United States Patent
Konradi et al.

(10) Patent No.: US 12,103,902 B2
(45) Date of Patent: Oct. 1, 2024

(54) BICYCLIC COMPOUNDS

(71) Applicant: Vivace Therapeutics, Inc., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

( * ) Notice: Subject to any disclaimer, the term of this patent is extended or adjusted under 35 U.S.C. 154(b) by 170 days.

(21) Appl. No.: 17/752,649

(22) Filed: May 24, 2022

(65) Prior Publication Data

US 2022/0298102 A1 Sep. 22, 2022

Related U.S. Application Data

(62) Division of application No. 16/849,728, filed on Apr. 15, 2020, now Pat. No. 11,420,935.

(60) Provisional application No. 62/834,671, filed on Apr. 16, 2019.

(51) Int. Cl.
| | |
|---|---|
| *C07C 235/66* | (2006.01) |
| *C07C 255/24* | (2006.01) |
| *C07C 311/51* | (2006.01) |
| *C07D 213/40* | (2006.01) |
| *C07D 213/61* | (2006.01) |
| *C07D 213/73* | (2006.01) |
| *C07D 217/24* | (2006.01) |
| *C07D 217/26* | (2006.01) |
| *C07D 233/64* | (2006.01) |
| *C07D 241/12* | (2006.01) |
| *C07D 257/04* | (2006.01) |
| *C07D 305/06* | (2006.01) |
| *C07D 305/08* | (2006.01) |
| *C07D 333/70* | (2006.01) |
| *C07D 401/12* | (2006.01) |

(52) U.S. Cl.
CPC .......... *C07C 235/66* (2013.01); *C07C 255/24* (2013.01); *C07C 311/51* (2013.01); *C07D 213/40* (2013.01); *C07D 213/61* (2013.01); *C07D 213/73* (2013.01); *C07D 217/24* (2013.01); *C07D 217/26* (2013.01); *C07D 233/64* (2013.01); *C07D 241/12* (2013.01); *C07D 257/04* (2013.01); *C07D 305/06* (2013.01); *C07D 305/08* (2013.01); *C07D 333/70* (2013.01); *C07D 401/12* (2013.01); *C07C 2601/02* (2017.05); *C07C 2601/04* (2017.05)

(58) Field of Classification Search
None
See application file for complete search history.

(56) References Cited

U.S. PATENT DOCUMENTS

| | | |
|---|---|---|
| 7,718,703 B2 | 5/2010 | Harada et al. |
| 7,960,409 B2 | 6/2011 | Grimm et al. |
| 8,362,000 B2 | 1/2013 | Bian et al. |
| 8,426,401 B2 | 4/2013 | Bian et al. |
| 8,748,417 B2 | 6/2014 | Zhang et al. |
| 9,012,443 B2 | 4/2015 | Boezio et al. |
| 9,452,986 B2 | 9/2016 | Bogdan et al. |
| 9,776,995 B2 | 10/2017 | Weiss et al. |
| 11,420,935 B2 | 8/2022 | Konradi et al. |
| 2002/0042426 A1 | 4/2002 | Makovec et al. |
| 2005/0059705 A1 | 3/2005 | Mjalli et al. |
| 2008/0188521 A1 | 8/2008 | Grimm et al. |
| 2012/0040936 A1 | 2/2012 | Kanno et al. |
| 2012/0302752 A1 | 11/2012 | Zhao et al. |
| 2014/0336182 A1 | 11/2014 | Cee et al. |
| 2015/0157584 A1 | 6/2015 | Guan et al. |
| 2015/0166500 A1 | 6/2015 | Zhao et al. |
| 2016/0194285 A1 | 7/2016 | Thompson et al. |
| 2020/0347009 A1 | 11/2020 | Konradi et al. |
| 2023/0061429 A1 | 3/2023 | Konradi et al. |
| 2024/0025913 A1 | 1/2024 | Konradi et al. |

FOREIGN PATENT DOCUMENTS

| | | |
|---|---|---|
| CN | 101679357 A | 3/2010 |
| CN | 107438598 A | 12/2017 |
| EP | 0765871 A1 | 4/1997 |
| EP | 0765871 B1 | 3/2004 |
| EP | 1042295 B1 | 9/2005 |
| WO | WO-9835967 A2 | 8/1998 |
| WO | WO-9932450 A1 | 7/1999 |
| WO | WO-0075145 A1 | 12/2000 |
| WO | WO-0200622 A2 | 1/2002 |
| WO | WO-0244166 A1 | 6/2002 |
| WO | WO-03010146 A1 | 2/2003 |
| WO | WO-2005014533 A2 | 2/2005 |

(Continued)

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Pobbati et al., Therapeutic targeting of TEAD transcription factors in cancer. Trends in Biochemical Sciences, 2023, 48, 450-462.*
Berge et al. Pharmaceutical Salts. Journal of Pharmaceutical Sciences 66(1):1-19 (Jan. 1977).
Bundgaard et al. Design of Prodrugs pp. 7-9, 21-24 (1985).
Dimauro et al. Application of a Parallel Synthetic Strategy in the Discovery of Biaryl Acyl Sulfonamides as Efficient and Selective NaV1.7 Inhibitors. J Med Chem 59(17):7818-39 (2016).

(Continued)

*Primary Examiner* — Po-Chih Chen
(74) *Attorney, Agent, or Firm* — WILSON SONSINI GOODRICH & ROSATI

(57) ABSTRACT

Provided herein are compounds and pharmaceutical compositions comprising said compounds that are useful for treating diseases, such as cancers. Specific cancers include those that are mediated by YAP/TAZ or those that are modulated by the interaction between YAP/TAZ and TEAD.

17 Claims, 2 Drawing Sheets

(56) References Cited

FOREIGN PATENT DOCUMENTS

| | | |
|---|---|---|
| WO | WO-2005082865 A1 | 9/2005 |
| WO | WO-2007090068 A2 | 8/2007 |
| WO | WO-2007097929 A1 | 8/2007 |
| WO | WO-2007099326 A1 | 9/2007 |
| WO | WO-2008023157 A1 | 2/2008 |
| WO | WO-2009018609 A1 | 2/2009 |
| WO | WO-2009073153 A2 | 6/2009 |
| WO | WO-2009075826 A1 | 6/2009 |
| WO | WO-2010124082 A1 | 10/2010 |
| WO | WO-2012003498 A1 | 1/2012 |
| WO | WO-2012054721 A1 | 4/2012 |
| WO | WO-2013066736 A1 | 5/2013 |
| WO | WO-2013188138 A1 | 12/2013 |
| WO | WO-2014177596 A1 | 11/2014 |
| WO | WO-2015144001 A1 | 10/2015 |
| WO | WO-2016118565 A1 | 7/2016 |
| WO | WO-2016153948 A1 | 9/2016 |
| WO | WO-2017058716 A1 | 4/2017 |
| WO | WO-2017064277 A1 | 4/2017 |
| WO | WO-2017087608 A1 | 5/2017 |
| WO | WO-2018028591 A1 | 2/2018 |
| WO | WO-2019040389 A1 | 2/2019 |
| WO | WO-2019148044 A1 | 8/2019 |
| WO | WO-2019152440 A1 | 8/2019 |
| WO | WO-2020097389 A1 | 5/2020 |
| WO | WO-2020214734 A1 | 10/2020 |
| WO | WO-2022087008 A1 | 4/2022 |

OTHER PUBLICATIONS

El-Feky et al. Design, Synthesis, and Anti-inflammatory Activity of Novel Quinazolines. Oriental Journal of Chemistry 33(2):707-716 (2017).

Fleisher et al. Improved oral drug delivery: solubility limitations overcome by the use of prodrugs. Advanced Drug Delivery Reviews 19:115-130 (1996).

Goodell et al. Acridine-based agents with topoisomerase II activity inhibit pancreatic cancer cell proliferation and induce apoptosis. J Med Chem 51(2):179-182 (2008).

Harvey et al. The Hippo pathway and human cancer. Nat Rev Cancer. 13(4):246-57 (2013).

La et al. The discovery of benzoxazine sulfonamide inhibitors of Na V 1.7: Tools that bridge efficacy and target engagement. Bioorg Med Chem Lett. 27(15):3477-3485 (2017).

Ma et al. The Hippo Pathway: Biology and Pathophysiology. Annu Rev Biochem 88:577-604 (2019).

Marx et al. Sulfonamides as Selective Na V 1.7 Inhibitors: Optimizing Potency and Pharmacokinetics to Enable in Vivo Target Engagement. ACS Med Chem Lett 7(12): 1062-1067 (2016).

Nara et al. Discovery of Novel, Highly Potent, and Selective Quinazoline-2-carboxamide-Based Matrix Metalloproteinase (MMP)-13 Inhibitors without a Zinc Binding Group Using a Structure-Based Design Approach. J Med Chem 57(21):8886-8902 (2014).

PCT/US2019/060350 International Search Report and Written Opinion dated Apr. 9, 2020.

PCT/US2019/060350 Invitation to Pay Additional Fees dated Feb. 4, 2020.

PCT/US2020/028363 International Search Report and Written Opinion dated Aug. 27, 2020.

PCT/US2020/028363 Invitation to Pay Additional Fees dated Jun. 25, 2020.

PCT/US2021/055668 International Search Report and Written Opinion dated Feb. 10, 2022.

PubChem-CID-59944252, Create Date: Aug. 20, 2012 (Aug. 20, 2012).

PubChem-CID-68784747, Create Date: Nov. 30, 2012 (Nov. 30, 2012).

PubChem-CID-70167127, Create Date: Dec. 1, 2012 (Dec. 1, 2012).

RN 1280135-65-0 Registry (Name: 2-Naphthalenecarboxamide, 5-[2,4-bis(1,1-dimethylpropyl)phenoxy]-N-butyl-1-hydroxy- (CA Index Name).

Roecker et al. Discovery of selective, orallybioavailable, N-linked arylsulfonamide Na v 1.7 inhibitors with pain efficacyin mice. Bioorg Med Chem Lett. 27(10):2087-2093(2017).

Science IP Report dated Jan. 18, 2019 (100 pgs).

Weiss et al. Sulfonamides as Selective Na V 1.7 Inhibitors: Optimizing Potency and Pharmacokinetics While Mitigating Metabolic Liabilities. J Med Chem 60(14):5969-5989 (2017).

Yu et al. Hippo Pathway in Organ Size Control, Tissue Homeostasis, and Cancer. Cell 163(4):811-28 (2015).

Golub et al., Molecular classification of cancer: class discovery and class prediction by gene expression monitoring. Science. 286(5439):531-537 (1999).

Lala et al. Role of nitric oxide in tumor progression: Lessons from experimental tumors. Cancer and Metastasis Reviews 17(1):91-106 (1998).

Registry No. 1310490-70-0, entered STN Jun. 27, 2011.

* cited by examiner

BICYCLIC COMPOUNDS

CROSS-REFERENCE

This application is a divisional of U.S. patent application Ser. No. 16/849,728, filed Apr. 15, 2020, which claims the benefit of U.S. Provisional Application No. 62/834,671, filed Apr. 16, 2019, each of which is incorporated by reference herein in its entirety.

BACKGROUND OF THE DISCLOSURE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferation. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSURE

Provided herein are bicyclic compounds and pharmaceutical compositions comprising said compounds. In some embodiments, the subject compounds are useful for the treatment of cancer.

In one aspect, the present disclosure provides a compound of Formula (I), or a pharmaceutically acceptable salt thereof

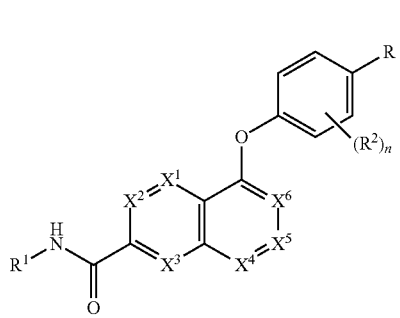

Formula (I)

wherein,
each $X^1$, $X^4$, $X^5$, and $X^6$, is independently N or $CR^X$;
each $X^2$ and $X^3$ is independently N or $CR^Y$;
each $R^X$ is independently hydrogen, halogen, nitro, —$OR^3$, —$SR^3$, —CN, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^Y$ is independently hydrogen, halogen, nitro, —CN, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
R is halogen, nitro, —CN, —$OR^3$, —$SR^3$, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, or substituted or unsubstituted $C_1$-$C_6$fluoroalkyl;
$R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)$_2R^4$;
each $R^2$ is independently halogen, nitro, —$N_3$, —CN, —$OR^3$, —$SR^3$, —S(=O)$_2R^3$, —N($R^3$)$_2$, —C(=O)O$R^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;
$R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —$NH_2$; and
n is 0, 1, 2, 3, or 4.

In another aspect, the present disclosure provides a compound of Formula (II), or a pharmaceutically acceptable salt thereof:

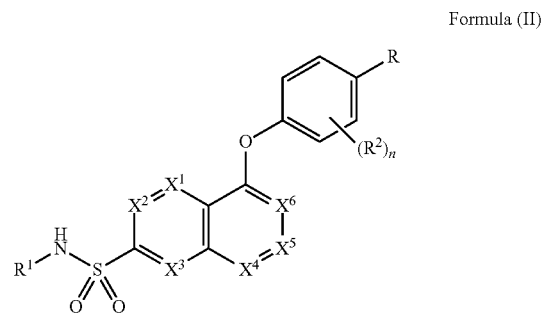

Formula (II)

wherein,
- each $X^1$, $X^2$, $X^3$, $X^4$, $X^5$, and $X^6$ is independently N or $CR^X$;
- each $R^X$ is independently hydrogen, halogen, nitro, $-OR^3$, $-SR^3$, $-CN$, $-C(=O)R^3$, $-C(=O)N(R^3)_2$, $-C(=O)OR^3$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
- R is halogen, nitro, $-CN$, $-OR^3$, $-SR^3$, $-C(=O)R^3$, $-C(=O)N(R^3)_2$, $-C(=O)OR^3$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, or substituted or unsubstituted $C_1$-$C_6$fluoroalkyl;
- $R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, $-CN$, or $-S(=O)_2R^4$;
- each $R^2$ is independently halogen, nitro, $-N_3$, $-CN$, $-OR^3$, $-SR^3$, $-S(=O)_2R^3$, $-N(R^3)_2$, $-C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
- each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;
- $R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or $-NH_2$; and
- n is 0, 1, 2, 3, or 4.

In another aspect, the present disclosure provides a compound of Formula (III), or a pharmaceutically acceptable salt thereof:

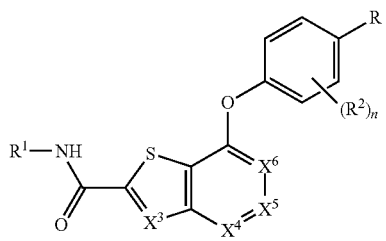

Formula (III)

wherein,
- each $X^3$, $X^5$, and $X^6$ is independently N or $CR^X$;
- $X^4$ is $CR^X$;
- each $R^X$ is independently hydrogen, halogen, nitro, $-OR^3$, $-SR^3$, $-CN$, $-C(=O)R^3$, $-C(=O)N(R^3)_2$, $-C(=O)OR^3$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
- R is halogen, nitro, $-CN$, $-OR^3$, $-SR^3$, $-C(=O)R^3$, $-C(=O)N(R^3)_2$, $-C(=O)OR^3$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, or substituted or unsubstituted $C_1$-$C_6$fluoroalkyl;
- $R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, $-CN$, or $-S(=O)_2R^4$;
- each $R^2$ is independently halogen, nitro, $-N_3$, $-CN$, $-OR^3$, $-SR^3$, $-S(=O)_2R^3$, $-N(R^3)_2$, $-C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
- each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;
- $R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or $-NH_2$; and
- n is 0, 1, 2, 3, or 4.

Any combination of the groups described above for the various variables is contemplated herein. Throughout the specification, groups and substituents thereof are chosen by one skilled in the field to provide stable moieties and compounds.

In another aspect, the present disclosure provides a compound or pharmaceutically acceptable salt thereof, wherein the compound is a compound from Table 1, or a pharmaceutically acceptable salt thereof.

In some embodiments, the compounds disclosed herein exhibits an $IC_{50}$ of no more than 10 μM.

In some embodiments, the compounds disclosed herein exhibits an $IC_{50}$ of no more than 3 μM.

In another aspect, the present disclosure provides a pharmaceutical composition comprising a pharmaceutically acceptable excipient and a compound disclosed herein or a pharmaceutically acceptable salt thereof.

In another aspect, the present disclosure provides a method for treating a cancer in a subject in need thereof comprising administering a therapeutically effective amount of a compound disclosed herein or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Certain Terminology

Figure 1:
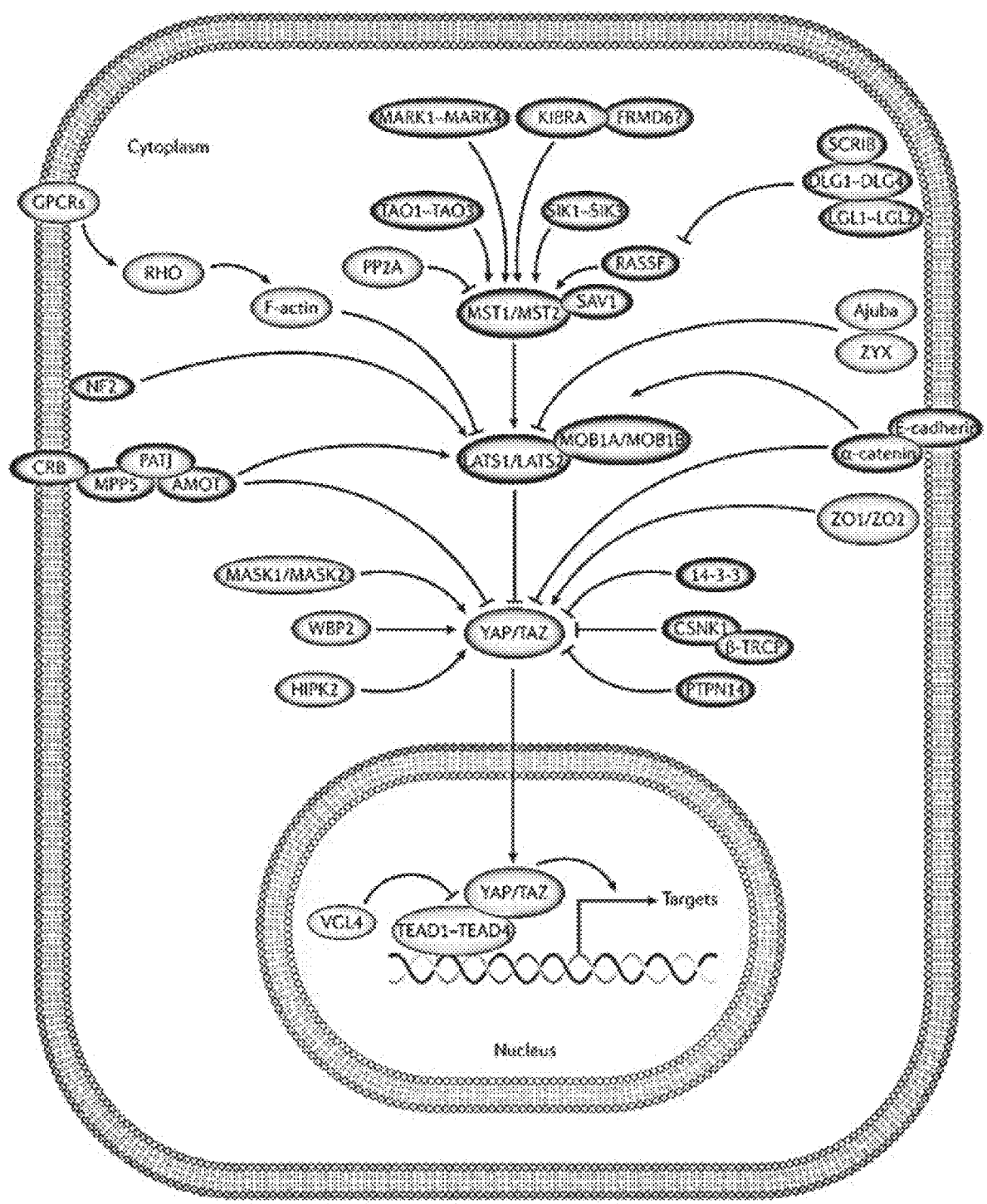
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK 1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Palsi-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" a particular value or range. About also includes the exact amount. Hence "about 5 μL" means "about 5 μL" and also "5 μL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —NH$_2$ radical.
"Cyano" refers to the —CN radical.
"Hydroxyl" refers to the —OH radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^8$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—

NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$NR$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Amino-alkyl" refers to a radical of the formula: -alkyl-NH$_2$.

"Hydroxyl-alkyl" refers to a radical of the formula: -alkyl-OH.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$NR$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$NR$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$) C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted hetero-cyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro, or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—CN, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tNR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroalkyl" refers to an alkyl group as defined above in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, the heteroalkyl comprises 1, 2, or 3 heteroatoms. In some embodiments, the alkyl part of the heteroalkyl radical is optionally substituted as defined for an alkyl group. Representative heteroalkyl groups include, but are not limited to —$CH_2NH_2$, —$CH_2NHCH_3$, —$CH_2N(CH_3)_2$, —$CH_2OH$, —$CH_2OCH_3$, —$CH_2CH_2NH_2$, —$CH_2CH_2NHCH_3$, —$CH_2CH_2N(CH_3)_2$, —$CH_2CH_2OH$, —$CH_2CH_2OCH_3$, —$CH_2CH_2OCH_2CH_2NH_2$, or —$CH_2CH_2OCH_2CH_2OH$.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, and 0-1 S atoms in the ring. In some embodiments, the heteroaryl is monocyclic heteroaryl. In some embodiments, the monocyclic heteroaryl is a 5-membered or 6-membered heteroaryl. In some embodiments, heteroaryl is a $C_1$-$C_9$ heteroaryl. In some embodiments, monocyclic heteroaryl is a $C_1$-$C_5$ heteroaryl. In some embodiments, a bicyclic heteroaryl is a $C_5$-$C_9$ heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above.

Likewise, all possible isomers, as well as their racemic and optically pure forms, and all tautomeric forms are also intended to be included. The term "geometric isomer" refers to E or Z geometric isomers (e.g., cis or trains) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

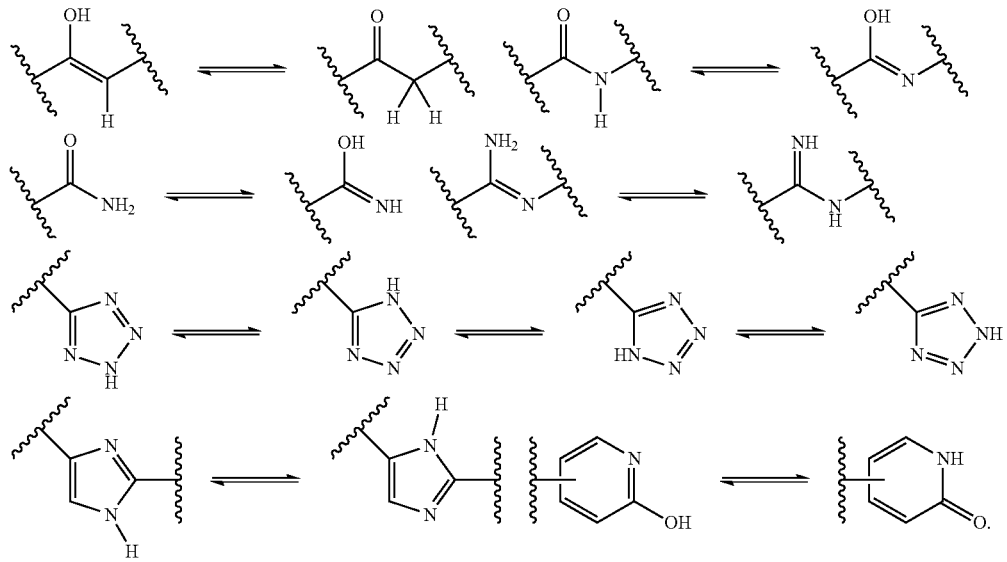

If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where R is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans).

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berg S. M. et al., "Pharmaceutical Salts," *Journal of Pharmaceutical Science*, 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines, and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are bicyclic compounds.

In one aspect, the present disclosure provides a compound of Formula (I), or a pharmaceutically acceptable salt thereof

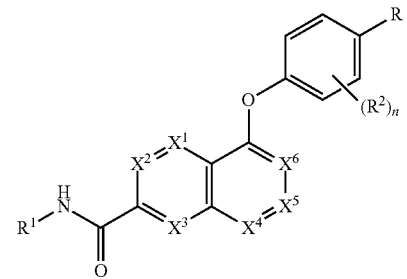

Formula (I)

wherein,
each $X^1$, $X^4$, $X^5$, and $X^6$, is independently N or $CR^X$;
each $X^2$ and $X^3$ is independently N or $CR^Y$;
each $R^X$ is independently hydrogen, halogen, nitro, —$OR^3$, —$SR^3$, —CN, —C(=O)$R^3$, —C(=O)N($R^3$)$_2$, —C(=O)$OR^3$, —S(=O)$R^3$, —S(=O)$_2R^3$, —N($R^3$)$_2$, —$NR^3S$(=O)$_2R^3$, —$NR^3C$(=O)$R^3$, —$NR^3C$(=O)$OR^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^Y$ is independently hydrogen, halogen, nitro, —CN, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2$$R^3$, —$NR^3$C(=O)$R^3$, —$NR^3$C(=O)O$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

R is halogen, nitro, —CN, —O$R^3$, —S$R^3$, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2$$R^3$, —$NR^3$C(=O)$R^3$, —$NR^3$C(=O)O$R^3$, or substituted or unsubstituted $C_1$-$C_6$fluoroalkyl;

$R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)$_2R^4$;

each $R^2$ is independently halogen, nitro, —$N_3$, —CN, —O$R^3$, —S$R^3$, —S(=O)$_2R^3$, —N($R^3$)$_2$, —C(=O)O$R^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;

$R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —NH$_2$; and n is 0, 1, 2, 3, or 4.

For any and all of the embodiments of a compound of Formula (I), substituents are selected from among a subset of the listed alternatives. For example, in some embodiments $X^1$ is N or $CR^X$. In other embodiments, $X^1$ is N. In some embodiments, $X^1$ is $CR^X$.

In some embodiments, $X^1$ is $CR^X$; and each $X^2$ and $X^3$ is $CR^Y$. In some embodiments, $X^1$ is N; and each $X^2$ and $X^3$ is $CR^Y$. In some embodiments, $X^1$ is $CR^X$; $X^2$ is $CR^Y$; and $X^3$ is N.

In some embodiments, each $X^4$, $X^5$, and $X^6$ is $CR^X$. In some embodiments, $X^4$ is N; and each $X^5$ and $X^6$ is $CR^X$. In some embodiments, each $X^4$ and $X^5$ is $CR^X$; and $X^6$ is N.

In some embodiments, each $R^X$ is independently hydrogen, halogen, —O$R^3$, —S$R^3$, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl. In some embodiments, each $R^X$ is independently hydrogen, halogen, —O$R^3$, —S$R^3$, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, each $R^X$ is independently hydrogen, F, Cl, Br, I, —CH$_3$, —CH$_2$CH$_3$, —CH$_2$OH, —CH$_2$CH$_2$OH, —CH$_2$CN, —CH$_2$C(=O)OH, —CH$_2$C(=O)OCH$_3$, —CH$_2$C(=O)OCH$_2$CH$_3$, —CH$_2$C(=O)NH$_2$, —CH$_2$C(=O)NHCH$_3$, —CH$_2$C(=O)N(CH$_3$)$_2$, —CH$_2$NH$_2$, —CH$_2$NHCH$_3$, —CH$_2$N(CH$_3$)$_2$, —CH$_2$F, —CHF$_2$, —CF$_3$, —CH=CH$_2$, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —OCH$_3$, —OCH$_2$CH$_3$, —OCH$_2$CH$_2$OH, —OCH$_2$CN, —OCF$_3$, —C(=O)OH, —C(=O)OCH$_3$, —C(=O)OCH$_2$CH$_3$, —C(=O)NH$_2$, —C(=O)NHCH$_3$, —C(=O)N(CH$_3$)$_2$, —NH$_2$, —NHCH$_3$, —N(CH$_3$)$_2$, —NHC(=O)CH$_3$, —N(CH$_3$)C(=O)CH$_3$, —NHC(=O)OCH$_3$, —N(CH$_3$)C(=O)OCH$_3$, —S(=O)CH$_3$, —S(=O)$_2$CH$_3$, —NHS(=O)$_2$CH$_3$, or —N(CH$_3$)S(=O)$_2$CH$_3$. In some embodiments, each $R^X$ is independently hydrogen, F, Cl, Br, I, —CH$_3$, —CH$_2$CH$_3$, cyclopropyl, —C≡CH, —OH, —OCH$_3$, —OCH$_2$CH$_3$, —OCF$_3$, —SCH$_3$, cyclopropyloxy, —NH$_2$, —NHC(=O)CH$_3$, —N(CH$_3$)C(=O)CH$_3$, —NHS(=O)$_2$CH$_3$, —N(CH$_3$)S(=O)$_2$CH$_3$, —S(=O)CH$_3$, or —S(=O)$_2$CH$_3$. In some embodiments, each $R^X$ is independently hydrogen, F, Cl, Br, I, —CH$_3$, —CH$_2$CH$_3$, cyclopropyl, —OH, —OCH$_3$, —OCH$_2$CH$_3$, —OCF$_3$, cyclopropyloxy, —NH$_2$, —NHC(=O)CH$_3$, —NHS(=O)$_2$CH$_3$, —S(=O)CH$_3$, or —S(=O)$_2$CH$_3$. In some embodiments, each $R^X$ is independently hydrogen, F, Cl, Br, —CH$_3$, —OH, —OCH$_3$, or —OCF$_3$. In some embodiments, each $R^X$ is independently hydrogen, F, Cl, —CH$_3$, —OCH$_3$, or —OCF$_3$. In some embodiments, each $R^X$ is independently hydrogen, F, or —OCH$_3$. In some embodiments, each $R^X$ is hydrogen.

In some embodiments, each $R^Y$ is independently hydrogen, halogen, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl. In some embodiments, each $R^Y$ is independently hydrogen, halogen, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, each $R^Y$ is independently hydrogen, F, Cl, Br, I, —$CH_3$, —$CH_2CH_3$, —$CH_2OH$, —$CH_2CH_2OH$, —$CH_2CN$, —$CH_2C$(=O)OH, —$CH_2C$(=O)O$CH_3$, —$CH_2C$(=O)OCH$_2CH_3$, —$CH_2C$(=O)$NH_2$, —$CH_2C$(=O)NH$CH_3$, —$CH_2C$(=O)N($CH_3$)$_2$, —$CH_2NH_2$, —$CH_2NHCH_3$, —$CH_2N(CH_3)_2$, —$CH_2F$, —$CHF_2$, —$CF_3$, —CH=$CH_2$, —C≡CH, —C(=O)$NH_2$, —C(=O)NH$CH_3$, —C(=O)N($CH_3$)$_2$, —$NH_2$, —$NHCH_3$, —N($CH_3$)$_2$, —NHC(=O)$CH_3$, —N($CH_3$)C(=O)$CH_3$, —NHC(=O)O$CH_3$, —N($CH_3$)C(=O)O$CH_3$, —S(=O)$CH_3$, —S(=O)$_2CH_3$, —NHS(=O)$_2CH_3$, or —N($CH_3$)S(=O)$_2CH_3$. In some embodiments, each $R^Y$ is independently hydrogen, F, Cl, Br, I, —$CH_3$, —$CH_2CH_3$, cyclopropyl, —C≡CH—$NH_2$, —NHC(=O)$CH_3$, —N($CH_3$)C(=O)$CH_3$, —NHS(=O)$_2CH_3$, —N($CH_3$)S(=O)$_2CH_3$, —S(=O)$CH_3$, or —S(=O)$_2CH_3$. In some embodiments, each $R^Y$ is independently hydrogen, F, Cl, Br, I, —$CH_3$, —$CH_2CH_3$, cyclopropyl, —$NH_2$, —NHC(=O)$CH_3$, —NHS(=O)$_2CH_3$, —S(=O)$CH_3$, or —S(=O)$_2CH_3$. In some embodiments, each $R^Y$ is independently hydrogen, F, Cl, or —$CH_3$. In some embodiments, each $R^Y$ is independently hydrogen or F. In some embodiments, each $R^Y$ is hydrogen.

In some embodiments, $R^1$ is substituted or unsubstituted $C_1$-$C_6$alkyl.

In some embodiments, $R^1$ is $C_1$-$C_6$alkyl substituted with substituted or unsubstituted $C_2$-$C_6$alkenyl, substituted or unsubstituted $C_2$-$C_6$alkynyl, or —CN.

In some embodiments, $R^1$ is $C_1$-$C_6$alkyl substituted with —O$R^3$; and $R^3$ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl.

In some embodiments, $R^1$ is $C_1$-$C_6$alkyl substituted with —C(=O)N($R^5$)$_2$ or —N($R^5$)$_2$; wherein each $R^5$ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —CN; or two $R^5$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with substituted or unsubstituted $C_3$-$C_8$cycloalkyl or substituted or unsubstituted $C_2$-$C_7$heterocycloalkyl.

In some embodiments, $R^1$ is $C_1$-$C_6$alkyl substituted with cyclopropyl, cyclobutyl, cyclopentyl, or cyclohexyl.

In some embodiments, $R^1$ is $C_1$-$C_6$alkyl substituted with oxetanyl, tetrahydrofuranyl, tetrahydropyranyl, azetidinyl, pyrrolidinyl, or piperidinyl.

In some embodiments, $R^1$ is $C_1$-$C_6$alkyl substituted with substituted or unsubstituted phenyl, wherein if phenyl is substituted, then it is substituted with 1, 2, 3, or 4 substituents selected from halogen, nitro, —CN, —O$R^3$, —N($R^3$)$_2$, —C(=O)$R^3$, —C(=O)N($R^3$)$_2$, —C(=O)O$R^3$, substituted or unsubstituted $C_1$-$C_6$alkyl, and substituted or unsubstituted $C_1$-$C_6$fluoroalkyl; and each $R^3$ is independently hydrogen, substituted or unsubstituted $C_1$-$C_6$alkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with 5-membered heteroaryl ring containing at least one nitrogen atom.

In some embodiments, $R^1$ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.

In some embodiments, $R^1$ is $C_1$-$C_6$alkyl substituted with 5-membered heteroaryl ring selected from

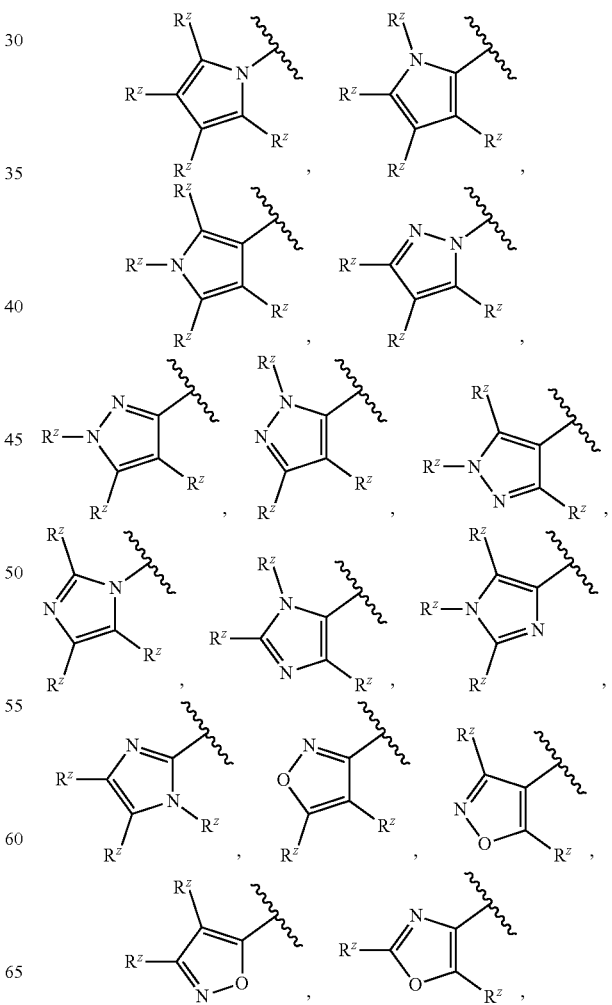

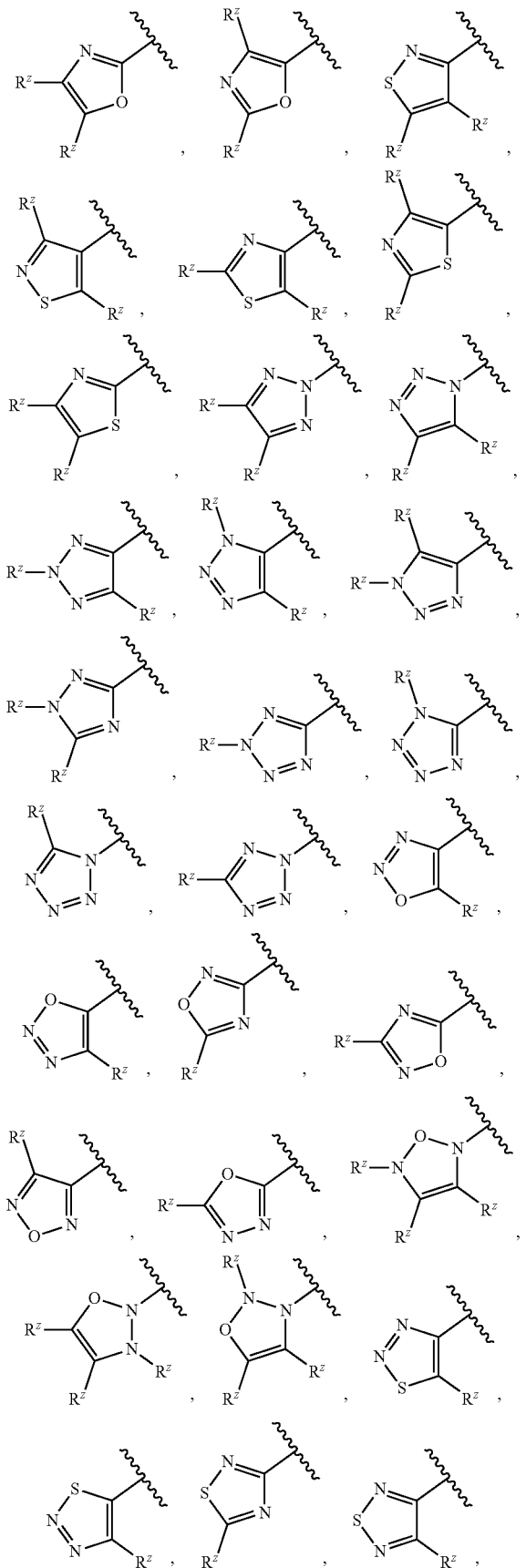

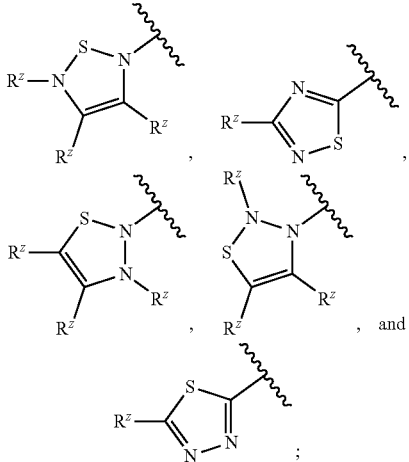

wherein
each $R^z$ is independently hydrogen, halogen, —CN, —$OR^3$, —$SR^3$, —$S(=O)_2R^3$, —$N(R^3)_2$, —$C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with a substituted or unsubstituted monocyclic 6-membered heteroaryl ring containing at least one nitrogen atom. In some embodiments, $R^1$ is $C_1$-$C_6$alkyl substituted with a substituted or unsubstituted monocyclic 6-membered heteroaryl ring containing 1, 2, or 3 nitrogen atoms. In some embodiments, $R^1$ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl. In some embodiments, $R^1$ is $C_1$-$C_6$alkyl substituted with substituted or unsubstituted pyridinyl. In some embodiments, $R^1$ is $C_1$-$C_6$alkyl substituted with pyridinyl. In some embodiments, $R^1$ is $C_1$-$C_6$alkyl substituted with 2-pyridinyl.

In some embodiments, $R^1$ is $C_1$-$C_6$alkyl substituted with 6-membered heteroaryl ring selected from

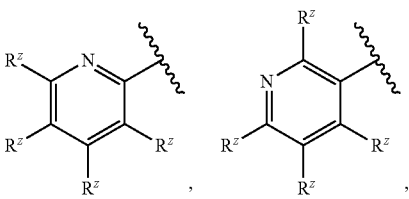

-continued

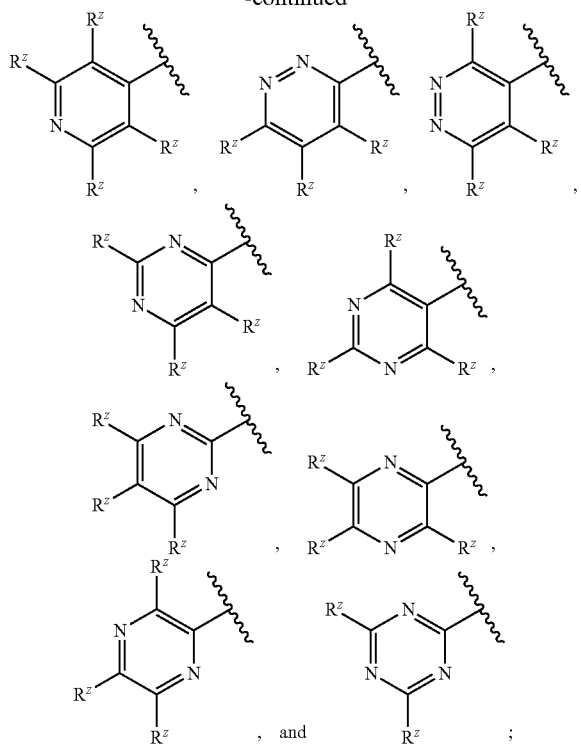

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$—C heterocycloalkyl.

In some embodiments, R$^1$ is C$_1$-C$_6$alkyl substituted with bicyclic 6/5 fused heteroaryl ring In some embodiments, R$^1$ is C$_1$-C$_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzoxadiazolyl, substituted or unsubstituted benzothiadiazolyl, substituted or unsubstituted indolizinyl, and substituted or unsubstituted imidazopyridinyl.

In some embodiments, R$^1$ is C$_1$-C$_6$alkyl substituted with bicyclic 6/5 fused heteroaryl ring selected from

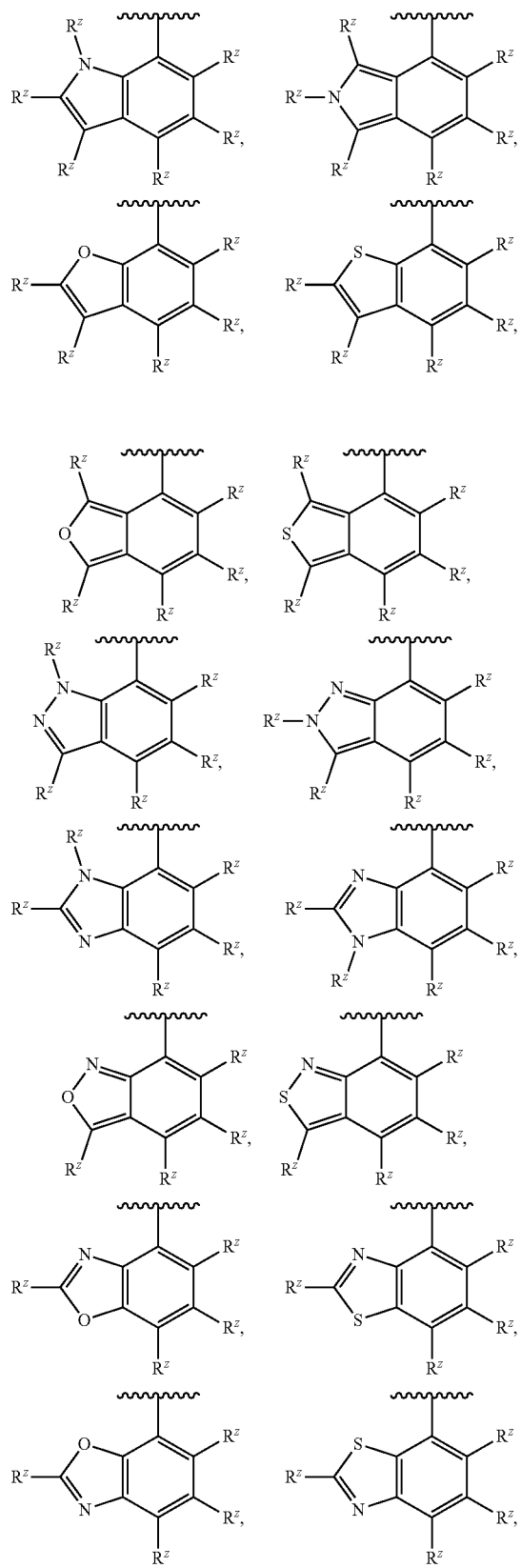

-continued

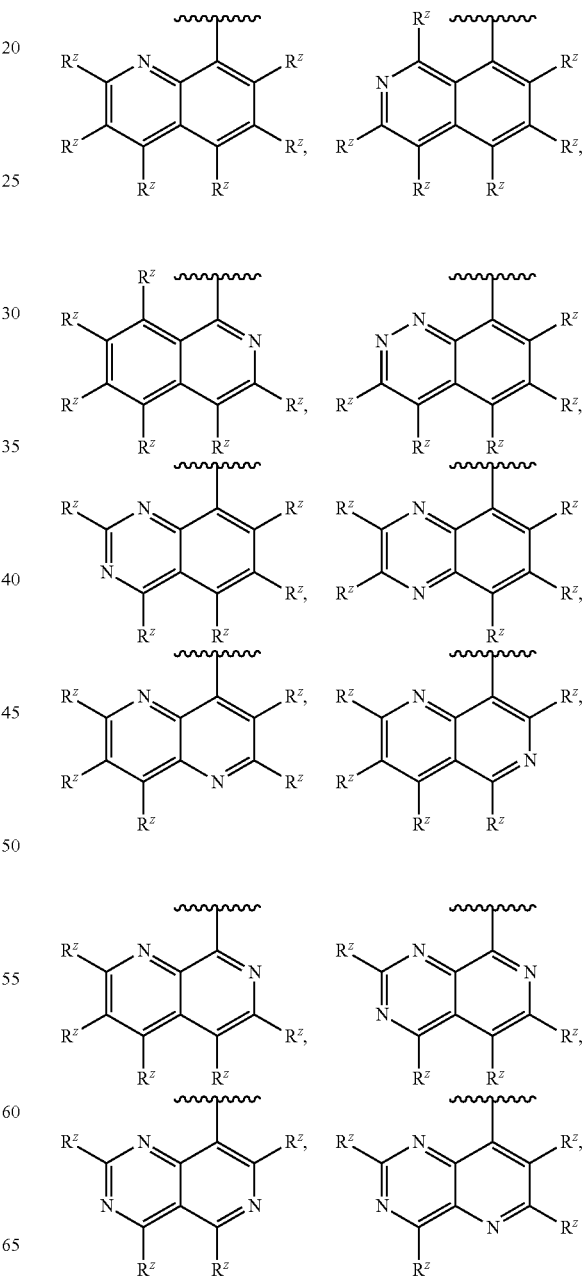

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

In some embodiments, R$^1$ is C$_1$-C$_6$alkyl substituted with a substituted or unsubstituted bicyclic 6/6 fused heteroaryl ring containing at least one nitrogen atom. In some embodiments, R$^1$ is C$_1$-C$_6$alkyl substituted with a substituted or unsubstituted bicyclic 6/6 fused heteroaryl ring containing 1, 2, 3, or 4 nitrogen atoms. In some embodiments, R$^1$ is C$_1$-C$_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or unsubstituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyrdazinyl, substituted or unsubstituted pyridopyrimidinyl, and substituted or unsubstituted pteridinyl.

In some embodiments, R$^1$ is C$_1$-C$_6$alkyl substituted with 6/6 fused heteroaryl ring selected from

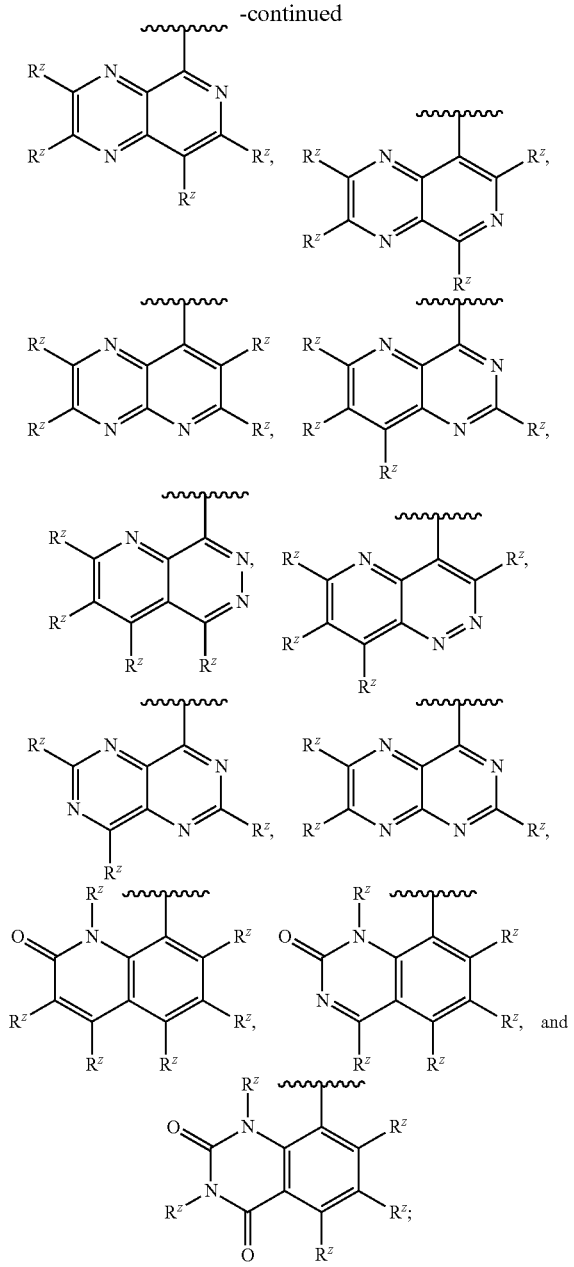

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

In some embodiments, $R^1$ is C$_1$-C$_6$alkyl substituted with 1, 2, or 3 substituents each independently selected from —OH, —OCH$_3$, —NH$_2$, NHCH$_3$, N(CH$_3$)$_2$, and pyridinyl. In some embodiments, $R^1$ is C$_1$-C$_6$alkyl substituted with 1 or 2 substituents each independently selected from —OH, —OCH$_3$, —NH$_2$, NHCH$_3$, N(CH$_3$)$_2$, and pyridinyl. In some embodiments, $R^1$ is C$_1$-C$_6$alkyl substituted with 1 or 2 substituents each independently selected from —OH and pyridinyl. In some embodiments, $R^1$ is C$_1$-C$_6$alkyl substituted with 1 or 2 substituents each independently selected from —NH$_2$ and pyridinyl. In some embodiments, $R^1$ is C$_1$-C$_6$alkyl substituted with 1 or 2 substituents each independently selected from —OH and —NH$_2$. In some embodiments, $R^1$ is C$_1$-C$_6$alkyl substituted with —OH. In some embodiments, $R^1$ is C$_1$-C$_6$alkyl substituted with —NH$_2$.

In some embodiments, each $R^z$ is independently hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, —OCF$_3$, —NH$_2$, —NHCH$_3$, or —N(CH$_3$)$_2$. In some embodiments, each $R^t$ is independently hydrogen, F, Cl, Br, —CH$_3$, —CN, —OCH$_3$, —NH$_2$, —NHCH$_3$, or —N(CH$_3$)$_2$. In some embodiments, each $R^z$ is independently hydrogen, Cl, Br, —CH$_3$, —OCH$_3$, —NH$_2$, or —N(CH$_3$)$_2$. In some embodiments, each $R^z$ is hydrogen.

In some embodiments, $R^1$ is C$_1$-C$_6$alkyl substituted with halogen, —CN, —OR$^3$, —SR$^3$, —S(=O) R$^3$, —S(=O)$_2$ R$^3$, —N(R$^3$)$_2$, —C(=O)OR$^3$, —C(=O)N(R$^3$)$_2$, —CR$^3$=C(R$^3$)$_2$, —C≡CR$^3$, substituted or unsubstituted C$_3$-C$_{10}$cycloalkyl, substituted or unsubstituted C$_2$-C$_{10}$heterocycloalkyl, or substituted or unsubstituted aryl; and each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_2$ heterocycloalkyl.

In some embodiments, $R^1$ is substituted or unsubstituted C$_3$-C$_{10}$cycloalkyl or substituted or unsubstituted C$_2$-C$_{10}$heterocycloalkyl. In some embodiments, $R^1$ is C$_3$-C$_6$cycloalkyl or C$_3$-C$_5$heterocycloalkyl substituted with C$_1$-C$_6$alkyl, phenyl, pyridinyl, pyrazinyl, pyrimidinyl, pyridazinyl, or triazinyl. In some embodiments, $R^1$ is C$_3$-C$_6$cycloalkyl or C$_3$-C$_5$heterocycloalkyl substituted with C$_1$-C$_6$alkyl, phenyl, or pyridinyl.

In some embodiments, R is halogen, nitro, —CN, —OR$^3$, —C(=O)R$^3$, —C(=O)N(R$^3$)$_2$, —C(=O)OR$^3$, —S(=O) R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl; and each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

In some embodiments, R is F, Cl, Br, I, nitro, —CN, —OCH$_2$F, —OCHF$_2$, —OCF$_3$, —C(=O)CH$_3$, —C(=O)OCH$_3$—C(=O)NH$_2$, —C(=O)NHCH$_3$, —C(=O)N(CH$_3$)$_2$, —S(=O)CH$_3$, —S(=O)$_2$CH$_1$, —NHS(=O)$_2$CH$_3$, —N(CH$_3$)S(=O)$_2$CH$_3$, —NHC(=O)CH$_3$, —N(CH$_3$)C —C(=O)CH$_3$, —NHC(=O)OCH$_3$, —N(CH$_3$)C(=O)OCH$_3$, —CH$_2$F, —CHF$_2$, or —CF$_3$. In some embodiments, R is F, Cl, —CN, —OCF$_3$, —CHF$_2$, or —CF$_3$. In some embodiments, R is F, Cl, —OCF$_3$, —CHF$_2$, or —CF$_3$. In some embodiments, R is F, Cl, or —CF$_3$. In some embodiments, R is —OCF$_3$. In some embodiments, R is —CF$_3$.

In some embodiments, each R$^2$ is independently halogen, nitro, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, or substituted or unsubstituted C$_1$-C$_6$fluoroalkyl; and each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

In some embodiments, each R$^2$ is independently F, Cl, Br, nitro, —CN, —OH, —OCH$_3$, —OCH$_2$CH$_3$, —OCH$_2$CH$_2$OH, —OCH$_2$CN, —OCF$_3$, —S(=O)$_2$CH$_3$, —NH$_2$, —NHCH$_3$, —N(CH$_3$)$_2$, —C(=O)OCH$_3$, —CH$_3$, —CH$_2$CH$_3$, —CH$_2$F, —CHF$_2$, or —CF$_3$. In some embodiments, each R$^2$ is independently F, Cl, —CN, —OCH$_3$, —OCF$_3$, —C(=O)OCH$_3$, —CH$_3$, or —CF$_3$. In some embodiments, each R$^2$ is independently F, Cl, —OCF$_3$, or —CF$_3$. In some embodiments, each R$^2$ is independently F or C$_1$.

In some embodiments, n is 0. In some embodiments, n is 1. In some embodiments, n is 2. In some embodiments, n is 3. In some embodiments, n is 4. In some embodiments, n is 0 or 1. In some embodiments, n is 1 or 2. In some embodiments, n is 2 or 3. In some embodiments, n is 3 or 4. In some embodiments, n is 1, 2, or 3. In some embodiments, n is 2, 3, or 4. In some embodiments, n is 1, 2, 3, or 4.

In another aspect, the present disclosure provides a compound of Formula (I), or a pharmaceutically acceptable salt thereof Formula (I)

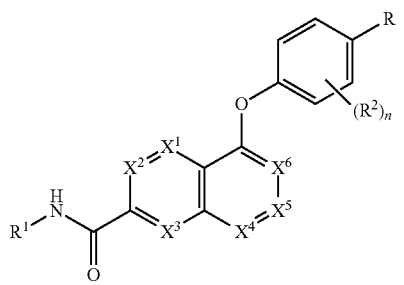

wherein,
each X$^1$, X$^4$, X$^5$, and X$^6$, is independently CR$^X$;
each X$^2$ and X$^3$ is independently CR$^Y$;
each R$^X$ is independently hydrogen, halogen, nitro, —OR$^3$, —SR$^3$, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, substituted or unsubstituted C$_1$-C$_6$ alkyl, substituted or unsubstituted C$_1$-C$_6$fluoroalkyl, or substituted or unsubstituted C$_3$-C$_6$cycloalkyl;
each R$^Y$ is independently hydrogen, halogen, nitro, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, substituted or unsubstituted C$_1$-C$_6$ alkyl, substituted or unsubstituted C$_1$-C$_6$fluoroalkyl, or substituted or unsubstituted C$_3$-C$_6$cycloalkyl;
R is halogen, nitro, —CN, or C$_1$-C$_4$fluoroalkyl;
R$^1$ is substituted or unsubstituted C$_1$-C$_6$alkyl or substituted or unsubstituted C$_3$-C$_{10}$cycloalkyl;
each R$^2$ is independently halogen, nitro, —N$_3$, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, or substituted or unsubstituted C$_3$-C$_6$cycloalkyl;
each R$^3$ is independently hydrogen or substituted or unsubstituted C$_1$-C$_6$alkyl; and
n is 0, 1, 2, 3, or 4.

In some embodiments, each R$^X$ is independently hydrogen, F, Cl, Br, —CH$_3$, —CH$_2$CH$_3$, —OH, —OCH$_3$, —OCH$_2$CH$_3$, —OCF$_3$, —OCF$_2$CH$_3$, or —OCH$_2$CF$_3$. In some embodiments, each X$^1$, X$^4$, X$^5$, and X$^6$, is CH. In some embodiments, each R$^Y$ is independently hydrogen, F, Cl, Br, —CH$_3$, —CH$_2$CH$_3$. In some embodiments, each X$^2$ and X$^3$ is CH. In some embodiments, R$^1$ is substituted or unsubstituted C$_1$-C$_6$alkyl. In some embodiments, R$^1$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, or —C(CH$_3$)$_3$. In some embodiments, R$^1$ is —CH$_3$. In some embodiments, R$^1$ is —CH$_2$CH$_3$. In some embodiments, R$^1$ is —CH$_2$CH$_2$CH$_3$. In some embodiments, R$^1$ is —CH(CH$_3$)$_2$. In some embodiments, R$^1$ is —CH$_2$CH$_2$CH$_2$CH$_3$. In some embodiments, R$^1$ is —CH(CH$_3$)CH$_2$CH$_3$. In some embodiments, R$^1$ is —CH$_2$CH(CH$_3$)$_2$. In some embodiments, R$^1$ is —C(CH$_3$)$_3$. In some embodiments, R$^1$ is C$_1$-C$_6$alkyl substituted with 0, 1, 2, or 3 substituents each independently selected from F, —CN, —NH$_2$, —NH(C$_1$-C$_6$alkyl), —N(C$_1$-C$_6$alkyl)$_2$, —OH, —O(C$_1$-C$_6$alkyl), C$_1$-C$_6$fluoroalkyl, amino-C$_1$-C$_6$alkyl, hydroxyl-C$_1$-C$_6$alkyl, C$_3$-C$_8$cycloalkyl, C$_2$-C$_7$heterocycloalkyl, or heteroaryl; wherein C$_2$-C$_7$heterocycloalkyl is having 1, 2, or 3 heteroatom ring members each independently selected from N, O, or S; wherein heteroaryl is 3-6 membered monocyclic or 9-10 membered bicyclic ring system having 1, 2, 3, or 4 heteroatom ring members each independently selected from N, O, and S; and wherein each instance of C$_3$-C$_8$cycloalkyl, C$_2$-C$_7$heterocycloalkyl, and heteroaryl is substituted with 0, 1, 2, or 3 substituents each independently selected from halogen, oxo, —CN, —NH$_2$, —NH(C$_1$-C$_6$alkyl), —N(C$_1$-C$_6$alkyl)$_2$, —OH, —O(C$_1$-C$_6$alkyl), C$_1$-C$_6$alkyl, C$_1$-C$_6$fluoroalkyl, amino-C$_1$-C$_6$alkyl, hydroxyl-C$_1$-C$_6$alkyl, and C$_3$-C$_8$cycloalkyl. In some embodiments, R$^1$ is C$_1$-C$_6$alkyl substituted with —N(R$^3$)$_2$ or —OR$^3$; and each R$^3$ is independently hydrogen or C$_1$-C$_6$alkyl. In some embodiments, R$^1$ is C$_1$-C$_6$alkyl substituted with —N(R$^3$)$_2$; and R$^3$ is hydrogen or C$_1$-C$_6$alkyl. In some embodiments, R$^1$ is C$_1$-C$_6$alkyl substituted with —OR$^3$; and R$^3$ is hydrogen or C$_1$-C$_6$alkyl. In some embodiments, R$^1$ is C$_1$-C$_6$alkyl substituted with —NH$_2$, —NHCH$_3$, —N(CH$_3$)$_2$, —OH, or —OCH$_3$. In some embodiments, R$^1$ is C$_1$-C$_6$alkyl substituted with —NH$_2$. In some embodiments, R$^1$ is —CH$_2$NH$_2$, —CH$_2$CH$_2$NH$_2$, —CH(NH$_2$)CH$_3$, —CH$_2$CH$_2$CH$_2$NH$_2$, —CH$_2$CH(NH$_2$)CH$_3$, —CH(NH$_2$)CH$_2$CH$_3$, —CH(CH$_3$)CH$_2$NH$_2$, or —C(CH$_3$)$_2$NH$_2$. In some embodiments, R$^1$ is —CH$_2$NH$_2$. In some embodiments, R$^1$ is —CH(NH$_2$)CH$_3$. In some embodiments, R$^1$ is —CH$_2$CH$_2$CH$_2$NH$_2$. In some embodiments, R$^1$ is —CH$_2$CH(NH$_2$)CH$_3$. In some embodiments, R$^1$ is —CH(NH$_2$)CH$_2$CH$_3$. In some embodiments, R$^1$ is —CH(CH$_3$)CH$_2$NH$_2$. In some embodiments, R$^1$ is —C(CH$_3$)$_2$NH$_2$. In some embodiments, R$^1$ is C$_1$-C$_6$alkyl substituted with —NHCH₃. In some embodiments, R¹ is —CH₂NHCH₃, —CH₂CH₂NHCH₃, —CH(NHCH₃)CH₃, —CH₂CH₂CH₂NHCH₃, —CH₂CH(NHCH₃)CH₃, —CH(NHCH₃)CH₂CH₃, —CH(CH₃)CH₂NHCH₃, or —C(CH₃)₂NHCH₃. In some embodiments, R¹ is —CH₂NHCH₃. In some embodiments, R¹ is —CH(NHCH₃)CH₃. In some embodiments, R¹ is —CH₂CH₂CH₂NHCH₃. In some embodiments, R¹ is —CH₂CH(NHCH₃)CH₃. In some embodiments, R¹ is —CH(NHCH₃)CH₂CH₃. In some embodiments, R¹ is —CH(CH₃)CH₂NHCH₃. In some embodiments, R¹ is —C(CH₃)₂NHCH₃. In some embodiments, R¹ is $C_1$-$C_6$alkyl substituted with —N(CH₃)₂. In some embodiments, R¹ is —CH₂N(CH₃)₂, —CH₂CH₂N(CH₃)₂, —CH(N(CH₃)₂)CH₃, —CH₂CH₂CH₂N(CH₃)₂, —CH₂CH(N(CH₃)₂)CH₃, —CH(N(CH₃)₂)CH₂CH₃, —CH(CH₃)CH₂N(CH₃)₂, or —C(CH₃)₂N(CH₃)₂. In some embodiments, R¹ is —CH₂N(CH₃)₂. In some embodiments, R¹ is —CH(N(CH₃)₂)CH₃. In some embodiments, R¹ is —CH₂CH₂CH₂N(CH₃)₂. In some embodiments, R¹ is —CH₂CH(N(CH₃)₂)CH₃. In some embodiments, R¹ is —CH(N(CH₃)₂)CH₂CH₃. In some embodiments, R¹ is —CH(CH₃)CH₂N(CH₃)₂. In some embodiments, R¹ is —C(CH₃)₂N(CH₃)₂. In some embodiments, R¹ is $C_1$-$C_6$alkyl substituted with —OH. In some embodiments, R¹ is —CH₂OH, —CH₂CH₂OH, —CH(OH)CH₃, —CH₂CH₂CH₂OH, —CH₂CH(OH)CH₃, —CH(OH)CH₂CH₃, —CH(CH₃)CH₂OH, or —C(CH₃)₂OH. In some embodiments, R¹ is —CH₂OH. In some embodiments, R¹ is —CH(OH)CH₃. In some embodiments, R¹ is —CH₂CH₂CH₂OH. In some embodiments, R¹ is —CH₂CH(OH)CH₃. In some embodiments, R¹ is —CH(OH)CH₂CH₃. In some embodiments, R¹ is —CH(CH₃)CH₂OH. In some embodiments, R¹ is —C(CH₃)₂OH. In some embodiments, R¹ is $C_1$-$C_6$alkyl substituted with —OCH₃. In some embodiments, R¹ is —CH₂OCH₃, —CH₂CH₂OCH₃, —CH(OCH₃)CH₃, —CH₂CH₂CH₂OCH₃, —CH₂CH(OCH₃)CH₃, —CH(OCH₃)CH₂CH₃, —CH(CH₃)CH₂OCH₃, or —C(CH₃)₂OCH₃. In some embodiments, R¹ is —CH₂OCH₃. In some embodiments, R¹ is —CH(OCH₃)CH₃. In some embodiments, R¹ is —CH₂CH₂CH₂OCH₃. In some embodiments, R¹ is —CH₂CH(OCH₃)CH₃. In some embodiments, R¹ is —CH(OCH₃)CH₂CH₃. In some embodiments, R¹ is —C(CH₃)₂OCH₃. In some embodiments, R¹ is $C_1$-$C_6$alkyl substituted with heteroaryl. In some embodiments, R¹ is $C_1$-$C_6$alkyl substituted with 6-membered heteroaryl ring. In some embodiments, R¹ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl. In some embodiments, R¹ is $C_1$-$C_6$alkyl substituted with substituted or unsubstituted pyridinyl. In some embodiments, R¹ is $C_1$-$C_6$alkyl substituted with pyridinyl. In some embodiments, the pyridinyl is 2-pyridinyl. In some embodiments, R is F, Cl, or —CF₃. In some embodiments, R is F. In some embodiments, R is $C_1$. In some embodiments, R is —CF₃. In some embodiments, each R² is independently F, Cl, —OCF₃, or —CF₃. In some embodiments, each R² is independently F or Cl. In some embodiments, n is 0. In some embodiments, n is 1. In some embodiments, n is 2. In some embodiments, n is 1 or 2.

In another aspect, the present disclosure provides a compound of Formula (II), or a pharmaceutically acceptable salt thereof:

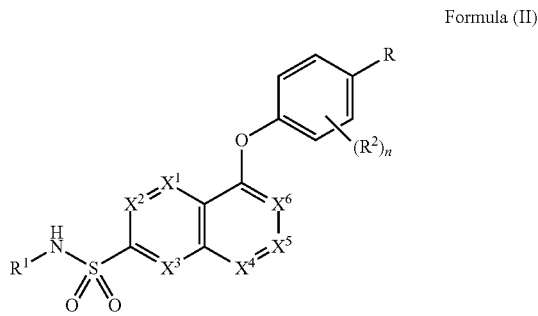

Formula (II)

wherein, each $X^1$, $X^2$, $X^3$, $X^4$, $X^5$, and $X^6$ is independently N or $CR^X$;

each $R^X$ is independently hydrogen, halogen, nitro, —OR³, —SR³, —CN, —C(=O)R³, —C(=O)N(R³)₂, —C(=O)OR³, —S(=O)R³, —S(=O)₂R³, —N(R³)₂, —NR³S(=O)₂R³, —NR³C(=O)R³, —NR³C(=O)OR³, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

R is halogen, nitro, —CN, —OR³, —SR³, —C(=O)R³, —C(=O)N(R³)₂, —C(=O)OR³, —S(=O)R³, —S(=O)₂R³, —N(R³)₂, —NR³S(=O)₂R³, —NR³C(=O)R³, —NR³C(=O)OR³, or substituted or unsubstituted $C_1$-$C_6$fluoroalkyl;

R¹ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)₂R⁴;

each R² is independently halogen, nitro, —N₃, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each R³ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two R³ are on the same nitrogen atom, then two R³ are taken together with the nitrogen atom to which they are attached to form a substituted or unsubstituted $C_3$—C; heterocycloalkyl;

R⁴ is substituted or unsubstituted $C_1$-$C_6$alkyl, substituted or unsubstituted $C_1$-$C_6$fluoroalkyl, substituted or unsubstituted $C_1$-$C_{10}$cycloalkyl, or —NH₂; and n is 0, 1, 2, 3, or 4.

For any and all of the embodiments of a compound of Formula (II), substituents are selected from among a subset of the listed alternatives. For example, in some embodiments $X^1$ is N or $CR^X$. In other embodiments, $X^1$ is N. In some embodiments, $X^1$ is $CR^X$.

In some embodiments, each $X^1$, $X^2$, and $X^3$ is $CR^X$. In some embodiments, $X^1$ is N; and each $X^2$ and $X^3$ is $CR^X$. In some embodiments, each $X^1$ and $X^2$ is $CR^X$; and $X^3$ is N.

In some embodiments, each $X^1$, $X^5$, and $X^6$ is $CR^X$. In some embodiments, $X^4$ is N; and each $X^5$ and $X^6$ is $CR^X$. In some embodiments, each $X^4$ and $X^5$ is $CR^X$; and $X^6$ is N.

In some embodiments, each $R^X$ is independently hydrogen, halogen, —$OR^3$, —$SR^3$, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl. In some embodiments, each $R^X$ is independently hydrogen, halogen, —$OR^3$, —$SR^3$, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, each $R^X$ is independently hydrogen, F, Cl, Br, I, —$CH_3$, —$CH_2CH_3$, —$CH_2OH$, —$CH_2CH_2OH$, —$CH_2CN$, —$CH_2C(=O)OH$, —$CH_2C(=O)OCH_3$, —$CH_2C(=O)OCH_2CH_3$, —$CH_2C(=O)NH_2$, —$CH_2C(=O)NHCH_3$, —$CH_2C(=O)N(CH_3)_2$, —$CH_2NH_2$, —$CH_2NHCH_3$, —$CH_2N(CH_3)_2$, —$CH_2F$, —$CHF_2$, —$CF_3$, —CH=$CH_2$, —C≡CH, cyclopropyloxy, cyclobutyloxy, cyclopentyloxy, oxetanyl, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —C(=O)OH, —C(=O)$OCH_3$, —C(=O)$OCH_2CH_3$, —C(=O)$NH_2$, —C(=O)$NHCH_3$, —C(=O)N($CH_3$)$_2$, —$NH_2$, —$NHCH_3$, —N($CH_3$)$_2$, —NHC(=O)$CH_3$, —N($CH_3$)C(=O)$CH_3$, —NHC(=O)$OCH_3$, —N($CH_3$)C(=O)$OCH_3$, —S(=O)$CH_3$, —S(=O)$_2CH_3$, —NHS(=O)$_2CH_3$, or —N($CH_3$)S(=O)$_2CH_3$. In some embodiments, each $R^X$ is independently hydrogen, F, Cl, Br, I, —$CH_3$, —$CH_2CH_3$, cyclopropyl, —C≡CH, —OH, —$OCH_3$, —$OCH_2CH_3$, —$OCF_3$, —$SCH_3$, cyclopropyloxy, —$NH_2$, —NHC(=O)$CH_3$, —N($CH_3$)C(=O)$CH_3$, —NHS(=O)$_2CH_3$, —N($CH_3$)S(=O)$_2CH_3$, —S(=O)$CH_3$, or —S(=O)$_2CH_3$. In some embodiments, each $R^X$ is independently hydrogen, F, Cl, Br, I, —$CH_3$, —$CH_2CH_3$, cyclopropyl, —OH, —$OCH_3$, —$OCH_2CH_3$, —$OCF_3$, cyclopropyloxy, —$NH_2$, —NHC(=O)$CH_3$, —NHS(=O)$_2CH_3$, —S(=O)$CH_3$, or —S(=O)$_2CH_3$. In some embodiments, each $R^X$ is independently hydrogen, F, Cl, Br, —$CH_3$, —OH, —$OCH_3$, or —$OCF_3$. In some embodiments, each $R^X$ is independently hydrogen, F, Cl, —$CH_3$, —$OCH_3$, or —$OCF_3$. In some embodiments, each $R^X$ is independently hydrogen, F, or —$OCH_3$. In some embodiments, each $R^X$ is hydrogen.

In some embodiments, $R^1$ is substituted or unsubstituted $C_1$-$C_6$alkyl.

In some embodiments, $R^1$ is $C_1$-$C_6$alkyl substituted with substituted or unsubstituted $C_2$-$C_6$alkenyl, substituted or unsubstituted $C_2$-$C_6$alkynyl, or —CN.

In some embodiments, $R^1$ is $C_1$-$C_6$alkyl substituted with —$OR^3$; and $R^3$ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl.

In some embodiments, $R^1$ is $C_1$-$C_6$alkyl substituted with —C(=O)N($R^5$)$_2$ or —N($R^5$)$_2$; wherein each $R^5$ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —CN; or two $R^5$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with substituted or unsubstituted $C_3$-$C_8$cycloalkyl or substituted or unsubstituted $C_2$-$C_7$heterocycloalkyl.

In some embodiments, $R^1$ is $C_1$-$C_6$alkyl substituted with cyclopropyl, cyclobutyl, cyclopentyl, or cyclohexyl.

In some embodiments, $R^1$ is $C_1$-$C_6$alkyl substituted with oxetanyl, tetrahydrofuranyl, tetrahydropyranyl, azetidinyl, pyrrolidinyl, or piperidinyl.

In some embodiments, $R^1$ is $C_1$-$C_6$alkyl substituted with substituted or unsubstituted phenyl, wherein if phenyl is substituted, then it is substituted with 1, 2, 3, or 4 substituents selected from halogen, nitro, —CN, —$OR^3$, —N($R^3$)$_2$, —C(=O)$R^3$, —C(=O)N($R^3$)$_2$, —C(=O)$OR^3$, substituted or unsubstituted $C_1$-$C_6$alkyl, and substituted or unsubstituted $C_1$-$C_6$fluoroalkyl; and each $R^3$ is independently hydrogen, substituted or unsubstituted $C_1$-$C_6$alkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with 5-membered heteroaryl ring containing at least one nitrogen atom.

In some embodiments, $R^1$ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.

In some embodiments, $R^1$ is $C_1$-$C_6$alkyl substituted with 5-membered heteroaryl ring selected from

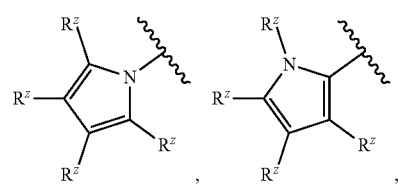

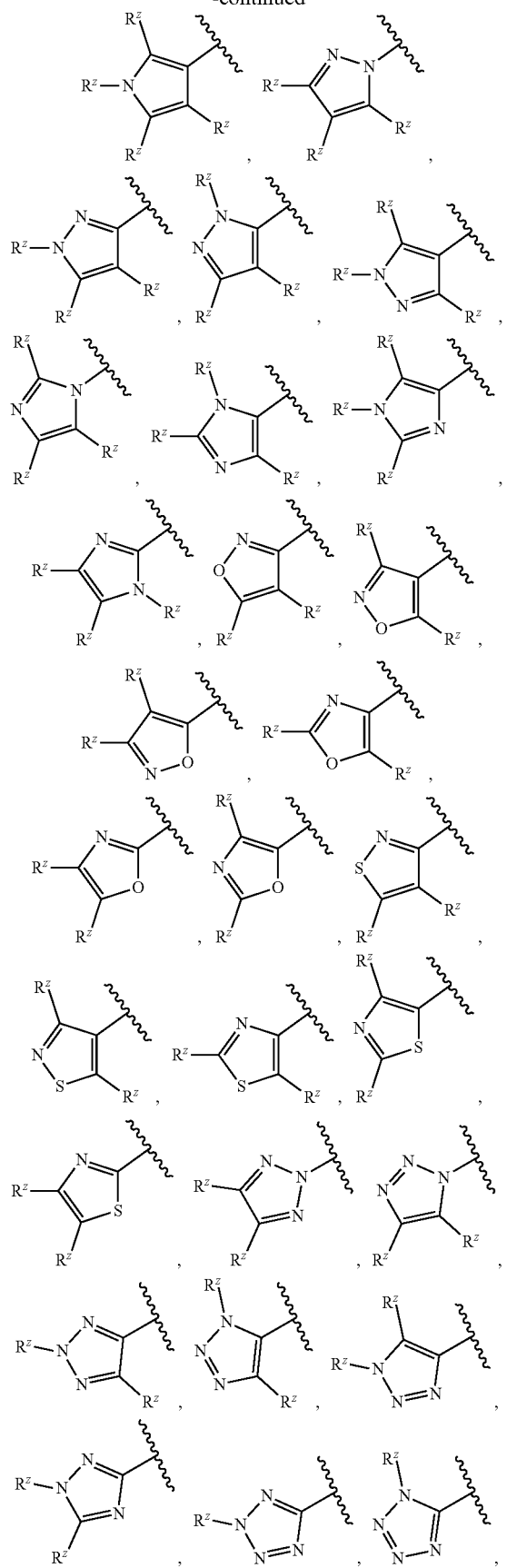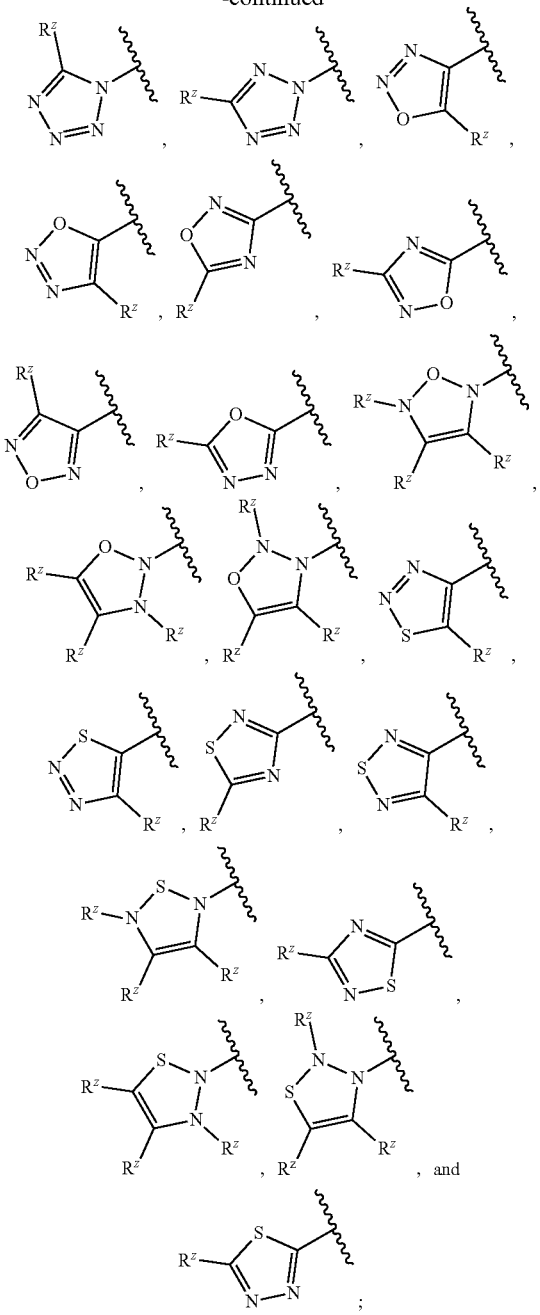

wherein
each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with a substituted or unsubstituted monocyclic 6-membered heteroaryl ring containing at least one nitrogen atom. In some embodiments, $R^1$ is $C_1$-$C_6$alkyl substituted with a substituted or unsubstituted monocyclic 6-membered heteroaryl ring containing 1, 2, or 3 nitrogen atoms. In some embodiments, $R^1$ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl. In some embodiments, $R^1$ is $C_1$-$C_6$alkyl substituted with substituted or unsubstituted pyridinyl. In some embodiments, $R^1$ is $C_1$-$C_6$alkyl substituted with pyridinyl. In some embodiments, $R^1$ is $C_1$-$C_6$alkyl substituted with substituted or unsubstituted pyridinyl. In some embodiments, $R^1$ is $C_1$-$C_6$alkyl substituted with pyridinyl. In some embodiments, $R^1$ is $C_1$-$C_6$alkyl substituted with 2-pyridinyl.

In some embodiments, $R^1$ is $C_1$-$C_6$alkyl substituted with 6-membered heteroaryl ring selected from

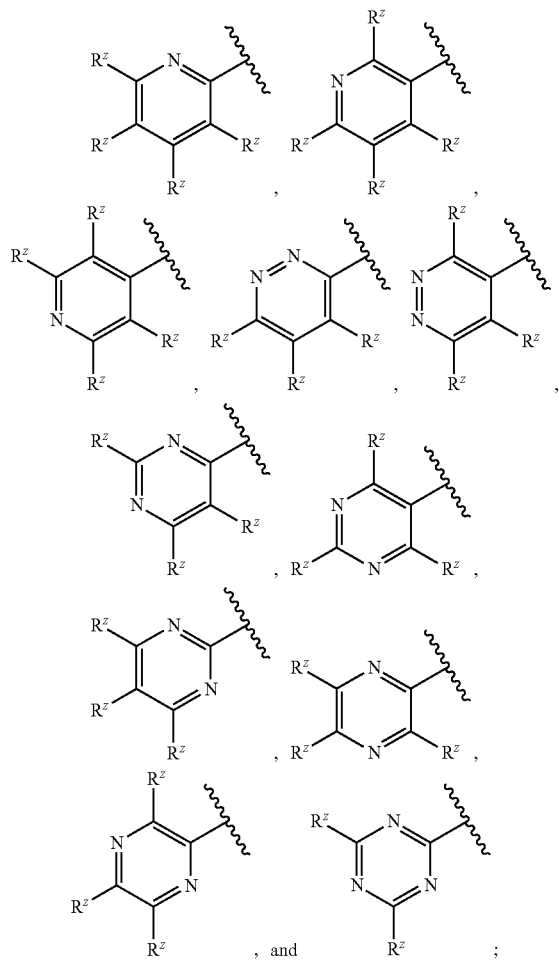

wherein
each $R^z$ is independently hydrogen, halogen, —CN, —$OR^3$, —$SR^3$, —$S(=O)_2R^3$, —$N(R^3)_2$, —$C(=O)$ $OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$—C heterocycloalkyl.

In some embodiments, $R^1$ is $C_1$-$C_6$alkyl substituted with bicyclic 6/5 fused heteroaryl ring In some embodiments, $R^1$ is $C_1$-$C_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzooxadiazolyl, substituted or unsubstituted benzothiadiazolyl, substituted or unsubstituted indolizinyl, and substituted or unsubstituted imidazopyridinyl.

In some embodiments, $R^1$ is $C_1$-$C_6$alkyl substituted with bicyclic 6/5 fused heteroaryl ring selected from

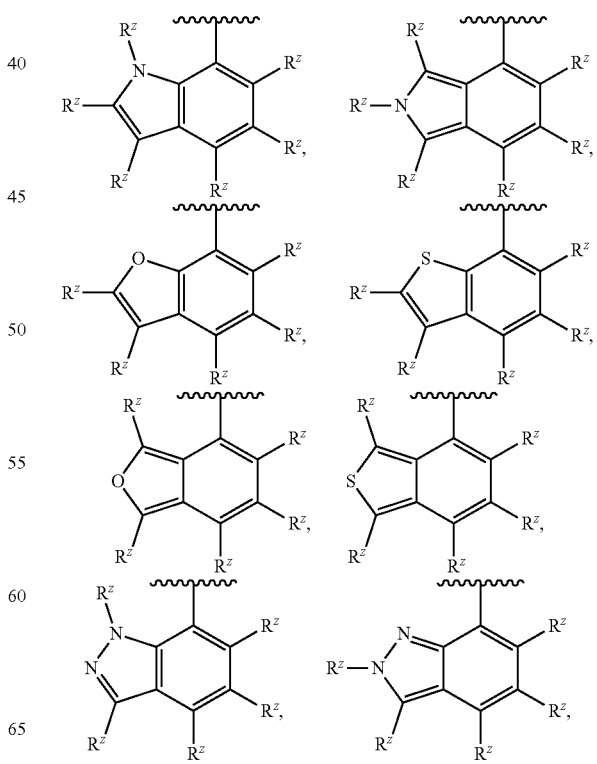

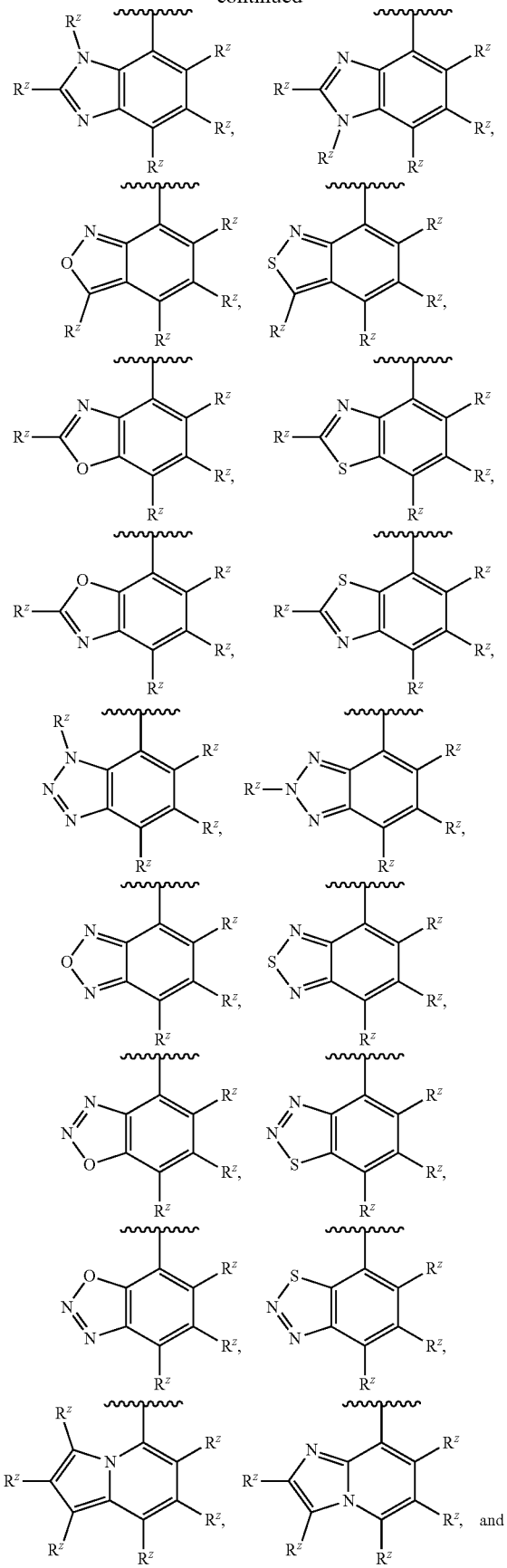

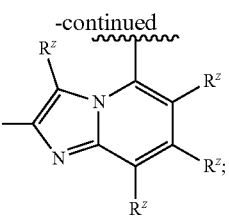

wherein each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with a substituted or unsubstituted bicyclic 6/6 fused heteroaryl ring containing at least one nitrogen atom. In some embodiments, $R^1$ is $C_1$-$C_6$alkyl substituted with a substituted or unsubstituted bicyclic 6/6 fused heteroaryl ring containing 1, 2, 3, or 4 nitrogen atoms. In some embodiments, $R^1$ is $C_1$-$C_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or un substituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyridazinyl, substituted or unsubstituted pyrimidopyrimidinyl, and substituted or unsubstituted pteridinyl.

In some embodiments, $R^1$ is $C_1$-$C_6$alkyl substituted with 6/6 fused heteroaryl ring selected from

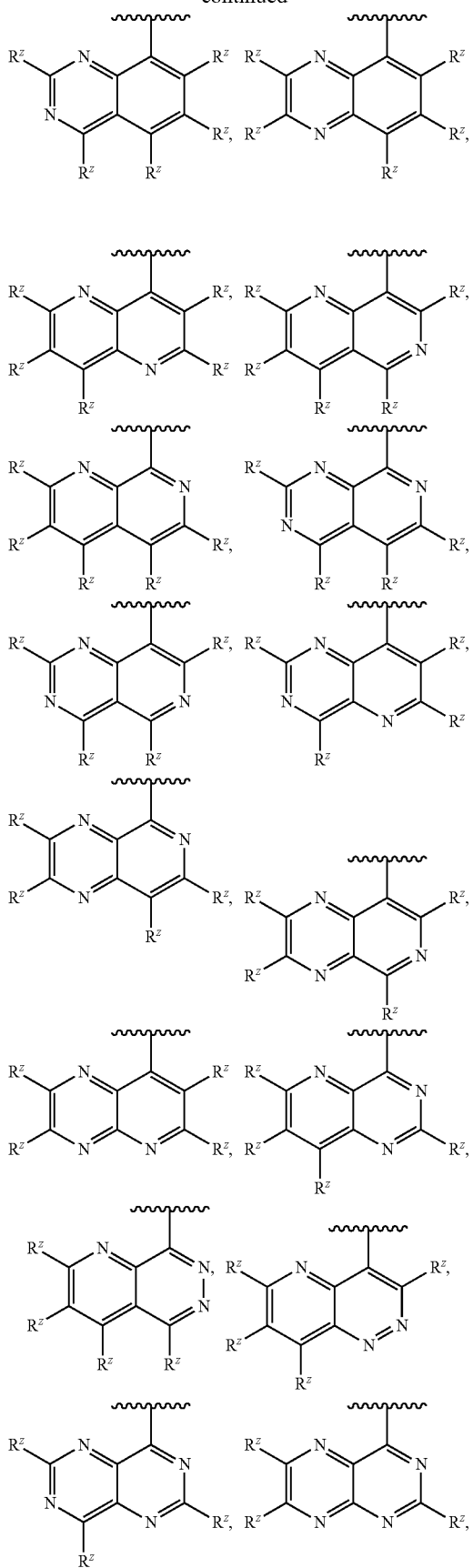

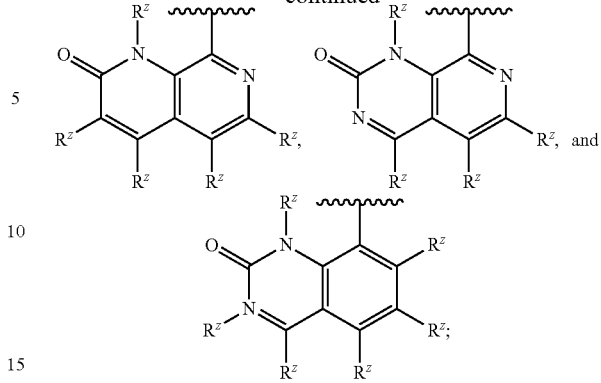

wherein
each $R^z$ is independently hydrogen, halogen, —CN, —OR³, —SR³, —S(═O)₂R³, —N(R³)₂, —C(═O)OR³, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl; and each $R^3$ is independently hydrogen, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, or substituted or unsubstituted C₂-C₁₀heterocycloalkyl; or if two R³ are on the same nitrogen atom, then two R³ are taken together with the nitrogen atom to which they are attached to form a substituted or unsubstituted C₃—C heterocycloalkyl.

In some embodiments, $R^1$ is C₁-C₆alkyl substituted with 1, 2, or 3 substituents each independently selected from —OH, —OCH₃, —NH₂, NHCH₃, N(CH₃)₂, and pyridinyl. In some embodiments, $R^1$ is C₁-C₆alkyl substituted with 1 or 2 substituents each independently selected from —OH, —OCH₃, —NH₂, NHCH₃, N(CH₃)₂, and pyridinyl. In some embodiments, $R^1$ is C₁-C₆alkyl substituted with 1 or 2 substituents each independently selected from —OH and pyridinyl. In some embodiments, $R^1$ is C₁-C₆alkyl substituted with 1 or 2 substituents each independently selected from —NH₂ and pyridinyl. In some embodiments, $R^1$ is C₁-C₆alkyl substituted with 1 or 2 substituents each independently selected from —OH and —NH₂. In some embodiments, $R^1$ is C₁-C₆alkyl substituted with —OH. In some embodiments, $R^1$ is C₁-C₆alkyl substituted with —NH₂.

In some embodiments, each $R^z$ is independently hydrogen, F, Cl, Br, —CH₃, —CH₂CH₃, —CH₂F, —CHF₂, —CF₃, —CN, —OH, —OCH₃, —OCH₂CH₃, —OCF₃, —NH₂, —NHCH₃, or —N(CH₃)₂. In some embodiments, each $R^z$ is independently hydrogen, F, Cl, Br, —CH₃, —CN, —OCH₃, —NH₂, —NHCH₃, or —N(CH₃)₂. In some embodiments, each $R^z$ is independently hydrogen, Cl, Br, —CH₃, —OCH₃, —NH₂, or —N(CH₃)₂. In some embodiments, each $R^z$ is hydrogen.

In some embodiments, $R^1$ is C₁-C₆alkyl substituted with halogen, —CN, —OR³, —SR³, —S(═O) R³, —S(═O)₂R³, —N(R³)₂, —C(═O)OR³, —C(═O)N(R³)₂, —CR³═C(R³)₂, —C≡CR³, substituted or unsubstituted C₃-C₁₀cycloalkyl, substituted or unsubstituted C₂-C₁₀heterocycloalkyl, or substituted or unsubstituted aryl; and each R³ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_2$ heterocycloalkyl.

In some embodiments, $R^1$ is substituted or unsubstituted $C_3$-$C_{10}$cycloalkyl or substituted or unsubstituted $C_2$-$C_{10}$heterocycloalkyl. In some embodiments, $R^1$ is $C_3$-$C_6$cycloalkyl or $C_1$-$C_5$heterocycloalkyl substituted with $C_1$-$C_6$alkyl, phenyl, pyridinyl, pyrazinyl, pyrimidinyl, pyridazinyl, or triazinyl. In some embodiments, $R^1$ is $C_3$-$C_6$cycloalkyl or $C_3$-$C_5$heterocycloalkyl substituted with $C_1$-$C_6$alkyl, phenyl, or pyridinyl.

In some embodiments, R is halogen, nitro, —CN, —OR$^3$, —C(=O)R$^3$, —C(=O)N(R$^3$)$_2$, —C(=O)OR$^3$, —S(=O) R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted $C_1$-$C_6$fluoroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, R is F, Cl, Br, I, nitro, —CN, —OCH$_2$F, —OCHF$_2$, —OCF$_3$, —C(=O)CH$_3$, —C(=O)OCH$_3$—C(=O)NH$_2$, —C(=O)NHCH$_3$, —C(=O)N (CH$_3$)$_2$, —S(=O)CH$_3$, —S(=O)$_2$CH$_3$, —NHS(=O)$_2$CH$_3$, —N(CH$_3$)S(=O)$_2$CH$_3$, —NHC(=O)CH$_3$, —N(CH$_3$)C (=O)CH$_3$, —NHC(=O)OCH$_3$, —N(CH$_3$)C(=O)OCH$_3$, —CH$_2$F, —CHF$_2$, or —CF$_3$. In some embodiments, R is F, Cl, —CN, —OCF$_3$, —CHF$_2$, or —CF$_3$. In some embodiments, R is F, Cl, —OCF$_3$, —CHF$_2$, or —CF$_3$. In some embodiments, R is F, Cl, or —CF$_3$. In some embodiments, R is —OCF$_3$. In some embodiments, R is —CF$_3$.

In some embodiments, each $R^2$ is independently halogen, nitro, —CN, —OR$^3$, —SR$^3$, —S(=O)$_2$R$^3$, —N(R$^3$)$_2$, —C(=O)OR$^3$, substituted or unsubstituted $C_1$-$C_6$alkyl, or substituted or unsubstituted $C_1$-$C_6$fluoroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, each $R^2$ is independently F, Cl, Br, nitro, —CN, —OH, —OCH$_3$, —OCH$_2$CH$_3$, —OCH$_2$CH$_2$OH, —OCH$_2$CN, —OCF$_3$, —S(=O)$_2$CH$_3$, —NH$_2$, —NHCH$_3$, —N(CH$_3$)$_2$, —C(=O)OCH$_3$, —CH$_3$, —CH$_2$CH$_3$, —CH$_2$F, —CHF$_2$, or —CF$_3$. In some embodiments, each $R^2$ is independently F, Cl, —CN, —OCH$_3$, —OCF$_3$, —C(=O)OCH$_3$, —CH$_3$, or —CF$_3$. In some embodiments, each $R^2$ is independently F, Cl, —OCF$_3$, or —CF$_3$. In some embodiments, each $R^2$ is independently F or Cl.

In some embodiments, n is 0. In some embodiments, n is 1. In some embodiments, n is 2. In some embodiments, n is 3. In some embodiments, n is 4. In some embodiments, n is 0 or 1. In some embodiments, n is 1 or 2. In some embodiments, n is 2 or 3. In some embodiments, n is 3 or 4.

In some embodiments, n is 1, 2, or 3. In some embodiments, n is 2, 3, or 4. In some embodiments, n is 1, 2, 3, or 4.

In another aspect, the present disclosure provides a compound of Formula (III), or a pharmaceutically acceptable salt thereof:

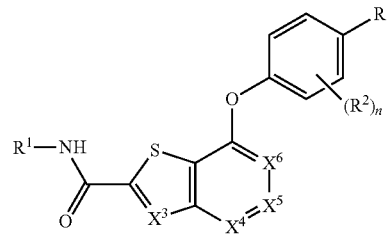

Formula (III)

wherein,
each $X^3$, $X^5$, and $X^6$ is independently N or CR$^X$;
$X^4$ is CR$^X$;
each $R^X$ is independently hydrogen, halogen, nitro, —OR$^3$, —SR$^3$, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O) OR$^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
R is halogen, nitro, —CN, —OR$^3$, —SR$^3$, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C (=O)R$^3$, —NR$^3$C(=O)OR$^3$, or substituted or unsubstituted $C_1$-$C_6$fluoroalkyl;
$R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)$_2$R$^4$;
each $R^2$ is independently halogen, nitro, —N$_3$, —CN, —OR$^3$, —SR$^3$, —S(=O)$_2$R$^3$, —N(R$^3$)$_2$, —C(=O) OR$^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;

R⁴ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —NH₂; and n is 0, 1, 2, 3, or 4.

For any and all of the embodiments of a compound of Formula (III), substituents are selected from among a subset of the listed alternatives. For example, in some embodiments $X^5$ is N or $CR^X$. In other embodiments, $X^5$ is N. In some embodiments, $X^5$ is $CR^X$.

In some embodiments, $X^3$ is $CR^X$. In some embodiments, $X^3$ is N.

In some embodiments, each $X^5$ and $X^6$ is $CR^X$. In some embodiments, $X^5$ is N; and $X^6$ is $CR^X$. In some embodiments, $X^5$ is $CR^X$; and $X^6$ is N.

In some embodiments, each $R^X$ is independently hydrogen, halogen, —OR³, —SR³, —CN, —S(=O)R³, —S(=O)₂R³, —N(R³)₂, —NR³S(=O)₂R³, —NR³C(=O)R³, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each R³ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two R³ are on the same nitrogen atom, then two R³ are taken together with the nitrogen atom to which they are attached to form a substituted or unsubstituted $C_3$-$C_7$ heterocycloalkyl.

In some embodiments, each $R^X$ is independently hydrogen, halogen, —OR³, —SR³, —S(=O)R³, —S(=O)₂R³, —N(R³)₂, —NR³S(=O)₂R³, —NR³C(=O)R³, substituted or unsubstituted $C_1$-$C_6$alkyl, substituted or unsubstituted $C_1$-$C_6$fluoroalkyl, or substituted or unsubstituted $C_2$-$C_4$alkynyl; and each R³ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two R³ are on the same nitrogen atom, then two R³ are taken together with the nitrogen atom to which they are attached to form a substituted or unsubstituted $C_3$-$C_7$ heterocycloalkyl.

In some embodiments, each $R^X$ is independently hydrogen, F, Cl, Br, I, —CH₃, —CH₂CH₃, —CH₂OH, —CH₂CH₂OH, —CH₂CN, —CH₂C(=O)OH, —CH₂C(=O)OCH₃, —CH₂C(=O)OCH₂CH₃, —CH₂C(=O)NH₂, —CH₂C(=O)NHCH₃, —CH₂C(=O)N(CH₃)₂, —CH₂NH₂, —CH₂NHCH₃, —CH₂N(CH₃)₂, —CH₂F, —CHF₂, —CF₃, —CH=CH₂, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —OCH₃, —OCH₂CH₃, —OCH₂CH₂OH, —OCH₂CN, —OCF₃, —C(=O)OH, —C(=O)OCH₃, —C(=O)OCH₂CH₃, —C(=O)NH₂, —C(=O)NHCH₃, —C(=O)N(CH₃)₂, —NH₂, —NHCH₃, —N(CH₃)₂, —NHC(=O)CH₃, —N(CH₃)C(=O)CH₃, —NHC(=O)OCH₃, —N(CH₃)C(=O)OCH₃, —S(=O)CH₃, —S(=O)₂CH₃, —NHS(=O)₂CH₃, or —N(CH₃)S(=O)₂CH₃. In some embodiments, each $R^X$ is independently hydrogen, F, Cl, Br, I, —CH₃, —CH₂CH₃, cyclopropyl, —C≡CH, —OH, —OCH₃, —OCH₂CH₃, —OCF₃, —SCH₃, cyclopropyloxy, —NH₂, —NHC(=O)CH₃, —N(CH₃)C(=O)CH₃, —NHS(=O)₂CH₃, —N(CH₃)S(=O)₂CH₃, —S(=O)CH₃, or —S(=O)₂CH₃. In some embodiments, each $R^X$ is independently hydrogen, F, Cl, Br, I, —CH₃, —CH₂CH₃, cyclopropyl, —OH, —OCH₃, —OCH₂CH₃, —OCF₃, cyclopropyloxy, —NH₂, —NHC(=O)CH₃, —NHS(=O)₂CH₃, —S(=O)CH₃, or —S(=O)₂CH₃. In some embodiments, each $R^X$ is independently hydrogen, F, Cl, Br, —CH₃, —OH, —OCH₃, or —OCF₃. In some embodiments, each $R^X$ is independently hydrogen, F, Cl, —CH₃, —OCH₃, or —OCF₃. In some embodiments, each $R^X$ is independently hydrogen, F, or —OCH₃. In some embodiments, each $R^X$ is hydrogen.

In some embodiments, R¹ is substituted or unsubstituted $C_1$-$C_6$alkyl.

In some embodiments, R¹ is $C_1$-$C_6$alkyl substituted with substituted or unsubstituted $C_2$-$C_6$alkenyl, substituted or unsubstituted $C_2$-$C_6$alkynyl, or —CN.

In some embodiments, R¹ is $C_1$-$C_6$alkyl substituted with —OR³; and R³ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl.

In some embodiments, R¹ is $C_1$-$C_6$alkyl substituted with —C(=O)N(R⁵)₂ or —N(R⁵)₂; wherein each R⁵ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —CN; or two R⁵ are taken together with the nitrogen atom to which they are attached to form a substituted or unsubstituted $C_3$-$C_7$ heterocycloalkyl.

In some embodiments, R¹ is $C_1$-$C_6$alkyl substituted with substituted or unsubstituted $C_3$-$C_8$cycloalkyl or substituted or unsubstituted $C_2$-$C_7$heterocycloalkyl.

In some embodiments, R¹ is $C_1$-$C_6$alkyl substituted with cyclopropyl, cyclobutyl, cyclopentyl, or cyclohexyl.

In some embodiments, R¹ is $C_1$-$C_6$alkyl substituted with oxetanyl, tetrahydrofuranyl, tetrahydropyranyl, azetidinyl, pyrrolidinyl, or piperidinyl.

In some embodiments, R¹ is $C_1$-$C_6$alkyl substituted with substituted or unsubstituted phenyl, wherein if phenyl is substituted, then it is substituted with 1, 2, 3, or 4 substituents selected from halogen, nitro, —CN, —OR³, —N(R³)₂, —C(=O)R³, —C(=O)N(R³)₂, —C(=O)OR³, substituted or unsubstituted $C_1$-$C_6$alkyl, and substituted or unsubstituted $C_1$-$C_6$fluoroalkyl; and each R³ is independently hydrogen, substituted or unsubstituted $C_1$-$C_6$alkyl, or substituted or unsubstituted $C_3$-$C_{10}$cycloalkyl; or if two R³ are on the same nitrogen atom, then two R³ are taken together with the nitrogen atom to which they are attached to form a substituted or unsubstituted $C_3$-$C_7$ heterocycloalkyl.

In some embodiments, R¹ is $C_1$-$C_6$alkyl substituted with 5-membered heteroaryl ring containing at least one nitrogen atom. In some embodiments, R¹ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.

In some embodiments, R¹ is $C_1$-$C_6$alkyl substituted with 5-membered heteroaryl ring selected from

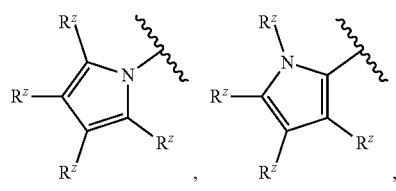

-continued

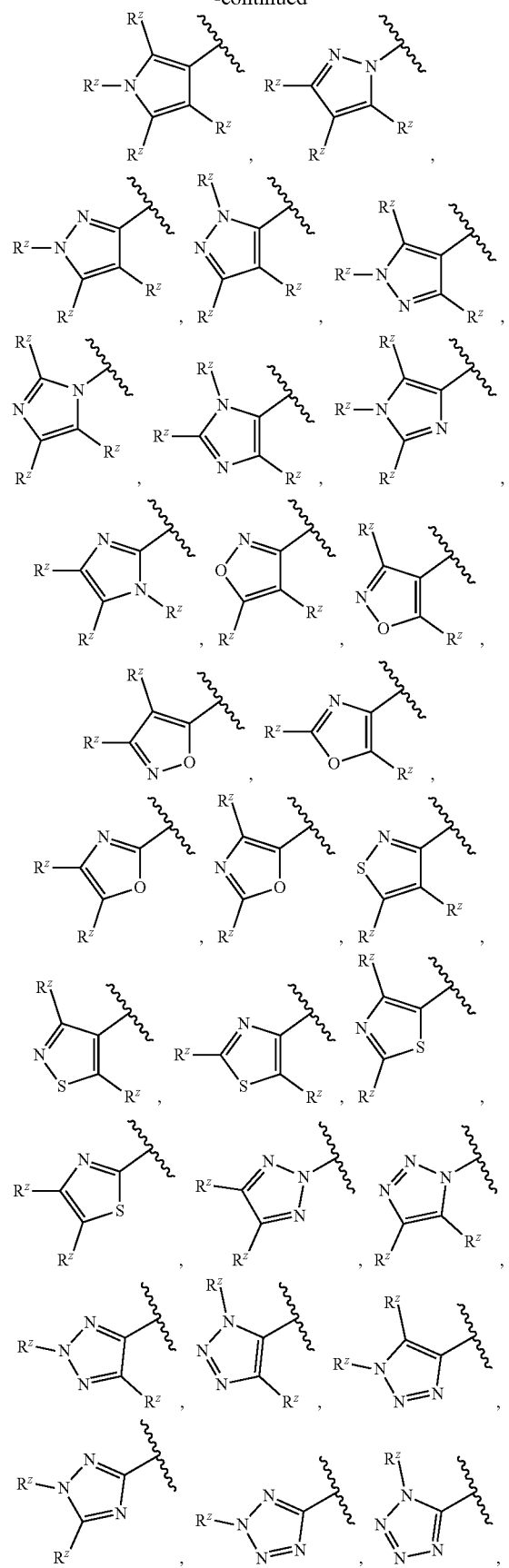

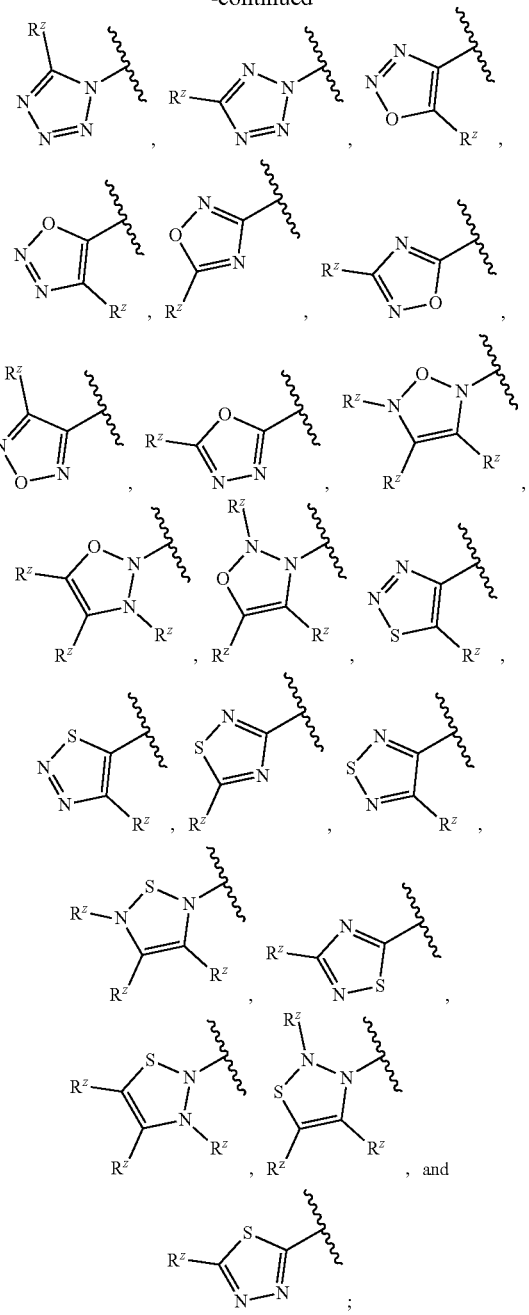

wherein
each $R^z$ is independently hydrogen, halogen, —CN, —$OR^3$, —$SR^3$, —$S(O)_2R^3$, —$N(R^3)_2$, —$C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_3$-$C_{10}$heterocycloalkyl; or if two $R^3$ are on the same nitrogen atom, then two $R^3$ are taken together with the nitrogen atom to which they are attached to form a substituted or unsubstituted $C_3$—C heterocycloalkyl.

In some embodiments, $R^1$ is $C_1$-$C_6$alkyl substituted with a substituted or unsubstituted monocyclic 6-membered heteroaryl ring containing at least one nitrogen atom. In some embodiments, $R^1$ is $C_1$-$C_6$alkyl substituted with a substituted or unsubstituted monocyclic 6-membered heteroaryl ring containing 1, 2, or 3 nitrogen atoms. In some embodiments, $R^1$ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl. In some embodiments, $R^1$ is $C_1$-$C_6$alkyl substituted with substituted or unsubstituted pyridinyl. In some embodiments, $R^1$ is $C_1$-$C_6$alkyl substituted with pyridinyl. In some embodiments, $R^1$ is $C_1$-$C_6$alkyl substituted with 2-pyridinyl.

In some embodiments, $R^1$ is $C_1$-$C_6$alkyl substituted with 6-membered heteroaryl ring selected from

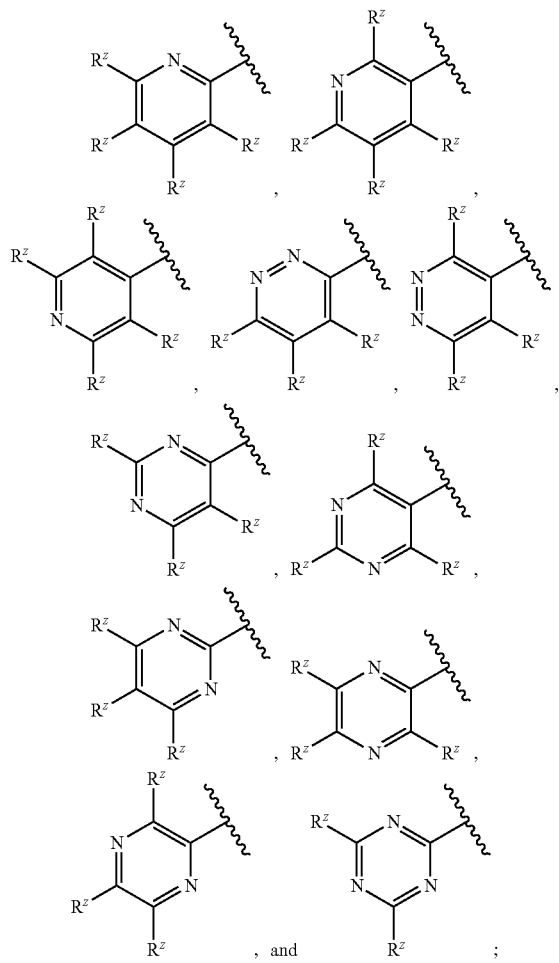

wherein
each $R^z$ is independently hydrogen, halogen, —CN, —$OR^3$, —$SR^3$, —$S(=O)_2R^3$, —$N(R^3)_2$, —$C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with bicyclic 6/5 fused heteroaryl ring In some embodiments, $R^1$ is $C_1$-$C_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzooxadiazolyl, substituted or unsubstituted benzothiadiazolyl, substituted or unsubstituted indolizinyl, and substituted or unsubstituted imidazopyridinyl.

In some embodiments, $R^1$ is $C_1$-$C_6$alkyl substituted with bicyclic 6/5 fused heteroaryl ring selected from

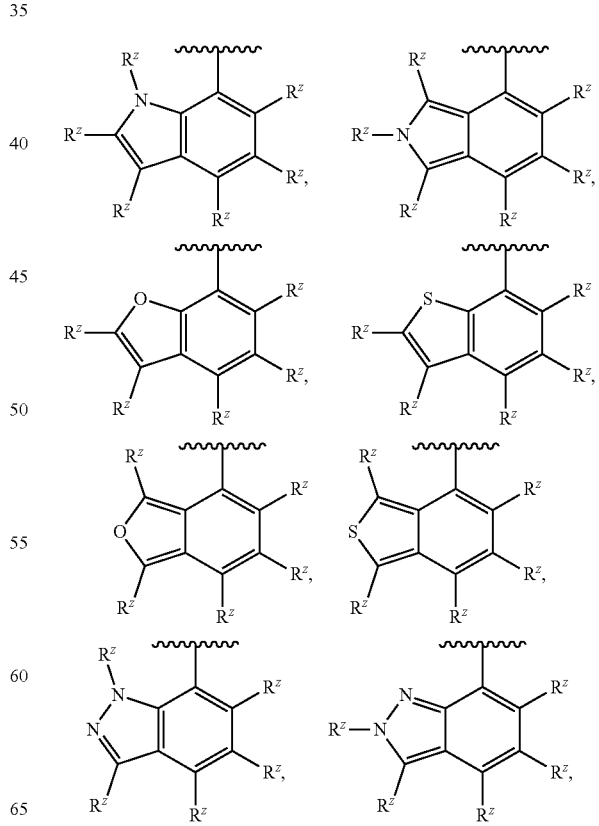

-continued

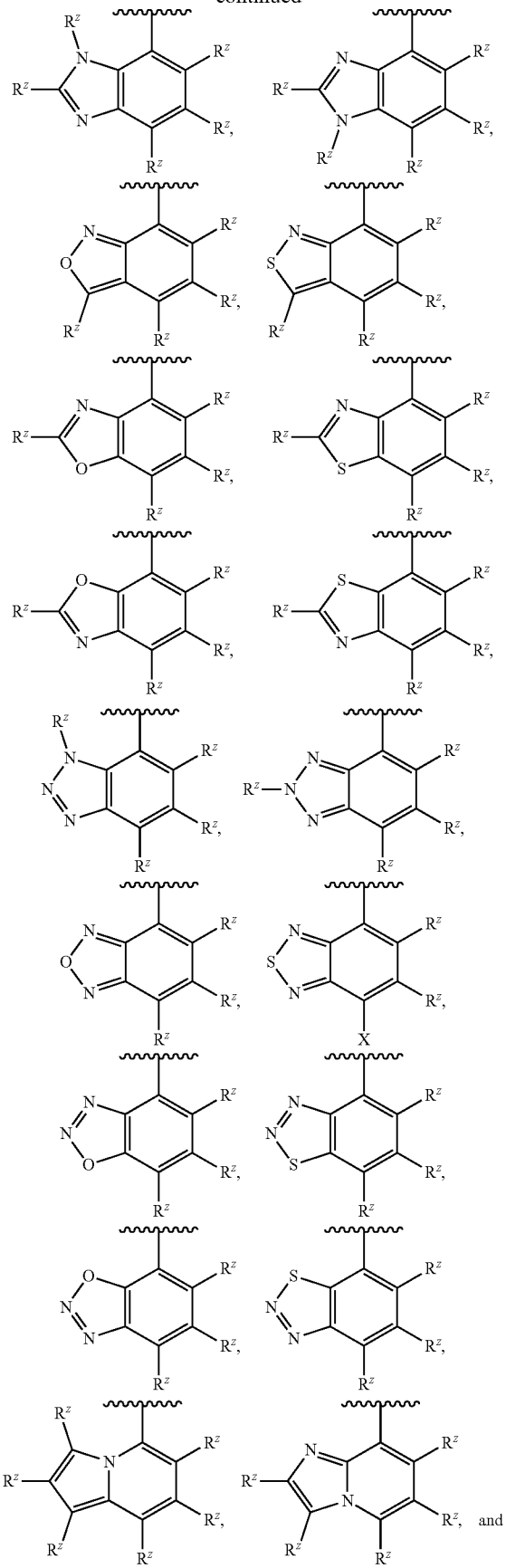

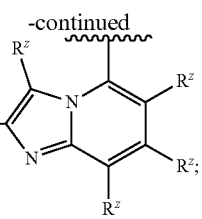

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

In some embodiments, $R^1$ is C$_1$-C$_6$alkyl substituted with a substituted or unsubstituted bicyclic 6/6 fused heteroaryl ring containing at least one nitrogen atom. In some embodiments, $R^1$ is C$_1$-C$_6$alkyl substituted with a substituted or unsubstituted bicyclic 6/6 fused heteroaryl ring containing 1, 2, 3, or 4 nitrogen atoms. In some embodiments, $R^1$ is C$_1$-C$_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or unsubstituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyridazinyl, substituted or unsubstituted pyrimidopyrimidinyl, and substituted or unsubstituted pteridinyl.

In some embodiments, $R^1$ is C$_1$-C$_6$alkyl substituted with 6/6 fused heteroaryl ring selected from

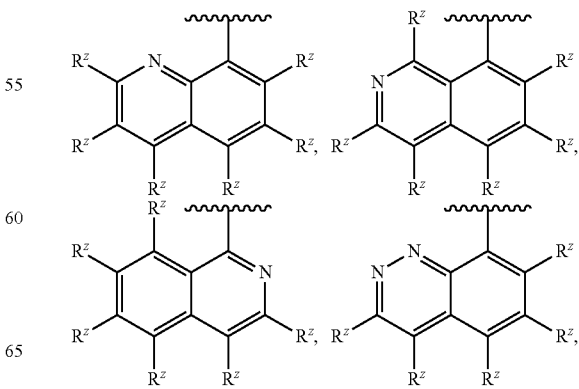

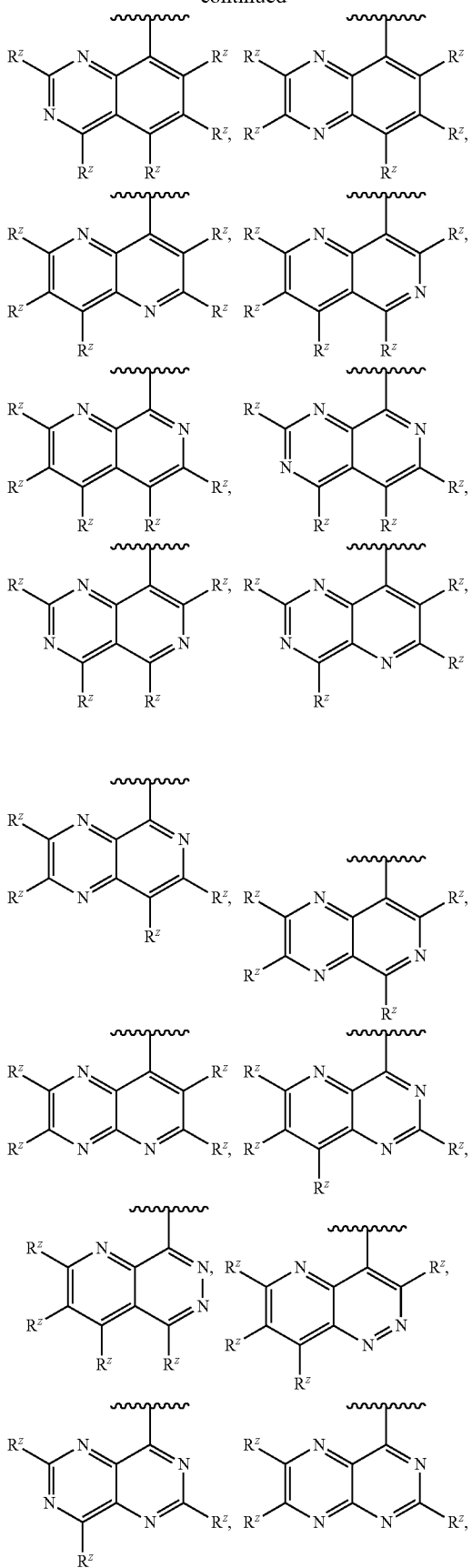

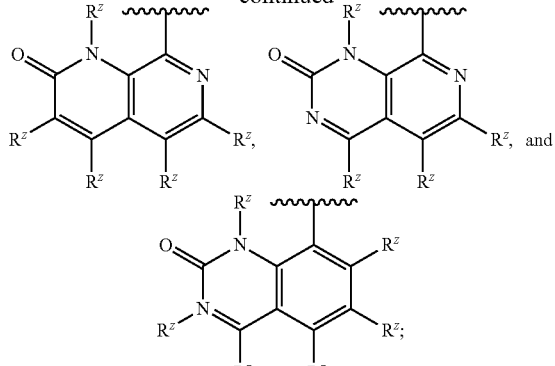

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, $R^1$ is $C_1$-$C_6$alkyl substituted with 1, 2, or 3 substituents each independently selected from —OH, —OCH$_3$, —NH$_2$, NHCH$_3$, N(CH$_3$)$_2$, and pyridinyl. In some embodiments, $R^1$ is $C_1$-$C_6$alkyl substituted with 1 or 2 substituents each independently selected from —OH, —OCH$_3$, —NH$_2$, NHCH$_3$, N(CH$_3$)$_2$, and pyridinyl. In some embodiments, $R^1$ is $C_1$-$C_6$alkyl substituted with 1 or 2 substituents each independently selected from —OH and pyridinyl. In some embodiments, $R^1$ is $C_1$-$C_6$alkyl substituted with 1 or 2 substituents each independently selected from —NH$_2$ and pyridinyl. In some embodiments, $R^1$ is $C_1$-$C_6$alkyl substituted with 1 or 2 substituents each independently selected from —OH and —NH$_2$. In some embodiments, $R^1$ is $C_1$-$C_6$alkyl substituted with —OH. In some embodiments, $R^1$ is $C_1$-$C_6$alkyl substituted with —NH$_2$.

In some embodiments, each $R^z$ is independently hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, —OCF$_3$, —NH$_2$, —NHCH$_3$, or —N(CH$_3$)$_2$. In some embodiments, each $R^z$ is independently hydrogen, F, Cl, Br, —CH$_3$, —CN, —OCH$_3$, —NH$_2$, —NHCH$_3$, or —N(CH$_3$)$_2$. In some embodiments, each $R^z$ is independently hydrogen, Cl, Br, —CH$_3$, —OCH$_3$, —NH$_2$, or —N(CH$_3$)$_2$. In some embodiments, each $R^z$ is hydrogen.

In some embodiments, $R^1$ is $C_1$-$C_6$alkyl substituted with halogen, —CN, —OR$^3$, —SR$^3$, —S(=O) R$^3$, —S(=O)$_2$R$^3$, —N(R$^3$)$_2$, —C(=O)OR$^3$, —C(=O)N(R$^3$)$_2$, —CR$^3$=C(R$^3$)$_2$, —C≡CR$^3$, substituted or unsubstituted $C_3$-$C_{10}$cycloalkyl, substituted or unsubstituted $C_2$-$C_{10}$heterocycloalkyl, or substituted or unsubstituted aryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_2$ heterocycloalkyl.

In some embodiments, $R^1$ is substituted or unsubstituted $C_3$-$C_{10}$cycloalkyl or substituted or unsubstituted $C_2$-$C_{10}$heterocycloalkyl. In some embodiments, $R^1$ is $C_3$-$C_6$cycloalkyl or $C_3$-$C_5$heterocycloalkyl substituted with $C_1$-$C_6$alkyl, phenyl, pyridinyl, pyrazinyl, pyrimidinyl, pyridazinyl, or triazinyl. In some embodiments, $R^1$ is $C_3$-$C_6$cycloalkyl or $C_3$-$C_5$heterocycloalkyl substituted with $C_1$-$C_6$alkyl, phenyl, or pyridinyl.

In some embodiments, R is halogen, nitro, —CN, —$OR^3$, —C(=O)$R^3$, —C(=O)N($R^3$)$_2$, —C(=O)$OR^3$, —S(=O)$R^3$, —S(=O)$_2R^3$, —$NR^3$S(=O)$_2R^3$, —$NR^3$C(=O)$R^3$, —$NR^3$C(=O)$OR^3$, or substituted or unsubstituted $C_1$-$C_6$fluoroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, R is F, Cl, Br, I, nitro, —CN, —$OCH_2F$, —$OCHF_2$, —$OCF_3$, —C(=O)$CH_3$, —C(=O)$OCH_3$, —C(=O)$NH_2$, —C(=O)$NHCH_3$, —C(=O)N($CH_3$)$_2$, —S(=O)$CH_3$, —S(=O)$_2CH_3$, —NHS(=O)$_2CH_3$, —N($CH_3$)S(=O)$_2CH_3$, —NHC(=O)$CH_3$, —N($CH_3$)C(=O)$CH_3$, —NHC(=O)$OCH_3$, —N($CH_3$)C(=O)$OCH_3$, —$CH_2F$, —$CHF_2$, or —$CF_3$. In some embodiments, R is F, Cl, —CN, —$OCF_3$, —$CHF_2$, or —$CF_3$. In some embodiments, R is F, Cl, —$OCF_3$, —$CHF_2$, or —$CF_3$. In some embodiments, R is F, Cl, or —$CF_3$. In some embodiments, R is —$OCF_3$. In some embodiments, R is —$CF_3$.

In some embodiments, each $R^2$ is independently halogen, nitro, —CN, —$OR^3$, —$SR^3$, —S(=O)$_2R^3$, —N($R^3$)$_2$, —C(=O)$OR^3$, substituted or unsubstituted $C_1$-$C_6$alkyl, or substituted or unsubstituted $C_1$-$C_6$fluoroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

In some embodiments, each $R^2$ is independently F, Cl, Br, nitro, —CN, —OH, —$OCH_3$, —$OCH_2CH_3$, —$OCH_2CH_2OH$, —$OCH_2CN$, —$OCF_3$, —S(=O)$_2CH_3$, —$NH_2$, —$NHCH_3$, —N($CH_3$)$_2$, —C(=O)$OCH_3$, —$CH_3$, —$CH_2CH_3$, —$CH_2F$, —$CHF_2$, or —$CF_3$. In some embodiments, each $R^2$ is independently F, Cl, —CN, —$OCH_3$, —$OCF_3$, —C(=O)$OCH_3$, —$CH_3$, or —$CF_3$. In some embodiments, each $R^2$ is independently F, Cl, —$OCF_3$, or —$CF_3$. In some embodiments, each $R^2$ is independently F or Cl.

In some embodiments, n is 0. In some embodiments, n is 1. In some embodiments, n is 2. In some embodiments, n is 3. In some embodiments, n is 4. In some embodiments, n is 0 or 1. In some embodiments, n is 1 or 2. In some embodiments, n is 2 or 3. In some embodiments, n is 3 or 4. In some embodiments, n is 1, 2, or 3. In some embodiments, n is 2, 3, or 4. In some embodiments, n is 1, 2, 3, or 4.

In another aspect, the present disclosure provides a compound or pharmaceutically acceptable salt thereof, wherein the compound is a compound from Table 1, or a pharmaceutically acceptable salt thereof.

TABLE 1

| Compound # | Structure | Name |
| --- | --- | --- |
| 1 | 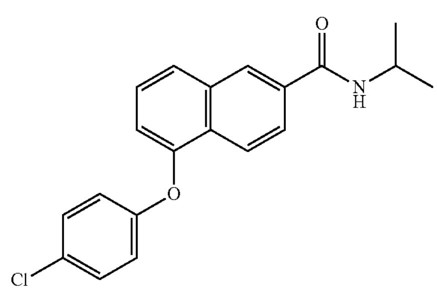 [SMILES: CC(C)NC(=O)c1ccc2c(Oc3ccc(Cl)cc3)cccc2c1] | 5-(4-chlorophenoxy)-N-isopropyl-2-naphthamide |
| 2 | 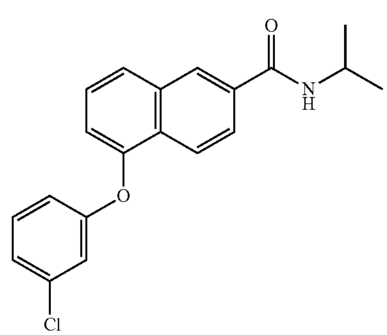 [SMILES: CC(C)NC(=O)c1ccc2c(Oc3cccc(Cl)c3)cccc2c1] | 5-(3-chlorophenoxy)-N-isopropyl-2-naphthamide |

TABLE 1-continued

| Compound # | Structure | Name |
|---|---|---|
| 3 | 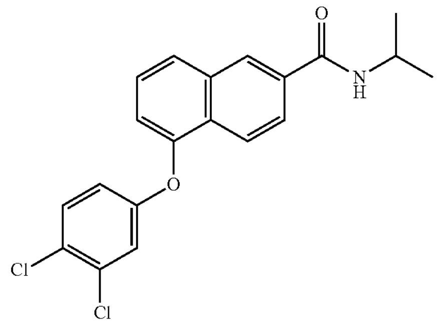 [SMILES: CC(C)NC(=O)c1ccc2c(Oc3ccc(Cl)c(Cl)c3)cccc2c1] | 5-(3,4-dichlorophenoxy)-N-isopropyl-naphthamide-2-carboxamide |
| 4 | 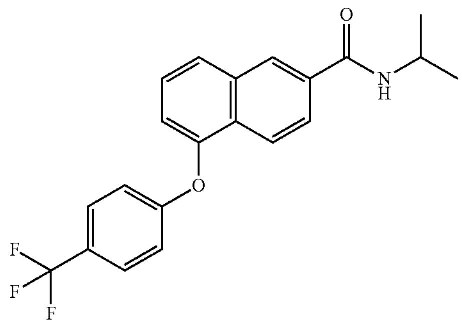 [SMILES: CC(C)NC(=O)c1ccc2c(Oc3ccc(C(F)(F)F)cc3)cccc2c1] | N-isopropyl-5-(4-(trifluoromethyl)phenoxy)-2-naphthamide |
| 5 | 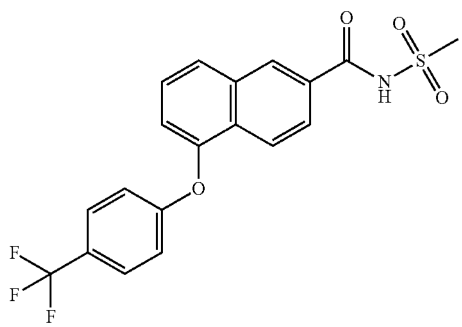 [SMILES: CS(=O)(=O)NC(=O)c1ccc2c(Oc3ccc(C(F)(F)F)cc3)cccc2c1] | N-(methylsulfonyl)-5-(4-(trifluoromethyl)phenoxy)-2-naphthamide |
| 6 | 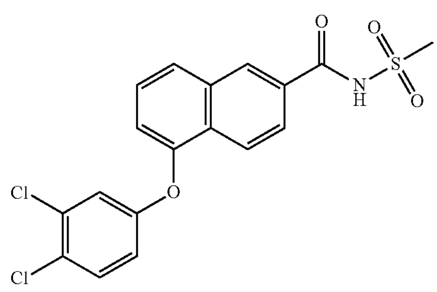 [SMILES: CS(=O)(=O)NC(=O)c1ccc2c(Oc3ccc(Cl)c(Cl)c3)cccc2c1] | 5-(3,4-dichlorophenoxy)-N-(methylsulfonyl)-2-naphthamide |
| 7 | 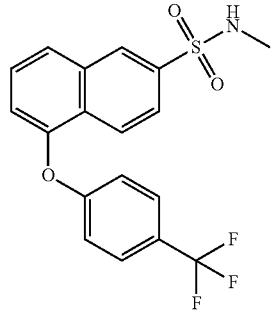 [SMILES: CNS(=O)(=O)c1ccc2c(Oc3ccc(C(F)(F)F)cc3)cccc2c1] | N-methyl-5-(4-(trifluoromethyl)phenoxy)naphthalene-2-sulfonamide |

TABLE 1-continued

| Compound # | Structure | Name |
|---|---|---|
| 8 | 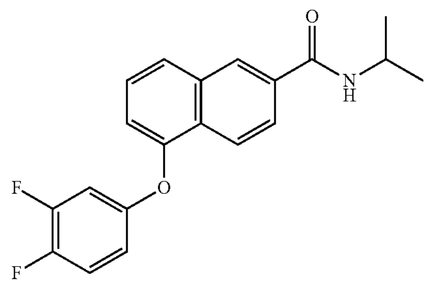 [SMILES: CC(C)NC(=O)c1ccc2c(Oc3ccc(F)c(F)c3)cccc2c1] | 5-(3,4-difluorophenoxy)-N-isopropyl-2-naphthamide |
| 9 | 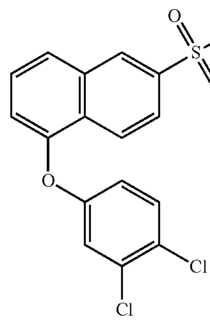 | 5-(3,4-dichlorophenoxy)-N-methylnaphalene-2-sulfonamide |
| 10 | 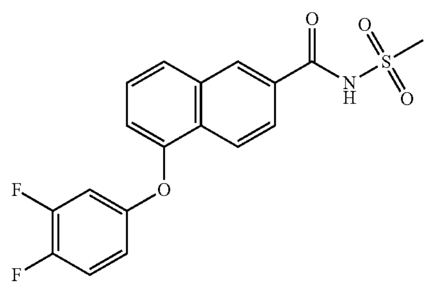 [SMILES: CS(=O)(=O)NC(=O)c1ccc2c(Oc3ccc(F)c(F)c3)cccc2c1] | 5-(3,4-difluorophenoxy)-N-(methylsulfonyl)-2-naphthamide |
| 11 | 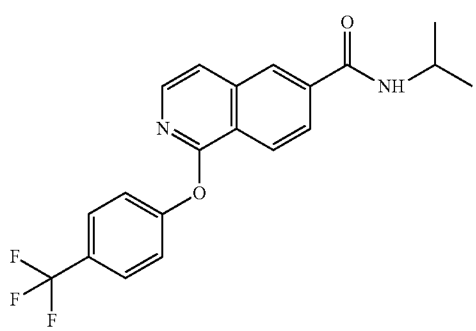 [SMILES: CC(C)NC(=O)c1ccc2c(Oc3ccc(C(F)(F)F)cc3)nccc2c1] | N-isopropyl-1-[4-(trifluoromethyl)phenoxy]isoquinoline-6-carboxamide |
| 12 | 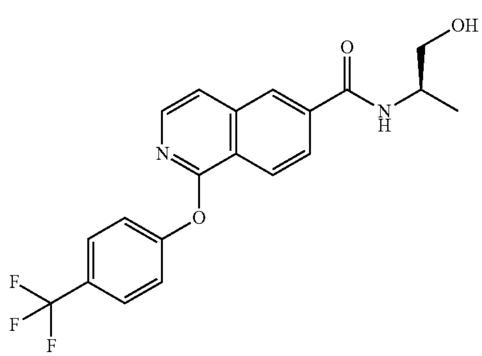 [SMILES: C[C@H](CO)NC(=O)c1ccc2c(Oc3ccc(C(F)(F)F)cc3)nccc2c1] | N-[(1R)-2-hydroxy-1-methyl-ethyl]-1-[4-(trifluoromethyl)phenoxy]isoquinoline-6-carboxamide |

TABLE 1-continued

| Compound # | Structure | Name |
|---|---|---|
| 13 | 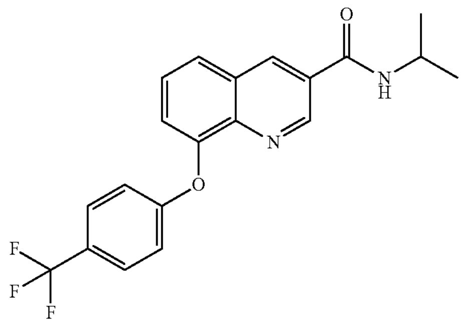 [SMILES: CC(C)NC(=O)c1cnc2c(Oc3ccc(C(F)(F)F)cc3)cccc2c1] | N-isopropyl-8-[4-(trifluoromethyl)phenoxy]quinoline-3-carboxamide |
| 14 | 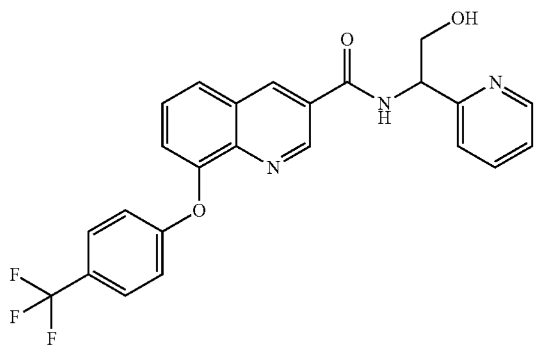 [SMILES: O=C(NC(CO)c1ccccn1)c1cnc2c(Oc3ccc(C(F)(F)F)cc3)cccc2c1] | N-[2-hydroxy-1-(2-pyridyl)ethyl]-8-[4-(trifluoromethyl)phenoxy]quinoline-3-carboxamide |
| 15 | 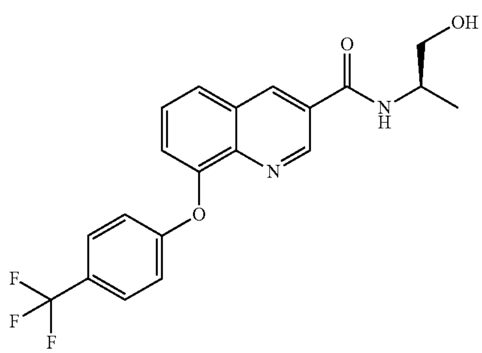 [SMILES: C[C@H](CO)NC(=O)c1cnc2c(Oc3ccc(C(F)(F)F)cc3)cccc2c1] | N-[(1R)-2-hydroxy-1-methyl-ethyl]-8-[4-(trifluoromethyl)phenoxy]quinoline-3-carboxamide |
| 16 | 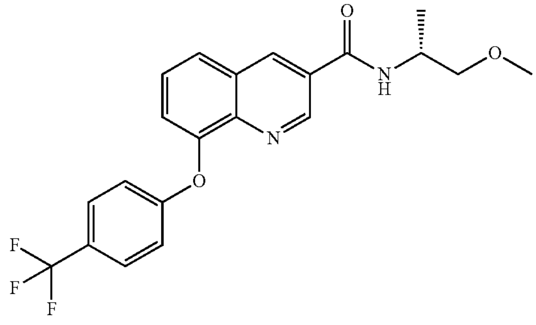 [SMILES: COC[C@@H](C)NC(=O)c1cnc2c(Oc3ccc(C(F)(F)F)cc3)cccc2c1] | N-[(1R)-2-methoxy-1-methyl-ethyl]-8-[4-(trifluoromethyl)phenoxy]quinoline-3-carboxamide |

TABLE 1-continued

| Compound # | Structure | Name |
|---|---|---|
| 17 | 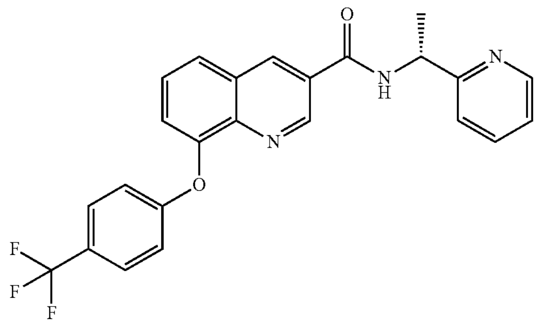 [SMILES: C[C@@H](NC(=O)c1cnc2c(Oc3ccc(C(F)(F)F)cc3)cccc2c1)c1ccccn1] | N-[(1R)-1-(2-pyridyl)ethyl]-8-[4-(trifluoromethyl)phenoxy]quinoline-3-carboxamide |
| 18 | 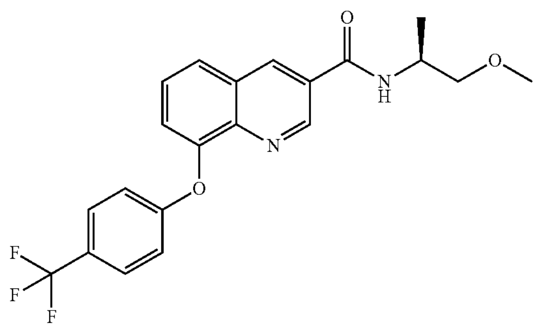 [SMILES: COC[C@H](C)NC(=O)c1cnc2c(Oc3ccc(C(F)(F)F)cc3)cccc2c1] | N-[(1S)-2-methoxy-1-methyl-ethyl]-8-[4-(trifluoromethyl)phenoxy]quinoline-3-carboxamide |
| 19 | 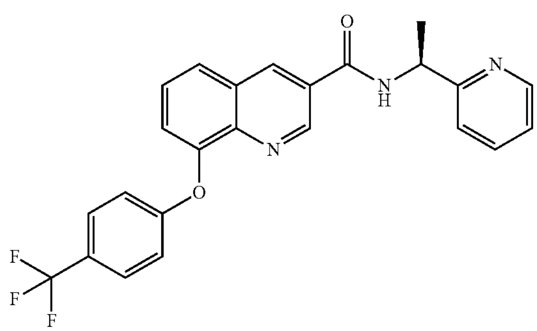 [SMILES: C[C@H](NC(=O)c1cnc2c(Oc3ccc(C(F)(F)F)cc3)cccc2c1)c1ccccn1] | N-[(1S)-1-(2-pyridyl)ethyl]-8-[4-(trifluoromethyl)phenoxy]quinoline-3-carboxamide |
| 20 | 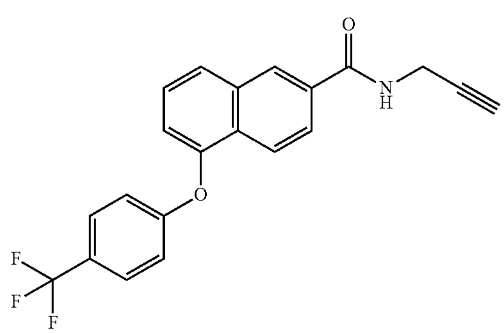 [SMILES: C#CCNC(=O)c1ccc2c(Oc3ccc(C(F)(F)F)cc3)cccc2c1] | N-(prop-2-yn-1-yl)-5-(4-(trifluoromethyl)phenoxy)-2-naphthamide |

TABLE 1-continued

| Compound # | Structure | Name |
|---|---|---|
| 21 | 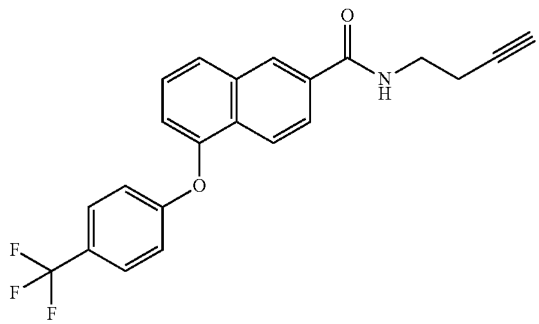 [SMILES: C#CCCNC(=O)c1ccc2c(Oc3ccc(C(F)(F)F)cc3)cccc2c1] | N-(but-3-yn-1-yl)-5-(4-(trifluoromethyl)phenoxy)-2-naphthamide |
| 22 | 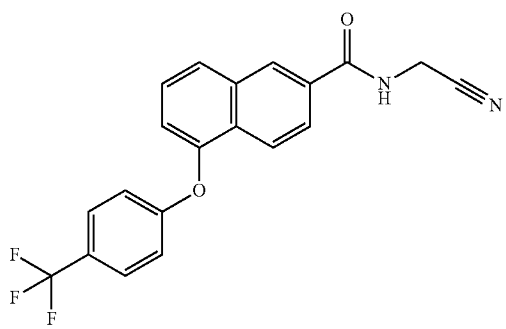 [SMILES: N#CCNC(=O)c1ccc2c(Oc3ccc(C(F)(F)F)cc3)cccc2c1] | N-(cyanomethyl)-5-(4-(trifluoromethyl)phenoxy)-2-naphthamid |
| 23 | 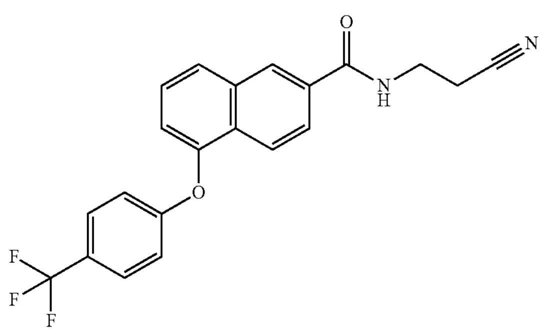 [SMILES: N#CCCNC(=O)c1ccc2c(Oc3ccc(C(F)(F)F)cc3)cccc2c1] | N-(2-cyanoethyl)-5-(4-(trifluoromethyl)phenoxy)-2-naphthamide |
| 24 | 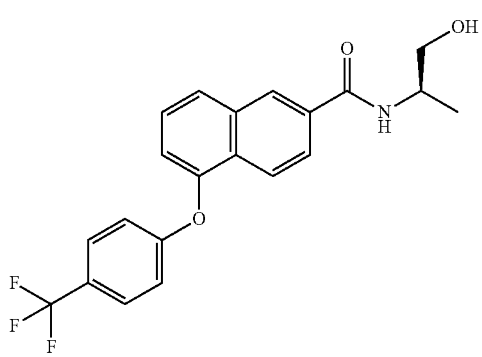 [SMILES: C[C@H](CO)NC(=O)c1ccc2c(Oc3ccc(C(F)(F)F)cc3)cccc2c1] | (R)-N-(1-hydroxypropan-2-yl)-5-(4-(trifluoromethyl)phenoxy)-2-naphthamide |

TABLE 1-continued

| Compound # | Structure | Name |
|---|---|---|
| 25 | 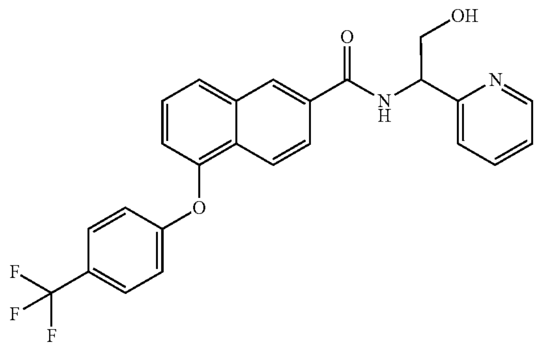 [SMILES: O=C(NC(CO)c1ccccn1)c1ccc2c(Oc3ccc(C(F)(F)F)cc3)cccc2c1] | N-(2-hydroxy-1-(pyridin-2-yl)ethyl)-5-(4-(trifluoromethyl)phenoxy)-2-naphthamide |
| 26 | 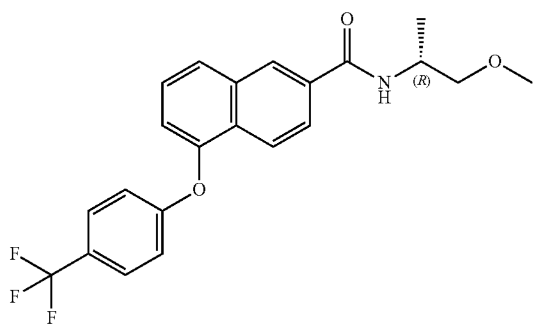 | (R)-N-(1-methoxypropan-2-yl)-5-(4-(trifluoromethyl)phenoxy)-2-naphthamide |
| 27 | 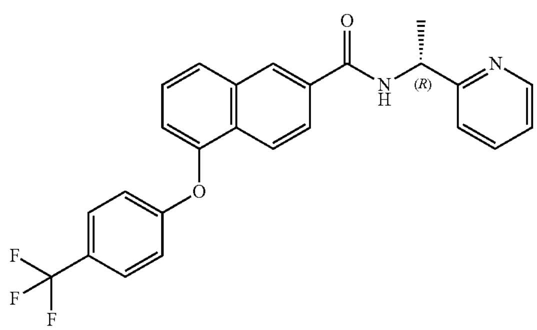 | N-[(1R)-1-(2-pyridyl)ethyl]-5-[4-(trifluoromethyl)phenoxy]naphthalene-2-carboxamide |
| 28 | 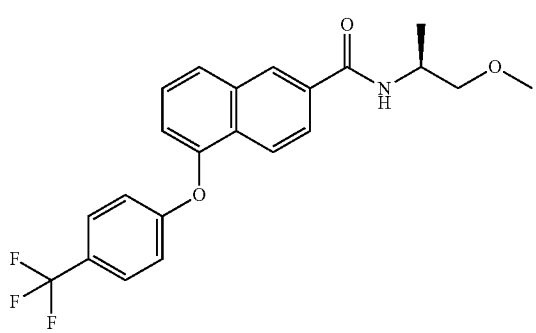 [SMILES: COC[C@H](C)NC(=O)c1ccc2c(Oc3ccc(C(F)(F)F)cc3)cccc2c1] | (S)-N-(1-methoxypropan-2-yl)-5-(4-(trifluoromethyl)phenoxy)-2-naphthamide |

TABLE 1-continued

| Compound # | Structure | Name |
|---|---|---|
| 29 | 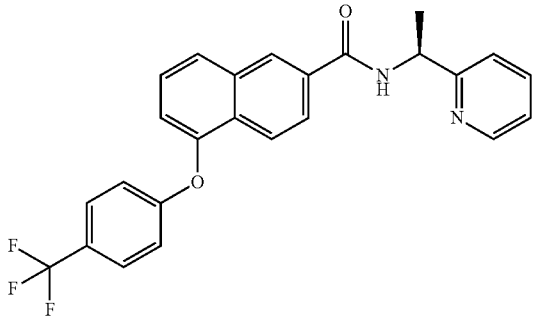 [SMILES: C[C@H](NC(=O)c1ccc2c(Oc3ccc(C(F)(F)F)cc3)cccc2c1)c1ccccn1] | (S)-N-(1-(pyridin-2-yl)ethyl)-5-(4-(trifluoromethyl)phenoxy)-2-naphthamide |
| 30 | 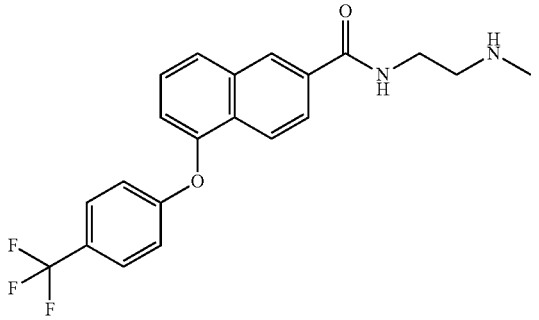 [SMILES: CNCCNC(=O)c1ccc2c(Oc3ccc(C(F)(F)F)cc3)cccc2c1] | N-(2-(methylamino)ethyl)-5-(4-(trifluoromethyl)phenoxy)-2-naphthamide |
| 31 | 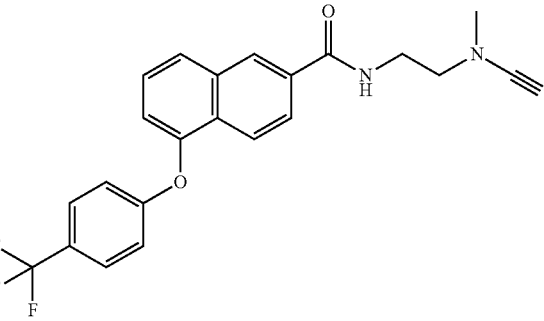 | N-(2-(N-methylcyanoamido)ethyl)-5-(4-(trifluoromethyl)phenoxy)-2-naphthamide |
| 32 | 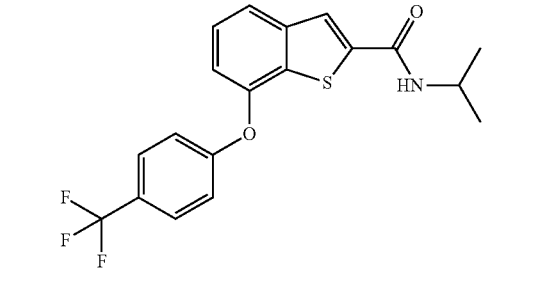 [SMILES: CC(C)NC(=O)c1cc2cccc(Oc3ccc(C(F)(F)F)cc3)c2s1] | N-isopropyl-7-(4-(trifluoromethyl)phenoxy)benzo[b]thiophene-2-carboxamide |
| 33 | 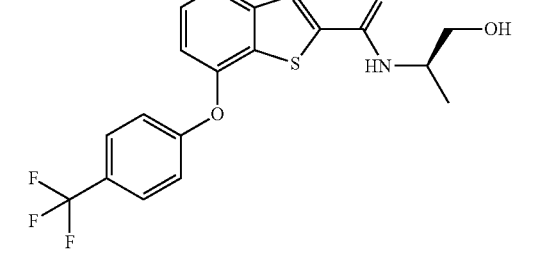 | (R)-N-(1-hydroxypropan-2-yl)-7-(4-(trifluoromethyl)phenoxy)benzo[b]thiophene-2-carboxamide |

TABLE 1-continued

| Compound # | Structure | Name |
|---|---|---|
| 34 | 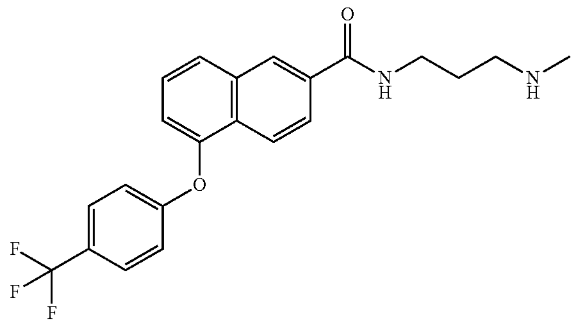 [SMILES: CNCCCNC(=O)c1ccc2c(Oc3ccc(C(F)(F)F)cc3)cccc2c1] | N-(3-(methylamino)propyl)-5-(4-(trifluoromethyl)phenoxy)-2-naphthamide |
| 35 | 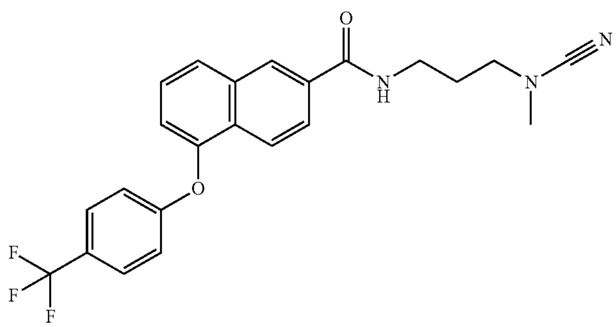 [SMILES: CN(C#N)CCCNC(=O)c1ccc2c(Oc3ccc(C(F)(F)F)cc3)cccc2c1] | N-(3-(N-methylcyanamido)propyl)-5-(4-(trifluoromethyl)phenoxy)-2-naphthamide |
| 36 | 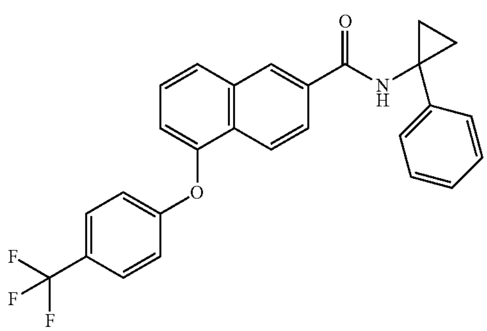 [SMILES: O=C(NC1(c2ccccc2)CC1)c1ccc2c(Oc3ccc(C(F)(F)F)cc3)cccc2c1] | N-(1-phenylcyclopropyl)-5-[4-(trifluoromethyl)phenoxy]naphthalene-2-carboxamide |
| 37 | 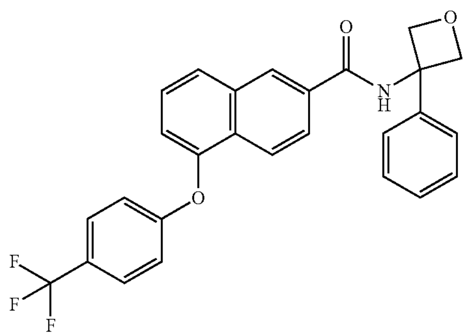 [SMILES: O=C(NC1(c2ccccc2)COC1)c1ccc2c(Oc3ccc(C(F)(F)F)cc3)cccc2c1] | N-(3-phenyloxetan-3-yl)-5-(4-(trifluoromethyl)phenoxy)-2-naphthamide |

TABLE 1-continued

| Compound # | Structure | Name |
|---|---|---|
| 38 | 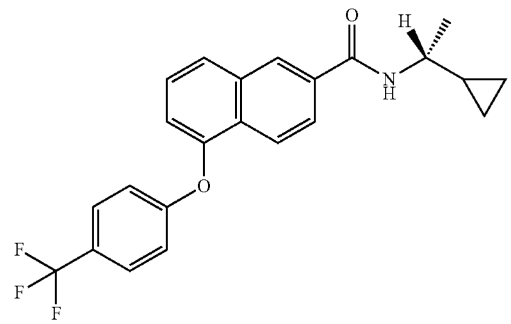 [SMILES: C[C@@H](NC(=O)c1ccc2c(Oc3ccc(C(F)(F)F)cc3)cccc2c1)C1CC1] | (R)-N-(1-cyclopropylethyl)-5-(4-(trifluoromethyl)phenoxy)-2-naphthamide |
| 39 | 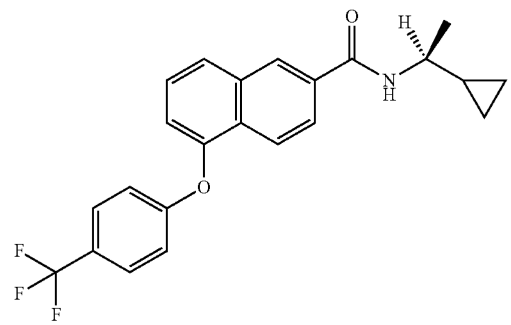 [SMILES: C[C@H](NC(=O)c1ccc2c(Oc3ccc(C(F)(F)F)cc3)cccc2c1)C1CC1] | (S)-N-(1-cyclopropylethyl)-5-(4-(trifluoromethyl)phenoxy)-2-naphthamide |
| 40 | 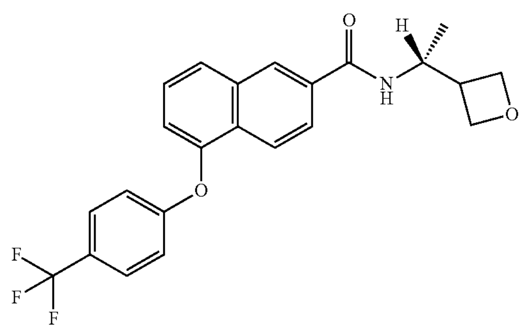 [SMILES: C[C@@H](NC(=O)c1ccc2c(Oc3ccc(C(F)(F)F)cc3)cccc2c1)C1COC1] | (R)-N-(1-(oxetan-3-yl)ethyl)-5-(4-(trifluoromethyl)phenoxy)-2-naphthamide |
| 41 | 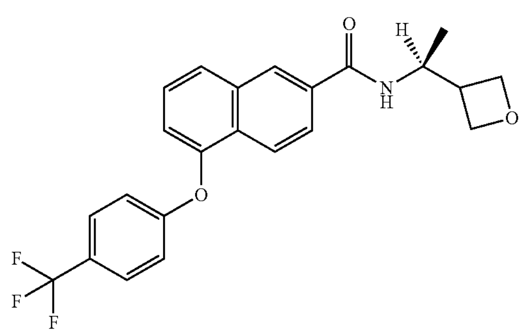 [SMILES: C[C@H](NC(=O)c1ccc2c(Oc3ccc(C(F)(F)F)cc3)cccc2c1)C1COC1] | (S)-N-(1-(oxetan-3-yl)ethyl)-5-(4-(trifluoromethyl)phenoxy)-2-naphthamide |

TABLE 1-continued

| Compound # | Structure | Name |
|---|---|---|
| 42 | 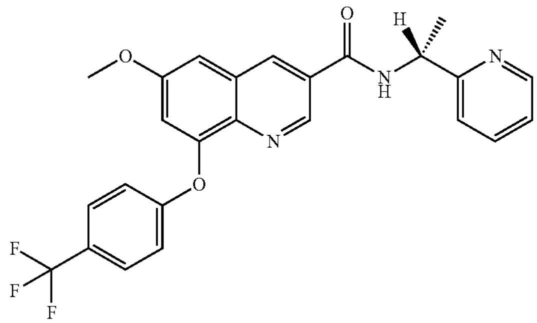 [SMILES: COc1cc(Oc2ccc(C(F)(F)F)cc2)c2ncc(C(=O)N[C@H](C)c3ccccn3)cc2c1] | (R)-6-methoxy-N-(1-(pyridin-2-yl)ethyl)-8-(4-(trifluoromethyl)phenoxy)quinoline-3-carboxamide |
| 43 | 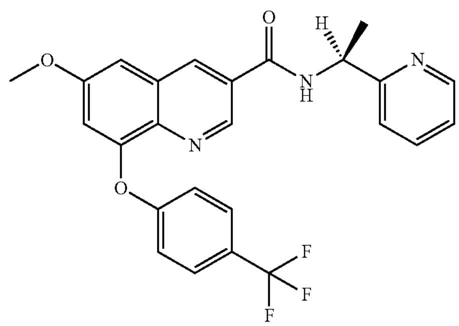 [SMILES: COc1cc(Oc2ccc(C(F)(F)F)cc2)c2ncc(C(=O)N[C@@H](C)c3ccccn3)cc2c1] | (S)-6-methoxy-N-(1-(pyridin-2-yl)ethyl)-8-(4-(trifluoromethyl)phenoxy)quinoline-3-carboxamide |
| 44 | 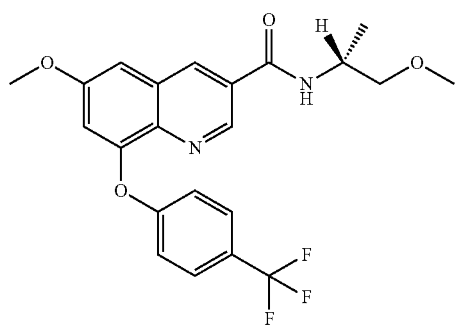 | (R)-6-methoxy-N-(1-methoxypropan-2-yl)-8-(4-(trifluoromethyl)phenoxy)quinoline-3-carboxamide |
| 45 | 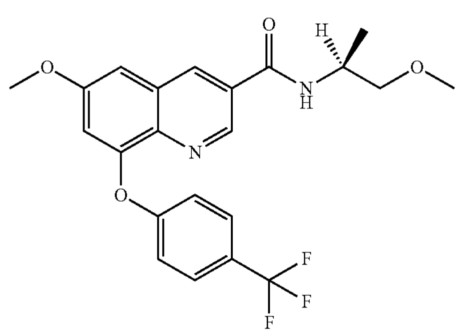 | (S)-6-methoxy-N-(1-methoxypropan-2-yl)-8-(4-(trifluoromethyl)phenoxy)quinoline-3-carboxamide |

TABLE 1-continued
| Compound # | Structure | Name |
|---|---|---|
| 46 | 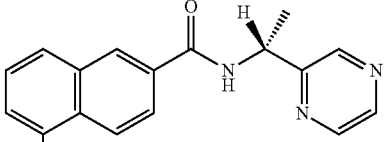 | (R)-N-(1-(pyrazin-2-yl)ethyl)-5-(4-(trifluoromethyl)phenoxy)-2-naphthamide |
| 47 | 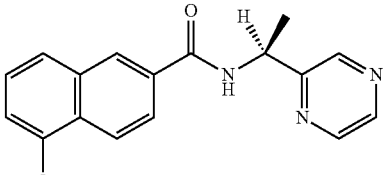 | (S)-N-(1-(pyrazin-2-yl)ethyl)-5-(4-(trifluoromethyl)phenoxy)-2-naphthamide |
| 48 | 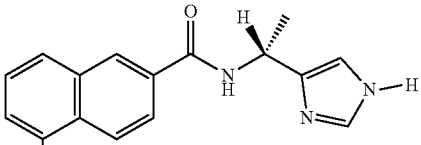 | (R)-N-(1-(1H-imidazol-4-yl)ethyl)-5-(4-(trifluoromethyl)phenoxy)-2-naphthamide |
| 49 | 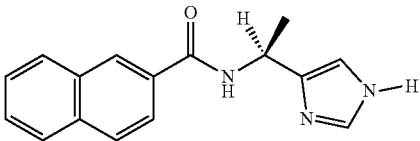 | (S)-N-(1-(1H-imidazol-4-yl)ethyl)-5-(4-(trifluoromethyl)phenoxy)-2-naphthamide |

TABLE 1-continued

| Compound # | Structure | Name |
|---|---|---|
| 50 | 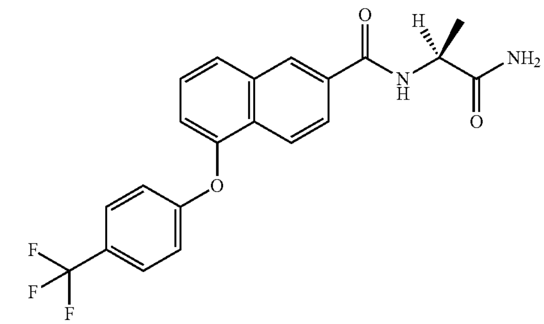 [SMILES: C[C@H](NC(=O)c1ccc2c(Oc3ccc(C(F)(F)F)cc3)cccc2c1)C(N)=O] | (S)-N-(1-amino-1-oxopropan-2-yl)-5-(4-(trifluoromethyl)phenoxy)-2-naphthamide |
| 51 | 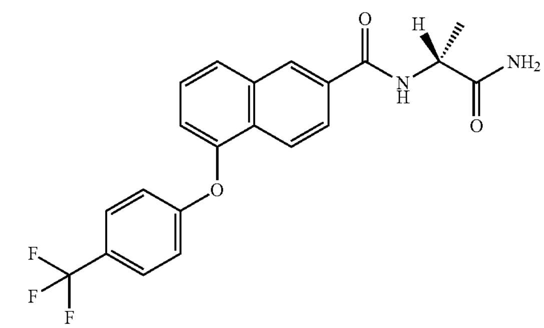 [SMILES: C[C@@H](NC(=O)c1ccc2c(Oc3ccc(C(F)(F)F)cc3)cccc2c1)C(N)=O] | (R)-N-(1-amino-1-oxopropan-2-yl)-5-(4-(trifluoromethyl)phenoxy)-2-naphthamide |
| 52 | 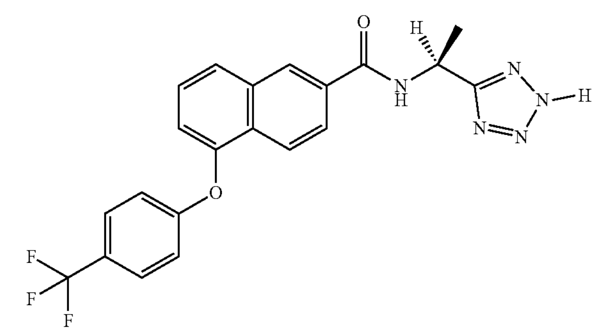 [SMILES: C[C@H](NC(=O)c1ccc2c(Oc3ccc(C(F)(F)F)cc3)cccc2c1)c1nn[nH]n1] | (S)-N-(1-(2H-tetrazol-5-yl)ethyl)-5-(4-(trifluoromethyl)phenoxy)-2-naphthamide |
| 53 | 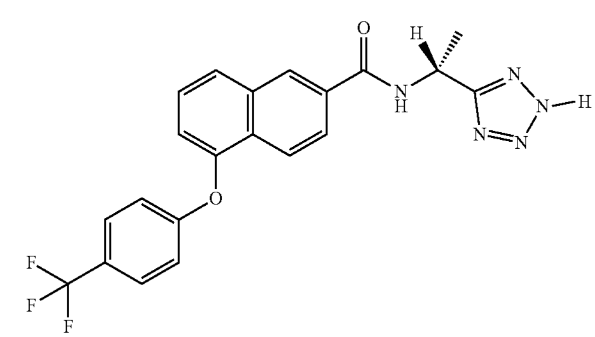 [SMILES: C[C@@H](NC(=O)c1ccc2c(Oc3ccc(C(F)(F)F)cc3)cccc2c1)c1nn[nH]n1] | (R)-N-(1-(2H-tetrazol-5-yl)ethyl)-5-(4-(trifluoromethyl)phenoxy)-2-naphthamide |

TABLE 1-continued

| Compound # | Structure | Name |
|---|---|---|
| 54 | 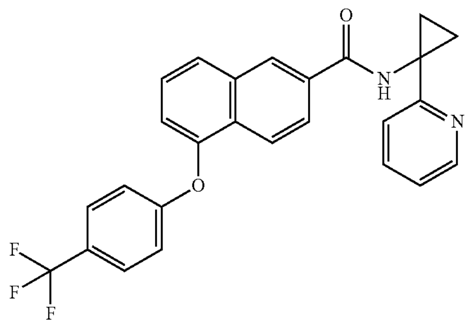 [SMILES: O=C(NC1(c2ccccn2)CC1)c1ccc2c(Oc3ccc(C(F)(F)F)cc3)cccc2c1] | N-(1-(pyridin-2-yl)cyclopropyl)-5-(4-(trifluoromethyl)phenoxy)-2-naphthamide |
| 55 | 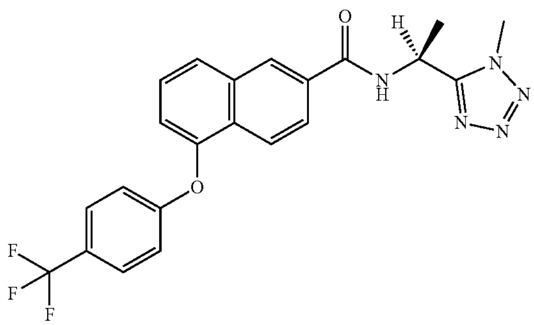 [SMILES: C[C@H](NC(=O)c1ccc2c(Oc3ccc(C(F)(F)F)cc3)cccc2c1)c1nnnn1C] | (S)-N-(1-(1-methyl-1H-tetrazol-5-yl)ethyl)-5-(4-(trifluoromethyl)phenoxy)-2-naphthamide |
| 56 | 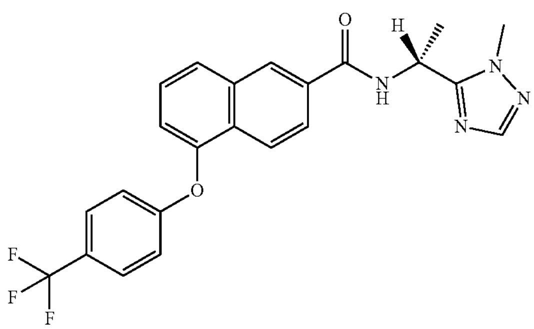 [SMILES: C[C@@H](NC(=O)c1ccc2c(Oc3ccc(C(F)(F)F)cc3)cccc2c1)c1ncnn1C] | (R)-N-(1-(1-methyl-1H-tetrazol-5-yl)ethyl)-5-(4-(trifluoromethyl)phenoxy)-2-naphthamide |
| 57 | 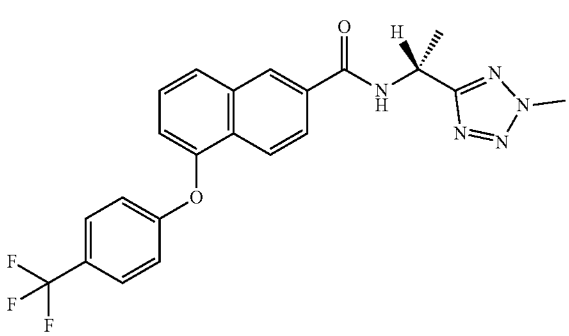 [SMILES: C[C@@H](NC(=O)c1ccc2c(Oc3ccc(C(F)(F)F)cc3)cccc2c1)c1nnn(C)n1] | (R)-N-(1-(2-methyl-2H-tetrazol-5-yl)ethyl)-5-(4-(trifluoromethyl)phenoxy)-2-naphthamide |

TABLE 1-continued
| Compound # | Structure | Name |
|---|---|---|
| 58 | 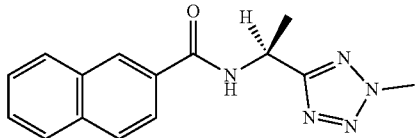 | (S)-N-(1-(2-methyl-2H-tetrazol-5-yl)ethyl)-5-(4-(trifluoromethyl)phenoxy)-2-naphthamide |
| 59 | 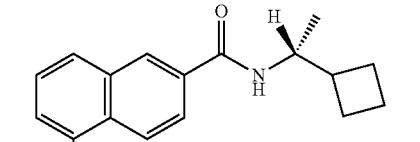 | (R)-N-(1-cyclobutylethyl)-5-(4-(trifluoromethyl)phenoxy)-2-naphthamide |
| 60 | 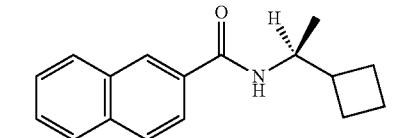 | (S)-N-(1-cyclobutylethyl)-5-(4-(trifluoromethyl)phenoxy)-2-naphthamide |
| 61 | 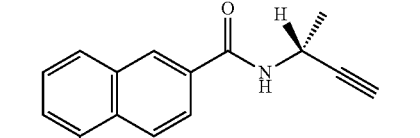 | (R)-N-(but-3-yn-2-yl)-5-(4-(trifluoromethyl)phenoxy)-2-naphthamide |

TABLE 1-continued

| Compound # | Structure | Name |
|---|---|---|
| 62 | 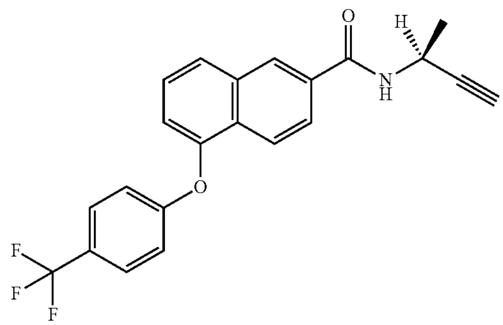 [SMILES: C#C[C@H](C)NC(=O)c1ccc2c(Oc3ccc(C(F)(F)F)cc3)cccc2c1] | (S)-N-(but-3-yn-2-yl)-5-(4-(trifluoromethyl)phenoxy)-2-naphthamide |
| 63 | 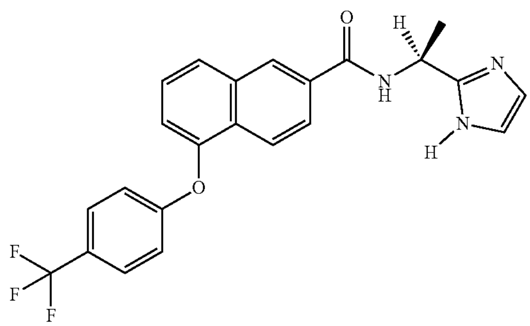 [SMILES: C[C@H](NC(=O)c1ccc2c(Oc3ccc(C(F)(F)F)cc3)cccc2c1)c1ncc[nH]1] | (S)-N-(1H-imidazol-2-yl)ethyl)-5-(4-(trifluoromethyl)phenoxy)-2-naphthamide |
| 64 | 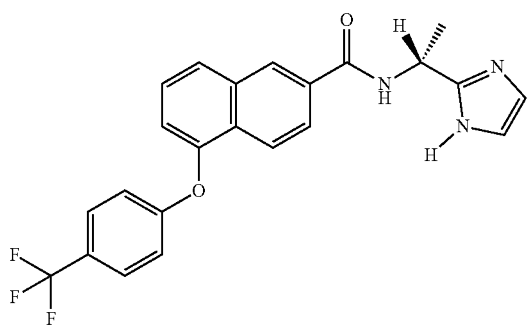 [SMILES: C[C@@H](NC(=O)c1ccc2c(Oc3ccc(C(F)(F)F)cc3)cccc2c1)c1ncc[nH]1] | (R)-N-(1-(1H-imidazol-2-yl)ethyl)-5-(4-(trifluoromethyl)phenoxy)-2-naphthamide |
| 65 | 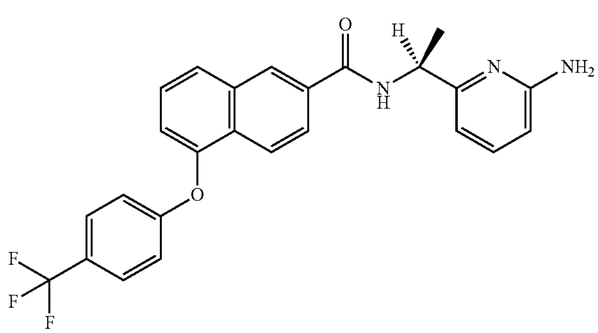 [SMILES: C[C@H](NC(=O)c1ccc2c(Oc3ccc(C(F)(F)F)cc3)cccc2c1)c1cccc(N)n1] | (S)-N-(1-(6-aminopyridin-2-yl)ethyl)-5-(4-(trifluoromethyl)phenoxy)-2-naphthamide |

TABLE 1-continued

| Compound # | Structure | Name |
|---|---|---|
| 66 | 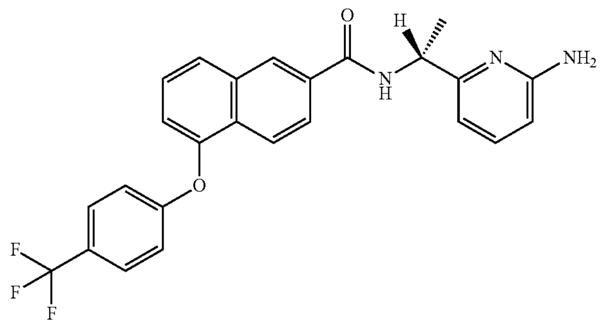 [SMILES: C[C@@H](NC(=O)c1ccc2c(Oc3ccc(C(F)(F)F)cc3)cccc2c1)c1cccc(N)n1] | (R)-N-(1-(6-aminopyridin-2-yl)ethyl)-5-(4-(trifluoromethyl)phenoxy)-2-naphthamide |
| 67 | 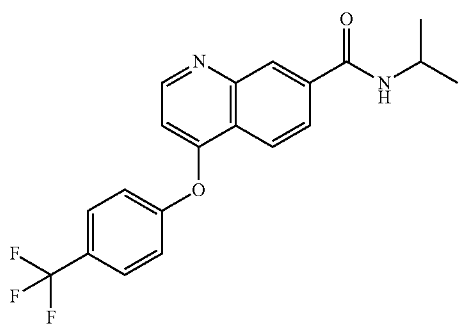 | N-Isopropyl-4-(4-(trifluoromethyl)phenoxy)quinoline-7-carboxamide |
| 68 | 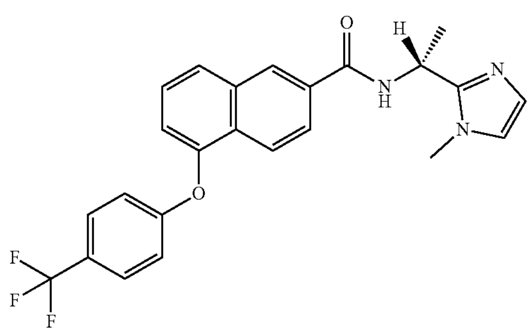 [SMILES: C[C@@H](NC(=O)c1ccc2c(Oc3ccc(C(F)(F)F)cc3)cccc2c1)c1nccn1C] | (R)-N-(1-(1-methyl-1H-imidazol-2-yl)ethyl)-5-(4-(trifluoromethyl)phenoxy)-2-naphthamide |
| 69 | 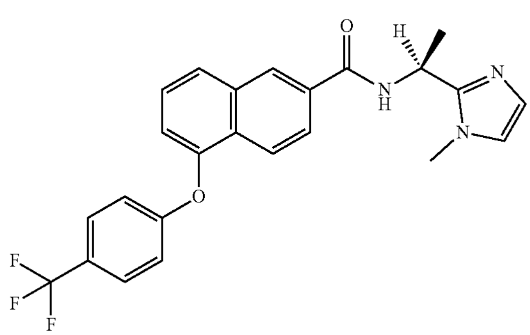 [SMILES: C[C@H](NC(=O)c1ccc2c(Oc3ccc(C(F)(F)F)cc3)cccc2c1)c1nccn1C] | (S)-N-(1-(1-methyl-1H-imidazol-2-yl)ethyl)-5-(4-(trifluoromethyl)phenoxy)-2-naphthamide |

TABLE 1-continued

| Compound # | Structure | Name |
|---|---|---|
| 70 | 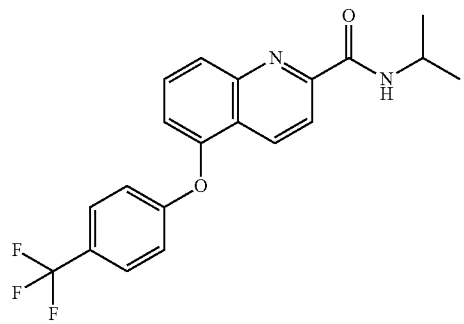 | N-Isopropyl-5-(4-(trifluoromethyl)phenoxy)quinoline-2-carboxamide |
| 71 | 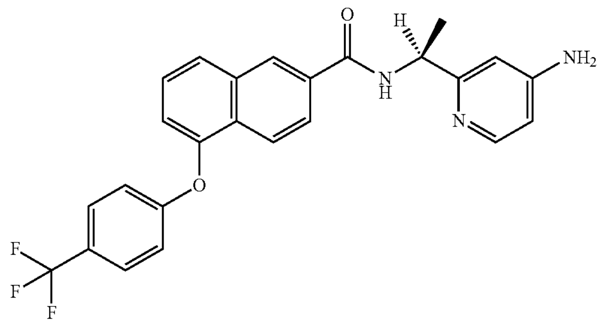 [SMILES: C[C@H](NC(=O)c1ccc2c(Oc3ccc(C(F)(F)F)cc3)cccc2c1)c1cc(N)ccn1] | (S)-N-(1-(4-aminopyridin-2-yl)ethyl)-5-(4-(trifluoromethyl)phenoxy)-2-naphthamide |
| 72 | 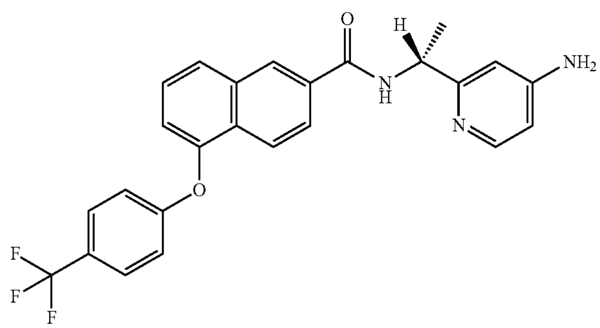 [SMILES: C[C@@H](NC(=O)c1ccc2c(Oc3ccc(C(F)(F)F)cc3)cccc2c1)c1cc(N)ccn1] | (R)-N-(1-(4-aminopyridin-2-yl)ethyl)-5-(4-(trifluoromethyl)phenoxy)-2-naphthamide |
| 73 | 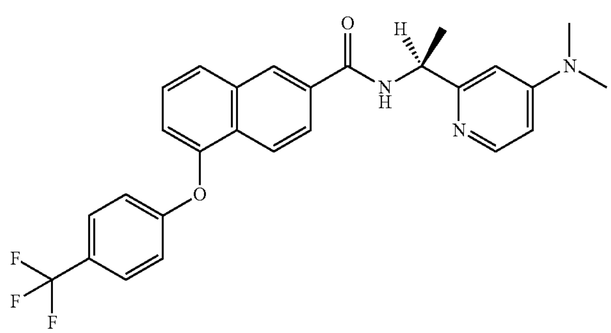 [SMILES: C[C@H](NC(=O)c1ccc2c(Oc3ccc(C(F)(F)F)cc3)cccc2c1)c1cc(N(C)C)ccn1] | (S)-N-(1-(4-(dimethylamino)pyridin-2-yl)ethyl)-5-(4-(trifluoromethyl)phenoxy)-2-naphthamide |

TABLE 1-continued

| Compound # | Structure | Name |
|---|---|---|
| 74 | 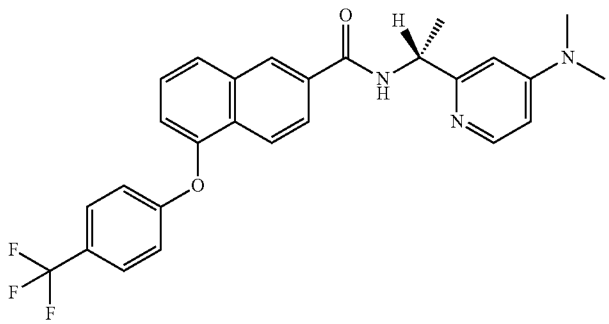 [SMILES: C[C@@H](NC(=O)c1ccc2c(Oc3ccc(C(F)(F)F)cc3)cccc2c1)c1cc(N(C)C)ccn1] | (R)-N-(1-(4-(dimethylamino)pyridin-2-yl)ethyl)-5-(4-(trifluoromethyl)phenoxy)-2-naphthamide |
| 75 | 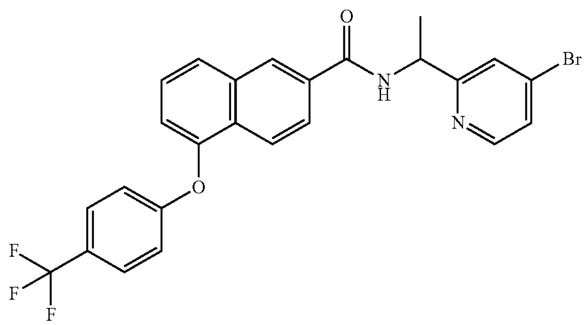 [SMILES: CC(NC(=O)c1ccc2c(Oc3ccc(C(F)(F)F)cc3)cccc2c1)c1cc(Br)ccn1] | N-(1-(4-bromopyridin-2-yl)ethyl)-5-(4-(trifluoromethyl)phenoxy)-2-naphthamide |
| 76 | 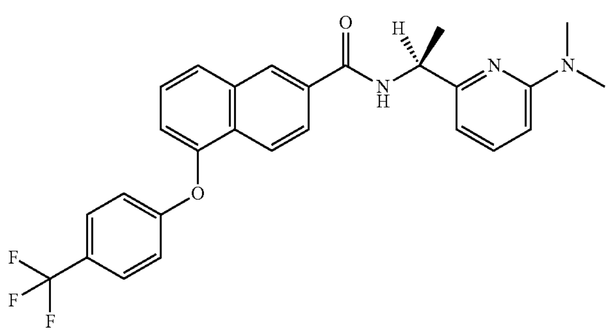 [SMILES: C[C@H](NC(=O)c1ccc2c(Oc3ccc(C(F)(F)F)cc3)cccc2c1)c1cccc(N(C)C)n1] | (S)-N-(1-(6-(dimethylamino)pyridin-2-yl)ethyl)-5-(4-(trifluoromethyl)phenoxy)-2-naphthamide |
| 77 | 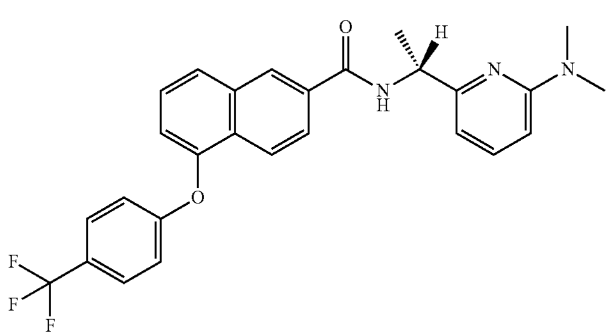 [SMILES: C[C@@H](NC(=O)c1ccc2c(Oc3ccc(C(F)(F)F)cc3)cccc2c1)c1cccc(N(C)C)n1] | (R)-N-(1-(6-(dimethylamino)pyridin-2-yl)ethyl)-5-(4-(trifluoromethyl)phenoxy)-2-naphthamide |

TABLE 1-continued
| Compound # | Structure | Name |
|---|---|---|
| 78 | 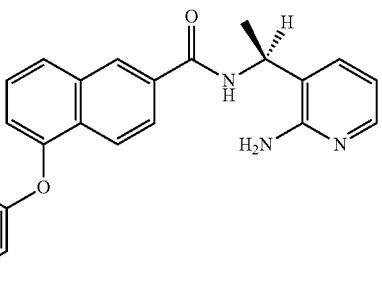 | (S)-N-(1-(2-aminopyridin-3-yl)ethyl)-5-(4-(trifluoromethyl)phenoxy)-2-naphthamide |
| 79 | 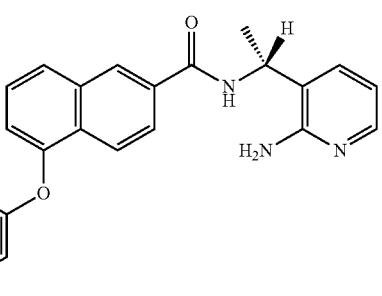 | (R)-N-(1-(2-aminopyridin-3-yl)ethyl)-5-(4-(trifluoromethyl)phenoxy)-2-naphthamide |
| 80 | 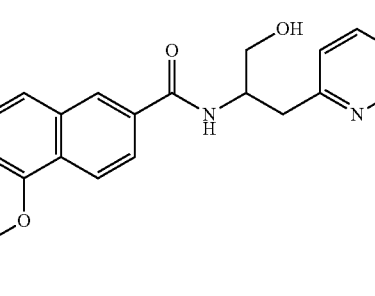 | N-[1-(hydroxymethyl)-2-(2-pyridyl)ethyl]-5-[4-(trifluoromethyl)phenoxy]naphthalene-2-carboxamide |
| 81 | 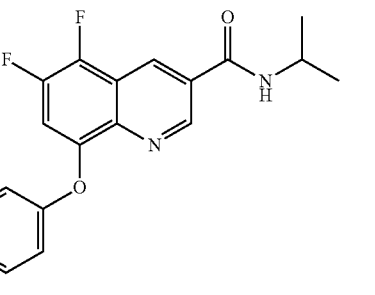 | 5,6-difluoro-N-isopropyl-8-(4-(trifluoromethyl)phenoxy)quinoline-3-carboxamide |

TABLE 1-continued

| Compound # | Structure | Name |
|---|---|---|
| 82 | 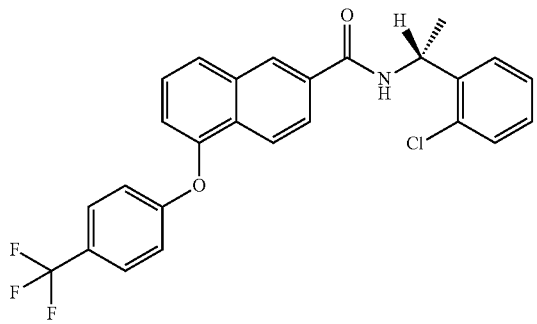 [SMILES: C[C@@H](NC(=O)c1ccc2c(Oc3ccc(C(F)(F)F)cc3)cccc2c1)c1ccccc1Cl] | (R)-N-(1-(2-chlorophenyl)ethyl)-5-(4-(trifluoromethyl)phenoxy)-2-naphthamide |
| 83 | 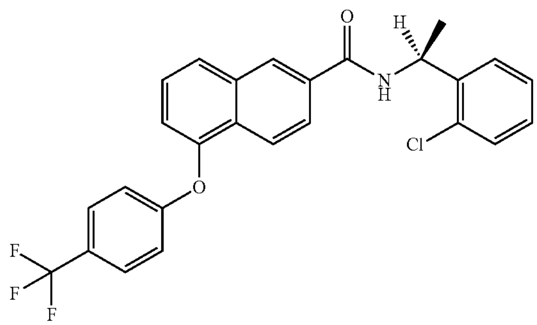 [SMILES: C[C@H](NC(=O)c1ccc2c(Oc3ccc(C(F)(F)F)cc3)cccc2c1)c1ccccc1Cl] | (S)-N-(1-(2-chlorophenyl)ethyl)-5-(4-(trifluoromethyl)phenoxy)-2-naphthamide |
| 84 | 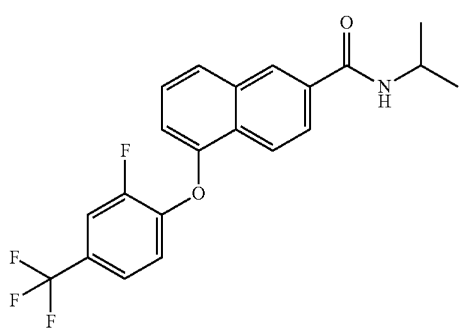 [SMILES: CC(C)NC(=O)c1ccc2c(Oc3ccc(C(F)(F)F)cc3F)cccc2c1] | 5-(2-fluoro-4-(trifluoromethyl)phenoxy)-N-isopropyl-2-naphthamide |
| 85 | 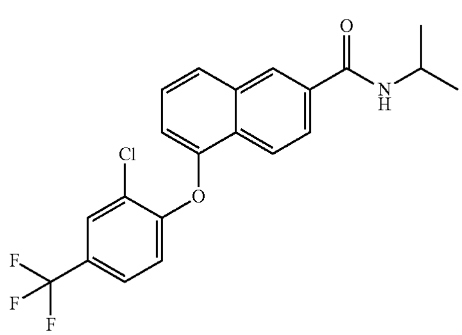 [SMILES: CC(C)NC(=O)c1ccc2c(Oc3ccc(C(F)(F)F)cc3Cl)cccc2c1] | 5-(2-chloro-4-(trifluoromethyl)phenoxy)-N-isopropyl-2-naphthamide |

TABLE 1-continued

| Compound # | Structure | Name |
|---|---|---|
| 86 | 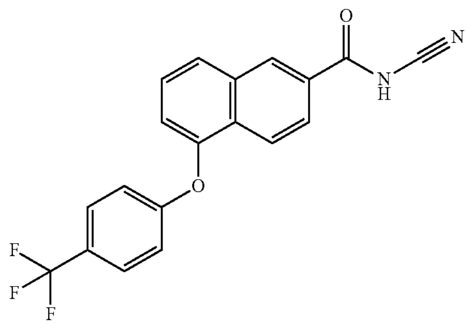 [SMILES: N#CNC(=O)c1ccc2c(Oc3ccc(C(F)(F)F)cc3)cccc2c1] | N-cyano-5-[4-(trifluoromethyl)phenoxy]naphthalene-2-carboxamide |
| 87 | 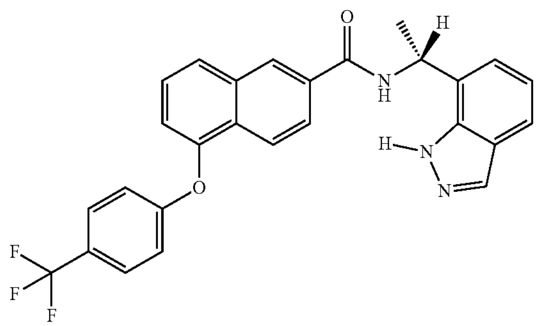 [SMILES: C[C@@H](NC(=O)c1ccc2c(Oc3ccc(C(F)(F)F)cc3)cccc2c1)c1cccc2cn[nH]c12] | N-[(1R)-1-(1H-indazol-7-yl)ethyl]-5-[4-(trifluoromethyl)phenoxy]naphthalene-2-carboxamide |
| 88 | 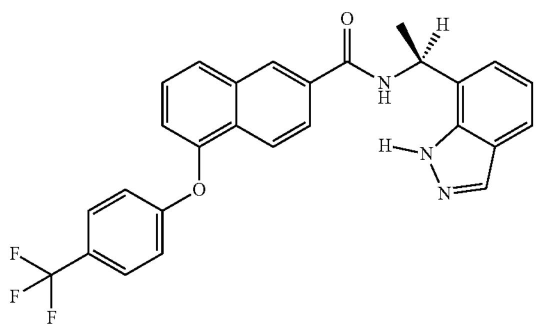 [SMILES: C[C@H](NC(=O)c1ccc2c(Oc3ccc(C(F)(F)F)cc3)cccc2c1)c1cccc2cn[nH]c12] | N-[(1S)-1-(1H-indazol-7-yl)ethyl]-5-[4-(trifluoromethyl)phenoxy]naphthalene-2-carboxamide |
| 89 | 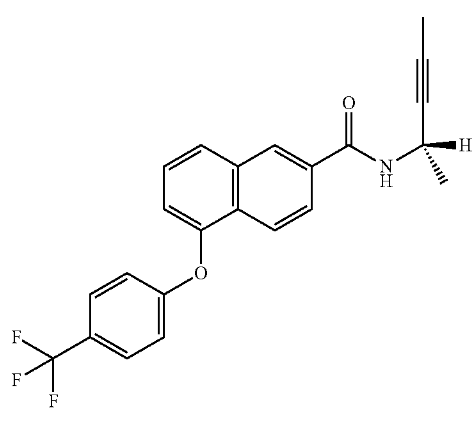 [SMILES: CC#C[C@H](C)NC(=O)c1ccc2c(Oc3ccc(C(F)(F)F)cc3)cccc2c1] | N-[(1S)-1-methylbut-2-ynyl]-5-[4-(trifluoromethyl)phenoxy]naphthalene-2-carboxamide |

TABLE 1-continued
| Compound # | Structure | Name |
|---|---|---|
| 90 | 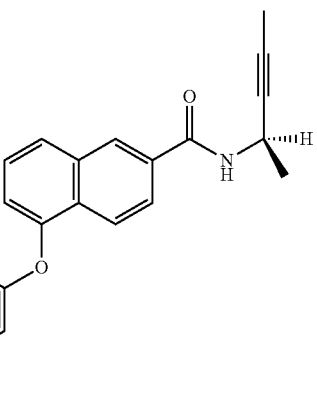 | N-[(1R)-1-methylbut-2-ynyl]-5-[4-(trifluoromethyl)phenoxy]naphthalene-2-carboxamide |
| 91 | 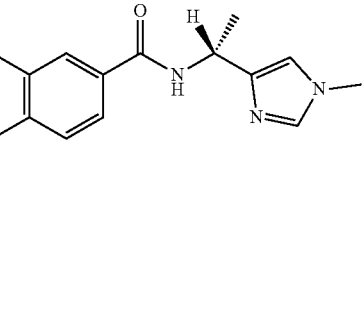 | N-[(1R)-1-(1-methylimidazol-4-yl)ethyl]-5-[4-(trifluoromethyl)phenoxy]naphthalene-2-carboxamide |
| 92 | 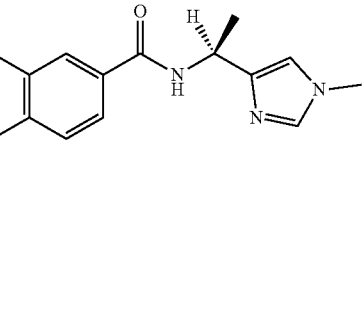 | N-[(1S)-1-(1-methylimidazol-4-yl)ethyl]-5-[4-(trifluoromethyl)phenoxy]naphthalene-2-carboxamide |
| 93 | 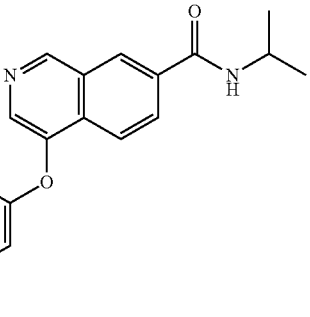 | N-isopropyl-4-(4-(trifluoromethyl)phenoxy)isoquinoline-7-carboxamide |

TABLE 1-continued

| Compound # | Structure | Name |
|---|---|---|
| 94 | 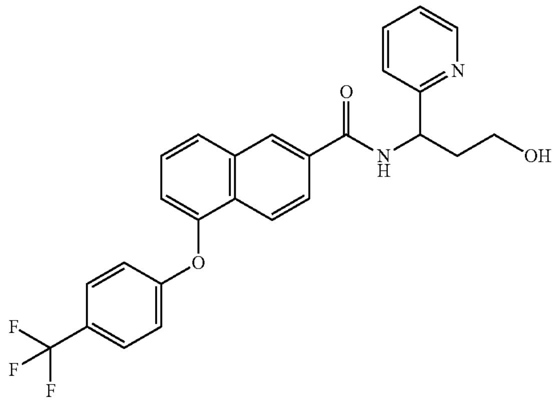 [SMILES: O=C(NC(CCO)c1ccccn1)c1ccc2c(Oc3ccc(C(F)(F)F)cc3)cccc2c1] | N-(3-hydroxy-1-(pyridin-2-yl)propyl)-5-(4-(trifluoromethyl)phenoxy)-2-naphthamide |
| 95 | 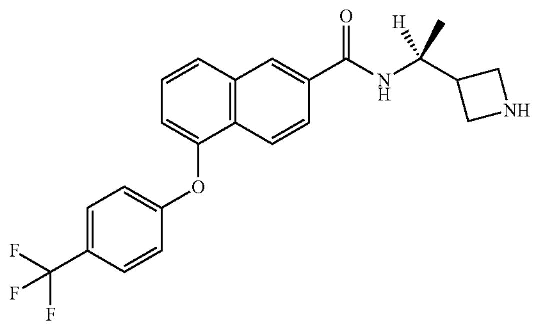 [SMILES: C[C@H](NC(=O)c1ccc2c(Oc3ccc(C(F)(F)F)cc3)cccc2c1)C1CNC1] | N-[(1S)-1-(azetidin-3-yl)ethyl]-5-[4-(trifluoromethyl)phenoxy]naphthalene-2-carboxamide |
| 96 | 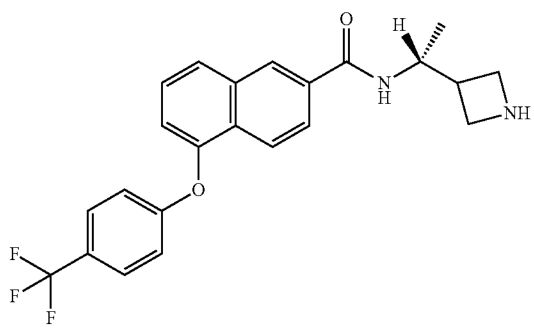 [SMILES: C[C@@H](NC(=O)c1ccc2c(Oc3ccc(C(F)(F)F)cc3)cccc2c1)C1CNC1] | N-[(1R)-1-(azetidin-3-yl)ethyl]-5-[4-(trifluoromethyl)phenoxy]naphthalene-2-carboxamide |
| 97 | 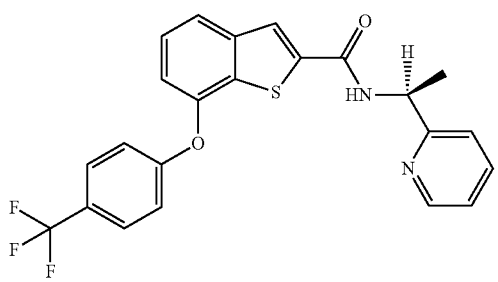 [SMILES: C[C@H](NC(=O)c1cc2cccc(Oc3ccc(C(F)(F)F)cc3)c2s1)c1ccccn1] | (S)-N-(1-(pyridin-2-yl)ethyl)-7-(4-(trifluoromethyl)phenoxy)benzothiophene-2-carboxamide |

TABLE 1-continued

| Compound # | Structure | Name |
|---|---|---|
| 98 | 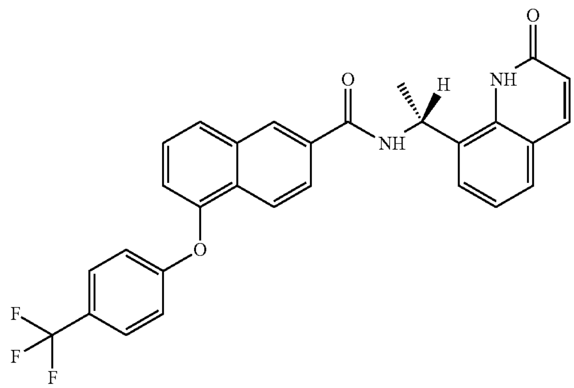 [SMILES: C[C@@H](NC(=O)c1ccc2c(Oc3ccc(C(F)(F)F)cc3)cccc2c1)c1cccc2ccc(=O)[nH]c12] | N-[(1R)-1-(2-oxo-1H-quinolin-8-yl)ethyl]-5-[4-(trifluoromethyl)phenoxy]naphthalene-2-carboxamide |
| 99 | 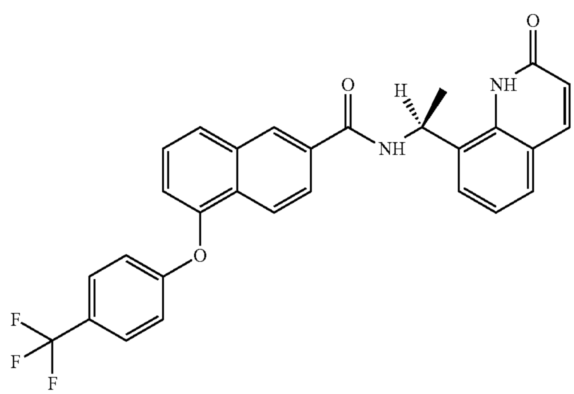 [SMILES: C[C@H](NC(=O)c1ccc2c(Oc3ccc(C(F)(F)F)cc3)cccc2c1)c1cccc2ccc(=O)[nH]c12] | N-[(1R)-1-(2-oxo-1H-quinolin-8-yl)ethyl]-5-[4-(trifluoromethyl)phenoxy]naphthalene-2-carboxamide |
| 100 | 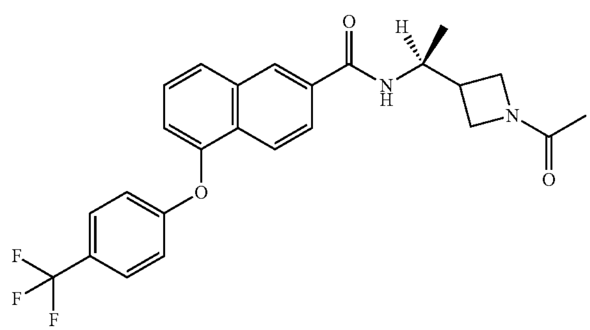 [SMILES: CC(=O)N1CC([C@H](C)NC(=O)c2ccc3c(Oc4ccc(C(F)(F)F)cc4)cccc3c2)C1] | (S)-N-(1-(1-acetylazetidin-3-yl)ethyl)-5-(4-(trifluoromethyl)phenoxy)-2-naphthamide |
| 101 | 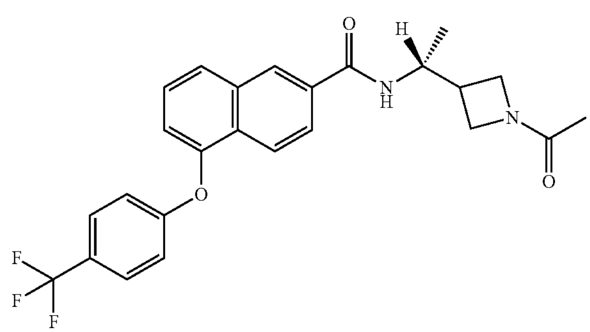 [SMILES: CC(=O)N1CC([C@@H](C)NC(=O)c2ccc3c(Oc4ccc(C(F)(F)F)cc4)cccc3c2)C1] | (R)-N-(1-(1-acetylazetidin-3-yl)ethyl)-5-(4-(trifluoromethyl)phenoxy)-2-naphthamide |

TABLE 1-continued

| Compound # | Structure | Name |
|---|---|---|
| 102 | 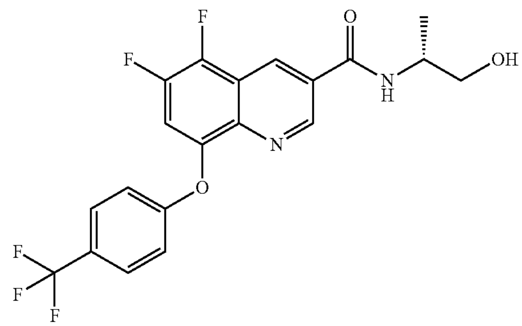 [SMILES: C[C@H](CO)NC(=O)c1cnc2c(Oc3ccc(C(F)(F)F)cc3)cc(F)c(F)c2c1] | (R)-5,6-difluoro-N-(1-hydroxypropan-2-yl)-8-(4-(trifluoromethyl)phenoxy)quinoline-3-carboxamide |
| 103 | 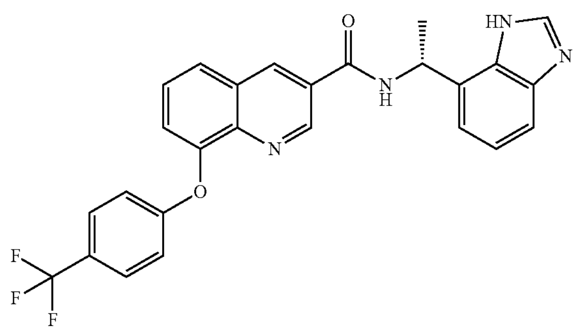 [SMILES: C[C@@H](NC(=O)c1cnc2c(Oc3ccc(C(F)(F)F)cc3)cccc2c1)c1cccc2nc[nH]c12] | (R)-N-(1-(1H-benzo[d]imidazol-7-yl)ethyl)-8-(4-(trifluoromethyl)phenoxy)quinoline-3-carboxamide |
| 104 | 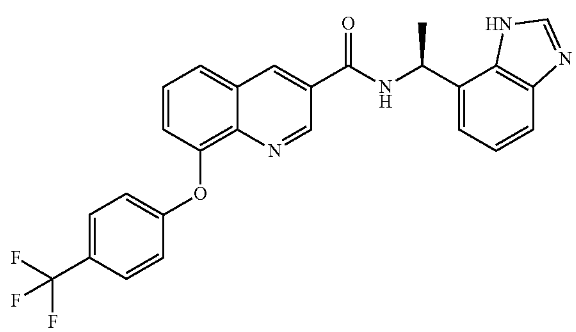 [SMILES: C[C@H](NC(=O)c1cnc2c(Oc3ccc(C(F)(F)F)cc3)cccc2c1)c1cccc2nc[nH]c12] | (S)-N-(1-(1H-benzo[d]imidazol-7-yl)ethyl)-8-(4-(trifluoromethyl)phenoxy)quinoline-3-carboxamide |
| 105 | 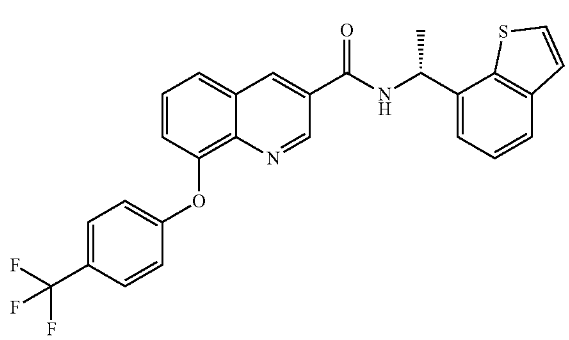 [SMILES: C[C@@H](NC(=O)c1cnc2c(Oc3ccc(C(F)(F)F)cc3)cccc2c1)c1cccc2ccsc12] | (R)-N-(1-(benzo[b]thiophen-7-yl)ethyl)-8-(4-(trifluoromethyl)phenoxy)quinoline-3-carboxamide |

TABLE 1-continued

| Compound # | Structure | Name |
|---|---|---|
| 106 | 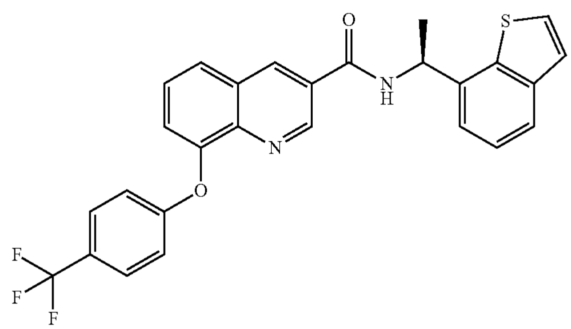 [SMILES: C[C@H](NC(=O)c1cnc2c(Oc3ccc(C(F)(F)F)cc3)cccc2c1)c1cccc2ccsc12] | (S)-N-(1-(benzo[b]thiophen-7-yl)ethyl)-8-(4-(trifluoromethyl)phenoxy)quinoline-3-carboxamide |
| 107 | 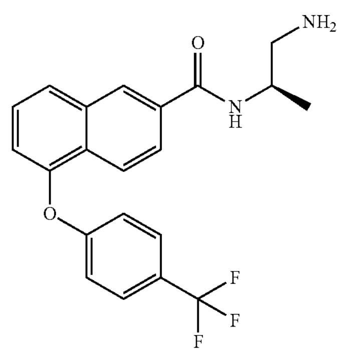 [SMILES: C[C@H](CN)NC(=O)c1ccc2c(Oc3ccc(C(F)(F)F)cc3)cccc2c1] | (R)-N-(1-aminopropan-2-yl)-5-(4-(trifluoromethyl)phenoxy)-2-naphthamide |
| 108 | 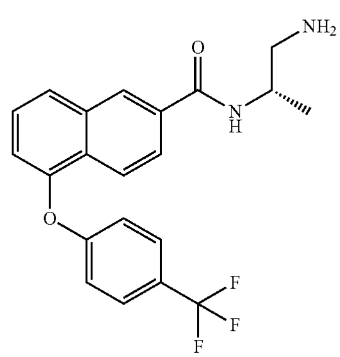 [SMILES: C[C@@H](CN)NC(=O)c1ccc2c(Oc3ccc(C(F)(F)F)cc3)cccc2c1] | (S)-N-(1-aminopropan-2-yl)-5-(4-(trifluoromethyl)phenoxy)-2-naphthamide |
| 109 | 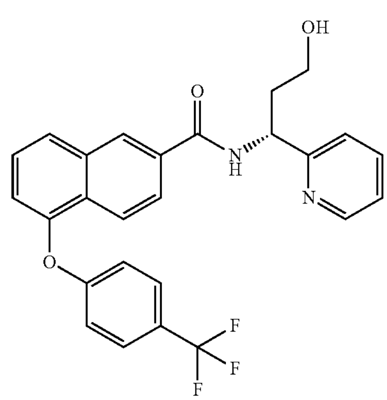 [SMILES: O=C(N[C@H](CCO)c1ccccn1)c1ccc2c(Oc3ccc(C(F)(F)F)cc3)cccc2c1] | (R)-N-(3-hydroxy-1-(pyridin-2-yl)propyl)-5-(4-(trifluoromethyl)phenoxy)-2-naphthamide |

TABLE 1-continued
| Compound # | Structure | Name |
|---|---|---|
| 110 | 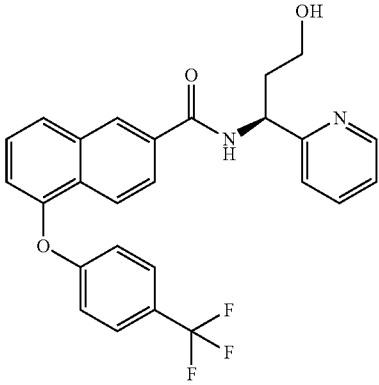 [SMILES: O=C(N[C@@H](CCO)c1ccccn1)c1ccc2c(Oc3ccc(C(F)(F)F)cc3)cccc2c1] | (S)-N-(3-hydroxy-1-(pyridin-2-yl)propyl)-5-(4-(trifluoromethyl)phenoxy)-2-naphthamide |
| 111 | 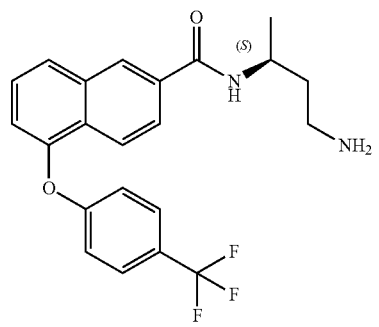 | (S)-N-(4-aminobutan-2-yl)-5-(4-(trifluoromethyl)phenoxy)-2-naphthamide |
| 112 | 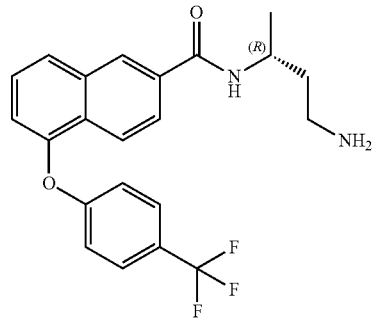 | (R)-N-(4-aminobutan-2-yl)-5-(4-(trifluoromethyl)phenoxy)-2-naphthamide |
| 113 | 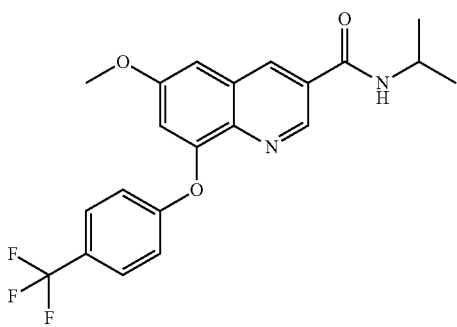 [SMILES: COc1cc(Oc2ccc(C(F)(F)F)cc2)c2ncc(C(=O)NC(C)C)cc2c1] | N-Isopropyl-6-methoxy-8-(4-(trifluoromethyl)phenoxy)quinoline-3-carboxamide |

TABLE 1-continued

| Compound # | Structure | Name |
|---|---|---|
| 114 | 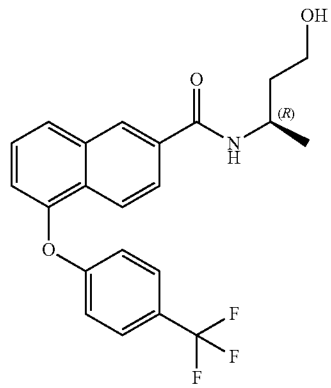 | (R)-N-(4-hydroxybutan-2-yl)-5-(4-(trifluoromethyl)phenoxy)-2-naphthamide |
| 115 | 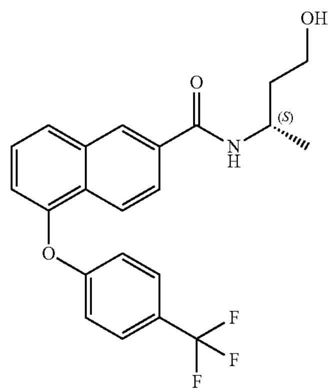 | (S)-N-(4-hydroxybutan-2-yl)-5-(4-(trifluoromethyl)phenoxy)-2-naphthamide |
| 116 | 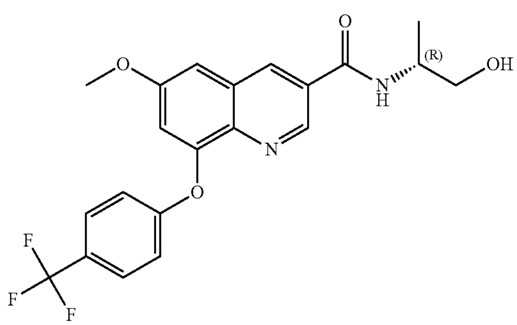 | (R)-N-(1-hydroxypropan-2-yl)-6-methoxy-8-(4-(trifluoromethyl)phenoxy)quinoline-3-carboxamide |
| 117 | 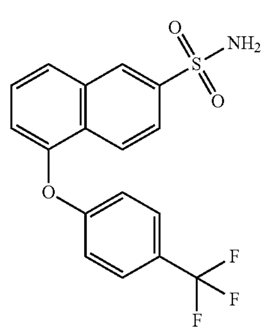 [SMILES: NS(=O)(=O)c1ccc2c(Oc3ccc(C(F)(F)F)cc3)cccc2c1] | 5-(4-(trifluoromethyl)phenoxy)naphthalene-2-sulfonamide |

TABLE 1-continued

| Compound # | Structure | Name |
|---|---|---|
| 118 | 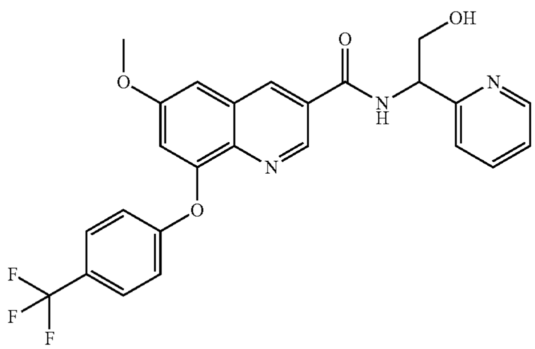 [SMILES: COc1cc(Oc2ccc(C(F)(F)F)cc2)c2ncc(C(=O)NC(CO)c3ccccn3)cc2c1] | N-(2-Hydroxy-1-(pyridin-2-yl)ethyl)-6-methoxy-8-(4-(trifluoromethyl)phenoxy)quinoline-3-carboxamide |
| 119 | 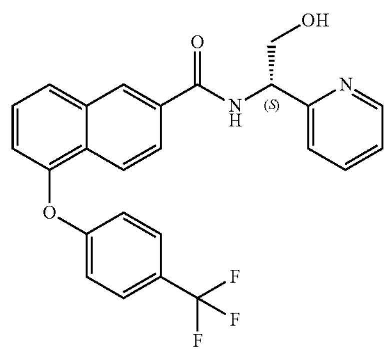 | (S)-N-(2-hydroxy-1-(pyridin-2-yl)ethyl)-5-(4-(trifluoromethyl)phenoxy)-2-naphthamide |
| 120 | 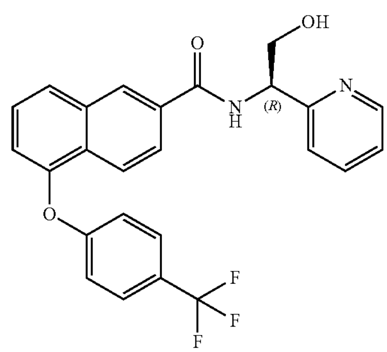 | (R)-N-(2-hydroxy-1-(pyridin-2-yl)ethyl)-5-(4-(trifluoromethyl)phenoxy)-2-naphthamide |
| 121 | 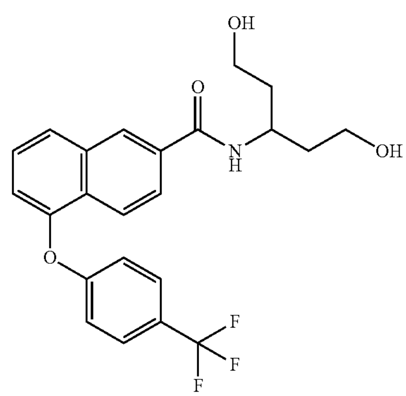 [SMILES: O=C(NC(CCO)CCO)c1ccc2c(Oc3ccc(C(F)(F)F)cc3)cccc2c1] | N-(1,5-dihydroxypentan-3-yl)-5-(4-(trifluoromethyl)phenoxy)-2-naphthamide |

TABLE 1-continued

| Compound # | Structure | Name |
|---|---|---|
| 122 | 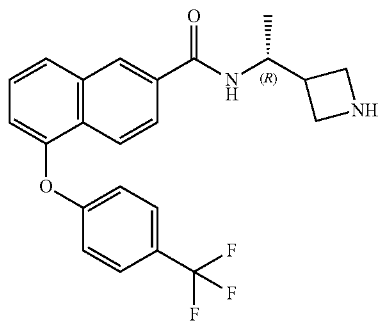 | (R)-N-(1-(azetidin-3-yl)ethyl)-5-(4-(trifluoromethyl)phenoxy)-2-naphthamide |
| 123 | 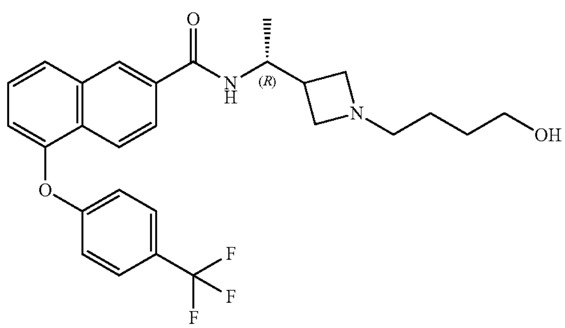 | (R)-N-(1-(1-(4-hydroxybutan)azetidin-3-yl)ethyl)-5-(4-(trifluoromethyl)phenoxy)-2-naphthamide |
| 124 | 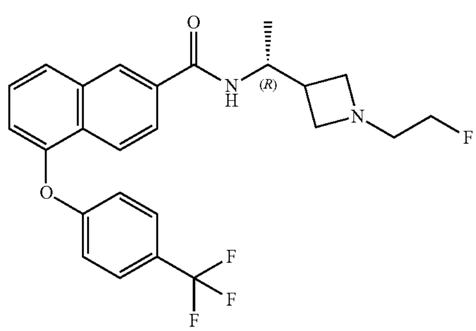 | (R)-N-(1-(1-(2-fluoroethyl)azetidin-3-yl)ethyl)-5-(4-(trifluoromethyl)phenoxy)-2-naphthamide |
| 125 | 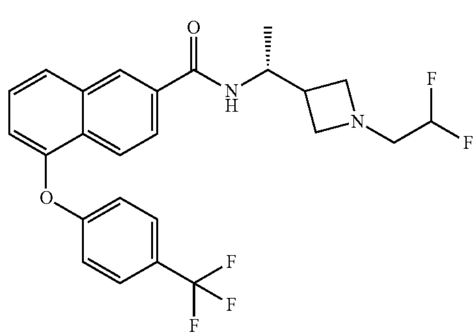 [SMILES: C[C@@H](NC(=O)c1ccc2c(Oc3ccc(C(F)(F)F)cc3)cccc2c1)C1CN(CC(F)F)C1] | (R)-N-(1-(1-(2,2-difluoroethyl)azetidin-3-yl)ethyl)-5-(4-(trifluoromethyl)phenoxy)-2-naphthamide |

TABLE 1-continued
| Compound # | Structure | Name |
|---|---|---|
| 126 | 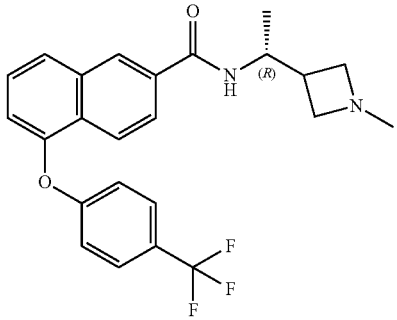 | (R)-N-(1-(1-methylazetidin-3-yl)ethyl)-5-(4-(trifluoromethyl)phenoxy)-2-naphthamide |
| 127 | 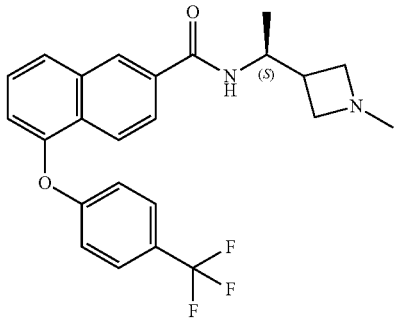 | (S)-N-(1-(1-methylazetidin-3-yl)ethyl)-5-(4-(trifluoromethyl)phenoxy)-2-naphthamide |
| 128 | 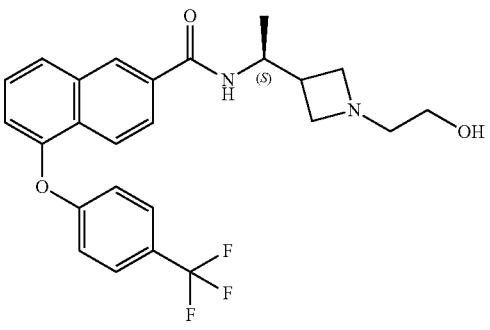 | (S)-N-(1-(1-(2-hydroxyethyl)azetidin-3-yl)ethyl)-5-(4-(trifluoromethyl)phenoxy)-2-naphthamide |
| 129 | 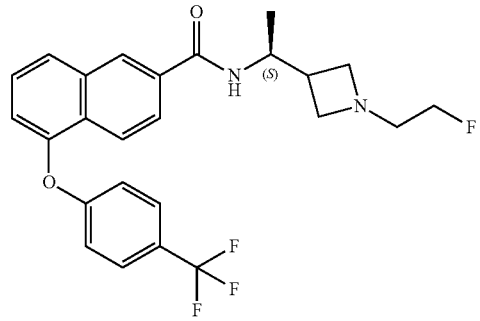 | (S)-N-(1-(1-(2-fluoroethyl)azetidin-3-yl)ethyl)-5-(4-(trifluoromethyl)phenoxy)-2-naphthamide |

TABLE 1-continued

| Compound # | Structure | Name |
|---|---|---|
| 130 | 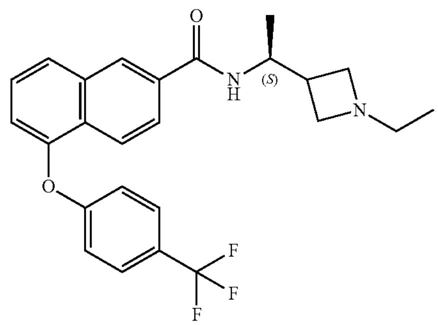 | (S)-N-(1-(1-ethylazetidin-3-yl)ethyl)-5-(4-(trifluoromethyl)propoxy)-2-naphthamide |
| 131 | 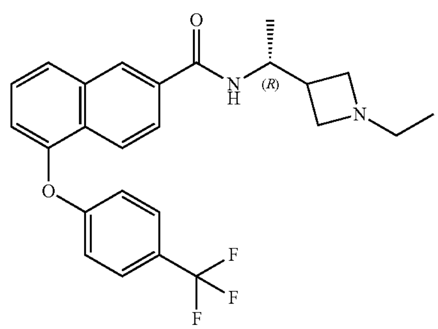 | (R)-N-(1-(1-ethylazetidin-3-yl)ethyl)-5-(4-(trifluoromethyl)phenoxy)-2-naphthamide |
| 132 | 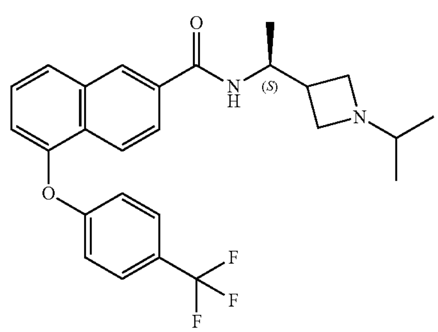 | (S)-N-(1-(1-isopropylazetidin-3-yl)ethyl)-5-(4-(trifluoromethyl)phenoxy)-2-naphthamide |
| 133 | 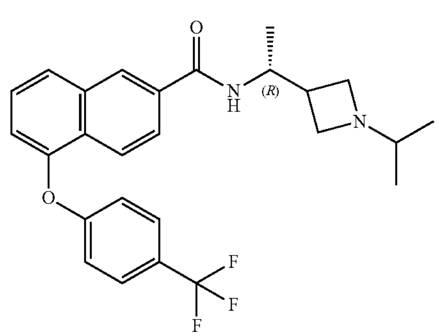 | (R)-N-(1-(1-isopropylazetidin-3-yl)ethyl)-5-(4-(trifluoromethyl)phenoxy)-2-naphthamide |

TABLE 1-continued

| Compound # | Structure | Name |
|---|---|---|
| 134 | 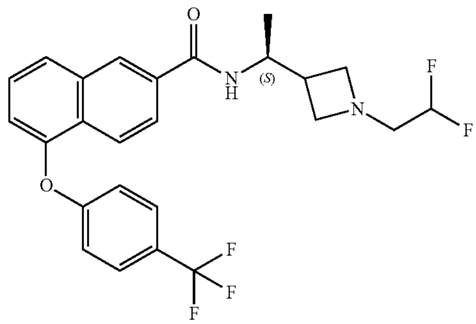 | (S)-N-(1-(1-(2,2-difluoroethyl)azetidin-3-yl)ethyl)-5-(4-(trifluoromethyl)phenoxy)-2-naphthamide |
| 135 | 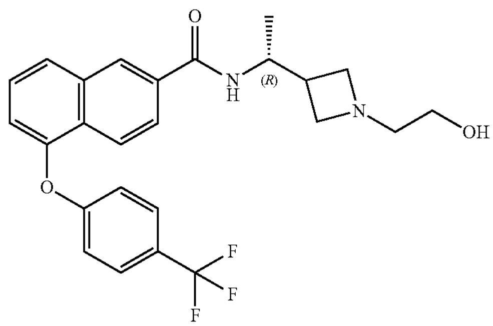 | (R)-N-(1-(1-(2-hydroxyethyl)azetidin-3-yl)ethyl)-5-(4-(trifluoromethyl)phenoxy)-2-naphthamide |
| 136 | 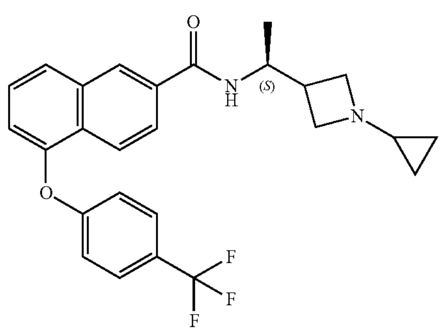 | (S)-N-(1-(1-cyclopropylazetidin-3-yl)ethyl)-5-(4-(trifluoromethyl)phenoxy)-2-naphthamide |
| 137 | 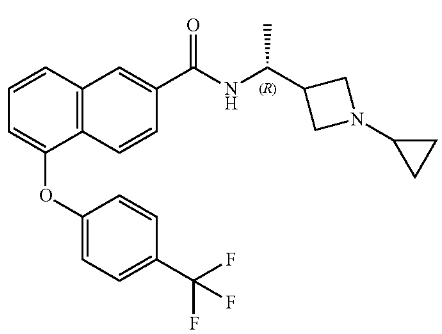 | (R)-N-(1-(1-cyclopropylazetidin-3-yl)ethyl)-5-(4-(trifluoromethyl)phenoxy)-2-naphthamide |

TABLE 1-continued

| Compound # | Structure | Name |
|---|---|---|
| 138 | 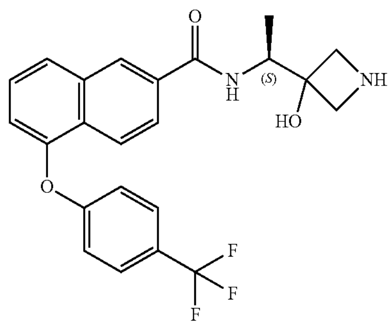 | (S)-N-(1-(3-hydroxyazetidin-3-yl)ethyl)-5-(4-(trifluoromethyl)phenoxy)-2-naphthamide |
| 139 | 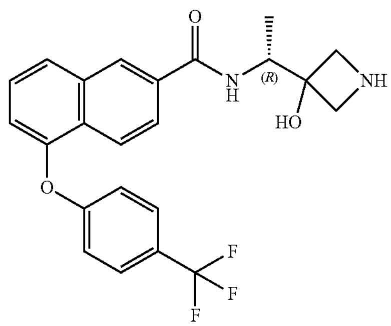 | (R)-N-(1-(3-hydroxyazetidin-3-yl)ethyl)-5-(4-(trifluoromethyl)phenoxy)-2-naphthamide |
| 140 | 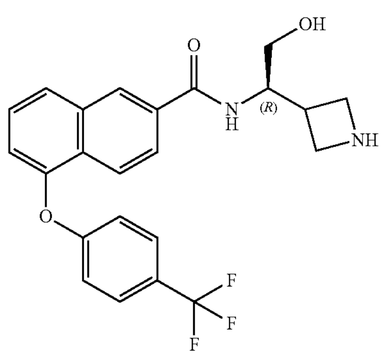 | (R)-N-(1-(azetidin-3-yl)-2-hydroxyethyl)-5-(4-(trifluoromethyl)phenoxy)-2-naphthamide |
| 141 | 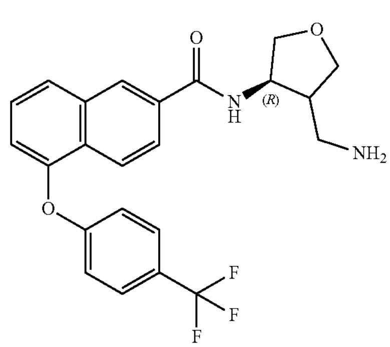 | N-((3R)-4-(aminomethyl)tetrahydrofuran-3-yl)-5-(4-(trifluoromethyl)phenoxy)-2-naphthamide |

TABLE 1-continued

| Compound # | Structure | Name |
|---|---|---|
| 142 | 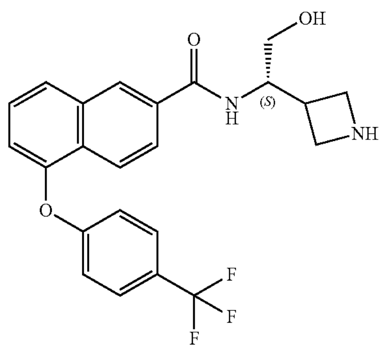 | (S)-N-(1-(azetidin-3-yl)-2-hydroxyethyl)-5-(4-(trifluoromethyl)phenoxy)-2-naphthamide |
| 143 | 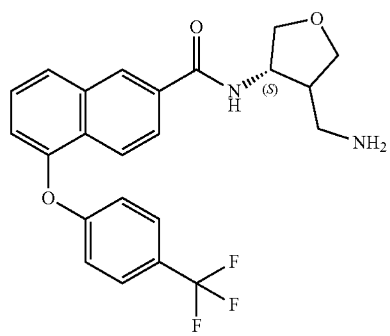 | N-((3S)-4-(aminomethyl)tetrahydrofuran-3-yl)-5-(4-(trifluoromethyl)phenoxy)-2-naphthamide |
| 144 | 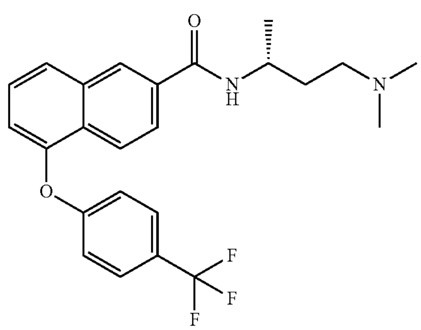 [SMILES: C[C@H](CCN(C)C)NC(=O)c1ccc2c(Oc3ccc(C(F)(F)F)cc3)cccc2c1] | (R)-N-(4-(dimethylamino)butan-2-yl)-5-(4-(trifluoromethyl)phenoxy)-2-naphthamide |
| 145 | 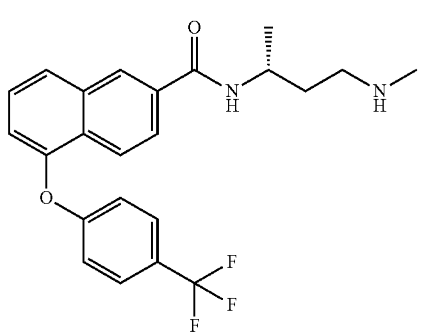 [SMILES: CNCC[C@@H](C)NC(=O)c1ccc2c(Oc3ccc(C(F)(F)F)cc3)cccc2c1] | (R)-N-(4-(methylamino)butan-2-yl)-5-(4-(trifluoromethyl)phenoxy)-2-naphthamide |

TABLE 1-continued

| Compound # | Structure | Name |
|---|---|---|
| 146 | 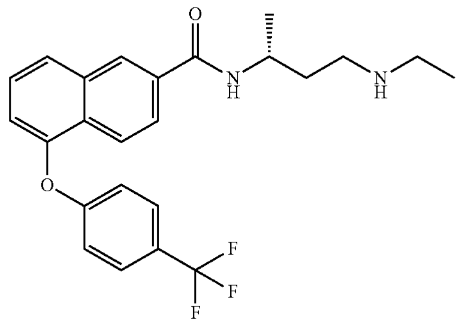 [SMILES: CCNCC[C@@H](C)NC(=O)c1ccc2c(Oc3ccc(C(F)(F)F)cc3)cccc2c1] | (R)-N-(4-(ethylamino)butan-2-yl)-5-(4-(trifluoromethyl)phenoxy)-2-naphthamide |
| 147 | 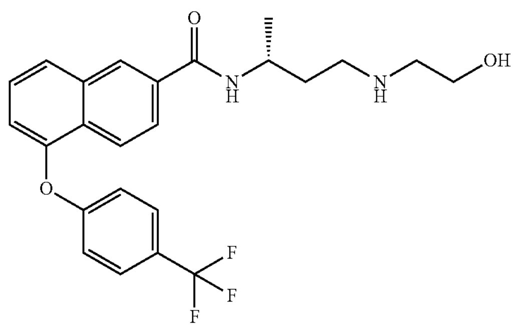 [SMILES: C[C@H](CCNCCO)NC(=O)c1ccc2c(Oc3ccc(C(F)(F)F)cc3)cccc2c1] | (R)-N-(4-((2-hydroxyethyl)amino)butan-2-yl)-5-(4-(trifluoromethyl)phenoxy)-2-naphthamide |
| 148 | 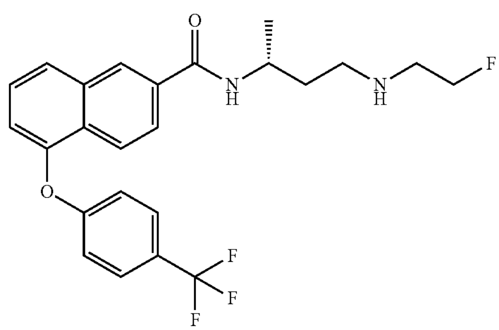 [SMILES: C[C@H](CCNCCF)NC(=O)c1ccc2c(Oc3ccc(C(F)(F)F)cc3)cccc2c1] | (R)-N-(4-((2-fluoroethyl)amino)butan-2-yl)-5-(4-(trifluoromethyl)phenoxy)-2-naphthamide |
| 149 | 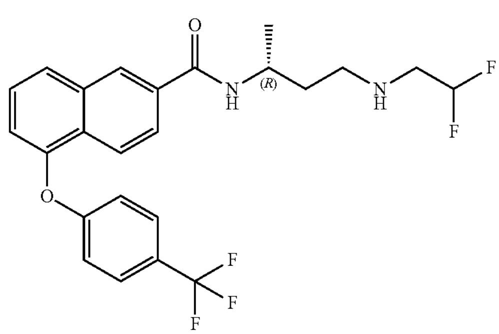 | (R)-N-(4-((2,2-difluoroethyl)amino)butan-2-yl)-5-(4-(trifluoromethyl)phenoxy)-2-naphthamide |

TABLE 1-continued

| Compound # | Structure | Name |
|---|---|---|
| 150 | 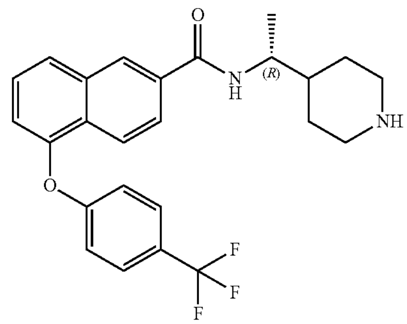 | (R)-N-(1-(piperidin-4-yl)ethyl)-5-(4-(trifluoromethyl)phenoxy)-2-naphthamide |
| 151 | 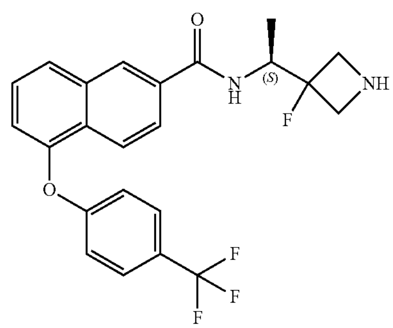 | (S)-N-(1-(3-fluoroazetidin-3-yl)ethyl)-5-(4-(trifluoromethyl)phenoxy)-2-naphthamide |
| 152 | 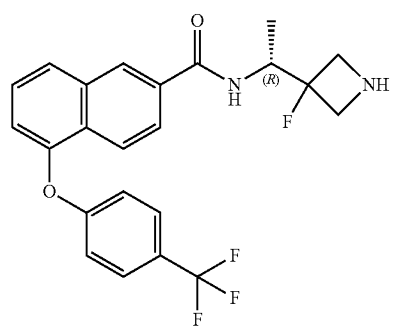 | (R)-N-(1-(3-fluoroazetidin-3-yl)ethyl)-5-(4-(trifluoromethyl)phenoxy)-2-naphthamide |
| 153 | 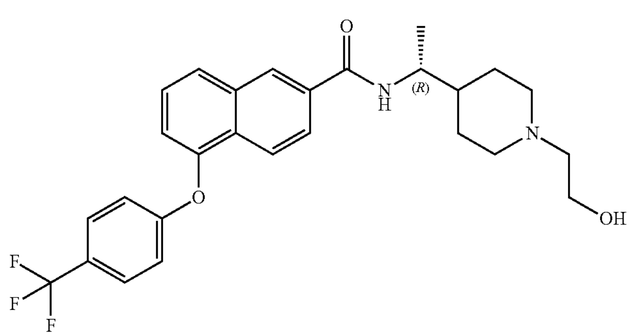 | (R)-N-(1-(1-(2-hydroxyethyl)piperidin-4-yl)ethyl)-5-(4-(trifluoromethyl)phenoxy)-2-naphthamide |

TABLE 1-continued

| Compound # | Structure | Name |
|---|---|---|
| 154 | 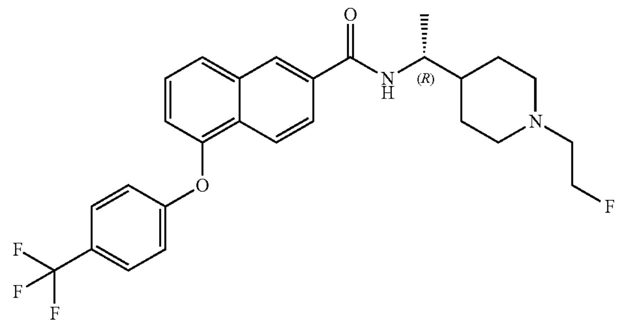 | (R)-N-(1-(1-(2-fluoroethyl)piperidin-4-yl)ethyl)-5-(4-(trifluoromethyl)phenoxy)-2-naphthamide |
| 155 | 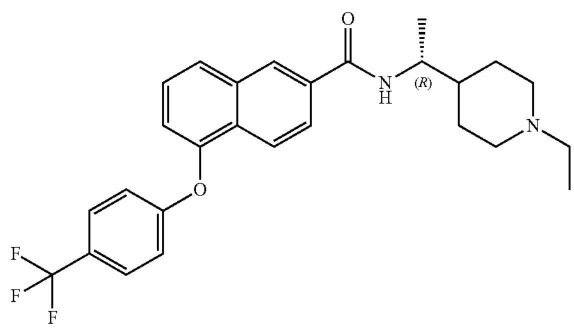 | (R)-N-(1-(1-ethylpiperidin-4-yl)ethyl)-5-(4-(trifluoromethyl)phenoxy)-2-naphthamide |
| 156 | 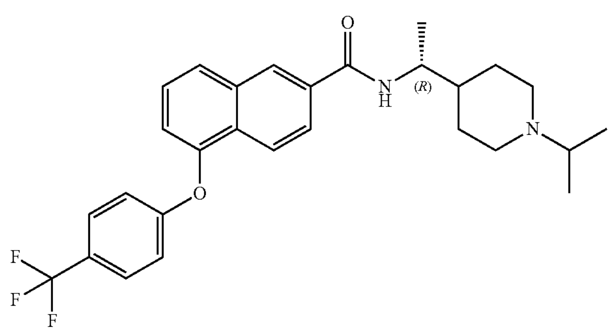 | (R)-N-(1-(1-isopropylpiperidin-4-yl)ethyl)-5-(4-(trifluoromethyl)phenoxy)-2-naphthamide |
| 157 | 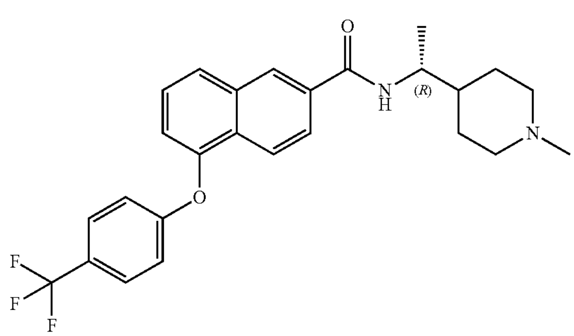 | (R)-N-(1-(1-methylpiperidin-4-yl)ethyl)-5-(4-(trifluoromethyl)phenoxy)-2-naphthamide |

TABLE 1-continued
| Compound # | Structure | Name |
|---|---|---|
| 158 | 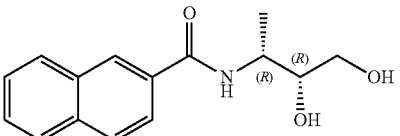 | N-((2R,3R)-3,4-dihydroxybutan-2-yl)-5-(4-(trifluoromethyl)phenoxy)-2-naphthamide |
| 159 | 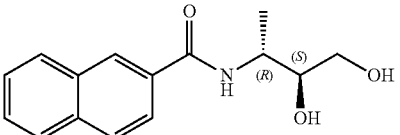 | N-((2R,3S)-3,4-dihydroxybutan-2-yl)-5-(4-(trifluoromethyl)phenoxy)-2-naphthamide |
| 160 | 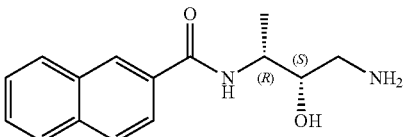 | N-((2R,3S)-4-amino-3-hydroxybutan-2-yl)-5-(4-(trifluoromethyl)phenoxy)-2-naphthamide |
| 161 | 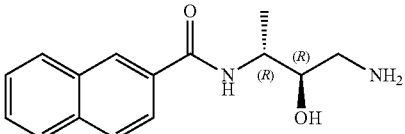 | N-((2R,3R)-4-amino-3-hydroxybutan-2-yl)-5-(4-(trifluoromethyl)phenoxy)-2-naphthamide |

TABLE 1-continued

| Compound # | Structure | Name |
|---|---|---|
| 162 | 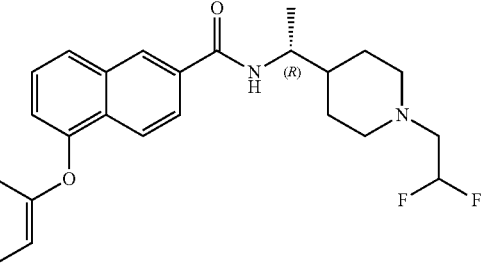 | (R)-N-(1-(1-(2,2-difluoroethyl)piperidin-4-yl)ethyl)-5-(4-(trifluoromethyl)phenoxy)-2-naphthamide |
| 163 | 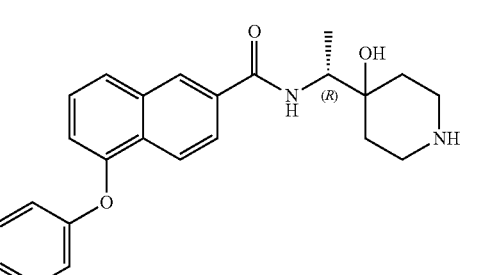 | (R)-N-(1-(4-hydroxypiperidin-4-yl)ethyl)-5-(4-(trifluoromethyl)phenoxy)-2-naphthamide |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CT), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972: T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, disclosed herein are dissociable complexes (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^{2}H$, $^{3}H$, $^{13}C$, $^{14}C$, $^{15}N$, $^{18}O$, $^{17}O$, $^{31}P$, $^{32}P$, $^{33}S$, $^{18}F$, and $^{36}Cl$, respectively. Compounds described herein, and the metabolites, pharmaceutically acceptable salts, esters, prodrugs, solvates, hydrates, or derivatives thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three, or four) amino acid residues is covalently joined through an amide or ester bond to a free amino, hydroxy, or carboxylic acid group of compounds of the present disclosure. The amino acid residues include, but are not limited to, the 20 naturally occurring amino acids and also includes 4-hydroxyproline, hydroxylysine, demosine, isodemosine, 3-methylhistidine, norvaline, beta-alanine, gamma-aminobutyric acid, citrulline, homocysteine, homoserine, ornithine, and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine, and carboxylic acid functionalities.

Hydroxy prodrugs include esters such as, though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to, the following groups and combinations of groups.

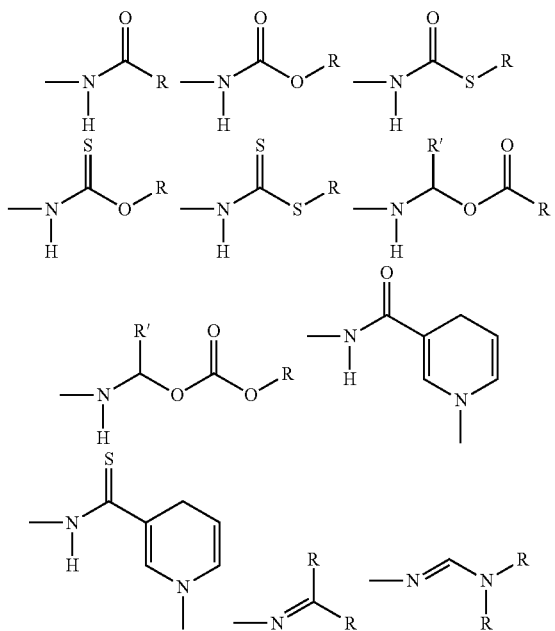

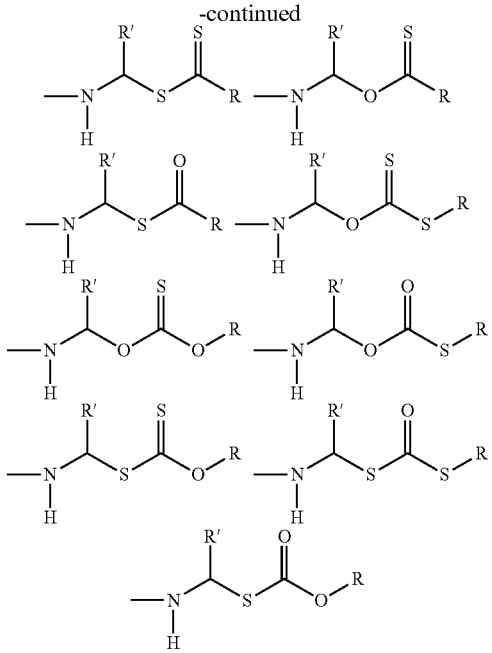

as well as sulfonamides and phosphonamides.

In certain instances, sites on any aromatic ring portions are susceptible to various metabolic reactions, therefore incorporation of appropriate substituents on the aromatic ring structures reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21st Ed. Mack Pub. Co., Easton, PA (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), Formula (II), or Formula (III), or a pharmaceutically acceptable salt or solvate thereof.

Another embodiment provides a pharmaceutical composition consisting essentially of a pharmaceutically acceptable carrier and a compound of Formula (I), Formula (II), or Formula (III), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butyleneglycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component is optionally mixed under sterile conditions with a pharmaceutically acceptable carrier, and with any preservatives, buffers, or propellants which are required in some embodiments.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure will recognize that it is not comprehensive and that there are other enteric materials that meet the objectives of the present disclosure.

In some embodiments, the doses of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1)(FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK 1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ atone or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes SCFV$^{\beta\text{-}TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxw1, hsSlimb, plkappaBalpha-E3 receptor subunit) and S-phase kinase-associated proteins 2 (SKP2). In some embodiments, the SCF complex (e.g. SCFP$^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1.

Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE21, UBE2.1, UBE2J2, UBE2K, UBE2L3, UBE2L6, UBE2M, UBE2N, UBE20, UBE2Q1, UBE2Q2, UBE2R1, UBE2R2, UBE2S, UBE2T, UBE2U, UBE2V1, UBE2V2, UBE2Z, AYG2, BIRC5, and UFC1. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
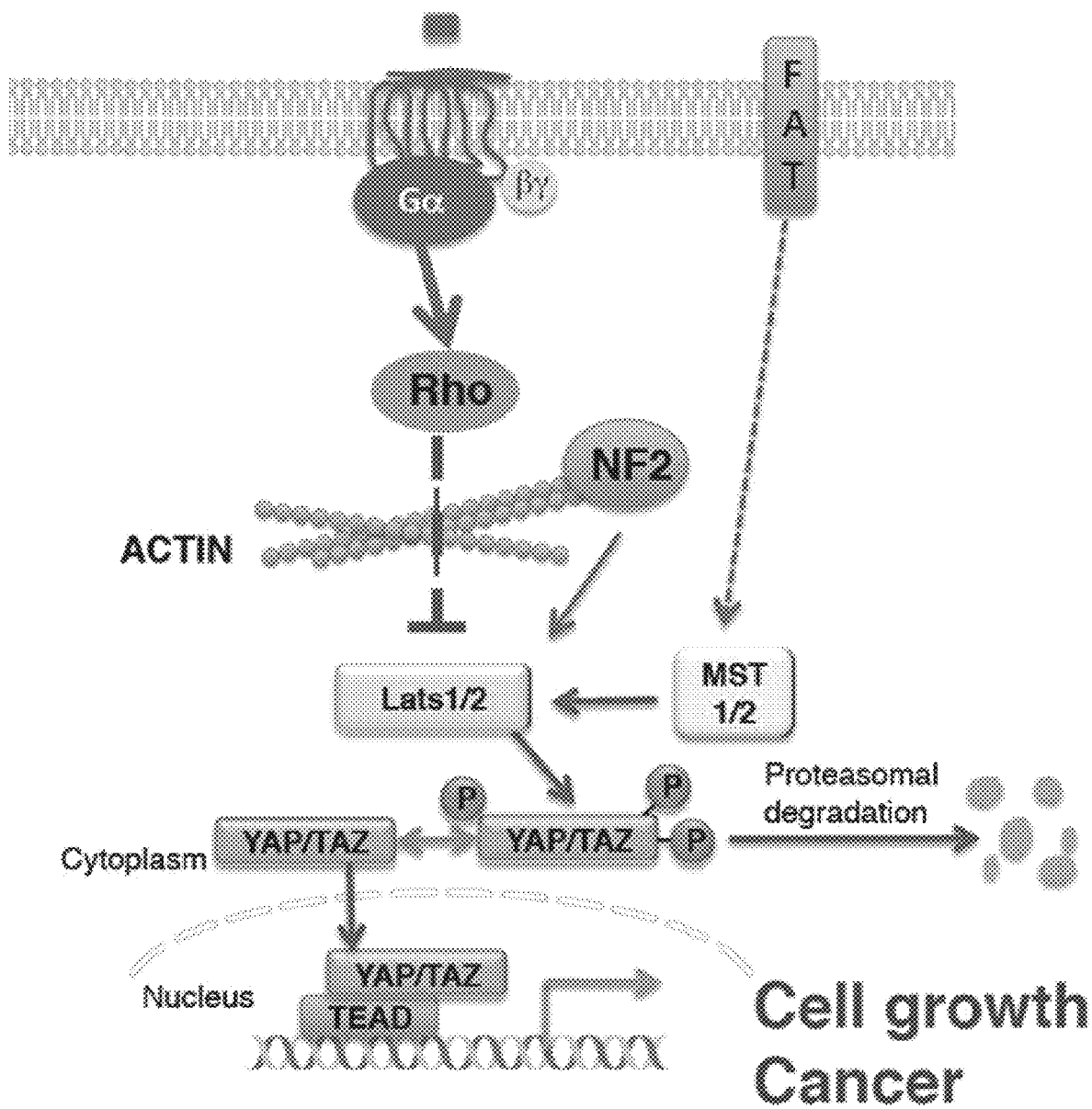
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $G_i\alpha$ (G inhibitory), $G_o\alpha$ (G other), $G_{q/11}\alpha$, and $G_{12/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q$a include, but are not limited to, 5-hydroxytryptamine receptor (5-HT receptor) types $5\text{-}HT_2$ and $5\text{-}HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12*13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g. $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g. $S1P_2$, $S1P_3$, $S1P_4$ and $S1P_5$); lysophosphatidic acid (e.g. $LPA_1$, $LPA_2$, $LPA_3$); angiotensin II (AT1); serotonin (5-$HT_{2c}$ and 5-$HT_4$): somatostatin (sst$_5$); endothelin ($ET_A$ and $ET_B$); cholecystokinin ($CCK_1$); $V_{1a}$ vasopressin receptors; DS dopamine receptors; fMLP formyl peptide receptors; $GAL_2$ galanin receptors; $EP_3$ prostanoid receptors; $A_1$ adenosine receptors; a, adrenergic receptors: $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{2/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other)(also known as $G_i/G_o$ or $G_i$ protein) suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types 5-HT, and 5-$HT_5$; muscarinic acetylcholine receptors such as $M_2$ and $M_4$, adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors sst1, sst2, sst3, sst4, and sst5; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$, and $G_z$. $G_i\alpha1$ is encoded by GNA1. $G_i\alpha2$ is encoded by GNA12. $G_i\alpha3$ is encoded by GNA13. $G_o\alpha$, the $a_o$ subunit, is encoded by GNAO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types 5-$HT_4$, 5-$HT_6$, and 5-$HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $\beta_1$, $\beta_2$, and $\beta_3$; calcitonin receptor; calcitonin gene-related peptide receptor; corticotropin-releasing hormone receptor; dopamine receptor $D_1$-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$ and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds of Formula (I), Formula (II), or Formula (III) disclosed herein are useful for treating cancer. In some embodiments, provided herein is a method for treating a cancer in a subject in need thereof comprising administering to the subject in need thereof a therapeutically effective amount of a compound disclosed herein or a pharmaceutically acceptable salt or solvate thereof. In some embodiments, provided herein is a compound for use in treating a cancer in a subject in need thereof comprising administering to the subject in need thereof a therapeutically effective amount of a compound disclosed herein or a pharmaceutically acceptable salt or solvate thereof. In some embodiments, provided herein is use of a compound disclosed herein or a pharmaceutically acceptable salt or solvate thereof in the manufacture of a medicament for treating cancer.

In some embodiments, the cancer is mediated by activation of transcriptional coactivator with PDZ binding motif/Yes-associated protein transcription coactivator (TAZ/YAP). In some embodiments, the cancer is mediated by modulation of the interaction of YAP/TAZ with TEAD. In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epithelioid cell differentiation, osteosarcoma, parosteal osteosarcoma, neoplasm with perivascular epithelioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, a hematologic malignancy is a leukemia, a lymphoma, a myeloma, a non-Hodgkin's lymphoma, a Hodgkin's lymphoma, a T-cell malignancy, or a B-cell malignancy. In some instances, a hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, a hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, a relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, a relapsed or refractory hematologic malignancy is a relapsed or refractory T-cell malignancy. In some instances, a relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is mesothelioma, hepatocellular carcinoma, meningioma, malignant peripheral nerve sheath tumor, Schwannoma, lung cancer, bladder carcinoma, cutaneous neurofibromas, prostate cancer, pancreatic cancer, glioblastoma, endometrial adenosquamous carcinoma, anaplastic thyroid carcinoma, gastric adenocarcinoma, esophageal adenocarcinoma, ovarian cancer, ovarian serous adenocarcinoma, melanoma, or breast cancer.

Non-Cancer Indications

In some embodiments, the compounds of Formula (I), Formula (II), or Formula (III) are useful for treating polycystic kidney disease. In some embodiments, the compounds of Formula (I), Formula (II), or Formula (III) are useful for treating liver fibrosis. In some embodiments, provided herein is a method for treating polycystic kidney disease in a subject in need thereof comprising administering to the subject in need thereof a therapeutically effective amount of a compound disclosed herein or a pharmaceutically acceptable salt or solvate thereof. In some embodiments, provided herein is a compound for use in treating polycystic kidney disease in a subject in need thereof comprising administering to the subject in need thereof a therapeutically effective amount of a compound disclosed herein or a pharmaceutically acceptable salt or solvate thereof. In some embodiments, provided herein is use of a compound disclosed herein or a pharmaceutically acceptable salt or solvate thereof in the manufacture of a medicament for treating polycystic kidney disease. In some embodiments, provided herein is a method for treating liver fibrosis in a subject in need thereof comprising administering to the subject in need thereof a therapeutically effective amount of a compound disclosed herein or a pharmaceutically acceptable salt or solvate thereof. In some embodiments, provided herein is a compound for use in treating liver fibrosis in a subject in need thereof comprising administering to the subject in need thereof a therapeutically effective amount of a compound disclosed herein or a pharmaceutically acceptable salt or solvate thereof. In some embodiments, provided herein is use of a compound or a pharmaceutically acceptable salt or solvate thereof disclosed herein in the manufacture of a medicament for treating liver fibrosis. Congenital Diseases In some embodiments, the compounds of Formula (I), Formula (II), or Formula (III) are useful for treating a congenital disease. In some embodiments, provided herein is a method for treating congenital disease in a subject in need thereof comprising administering to the subject in need thereof a therapeutically effective amount of a compound disclosed herein or a pharmaceutically acceptable salt or solvate thereof. In some embodiments, provided herein is a compound for use in treating congenital disease in a subject in need thereof comprising administering to the subject in need thereof a therapeutically effective amount of a compound disclosed herein or a pharmaceutically acceptable salt or solvate thereof. In some embodiments, provided herein is use of a compound disclosed herein or a pharmaceutically acceptable salt or solvate thereof in the manufacture of a medicament for treating congenital disease. In some embodiments, the congenital disease is mediated by activation of transcriptional coactivator with PDZ binding motif/Yes-associated protein transcription coactivator (TAZ/YAP). In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is $G_s$.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase deficiency, myasthenia gravis, neural tube defects, phenylketonuria, Pompe disease, severe combined immunodeficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

List of Abbreviations

As used above, and throughout the disclosure, the following abbreviations, unless otherwise indicated, shall be understood to have the following meanings:
ACN or MeCN acetonitrile
Ac acetyl
BOC or Boc tert-butyl carbamate
t-Bu tert-butyl
° C. degrees Celsius
DAST diethylaminosulfur trifluoride
DBA or dba dibenzylideneacetone
DCE dichloroethane ($CCH_2CH_2Cl$)
DCM dichloromethane ($CH_2Cl_2$)
DIPEA or DIEA diisopropylethylamine
DMF dimethylformamide
DMSO dimethylsulfoxide
Dppf or dppf 1,1'-bis(diphenylphosphino)ferrocene
EA or EtOAc ethyl acetate
Et ethyl
EtOH ethanol
g gram(s)
h, hr, hrs hour(s)
HATU 1-[bis(dimethylamino)methylene]-1H-1,2,3-triazolo[4,5-b]pyridinium 3-oxid hexafluorophosphate
HPLC high performance liquid chromatography
Hz hertz
LAH lithium aluminum anhydride
LCMS liquid chromatography mass spectrometry
m/z mass-to-charge ratio
M molar
Me methyl
MeOH methanol
mg milligram(s)
MHz megahertz
umol micromole(s)
uL microliter(s)
mL milliliter(s)
mmol millimole(s)
MS mass spectroscopy
NMR nuclear magnetic resonance
PE petroleum ether
Ph phenyl
prep-HPLC preparative high pressure liquid chromatography
prep-TLC preparative thin layer chromatography
Py pyridine
RT retention time
TEA triethylamine
TFA trifluoroacetic acid
THF tetrahydrofuran
TLC thin layer chromatography
XPhos 2-dicyclohexylphosphino-2',4',6'-triisopropylbiphenyl 1. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were not optimized. Column chromatography and thin layer chromatography (TLC) were performed on silica gel unless otherwise noted. In some embodiments, in case of a discrepancy between a reaction scheme and a written procedure, the written procedure should be followed.

Example 1:
5-(4-chlorophenoxy)-N-isopropyl-2-naphthamide
(Compound 1)

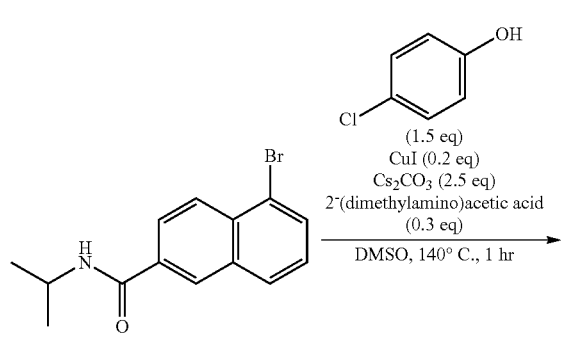

Compound 1

A mixture of 5-bromo-N-isopropyl-naphthalene-2-carboxamide (0.15 g, 0.51 mmol, 1 eq), 4-chlorophenol (99.0 mg, 0.77 mmol, 75.6 uL, 1.5 eq), CuI (19.5 mg, 0.10 mmol, 0.2 eq), $Cs_2CO_3$ (418.2 mg, 1.28 mmol, 2.5 eq) and 2-(dimethylamino)acetic acid (15.9 mg, 0.15 mmol, 0.3 eq) in DMSO (2 mL) was degassed and purged with $N_2$ for 3 times, and then the mixture was stirred at 140° C. for 1 hr under $N_2$ atmosphere under microwave. $H_2O$ (8 mL) was added to the solution. The mixture was extracted with ethyl acetate (15 mL*3). The combined organic layers were washed with brine (25 mL*2), dried over anhydrous $Na_2SO_4$, filtered and concentrated in vacuum. The residue was purified by prep-HPLC. Compound 5-(4-chlorophenoxy)-N-isopropyl-naphthalene-2-carboxamide (14.5 mg, 42.6 umol, 8.3% yield) was obtained. LCMS (ESI): RT=0.877 min, mass calc. for $C_{20}H_{18}ClNO_2$ 339.10, m/z found 339.9 $[M+H]^+$; $^1H$ NMR (400 MHz, $CDOD_3$) δ 8.36 (d, J=1.5 Hz, 1H), 8.13 (d, J=8.8 Hz, 1H), 7.85 (dd, J=1.8, 8.8 Hz, 1H), 7.75 (d, J=8.3 Hz, 1H), 7.46 (t, J=8.0 Hz, 1H), 7.34-7.30 (m, 2H), 7.03-6.96 (m, 3H), 4.23 (s, 1H), 1.25 (d, J=6.5 Hz, 7H).

Example 2:
5-(3-chlorophenoxy)-N-isopropyl-2-naphthamide
(Compound 2)

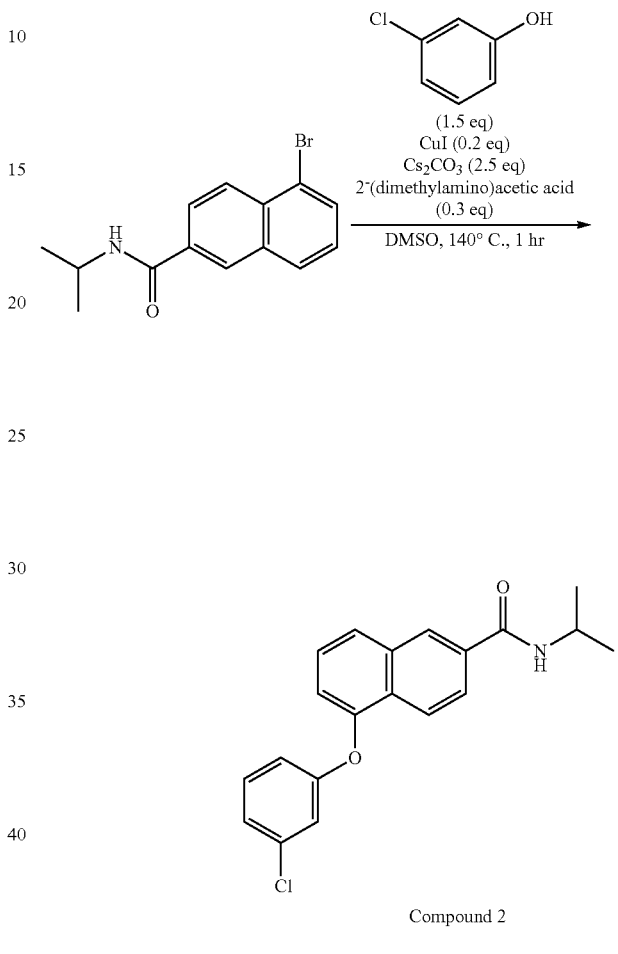

Compound 2

A mixture of 5-bromo-N-isopropyl-naphthalene-2-carboxamide (0.15 g, 0.51 mmol, 1 eq), 3-chlorophenol (99.0 mg, 0.77 mmol, 81.1 uL, 1.5 eq), CuI (19.6 mg, 0.10 mmol, 0.2 eq), $Cs_2CO_3$ (418.2 mg, 1.28 mmol, 2.5 eq) and 2-(dimethylamino)acetic acid (15.9 mg, 0.15 mmol, 0.3 eq) in DMSO (2 mL) was degassed and purged with $N_2$ for 3 times, and then the mixture was stirred at 140° C. for 1 hr under $N_2$ atmosphere under microwave. $H_2O$ (8 mL) was added to the solution. The mixture was extracted with ethyl acetate (15 mL*3). The combined organic layers were washed with brine (25 mL*2), dried over anhydrous $Na_2SO_4$, filtered and concentrated in vacuum. The residue was purified by prep-HPLC. Compound 5-(3-chlorophenoxy)-N-isopropyl-naphthalene-2-carboxamide (13.5 mg, 39.9 umol, 7.7% yield) was obtained. LCMS (ESI): RT=0.873 min, mass calc. for $C_{20}H_{18}ClNO_2$ 339.10, m/z found 339.9 $[M+H]^+$; $^1H$ NMR (400 MHz, $CDOD_3$) δ 8.42 (d, J=1.3 Hz, 1H), 8.13 (d, J=8.8 Hz, 1H), 7.92-7.81 (m, 2H), 7.54 (t, J=8.0 Hz, 1H), 7.38-7.30 (m, 1H), 7.16-7.10 (m, 2H), 7.01 (t, J=2.1 Hz, 1H), 6.95 (dd, J=1.8, 8.3 Hz, 1H), 4.35-4.21 (m, 1H), 1.30 (d, J=6.5 Hz, 6H).

Example 3: 5-(3,4-dichlorophenoxy)-N-isopropyl-naphthalene-2-carboxamide (Compound 3)

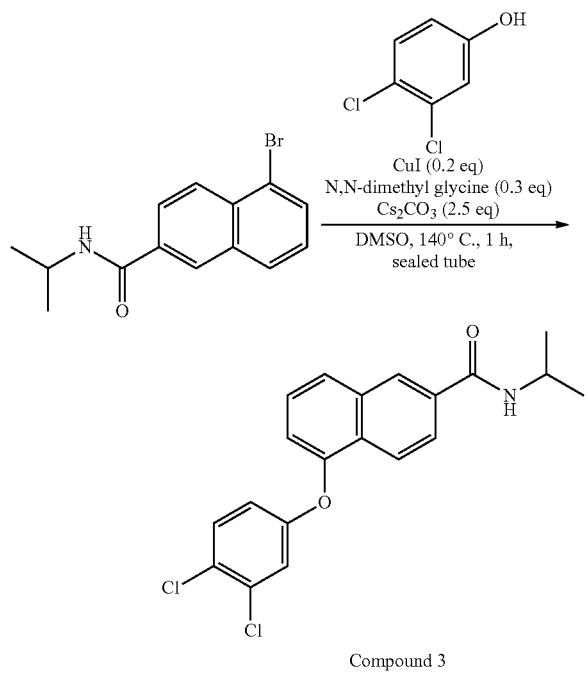

Compound 3

A mixture of compound 5-bromo-N-isopropyl-2-naphthamide (140 mg, 0.5 mmol, 1 eq), compound 3,4-dichlorophenol (117.2 mg, 0.7 mmol, 27.1 uL, 1.5 eq), CuI (18.3 mg, 95.8 umol, 0.2 eq), $Cs_2CO_3$ (390.3 mg, 1.2 mmol, 2.5 eq) and N, N-dimethyl glycine (14.8 mg, 0.1 mmol, 0.3 eq) were taken up into microwave tube in DMSO (3 mL). The sealed tube was heated at 140° C. for 1 hr under microwave. The residue was poured into $H_2O$ (50 mL) and stirred for 5 min. The aqueous phase was extracted with EA (20 mL*3). The combined organic phase was washed with brine (50 mL), dried with anhydrous $Na_2SO_4$, filtered and concentrated in vacuum. The residue was purified by prep-HPLC to give the title compound (58.6 mg, 0.2 mmol, 32.7% yield). LCMS (ESI). RT=0.920 min, mass calc. for $C_{20}H_{17}Cl_2NO_2$ 373.1.1, m/z found 373.9 [M+H]$^+$; $^1$H NMR (400 MHz, DMSO-d$_6$) δ 8.64-8.36 (m, 2H), 8.16-7.84 (m, 3H), 7.61 (d, J=12.3 Hz, 2H), 7.37 (s, 1H), 7.22 (s, 1H), 7.01 (d, J=5.8 Hz, 1H), 4.15 (s, 1H), 1.20 (d, J=5.8 Hz, 6H).

Example 4: N-isopropyl-5-(4-(trifluoromethyl)phenoxy)-2-naphthamide (Compound 4)

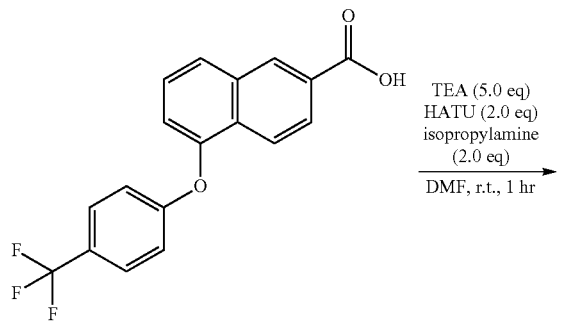

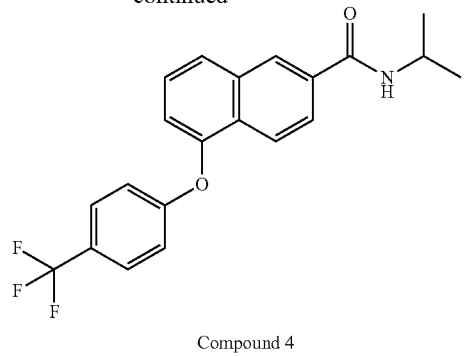

Compound 4

To a solution of 5-[4-(trifluoromethyl)phenoxy]naphthalene-2-carboxylic acid (0.1, 0.30 mmol, 1 eq) in DMF (2 mL) was added HATU (228.8 mg, 0.60 mmd, 2 eq) and TEA (152.2 mg, 1.50 mmol, 0.20 mL, 5 eq). The mixture was stirred for 0.5 hrs at 25° C. Iso-propylamine (35.5 mg 0.60 mmol, 51.7 uL, 2 eq) was added to the mixture and the mixture was stirred for 0.5 hr at 25° C. The mixture was quenched by $H_2O$ (30 mL), and the mixture was extracted with EA (20 mL*3). The combined organic phase was washed with brine (20 mL*3), dried with anhydrous $Na_2SO_4$, filtered and concentrated in vacuum. The residue was purified by prep-HPLC (column: Xtimate C18 150*25 mm*5 um; mobile phase: [water (0.05% HCl)-ACN]; B %: 60%-90%, 9.5 min) to give the title compound (13.26 mg, 35.5 umol, 11.8% yield). LCMS(ESI): RT=0.881 min, mass calc. for: $C_{21}H_{18}F_3NO_2$ 373.37, m/z found 373.9: $^1$H NMR (400 MHz, METHANOL-d4) Shift=8.45 (d, J=1.5 Hz, 1H), 8.10 (d, J=8.9 Hz, 1H), 7.91 (d, J=8.7 Hz, 2H), 7.71-7.64 (m, J=8.5 Hz, 2H), 7.59 (t, J=7.9 Hz, 1H), 7.23 (dd, J=0.8, 7.6 Hz, 1H), 7.18-7.12 (m, J=8.6 Hz, 2H), 4.34-4.24 (m, 1H), 1.31 (d, J=6.6 Hz, 6H).

Example 5: N-(methylsulfonyl)-5-(4-(trifluoromethyl)phenoxy)-2-naphthamide (Compound 5)

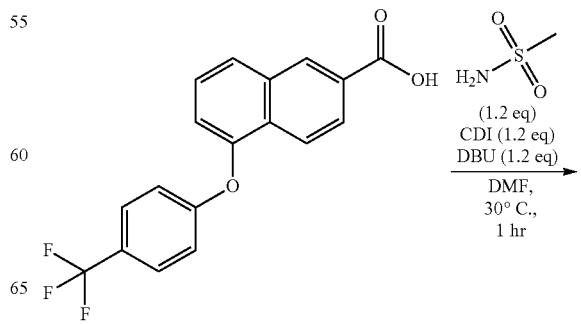

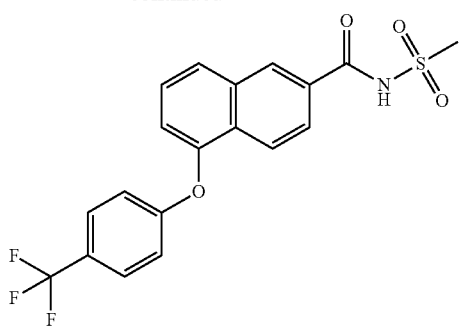

Compound 5

To a solution of 5-[4-(trifluoromethyl)phenoxy]naphthalene-2-carboxylic acid (0.05 g 0.15 mmol, 1 eq) in DMF (2 mL) was added CDI (29.2 mg, 0.18 mmol, 1.2 eq). The mixture was stirred for 0.5 hrs at 30° C. Methanesulfonamide (17.1 mg, 0.18 mmol, 1.2 eq) and DBU (27.4 mg, 0.18 mmol, 27.2 uL, 1.2 eq) was added to the mixture and the mixture was stirred for 0.5 hr at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC to give the title compound (8.3 mg, 20.3 umol, 13.5% yield). ¹H NMR (400 MHz, METHANOL-d4) Shift=8.59 (d, J=1.6 Hz, 1H), 8.18 (d, J=8.9 Hz, 1H), 7.97 (t, J=7.6 Hz, 2H), 7.73-7.62 (m, 3H), 7.30 (d, J=7.4 Hz, 1H), 7.17 (d, J=8.6 Hz, 2H), 3.43 (s, 3H).

Example 6: 5-(3,4-dichlorophenoxy)-N-(methylsulfonyl)-2-naphthamide (Compound 6)

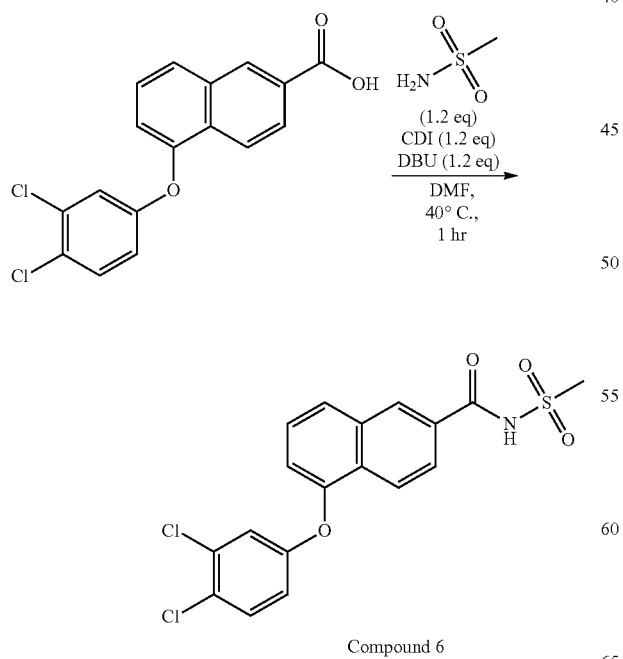

Compound 6

To a solution of 5-(3,4-dichlorophenoxy)naphthalene-2-carboxylic acid (50.1 mg, 0.15 mmol, 1 eq) in DMF (2 mL) was added DBU (27.4 mg, 0.18 mmol, 27.2 uL, 1.2 eq). The mixture was stirred for 0.5 hrs at 40° C. Methanesulfonamide (17.1 mg, 0.18 mmol, 1.2 eq) and CDI (29.2 mg, 0.18 mmol, 1.2 eq) was added to the mixture and the mixture was stirred for 0.5 hr at 25° C. H₂O (6 mL) was added to the solution. The mixture was extracted with ethyl acetate (10 mL*3). The combined organic layers were washed with brine (15 mL*2), dried over anhydrous Na₂SO₄, filtered and concentrated in vacuum. The residue was purified by prep-HPLC to give the title compound (9.1 mg, 21.6 umol, 14.3% yield). LCMS(ESI): RT=0.881 min, mass calc. for $C_{18}H_{13}Cl_2NO_4S$ 410.27, m/z found 409.8 [M+H]⁺; ¹H NMR (400 MHz, DMSO-de) δ=12.34 (br s, 1H), 8.68 (s, 1H), 8.09 (d, J=8.8 Hz, 1H), 8.00-7.91 (m, 2H), 7.65-7.58 (m, 2H), 7.38 (d, J=2.7 Hz, 1H), 7.27 (d, J=7.6 Hz, 1H), 7.01 (dd, J=2.8, 8.9 Hz, 1H), 3.39 (s, 3H).

Example 7: N-methyl-5-(4-(trifluoromethyl)phenoxy)naphthalene-2-sulfonamide (Compound 7)

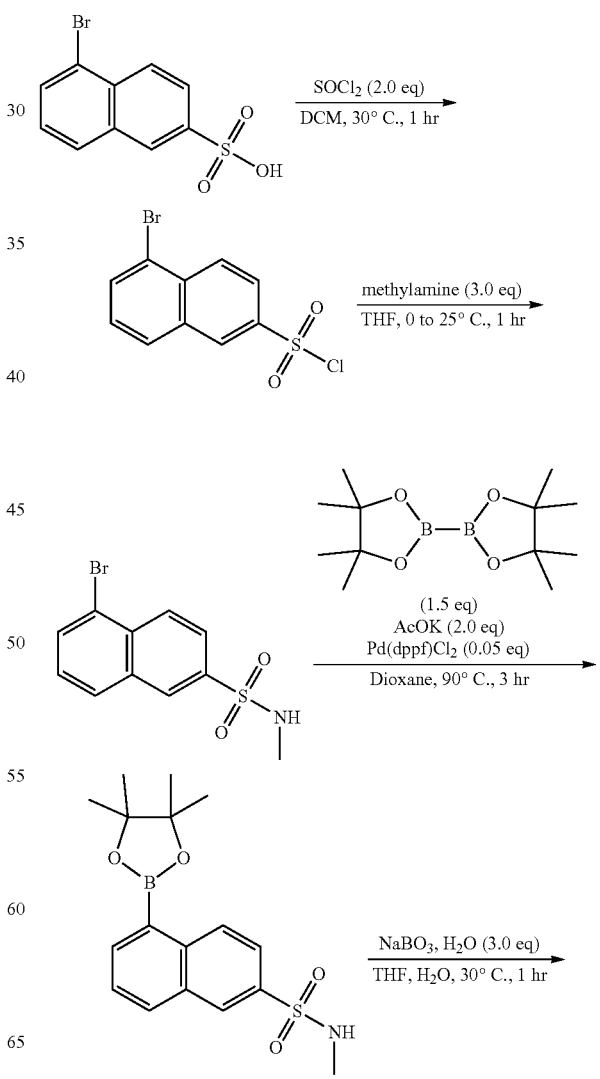

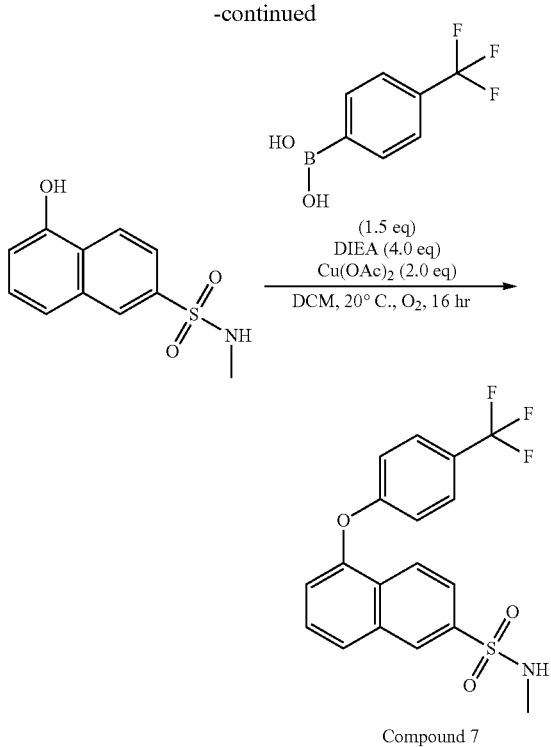

Compound 7

5-bromonaphthalene-2-sulfonyl Chloride

The mixture of 5-bromonaphthalene-2-sulfonic acid (900 mg, 3.13 mmol, 1 eq) and $SOCl_2$ (745.8 mg, 6.27 mmol, 0.45 mL, 2 eq) in DMF (2 mL) was stirred at 30° C. for 1 hr. The reaction mixture was diluted with $H_2O$ (5 mL) and the mixture was extracted with EA (15 mL*3). The combined organic phase was washed with brine (10 mL*6), dried with anhydrous $Na_2SO_4$, filtered and concentrated in vacuum. The residue was purified by silica gel column chromatography. Compound 5-bromonaphthalene-2-sulfonyl chloride (800 mg, 2.62 mmol, 83.5% yield) was obtained.

5-bromo-N-methylnaphthalene-2-sulfonamide

Methylamine (2 M, 3.93 mL, 3 eq) was added at the mixture of 5-bromonaphthalene-2-sulfonyl chloride (800 mg, 2.62 mmol, 1 eq) in THF (1 mL) dropwise at 0° C. Then the mixture was stirred at 25° C. for 1 hr. The reaction mixture was diluted with $H_2O$ (10 mL) and the mixture was extracted with EA (30 mL*3). The combined organic phase was washed with brine (20 mL*3), dried with anhydrous $Na_2SO_4$, filtered and concentrated in vacuum. The residue was purified by silica gel column chromatography. Compound 5-bromo-N-methyl-naphthalene-2-sulfonamide (600 mg, 2.00 mmol, 76.3% yield) was obtained.

N-methyl-5-(4,4,5,5-tetramethyl-1,3,2-dioxaborolan-2-yl)naphthalene-2-sulfonamide The mixture of 5-bromo-N-methyl-naphthalene-2-sulfonamide (400 mg, 1.33 mmol, 1 eq), 4,4,5,5-tetramethyl-2-(4,4,5,5-tetramethyl-1,3,2-dioxaborolan-2-yl)-1,3,2-dioxaborolane (507.5 mg, 2.00 mmol, 1.5 eq), AcOK (261.5 mg, 2.67 mmd, 2 eq) and $Pd(dppf)Cl_2$ (48.7 mg, 66.6 umol, 0.05 eq) in dioxane (3 mL) was degassed and purged with $N_2$ for 3 times, and then the mixture was stirred at 90° C. for 3 hr under $N_2$ atmosphere. The reaction mixture was diluted with $H_2O$ (10 mL) and the mixture was extracted with EA (10 mL*3). The combined organic phase was washed with brine (10 mL*3), dried with anhydrous $Na_2SO_4$, filtered and concentrated in vacuum. The residue was purified by silica gel column chromatography. Compound N-methyl-5-(4,4,5,5-tetramethyl-1,3,2-dioxaborolan-2-yl)naphthalene-2-sulfonamide (350 mg, 1.01 mmol, 75.6% yield) was obtained.

5-hydroxy-N-methylnaphthalene-2-sulfonamide

The mixture of N-methyl-5-(4,4,5,5-tetramethyl-1,3,2-dioxaborolan-2-yl)naphthalene-2-sulfonamide (350 mg, 1.01 mmol, 1 eq) and sodium; 3-oxidodioxaborirane tetrahydrate (465.2 mg, 3.02 mmol, 0.58 mL, 3 eq) in THF (2 mL) and $H_2O$ (1 mL) was stirred at 30° C. for 1 hr. The reaction mixture was diluted with $H_2O$ (10 mL) and the mixture was extracted with EA (10 mL*3). The combined organic phase was washed with brine (10 mL*3), dried with anhydrous $Na_2SO_4$, filtered and concentrated in vacuum. Compound 5-hydroxy-N-methyl-naphthalene-2-sulfonamide (250 mg, crude) was obtained, which was used into the next step without further purification.

N-methyl-5-(4-(trifluoromethyl)phenoxy)naphthalene-2-sulfonamide

The mixture of 5-hydroxy-N-methyl-naphthalene-2-sulfonamide (100 mg, 0.42 mmol, 1 eq), [4-(trifluoromethyl)phenyl]boronic acid (120.0 mg, 0.63 mmol, 1.5 eq), DIEA (217.8 mg, 1.69 mmol, 0.29 mL, 4 eq) and $Cu(OAc)_2$ (153.1 mg, 0.84 mmol, 2 eq) in DCM (5 mL) was degassed and purged with $O_2$ for 3 times, and then the mixture was stirred at 20° C. for 16 hr under $O_2$ atmosphere. The reaction mixture was diluted with $H_2O$ (10 mL) and the mixture was extracted with EA (10 mL*3). The combined organic phase was washed with brine (10 mL*3), dried with anhydrous $Na_2SO_4$, filtered and concentrated in vacuum. The residue was purified by prep-HPLC to give the title compound (20 mg, 51.9 umol, 12.3% yield). LCMS (ESI): RT=0.828 min, mass calc. for $C_{18}H_{14}F_3NO_3S$ 381.37, m/z found 382.06 $[M+H]^+$; $^1H$ NMR (400 MHz, METHANOL-$d_4$) δ=8.51 (d, J=1.5 Hz, 1H), 8.26 (d, J=8.8 Hz, 1H), 7.97 (d, J=8.3 Hz, 1H), 7.88 (dd, J=1.8, 8.8 Hz, 1H), 7.72-7.65 (m, 3H), 7.31 (d, J=7.0 Hz, 1H), 7.18 (d, J=8.8 Hz, 2H), 2.58 (s, 3H).

Example 8: 5-(3,4-difluorophenoxy)-N-isopropyl-2-naphthamide (Compound 8)

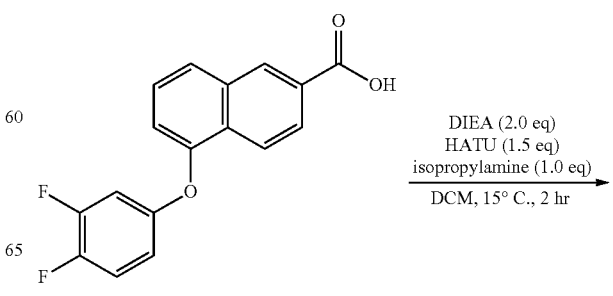

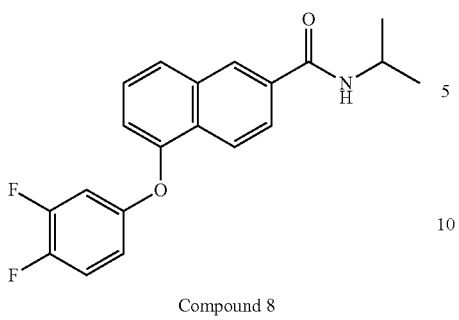

Compound 8

To a solution of 5-(3,4-difluorophenoxy)naphthalene-2-carboxylic acid (70 mg, 0.23 mmol, 1 eq) in DCM (1.5 mL) was added HATU (132.9 mg, 0.34 mmol, 1.5 eq). The mixture was stirred at 15° C. for 1 hr. DIEA (60.2 mg, 0.46 mmol, 81.2 uL, 2 eq) and iso-propylamine (13.7 mg, 0.23 mmol, 20.0 uL, 1 eq) was added to the solution. The reaction was stirred at 15° C. for 1 hr. H$_2$O (6 mL) was added to the solution. The mixture was extracted with ethyl acetate (10 mL*3). The combined organic layers were washed with brine (15 mL*2), dried over anhydrous Na$_2$SO$_4$, filtered and concentrated in vacuum. The residue was purified by prep-HPLC to give the title compound (10.5 mg, 30.8 umol, 13.2% yield). LCMS (ESI): RT=0.847 min, mass calc. for C$_{20}$H$_{17}$F$_2$NO$_2$ 341.35, m/z found 341.9 [M+H]$^+$; $^1$H NMR (400 MHz, DMSO-d$_6$) δ=8.51 (s, 1H), 8.48-8.43 (m, 1H), 8.11 (d, J=8.8 Hz, 1H), 7.98 (dd, J=1.4, 8.9 Hz, 1H), 7.87 (d, J=8.3 Hz, 1H), 7.56 (t, J=7.9 Hz, 1H), 7.52-7.42 (m, 1H), 7.36-7.27 (m, 1H), 7.15-7.09 (m, 1H), 6.94-6.86 (m, 1H), 4.16 (qd, J=6.8, 13.7 Hz, 1H), 1.22 (d, J=6.5 Hz, 6H).

Example 9: 5-(3,4-dichlorophenoxy)-N-methylnaphthalene-2-sulfonamide (Compound 9)

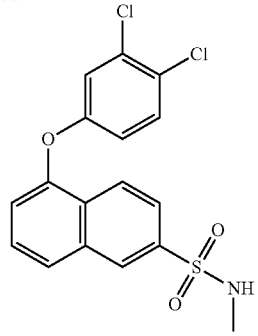

Compound 9

A mixture of 5-hydroxy-N-methyl-naphthalene-2-sulfonamide (80 mg, 0.33 mmol, 1 eq), (3,4-dichlorophenyl)boronic acid (96.5 mg, 0.50 mmol, 1.5 eq), Cu(OAc)$_2$ (122.4 mg, 0.67 mmol, 2 eq), DIEA (174.3 mg, 1.35 mmol, 0.23 mL, 4 eq) in DCM (3 mL) was degassed and purged with O$_2$ for 3 times, and then the mixture was stirred at 25° C. for 16 hr under O$_2$ atmosphere. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC to give the title compound (5 mg, 12.8 umol, 3.8% yield). $^1$H NMR (400 MHz, METHANOL-d$_4$) δ=8.50 (d, J=1.5 Hz, 1H), 8.29 (d, J=9.0 Hz, 1H), 7.94 (d, J=8.5 Hz, 1H), 7.89 (dd, J=1.8, 9.0 Hz, 1H), 7.65 (t, J=8.0 Hz, 1H), 7.54 (d, J=8.8 Hz, 1H), 7.26-7.22 (m, 2H), 7.01 (dd, J=2.8, 8.8 Hz, 1H), 2.58 (s, 3H).

Example 10: 5-(3,4-difluorophenoxy)-N-(methylsulfonyl)-2-naphthamide (Compound 10)

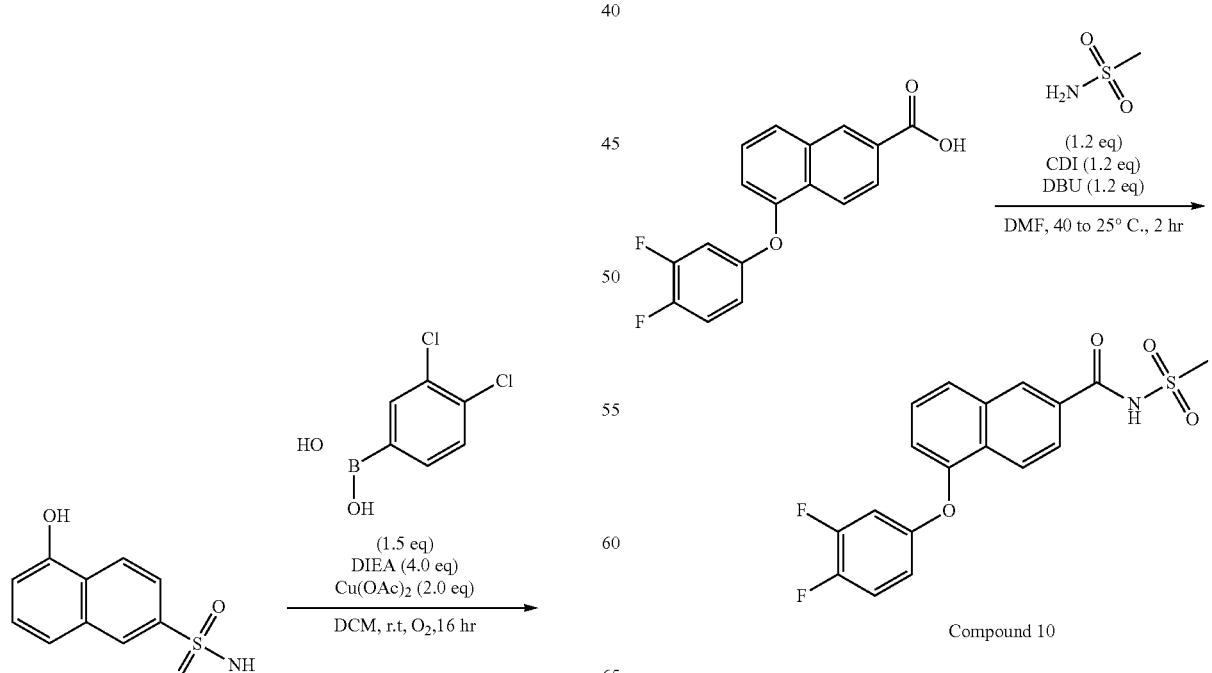

Compound 10

To a solution of 5-(3,4-difluorophenoxy)naphthalene-2-carboxylic acid (70 mg, 0.23 mmol, 1 eq) in DMF (2 mL)

was added CDI (45.3 mg, 0.27 mmol, 1.2 eq). The mixture was stirred at 40° C. for 1 hr. DBU (42.5 mg, 0.27 mmol, 42.1 uL, 1.2 eq) and methanesulfonamide (26.6 mg, 0.27 mmol, 1.2 eq) was added to the solution. The mixture was stirred at 25° C. for 1 hr. H₂O (5 mL) was added to the solution. The mixture was extracted with ethyl acetate (8 mL*3). The combined organic layers were washed with brine (12 mL*2), dried over anhydrous Na₂SO₄, filtered and concentrated in vacuum. The residue was purified by prep-HPLC to give the title compound (5.9 mg, 15.6 umol, 6.7% yield). LCMS (ESI): RT=0.808 min, mass calc. for C₁₈H₁₃F₂NO₄S 377.36, m/z found 377.8; ¹H NMR (400 MHz, DMSO-d₆) δ=8.56 (s, 1H), 8.11 (dd, J=1.3, 8.8 Hz, 1H), 8.00 (d, J=8.8 Hz, 1H), 7.85 (d, J=8.3 Hz, 1H), 7.52-7.42 (m, 2H), 7.35-7.26 (m, 1H), 7.04 (d, J=7.5 Hz, 1H), 6.89 (br s, 1H), 2.90 (s, 3H).

Example 11: N-isopropyl-1-[4-(trifluoromethyl)phenoxy]isoquinoline-6-carboxamide (Compound 11)

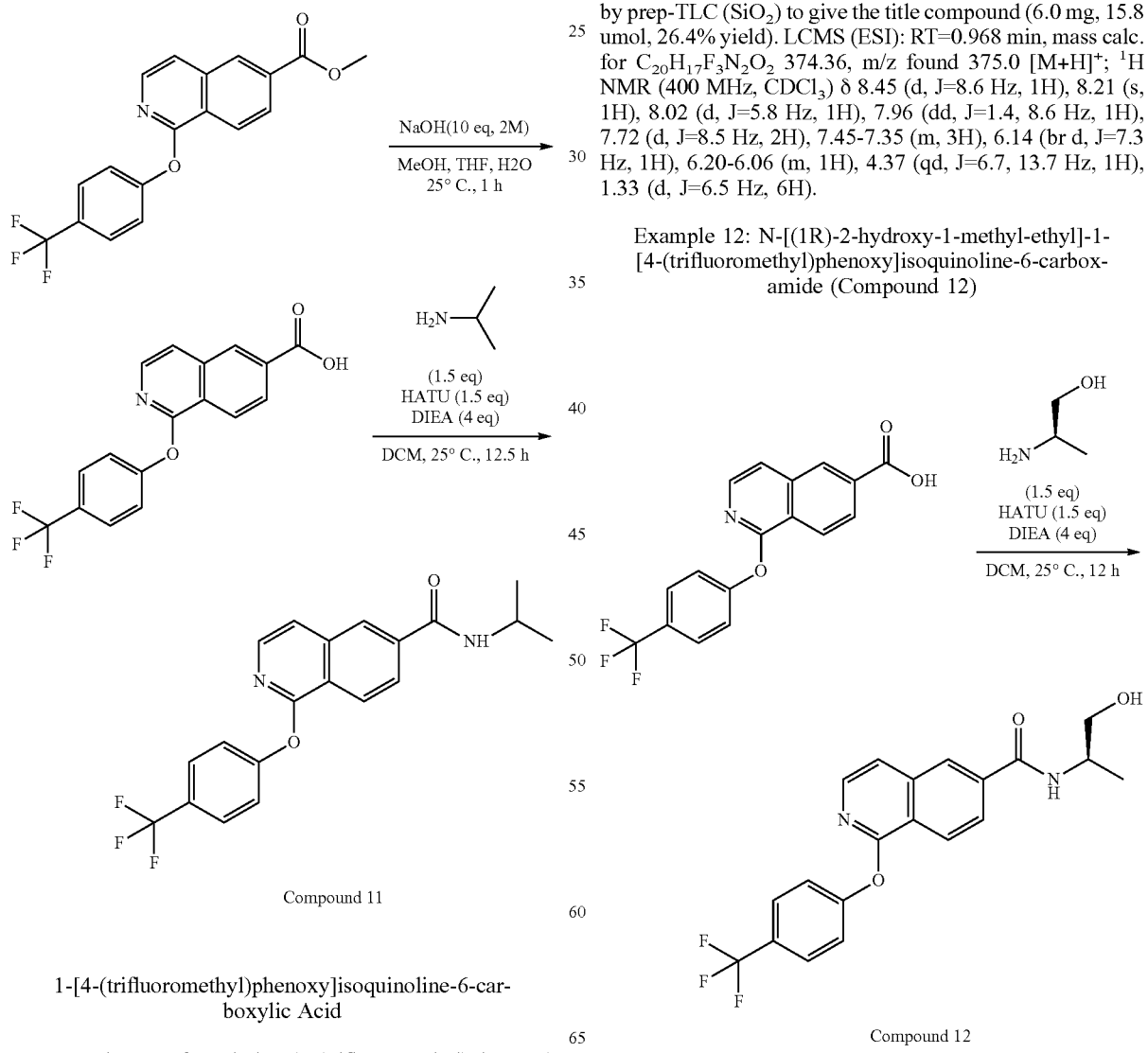

Compound 11

1-[4-(trifluoromethyl)phenoxy]isoquinoline-6-carboxylic Acid

To a mixture of methyl 1-(4-(trifluoromethyl)phenoxy)isoquinoline-6-carboxylate (120 mg, 0.35 mmol, 1 eq) in MeOH (5 mL), THF (1.5 mL) and H₂O (1.5 mL) was added NaOH (2 M, 1.73 mL, 10 eq). The mixture was stirred at 25° C. for 1 h. The mixture was concentrated. The residue was diluted with H₂O (10 mL) and adjusted PH=6-7 with 1N HCl. The mixture was extracted with EA (20 mL*3). The combined organic layers were washed with brine (15 mL), dried over Na₂SO₄, filtered and concentrated under reduced pressure to give 1-(4-(trifluoromethyl)phenoxy)isoquinoline-6-carboxylic acid (90 mg, crude).

N-isopropyl-1-[4-(trifluoromethyl)phenoxy]isoquinoline-6-carboxamide

To a solution of 1-(4-(trifluoromethyl)phenoxy)isoquinoline-6-carboxylic acid (20 mg, 60.0 umol, 1 eq) in DCM (2.5 mL) were added DIEA (31.0 mg, 0.24 mmol, 42 uL, 4 eq) and HATU (34.2 mg, 90.0 umol, 1.5 eq). The mixture was stirred at 25° C. for 0.5 h. Iso-propylamine (5.3 mg, 90.0 umol, 8 uL, 1.5 eq) was added into the mixture. The mixture was stirred at 25° C. for 12 h. The mixture was diluted with H₂O (10 mL), extracted with EA (20 mL*3). The combined organic layer was washed with brine (10 mL), dried over Na₂SO₄, filtered and concentrated. The residue was purified by prep-TLC (SiO₂) to give the title compound (6.0 mg, 15.8 umol, 26.4% yield). LCMS (ESI): RT=0.968 min, mass calc. for C₂₀H₁₇F₃N₂O₂ 374.36, m/z found 375.0 [M+H]⁺; ¹H NMR (400 MHz, CDCl₃) δ 8.45 (d, J=8.6 Hz, 1H), 8.21 (s, 1H), 8.02 (d, J=5.8 Hz, 1H), 7.96 (dd, J=1.4, 8.6 Hz, 1H), 7.72 (d, J=8.5 Hz, 2H), 7.45-7.35 (m, 3H), 6.14 (br d, J=7.3 Hz, 1H), 6.20-6.06 (m, 1H), 4.37 (qd, J=6.7, 13.7 Hz, 1H), 1.33 (d, J=6.5 Hz, 6H).

Example 12: N-[(1R)-2-hydroxy-1-methyl-ethyl]-1-[4-(trifluoromethyl)phenoxy]isoquinoline-6-carboxamide (Compound 12)

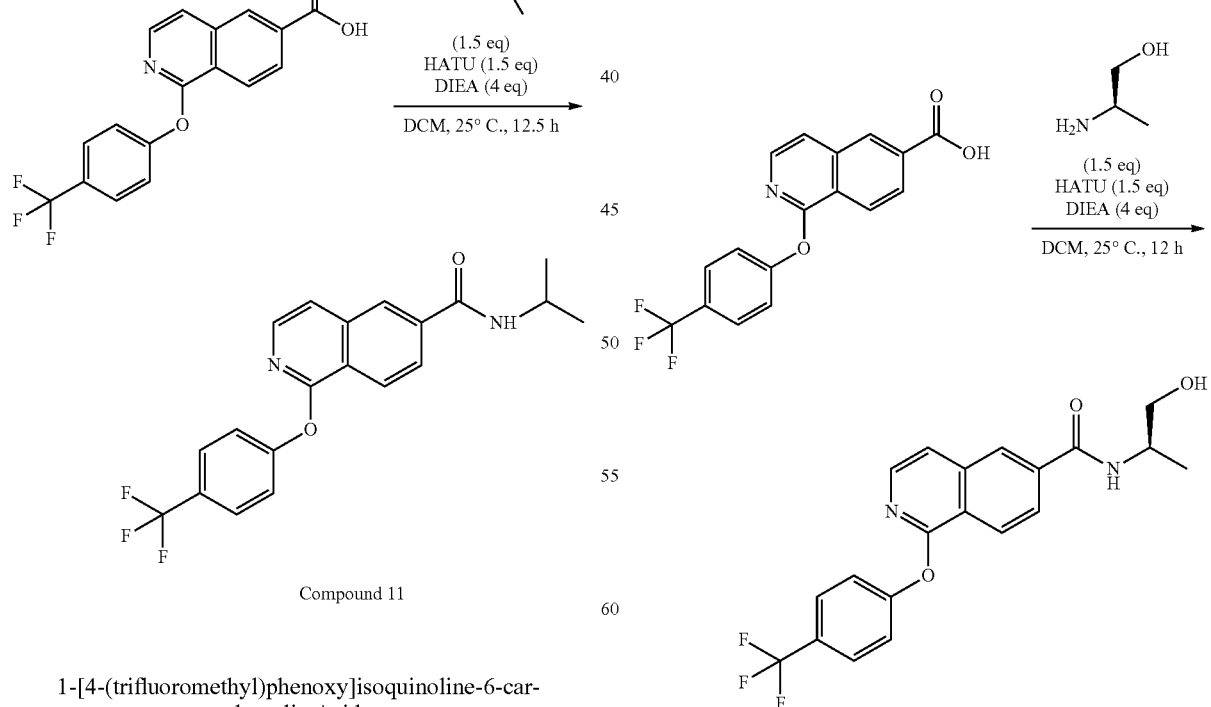

Compound 12

To a solution of 1-(4-(trifluoromethyl)phenoxy)isoquinoline-6-carboxylic acid (20 mg, 60.0 umol, 1 eq) and (R)-2-aminopropan-1-ol (6.8 mg, 90.0 umol, 7 uL, 1.5 eq) in DCM (1 mL) were added DIEA (31.0 mg, 0.24 mmol, 42 uL, 4 eq) and HATU (34.2 mg, 90 umol, 1.5 eq). The mixture was stirred at 25° C. for 12 h. The mixture was diluted with $H_2O$ (10 mL), extracted with EA (20 mL*3). The combined organic layer was washed with brine (10 mL), dried over $Na_2SO_4$, filtered and concentrated. The residue was purified by prep-HPLC to give the title compound (5.5 mg, 14.2 umol, 23.6% yield). LCMS (ESI): RT=0.882 min, mass calc. for $C_{20}H_{17}F_3N_2O_3$ 390.36, m/z found 391.0 [M+H]$^+$; $^1$H NMR (400 MHz, CDCl$_3$) δ 8.48 (d, J=8.5 Hz, 1H), 8.25 (d, J=1.0 Hz, 1H), 8.03 (d, J=5.8 Hz, 1H), 7.99 (dd, J=1.5, 8.8 Hz, 1H), 7.73 (d, J=8.5 Hz, 2H), 7.44 (d, J=5.5 Hz, 1H), 7.40 (d, J=8.5 Hz, 2H), 6.57-6.44 (m, 1H), 4.46-4.31 (m, 1H), 3.93-3.81 (m, 1H), 3.79-3.68 (m, 1H), 2.40 (br s, 1H), 1.37 (d, J=6.8 Hz, 3H).

Example 13: N-isopropyl-8-[4-(trifluoromethyl)phenoxy]quinoline-3-carboxamide (Compound 13)

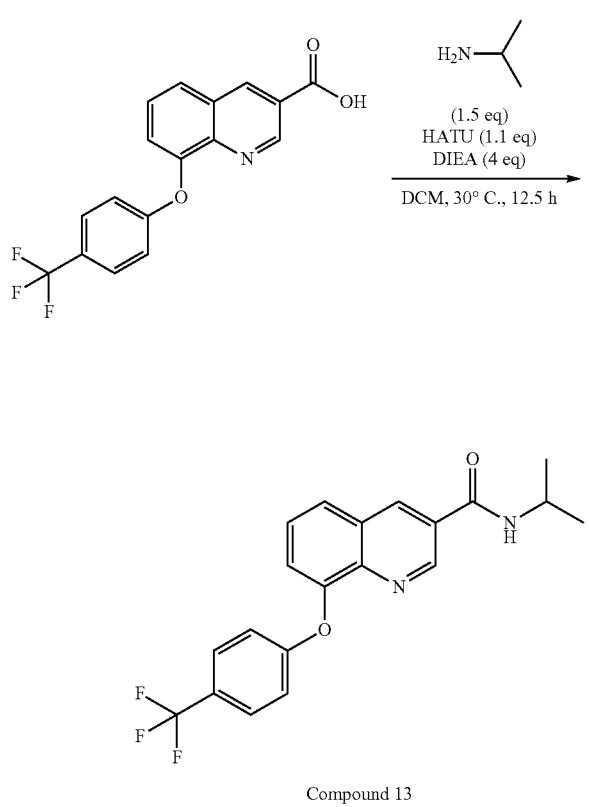

Compound 13

To a solution of 8-[4-(trifluoromethyl)phenoxy]quinoline-3-carboxylic acid (50 mg, 150.0 umol, 1 eq) and HATU (62.8 mg, 0.16 mmol, 1.1 eq) in DCM (1 mL) was added DIEA (77.6 mg, 0.6 mmol, 0.1 mL, 4 eq). The mixture was stirred at 30° C. for 30 min. Iso-propylamine (13.3 mg, 0.22 mmol, 19.3 uL, 1.5 eq) was added into the mixture. The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC. The title compound (7.9 mg, 21.2 umol, 14.1% yield) was obtained. LCMS (ESI): RT=0.802 min, mass calcd. for $C_{20}H_{17}F_3N_2O_2$ 374.12, m/z found 374.9[M+H]$^+$; $^1$H NMR (400 MHz, CDCl$_3$) δ 9.20 (d, J=2.4 Hz, 1H), 8.64 (d, J=2.0 Hz, 1H), 7.76 (d, J=8.0 Hz, 1H), 7.60-7.56 (m, 3H), 7.35 (d, J=6.8 Hz, 1H), 7.10 (d, J=8.8 Hz, 2H), 6.09 (d, J=7.2 Hz, 1H), 4.39-4.34 (m, 1H), 1.32 (d, J=6.4 Hz, 6H).

Example 14: N-[2-hydroxy-1-(2-pyridyl)ethyl]-8-[4-(trifluoromethyl)phenoxy]quinoline-3-carboxamide (Compound 14)

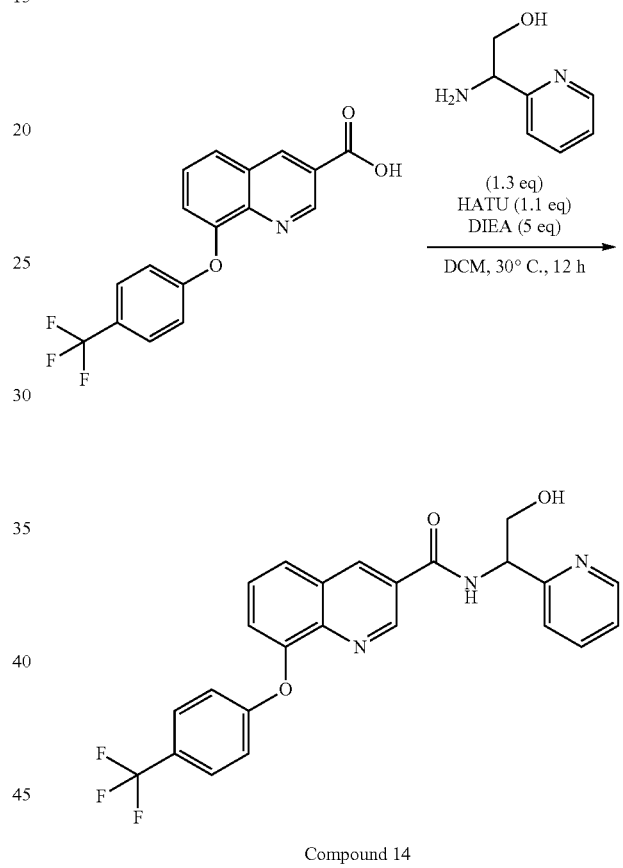

Compound 14

To a solution of 8-[4-(trifluoromethyl)phenoxy]quinoline-3-carboxylic acid (50 mg, 150.0 umol, 1 eq) and HATU (62.8 mg, 0.16 mmol, 1.1 eq) in DCM (2 mL) were added DIEA (96.9 mg, 0.75 mmol, 0.13 mL, 5 eq) and 2-amino-2-pyridin-2-yl-ethanol (40 mg, 0.19 mmol, 1.3 eq, 2HCl). The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC to give the title compound (15.7 mg, 34.7 umol, 23.1% yield). LCMS (ESI): RT=0.695 min, mass calcd. for $C_{24}H_{18}F_3N_3O_3$ 453.13, m/z found 454.0 [M+H]$^+$; $^1$H NMR (400 MHz, CDCl$_3$) δ 9.35 (d, J=2.0 Hz, 1H), 8.73 (d, J=2.0 Hz, 1H), 8.56 (d, J=4.4 Hz, 1H), 8.22 (br d, J=6.8 Hz, 1H), 7.78-7.76 (m, 2H), 7.59-7.51 (m, 4H), 7.36-7.34 (m, 2H), 7.10 (d, J=8.4 Hz, 2H), 5.43-5.39 (m, 1H), 4.20-4.16 (m, 1H), 4.10-4.06 (m, 1H), 2.7 (br s, 1H).

Example 15: N-[(1R)-2-hydroxy-1-methyl-ethyl]-8-[4-(trifluoromethyl)phenoxy] quinoline-3-carboxamide (Compound 15)

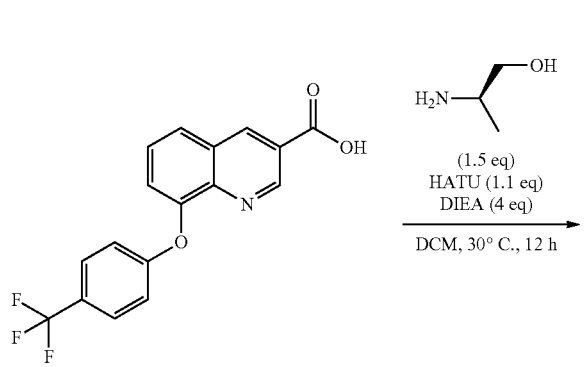

Example 16: N-[(1R)-2-methoxy-1-methyl-ethyl]-8-[4-(trifluoromethyl)phenoxy]quinoline-3-carboxamide (Compound 16)

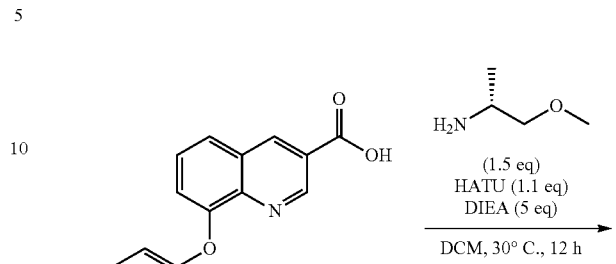

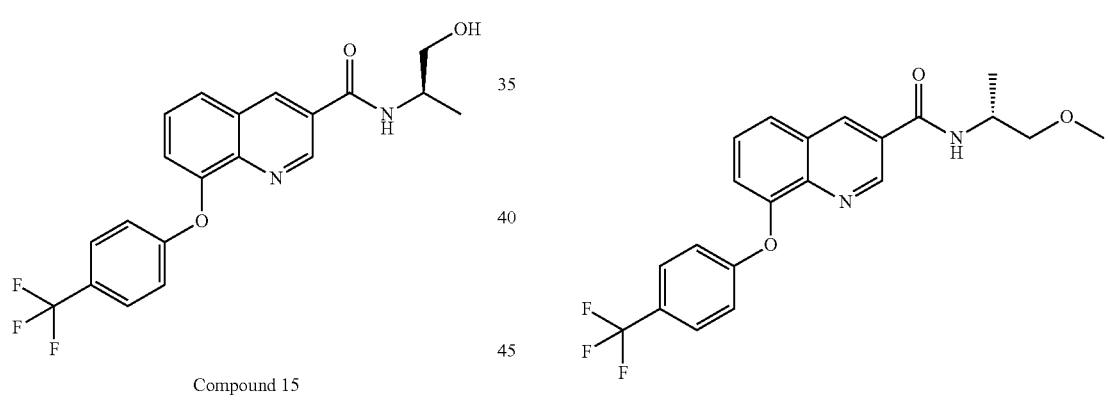

Compound 15

Compound 16

To a solution of 8-[4-(trifluoromethyl)phenoxy]quinoline-3-carboxylic acid (50 mg, 0.15 mmol, 1 eq) and HATU (62.8 mg, 0.16 mmol, 1.1 eq) in DCM (2 mL) were added DIEA (77.6 mg, 0.60 mmol, 0.1 mL, 4 eq) and (2R)-2-aminopropan-1-ol (16.9 mg, 0.23 mmol, 17.6 uL, 1.5 eq). The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC to give the title compound (5.3 mg, 13.6 umol, 9.1% yield). LCMS(ESI): RT=0.733 min, mass calcd. for $C_{20}H_{17}F_3N_2O_3$ 390.12, m/z found 390.9[M+H]$^+$; $^1$H NMR (400 MHz, CDCl$_3$) δ 9.26 (d, J=2.0 Hz, 1H), 8.67 (d, J=2.0 Hz, 1H), 7.74 (d, J=7.2 Hz, 1H), 7.73-7.57 (m, 3H), 7.34 (d, J=7.2 Hz, 1H), 7.09 (d, J=8.4 Hz, 2H), 6.71 (br d, J=7.2 Hz, 1H), 4.44-4.37 (m, 1H), 3.83-3.83 (m, 1H), 3.72-3.68 (m, 1H), 1.34 (d, J=6.8 Hz, 3H).

To a solution of 8-[4-(trifluoromethyl)phenoxy]quinoline-3-carboxylic acid (50 mg, 0.15 mmol, 1 eq) and HATU (62.8 mg, 0.16 mmol, 1.1 eq) in DCM (2 mL) were added DIEA (96.9 mg, 0.75 mmol, 0.13 mL, 5 eq) and (2R)-1-methoxypropan-2-amine (28.3 mg, 0.22 mmol, 17.6 uL, 1.5 eq, HCl). The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC to give the title compound (16.9 mg, 41.9 umol, 27.9% yield). LCMS (ESI): RT=0.778 min, mass calcd. for $C_{21}H_{19}F_3N_2O_3$ 404.13, m/z found 404.9[M+H]$^+$; $^1$H NMR (400 MHz, CDCl$_3$) δ 9.24 (d, J=2.0 Hz, 1H), 8.65 (d, J=2.0 Hz, 1H), 7.77 (d, J=8.4 Hz, 1H), 7.60-7.56 (m, 3H), 7.36 (d, J=8.4 Hz, 1H), 7.10 (d, J=8.8 Hz, 2H), 6.58 (br d, J=5.6 Hz, 1H), 4.45-4.42 (m, 1H), 3.58-3.54 (m, 1H), 3.49-3.46 (m, 1H), 3.41 (s, 3H), 1.35 (d, J=6.4 Hz, 3H).

Example 17: N-[(1R)-1-(2-pyridyl)ethyl]-8-[4-(trifluoromethyl)phenoxy]quinoline-3-carboxamide (Compound 17)

Example 18: N-[(1S)-2-methoxy-1-methyl-ethyl]-8-[4-(trifluoromethyl)phenoxy]quinoline-3-carboxamide (Compound 18)

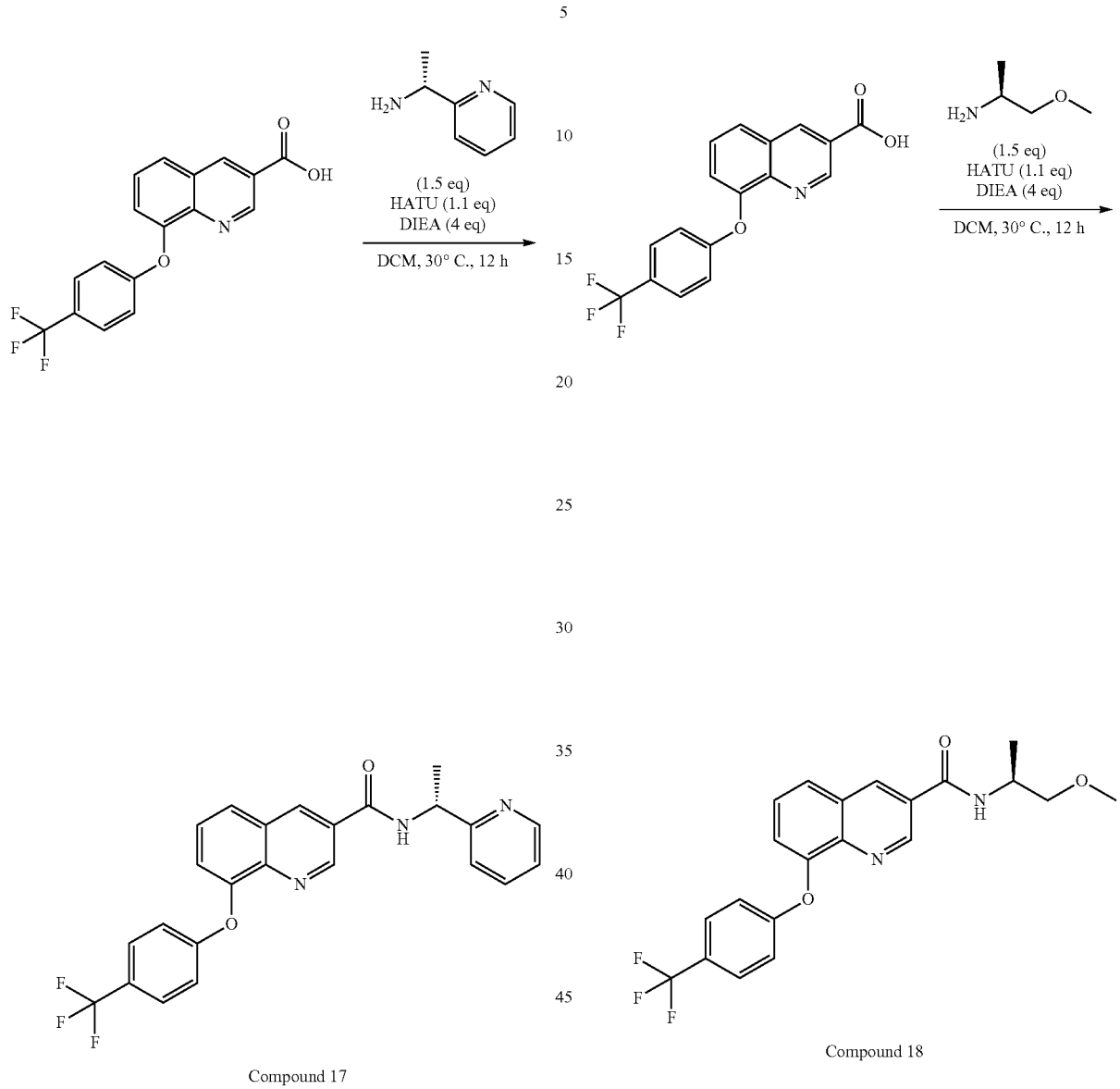

Compound 17

Compound 18

To a solution of 8-[4-(trifluoromethyl)phenoxy]quinoline-3-carboxylic acid (50 mg, 0.15 mmol, 1 eq) and HATU (62.8 mg, 0.16 mmol, 1.1 eq) in DCM (2 mL) were added DIEA (77.6 mg, 0.60 mmol, 0.1 mL, 4 eq) and (1R)-1-(2-pyridyl)ethanamine (27.5 mg, 0.22 mmol, 17.55 uL, 1.5 eq). The mixture was stirred at 30° C. for 12 h. The mixture was diluted with water (10 mL), extracted with EtOAc (20 mL*3). The combined organic layer was washed with brine (20 mL), dried over $Na_2SO_4$, filtered and concentrated. The residue was purified by prep-HPLC to give the title compound (26.7 mg, 61.2 umol, 40.8% yield). LCMS(ESI): RT=0.709 min, mass calcd. for $C_{24}H_{17}F_3N_3O_2$ 437.14, m/z found 438.0 [M+H]$^+$; $^1$H NMR (400 MHz, CDCl$_3$) δ 9.36 (d, J=2.4 Hz, 1H), 8.78 (d, J=2.0 Hz, 1H), 8.58 (d, J=4.8 Hz, 1H), 8.24 (br d, J=6.4 Hz, 1H), 7.81-7.79 (m, 2H), 7.60-7.56 (m, 3H), 7.38-7.35 (m, 2H), 7.31-7.27 (m, 1H), 7.11 (d, J=8.4 Hz, 2H), 5.44-5.37 (m, 1H), 1.65 (d, J=6.8 Hz, 3H).

To a solution of 8-[4-(trifluoromethyl)phenoxy]quinoline-3-carboxylic acid (50 mg, 0.15 mmol, 1 eq) and HATU (62.8 mg, 0.16 mmol, 1.1 eq) in DCM (2 mL) were added DIEA (77.6 mg, 0.6 mmol, 0.1 mL, 4 eq) and (2S)-1-methoxypropan-2-amine (20.1 mg, 0.22 mmol, 17.6 uL, 1.5 eq). The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC to give the title compound (25.0 mg, 61.4 umol, 40.9% yield). LCMS (ESI): RT=0.782 min, mass calcd. for $C_{21}H_{19}F_3N_2O_3$ 404.13, m/z found 404.9[M+H]$^+$; $^1$H NMR (400 MHz, CDCl$_3$) δ 9.23 (d, J=2.4 Hz, 1H), 8.65 (d, J=2.0 Hz, 1H), 7.77 (d, J=7.6 Hz, 1H), 7.60-7.56 (m, 3H), 7.36 (d, J=6.4 Hz, 1H), 7.10 (d, J=8.4 Hz, 2H), 6.59 (br d, J=8.0 Hz, 1H), 4.46-4.42 (m, 1H), 3.58-3.54 (m, 1H), 3.49-3.46 (m, 1H), 3.41 (s, 3H), 1.35 (d, J=6.8 Hz, 3H).

Example 19: N-[(1S)-1-(2-pyridyl)ethyl]-8-[4-(trifluoromethyl)phenoxy]quinoline-3-carboxamide (Compound 19)

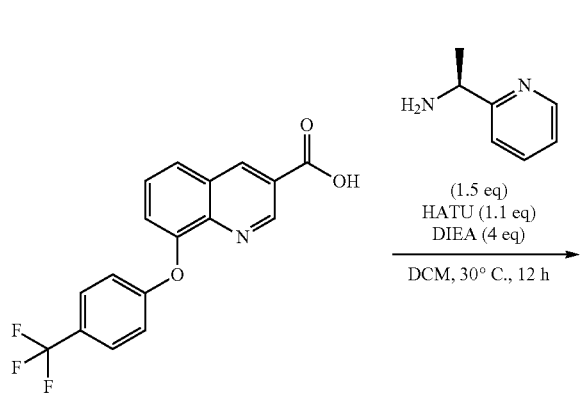

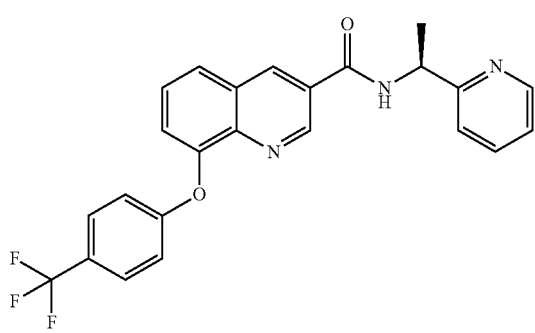

Compound 19

To a solution of 8-[4-(trifluoromethyl)phenoxy]quinoline-3-carboxylic acid (50 mg, 0.15 mmol, 1 eq) and HATU (62.8 mg, 0.16 mmol, 1.1 eq) in DCM (2 mL) were added DIEA (77.6 mg, 0.6 mumol, 0.1 mL, 4 eq) and (1S)-1-(2-pyridyl)ethanamine (27.5 mg, 0.22 mmol, 17.6 uL, 1.5 eq). The mixture was stirred at 30° C. for 12 h. The mixture was diluted with water (10 mL), extracted with EA (20 mL*3). The combined organic layer was washed with brine (20 mL), dried over $Na_2SO_4$, filtered and concentrated. The residue was purified by prep-HPLC to give the title compound (19.6 mg, 44.9 umol, 29.9% yield). LCMS (ESI): RT=0.717 min, mass calcd. for $C_{24}H_{18}F_3N_3O_2$ 437.14, m/z found 437.9[M+H]$^+$; $^1$H NMR (400 MHz, $CDCl_3$) δ 9.36 (d, J=2.0 Hz, 1H), 8.74 (d, J=2.0 Hz, 1H), 8.57 (d, J=4.8 Hz, 1H), 8.16 (br d, J=6.8 Hz, 1H), 7.79 (d, J=8.4 Hz, 1H), 7.72 (t, J=8.0 Hz, 1H), 7.60-7.53 (m, 3H), 7.36-7.34 (m, 2H), 7.26-7.21 (m, 1H), 7.11 (d, J=8.4 Hz, 2H), 5.42-5.35 (m, 1H), 1.63 (d, J=6.8 Hz, 3H).

Example 20: N-(prop-2-yn-1-yl)-5-(4-(trifluoromethyl)phenoxy)-2-naphthamide (Compound 20)

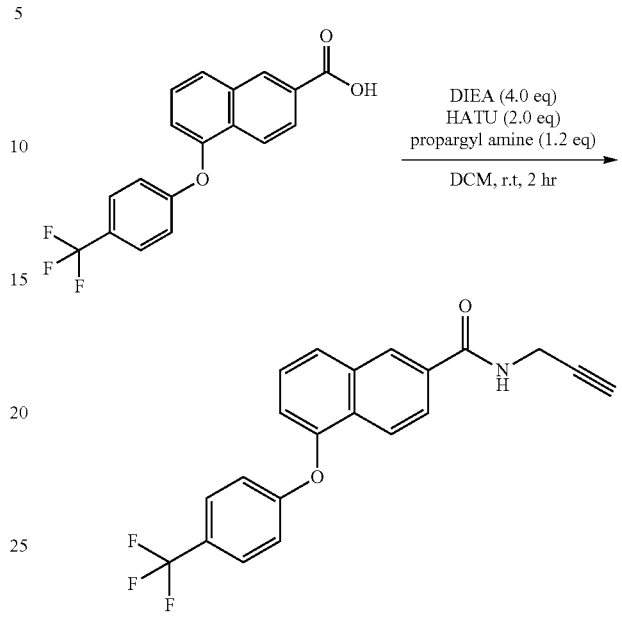

Compound 20

To a solution of 5-[4-(trifluoromethyl)phenoxy]naphthalene-2-carboxylic acid (50 mg, 0.15 mmol, 1 eq) and prop-2-yn-1-amine (9.9 mg, 0.18 mmol, 11.5 uL, 1.2 eq) in DMF (1 mL) was added HATU (114.4 mg, 0.3 mmol, 2 eq) and DIEA (77.7 mg, 0.6 mmol, 0.1 mL, 4 eq). The mixture was stirred at 25° C. for 2 hr. $H_2O$ (5 mL) was added to the solution. The mixture was extracted with ethyl acetate (8 mL*3). The combined organic layers were washed with brine (12 mL*2), dried over anhydrous $Na_2SO_4$, filtered and concentrated in vacuum. The residue was purified by prep-HPLC to give the title compound (5.2 mg, 14.1 umol, 9.41% yield). LCMS (ESI). RT=0.875 min, mass calcd for $C_{21}H_{14}F_3NO_2$ 369.34 m/z found 369.9 [M+H]$^+$; $^1$H NMR (400 MHz, DMSO-$d_6$) δ 9.16 (t, J=5.5 Hz, 1H), 8.58 (d, J=1.1 Hz, 1H), 8.05-8.01 (m, 1H), 8.01-7.94 (m, 2H), 7.75 (d, J=8.8 Hz, 2H), 7.64 (t, J=7.9 Hz, 1H), 7.34 (d, J=7.1 Hz, 1H), 7.18 (d, J=8.6 Hz, 2H), 4.12 (dd, J=2.5, 5.5 Hz, 2H), 3.17 (t, J=2.5 Hz, 1H).

Example 21: N-(but-3-yn-1-yl)-5-(4-(trifluoromethyl)phenoxy)-2-naphthamide (Compound 21)

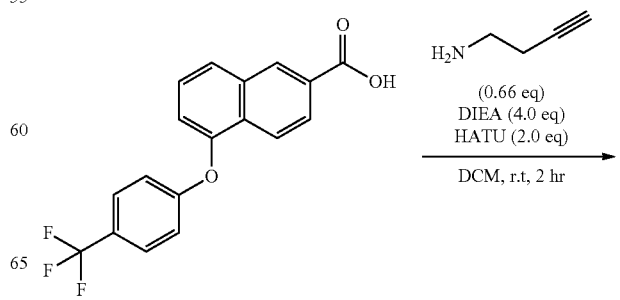

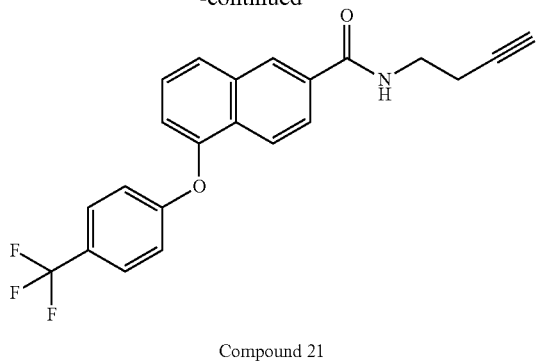

Compound 21

To a solution of 5-[4-(trifluoromethyl)phenoxy]naphthalene-2-carboxylic acid (50 mg, 0.15 mmol, 1 eq) and but-3-yn-1-amine hydrochloride (10.4 mg, 98.5 umol, 0.66 eq) in DMF (1 mL) was added HATU (114.4 mg, 0.3 mmol, 2 eq) and DIEA (77.7 mg, 0.6 mmol, 0.1 mL, 4 eq). The mixture was stirred at 25° C. for 2 hr. H$_2$O (5 mL) was added to the solution. The mixture was extracted with ethyl acetate (8 mL*3). The combined organic layers were washed with brine (12 mL*2), dried over anhydrous Na$_2$SO$_4$, filtered and concentrated in vacuum. The residue was purified by prep-HPLC to give the title compound (12.6 mg, 33.1 umol, 22% yield). LCMS (ESI): RT=0.878 min, mass calcd for C$_{22}$H$_{16}$F$_3$NO$_2$ 383.36 m/z found 383.9 [M+H]$^+$; $^1$H NMR (400 MHz, DMSO-d$_6$) δ 8.88 (t, J=5.5 Hz, 1H), 8.55 (s, 1H), 8.05-7.99 (m, 1H), 7.99-7.92 (m, 2H), 7.75 (d, J=8.5 Hz, 2H), 7.64 (t, J=7.9 Hz, 1H), 7.33 (d, J=7.0 Hz, 1H), 7.17 (d, J=8.5 Hz, 2H), 3.48-3.41 (m, 2H), 2.87 (t, J=2.6 Hz, 1H), 2.49-2.44 (m, 2H).

Example 22: N-(cyanomethyl)-5-(4-(trifluoromethyl)phenoxy)-2-naphthamid (Compound 22)

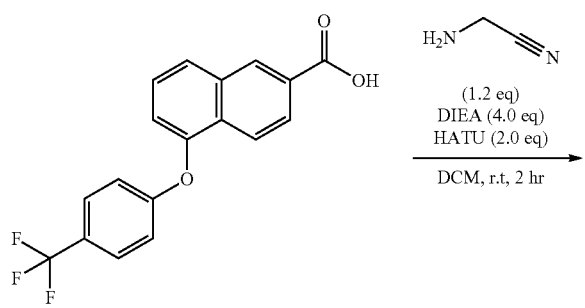

Compound 22

To a solution of 5-[4-(trifluoromethyl)phenoxy]naphthalene-2-carboxylic acid (50 mg, 0.15 mmol, 1 eq) and 2-aminoacetonitrile (16.7 mg, 0.18 mmol, 1.2 eq, HCl) in DMF (1 mL) was added HATU (114.4 mg, 0.3 mmol, 2 eq) and DIEA (77.7 mg, 0.6 mmol, 0.1 mL, 4 eq). The mixture was stirred at 25° C. for 2 hr. H$_2$O (5 mL) was added to the solution. The mixture was extracted with ethyl acetate (8 mL*3). The combined organic layers were washed with brine (12 mL*2), dried over anhydrous Na$_2$SO$_4$, filtered and concentrated in vacuum. The residue was purified by prep-HPLC (column: Xtimate C18 150*25 mm*5 um; mobile phase: [water (0.05% ammonia hydroxide v/v)-ACN]; B %: 65%-95%, 7 min) to give the title compound (20.4 mg, 55.2 umol, 36.7% yield). LCMS (ESI): RT=0.852 min, mass calcd for C$_{20}$H$_{13}$F$_3$N$_2$O$_2$ 370.32 m/z found 370.8 [M+H]$^+$; $^1$H NMR (400 MHz, CD$_3$OD) δ 8.51 (d, J=1.4 Hz, 1H), 8.14 (d, J=8.8 Hz, 1H), 7.96-7.89 (m, 2H), 7.68 (d, J=8.6 Hz, 2H), 7.61 (t, J=7.9 Hz, 1H), 7.25 (d, J=7.1 Hz, 1H), 7.15 (d, J=8.6 Hz, 2H), 4.44-4.39 (m, 2H).

Example 23: N-(2-cyanoethyl)-5-(4-(trifluoromethyl)phenoxy)-2-naphthamide (Compound 23)

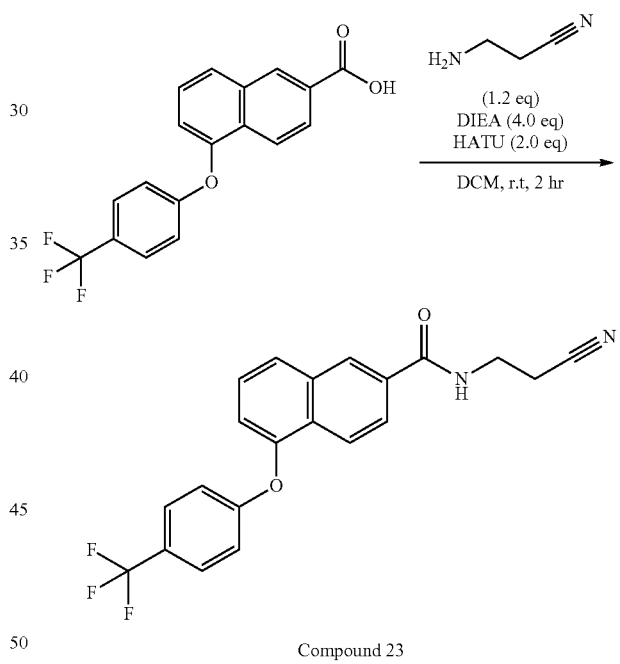

Compound 23

To a solution of 5-[4-(trifluoromethyl)phenoxy]naphthalene-2-carboxylic acid (50 mg, 0.15 mmol, 1 eq) and 3-aminopropanenitrile (12.6 mg, 0.18 mmol, 13.3 uL, 1.2 eq) in DMF (1 mL) was added HATU (114.4 mg, 0.3 mmol, 2 eq) and DIEA (77.7 mg, 0.6 mmol, 0.1 mL, 4 eq). The mixture was stirred at 25° C. for 2 hr. H$_2$O (5 mL) was added to the solution. The mixture was extracted with ethyl acetate (8 mL*3). The combined organic layers were washed with brine (12 mL*2), dried over anhydrous Na$_2$SO$_4$, filtered and concentrated in vacuum. The residue was purified by prep-HPLC to give the title compound (5.7 mg, 14.6 umol, 9.7% yield). LCMS (ESI): RT=0.843 min, mass calcd for C$_{21}$H$_{15}$F$_3$N$_2$O$_2$ 384.35 m/z found 384.9 [M+H]$^+$; $^1$H NMR (400 MHz, DMSO-d$_6$) δ 9.08 (t, J=5.6 Hz, 1H), 8.57 (s, 1H), 8.08-8.02 (m, 1H), 8.00-7.94 (m, 2H), 7.75 (d, J=8.8 Hz, 2H), 7.65 (t, J=7.9 Hz, 1H), 7.34 (d, J=7.4 Hz, 1H), 7.18 (d, J=8.6 Hz, 2H), 3.57 (q, J=6.3 Hz, 2H), 2.83 (t, J=6.5 Hz, 2H).

Example 24: (R)-N-(1-hydroxypropan-2-yl)-5-(4-(trifluoromethyl)phenoxy)-2-naphthamide (Compound 24)

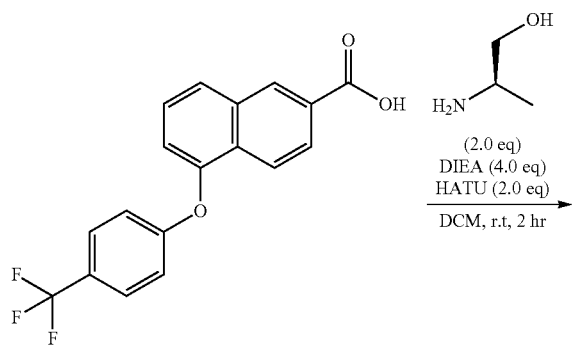

Compound 24

The mixture of 5-[4-(trifluoromethyl)phenoxy]naphthalene-2-carboxylic acid (50 mg 0.15 mmol, 1 eq), DIPEA (77.7 mg, 0.6 mmol, 0.1 mL, 4 eq) and HATU (114.4 mg, 0.3 mmol, 2 eq) in DCM (1 mL) was stirred at 25° C. for 1 hr. Then (R)-2-aminopropan-1-ol (22.6 mg, 0.3 mmol, 23.9 uL, 2 eq) was added at the mixture and the mixture was stirred for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (0.05% ammonia hydroxide v/v)–ACN]; B %: 60%-88.4%, 5.6 min) to give the title compound (30 mg, 76.2 umol, 50.6% yield). LCMS (ESI): RT=0.930 min, mass calcd for C$_{21}$H$_{18}$F$_3$NO$_3$ 389.37 m/z found 390.0 [M+H]$^+$; $^1$H NMR (400 MHz, DMSO-d$_6$) δ 8.56 (s, 1H), 8.33 (d, J=7.9 Hz, 1H), 8.01-7.94 (m, 3H), 7.75 (d, J=8.6 Hz, 2H), 7.63 (t, J=7.9 Hz, 1H), 7.33 (d, J=7.5 Hz, 1H), 7.17 (d, J=8.6 Hz, 2H), 4.77 (t, J=5.8 Hz, 1H), 4.12-4.03 (m, 1H), 3.55-3.46 (m, 1H), 3.42-3.39 (m, 1H), 1.19-1.15 (m, 3H).

Example 25: N-(2-hydroxy-1-(pyridin-2-yl)ethyl)-5-(4-(trifluoromethyl)phenoxy)-2-naphthamide (Compound 25)

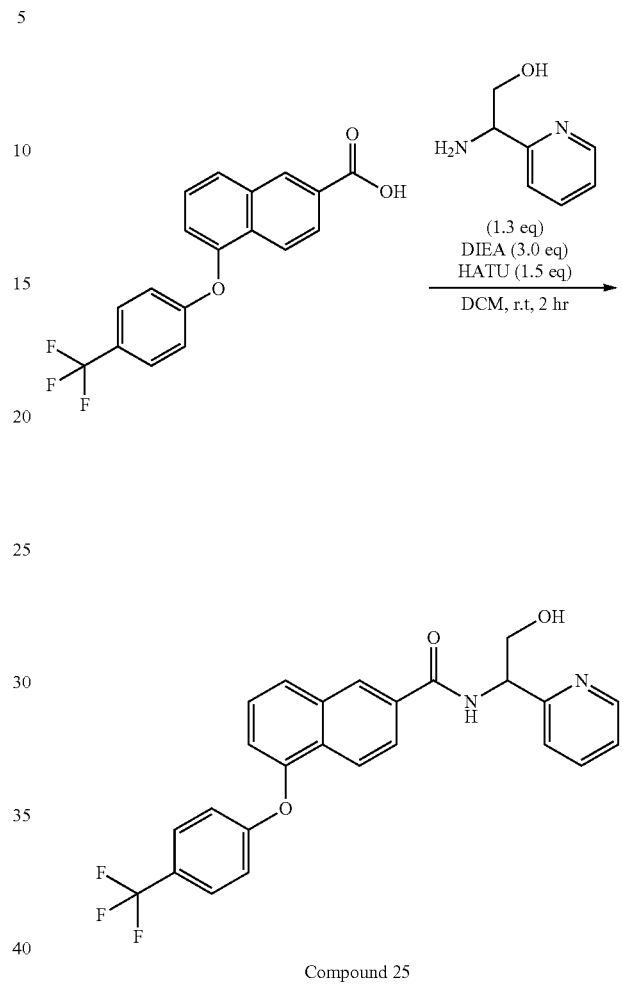

Compound 25

The mixture of 5-[4-(trifluoromethyl)phenoxy]naphthalene-2-carboxylic acid (60 mg, 0.18 mmol, 1 eq), HATU (102.9 mg, 0.27 mmol, 1.5 eq) and DIPEA (70 mg, 0.54 mmol, 94.3 uL, 3 eq) in DCM (2 mL) was stirred at 25° C. for 1 hr. Then 2-amino-2-pyridin-2-yl-ethanol (50 mg, 0.23 mmol, 1.31 eq, 2 HCl) was added at the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (0.05% ammonia hydroxide v/v)–ACN]; B %: 60%-90%, 7.8 min) to give the title compound (32 mg, 70.7 umol, 39.1% yield). LCMS (ESI): RT=0.868 min, mass calcd for C$_{25}$H$_{19}$F$_3$N$_2$O$_3$ 452.34 m/z found 453.0 [M+H]$^+$; $^1$H NMR (400 MHz, DMSO-d$_6$) δ 8.90 (d, J=7.8 Hz, 1H), 8.67 (s, 1H), 8.58-8.53 (m, 1H), 8.04-7.97 (m, 3H), 7.80-7.73 (m, 4H), 7.69-7.62 (m, 1H), 7.47 (d, J=7.8 Hz, 1H), 7.34 (d, J=7.5 Hz, 1H), 7.31-7.21 (m, 2H), 7.18 (d, J=8.5 Hz, 2H), 5.26-5.18 (m, 1H), 4.98 (br s, 1H), 3.85 (br dd, J=5.8, 12.0 Hz, 2H).

Example 26: (R)-N-(1-methoxypropan-2-yl)-5-(4-(trifluoromethyl)phenoxy)-2-naphthamide (Compound 26)

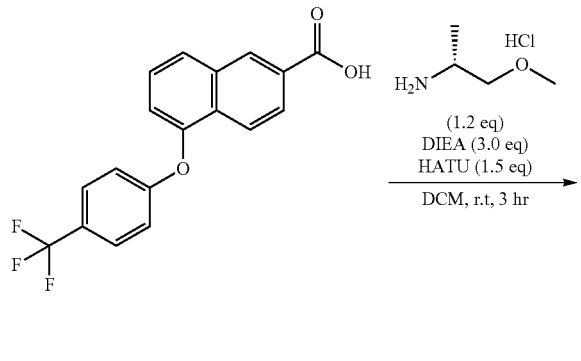

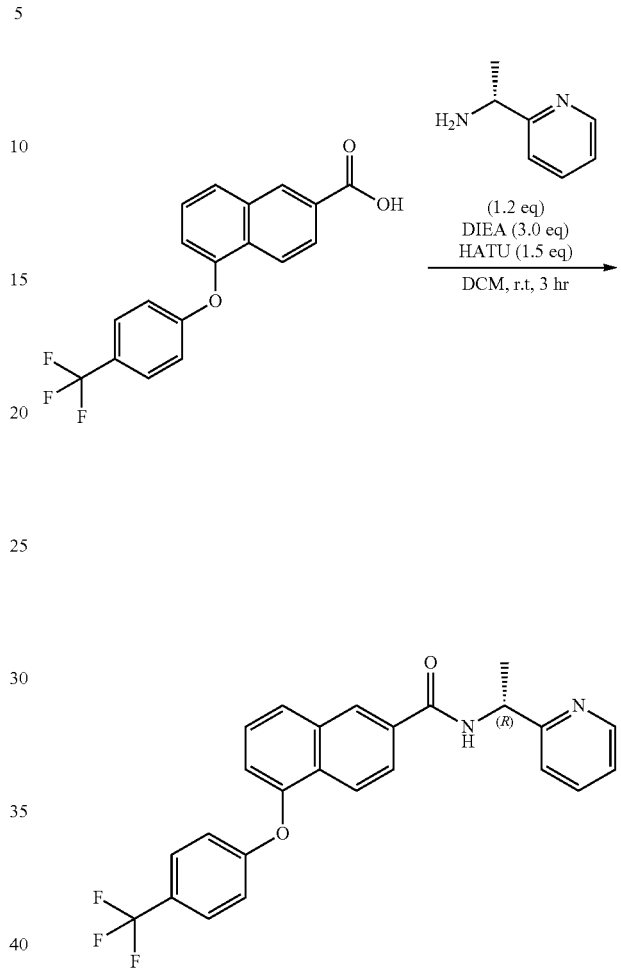

Compound 26

Compound 27

Example 27: N-[(1R)-1-(2-pyridyl)ethyl]-5-[4-(trifluoromethyl)phenoxy]naphthalene-2-carboxamide (Compound 27)

The mixture of 5-[4-(trifluoromethyl)phenoxy]naphthalene-2-carboxylic acid (50 mg, 0.15 mmol, 1 eq), DIPEA (58.3 mg, 0.45 mmol, 78.6 uL, 3 eq) and HATU (85.8 mg, 0.22 mmol, 1.5 eq) in DCM (2 mL) was stirred at 25° C. for 1 hr. Then (2R)-1-methoxypropan-2-amine hydrochloride (22.6 mg, 0.18 mmol, 1.2 eq) was added at the mixture and the mixture was stirred at 25° C. for 2 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (0.05% HCl)–ACN]; B %: 60%-90%, 7 min) to give the title compound (40 mg, 99.1 umol, 65.9% yield). LCMS (ESI): RT=0.863 min, mass calcd for C$_{22}$H$_{20}$F$_3$NO$_3$ 403.39 m/z found 404.0 [M+H]$^+$; $^1$H NMR (400 MHz, CD$_3$OD) δ 8.46 (d, J=1.3 Hz, 1H), 8.10 (d, J=8.8 Hz, 1H), 7.94-7.87 (m, 2H), 7.68 (d, J=8.5 Hz, 2H), 7.60 (t, J=7.9 Hz, 1H), 7.26-7.20 (m, 1H), 7.15 (d, J=8.5 Hz, 2H), 4.40 (sxt, J=6.5 Hz, 1H), 3.59-3.53 (m, 1H), 3.50-3.45 (m, 1H), 3.42 (s, 3H), 1.30 (d, J=6.8 Hz, 4H).

The mixture of 5-[4-(trifluoromethyl)phenoxy]naphthalene-2-carboxylic acid (50 mg, 0.15 mmol, 1 eq), DIPEA (58.3 mg, 0.45 mmol, 78.6 uL, 3 eq) and HATU (85.8 mg, 0.22 mmd, 1.5 eq) in DCM (3 mL) was stirred at 25° C. for 1 hr. Then (1R)-1-(2-pyridyl)ethanamine (22 mg, 0.18 mmol, 1.2 eq) was added at the mixture and the mixture was stirred at 25° C. for another 2 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (0.05% HCl)–ACN]; B %: 65%-95%, 7 min) to give the title compound (30 mg, 68 umol, 45.2% yield). LCMS (ESI): RT=0.891 min, mass calcd for C$_{21}$H$_{19}$F$_3$N$_2$O$_2$ 436.43 m/z found 437.0 [M+H]$^+$; $^1$H NMR (400 MHz, CD$_3$OD) δ 8.54 (d, J=1.5 Hz, 2H), 8.10 (d, J=8.8 Hz, 1H), 7.98-7.88 (m, 2H), 7.83 (dt, J=1.8, 7.7 Hz, 1H), 7.66 (d, J=8.6 Hz, 2H), 7.59 (t, J=7.9 Hz, 1H), 7.52 (d, J=8.0 Hz, 1H), 7.32 (ddd, J=0.9, 5.0, 7.5 Hz, 1H), 7.23 (d, J=7.0 Hz, 1H), 7.13 (d, J=8.6 Hz, 2H), 5.34 (q, J=7.0 Hz, 1H), 1.64 (d, J=7.1 Hz, 3H).

Example 28: (S)-N-(1-methoxypropan-2-yl)-5-(4-(trifluoromethyl)phenoxy)-2-naphthamide (Compound 28)

Example 29: (S)-N-(1-(pyridin-2-yl)ethyl)-5-(4-(trifluoromethyl)phenoxy)-2-naphthamide (Compound 29)

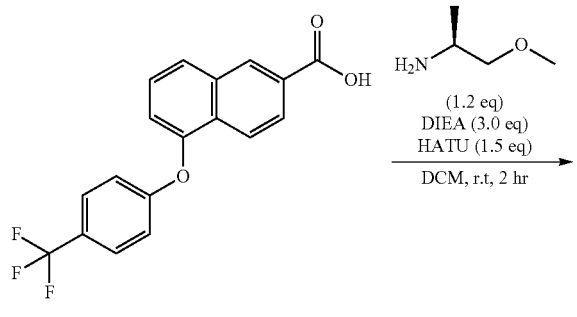

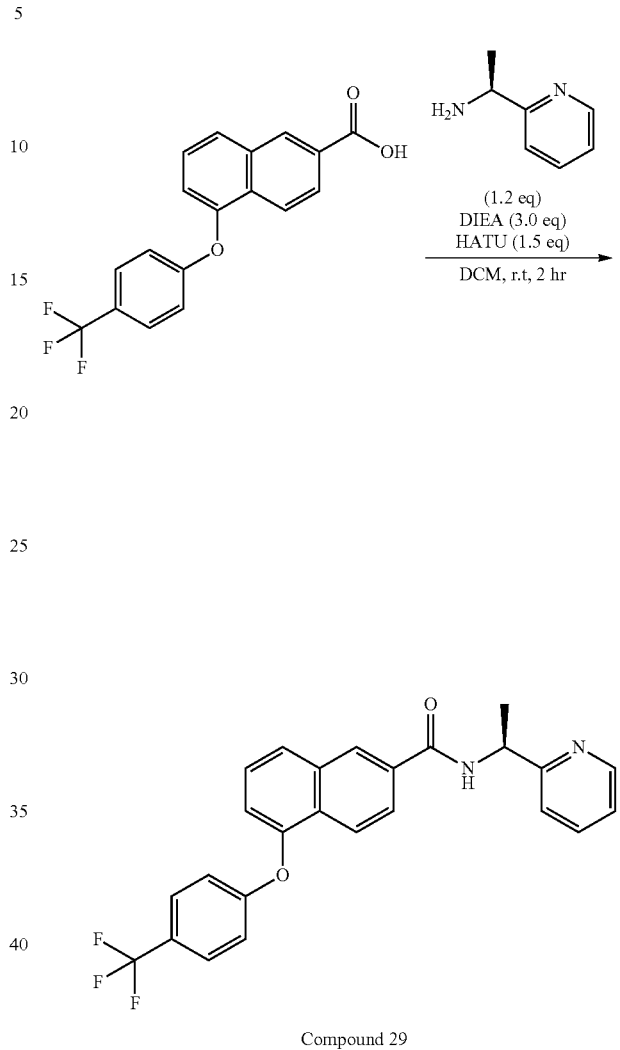

Compound 28

Compound 29

The mixture of 5-[4-(trifluoromethyl)phenoxy]naphthalene-2-carboxylic acid (50 mg, 0.15 mmol, 1 eq), DIPEA (58.3 mg, 0.45 mmol, 78.6 uL, 3 eq) and HATU (85.8 mg, 0.22 mmol, 1.5 eq) in DCM (3 mL) was stirred at 25° C. for 1 hr. Then (2S)-1-methoxypropan-2-amine (16.1 mg, 0.18 mmol, 1.2 eq) was added at the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate C18 150*25 mm*5 um; mobile phase: [water (0.05% ammonia hydroxide v/v)–ACN]; B %: 60%-90%, 7 min) to give the title compound (40 mg, 99.1 umol, 65.9% yield). LCMS (ESI): RT=0.995 min, mass calcd for $C_{22}H_{20}F_3NO_3$ 403.39 m/z found 404.0 [M+H]+; 1H NMR (400 MHz, $CD_3OD$) δ 8.46 (d, J=1.5 Hz, 1H), 8.09 (d, J=8.8 Hz, 1H), 7.96-7.87 (m, 2H), 7.66 (d, J=8.8 Hz, 2H), 7.58 (t, J=7.9 Hz, 1H), 7.22 (d, J=7.6 Hz, 1H), 7.13 (d, J=8.6 Hz, 2H), 4.40 (sxt, J=6.5 Hz, 1H), 3.59-3.53 (m, 1H), 3.50-3.45 (m, 1H), 3.44-3.39 (m, 3H), 1.30 (d, J=6.8 Hz, 3H).

The mixture of 5-[4-(trifluoromethyl)phenoxy]naphthalene-2-carboxylic acid (50 mg, 0.15 mmol, 1 eq), DIPEA (58.3 mg, 0.45 mmol, 78.6 uL, 3 eq) and HATU (85.8 mg, 0.22 mmol, 1.5 eq) in DCM (3 mL) was stirred at 25° C. for 1 hr. Then (1 S)-1-(2-pyridyl)ethanamine (22 mg, 0.18 mmol, 1.2 eq) was added at the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate C18 150*25 mm*5 um; mobile phase: [water (10 mM $NH_4HCO3$)–ACN]; B %: 66%-76%, 8 min) to give the title compound (32 mg, 72.5 umol, 48.2% yield). LCMS (ESI): RT=0.886 min, mass calcd for $C_{25}H_{19}F_3N_2O_2$ 436.34 m/z found 437.0 [M+H]+; 1H NMR (400 MHz, $CD_3OD$ S 8.58-8.51 (m, 2H), 8.12 (d, J=8.8 Hz, 1H), 7.99-7.90 (m, 2H), 7.84 (dt, J=1.6, 7.8 Hz, 1H), 7.68 (d, J=8.6 Hz, 2H), 7.61 (t, J=7.9 Hz, 1H), 7.53 (d, J=7.9 Hz, 1H), 7.33 (dd, J=5.1, 6.9 Hz, 1H), 7.25 (d, J=7.5 Hz, 1H), 7.15 (d, J=8.6 Hz, 2H), 5.34 (q, J=7.1 Hz, 1H), 1.65 (d, J=7.0 Hz, 3H).

Example 30: N-(2-(methylamino)ethyl)-5-(4-(trifluoromethyl)phenoxy)-2-naphthamide (Compound 30)

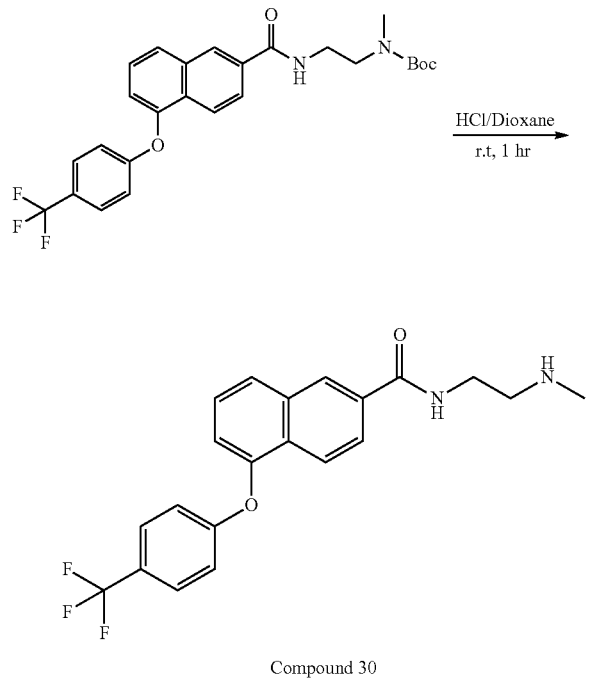 [SMILES: CN(CCNC(=O)c1ccc2c(Oc3ccc(C(F)(F)F)cc3)cccc2c1)C(=O)OC(C)(C)C ; CNCCNC(=O)c1ccc2c(Oc3ccc(C(F)(F)F)cc3)cccc2c1]

Compound 30

To a solution of tert-butyl N-methyl-N-[2-[[5-[4-(trifluoromethyl)phenoxy]naphthalene-2-carbonyl]amino]ethyl]carbamate (20 mg, 40.9 umol, 1 eq) in HCl/dioxane (4 M, 51.1 uL, 5 eq) was stirred at 25° C. for 1 hr. The reaction mixture was concentrated under reduced pressure to remove solvent. The residue was purified by prep-HPLC to give the title compound (5.0 mg, 11.8 umol, 28.8% yield, HCl). LCMS (ESI): RT=0.742 min, mass calcd for $C_{21}H_{19}F_3N_2O_2$ 388.38 m/z found 389.0 [M+H]$^+$; $^1$H NMR (400 MHz, CD$_3$OD) δ 8.56 (s, 1H), 8.14 (d, J=8.8 Hz, 1H), 7.98 (d, J=8.8 Hz, 1H), 7.93 (d, J=8.3 Hz, 1H), 7.68 (d, J=8.5 Hz, 2H), 7.62 (t, J=7.9 Hz, 1H), 7.26 (d, J=7.5 Hz, 1H), 7.15 (d, J=8.5 Hz, 2H), 3.79 (br t, J=5.4 Hz, 2H), 3.30 (br s, 2H), 2.80 (s, 3H).

Example 31: N-(2-(N-methylcyanamido)ethyl)-5-(4-(trifluoromethyl)phenoxy)-2-naphthamide (Compound 31)

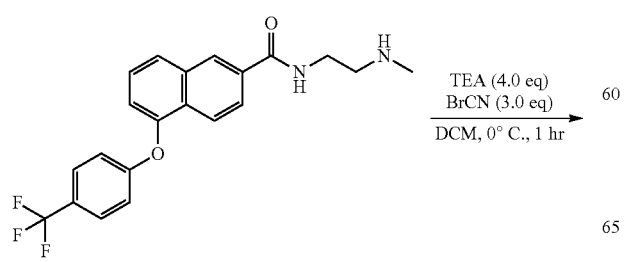

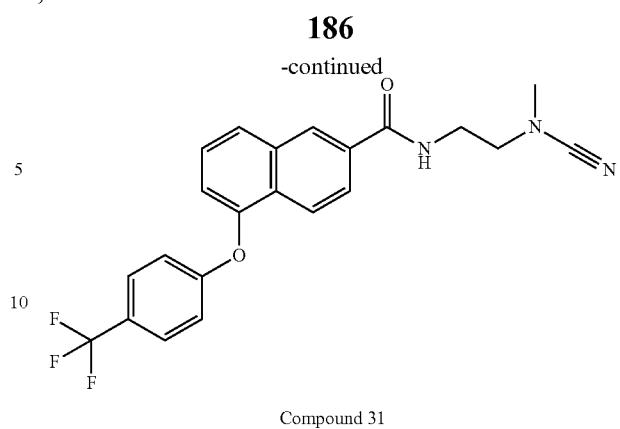

Compound 31

To a solution of N-[2-(methylamino)ethyl]-5-[4-(trifluoromethyl)phenoxy]naphthalene-2-carboxamide (50 mg, 0.12 mmol, 1 eq) in DCM (1 mL) was added TEA (52.1 mg, 0.51 mmol, 71.6 uL, 4 eq) and BrCN (40.9 mg, 0.38 mmol, 28.4 uL, 3 eq). The mixture was stirred at 0° C. for 1 hr. H$_2$O (5 mL) was added to the solution. The mixture was extracted with ethyl acetate (8 mL*3). The combined organic layers were washed with brine (12 mL*2), dried over anhydrous Na$_2$SO$_4$, filtered and concentrated in vacuum. The residue was purified by prep-HPLC to give the title compound (2.8 mg, 6.6 umol, 5.1% yield). LCMS (ESI): RT=0.819 min, mass calcd for $C_{22}H_{18}F_3N_3O_2$ 413.39 m/z found 435.9 [M+Na]$^+$; $^1$H NMR (400 MHz, CD$_3$OD) δ 8.50 (d, J=1.5 Hz, 1H), 8.12 (d, J=8.8 Hz, 1H), 7.97-7.89 (m, 2H), 7.68 (d, J=8.5 Hz, 2H), 7.61 (t, J=7.9 Hz, 1H), 7.25 (d, J=7.5 Hz, 1H), 7.15 (d, J=8.8 Hz, 2H), 3.70 (t, J=5.6 Hz, 2H), 3.38-3.34 (m, 2H), 3.00 (s, 3H).

Example 32: N-isopropyl-7-(4-(trifluoromethyl)phenoxy)benzo[b]thiophene-2-carboxamide (Compound 32)

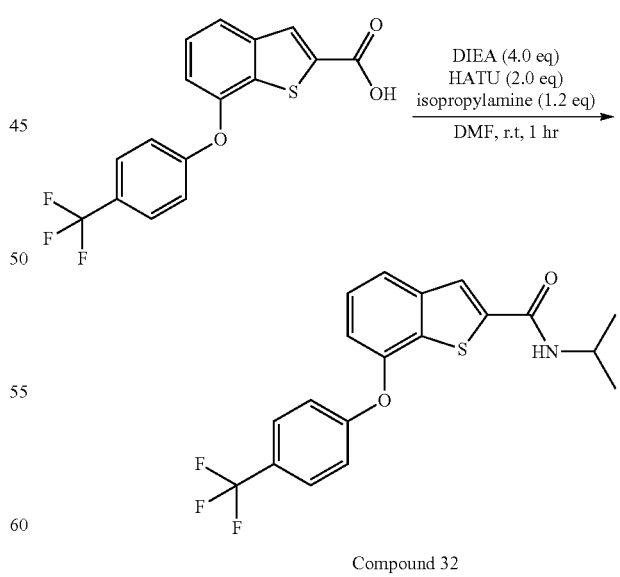

Compound 32

To a solution of 7-[4-(trifluoromethyl)phenoxy]benzothiophene-2-carboxylic acid (30 mg 88.6 umol, 1.2 eq) in DMF (1 mL) was added HATU (56.2 mg, 0.14 mmol, 2 eq) and DIEA (38.2 mg, 0.29 mmol, 51.4 uL, 4 eq). The mixture was stirred at 25° C. for 0.5 hr. Iso-propylamine (4.3 mg, 73.9 umol, 6.3 uL, 1 eq) was added to the solution. The mixture was stirred at 25° C. for 0.5 hr. H₂O (5 mL) was added to the solution. The mixture was extracted with ethyl acetate (8 mL*3). The combined organic layers were washed with brine (12 mL*2), dried over anhydrous Na₂SO₄, filtered and concentrated in vacuum. The residue was purified by prep-HPLC to give the title compound (9.6 mg, 25.4 umol, 34.3% yield). LCMS(ESI): RT=0.889 min, mass calcd for $C_{19}H_{16}F_3NO_2S$ 379.40 m/z found 379.9 [M+H]⁺; ¹H NMR (400 MHz, DMSO-d₆) δ 8.60 (d, J=7.6 Hz, 1H), 8.20 (s, 1H), 7.85 (d, J=7.8 Hz, 1H), 7.77 (d, J=8.6 Hz, 2H), 7.52 (t, =7.9 Hz, 1H), 7.22 (dd, J=2.3, 8.3 Hz, 3H), 4.06 (qd, J=6.7, 13.8 Hz, 1H), 1.18 (d, J=6.6 Hz, 6H).

Example 33: (R)-N-(1-hydroxypropan-2-yl)-7-(4-(trifluoromethyl)phenoxy)benzo[b]thiophene-2-carboxamide (Compound 33)

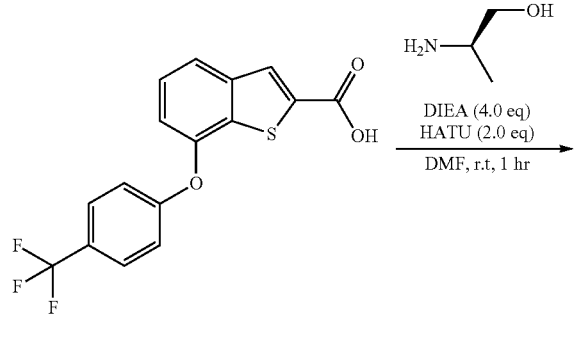

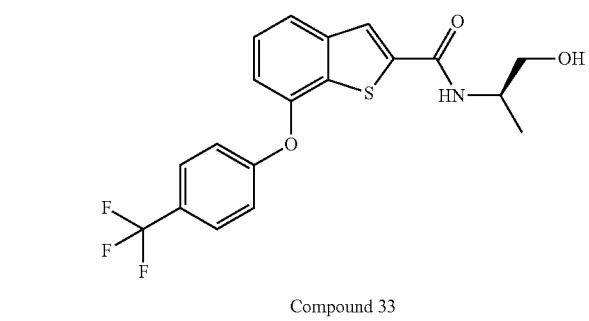

Compound 33

To a solution of (2R)-2-aminopropan-1-ol (5.5 mg, 73.9 umol, 5.7 uL, 1 eq) and 7-[4-(trifluoromethyl)phenoxy]benzothiophene-2-carboxylic acid (30 mg, 88.6 umol, 1.2 eq) in DMF (1 mL) was added DIEA (38.2 mg, 0.29 mmol, 51.4 uL, 4 eq) and HATU (56.2 mg, 0.14 mmol, 2 eq). The mixture was stirred at 25° C. for 1 hr. H₂O (5 mL) was added to the solution. The mixture was extracted with ethyl acetate (8 mL*3). The combined organic layers were washed with brine (12 mL*2), dried over anhydrous Na₂SO₄, filtered and concentrated in vacuum. The residue was purified by prep-HPLC to give the title compound (3.0 mg, 7.5 umol, 10.2% yield). LCMS (ESI): RT=0.803 min, mass calcd for $C_{19}H_{16}F_3NO_3S$ 395.40 m/z found 395.9 [M+H]⁺, ¹H NMR (400 MHz, CD₃OD) δ 8.07 (s, 1H), 7.80 (d, J=7.5 Hz, 1H), 7.70 (d, J=8.5 Hz, 2H), 7.49 (t, J=7.9 Hz, 1H), 7.19 (d, J=8.5 Hz, 2H), 7.13 (d, J=7.3 Hz, 1H), 4.22-4.14 (m, 1H), 3.67-3.58 (m, 2H), 1.28 (d, J=6.8 Hz, 3H).

Example 34: N-(3-(methylamino)propyl)-5-(4-(trifluoromethyl)phenoxy)-2-naphthamide (Compound 34)

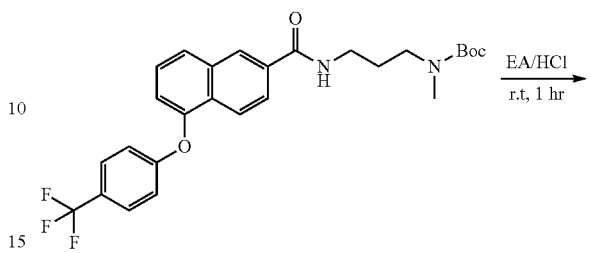

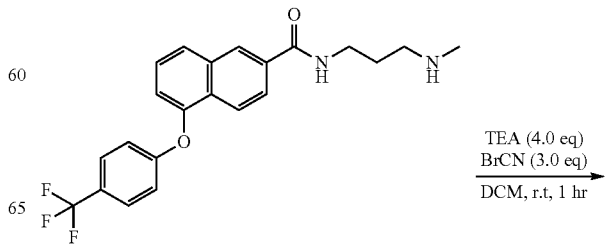

Compound 34

The mixture of tert-butyl N-methyl-N-[3-[[5-[4-(trifluoromethyl)phenoxy]naphthalene-2-carbonyl]amino]propyl]carbamate (0.02 g, 39.8 umol, 1 eq) in HCl/EtOAc (4 M, 0.49 mL, 50 eq) was stirred at 25° C. for 1 hr. The mixture was concentrated in vacuum to afford the crude product. The residue was purified by prep-HPLC to give the title compound (8.5 mg, 19.3 umol, 48.6% yield, HCl). LCMS (ESI): RT=0.745 min, mass calcd for $C_{22}H_{21}F_3N_2O_2$ 402.41 m/z found 403.0 [M+H]⁺; ¹H NMR (400 MHz, CD₃OD) δ 8.52 (s, 1H), 8.13 (d, J=8.8 Hz, 1H), 7.92 (d, J=8.4 Hz, 2H), 7.68 (d, J=8.6 Hz, 2H), 7.62 (t, J=7.9 Hz, 1H), 7.26 (d, J=7.5 Hz, 1H), 7.15 (d, J=8.5 Hz, 2H), 3.58 (t, J=6.6 Hz, 2H), 3.11 (br t, J=7.2 Hz, 2H), 2.05 (quin, J=7.0 Hz, 2H).

Example 35: N-(3-(N-methylcyanamido)propyl)-5-(4-(trifluoromethyl)phenoxy)-2-naphthamide (Compound 35)

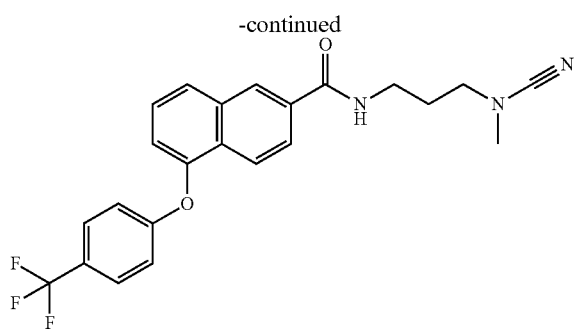

The mixture of N-[3-(methylamino)propyl]-5-[4-(trifluoromethyl)phenoxy]naphthalene-2-carboxamide (0.048 g, 0.11 mmol, 1 eq), TEA (48.2 mg, 0.47 mmol, 66.4 uL, 4 eq) and BrCN (37.9 mg, 0.35 mmol, 26.3 uL, 3 eq) in DCM (2 mL) was stirred at 25° C. for 1 hr. The mixture was washed with brine (3 mL), dried over anhydrous $Na_2SO_4$ and concentrated in vacuum to afford the crude product. The residue was purified by prep-HPLC to give the title compound (30.5 mg, 71.3 umol, 59.8% yield). LCMS (ESI): RT=0.957 min, mass calcd for $C_{23}H_{20}F_3N_3O_2$ 427.42 m/z found 428.0 $[M+H]^+$; $^1H$ NMR (400 MHz, $CD_3OD$) δ 8.48 (d, J=1.3 Hz, 1H), 8.11 (d, J=8.8 Hz, 1H), 7.95-7.88 (m, 2H), 7.68 (d, J=8.6 Hz, 2H), 7.60 (t, J=7.9 Hz, 1H), 7.24 (d, J=7.4 Hz, 1H), 7.15 (d, J=8.5 Hz, 2H), 3.55 (t, J=6.9 Hz, 2H), 3.17 (t, J=7.1 Hz, 2H), 2.93 (s, 3H), 2.07-1.98 (m, 2H).

Example 36: N-(1-phenylcyclopropyl)-5-[4-(trifluoromethyl)phenoxy]naphthalene-2-carboxamide (Compound 36)

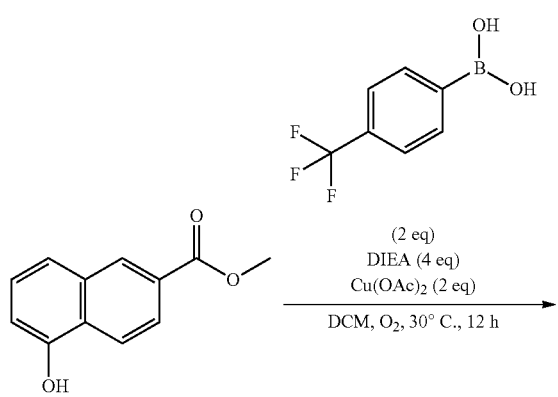

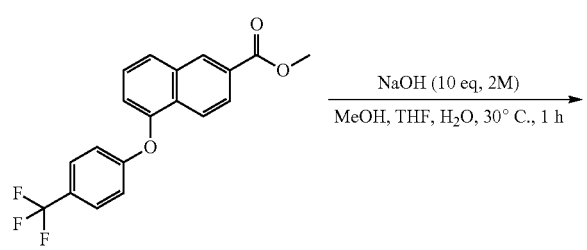

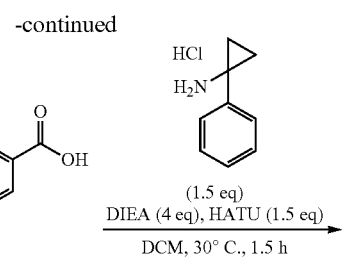

Compound 36

Methyl 5-[4-(trifluoromethyl)phenoxy]naphthalene-2-carboxylate

To a solution of methyl 5-hydroxy-2-naphthoate (3.6 g, 17.80 mmol, 1 eq) and (4-(trifluoromethyl)phenyl)boronic acid (6.76 g, 35.61 mmol, 2 eq) in DCM (120 mL) were added DIEA (9.20 g, 71.21 mmol, 12.40 mL, 4 eq) and $Cu(OAc)_2$ (6.47 g, 35.61 mmol, 2 eq) under $O_2$. The mixture was degassed under vacuum and purged with $O_2$ 3 times. The mixture was stirred under $O_2$ (15 psi) at 30° C. for 12 hours. The mixture was filtered. The filtrate was diluted with $H_2O$ (250 mL), extracted with EA (500 mL*3). The combined organic layers were washed with brine (300 mL), dried over $Na_2SO_4$, filtered and concentrated under reduced pressure to give a residue. The residue was purified by flash silica gel chromatography to give methyl 5-[4-(trifluoromethyl)phenoxy]naphthalene-2-carboxylate (2.5 g, 7.22 mmol, 20.3% yield) and 1 (1.5 g, 7.42 mmol, 20.8% yield).

5-[4-(trifluoromethyl)phenoxy]naphthalene-2-carboxylic Acid

To a mixture of methyl 5-[4-(trifluoromethyl)phenoxy]naphthalene-2-carboxylate (200 mg, 0.58 mmol, 1 eq) in MeOH (1.5 mL), THF (0.5 mL) and $H_2O$ (0.5 mL) was added NaOH (2 M, 2.89 mL, 10 eq). The mixture was stirred at 30° C. for 1 h. The mixture was concentrated. The residue was diluted with $H_2O$ (20 mL) and adjusted pH=6-7 with 1N HCl. The mixture was extracted with EA (40 mL*3). The combined organic layers were washed with brine (30 mL), dried over $Na_2SO_4$, filtered and concentrated under reduced pressure to give 5-[4-(trifluoromethyl)phenoxy]naphthalene-2-carboxylic acid (220 mg, crude).

N-(1-phenylcyclopropyl)-5-[4-(trifluoromethyl)phenoxy]naphthalene-2-carboxamide To a solution of 5-[4-(trifluoromethyl)phenoxy]naphthalene-2-carboxylic acid (30 mg, 90.3 umol, 1 eq) in DCM (1 mL) were added DIEA (46.7 mg, 0.36 mmd, 63 uL, 4 eq) and HATU (51.5 mg, 0.14 mmol, 1.5 eq). The mixture was stirred at 30° C. for 0.5 h. 1-Phenylcyclopropan-1-amine (23.0 mg, 0.14 mmol, 1.5 eq, HCl) was added into the mixture. The mixture was stirred at 30° C. for 1 h. The mixture was diluted with $H_2O$ (10 mL), extracted with EA (20 mL*3). The combined organic layers were washed with brine (10 mL), dried over $Na_2SO_4$, filtered and concentrated. The residue was purified by prep-HPLC to give the title compound (16.6 mg, 36.9 umol, 40.8% yield). LCMS (ESI): RT=1.053 min, mass calc. for $C_{27}H_{20}F_3NO_2$ 447.14, m/z found 448.0 [M+H]$^+$, $^1$H NMR (400 MHz, CDCl$_3$) 58.37 (d, J=1.0 Hz, 1H), 8.12 (d, J=8.8 Hz, 1H), 7.84 (dd, J=1.6, 8.8 Hz, 1H), 7.78 (d, J=8.3 Hz, 1H), 7.59 (d, J=8.6 Hz, 2H), 7.50 (t, J=7.9 Hz, 1H), 7.38-7.27 (m, 4H), 7.24-7.17 (m, 1H), 7.14 (d, J=7.4 Hz, 1H), 7.06 (d, J=8.6 Hz, 2H), 6.98 (s, 1H), 1.47-1.35 (m, 4H).

Example 37: N-(3-phenyloxetan-3-yl)-5-(4-(trifluoromethyl)phenoxy)-2-naphthamide (Compound 37)

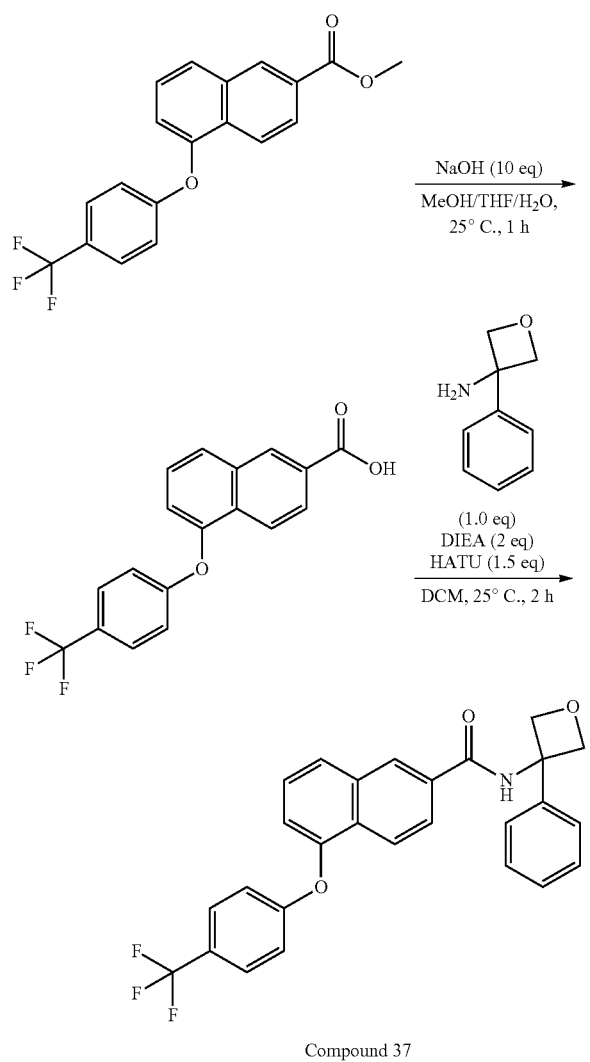

Compound 37

5-(4-(trifluoromethyl)phenoxy)-2-naphthoic Acid

To a solution of compound methyl 5-(4-(trifluoromethyl)phenoxy)-2-naphthoate (2 g, 5.78 mmol, 1 eq) in MeOH (16 mL) and THF (4 mL) was added NaOH (2.31 g, 57.75 mmol, 10 eq) in $H_2O$ (4 mL). The mixture was stirred at 25° C. for 1 hr. The mixture was concentrated. 1 N HC was added to the residue until pH=6-7. The mixture was extracted with EA (20 mL*3). The organic layer was dried over $Na_2SO_4$, filtered and concentrated to give compound 5-(4-(trifluoromethyl)phenoxy)-2-naphthoic acid (2.5 g, crude).

N-(3-phenyloxetan-3-yl)-5-(4-(trifluoromethyl)phenoxy)-2-naphthamide

To a solution of compound 5-(4-(trifluoromethyl)phenoxy)-2-naphthoic acid (50.0 mg, 0.15 mmol, 1 eq), compound 3-phenyloxetan-3-amine (22.5 mg, 0.15 mmol, 1 eq) and HATU (85.8 mg, 0.23 mmol, 1.5 eq) in DCM (0.5 mL) was added DIEA (38.9 mg, 0.30 mmol, 52 uL, 2 eq). The mixture was stirred at 25° C. for 2 hr. The mixture was diluted with water (5 mL). The mixture was extracted with EA (10 mL*3). The organic layer was dried over $Na_2SO_4$, filtered and concentrated The residue was purified by prep-HPLC to give the title compound (2.0 mg, 4.4 umol, 2.9% yield). LCMS (ESI). RT=0.895 min, mass calc. for $C_{27}H_{20}F_3NO_3$ 463.14, m/z found 464.0 [M+H]$^+$, $^1$H NMR (400 MHz, CDCl$_3$) δ 8.45 (d, J=1.4 Hz, 1H), 8.17 (d, J=8.9 Hz, 1H), 7.89 (dd, J=1.8, 8.8 Hz, 1H), 7.81 (d, J=8.4 Hz, 1H), 7.61 (br d, J=7.8 Hz, 4H), 7.54 (t, J=7.9 Hz, 1H), 7.42 (t, J=7.6 Hz, 2H), 7.36-7.30 (m, 1H), 7.17 (d, J=7.5 Hz, 1H), 7.09 (d, J=8.5 Hz, 2H), 7.05 (s, 1H), 5.21 (d, J=6.8 Hz, 2H), 5.08 (d, J=6.9 Hz, 2H).

Example 38: (R)-N-(1-cyclopropylethyl)-5-(4-(trifluoromethyl)phenoxy)-2-naphthamide (Compound 38) and (S)-N-(1-cyclopropylethyl)-5-(4-(trifluoromethyl)phenoxy)-2-naphthamide (Compound 39)

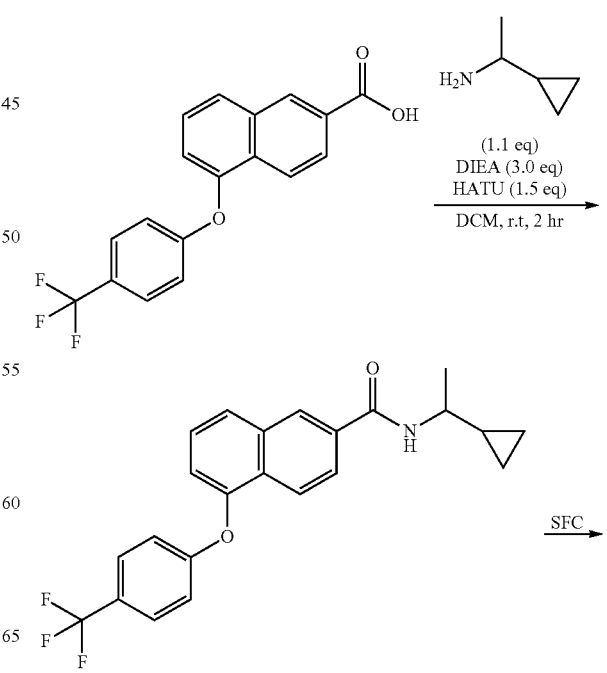

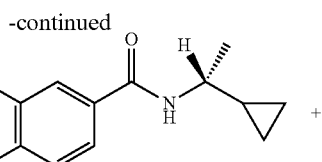

Compound 38

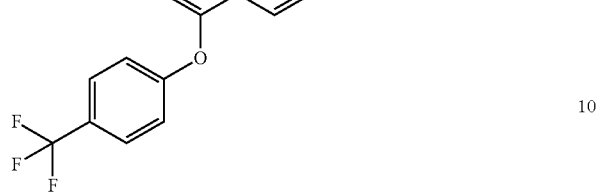

Compound 39

N-(1-cyclopropylethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-cyclopropylmethanamine (28.1 mg, 0.33 mmol, 1.1 eq) was added into the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC. Compound N-(1-cyclopropylethyl)-5-[4-(trifluoromethyl)phenoxy]naphthalene-2-carboxamide (99 mg, 0.24 mmol, 82.3% yield) was obtained.

(R)-N-(1-cyclopropylethyl)-5-(4-(trifluoromethyl)phenoxy)-2-naphthamide (Compound 38) and (S)-N-(1-cyclopropylethyl)-S-(4-(trifluoromethyl)phenoxy)-2-naphthamide (Compound 39)

The racemic compound N-(1-cyclopropylethyl)-5-[4-(trifluoromethyl)phenoxy]naphthalene-2-carboxamide (99 mg, 0.24 mmol, 1 eq) was separated by SFC (column: DAICEL CHIRALPAK AS-H (250 mm*30 mm, 5 um); mobile phase: [0.1% $NH_3H_2O$ ETOH]; B %: 30%-30%, min) to give Compound 38 (20 mg, 49.6 umol, 20% yield) LCMS (ESI): RT=1.042 min, mass calcd for $C_{23}H_{20}F_3NO_2$ 399.41 m/z found 400.0 $[M+H]^+$; $^1H$ NMR (400 MHz, $CD_3OD$) δ 8.46 (s, 1H), 8.09 (br d, J=8.8 Hz, 1H), 7.95-7.84 (m, 2H), 7.69-7.54 (m, 3H), 7.25-7.18 (m, 1H), 7.14 (br d, J=8.3 Hz, 2H), 3.63-3.50 (m, 1H), 1.37 (d, J=6.8 Hz, 4H), 1.07 (dt, J=4.3, 8.8 Hz, 1H), 0.65-0.37 (m, 3H), 0.36-0.25 (m, 1H) and Compound 39 (20 mg, 49.6 umol, 20% yield) LCMS (ESI): RT=1.036 min, mass calcd for $C_{23}H_{20}F_3NO_2$ 399.41 m/z found 400.0 $[M+H]^+$; $^1H$ NMR (400 MHz, $CD_3OD$) δ 8.45 (s, 1H), 8.08 (dd, J=4.1, 8.7 Hz, 1H), 7.95-7.83 (m, 2H), 7.68-7.52 (m, 3H), 7.23-7.08 (m, 3H), 3.62-3.49 (m, 1H), 1.37 (d, J=6.8 Hz, 3H), 1.13-1.01 (m, 1H), 0.63-0.37 (m, 3H), 0.36-0.23 (m, 1H).

Example 39: (R)-N-(1-(oxetan-3-yl)ethyl)-5-(4-(trifluoromethyl)phenoxy)-2-naphthamide (Compound 40) and (S)-N-(1-(oxetan-3-yl)ethyl)-5-(4-(trifluoromethyl)phenoxy)-2-naphthamide (Compound 41)

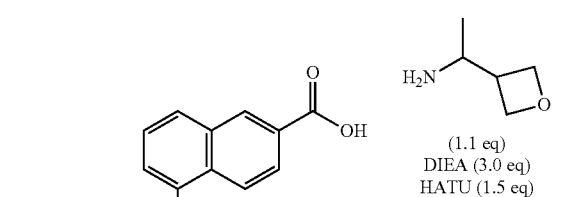

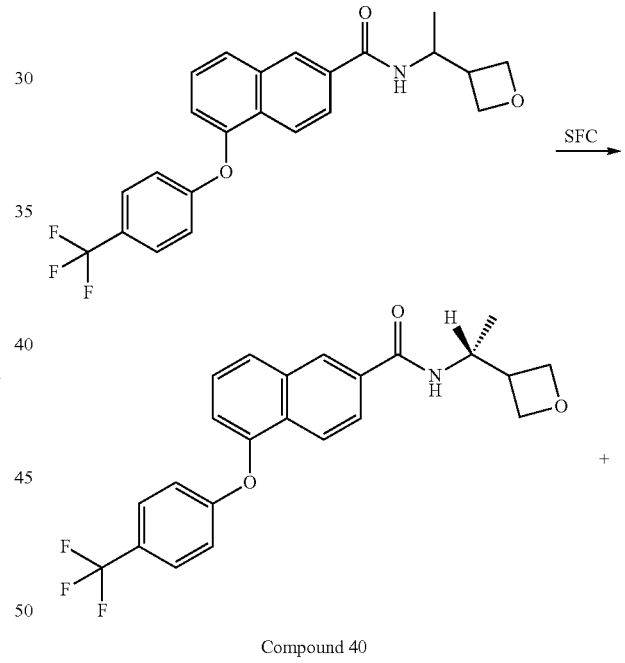

Compound 40

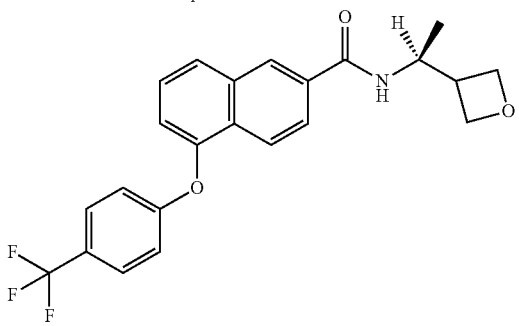

Compound 41

N-(1-(oxetan-3-yl)ethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-(oxetan-3-yl)ethanamine (33.4 mg, 0.33 mmol, 1.1 eq) was added into the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC. Compound N-[1-(oxetan-3-yl)ethyl]-5-[4-(trifluoromethyl)phenoxy]naphthalene-2-carboxamide (66.2 mg, 0.15 mmol, 50.8% yield) was obtained.

(R)-N-(1-(oxetan-3-yl)ethyl)-5-(4-(trifluoromethyl)phenoxy)-2-naphthamide (Compound 40) and (S)-N-(1-(oxetan-3-yl)ethyl)-5-(4-(trifluoromethyl)phenoxy)-2-naphthamide (Compound 41)

The racemic compound N-[1-(oxetan-3-yl)ethyl]-5-[4-(trifluoromethyl)phenoxy]naphthalene-2-carboxamide (66.2 mg, 0.15 mmol, 1 eq) was separated by SFC (column: DAICEL CHIRALPAK AD-H (250 mm*30 mm, 5 um); mobile phase: [0.1% $NH_3H_2O$ ETOH]; B %: 30%-30%, min) to give Compound 40 (10.8 mg, 25.6 umol, 16.1% yield) LCMS (ESI): RT=0.954 min, mass calcd for $C_{23}H_{20}F_3NO_3$ 415.41 m/z found 416.0 $[M+H]^+$, $^1H$ NMR (400 MHz, $CD_3OD$) δ 8.46 (d, J=1.5 Hz, 1H), 8.11 (d, J=8.8 Hz, 1H), 7.93-7.87 (m, 2H), 7.70-7.57 (m, 3H), 7.24 (d, J=7.5 Hz, 1H), 7.15 (br d, J=8.5 Hz, 2H), 4.67-4.51 (m, 5H), 1.24 (d, J=6.8 Hz, 3H) and Compound 41 (19.1 mg, 45.2 umol, 28.4% yield) LCMS (ESI): RT=0.949 min, mass calcd for $C_{23}H2F_3NO_3$ 415.41 m/z found 416.0 $[M+H]^+$, $^1H$ NMR (400 MHz, $CD_3OD$) δ 8.34 (s, 1H), 7.99 (d, J=8.8 Hz, 1H), 7.81-7.76 (m, 2H), 7.56 (br d, J=8.5 Hz, 2H), 7.48 (t, J=7.9 Hz, 1H), 7.12 (d, J=7.5 Hz, 1H), 7.03 (br d, J=8.5 Hz, 2H), 4.55 (s, 1H), 4.51-4.45 (m, 4H), 4.43 (t, J=6.1 Hz, 1H), 1.15-1.05 (m, 4H).

Example 40: (R)-6-methoxy-N-(1-(pyridin-2-yl)ethyl)-8-(4-(trifluoromethyl)phenoxy)quinoline-3-carboxamide (Compound 42)

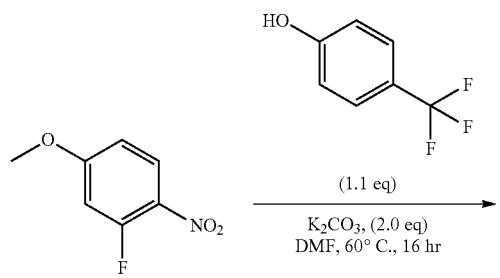

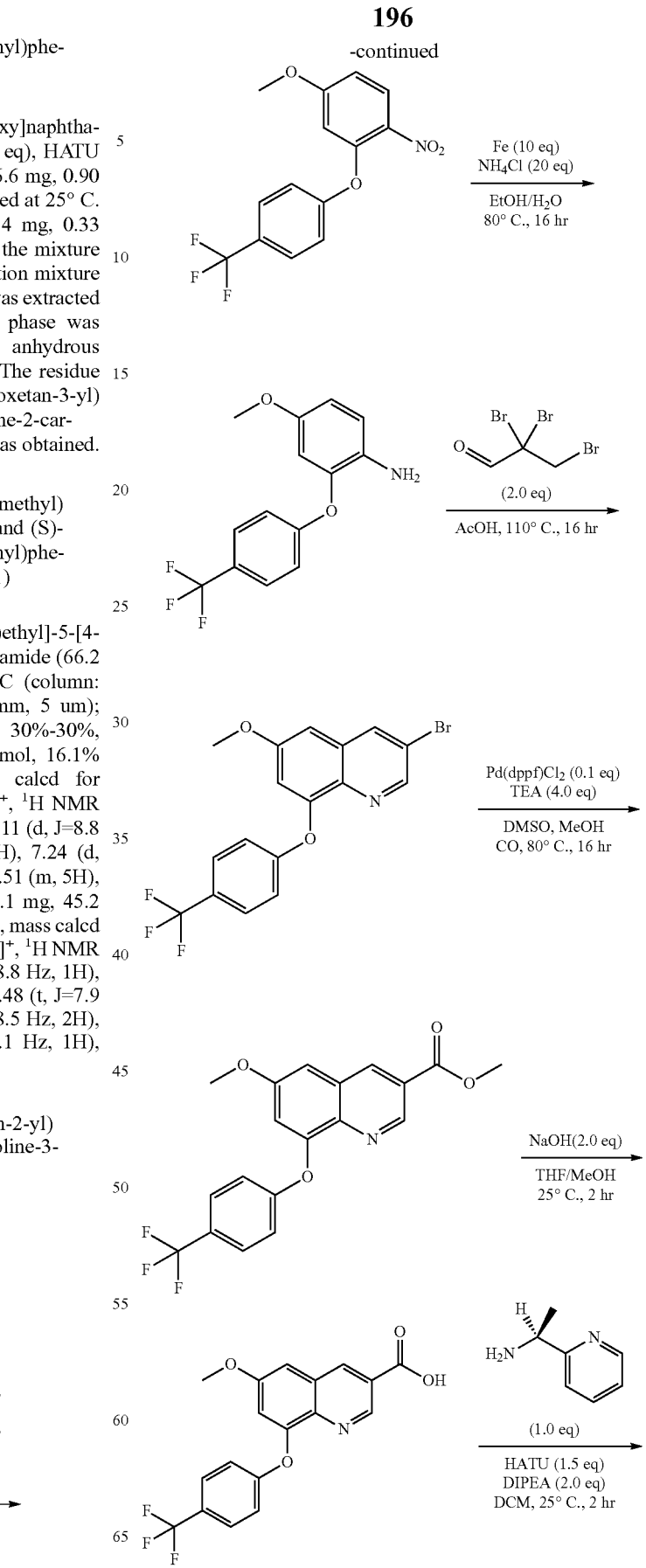

-continued

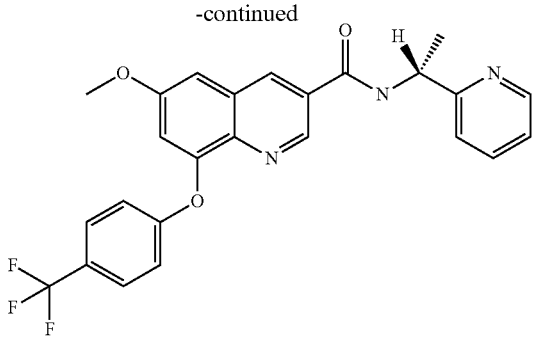

Compound 42

4-methoxy-1-nitro-2-(4-(trifluoromethyl)phenoxy)benzene

To a solution of compound 2-fluoro-4-methoxy-1-nitrobenzene (3.00 g, 17.53 mmol, 1.0 eq) and compound 4-(trifluoromethyl)phenol (3.13 g, 19.28 mmol, 1.1 eq) in DMF (30 mL) was added $K_2CO_3$ (4.85 g, 35.06 mmol, 2.0 eq). The reaction mixture was stirred at 60° C. for 16 hours. The reaction mixture was concentrated under reduced pressure. The mixture was diluted with water (20 mL) and the resultant mixture was extracted with EA (30 mL*3). The combined organic layers were dried over $Na_2SO_4$, filtered and concentrated to dryness under reduced pressure. The residue was purified by silica gel column chromatography to give 4-methoxy-1-nitro-2-(4-(trifluoromethyl)phenoxy)benzene (5.2 g, 94.7% yield). $^1$H NMR (400 MHz, $CDCl_3$) δ 8.13 (d, J=9.3 Hz, 1H), 7.62 (d, J=8.6 Hz, 2H), 7.08 (d, J=8.5 Hz, 2H), 6.82 (dd, J=2.6, 9.3 Hz, 1H), 6.58 (d, J=2.6 Hz, 1H), 3.86 (s, 3H).

4-methoxy-2-(4-(trifluoromethyl)phenoxy)aniline

To a solution of compound 4-methoxy-1-nitro-2-(4-(trifluoromethyl)phenoxy)benzene (5.20 g, 16.60 mmol, 1.0 eq) in EtOH (50 mL) and $H_2O$ (10 mL) were Fe (9.27 g, 0.17 mol, 10 eq) and $NH_4Cl$ (17.76 g, 0.33 mol, 20 eq). The reaction mixture was stirred at 80° C. for 16 hours. The reaction mixture was filtered and washed with EA (80 mL) and $H_2O$ (40 mL). The suspension was separated, and then the organic layer was dried over $Na_2SO_4$, filtered and concentrated under reduce pressure to give 4-methoxy-2-(4-(trifluoromethyl)phenoxy)aniline (4.6 g, crude).

3-bromo-6-methoxy-8-(4-(trifluoromethyl)phenoxy)quinoline

A mixture of compound 4-methoxy-2-(4-(trifluoromethyl)phenoxy)aniline (1.00 g, 3.53 mmol, 1.0 eq) and compound 2,2,3-tribromopropanal (2.08 g, 7.06 mmol, 2.0 eq) in AcOH (10 mL) was stirred at 110° C. for 16 hours. The reaction mixture was concentrated under reduced pressure. The mixture was diluted with water (20 mL) and then the suspension was based with NaOH (1 M) to pH=10. The resultant mixture was extracted with EA (30 mL*3). The combined organic layers were dried over $Na_2SO_4$, filtered and concentrated to dryness under reduced pressure. The residue was purified by silica gel column chromatography to give 3-bromo-6-methoxy-8-(4-(trifluoromethyl)phenoxy)quinoline (230 mg, 16.3% yield).

Methyl 6-methoxy-84-(4-(trifluoromethyl)phenoxy)quinoline-3-carboxylate

To a solution of compound 3-bromo-6-methoxy-8-(4-(trifluoromethyl)phenoxy)quinoline (180.0 mg, 0.45 mmol, 1.0 eq) and TEA (183.0 mg, 1.81 mmol, 4.0 eq) in DMSO (3 mL) and MeOH (2.4 mL) was added $Pd(dppf)Cl_2$ (33.1 mg, 45.2 umol, 0.1 eq) under $N_2$. The suspension was degassed under vacuum and purged with CO several times. The mixture was stirred under CO (45 Psi) at 80° C. for 16 hours. The reaction mixture was concentrated under reduced pressure. The mixture was diluted with water (10 mL) and the resultant mixture was extracted with EA (30 mL*3). The combined organic layers were dried over $Na_2SO_4$, filtered and concentrated to dryness under reduced pressure. The residue was purified by silica gel column chromatography to give methyl 6-methoxy-8-(4-(trifluoromethyl)phenoxy)quinoline-3-carboxylate (140 mg, 82.0% yield).

6-methoxy-8-(4-(trifluoromethyl)phenoxy)quinoline-3-carboxylic Acid

To a solution of compound methyl 6-methoxy-8-(4-(trifluoromethyl)phenoxy)quinoline-3-carboxylate (25.0 mg, 66.2 umol, 1.0 eq) in THF (0.45 mL) and MeOH (0.15 mL) was added NaOH (1 M, 0.13 mL, 2.0 eq). The reaction mixture was stirred at 25° C. for 2 hours. The suspension was adjusted with HCl (1 M) to pH=5, and then the resultant mixture was extracted with EA (10 mL*3). The combined organic layers were dried over $Na_2SO_4$, filtered and concentrated to dryness under reduced pressure to give 6-methoxy-8-(4-(trifluoromethyl)phenoxy)quinoline-3-carboxylic acid (20 mg, crude).

(R)-6-methoxy-N-(1-(pyridin-2-yl)ethyl)-4-(4-(trifluoromethyl)phenoxy)quinoline-3-carboxamide To a solution of compound 6-methoxy-8-(4-(trifluoromethyl)phenoxy)quinoline-3-carboxylic acid (20.0 mg, 55.0 umol, 1.0 eq), compound (R)-1-(pyridin-2-yl)ethan-1-amine (6.7 mg, 55.0 umol, 1.0 eq) and DIPEA (14.2 mg, 0.11 umol, 2.0 eq) in DCM (1 mL) was added HATU (31.4 mg, 82.5 umol, 1.5 eq). The reaction mixture was stirred at 25° C. for 2 hours. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC to give the title compound (8.33 mg, 32.3% yield). LCMS(ESI): RT=0.840 min, mass calcd. for $C_{25}H_{20}F_3N_3O_3$ 467.15, m/z found 468.0 $[M+H]^+$; $^1$H NMR (400 MHz, $CDCl_3$) δ 9.21 (d, J=2.0 Hz, 1H), 8.67 (s, 1H), 8.59 (d, J=5.0 Hz, 1H), 8.28-8.16 (m, 1H), 7.82-7.74 (m, 1H), 7.62 (d, J=8.6 Hz, 2H), 7.40 (d, J=7.5 Hz, 1H), 7.34-7.28 (m, 1H), 7.16 (d, J=8.5 Hz, 2H), 7.03 (d, J=2.4 Hz, 1H), 6.95 (d, J=2.6 Hz, 1H), 5.46-5.36 (m, 1H), 3.94 (s, 3H), 1.67 (d, J=6.6 Hz, 3H).

Example 41: (S)-6-methoxy-N-(1-(pyridin-2-yl)ethyl)-8-(4-(trifluoromethyl)phenoxy)quinoline-3-carboxamide (Compound 43)

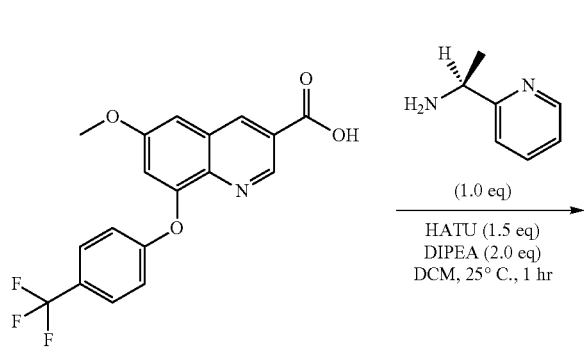

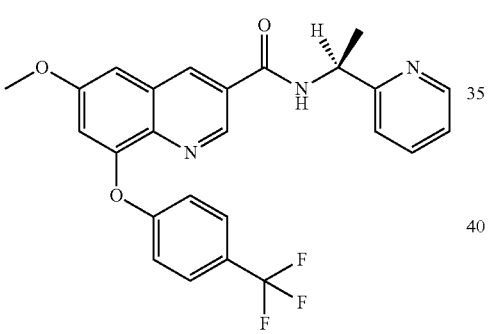

Compound 43

To a solution of 6-methoxy-8-(4-(trifluoromethyl)phenoxy)quinoline-3-carboxylic acid (prepared as described in Example 40) (25.0 mg, 68.8 umol, 1.0 eq), compound (S)-1-(pyridin-2-yl)ethan-1-amine (8.4 mg, 68.8 umol, 1.0 eq) and DIPEA (17.8 mg, 0.14 mol, 2.0 eq) in DCM (1 mL) was added HATU (39.2 mg, 0.10 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC to give the title compound (11.25 mg, 34.9% yield). LCMS (ESI): RT=0.843 min, mass calcd. for $C_{25}H_{20}F_3N_3O_3$ 467.44, m/z found 468.0 [M+H]$^+$; $^1$H NMR (400 MHz, CDCl$_3$) δ 9.20 (d, J=1.9 Hz, 1H), 8.62 (d, J=1.9 Hz, 1H), 8.57 (d, J=4.6 Hz, 1H), 8.14 (d, J=6.6 Hz, 1H), 7.76-7.68 (m, 1H), 7.62 (d, J=8.6 Hz, 2H), 7.34 (d, J=7.8 Hz, 1H), 7.27-7.23 (m, 1H), 7.16 (d, J=8.5 Hz, 2H), 7.02 (d, J=2.4 Hz, 1H), 6.95 (d, J=2.5 Hz, 1H), 5.44-5.34 (m, 1H), 3.94 (s, 3H), 1.63 (d, J=6.8 Hz, 3H).

Example 42: (R)-6-methoxy-N-(1-methoxypropan-2-yl)-8-(4-(trifluoromethyl)phenoxy)quinoline-3-carboxamide (Compound 44)

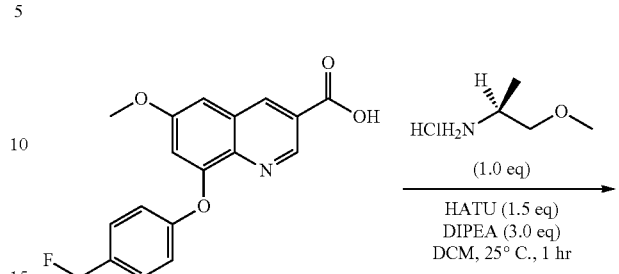

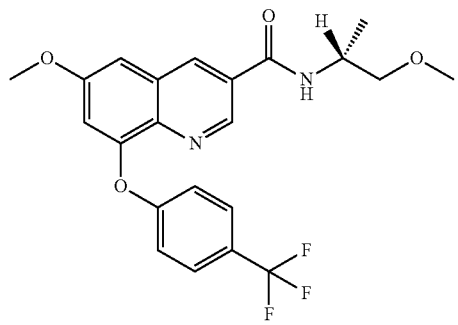

Compound 44

To a solution of 6-methoxy-8-(4-(trifluoromethyl)phenoxy)quinoline-3-carboxylic acid (prepared as described in Example 40) (25.0 mg, 68.8 umol, 1.0 eq), compound (R)-1-methoxypropan-2-amine (8.6 mg, 68.8 umol, 1.0 eq, HCl) and DIPEA (26.6 mg, 0.20 mmol, 3.0 eq) in DCM (1 mL) was added HATU (39.2 mg, 0.10 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC to give the title compound (11.71 mg, 38.7% yield). LCMS (ESI): RT=0.910 min, mass calcd. for $C_{22}H_{21}F_3N_2O_4$ 434.15, m/z found 435.0 [M+H]$^+$; $^1$H NMR (400 MHz, CDCl$_3$) δ 9.07 (d, J=2.0 Hz, 1H), 8.54 (d, J=1.9 Hz, 1H), 7.61 (d, J=8.5 Hz, 2H), 7.15 (d, J=8.5 Hz, 2H), 7.00 (d, J=2.5 Hz, 1H), 6.94 (d, J=2.5 Hz, 1H), 6.60 (d, J=7.8 Hz, 1H), 4.50-4.37 (m, 1H), 3.93 (s, 3H), 3.58-3.53 (m, 1H), 3.51-3.45 (m, 1H), 3.41 (s, 3H), 1.35 (d, J=6.8 Hz, 3H).

Example 43: (S)-6-methoxy-N-(1-methoxypropan-2-yl)-8-(4-(trifluoromethyl)phenoxy)quinoline-3-carboxamide (Compound 45)

Example 44: (R)-N-(1-(pyrazin-2-yl)ethyl)-5-(4-(trifluoromethyl)phenoxy)-2-naphthamide (Compound 46) and (S)-N-(1-(pyrazin-2-yl)ethyl)-5-(4-(trifluoromethyl)phenoxy)-2-naphthamide (Compound 47)

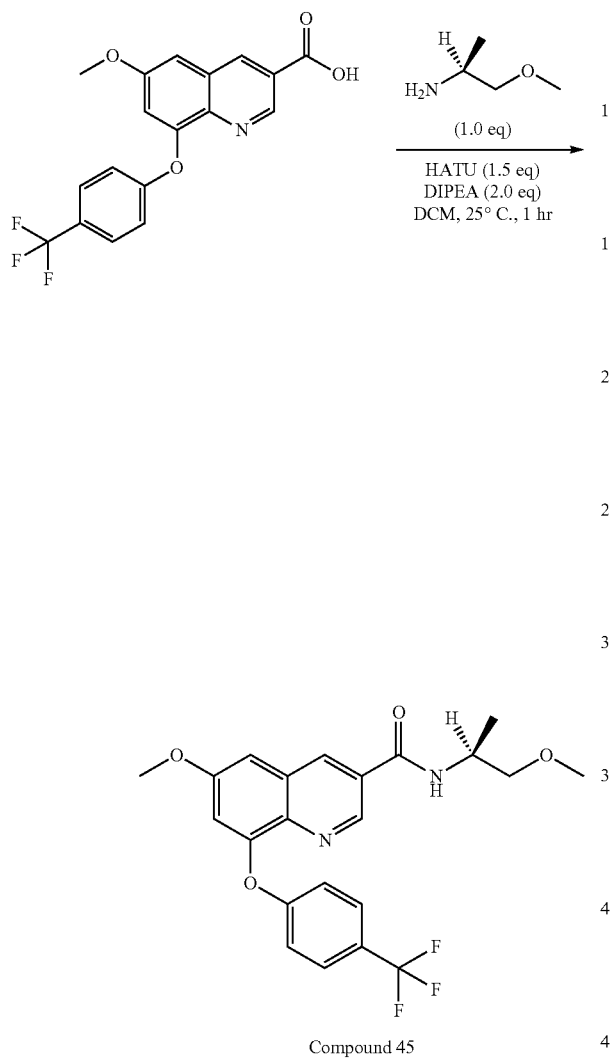

Compound 45

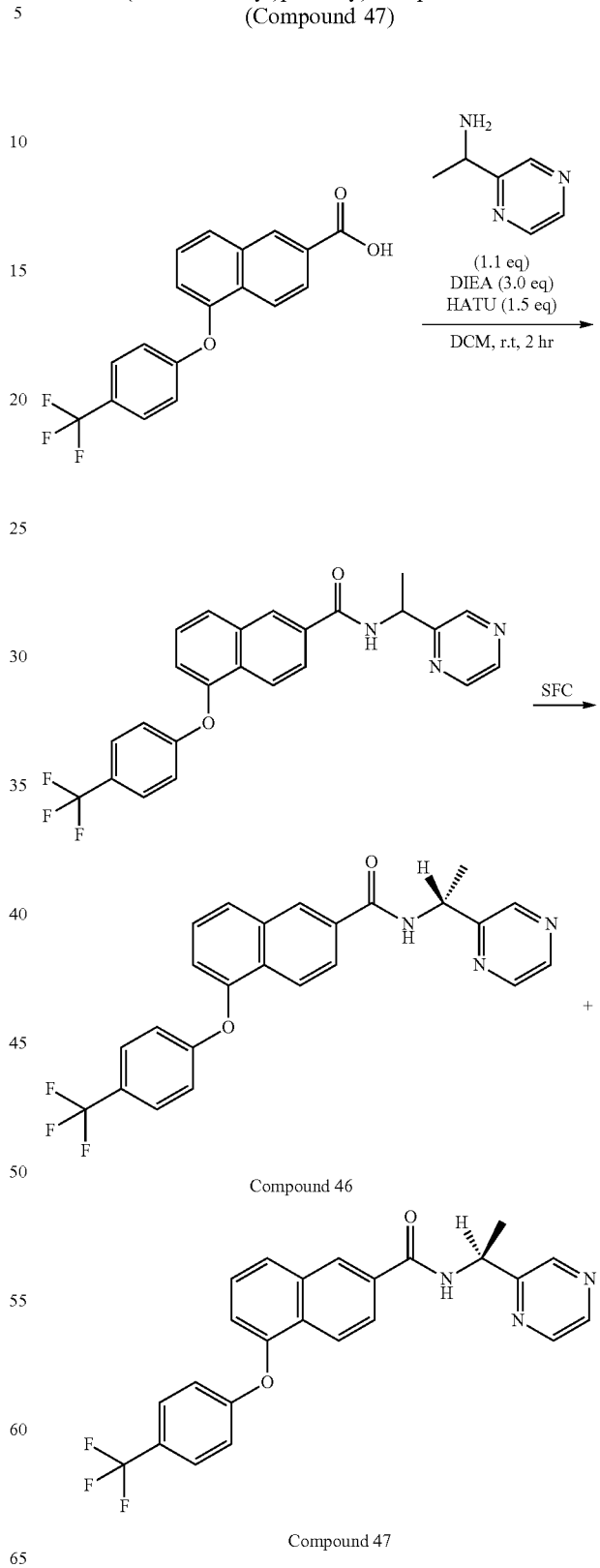

Compound 46

Compound 47

To a solution of 6-methoxy-8-(4-(trifluoromethyl)phenoxy)quinoline-3-carboxylic acid (prepared as described in Example 40) (25.0 mg, 68.8 umol, 1.0 eq), compound (S)-1-methoxypropan-2-amine (6.1 mg, 68.8 umol, 1.0 eq) and DIPEA (17.8 mg, 0.14 mol, 2.0 eq) in DCM (1 mL) was added HATU (39.2 mg, 0.10 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC to give the title compound (13.85 mg, 46.3% yield). LCMS (ESI): RT=0.906 min, mass calcd. for $C_{22}H_{21}F_3N_2O_4$ 434.15, m/z found 435.0 $[M+H]^+$; $^1$H NMR (400 MHz, $CDCl_3$) δ 9.07 (d, J=1.9 Hz, 1H), 8.54 (d, J=1.6 Hz, 1H), 7.62 (d, J=8.5 Hz, 2H), 7.15 (d, J=8.5 Hz, 2H), 7.00 (d, J=2.4 Hz, 1H), 6.95 (d, J=2.4 Hz, 1H), 6.59 (d, J=8.0 Hz, 1H), 4.49-4.37 (m, 1H), 3.93 (s, 3H), 3.58-3.53 (m, 1H), 3.51-3.46 (m, 1H), 3.41 (s, 3H), 1.35 (d, J=6.8 Hz, 3H).

N-(1-(pyrazin-2-yl)ethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-pyrazin-2-ylethanamine (40.7 mg, 0.33 mmol, 1.1 eq) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. Compound N-(1-pyrazin-2-ylethyl)-5-[4-(trifluoromethyl)phenoxy]naphthalene-2-carboxamide (22 mg, 49.7 umol, 16.5% yield) was obtained.

(R)-N-(1-(pyrazin-2-yl)ethyl)-5-(4-(trifluoromethyl)phenoxy)-2-naphthamide (Compound 46) and (S)-N-(1-(pyrazin-2-yl)ethyl)-5-(4-(trifluoromethyl)phenoxy)-2-naphthamide (Compound 47)

The racemic compound N-(1-pyrazin-2-ylethyl)-5-[4-(trifluoromethyl)phenoxy]naphthalene-2-carboxamide (22 mg, 50.30 umol, 1 eq) was separated by SFC (column: REGIS (s,s) WHELK-O1 (250 mm*30 mm, 5 um); mobile phase: [0.1% NH₃H₂O ETOH]; B %: 50%-50%, min) to give Compound 46 (6 mg, 13.6 umol, 27.2% yield) LCMS (ESI): RT=0.970 min, mass calcd for $C_{24}H_{18}F_3N_3O_2$ 437.41 m/z found 438.0 [M+H]⁺; ¹H NMR (400 MHz, CD₃OD) δ8.75 (s, 1H), 8.65-8.62 (m, 1H), 8.56-8.51 (m, 2H), 8.13 (d, J=8.8 Hz, 1H), 7.97-7.91 (m, 2H), 7.68 (d, J=8.5 Hz, 2H), 7.61 (t, J=7.9 Hz, 1H), 7.25 (dd, J=0.8, 7.8 Hz, 1H), 7.16 (d, J=8.5 Hz, 2H), 5.42 (q, J=7.2 Hz, 1H), 1.70 (d, J=7.3 Hz, 3H); and Compound 47 (5 mg, 11.4 umol, 22.6% yield) LCMS (ESI): RT=0.974 min, mass calcd for $C_{24}H_{18}F_3N_3O_2$ 437.41 m/z found 438.0 [M+H]⁺; ¹H NMR (400 MHz, CD₃OD) δ 8.75 (br s, 1H), 8.64 (s, 1H), 8.54 (d, J=1.5 Hz, 2H), 8.12 (d, J=8.8 Hz, 1H), 7.98-7.90 (m, 2H), 7.68 (d, J=8.5 Hz, 2H), 7.61 (t, J=7.9 Hz, 1H), 7.27-7.23 (m, 1H), 7.15 (d, J=8.5 Hz, 2H), 5.42 (q, J=7.0 Hz, 1H), 1.70 (d, J=7.0 Hz, 3H).

Example 45: (R)-N-(1-(1H-imidazol-4-yl)ethyl)-5-(4-(trifluoromethyl)phenoxy)-2-naphthamide (Compound 48) and (S)-N-(1-(1H-imidazol-4-yl)ethyl)-5-(4-(trifluoromethyl)phenoxy)-2-naphthamide (Compound 49)

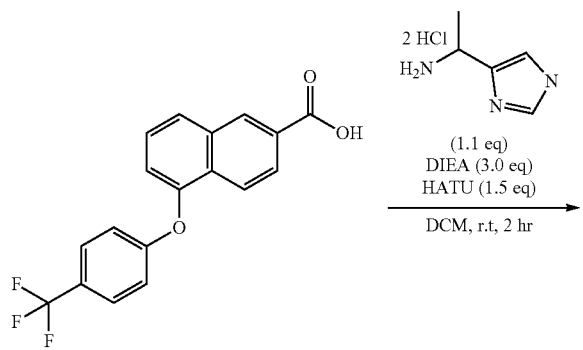

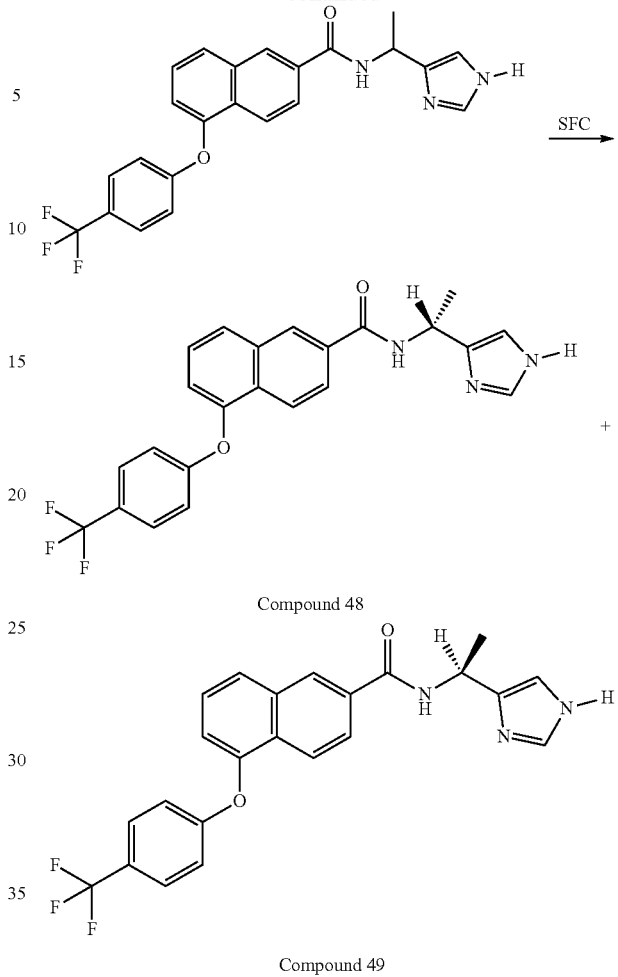

Compound 48

Compound 49

N-(1-(1H-imidazol-4-yl)ethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq) HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-(1H-imidazol-4-yl)ethanamine (60.9 mg, 0.33 mmol, 1.1 eq, 2HCl) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. Compound N-[1-(1H-imidazol-4-yl)ethyl]-5-[4-(trifluoromethyl)phenoxy]naphthalene-2-carboxamide (103 mg, 0.23 mmol, 79.6% yield) was obtained.

(R)-N-(1-(1H-imidazol-4-yl)ethyl)-5-(4-(trifluoromethyl)phenoxy)-2-naphthamide (Compound 48) and (S)-N-(1-(1H-imidazol-4-yl)ethyl)-5-(4-(trifluoromethyl)phenoxy)-2-naphthamide (Compound 49)

The racemic compound N-[1-(1H-imidazol-4-yl)ethyl]-5-[4-(trifluoromethyl)phenoxy]naphthalene-2-carboxamide (70 mg, 0.16 mmol, 1 eq) was purified by SFC (column: DAICEL CHIRALPAK IC (250 mm*30 mm, 5 um); mobile phase: [0.1% NH$_3$H$_2$O IPA]; B %: 45%-45%, min) to give Compound 48 (13 mg, 30.2 umol, 18.3% yield) LCMS (ESI): RT=0.860 min, mass calcd for C$_{23}$H$_{18}$F$_3$N$_3$O$_2$ 425.40 m/z found 426.0 [M+H]$^+$; $^1$H NMR (400 MHz, CD$_3$OD) δ 8.34 (s, 1H), 7.99 (d, J=8.8 Hz, 1H), 7.81-7.76 (m, 2H), 7.56 (br d, J=8.5 Hz, 2H), 7.48 (t, J=7.9 Hz, 1H), 7.12 (d, J=7.5 Hz, 1H), 7.03 (br d, J=8.5 Hz, 2H), 4.55 (s, 1H), 4.51-4.45 (m, 4H), 4.43 (t, J=6.1 Hz, 1H), 1.15-1.05 (m, 4H); and Compound 49 (15 mg, 34.9 umol, 21.2% yield) LCMS (ESI): RT=0.860 min, mass calcd for C$_{23}$H$_{18}$F$_3$N$_3$O$_2$ 425.40 m/z found 426.0 [M+H]$^+$; $^1$H NMR (400 MHz, CD$_3$OD) δ 8.37 (d, J=1.5 Hz, 1H), 7.96 (d, J=8.9 Hz, 1H), 7.84-7.73 (m, 2H), 7.58-7.51 (m, 3H), 7.45 (t, J=7.9 Hz, 1H), 7.09 (dd, J=0.8, 7.6 Hz, 1H), 7.00 (d, J=8.5 Hz, 2H), 6.94 (s, 1H), 5.26 (q, J=6.9 Hz, 1H), 1.52 (d, J=6.9 Hz, 3H).

Example 46: (S)-N-(1-amino-1-oxopropan-2-yl)-5-(4-(trifluoromethyl)phenoxy)-2-naphthamide (Compound 50)

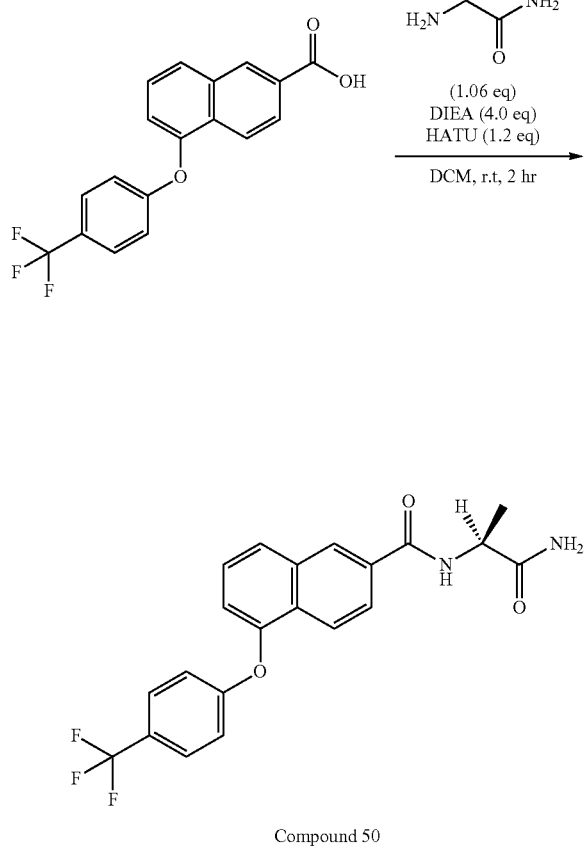

Compound 50

To a solution of 5-[4-(trifluoromethyl)phenoxy]naphthalene-2-carboxylic acid (50 mg, 0.15 mmol, 1 eq) and HATU (68.6 mg, 0.18 mmol, 1.2 eq) in DCM (2 mL) was added DIPEA (77.7 mg, 0.60 mmol, 0.10 mL, 4 eq). After addition, the mixture was stirred at 25° C. for 0.5 hr, and then (2S)-2-aminopropanamide (19.8 mg, 0.15 mmol, 1.06 eq, HCl) was added. The resulting mixture was stirred at 25° C. for 2 hr. The reaction mixture was added H$_2$O (50 mL) and extracted with EA (30 mL*3). The combined organic layers were washed with brine (20 mL), dried with anhydrous Na$_2$SO$_4$, filtered and concentrated under reduced pressure to give a residue. The residue was purified by prep-HPLC to give the title compound (31 mg, 77.0 umol, 51.2% yield). LCMS (ESI): RT=0.785 min, mass calcd for C$_{21}$H$_{17}$F$_3$N$_2$O$_3$ 402.37 m/z found 425.1 [M+Na]$^+$; $^1$H NMR (400 MHz, DMSO-d$_6$) δ 8.68-8.58 (m, 2H), 8.03-7.94 (m, 3H), 7.74 (d, J=8.8 Hz, 2H), 7.64 (t, J=8.0 Hz, 1H), 7.43 (br s, 1H), 7.33 (d, J=7.0 Hz, 1H), 7.17 (d, J=8.5 Hz, 2H), 7.03 (s, 1H), 4.47 (quin, J=7.2 Hz, 1H), 1.37 (d, J=7.3 Hz, 3H).

Example 47: (R)-N-(1-amino-1-oxopropan-2-yl)-5-(4-(trifluoromethyl)phenoxy)-2-naphthamide (Compound 51)

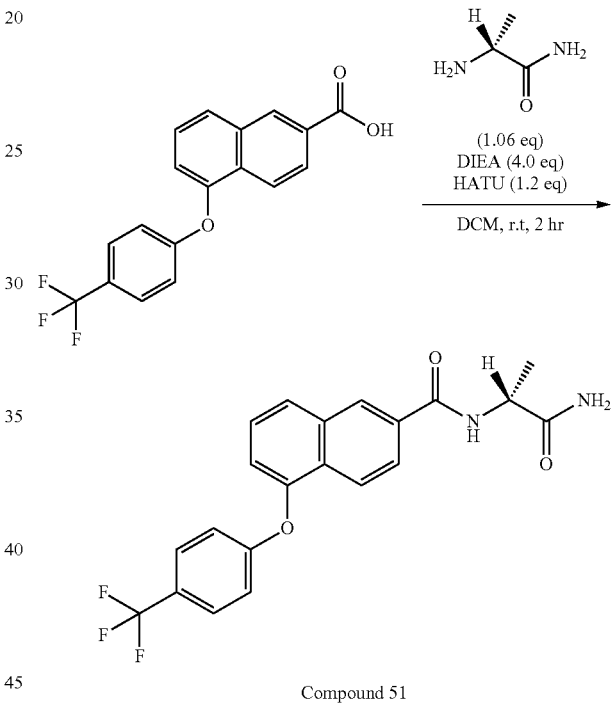

Compound 51

To a solution of 5-[4-(trifluoromethyl)phenoxy]naphthalene-2-carboxylic acid (50 mg, 0.15 mmol, 1 eq) and HATU (68.6 mg, 0.18 mmol, 1.2 eq) in DCM (2 mL) was added DIPEA (77.7 mg, 0.60 mmol, 0.10 mL, 4 eq). After addition, the mixture was stirred at 25° C. for 0.5 hr, and then (2R)-2-aminopropanamide (19.8 mg, 0.15 mmol, 1.06 eq, HCl) was added. The resulting mixture was stirred at 25° C. for 2 hr. The reaction mixture was added H$_2$O (20 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC to give the title compound (30.5 mg, 75.8 umol, 50.3% yield). LCMS (ESI): RT=0.790 min, mass calcd for C$_{21}$H$_{17}$F$_3$N$_2$O$_3$ 402.37 m/z found 425.1.0 [M+Na]; $^1$H NMR (400 MHz, DMSO-d$_6$) δ 8.69-8.57 (m, 2H), 8.04-7.93 (m, 3H), 7.74 (d, J=8.8 Hz, 2H), 7.63 (t, J=7.9 Hz, 1H), 7.43 (br s, 1H), 7.33 (d, J=7.5 Hz, 1H), 7.16 (d, J=8.5 Hz, 2H), 7.03 (br s, 1H), 4.47 (quin, J=7.1 Hz, 1H), 1.37 (d, J=7.3 Hz, 3H).

Example 48: (S)-N-(1-(2H-tetrazol-5-yl)ethyl)-5-(4-(trifluoromethyl)phenoxy)-2-naphthamide (Compound 52) and (R)-N-(1-(2H-tetrazol-5-yl)ethyl)-5-(4-(trifluoromethyl)phenoxy)-2-naphthamide (Compound 53)

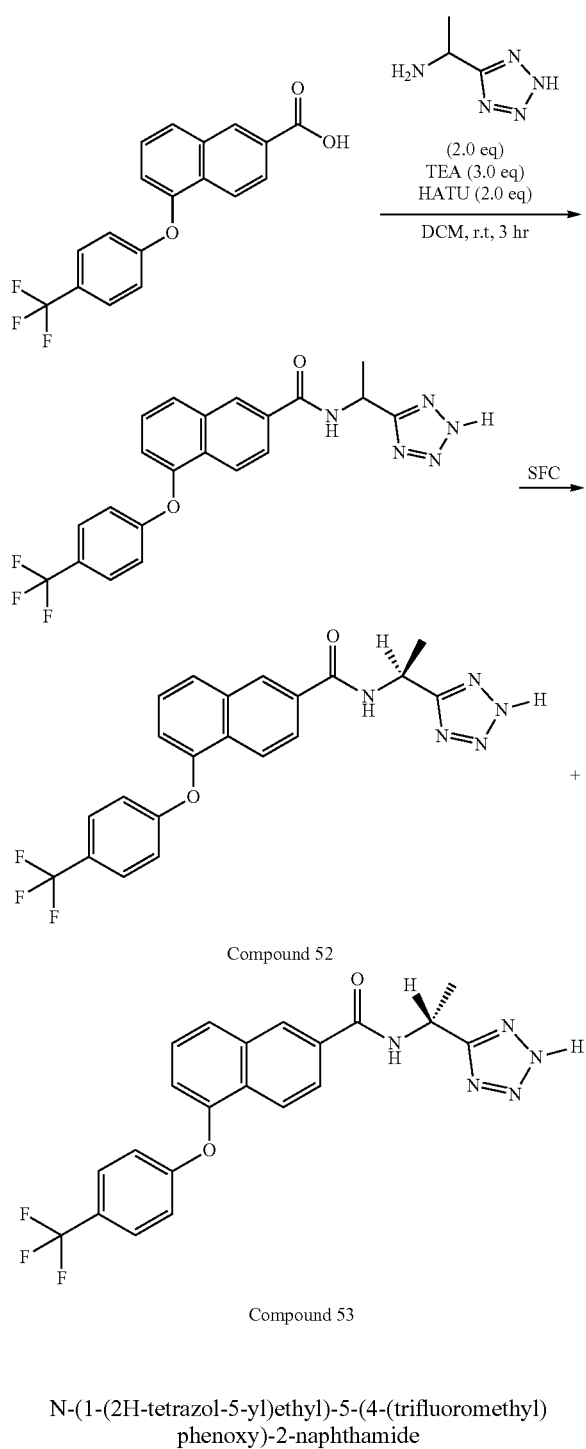

Compound 52

Compound 53

N-(1-(2H-tetrazol-5-yl)ethyl)-5-(4-(trifluoromethyl)phenoxy)-2-naphthamide

To a solution of 5-[4-(trifluoromethyl)phenoxy]naphthalene-2-carboxylic acid (0.05 g, 0.15 mmol, 1 eq) in DMF (3 mL) was added HATU (114.4 mg, 0.30 mmol, 2 eq) and $Et_3N$ (45.6 mg, 0.45 mmol, 62.8 uL, 3 eq). The mixture was stirred for 0.5 hrs at 25° C. 1-(2H-tetrazol-5-yl)ethanamine (34.0 mg, 0.30 mmol, 2 eq) was added to the mixture. The mixture was stirred for 2.5 h at 25° C. The mixture was quenched by $H_2O$ (30 mL), and the mixture was extracted with EA (20 mL*3). The combined organic phase was washed with brine (20 mL*3), dried with anhydrous $Na_2SO_4$, filtered and concentrated in vacuum. The residue was purified by pre-HPLC. Compound N-[1-(2H-tetrazol-5-yl)ethyl]-5-[4-(trifluoromethyl)phenoxy]naphthalene-2-carboxamide (30 mg, 70.2 umol, 46.6% yield) was obtained.

(S)-N-(1-(2H-tetrazol-5-yl)ethyl)-5-(4-(trifluoromethyl)phenoxy)-2-naphthamide (Compound 52) and (R)-N-(1-(2H-tetrazol-5-yl)ethyl)-5-(4-(trifluoromethyl)phenoxy)-2-naphthamide (Compound 53)

The racemic compound N-[1-(2H-tetrazol-5-yl)ethyl]-5-[4-(trifluoromethyl)phenoxy]naphthalene-2-carboxamide (0.02 g, 46.8 umol, 1 eq) was separated by SFC (column: REGIS (s,s) WHELK-O1 (250 mm*30 mm, 5 um); mobile phase: [0.1% $NH_3H_2O$ ETOH]; B %: 40%-40%, min) twice to give Compound 52 (1.1 mg, 2.6 umol, 11.1% yield) LCMS (ESI): RT=0.929 min, mass calcd for $C_{21}H_{16}F_3N_5O_2$ 427.38 m/z found 428.1 $[M+H]^+$; $^1$H NMR (400 MHz, $CD_3OD$) δ 8.44 (s, 1H), 8.00 (d, J=8.8 Hz, 1H), 7.86 (br d, J=8.6 Hz, 1H), 7.80 (d, J=8.3 Hz, 1H), 7.56 (d, J=8.6 Hz, 2H), 7.49 (t, J=7.9 Hz, 1H), 7.13 (d, J=7.4 Hz, 1H), 7.03 (d, J=8.6 Hz, 2H), 5.54 (br d, J=6.8 Hz, 1H), 1.66 (br d, J=6.5 Hz, 3H); and Compound 53 (3.2 mg, 7.6 umol, 32.5% yield) LCMS (ESI): RT=0.923 min, mass calcd for $C_{21}H_{16}F_3N_5O_2$ 427.38 m/z found 428.0 $[M+H]^+$; $^1$H NMR (400 MHz, $CD_3OD$) δ 8.41 (s, 1H), 7.96 (d, J=8.6 Hz, 1H), 7.87-7.72 (m, 2H), 7.53 (d, J=8.6 Hz, 2H), 7.45 (t, J=7.9 Hz, 1H), 7.09 (d, J=7.5 Hz, 1H), 7.00 (d, J=8.5 Hz, 2H), 5.52 (br s, 1H), 1.61 (br d, J=5.6 Hz, 3H).

Example 49: N-(1-(pyridin-2-yl)cyclopropyl)-5-(4-(trifluoromethyl)phenoxy)-2-naphthamide (Compound 54)

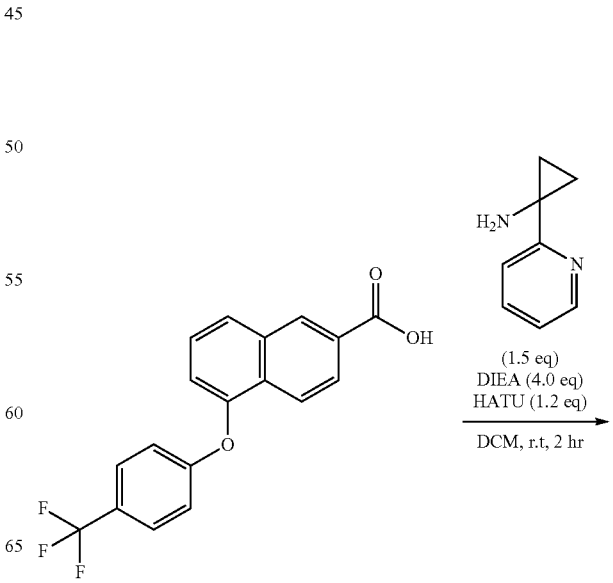

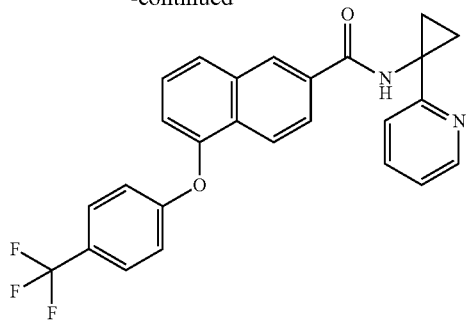

Compound 54

To a solution of 5-[4-(trifluoromethyl)phenoxy]naphthalene-2-carboxylic acid (50 mg, 0.15 mmol, 1 eq) and HATU (68.6 mg, 0.18 mmol, 1.2 eq) in DCM (2 mL) was added DIEA (77.7 mg, 0.60 mmol, 0.10 mL, 4 eq). After addition, the mixture was stirred at 25° C. for 0.5 hr, and then 1-(2-pyridyl)cyclopropanamine (121.1 mg, 0.22 mmol, 1.5 eq) was added. The resulting mixture was stirred at 25° C. for 2 hr. The reaction mixture was added H$_2$O (20 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC. The title compound (17 mg, 37.9 umol, 25.1% yield) was obtained. LCMS (ESI): RT=0.783 min, mass calcd for C$_{26}$H$_{19}$F$_3$N$_2$O$_2$ 448.44 m/z found 449.1 [M+H]$^+$; $^1$H NMR (400 MHz, DMSO-d$_6$) δ 9.47 (s, 1H), 8.66 (s, 1H), 8.48-8.44 (m, 1H), 8.03-7.97 (m, 3H), 7.75 (d, J=8.5 Hz, 2H), 7.70-7.63 (m, 2H), 7.40-7.34 (m, 2H), 7.19-7.13 (m, 3H), 1.61-1.55 (m, 2H), 1.34-1.28 (m, 2H).

Example 50: (S)-N-(1-(1-methyl-1H-tetrazol-5-yl)ethyl)-5-(4-(trifluoromethyl)phenoxy)-2-naphthamide (Compound 55) and (R)-N-(1-(1-methyl-1H-tetrazol-5-yl)ethyl)-5-(4-(trifluoromethyl)phenoxy)-2-naphthamide (Compound 56)

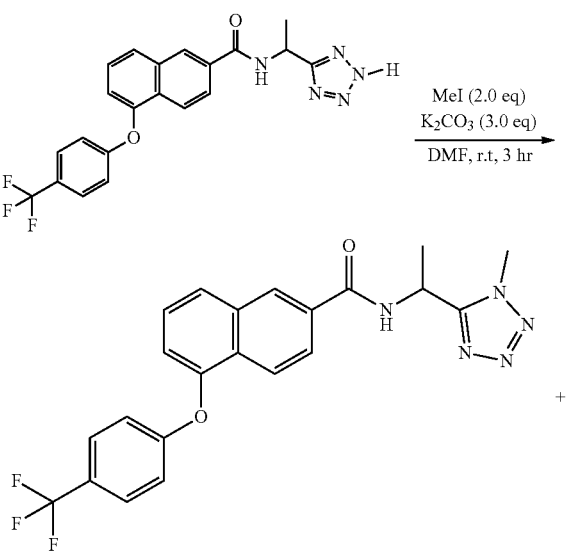

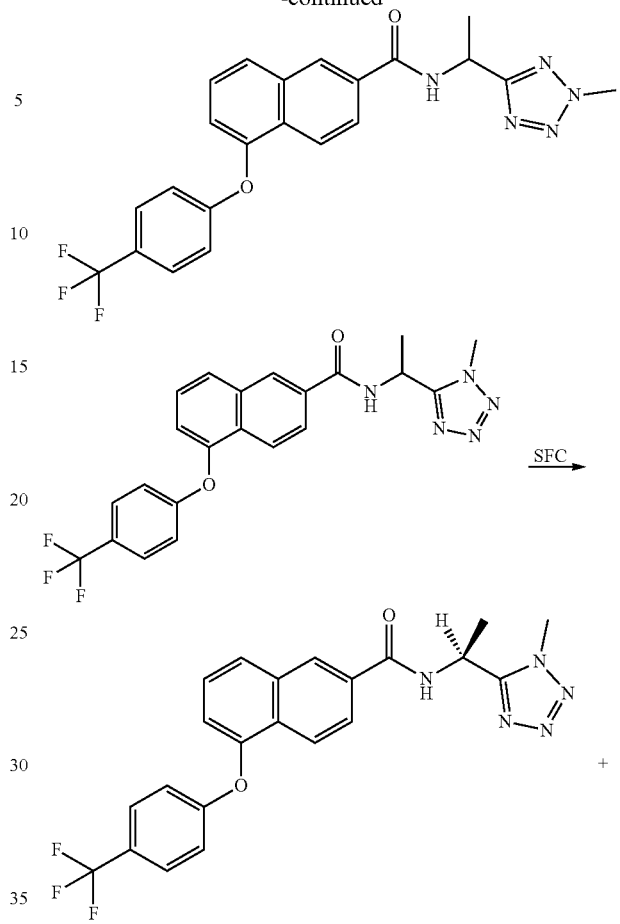

Compound 55

Compound 56

N-(1-(1-methyl-1H-tetrazol-5-yl)ethyl)-5-(4-(trifluoromethyl)phenoxy)-2-naphthamide and N-(1-(2-methyl-2H-tetrazol-5-yl)ethyl)-5-(4-(trifluoromethyl)phenoxy)-2-naphthamide To the solution of N-[1-(2H-tetrazol-5-yl)ethyl]-5-[4-(trifluoromethyl)phenoxy]naphthalene-2-carboxamide (0.2 g, 0.46 mmol, 1 eq) in DMF (3 mL) was added CH$_3$I (132.8 mg, 0.93 mmol, 58.2 uL, 2 eq) and K$_2$CO$_3$ (194.0 mg, 1.40 mmol, 3 eq). The mixture was stirred at 25° C. for 3 hr. The reaction solution was added to H$_2$O (10 mL). The mixture was extracted with ethyl acetate (20 mL*3). The combined organic phase was washed with brine (20 mL*3), dried with anhydrous Na$_2$SO$_4$, filtered and concentrated in vacuum.

The residue was purified by prep-HPLC to give N-[1-(2-methyltetrazol-5-yl)ethyl]-5-[4-(trifluoromethyl)phenoxy]naphthalene-2-carboxamide (20.9 mg, 47.3 umol, 10.1% yield) and N-[1-(1-methyltetrazol-5-yl)ethyl]-5-[4-(trifluoromethyl)phenoxy]naphthalene-2-carboxamide (20.8 mg, 47.3 umol, 10.1% yield).

(S)-N-(1-(1-methyl-1H-tetrazol-5-yl)ethyl)-5-(4-(trifluoromethyl)phenoxy)-2-naphthamide (Compound 55) and (R)-N-(1-(1-methyl-1H-tetrazol-5-yl)ethyl)-5-(4-(trifluoromethyl)phenoxy)-2-naphthamide (Compound 56)

The racemic N-(1-(1-methyl-1H-tetrazol-5-yl)ethyl)-5-(4-(trifluoromethyl)phenoxy)-2-naphthamide (0.02 g, 45.3 umol, 1 eq) was separated by SFC (column: DAICEL CHIRALPAK AD-H (250 mm*30 mm, 5 um); mobile phase: [0.1% NH$_3$H$_2$O ETOH]; B %: 40%-40%, min) to give Compound 55 (2.2 mg, 4.9 umol, 21.9% yield) LCMS (ESI): RT=0.954 min, mass calcd for C$_{22}$H$_{18}$F$_3$N$_5$O$_2$ 441.41 m/z found 442.0 [M+H]$^+$; $^1$H NMR (400 MHz, CD$_3$OD) δ 8.40 (s, 1H), 8.00 (d, J=8.8 Hz, 1H), 7.85-7.74 (m, 2H), 7.58-7.42 (m, 3H), 7.14 (d, J=7.5 Hz, 1H), 7.03 (d, J=8.6 Hz, 2H), 5.54 (q, J=7.2 Hz, 1H), 4.15-4.04 (m, 3H), 1.69 (d, J=7.0 Hz, 3H); and Compound 56 (2.6 mg, 6.0 umol, 26.9% yield) LCMS (ESI). RT=0.957 min, mass calcd for C$_{22}$H$_{18}$F$_3$N$_5$O$_2$ 441.41 m/z found 442.0 [M+H]$^+$; $^1$H NMR (400 MHz, CD$_3$OD) δ 8.39 (s, 1H), 8.00 (d, J=8.8 Hz, 1H), 7.84-7.77 (m, 2H), 7.56 (d, J=8.6 Hz, 2H), 7.49 (t, J=7.9 Hz, 1H), 7.13 (d, J=7.5 Hz, 1H), 7.03 (d, J=8.6 Hz, 2H), 5.54 (q, J=7.0 Hz, 1H), 4.09 (s, 3H), 1.69 (d, J=7.0 Hz, 3H).

Example 51: (R)-N-(1-(2-methyl-2H-tetrazol-5-yl)ethyl)-5-(4-(trifluoromethyl)phenoxy)-2-naphthamide (Compound 57) and (S)-N-(1-(2-methyl-2H-tetrazol-5-yl)ethyl)-5-(4-(trifluoromethyl)phenoxy)-2-naphthamide (Compound 58)

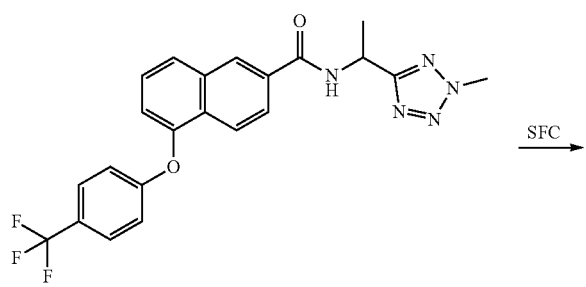

Compound 57

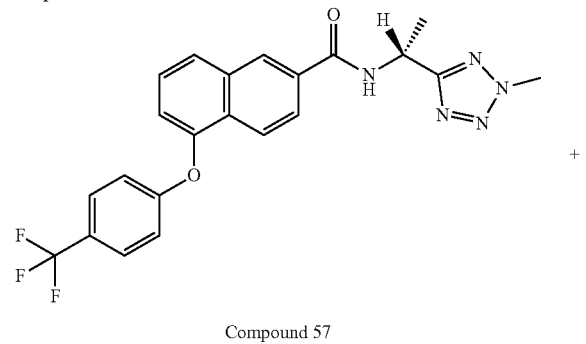

Compound 58

(R)-N-(1-(2-methyl-2H-tetrazol-5-yl)ethyl)-5-(4-(trifluoromethyl)phenoxy)-2-naphthamide (Compound 57) and (S)-N-(1-(2-methyl-2H-tetrazol-5-yl)ethyl)-5-(4-(trifluoromethyl)phenoxy)-2-naphthamide (Compound 58)

The racemic compound N-[1-(2-methyltetrazol-5-yl)ethyl]-5-[4-(trifluoromethyl)phenoxy]naphthalene-2-carboxamide (prepared as described in Example 50) (0.02 g, 45.3 umol, 1 eq) was separated by SFC (column: Phenomenex-Cellulose-2 (250 mm*30 mm, 10 um); mobile phase: [0.1% NH$_3$H$_2$O IPA]; B %: 35%-35%, min) to give Compound 57 (4.8 mg, 10.8 umol, 48.0% yield) LCMS (ESI): RT=0.960 min, mass calcd for C$_{22}$H$_{18}$F$_3$N$_5$O$_2$ 441.41 m/z found 442.0 [M+H]$^+$; $^1$H NMR (400 MHz, CD$_3$OD) δ 8.41 (d, J=1.0 Hz, 1H), 8.00 (d, J=8.8 Hz, 1H), 7.86-7.76 (m, 2H), 7.56 (d, J=8.6 Hz, 2H), 7.49 (t, J=7.9 Hz, 1H), 7.13 (d, J=7.6 Hz, 1H), 7.04 (d, J=8.5 Hz, 2H), 5.50 (q, J=7.1 Hz, 1H), 4.25 (s, 3H), 1.63 (d, J=7.1 Hz, 3H); and Compound 58 (4.5 mg, 10.1 umol, 45.0% yield) LCMS(ESI): RT=0.959 min, mass calcd for C$_{22}$H$_{18}$F$_3$N$_5$O$_2$ 441.41 m/z found 442.0 [M+H]$^+$; $^1$H NMR (400 MHz, CD$_3$OD) S 8.41 (s, 1H), 8.00 (d, J=8.8 Hz, 1H), 7.86-7.75 (m, 2H), 7.56 (d, J=8.6 Hz, 2H), 7.48 (t, J=7.9 Hz, 1H), 7.13 (d, J=7.5 Hz, 1H), 7.03 (d, J=8.6 Hz, 2H), 5.50 (q, J=7.1 Hz, 1H), 4.30-4.20 (m, 3H), 1.63 (d, J=7.1 Hz, 3H).

Example 52: (R)-N-(1-cyclobutylethyl)-5-(4-(trifluoromethyl)phenoxy)-2-naphthamide (Compound 59) and (S)-N-(1-cyclobutylethyl)-5-(4-(trifluoromethyl)phenoxy)-2-naphthamide (Compound 60)

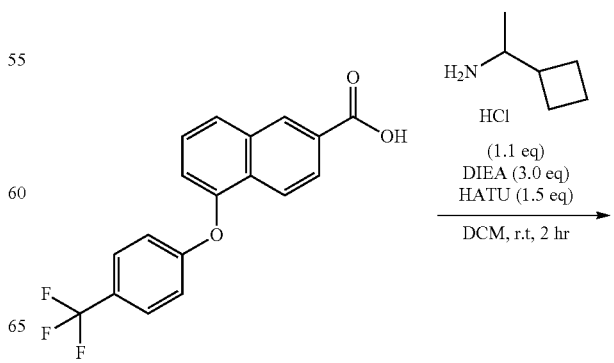

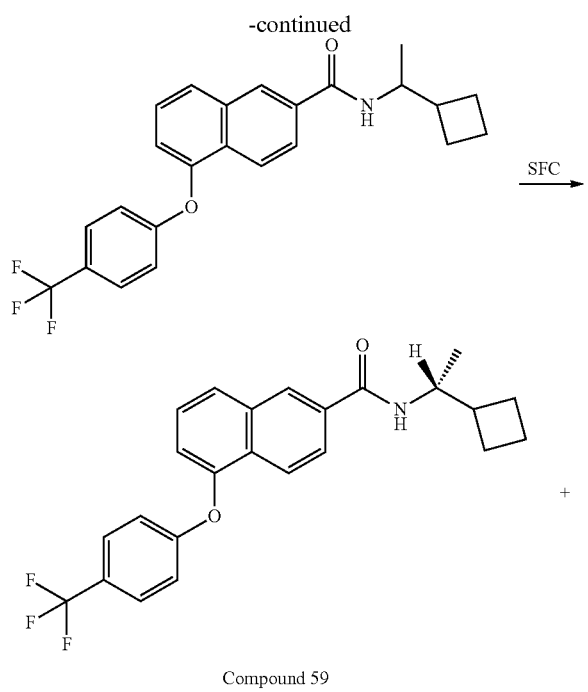

Compound 59

Compound 60

N-(1-cyclobutylethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-cyclobutylethanamine (44.9 mg, 0.33 mmol, 1.1 eq, HCl) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by silica gel column chromatography. Compound N-(1-cyclobutylethyl)-5-[4-(trifluoromethyl)phenoxy]naphthalene-2-carboxamide (91 mg, 0.21 mmol, 71.6% yield) was obtained.

(R)-N-(1-cyclobutylethyl)-5-(4-(trifluoromethyl)phenoxy)-2-naphthamide (Compound 59) and (S)-N-(1-cyclobutylethyl)-5-(4-(trifluoromethyl)phenoxy)-2-naphthamide (Compound 60)

The racemic compound N-(1-cyclobutylethyl)-5-[4-(trifluoromethyl)phenoxy]naphthalene-2-carboxamide (91 mg, 0.22 mmol, 1 eq) was purified by SFC (column: DAICEL CHIRALPAK AS-H (250 mm*30 mm, 5 um); mobile phase: [0.1% NH₃H2O ETOH]; B %: 30%-30%, min) to give Compound 59 (26.7 mg, 64.5 umol, 29.3% yield) LCMS (ESI): RT=1.068 min, mass calcd for C₂₄H₂₂F₃NO₂ 413.43 m/z found 414.0 [M+H]⁺; ¹H NMR (400 MHz, CD₃OD) δ 8.44 (d, J=1.5 Hz, 1H), 8.10 (d, J=8.8 Hz, 1H), 7.93-7.87 (m, 2H), 7.72-7.55 (m, 3H), 7.24 (d, J=7.8 Hz, 1H), 7.15 (br d, J=8.5 Hz, 2H), 4.23-4.13 (m, 1H), 2.56-2.46 (m, 1H), 2.15-2.04 (m, 2H), 1.97-1.78 (m, 4H), 1.18 (d, J=6.5 Hz, 3H); and Compound 60 (18.9 mg, 45.6 umol, 20.7% yield) LCMS (ESI): RT=1.069 min, mass calcd for C₂₄H₂₂F₃NO₂ 413.43 m/z found 414.0 [M+H]⁺; ¹H NMR (400 MHz, CD₃OD) δ 8.44 (d, J=1.5 Hz, 1H), 8.10 (d, J=8.8 Hz, 1H), 7.90 (td, J=1.9, 8.7 Hz, 2H), 7.70-7.56 (m, 3H), 7.24 (d, J=7.5 Hz, 1H), 7.15 (d, J=8.8 Hz, 2H), 4.22-4.13 (m, 1H), 2.57-2.45 (m, 1H), 2.16-2.03 (m, 2H), 1.97-1.80 (m, 4H), 1.18 (d, J=6.8 Hz, 3H).

Example 53: (R)-N-(but-3-yn-2-yl)-5-(4-(trifluoromethyl)phenoxy)-2-naphthamide (Compound 61) and (S)-N-(but-3-yn-2-yl)-5-(4-(trifluoromethyl)phenoxy)-2-naphthamide (Compound 62)

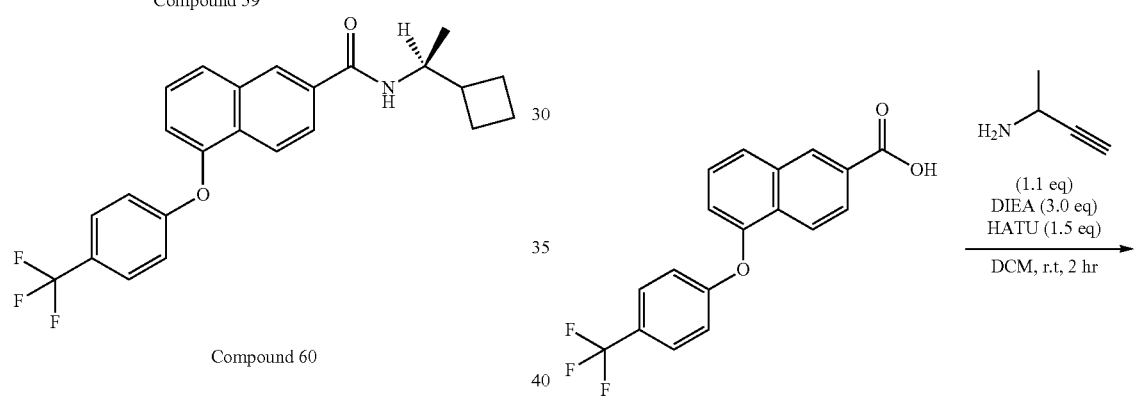

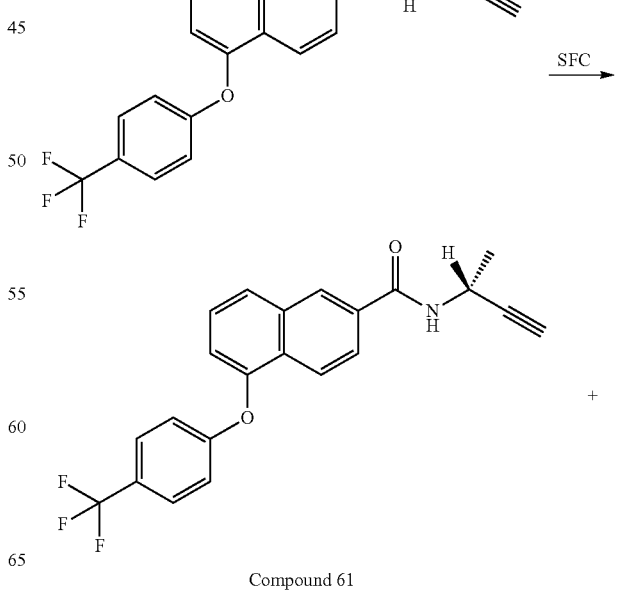

Compound 61

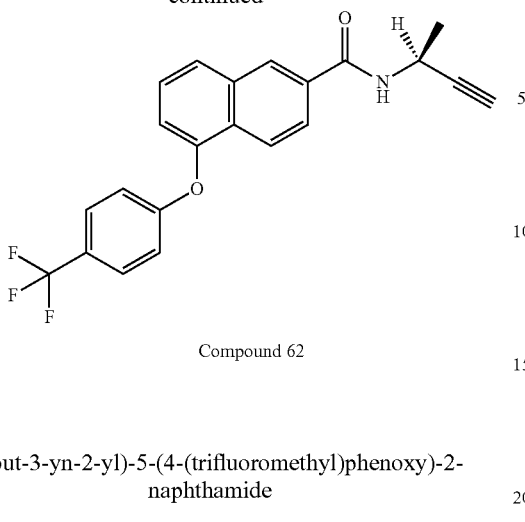

Compound 62

N-(but-3-yn-2-yl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then but-3-yn-2-amine hydrochloride (34.9 mg, 0.33 mmol, 1.1 eq) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by silica gel column chromatography. Compound N-(1-methylprop-2-ynyl)-5-[4-(trifluoromethyl)phenoxy]naphth alene-2-carboxamide (112 mg, 0.29 mmol, 96.6% yield) was obtained.

(R)-N-(but-3-yn-2-yl)-5-(4-(trifluoromethyl)phenoxy)-2-naphthamide (Compound 61) and (S)-N-(but-3-yn-2-yl)-5-(4-(trifluoromethyl)phenoxy)-2-naphthamide (Compound 62)

The racemic compound N-(1-methylprop-2-ynyl)-5-[4-(trifluoromethyl)phenoxy]naphthalene-2-carboxamide (98 mg, 0.25 mmol, 1 eq) was purified by SFC to give Compound 61 (24.6 mg, 64.1 umol, 25.1% yield) LCMS (ESI): RT=0.999 min, mass calcd for $C_{22}H_{16}F_3NO_2$ 383.36 m/z found 384.0 [M+H]⁺; ¹H NMR (400 MHz, CD₃OD) δ 8.48 (d, J=1.5 Hz, 1H), 8.12 (d, J=8.8 Hz, 1H), 7.95-7.89 (m, 2H), 7.68 (d, J=8.8 Hz, 2H), 7.60 (t, J=7.9 Hz, 1H), 7.25 (d, J=7.0 Hz, 1H), 7.15 (d, J=8.5 Hz, 2H), 5.02 (dd, J=2.4, 6.9 Hz, 1H), 2.72 (d, J=2.3 Hz, 1H), 1.56 (d, J=7.0 Hz, 4H); and Compound 62 (24.8 mg, 64.8 umol, 25.3% yield) LCMS (ESI): RT=0.999 min, mass calcd for $C_{22}H_{16}F_3NO_2$ 383.36 m/z found 383.9 [M+H]⁺; ¹H NMR (400 MHz, CD₃OD) δ 8.48 (d, J=1.5 Hz, 1H), 8.12 (d, J=8.8 Hz, 1H), 7.95-7.89 (m, 2H), 7.68 (d, J=8.8 Hz, 2H), 7.60 (t, J=8.0 Hz, 1H), 7.25 (d, J=7.5 Hz, 1H), 7.15 (d, J=8.8 Hz, 2H), 5.02 (dq, J=2.3, 7.0 Hz, 1H), 2.72 (d, J=2.5 Hz, 1H), 1.56 (d, J=7.0 Hz, 4H).

Example 54: (S)-N-(1-(1H-imidazol-2-yl)ethyl)-5-(4-(trifluoromethyl)phenoxy)-2-naphthamide (Compound 63) and (R)-N-(1-(1H-imidazol-2-yl)ethyl)-5-(4-(trifluoromethyl)phenoxy)-2-naphthamide (Compound 64)

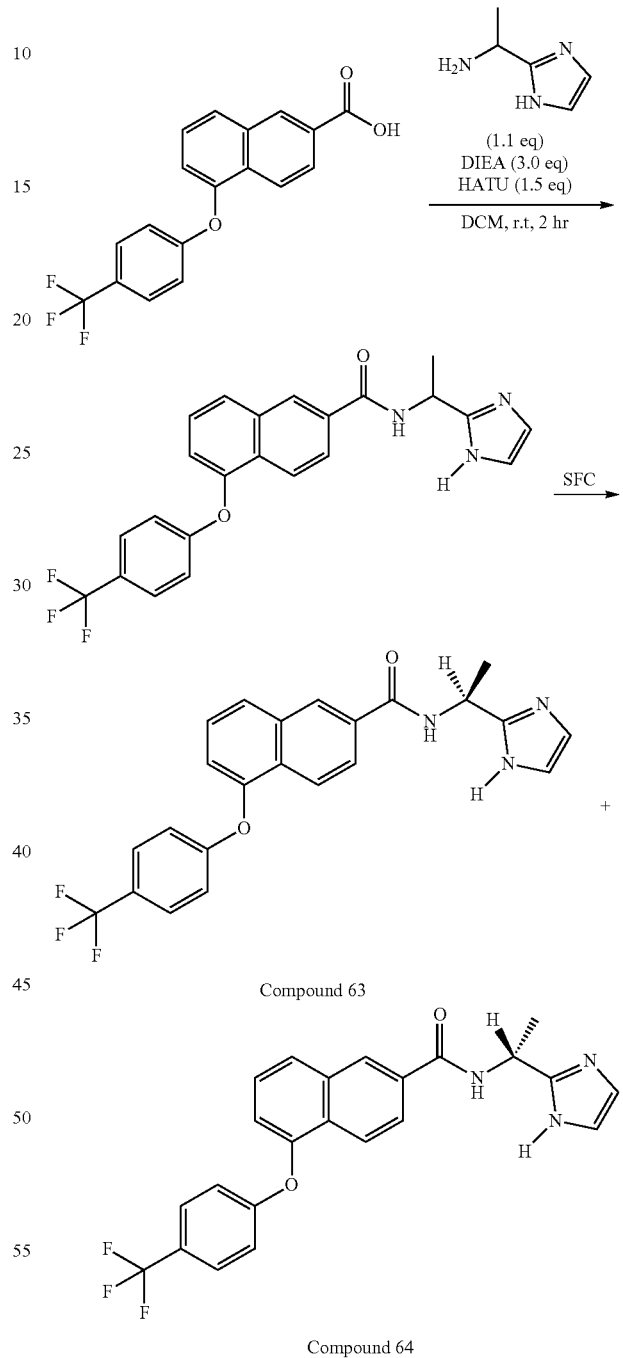

Compound 63

Compound 64

N-(1-(1H-imidazol-2-yl)ethyl)-5-(4-(trifluoromethyl)phenoxy)-2-naphthamide

The mixture of 5-[4-(trifluoromethyl)phenoxy]naphthalene-2-carboxylic acid (100 mg, 0.30 mmol, 1 eq), HATU (171.6 mg, 0.45 mmol, 1.5 eq) and DIPEA (116.6 mg, 0.90 mmol, 0.15 mL, 3 eq) in DCM (2 mL) was stirred at 25° C. for 1 hr. Then 1-(1H-imidazol-2-yl)ethanamine (48.8 mg, 0.33 mmol, 1.1 eq, HCl) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. Compound N-[1-(1H-imidazol-2-yl)ethyl]-5-[4-(trifluoromethyl)phenoxy]naphthalene-2-carboxamide (52 mg, 0.12 mmol, 40.2% yield) was obtained.

(S)-N-(1-(1H-imidazol-2-yl)ethyl)-5-(4-(trifluoromethyl)phenoxy)-2-naphthamide (Compound 63) and (R)-N-(1-(1H-imidazol-2-yl)ethyl)-5-(4-(trifluoromethyl)phenoxy)-2-naphthamide (Compound 64)

The racemic compound N-[1-(1H-imidazol-2-yl)ethyl]-5-[4-(trifluoromethyl)phenoxy]naphthalene-2-carboxamide (52 mg, 0.12 mmol, 1 eq) was purified by SFC to give Compound 63 (5.2 mg, 12.3 umol, 10.1% yield) LCMS (ESI): RT=0.855 min, mass calcd for C₂₃H₁₈F₃N₃O₂ 425.40 m/z found 426.0 [M+H]⁺; ¹H NMR (400 MHz, CD₃OD) δ 8.43 (d, J=1.3 Hz, 1H), 8.00 (d, J=8.8 Hz, 1H), 7.85 (dd, J=1.8, 8.8 Hz, 1H), 7.80 (d, J=8.3 Hz, 1H), 7.56 (d, J=8.8 Hz, 2H), 7.48 (t, J=8.0 Hz, 1H), 7.16-7.10 (m, 1H), 7.03 (d, J=8.5 Hz, 2H), 6.89 (s, 2H), 5.31 (q, J=7.0 Hz, 1H), 1.58 (d, J=7.0 Hz, 3H); and Compound 64 (21.5 mg, 50.6 umol, 41.4% yield) LCMS (ESI): RT=0.855 min, mass calcd for C₂₃H₁₈F₃N₃O₂ 425.40 m/z found 426.0 [M+H]⁺; ¹H NMR (400 MHz, CD₃OD) δ 8.55 (d, J=1.5 Hz, 1H), 8.11 (d, J=8.8 Hz, 1H), 8.00-7.89 (m, 2H), 7.68 (d, J=8.5 Hz, 2H), 7.60 (t, J=8.0 Hz, 1H), 7.24 (dd, J=0.8, 7.5 Hz, 1H), 7.15 (d, J=8.5 Hz, 2H), 7.01 (s, 2H), 5.43 (q, J=7.0 Hz, 1H), 1.70 (d, J=7.0 Hz, 3H).

Example 55: (S)-N-(1-(6-aminopyridin-2-yl)ethyl)-5-(4-(trifluoromethyl)phenoxy)-2-naphthamide (Compound 65) and (R)-N-(1-(6-aminopyridin-2-yl)ethyl)-5-(4-(trifluoromethyl)phenoxy)-2-naphthamide (Compound 66)

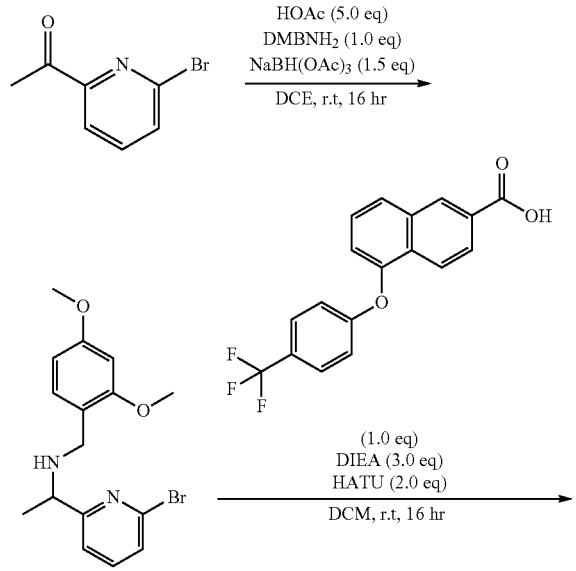

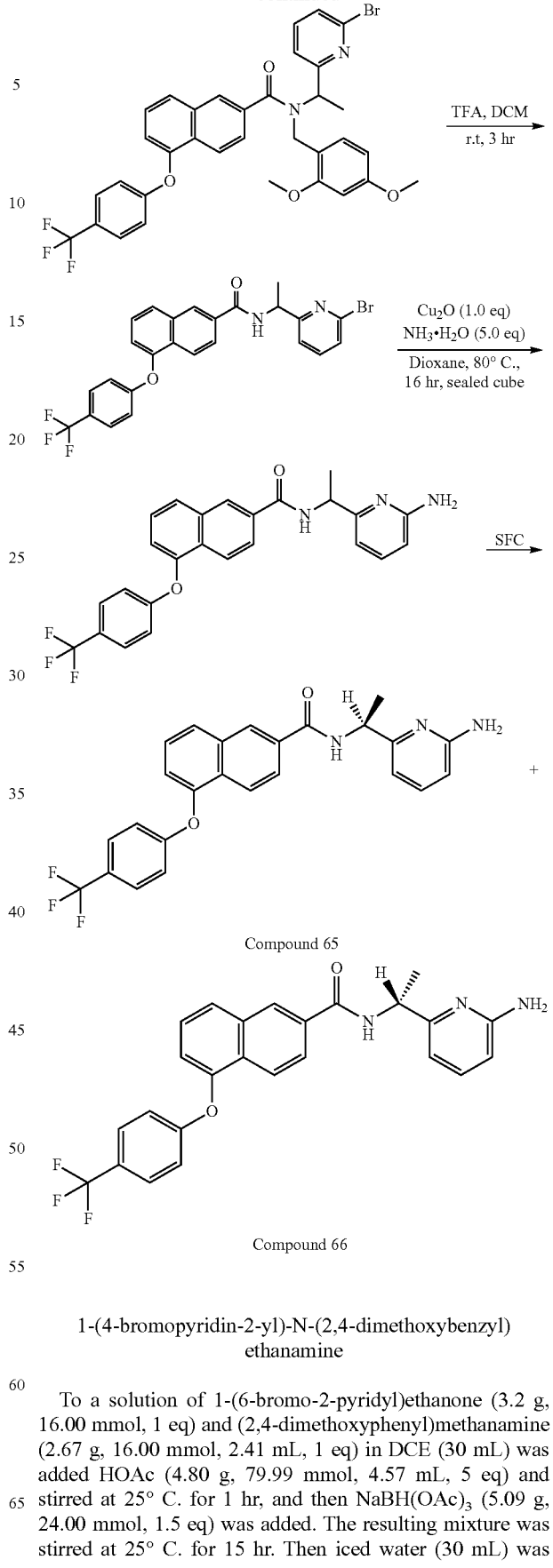

Compound 65

Compound 66

1-(4-bromopyridin-2-yl)-N-(2,4-dimethoxybenzyl)ethanamine

To a solution of 1-(6-bromo-2-pyridyl)ethanone (3.2 g, 16.00 mmol, 1 eq) and (2,4-dimethoxyphenyl)methanamine (2.67 g, 16.00 mmol, 2.41 mL, 1 eq) in DCE (30 mL) was added HOAc (4.80 g, 79.99 mmol, 4.57 mL, 5 eq) and stirred at 25° C. for 1 hr, and then NaBH(OAc)₃ (5.09 g, 24.00 mmol, 1.5 eq) was added. The resulting mixture was stirred at 25° C. for 15 hr. Then iced water (30 mL) was added and the mixture was neutralized to pH=9-10 with aq. NaOH (2 M). The aqueous phase was extracted with EA (30 mL*3). The combined organic phase was washed with brine (60 mL), dried with anhydrous $Na_2SO_4$, filtered and concentrated in vacuo. The residue was purified by flash silica gel chromatography. Compound 1-(6-bromo-2-pyridyl)-N-[(2,4-dimethoxyphenyl)methyl]ethanamine (1.6 g, 4.42 mmol, 27.6% yield) was obtained.

N-(1-(6-bromopyridin-2-yl)ethyl)-N-(2,4-dimethoxybenzyl)-5-(4-(trifluoromethyl)phenoxy)-2-naphthamide A mixture of 5-[4-(trifluoromethyl)phenoxy]naphthalene-2-carboxylic acid (473.0 mg, 1.42 mmol, 1 eq), HATU (1.08 g, 2.85 mmol, 2 eq) in DCM (10 mL) was added DIPEA (551.9 mg 4.27 mmol, 0.74 mL, 3 eq) at 25° C. After addition, the mixture was stirred at 25° C. for 1 hr, and then 1-(6-bromo-2-pyridyl)-N-[(2,4-dimethoxyphenyl)methyl]ethanamine (500 mg, 1.42 mmol, 1 eq) (in DCM (3 mL)) was added. The resulting mixture was stirred at 25° C. for 15 hr. The residue was poured into $H_2O$ (50 mL) and stirred for 5 min. The aqueous phase was extracted with EA (30 mL*3). The combined organic phase was washed with brine (50 mL), dried with anhydrous $Na_2SO_4$, filtered and concentrated in vacuum. The residue was purified by flash silica gel chromatography. Compound N-[1-(6-bromo-2-pyridyl)ethyl]-N-[(2,4-dimethoxyphenyl)methyl]-5-[4-(trifluoromethyl)phenoxy]naphthalene-2-carboxamide (650 mg, 0.97 mmol, 68.6% yield) was obtained.

N-(1-(6-bromopyridin-2-yl)ethyl)-5-(4-(trifluoromethyl)phenoxy)-2-naphthamide To a solution of N-[1-(6-bromo-2-pyridyl)ethyl]-N-[(2,4-dimethoxyphenyl)methyl]-5-[4-(trifluoromethyl)phenoxy]naphthalene-2-carboxamide (590 mg, 0.88 mmol, 1 eq) in DCM (0.5 mL) was added TFA (9.09 g, 79.69 mmol, 5.90 mL, 89.88 eq). The mixture was stirred at 25° C. for 3 hr. Then iced water (30 mL) was added and the mixture was neutralized to pH=9-10 with aq. NaOH (2 M). The aqueous phase was extracted with EA (30 mL*3). The combined organic phase was washed with brine (60 mL), dried with anhydrous $Na_2SO_4$, filtered and concentrated in vacuo to give crude product. The residue was purified by flash silica gel chromatography. CompoundN-[1-(6-bromo-2-pyridyl)ethyl]-5-[4-(trifluoromethyl)phenoxy]naphthalene-2-carboxamide (425 mg, 0.82 mmol, 93.0% yield) was obtained.

N-(1-(6-aminopyridin-2-yl)ethyl)-5-(4-(trifluoromethyl)phenoxy)-2-naphthamide A mixture of N-[1-(6-bromo-2-pyridyl)ethyl]-5-[4-(trifluoromethyl)phenoxy]naphthalene-2-carboxamide (150 mg, 0.29 mmd, 1 eq), $Cu_2O$ (41.6 mg, 0.29 mmol, 29.7 uL, 1 eq), $NH_3.H_2O$ (134.2 mg, 1.46 mmol, 0.14 mL, 38%, 5 eq) in dioxane (1 mL) were loaded in a sealed reaction tube. The reaction temperature was increased to 80° C. and the reaction mixture was stirred at 80° C. for 16 hr. The mixture was poured into $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuo. The residue was purified by flash silica gel chromatography. Compound N-[1-(6-amino-2-pyridyl)ethyl]-5-[4-(trifluoromethyl)phenoxy]naphthalene-2-carboxamide (98 mg, 0.21 mmol, 74.5% yield) was obtained.

(S)-N-(1-(6-aminopyridin-2-yl)ethyl)-5-(4-(trifluoromethyl)phenoxy)-2-naphthamide (Compound 65) and (R)-N-(1-(6-aminopyridin-2-yl)ethyl)-5-(4-(trifluoromethyl)phenoxy)-2-naphthamide (Compound 66)

The racemic compound N-[1-(6-amino-2-pyridyl)ethyl]-5-[4-(trifluoromethyl)phenoxy]naphthalene-2-carboxamide (85 mg, 0.18 mmol, 1 eq) was purified by SFC to give Compound 65 (20.2 mg, 42.0 umol, 22.3% yield) LCMS (ESI). RT=0.776 min, mass calcd for $C_{25}H_{20}F_3N_3O_2$ 451.44 m/z found 452.1 [M+H]$^+$; $^1$H NMR (400 MHz, $CD_3OD$) δ 8.51 (s, 1H), 8.10 (d, J=8.9 Hz, 1H), 7.98-7.87 (m, 2H), 7.66 (d, J=8.5 Hz, 2H), 7.58 (t, J=8.0 Hz, 1H), 7.43 (t, J=7.7 Hz, 1H), 7.23 (d, J=7.6 Hz, 1H), 7.13 (d, J=8.6 Hz, 2H), 6.66 (d, J=7.3 Hz, 1H), 6.46 (d, J=8.1 Hz, 1H), 5.18-5.07 (m, 1H), 1.56 (d, J=7.0 Hz, 3H); and Compound 66 (17.6 mg, 37.4 umol, 19.8% yield) LCMS (ESI): RT=0.773 min, mass calcd for $C_{25}H_{20}F_3N_3O_2$ 451.44 m/z found 452.1 [M+H]$^+$; $^1$H NMR (400 MHz, $CD_3OD$) δ 8.51 (s, 1H), 8.10 (d, J=8.8 Hz, 1H), 7.98-7.88 (m, 2H), 7.66 (d, J=8.5 Hz, 2H), 7.59 (t, J=7.9 Hz, 1H), 7.42 (t, J=7.8 Hz, 1H), 7.23 (d, J=7.5 Hz, 1H), 7.13 (d, J=8.4 Hz, 2H), 6.66 (d, J=7.5 Hz, 1H), 6.46 (d, J=8.3 Hz, 1H), 5.12 (q, J=6.9 Hz, 1H), 1.56 (d, J=6.9 Hz, 3H).

Example 56: N-isopropyl-4-(4-(trifluoromethyl)phenoxy)quinoline-7-carboxamide (Compound 67)

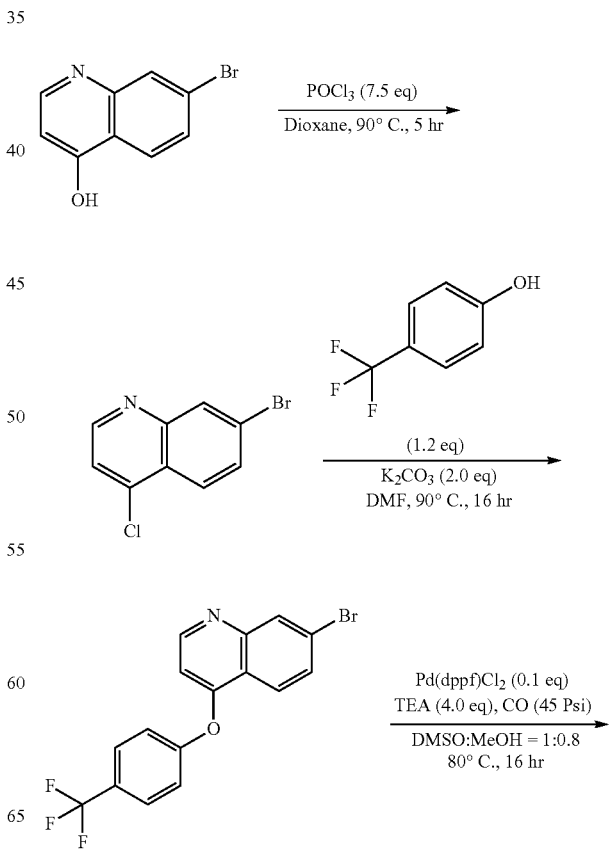

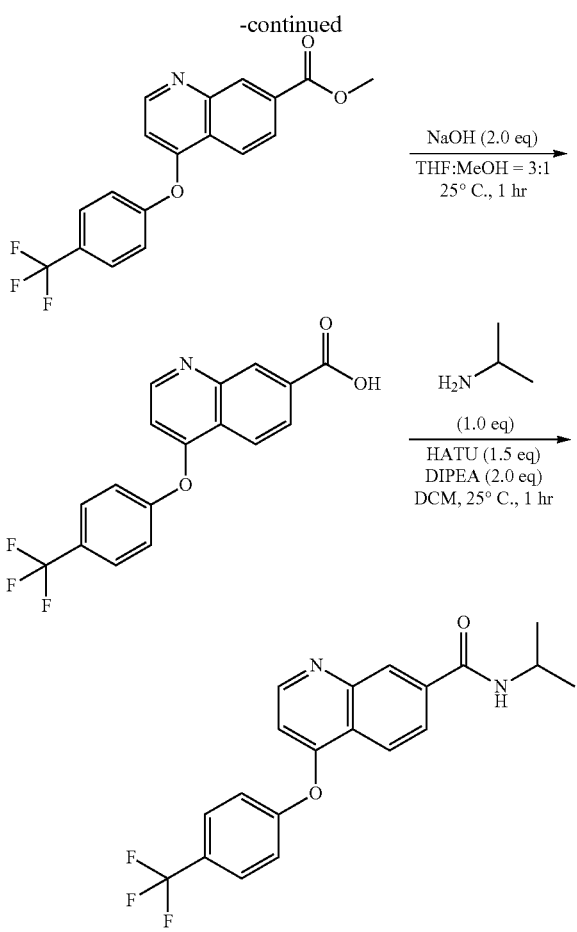

Compound 67

7-bromo-4-chloroquinoline

POCl$_3$ (1.03 g, 6.72 mmol, 7.53 eq) was added to a mixture of compound 7-bromoquinolin-4-ol (200.0 mg, 0.89 mmol, 1.0 eq) in Dioxane (2 mL) and the mixture was stirred at 90° C. for 5 hours. The reaction mixture was cooled to 25° C. The mixture was poured into water (10 mL) and adjusted to pH=8 with solid Na$_2$CO$_3$. The resultant mixture was extracted with EA (50 mL*3). The combined organic layers were dried over Na$_2$SO$_4$, filtered and concentrated to dryness under reduced pressure. The residue was purified by silica gel column chromatography to give 7-bromo-4-chloroquinoline (170 mg, 78.5% yield). $^1$H NMR (400 MHz, CDCl$_3$) δ 8.81 (d, J=4.5 Hz, 1H), 8.34 (d, J=1.8 Hz, 1H), 8.13 (d, J=9.0 Hz, 1H), 7.80-7.74 (m, 1H), 7.76 (dd, J=2.0, 9.0 Hz, 1H), 7.53 (d, J=4.8 Hz, 1H).

7-bromo-4-(4-(trifluoromethyl)phenoxy)quinoline

To a solution of compound 7-bromo-4-chloroquinoline (120.0 mg, 0.49 mmol, 1.0 eq) and compound 4-(trifluoromethyl)phenol (96.2 mg, 0.59 mmol, 1.2 eq) in DMF (1.5 mL) was added K$_2$CO$_3$ (136.7 mg, 0.98 mmol, 2.0 eq). The reaction mixture was stirred at 90° C. for 16 hours. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by silica gel column chromatography to give 7-bromo-4-(4-(trifluoromethyl)phenoxy)quinoline (52 mg, 27.6% yield). LCMS (ESI): RT=0.894 min, mass calcd. for C$_{16}$H$_9$BrF$_3$NO 366.98, m/z found 369.9 [M+H]$^+$; $^1$H NMR (400 MHz, CDCl$_3$) δ 8.73 (d, J=5.1 Hz, 1H), 8.36 (d, J=1.3 Hz, 1H), 8.21 (d, J=8.8 Hz, 1H), 7.77 (d, J=8.6 Hz, 2H), 7.72 (dd, J=1.8, 8.8 Hz, 1H), 7.31 (d, J=8.4 Hz, 2H), 6.65 (d, J=5.1 Hz, 1H).

Methyl 4-(4-(trifluoromethyl)phenoxy)quinoline-7-carboxylate

To a solution of compound 7-bromo-4-(4-(trifluoromethyl)phenoxy)quinoline (50.0 mg, 0.13 mmol, 1.0 eq) and TEA (54.9 mg, 0.54 mmol, 4.0 eq) in MeOH (0.8 mL) and DMSO (1 mL) was added Pd(dppf)Cl$_2$ (9.9 mg, 13.5 umol, 0.1 eq) under N$_2$. The suspension was degassed under vacuum and purged with CO several times. The mixture was stirred under CO (45 psi) at 80° C. for 16 hours. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by silica gel column chromatography to give methyl 4-(4-(trifluoromethyl)phenoxy)quinoline-7-carboxylate (40 mg, 80.5% yield). LCMS (ESI): RT=0.867 min, mass calcd. for C$_{18}$H$_{12}$F$_3$NO$_3$ 347.08, m/z found 348.0 [M+H]$^+$.

Methyl 4-(4-(trifluoromethyl)phenoxy)quinoline-7-carboxylate

To a solution of compound methyl 4-(4-(trifluoromethyl)phenoxy)quinoline-7-carboxylate (25.0 mg, 72.0 umol, 1.0 eq) in THF (0.6 mL) and MeOH (0.2 mL) was added NaOH (1 M, 0.14 mL, 2.0 eq). The reaction mixture was stirred at 25° C. for 1 hour. H$_2$O (5 mL) was added, and then the mixture was adjusted with HCl (1M) to pH=5. The resultant mixture was extracted with EA (10 mL*3). The combined organic layers were dried over Na$_2$SO$_4$, filtered and concentrated to dryness under reduced pressure to give methyl 4-(4-(trifluoromethyl)phenoxy)quinoline-7-carboxylate (20 mg, 83.3% yield).

N-isopropyl-4-(4-(trifluoromethyl)phenoxy)quinoline-7-carboxamide

To a solution of compound methyl 4-(4-(trifluoromethyl)phenoxy)quinoline-7-carboxylate (20.0 mg, 60.0 umol, 1.0 eq), iso-propylamine (3.6 mg, 60.0 umol, 1.0 eq) and DIPEA (15.5 mg, 0.12 mmol, 2.0 eq) in DCM (1 mL) was added HATU (34.2 mg, 90.0 umol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (10.42 mg, 45.4% yield). LCMS(ESI): RT=0.820 min, mass calcd. for C$_{20}$H$_{17}$F$_3$N$_2$O$_2$ 374.12, m/z found 375.0 [M+H]$^+$; $^1$H NMR (400 MHz, CDCl$_3$) δ 8.79 (d, J=5.3 Hz, 1H), 8.42-8.35 (m, 2H), 8.09-8.03 (m, 1H), 7.76 (d, J=8.5 Hz, 2H), 7.32 (d, J=8.5 Hz, 2H), 6.69 (d, J=5.0 Hz, 1H), 6.19 (d, J=7.5 Hz, 1H), 4.43-4.30 (m, 1H), 1.33 (d, J=6.5 Hz, 6H).

Example 57: (R)-N-(1-(1-methyl-1H-imidazol-2-yl)ethyl)-5-(4-(trifluoromethyl)phenoxy)-2-naphthamide (Compound 68) and (S)-N-(1-(1-methyl-1H-imidazol-2-yl)ethyl)-5-(4-(trifluoromethyl)phenoxy)-2-naphthamide (Compound 69)

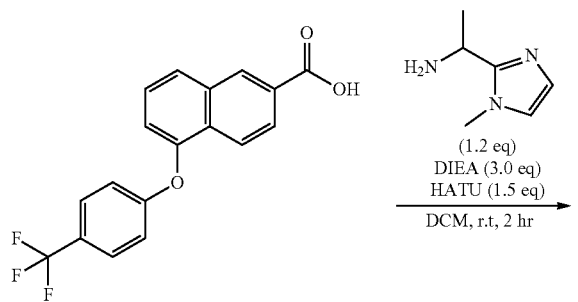

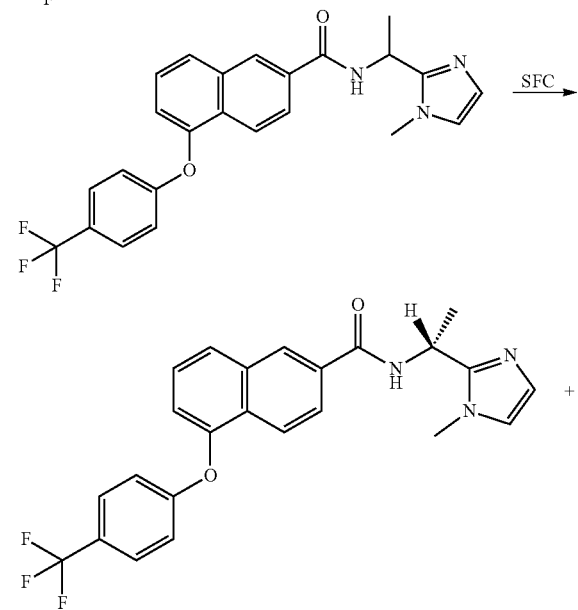

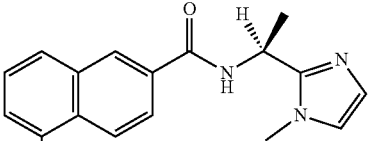

Compound 69

N-(1-(1-methyl-1H-imidazol-2-yl)ethyl)-5-(4-(trifluoromethyl)phenoxy)-2-naphthamide The mixture of 5-[4-(trifluoromethyl)phenoxy]naphthalene-2-carboxylic acid (200 mg, 0.60 mmol, 1 eq), DIPEA (233.3 mg, 1.81 mmol, 0.31 mL, 3 eq) and HATU (343.3 mg, 0.90 mmol, 1.5 eq) in DCM (2 mL) was stirred at 25° C. for 1 hr. Then 1-(1-methylimidazol-2-yl)ethanamine (90.4 mg, 0.72 mmol, 1.2 eq) was added at the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. Compound N-[1-(1-methylimidazol-2-yl)ethyl]-5-[4-(trifluoromethyl)phenoxy]naphthalene-2-carboxamide (90 mg, 0.20 mmol, 34.0% yield) was obtained.

(R)-N-(1-(1-methyl-1H-imidazol-2-yl)ethyl)-5-(4-(trifluoromethyl)phenoxy)-2-naphthamide (Compound 68) and (S)-N-(1-(1-methyl-1H-imidazol-2-yl)ethyl)-5-(4-(trifluoromethyl)phenoxy)-2-naphthamide (Compound 69)

N-[1-(1-methylimidazol-2-yl)ethyl]-5-[4-(trifluoromethyl)phenoxy]naphthalene-2-carboxamide (90 mg, 0.20 mmol, 1 eq) was separated by SFC to give Compound 68 (22.6 mg, 51.6 umol, 25.2% yield) LCMS (ESI): RT=0.872 min, mass calcd for $C_{24}H_{20}F_3N_3O_2$ 439.43 m/z found 440.0 [M+H]⁺; ¹H NMR (400 MHz, CD₃OD) δ 8.48 (s, 1H), 8.08 (d, J=8.8 Hz, 1H), 7.94-7.86 (m, 2H), 7.65 (d, J=8.8 Hz, 2H), 7.58 (t, J=7.9 Hz, 1H), 7.22 (d, J=7.5 Hz, 1H), 7.12 (d, J=8.5 Hz, 2H), 7.03 (s, 1H), 6.91 (d, J=1.3 Hz, 1H), 5.50 (q, J=7.0 Hz, 1H), 3.76 (s, 3H), 1.69-1.64 (m, 1H), 1.66 (d, J=7.0 Hz, 2H); and Compound 69 (10.5 mg, 23.8 umol, 11.6% yield) LCMS (ESI): RT=0.872 min, mass calcd for $C_{24}H_{20}F_3N_3O_2$ 439.43 m/z found 440.0 [M+H]⁺; ¹H NMR (400 MHz, CD₃OD) δ 8.46 (d, J=1.5 Hz, 1H), 8.06 (d, J=8.8 Hz, 1H), 7.92-7.83 (m, 2H), 7.63 (d, J=8.5 Hz, 2H), 7.55 (t, J=8.0 Hz, 1H), 7.19 (dd, J=0.8, 7.5 Hz, 1H), 7.10 (d, J=8.5 Hz, 2H), 7.01 (d, J=1.3 Hz, 1H), 6.90 (d, J=1.3 Hz, 1H), 5.49 (q, J=6.9 Hz, 1H), 3.74 (s, 3H), 1.65 (d, J=7.0 Hz, 3H).

Example 58: N-Isopropyl-5-(4-(trifluoromethyl)phenoxy)quinoline-2-carboxamide (Compound 70)

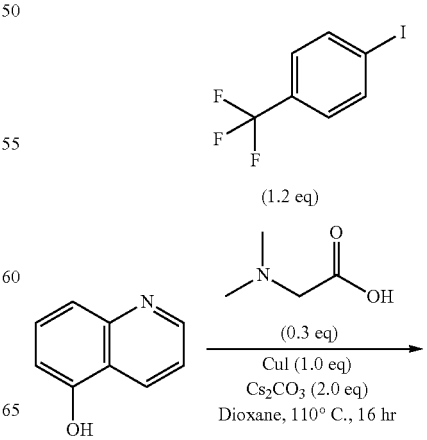

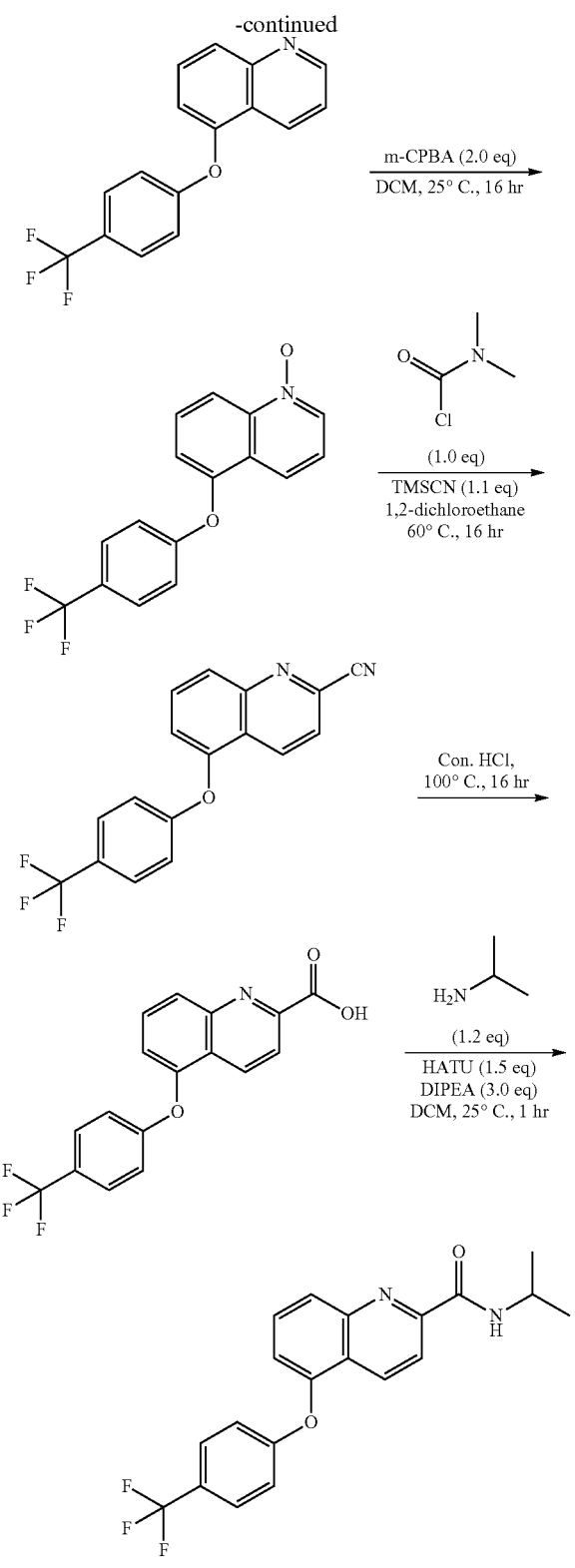

Compound 70

5-(4-(trifluoromethyl)phenoxy)quinoline

To a solution of compound quinolin-5-ol (400.0 mg, 2.76 mmol, 1.0 eq), compound 1-iodo-4-(trifluoromethyl)benzene (899.4 mg, 3.31 mmol, 1.2 eq), CuI (524.8 mg, 2.76 mmol, 1.0 eq) and compound dimethylglycine (85.2 mg, 0.82 mmol, 0.3 eq) in Dioxane (10 mL) was added $Cs_2CO_3$ (1.80 g, 5.51 mmol, 2.0 eq). The reaction mixture was stirred at 110° C. for 16 hours under $N_2$. The reaction mixture was concentrated under reduced pressure. The mixture was diluted with water (30 mL) and the resultant mixture was extracted with EA (50 mL*3). The combined organic layers were dried over $Na_2SO_4$, filtered and concentrated to dryness under reduced pressure. The residue was purified by silica gel column chromatography to give 5-(4-(trifluoromethyl)phenoxy)quinoline (270 mg, 33.2% yield). LCMS (ESI): RT=0.848 min, mass calcd. for $C_{16}H_{10}F_3NO$ 289.07, m/z found 290.0 $[M+H]^+$.

5-(4-(trifluoromethyl)phenoxy)quinoline 1-oxide

To a solution of compound 5-(4-(trifluoromethyl)phenoxy)quinoline (250.0 mg, 0.86 mmol, 1.0 eq) in DCM (5 mL) was added m-CPBA (350.9 mg, 1.73 mmol, 85%, 2.0 eq). The reaction mixture was stirred at 25° C. for 16 hours. The mixture was diluted with NaOH (30 mL, 1M) and the resultant mixture was extracted with DCM (50 mL*2). The combined organic layers were washed with NaOH (25 mL, 1M), brine (25 mL), dried over $Na_2SO_4$, filtered and concentrated to dryness under reduced pressure to give 5-(4-(trifluoromethyl)phenoxy)quinoline 1-oxide (220 mg, 83.3% yield).

5-(4-(trifluoromethyl)phenoxy)quinoline-2-carbonitrile

To a solution of compound 5-(4-(trifluoromethyl)phenoxy)quinoline 1-oxide (100.0 mg, 0.32 mmol, 1.0 eq) in 1,2-dichloroethane (2 mL) were added TMSCN (35.7 mg, 0.36 mmol, 1.1 eq) and dimethylcarbamic chloride (35.2 mg, 0.32 mmol, 1.0 eq). The reaction mixture was stirred at 60° C. for 16 hours. The reaction mixture was concentrated under reduced pressure. The mixture was diluted with water (20 mL) and the resultant mixture was extracted with EA (30 mL*3). The combined organic layers were dried over $Na_2SO_4$, filtered and concentrated to dryness under reduced pressure. The residue was purified by silica gel column chromatography to give 5-(4-(trifluoromethyl)phenoxy)quinoline-2-carbonitrile (75 mg, 72.8% yield).

5-(4-(trifluoromethyl)phenoxy)quinoline-2-carboxylic acid

A mixture of compound 5-(4-(trifluoromethyl)phenoxy)quinoline-2-carbonitrile (40.0 mg, 0.12 mmol, 1.0 eq) in conc. HCl (1 mL) was stirred at 100° C. for 16 hours. The reaction mixture was cooled to 25° C., and then the suspension was filtered to give 5-(4-(trifluoromethyl)phenoxy)quinoline-2-carboxylic acid (35 mg, crude).

N-isopropyl-5-(4-(trifluoromethyl)phenoxy)quinoline-2-carboxamide

To a solution of compound 5-(4-(trifluoromethyl)phenoxy)quinoline-2-carboxylic acid (35.0 mg, 94.6 umol, 1 eq, HCl), iso-propylamine (6.7 mg, 0.11 mmol, 1.2 eq) and DIPEA (36.7 mg, 0.28 mmol, 3.0 eq) in DCM (1 mL) was added HATU (54.0 mg, 0.14 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over Na₂SO₄, filtered and concentrated to dryness under reduced pressure. The residue was purified by prep-HPLC to give the title compound (5.81 mg, 16.2% yield). LCMS (ESI): RT=1.048 min, mass calcd. for $C_{21}H_{18}F_4N_2O_3$ 374.12, m/z found 375.0 [M+H]⁺; ¹H NMR (400 MHz, CDCl₃) δ 8.61 (d, J=8.6 Hz, 1H), 8.34 (d, J=8.6 Hz, 1H), 8.09 (d, J=7.8 Hz, 1H), 7.98 (d, J=8.6 Hz, 1H), 7.71 (t, J=8.1 Hz, 1H), 7.64 (d, J=8.1 Hz, 2H), 7.13 (d, J=8.0 Hz, 3H), 4.42-4.28 (m, 1H), 1.37 (d, J=6.5 Hz, 6H).

Example 59: (S)-N-(1-(4-aminopyridin-2-yl)ethyl)-5-(4-(trifluoromethyl)phenoxy)-2-naphthamide (Compound 71) and (R)-N-(1-(4-aminopyridin-2-yl)ethyl)-5-(4-(trifluoromethyl)phenoxy)-2-naphthamide (Compound 72)

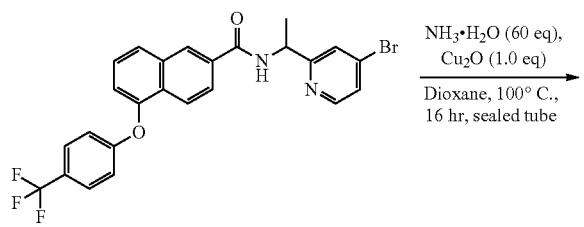

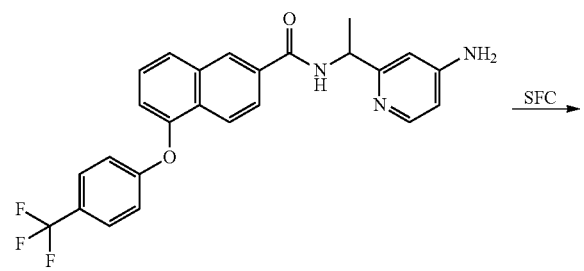

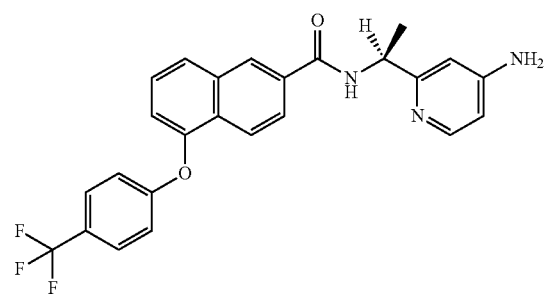

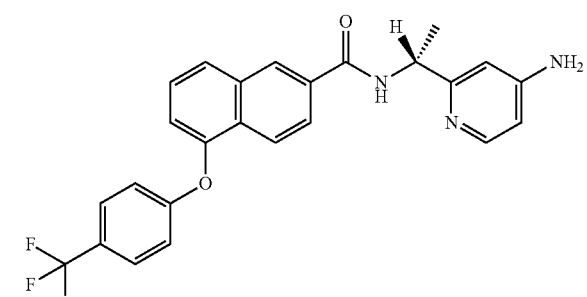

Compound 71

Compound 72

N-(1-(4-aminopyridin-2-yl)ethyl)-5-(4-(trifluoromethyl)phenoxy)-2-naphthamide

To a solution of N-[1-(4-bromo-2-pyridyl)ethyl]-5-[4-(trifluoromethyl)phenoxy]naphthalene-2-carboxamide (200 mg, 0.38 mmol, 1 eq) in dioxane (1 mL) was added NH₃·H₂O (2.73 g, 23.37 mmol, 3 mL, 30%, 60.21 eq) and Cu2O (55.53 mg, 0.38 mmol, 39.6 uL, 1 eq). The mixture was stirred at 100° C. for 16 hr in a sealed tube. The mixture was added H₂O (20 mL) and extracted with EA (15 mL*3). The combined organic layers were washed with brine (20 mL), dried with anhydrous Na₂SO₄, filtered and concentrated under reduced pressure to give a residue. The residue was purified by flash silica gel chromatography to affordN-[1-(4-amino-2-pyridyl)ethyl]-5-[4-(trifluoromethyl)phenoxy]naphthalene-2-carboxamide (88 mg, 0.19 mmol, 49.7% yield).

(S)-N-(1-(4-aminopyridin-2-yl)ethyl)-5-(4-(trifluoromethyl)phenoxy)-2-naphthamide (Compound 71) and (R)-N-(1-(4-aminopyridin-2-yl)ethyl)-5-(4-(trifluoromethyl)phenoxy)-2-naphthamide (Compound 72)

The racemic compound N-[1-(4-amino-2-pyridyl)ethyl]-5-[4-(trifluoromethyl)phenoxy]naphthalene-2-carboxamide (88 mg, 0.19 mmol, 1 eq) was purified by SFC to give Compound 71 (22.6 mg, 50.0 umol, 25.6% yield) LCMS (ESI): RT=0.879 min, mass calcd for $C_{25}H_{20}F_3N_3O_2$ 451.44 m/z, found 452.1 [M+H]⁺; ¹H NMR (400 MHz, DMSO-d₆) δ 8.88 (br d, J=7.8 Hz, 1H), 8.64 (s, 1H), 8.04-7.91 (m, 4H), 7.74 (d, J=8.5 Hz, 2H), 7.64 (t, J=7.9 Hz, 1H), 7.33 (d, J=7.5 Hz, 1H), 7.16 (d, J=8.4 Hz, 2H), 6.52 (s, 1H), 6.34 (br d, J=5.5 Hz, 1H), 5.96 (s, 2H), 5.08-4.98 (m, 1H), 1.48 (d, J=7.0 Hz, 3H); and Compound 72 (24.5 mg, 53.1 umol, 27.28% yield) LCMS (ESI): RT=0.823 min, mass calcd for $C_{25}H_{20}F_3N_3O_2$ 451.44 m/z, found 452.1 [M+H]⁺; ¹H NMR (400 MHz, DMSO-d₆) δ 8.92 (br d, J=7.8 Hz, 1H), 8.65 (s, 1H), 8.06-7.90 (m, 4H), 7.75 (d, J=8.5 Hz, 2H), 7.64 (t, J=7.9 Hz, 1H), 7.34 (d, J=7.5 Hz, 1H), 7.16 (d, J=8.4 Hz, 2H), 6.54 (s, 1H), 6.37 (br d, J=5.6 Hz, 1H), 6.15 (br s, 2H), 5.04 (quin, J=7.0 Hz, 1H), 1.49 (d, J=7.0 Hz, 3H).

Example 60: (S)-N-(1-(4-(dimethylamino)pyridin-2-yl)ethyl)-5-(4-(trifluoromethyl)phenoxy)-2-naphthamide (Compound 73) and (R)-N-(1-(4-(dimethylamino)pyridin-2-yl)ethyl)-5-(4-(trifluoromethyl)phenoxy)-2-naphthamide (Compound 74)

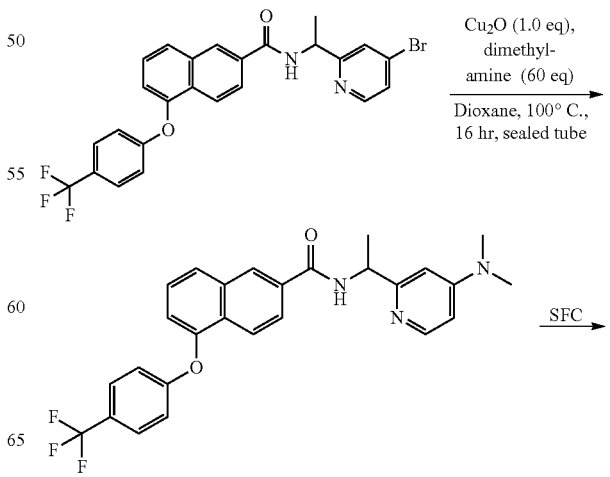

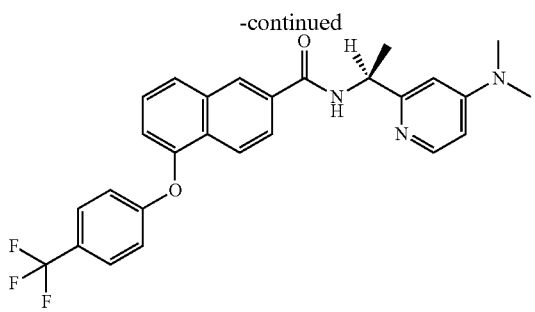

Compound 73

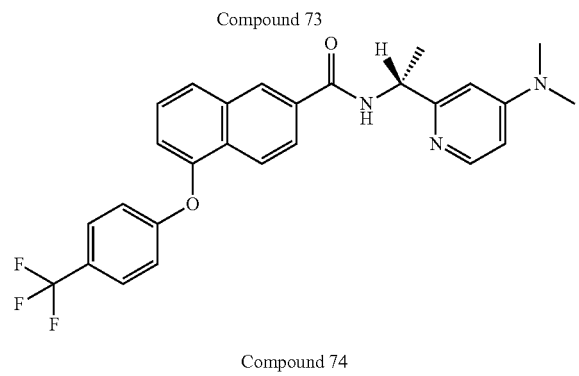

Compound 74

N-(1-(4-(dimethylamino)pyridin-2-yl)ethyl)-5-(4-(trifluoromethyl)phenoxy)-2-naphthamide To a solution of N-[1-(4-bromo-2-pyridyl)ethyl]-5-[4-(trifluoromethyl)phenoxy]naphthalene-2-carboxamide (200 mg, 0.38 mmol, 1 eq) in dioxane (1 mL) was added N-methylmethanamine (2.67 g, 23.69 mmol, 3 mL, 40%, 60 eq) and Cu$_2$O (55.5 mg, 0.38 mmol, 39.6 uL, 1 eq). The mixture was stirred at 100° C. for 16 hr in a sealed tube. The reaction mixture was added H$_2$O (20 mL) and extracted with EA (20 mL*3). The combined organic layers were washed with brine (30 mL), dried with anhydrous Na$_2$SO$_4$, filtered and concentrated under reduced pressure to give a residue. The residue was purified by flash silica gel chromatography to afford N-[1-[4-(dimethylamino)-2-pyridyl]ethyl]-5-[4-(trifluoromethyl)phenoxy]naphthalene-2-carboxamide (134 mg, 0.27 mmd, 69.8% yield).

(S)-N-(1-(4-(dimethylamino)pyridin-2-yl)ethyl)-5-(4-(trifluoromethyl)phenoxy)-2-naphthamide (Compound 73) and (R)-N-(1-(4-(dimethylamino)pyridin-2-yl)ethyl)-5-(4-(trifluoromethyl)phenoxy)-2-naphthamide (Compound 74)

The racemic compound N-[1-[4-(dimethylamino)-2-pyridyl]ethyl]-5-[4-(trifluoromethyl)phenoxy]naphthalene-2-carboxamide (95 mg, 0.19 mmol, 1 eq) was purified by SFC to give Compound 73 (24.3 mg, 50.0 umol, 25.2% yield) LCMS (ESI): RT=0.885 min, mass calcd for C$_{27}$H$_{24}$F$_3$N$_3$O$_2$ 479.49 m/z, found 480.1 [M+H]$^+$; $^1$H NMR (400 MHz, DMSO-d$_6$) δ 8.88 (d, J=8.0 Hz, 1H), 8.61 (s, 1H), 8.08 (d, J=5.9 Hz, 1H), 8.03-7.95 (m, 3H), 7.74 (d, J=8.5 Hz, 2H), 7.63 (t, J=7.9 Hz, 1H), 7.33 (d, J=7.6 Hz, 1H), 7.17 (d, J=8.6 Hz, 2H), 6.68 (s, 1H), 6.54-6.47 (m, 1H), 5.13 (quin, J=7.2 Hz, 1H), 2.98-2.90 (m, 6H), 1.49 (d, J=7.0 Hz, 3H) Compound 74 (39.6 mg, 81.1 umol, 40.9% yield) LCMS (ESI): RT=0.882 min, mass calcd for C$_{27}$H$_{24}$F$_3$N$_3$O$_2$ 479.49 m/z, found 480.1 [M+H]$^+$; $^1$H NMR (400 MHz, DMSO-d$_6$) δ 8.88 (br d, J=7.9 Hz, 1H), 8.61 (s, 1H), 8.08 (d, J=5.9 Hz, 1H), 8.02-7.95 (m, 3H), 7.74 (d, J=8.5 Hz, 2H), 7.63 (t, J=7.9 Hz, 1H), 7.33 (d, J=7.6 Hz, 1H), 7.17 (d, J=8.4 Hz, 2H), 6.68 (s, 1H), 6.50 (br d, J=5.8 Hz, 1H), 5.13 (quin, J=7.0 Hz, 1H), 2.94 (s, 6H), 1.50 (d, J=6.9 Hz, 3H).

Example 61: N-(1-(4-bromopyridin-2-yl)ethyl)-5-(4-(trifluoromethyl)phenoxy)-2-naphthamide (Compound 75)

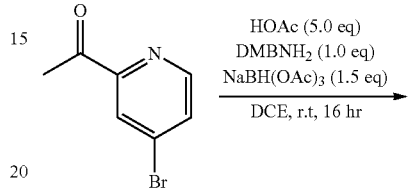

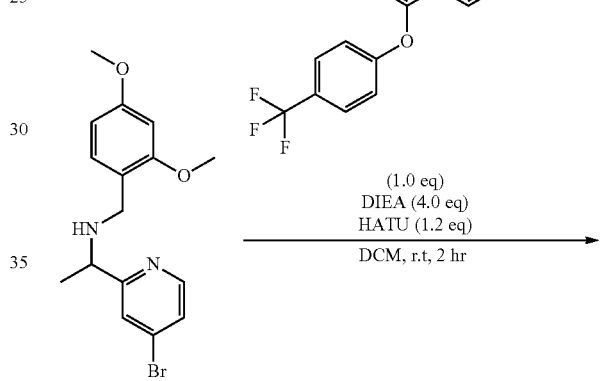

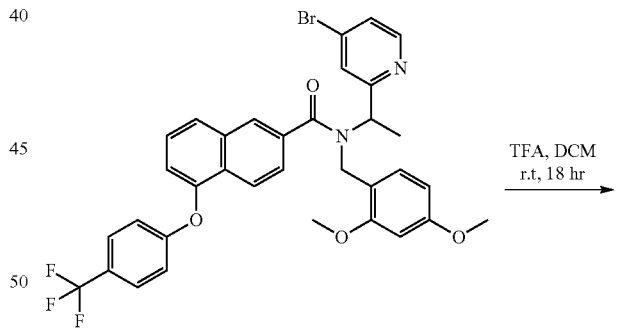

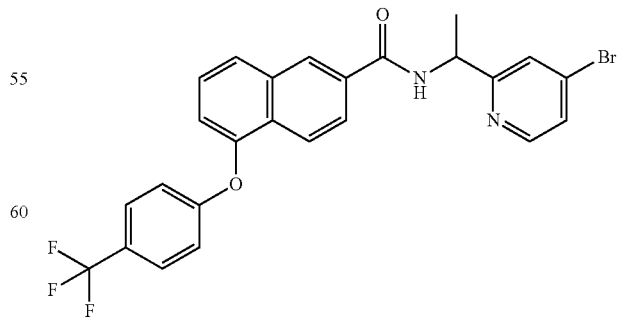

Compound 75

1-(4-bromopyridin-2-yl)-N-(2,4-dimethoxybenzyl)ethanamine

To a solution of 1-(4-bromo-2-pyridyl)ethanone (10 g, 49.99 mmol, 1 eq) and (2,4-dimethoxyphenyl)methanamine (8.36 g, 49.99 mmol, 7.53 mL, 1 eq) in DCE (120 mL) was added HOAc (15.01 g, 249.96 mmol, 14.30 mL, 5 eq) and stirred at 25° C. for 1 hr. Then NaBH(OAc)$_3$ (15.89 g, 74.99 mmol, 1.5 eq) was added. The resulting mixture was stirred at 25° C. for 15 hr. Then iced water (50 mL) was added and the mixture was neutralized to pH=9-10 with aq. NaOH (4 M). The aqueous phase was extracted with EA (100 mL*3). The combined organic phase was washed with brine (150 mL), dried with anhydrous Na$_2$SO$_4$, filtered and concentrated in vacuo. The residue was purified by flash silica gel chromatography. Compound 1-(4-bromo-2-pyridyl)-N-[(2,4-dimethoxyphenyl)methyl]ethanamine (7.16 g, 15.29 mmol, 30.5% yield) was obtained.

N-(1-(4-bromopyridin-2-yl)ethyl)-N-(2,4-dimethoxybenzyl)-5-(4-(trifluoromethyl)phenoxy)-2-naphthamide To a solution of 5-[4-(trifluoromethyl)phenoxy]naphthalene-2-carboxylic acid (2 g, 6.02 mmol, 1 eq) and HATU (2.75 g, 7.22 mmol, 1.2 eq) in DCM (35 mL) was added DIPEA (3.11 g, 24.08 mmol, 4.19 mL, 4 eq). After addition, the mixture was stirred at 25° C. for 0.5 hr, then 1-(4-bromo-2-pyridyl)-N-[(2,4-dimethoxyphenyl)methyl]ethanamine (2.82 g, 6.02 mmol, 1 eq) was added. The resulting mixture was stirred at 25° C. for 1.5 hr. The reaction mixture was added H$_2$O (50 mL) and extracted with EA (50 mL*3). The combined organic layers were washed with brine (60 mL), dried with anhydrous Na$_2$SO$_4$, filtered and concentrated under reduced pressure to give a residue. The residue was purified by flash silica gel chromatography to afford N-[1-(4-bromo-2-pyridyl)ethyl]-N-[(2,4-dimethoxyphenyl)methyl]-5-[4-(trifluoromethyl)phenoxy]naphthalene-2-carboxamide (3.5 g, 5.15 mmol, 85.6% yield).

N-(1-(4-bromopyridin-2-yl)ethyl)-5-(4-(trifluoromethyl)phenoxy)-2-naphthamide To a solution of N-[1-(4-bromo-2-pyridyl)ethyl]-N-[(2,4-dimethoxyphenyl)methyl]-5-[4-(trifluoromethyl)phenoxy]naphthalene-2-carboxamide (3.5 g, 5.26 mmol, 1 eq) in DCM (10 mL) was added TFA (61.60 g, 540.24 mmol, 40 mL, 102.7 eq). The mixture was stirred at 25° C. for 16 hr. Iced water (30 mL) was added and the mixture was neutralized to pH=9-10 with aq. NaOH (4 M). The aqueous phase was extracted with EA (40 mL*3). The combined organic phase was washed with brine (60 mL), dried with anhydrous Na$_2$SO$_4$, filtered and concentrated in vacuo to give a residue. The residue was purified by flash silica gel chromatography to afford N-[1-(4-bromo-2-pyridyl)ethyl]-5-[4-(trifluoromethyl)phenoxy]naphthalene-2-carboxamide (2.68 g, 4.99 mmol, 94.9% yield). The crude product was purified by prep-HPLC. The title compound (72 mg, 0.13 mmol, 75.0% yield) was obtained. LCMS (ESI): RT=0.951 min, mass calcd for C$_{25}$H$_{18}$BrF$_3$N$_2$O$_2$ 515.32 m/z, found 517.0 [M+H]$^+$; $^1$H NMR (400 MHz, DMSO-d$_6$) δ 9.08 (d, J=7.5 Hz, 1H), 8.64 (s, 1H), 8.44 (d, J=5.3 Hz, 1H), 8.06-7.96 (m, 3H), 7.78-7.62 (m, 4H), 7.57 (dd, J=1.8, 5.3 Hz, 1H), 7.34 (d, J=7.3 Hz, 1H), 7.17 (d, J=8.5 Hz, 2H), 5.24 (quin, J=7.2 Hz, 1H), 1.55 (d, J=7.0 Hz, 3H).

Example 62: (S)-N-(1-(6-(dimethylamino)pyridin-2-yl)ethyl)-5-(4-(trifluoromethyl)phenoxy)-2-naphthamide (Compound 76) and (R)-N-(1-(6-(dimethylamino)pyridin-2-yl)ethyl)-5-(4-(trifluoromethyl)phenoxy)-2-naphthamide (Compound 77)

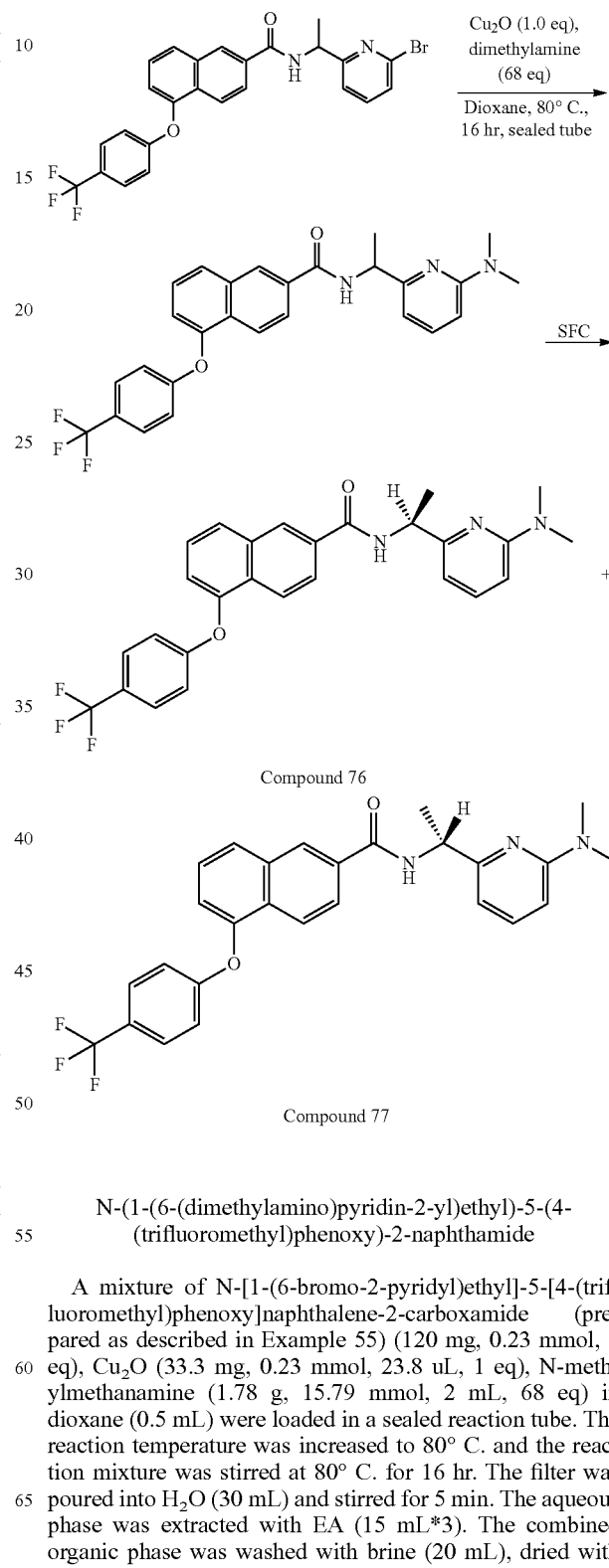

Compound 76

Compound 77

N-(1-(6-(dimethylamino)pyridin-2-yl)ethyl)-5-(4-(trifluoromethyl)phenoxy)-2-naphthamide A mixture of N-[1-(6-bromo-2-pyridyl)ethyl]-5-[4-(trifluoromethyl)phenoxy]naphthalene-2-carboxamide (prepared as described in Example 55) (120 mg, 0.23 mmol, 1 eq), Cu$_2$O (33.3 mg, 0.23 mmol, 23.8 uL, 1 eq), N-methylmethanamine (1.78 g, 15.79 mmol, 2 mL, 68 eq) in dioxane (0.5 mL) were loaded in a sealed reaction tube. The reaction temperature was increased to 80° C. and the reaction mixture was stirred at 80° C. for 16 hr. The filter was poured into H$_2$O (30 mL) and stirred for 5 min. The aqueous phase was extracted with EA (15 mL*3). The combined organic phase was washed with brine (20 mL), dried with anhydrous Na$_2$SO$_4$, filtered and concentrated in vacuo. The residue was purified by flash silica gel chromatography. Compound N-[1-[6-(dimethylamino)-2-pyridyl]ethyl]-5-[4-(trifluoromethyl)phenoxy]naphthalene-2-carboxamide (88 mg, 0.18 mmol, 78.8% yield) was obtained.

(S)-N-(1-(6-(dimethylamino)pyridin-2-yl)ethyl)-5-(4-(trifluoromethyl)phenoxy)-2-naphthamide (Compound 76) and (R)-N-(1-(6-(dimethylamino)pyridin-2-yl)ethyl)-5-(4-(trifluoromethyl)phenoxy)-2-naphthamide (Compound 77)

The racemic compound N-[1-[6-(dimethylamino)-2-pyridyl]ethyl]-5-[4-(trifluoromethyl)phenoxy]naphthalene-2-carboxamide (88 mg, 0.18 mmol, 1 eq) was purified by SFC to give Compound 76 (20.7 mg, 41.0 umol, 22.3% yield) LCMS (ESI): RT=0.808 min, mass calcd for C$_{27}$H$_{24}$F$_3$N$_3$O$_2$ 479.49 m/z found 480.2 [M+H]$^+$; $^1$H NMR (400 MHz, CD$_3$OD) δ 8.49 (s, 1H), 8.10 (d, J=8.8 Hz, 1H), 7.96-7.84 (m, 2H), 7.65 (d, J=8.5 Hz, 2H), 7.57 (t, J=7.9 Hz, 1H), 7.46 (t, J=7.9 Hz, 1H), 7.21 (d, J=7.5 Hz, 1H), 7.12 (d, J=8.5 Hz, 2H), 6.61 (d, J=7.3 Hz, 1H), 6.50 (d, J=8.5 Hz, 1H), 5.18 (q, J=6.8 Hz, 1H), 3.09 (s, 6H), 1.59 (d, J=6.9 Hz, 3H); and Compound 77 (22.3 mg, 46.5 umol, 25.3% yield) LCMS (ESI): RT=0.790 min, mass calcd for C$_{27}$H$_{24}$F$_3$N$_3$O$_2$ 479.49 m/z found 480.1 [M+H]$^+$; $^1$H NMR (400 MHz, CD$_3$OD) δ 8.49 (s, 1H), 8.10 (d, J=8.9 Hz, 1H), 7.96-7.84 (m, 2H), 7.65 (d, J=8.5 Hz, 2H), 7.57 (t, J=7.9 Hz, 1H), 7.47 (t, J=7.9 Hz, 1H), 7.21 (d, J=7.5 Hz, 1H), 7.12 (d, J=8.5 Hz, 2H), 6.62 (d, J=7.4 Hz, 1H), 6.50 (d, J=8.5 Hz, 1H), 5.18 (q, J=6.8 Hz, 1H), 3.09 (s, 6H), 1.59 (d, J=6.9 Hz, 3H).

Example 63: (S)-N-(1-(2-aminopyridin-3-yl)ethyl)-5-(4-(trifluoromethyl)phenoxy)-2-naphthamide (Compound 78) and (R)-N-(1-(2-aminopyridin-3-yl)ethyl)-5-(4-(trifluoromethyl)phenoxy)-2-naphthamide (Compound 79)

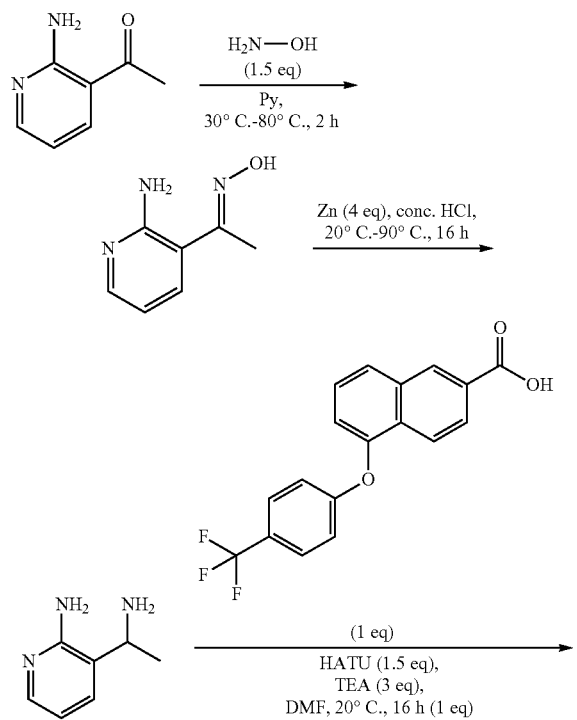

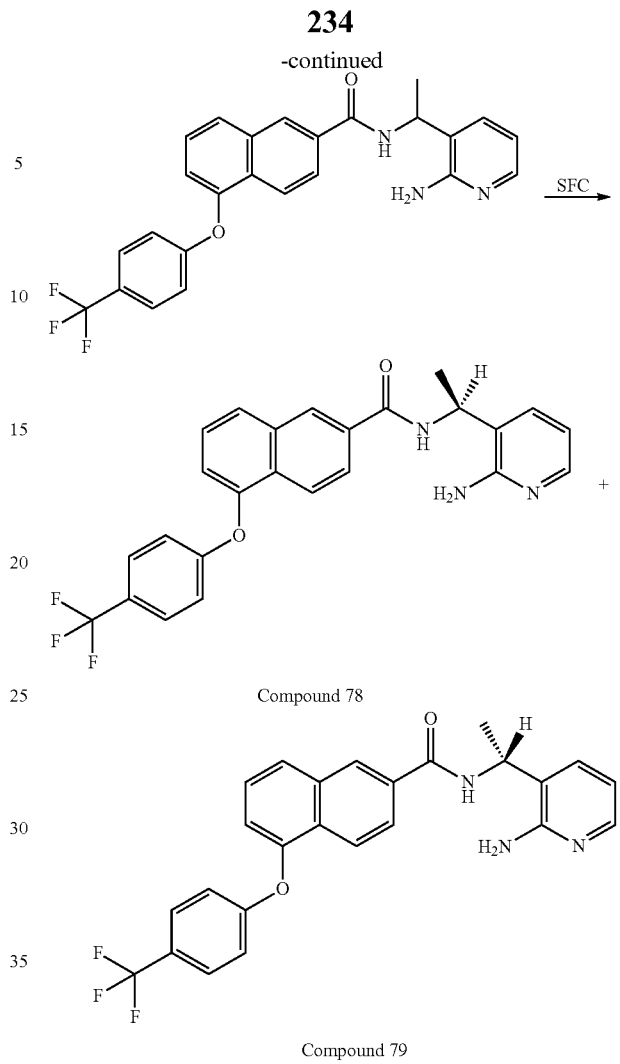

Compound 78

Compound 79

(E)-1-(2-aminopyridin-3-yl)ethanone Oxime

To a solution of 1-(2-aminopyridin-3-yl)ethan-1-one (300 mg, 2.2 mmol, 1 eq) in Py (6 mL) at 30° C. was added hydroxylamine (229.7 mg, 3.31 mmol, 1.5 eq). The mixture was stirred at 80° C. for 2 h. The reaction mixture was concentrated under reduced pressure to give the residue which purified by flash silica gel chromatography to give (E)-1-(2-aminopyridin-3-yl)ethanone oxime (375 mg, 2.2 mmol, 99.1% yield). LCMS(ESI): RT=0.333 min, mass calc. for C$_7$H9N$_3$O 151.07, m/z found 152.1 [M+H]$^+$.

3-(1-aminoethyl)pyridin-2-amine

To a mixture of (E)-1-(2-aminopyridin-3-yl)ethanone oxime (200 mg, 1.3 mmol, 1 eq) and Zn (345.3 mg, 5.3 mmol, 4 eq) at 20° C. was slowly added con. HCl (3 mL) with vigorous stirring. The mixture was heated at 90° C. for 16 hours The reaction mixture was concentrated under reduced pressure to remove solvent. The residue was diluted with water (20 mL), then basified with 2N NaOH at 20° C. to pH=9-10, and then extracted with EA (20 mL*3). The combined organic layers were washed with brine (20 mL), dried over anhydrous Na$_2$SO$_4$, filtered and concentrated under reduced pressure to give 3-(1-aminoethyl)pyridin-2-amine (70 mg, 0.46 mmol, 34.8% yield). $^1$H NMR (400

MHz, CDCl₃) δ 7.93 (br d, J=4.8 Hz, 1H), 7.32 (br d, J=7.3 Hz, 1H), 6.60 (br t, J=6.1 Hz, 1H), 6.01 (brs, 2H), 4.16 (brs, 1H), 1.46 (br d, J=6.3 Hz, 3H).

N-(1-(2-aminopyridin-3-yl)ethyl)-5-(4-(trifluoromethyl)phenoxy)-2-naphthamide To a solution of 3-(1-aminoethyl)pyridin-2-amine (50 mg, 0.36 mmol, 1.6 eq) and HATU (129.9 mg 0.34 mmol, 1.5 eq) in DMF (1 mL) at 20° C. were added 5-(4-(trifluoromethyl)phenoxy)-2-naphthoic acid (75.7 mg, 0.23 mmol, 1 eq) and TEA (69.2 mg, 0.68 mmol, 95 uL, 3 eq). The mixture was stirred at 20° C. for 16 h. The reaction mixture was concentrated under reduced pressure to give the residue which was purified by prep-HPLC to give N-(1-(2-aminopyridin-3-yl)ethyl)-5-(4-(trifluoromethyl)phenoxy)-2-naphthamide (50 mg, 0.11 mmol, 48.1% yield). LCMS (ESI): RT=0.796 min, mass calc. for $C_{25}H_{20}F_3N_3O_2$ 451.15, m/z found 452.0 [M+H⁺].

(S)-N-(1-(2-aminopyridin-3-yl)ethyl)-5-(4-(trifluoromethyl)phenoxy)-2-naphthamide (Compound 78) and (R)-N-(1-(2-aminopyridin-3-yl)ethyl)-5-(4-(trifluoromethyl)phenoxy)-2-naphthamide (Compound 79)

N-(1-(2-aminopyridin-3-yl)ethyl)-5-(4-(trifluoromethyl)phenoxy)-2-naphthamide (42 mg, 93 umol, 1 eq) was purified by SFC (column: DAICEL CHIRALCEL OD-H (250 mm*30 mm, 5 um); mobile phase: [0.1% NH₃H₂O ETOH]; B %: 25%-25%, min) to give Compound 78 (7 mg, 15 umol, 16.3% yield) LCMS (ESI): RT=0.876 min, mass calc. for $C_{25}H_{20}F_3N_3O_2$ 451.15, m/z found 452.1 [M+H⁺]; ¹H NMR (400 MHz, CDCl3) δ 8.37 (d, J=1.3 Hz, 1H), 8.14 (d, J=8.8 Hz, 1H), 7.88 (br d, J=5.0 Hz, 1H), 7.84-7.76 (m, 2H), 7.64-7.57 (m, 3H), 7.54-7.48 (m, 1H), 7.15 (d, J=7.0 Hz, 1H), 7.07 (d, J=8.5 Hz, 2H), 6.64 (dd, J=5.4, 7.2 Hz, 1H), 6.54 (br d, J=9.3 Hz, 1H), 6.03 (brs, 1H), 5.52-5.43 (m, 1H), 1.73 (d, J=7.0 Hz, 3H); and Compound 79 (6 mg, 13 umol, 14% yield) LCMS (ESI): RT=0.876 min, mass calc. for $C_{23}H_{20}F_3N_3O_2$ 451.15, m/z found 452.0 [M+H⁺]; ¹H NMR (400 MHz, CDCl₃) δ 8.37 (d, J=1.5 Hz, 1H), 8.14 (d, J=8.8 Hz, 1H), 7.91 (br d, J=4.3 Hz, 1H), 7.82-7.77 (m, 2H), 7.62-7.58 (m, 3H), 7.52 (t, J=7.9 Hz, 1H), 7.15 (d, J=7.0 Hz, 1H), 7.07 (d, J=8.5 Hz, 2H), 6.64 (dd, J=5.3, 7.5 Hz, 1H), 6.48 (br d, J=9.5 Hz, 1H), 5.91 (br s, 1H), 5.55-5.42 (m, 1H), 1.73 (d, J=6.8 Hz, 3H).

Example 64: N-[1-(hydroxymethyl)-2-(2-pyridyl)ethyl]-5-[4-(trifluoromethyl)phenoxy]naphthalene-2-carboxamide (Compound 80)

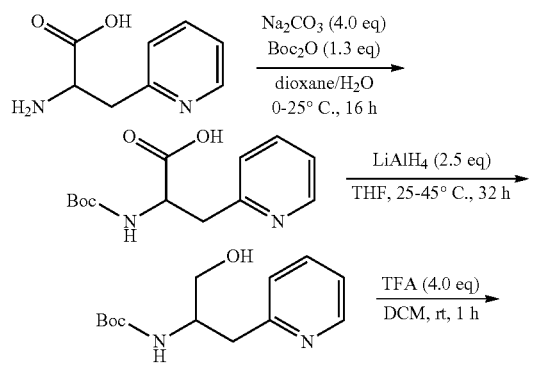

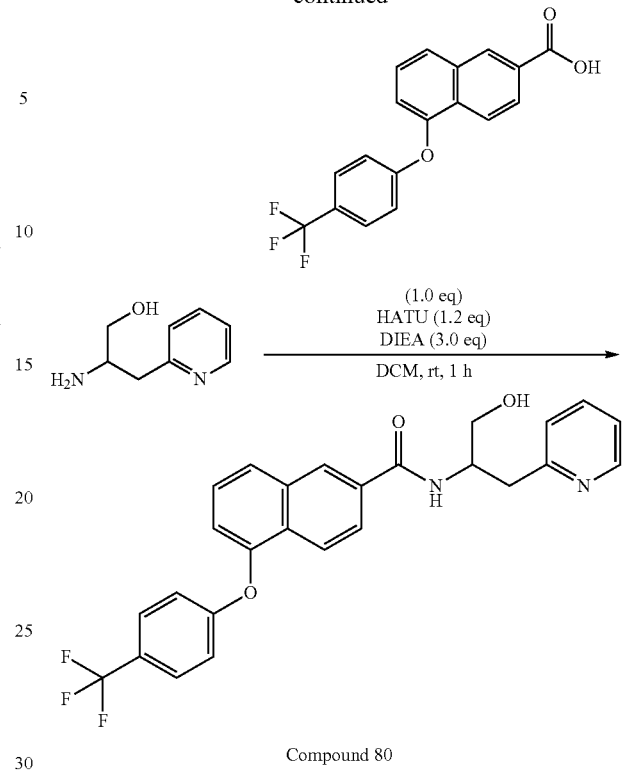

2-(tert-butoxycarbonylamino)-3-(2-pyridyl)propanoic Acid

To a solution of compound 2-amino-3-(pyridin-2-yl)propanoic acid (0.2 g, 0.83 mmol, 1 eq, 2HCl) in dioxane (10 mL) and H₂O (5 mL) was added Na₂CO₃ (354.6 mg, 3.35 mmol, 4 eq) at 0° C. And then Boc₂O (237.3 mg, 1.0 mmol, 0.24 mL, 1.3 eq) was added drop-wise to the solution. The reaction was stirred at 25° C. for 16 hr. The reaction was diluted with H₂O (10 mL) and extracted with EA (20 mL). The aqueous layer was adjusted pH to 3-4 with 0.5M aq. citric and extracted with EA (5*10 mL). The organic layer was dried over Na₂SO₄ and concentrated. Compound 2-(tert-butoxycarbonylamino)-3-(2-pyridyl)propanoic acid (75 mg, 0.25 mmol, 29.9% yield) was used for next step directly.

Tert-butyl N-[1-(hydroxymethyl)-2-(2-pyridyl)ethyl] carbamate

To a solution of compound 2-(tert-butoxycarbonylamino)-3-(2-pyridyl)propanoic acid (75 mg, 0.28 mmol, 1 eq) in THF (1 mL) was added LiAlH₄ (26.7 mg, 0.7 mmol, 2.5 eq). The reaction was stirred at 25° C. for 16 hr. The reaction was heated at 45° C. for 16 hr. The reaction was quenched by H₂O (1 mL), 2M aq. NaOH (1 mL), H₂O (10 mL) and extracted with EA (2*10 mL). The organic layer was dried over Na₂SO₄ and concentrated. Compound tert-butyl N-[1-(hydroxymethyl)-2-(2-pyridyl)ethyl]carbamate (60 mg, 0.12 mmol, 44.7% yield) was used for next step directly.

2-amino-3-(2-pyridyl)propan-1-ol

To a solution of compound tert-butyl N-[1-(hydroxymethyl)-2-(2-pyridyl)ethyl]carbamate (60 mg, 0.12 mmol, 1 eq) in DCM (1 mL) was added TFA (57.4 mg, 0.5 mmol, 37 uL, 4 eq). The reaction was stirred at 25° C. for 1 hr. The reaction mixture was concentrated to give 2-amino-3-(2-pyridyl)propan-1-ol (50 mg, crude, 2TFA), which was used for next step directly.

N-[1-(hydroxymethyl)-2-(2-pyridyl)ethyl]-5-[4-(trifluoromethyl)phenoxy]naphthalene-2-carboxamide To a solution of compound 5-(4-(trifluoromethyl)phenoxy)-2-naphthoic acid (21.8 mg, 65.7 umol, 1 eq) and HATU (30 mg, 78.9 umol, 1.2 eq) in DCM (1 mL) was added compound 2-amino-3-(2-pyridyl)propan-1-ol (25 mg, 65.7 umol, 1 eq, 2TFA) followed by DIEA (25.4 mg, 0.19 mmol, 34 uL, 3 eq). The reaction was stirred at 25° C. for 1 hr. The reaction was diluted with DCM (15 mL) and washed with H$_2$O (2*10 mL). The organic layer was dried over Na$_2$SO$_4$ and concentrated. The residue was purified by prep-HPLC to give the title compound (2.1 mg, 4.5 umol, 6.8% yield). LCMS(ESI): RT=0.825 min, mass calcd. for C$_{26}$H$_{21}$F$_3$N$_2$O$_3$ 466.15, m/z found 467.1 [M+H]$^+$, (H NMR (400 MHz, CDCl$_3$) δ 8.60-8.55 (m, 1H), 8.36 (d, J=1.5 Hz, 1H), 8.12 (d, J=8.8 Hz, 1H), 7.83 (dd, J=1.8, 8.8 Hz, 2H), 7.79 (d, J=8.3 Hz, 1H), 7.68 (dt, J=1.8, 7.7 Hz, 1H), 7.60 (d, J=8.5 Hz, 2H), 7.54-7.49 (m, 1H), 7.30 (d, J=7.6 Hz, 1H), 7.25-7.19 (m, 1H), 7.15 (dd, J=0.8, 7.5 Hz, 1H), 7.08 (d, J=8.4 Hz, 2H), 4.59-4.48 (m, 1H), 3.89-3.73 (m, 2H), 3.41-3.32 (m, 1H), 3.28-3.18 (m, 1H).

Example 65: 5,6-difluoro-N-isopropyl-8-(4-(trifluoromethyl)phenoxy)quinoline-3-carboxamide (Compound 81)

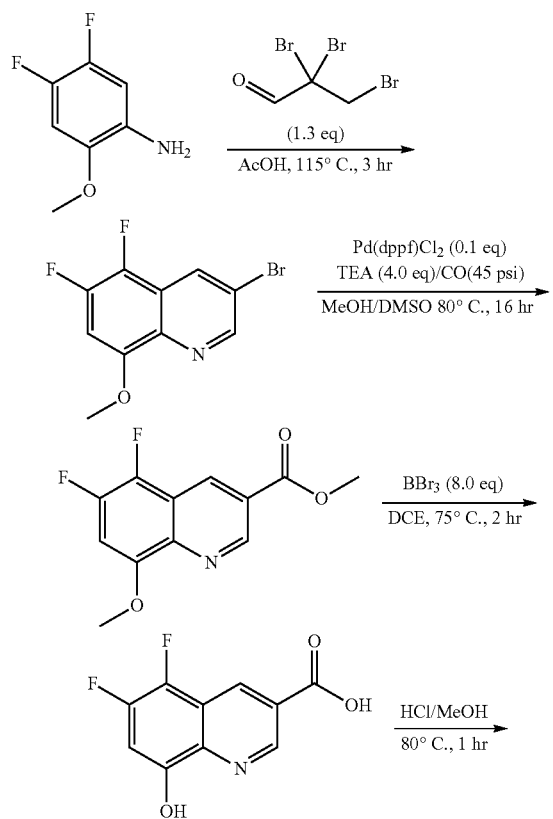

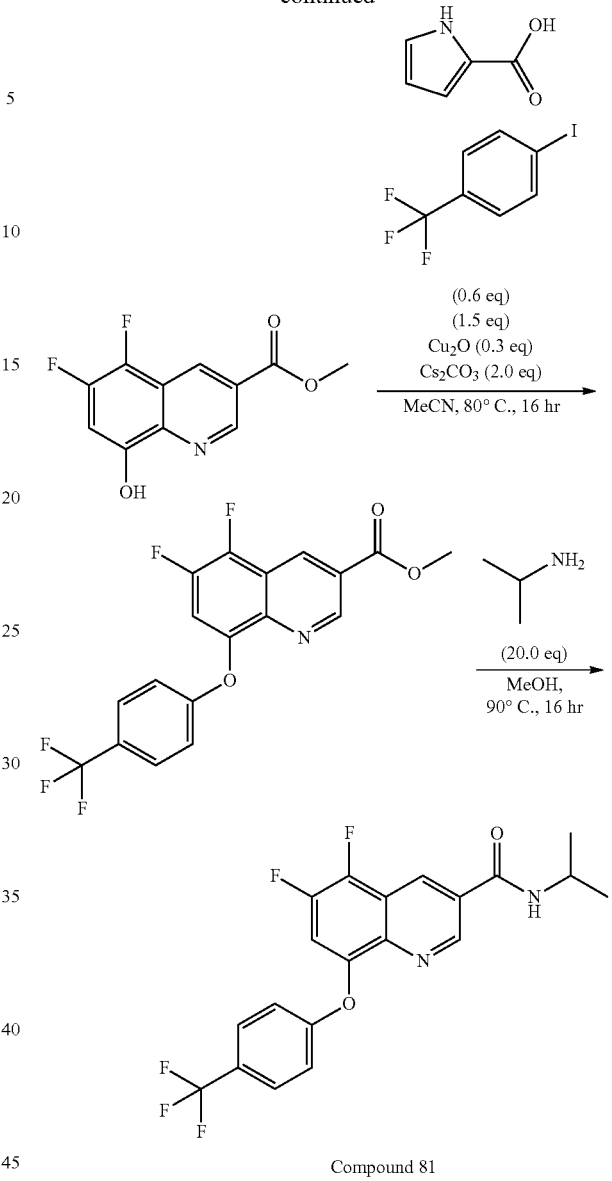

Compound 81

3-bromo-5,6-difluoro-8-methoxyquinoline

To a solution of 4,5-difluoro-2-methoxy-aniline (0.5 g, 3.14 mmol, 1 eq) in AcOH (8 mL) was added 2,2,3-tribromopropanal (1.20 g, 4.08 mmol, 1.3 eq) at 115° C. The mixture was stirred at 115° C. for 3 hr. The reaction mixture was quenched by addition saturated Na$_2$CO$_3$ (50 mL) and extracted with EtOAc (30 mL*3). The combined organic layers were washed with brine (50 mL*2), dried over Na$_2$SO$_4$, filtered and concentrated under reduced pressure to give a residue. The residue was purified by silica gel column chromatography to give a 3-bromo-5,6-difluoro-8-methoxyquinoline (400 mg, 1.39 mmol, 44.1% yield).

Methyl 5,6-difluoro-8-methoxyquinoline-3-carboxylate

To a solution of 3-bromo-5,6-difluoro-8-methoxy-quinoline (0.4 g, 1.46 mmol, 1 eq) in MeOH (4 mL) and DMSO (6 mL) were added Pd(dppf)Cl$_2$ (106.8 mg, 0.14 mmol, 0.1 eq), and TEA (590.7 mg, 5.84 mmol, 0.81 mL, 4.0 eq) under N$_2$. The suspension was degassed under vacuum and purged with CO several times. The mixture was stirred under CO (45 psi) at 80° C. for 16 hrs. The reaction mixture was filtered and diluted with H$_2$O (60 mL) and extracted with EtOAc (40 mL*3). The combined organic layers were dried over Na$_2$SO$_4$, filtered and concentrated under reduced pressure to give a residue. The residue was purified by silica gel column chromatography to give methyl 5,6-difluoro-8-methoxy-quinoline-3-carboxylate (250 mg, 0.98 mmol, 67.6% yield)s. Compound methyl 5,6-difluoro-8-methoxy-quinoline-3-carboxylate (250 mg, 0.98 mmol, 67.6% yield) was obtained.

5,6-difluoro-8-hydroxyquinoline-3-carboxylic Acid

To a solution of methyl 5,6-difluoro-8-methoxy-quinoline-3-carboxylate (0.2 g, 0.78 mmol, 1 eq) in DCE (3 mL) was added BBr$_3$ (1.58 g, 6.32 mmol, 0.60 mL, 8.0 eq) in DCE (1 mL). The mixture was stirred at 75° C. for 2 hr. The reaction mixture was quenched by addition saturated Na$_2$CO$_3$ (20 mL), and then extracted with EtOAc (20 mL*2). Then the pH of the aqueous phase was adjusted with HCl (2 M) to 5-6 and the mixture was extracted with EtOAc (20 mL*3). The combined organic layers were dried over Na$_2$SO$_4$, filtered and concentrated under reduced pressure to give 5,6-difluoro-8-hydroxy-quinoline-3-carboxylic acid (120 mg, crude). The crude product was used into the next step without further purification. Compound 5,6-difluoro-8-hydroxy-quinoline-3-carboxylic acid (120 mg, crude) was obtained.

Methyl 5,6-difluoro-8-hydroxyquinoline-3-carboxylate

A solution of 5,6-difluoro-8-hydroxy-quinoline-3-carboxylic acid (120 mg, 0.53 mmol, 1 eq) in HCl/MeOH (4 M, 12.00 mL, 90.06 eq) was stirred at 80° C. for 1 hr. The reaction mixture was concentrated under reduced pressure to give methyl 5,6-difluoro-8-hydroxy-quinoline-3-carboxylate (130 mg, crude). The crude product was used into the next step without further purification.

Methyl 5,6-difluoro-8-(4-(trifluoromethyl)phenoxy) quinoline-3-carboxylate

To a solution of methyl 5,6-difluoro-8-hydroxy-quinoline-3-carboxylate (100 mg, 0.41 mmol, 1 eq) in MeCN (0.5 mL) were added 1-iodo-4-(trifluoromethyl)benzene (170.5 mg, 0.62 mmol, 92.2 uL, 1.5 eq), Cs$_2$CO$_3$ (272.4 mg, 0.83 mmol, 2.0 eq) and Cu$_2$O (17.9 mg, 0.12 mmol, 12.8 uL, 0.3 eq), 1H-imidazole-5-carboxylic acid (28.1 mg, 0.25 mmol, 0.6 eq). The mixture was stirred in microwave at 80° C. for 16 hr. The reaction mixture was filtered and concentrated under reduced pressure to give a residue. The residue was purified by silica gel column chromatography to give methyl 5,6-difluoro-8-[4-(trifluoromethyl)phenoxy]quinoline-3-carboxylate (20 mg, 52.1 umol, 12.4% yield).

5,6-difluoro-N-isopropyl-8-(4-(trifluoromethyl)phenoxy)quinoline-3-carboxamide

To a solution of methyl 5,6-difluoro-8-[4-(trifluoromethyl)phenoxy]quinoline-3-carboxylate (20 mg, 52.1 umol, 1 eq) in MeOH (1 mL) was added iso-propylamine (61.6 mg, 1.04 mmol, 89.6 uL, 20 eq). The mixture was stirred at 90° C. for 16 hr. The reaction mixture was concentrated under reduced pressure to give a residue. The residue was purified by prep-HPLC to give the title compound (1.9 mg, 4.6 umol, 8.9% yield). LCMS (ESI): RT=0.793 min, mass calcd for C$_{20}$H$_{15}$F$_5$N$_2$O$_2$ 410.34 m/z found 411.0 [M+H]$^+$; $^1$H NMR (400 MHz, CDCl$_3$) δ 9.24 (br s, 1H), 8.82 (s, 1H), 7.64 (d, J=8.3 Hz, 2H), 7.22 (dd, J=7.2, 10.9 Hz, 1H), 7.13 (br d, J=8.5 Hz, 2H), 6.08 (br s, 1H), 4.39 (br s, 1H), 1.35 (d, J=6.3 Hz, 6H).

Example 66: (R)-N-(1-(2-chlorophenyl)ethyl)-5-(4-(trifluoromethyl)phenoxy)-2-naphthamide (Compound 82) and (S)-N-(1-(2-chlorophenyl)ethyl)-5-(4-(trifluoromethyl)phenoxy)-2-naphthamide (Compound 83)

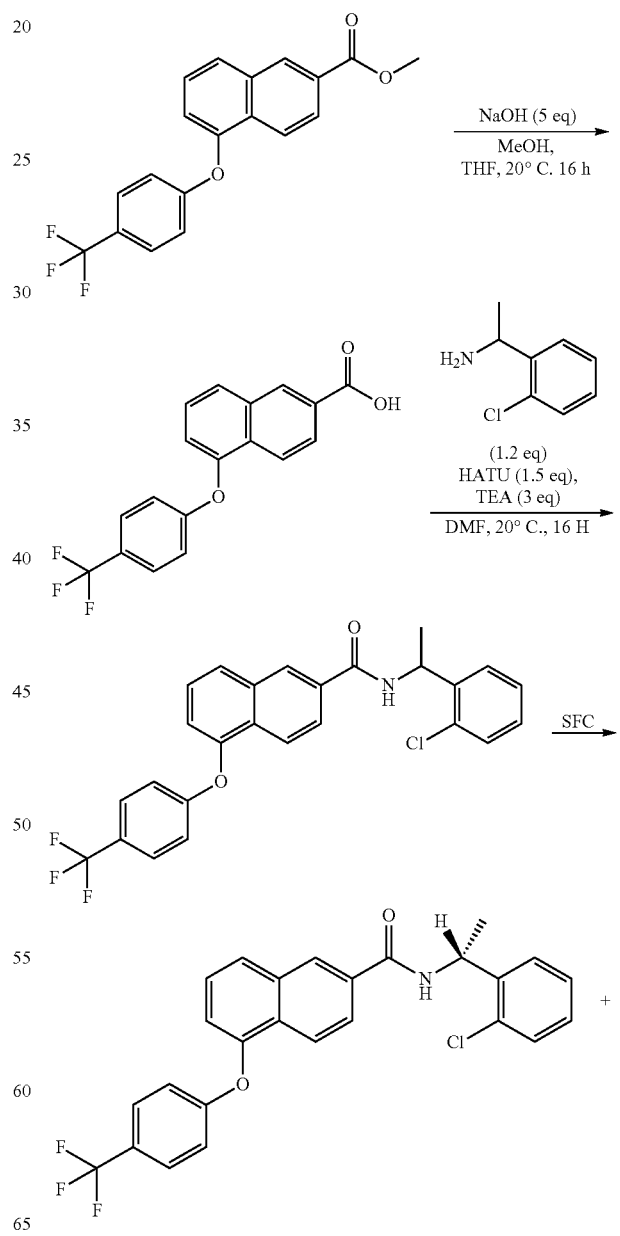

Compound 82

-continued

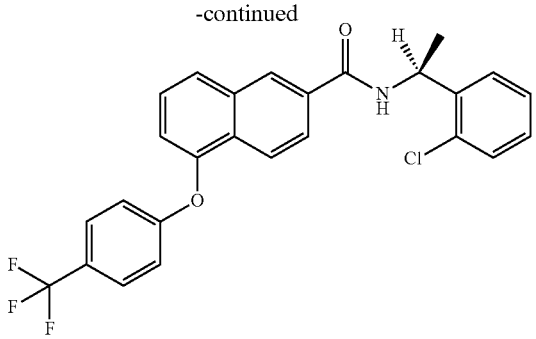

Compound 83

5-(4-(trifluoromethyl)phenoxy)-2-naphthoic Acid

To a solution of methyl 5-(4-(trifluoromethyl)phenoxy)-2-naphthoate (500 mg, 1.44 mmol, 1 eq) in MeOH (8 mL) at 20° C. was added NaOH (2 M, 3.6 mL, 5 eq) and THF (3 mL). The mixture was stirred at 20° C. for 16 h. The reaction mixture was concentrated under reduced pressure to remove solvent. The residue was diluted with water (20 mL), then acidified with 2N HCl at 0° C. to pH=2-3, and then extracted with EA (20 mL*3). The combined organic layers were washed with brine (20 mL), dried over anhydrous $Na_2SO_4$, filtered and concentrated under reduced pressure to give 5-(4-(trifluoromethyl)phenoxy)-2-naphthoic acid (440 mg, 1.28 mmol, 89% yield).

N-(1-(2-chlorophenyl)ethyl)-5-(4-(trifluoromethyl)phenoxy)-2-naphthamide

To a solution of 5-(4-(trifluoromethyl)phenoxy)-2-naphthoic acid (50 mg, 0.15 mmol, 1 eq) and HATU (85.8 mg, 0.23 mmol, 1.5 eq) in DMF (1 mL) at 20° C. was added 1-(2-chlorophenyl)ethan-1-amine (28.1 mg, 0.18 mmol, 1.2 eq) and TEA (45.7 mg, 0.45 mmol, 62 uL, 3 eq). The mixture was stirred at 20° C. for 16 h. The reaction mixture was concentrated under reduced pressure to give the residue which was purified by prep-HPLC to give N-(1-(2-chlorophenyl)ethyl)-5-(4-(trifluoromethyl)phenoxy)-2-naphthamide (52 mg, 0.11 mmol, 73.5% yield). LCMS (ESI): RT=0.993 min, mass calc. for $C_{26}H_{19}ClF_3NO_2$ 469.11, m/z found 470.0 $[M+H]^+$.

(R)-N-(1-(2-chlorophenyl)ethyl)-5-(4-(trifluoromethyl)phenoxy)-2-naphthamide (Compound 82) and (S)-N-(1-(2-chlorophenyl)ethyl)-5-(4-(trifluoromethyl)phenoxy)-2-naphthamide (Compound 83)

N-(1-(2-chlorophenyl)ethyl)-5-(4-(trifluoromethyl)phenoxy)-2-naphthamide (50 mg, 0.11 mmol, 1 eq) was purified SFC to give Compound 82 (12 mg, 25 umol, 23.8% yield) LCMS (ESI): RT=1.049 min, mass calc. for $C_{26}H_{19}ClF_3NO_2$ 469.11, m/z found 470.0 $[M+H]^+$; $^1$H NMR (400 MHz, CDCl$_3$) δ 8.37 (d, J=1.5 Hz, 1H), 8.12 (d, J=8.8 Hz, 1H), 7.86-7.78 (m, 2H), 7.59 (d, J=8.5 Hz, 2H), 7.51 (t, J=8.0 Hz, 1H), 7.43 (ddd, J=1.6, 7.7, 14.3 Hz, 2H), 7.31-7.27 (m, 1H), 7.26-7.22 (m, 1H), 7.15 (d, J=7.5 Hz, 1H), 7.07 (d, J=8.5 Hz, 2H), 6.75 (br d, J=7.3 Hz, 1H), 5.65 (quin, J=7.1 Hz, 1H), 1.68 (d, J=7.0 Hz, 3H); and Compound 83 (13 mg, 28 umol, 26% yield) LCMS (ESI): RT=1.056 min, mass calc. for $C_{26}H_{19}ClF_3NO_2$ 469.11, m/z found 470.0 $[M+H]^+$; $^1$H NMR (400 MHz, CDCl$_3$) δ 8.37 (d, J=1.5 Hz, 1H), 8.12 (d, J=8.8 Hz, 1H), 7.86-7.78 (m, 2H), 7.59 (d, J=8.5 Hz, 2H), 7.51 (t, J=7.9 Hz, 1H), 7.43 (ddd, J=1.6, 7.7, 14.3 Hz, 2H), 7.32-7.28 (m, 1H), 7.32-7.27 (m, 1H), 7.26-7.22 ((m, 1H), 7.17-7.14 (m, 1H), 7.07 (d, J=8.3 Hz, 2H), 6.75 (br d, J=7.3 Hz, 1H), 5.65 (quin, J=7.0 Hz, 1H), 1.68 (d, J=7.0 Hz, 3H).

Example 67: 5-(2-fluoro-4-(trifluoromethyl)phenoxy)-N-isopropyl-2-naphthamide (Compound 84)

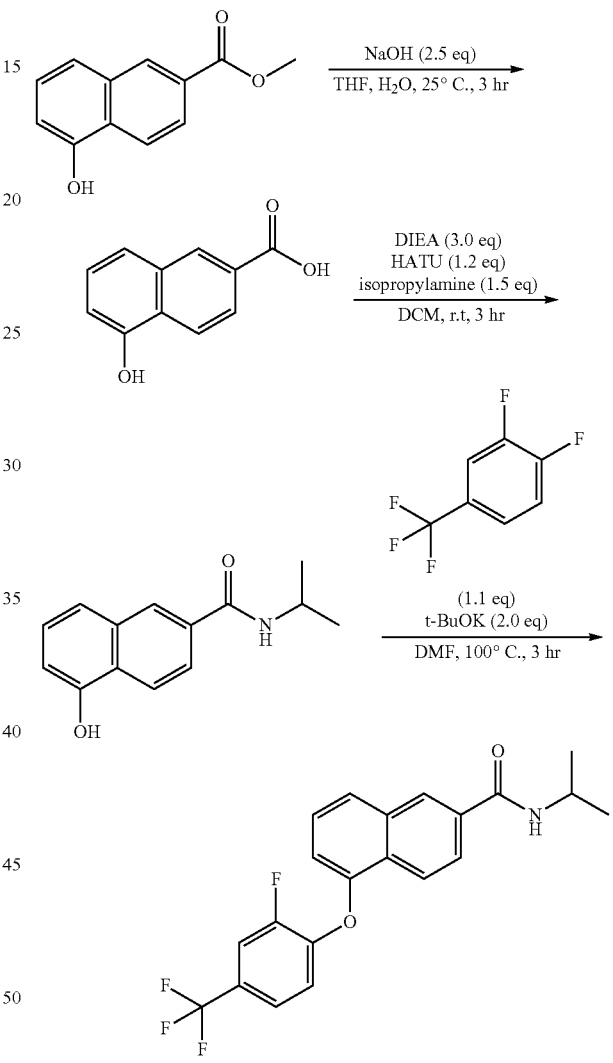

Compound 84

5-hydroxy-2-naphthoic Acid

To a solution of methyl 5-hydroxynaphthalene-2-carboxylate (1.5 g, 7.42 mmol, 1 eq) in THF (25 mL) was added NaOH (741.8 mg, 18.55 mmol, 2.5 eq) in $H_2O$ (5 mL). The mixture was stirred at 25° C. for 3 hr. The $H_2O$ (20 mL) was added and the mixture was neutralized to pH=3~4 with aq. HCl (2 M), The aqueous phase was extracted with EA (35 mL*3). The combined organic phase was washed with brine (40 mL), dried with anhydrous $Na_2SO_4$, filtered and concentrated in vacuum to give crude product. The crude product was triturated with PE (30 mL*3). Compound 5-hydroxynaphthalene-2-carboxylic acid (1.35 g, crude) was obtained.

5-hydroxy-N-isopropyl-2-naphthamide

A mixture of 5-hydroxynaphthalene-2-carboxylic acid (500 mg, 2.66 mmol, 1 eq) HATU (1.21 g, 3.19 mmol, 1.2 eq) in DCM (15 mL) was added DIPEA (1.03 g, 7.97 mmol, 1.39 mL, 3 eq) at 25° C. After addition, the mixture was stirred at 25° C. for 1 hr, and then iso-propylamine (235.5 mg, 3.99 mmol, 0.34 mL, 1.5 eq) was added. The resulting mixture was stirred at 25° C. for 2 hr. The residue was poured into $H_2O$ (50 mL) at 0° C. and stirred for 5 min. The aqueous phase was extracted with EA (30 mL*3). The combined organic phase was washed with brine (40 mL), dried with anhydrous $Na_2SO_4$, filtered and concentrated in vacuum. The residue was purified by flash silica gel chromatography. Compound 5-hydroxy-N-isopropyl-naphthalene-2-carboxamide (410 mg, 1.79 mmol, 67.3% yield) was obtained.

5-(2-fluoro-4-(trifluoromethyl)phenoxy)-N-isopropyl-2-naphthamide

A mixture of 5-hydroxy-N-isopropyl-naphthalene-2-carboxamide (120 mg, 0.52 mmol, 1 eq), 1,2-difluoro-4-(trifluoromethyl)benzene (104.8 mg, 0.57 mmol, 1.1 eq), t-BuOK (117.4 mg, 1.05 mmol, 2 eq) in DMF (3 mL) and the mixture was stirred at 100° C. for 3 hr. The mixture was poured into $H_2O$ (30 mL) at 0° C. and stirred for 5 min. The aqueous phase was extracted with EA (20 mL*3). The combined organic phase was washed with brine (30 mL), dried with anhydrous $Na_2SO_4$, filtered and concentrated in vacuum. The residue was purified by flash silica gel chromatography to give the title compound (49.8 mg, 0.12 mmol, 23.8% yield). LCMS (ESI): RT=0.879 min, mass calcd for $C_{21}H_{17}F_4NO_2$ 391.36, m/z found 392.0 $[M+H]^+$; $^1H$ NMR (400 MHz, DMSO-$d_6$) δ 8.53 (d, J=1.3 Hz, 1H), 8.46 (br d, J=7.8 Hz, 1H), 8.10 (d, J=8.8 Hz, 1H), 8.02-7.90 (m, 3H), 7.61-7.53 (m, 2H), 7.23-7.12 (m, 2H), 4.16 (qd, J=6.8, 13.8 Hz, 1H), 1.21 (d, J=6.8 Hz, 6H).

Example 68: 5-(2-chloro-4-(trifluoromethyl)phenoxy)-N-isopropyl-2-naphthamide (Compound 85)

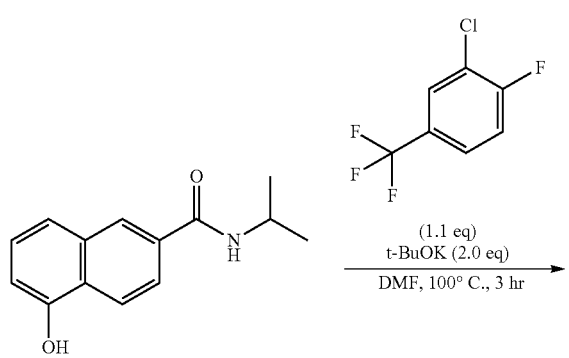

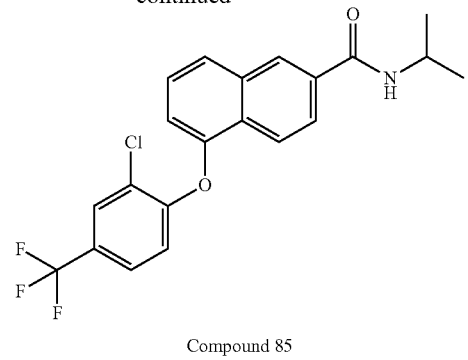

Compound 85

A mixture of 5-hydroxy-N-isopropyl-naphthalene-2-carboxamide (120 mg, 0.52 mmol, 1 eq), 2-chloro-1-fluoro-4-(trifluoromethyl)benzene (114.3 mg, 0.57 mmol, 1.1 eq), t-BuOK (117.4 mg, 1.05 mmol, 2 eq) in DMF (3 mL) and the mixture was stirred at 100° C. for 3 hr. The mixture was poured into $H_2O$ (30 mL) at 0° C. and stirred for 5 min. The aqueous phase was extracted with EA (20 mL*3). The combined organic phase was washed with brine (30 mL), dried with anhydrous $Na_2SO_4$, filtered and concentrated in vacuum. The crude product was purified by prep-HPLC. The title compound (45.6 mg, 0.11 mmol, 21.1% yield) was obtained. LCMS (ESI): RT=0.951 min, mass calcd for $C_{21}H_{17}ClF_3NO_2$ 407.81, m/z found 408.0 $[M+H]^+$; $^1H$ NMR (400 MHz, DMSO-$d_6$) δ 8.54 (s, 1H), 8.46 (br d, J=7.5 Hz, 1H), 8.12 (s, 1H), 8.05-7.92 (m, 3H), 7.70-7.57 (m, 2H), 7.23 (d, J=7.5 Hz, 1H), 7.04 (d, J=8.6 Hz, 1H), 4.16 (qd, J=6.6, 13.2 Hz, 1H), 1.22 (d, J=6.4 Hz, 6H).

Example 69: N-cyano-5-[4-(trifluoromethyl)phenoxy]naphthalene-2-carboxamide (Compound 86)

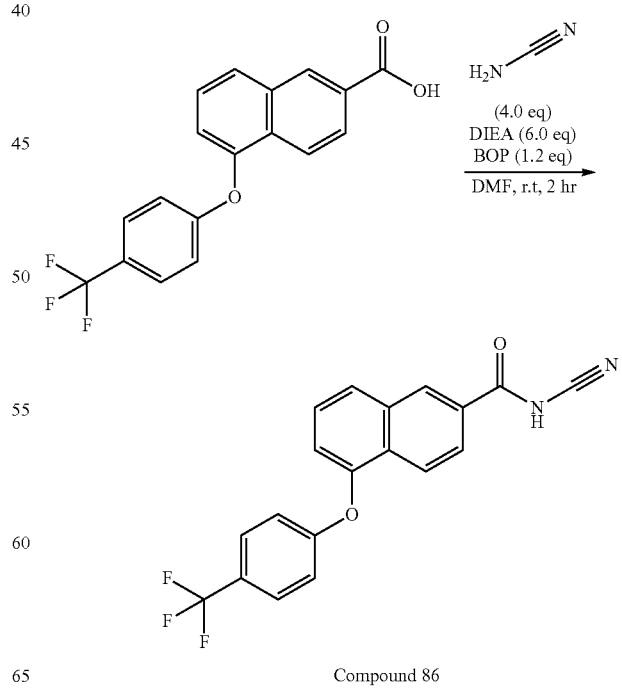

Compound 86

To a solution of 5-[4-(trifluoromethyl)phenoxy]naphthalene-2-carboxylic acid (50 mg, 0.15 mmol, 1 eq) in DMF (2 mL) was added cyanamide (25.3 mg, 0.60 mmol, 25 uL, 4 eq), DIPEA (116.6 mg, 0.90 mmol, 0.15 mL, 6 eq) and BOP (79.8 mg, 0.18 mmol, 1.2 eq). The mixture was stirred at 25° C. for 2 hr. The reaction mixture was diluted with H$_2$O (10 mL) and extracted with EA (10 mL*3). The combined organic phase was washed with brine (10 mL*2), dried with anhydrous Na$_2$SO$_4$, filtered and concentrated in vacuum. The residue was purified by prep-HPLC to give the title compound (1.9 mg, 33.2 umol, 22.1% yield). LCMS (ESI). RT=3.083 min, mass calcd for C$_{19}$H$_{11}$F$_3$N$_2$O 2356.30 m/z found 354.9 [M−H]$^-$; $^1$H NMR (400 MHz, CD$_3$OD) δ 8.58 (d, J=1.5 Hz, 1H), 8.20 (d, J=8.8 Hz, 1H), 7.96 (d, J=7.5 Hz, 2H), 7.71 (s, 1H), 7.69-7.63 (m, 2H), 7.31 (d, J=7.8 Hz, 1H), 7.17 (d, J=8.5 Hz, 2H).

Example 70: N-[(1R)-1-(1H-indazol-7-yl)ethyl]-5-[4-(trifluoromethyl)phenoxy]naphthalene-2-carboxamide (Compound 87) and N-[(S)-1-(1H-indazol-7-yl)ethyl]-5-[4-(trifluoromethyl)phenoxy]naphthalene-2-carboxamide (Compound 88)

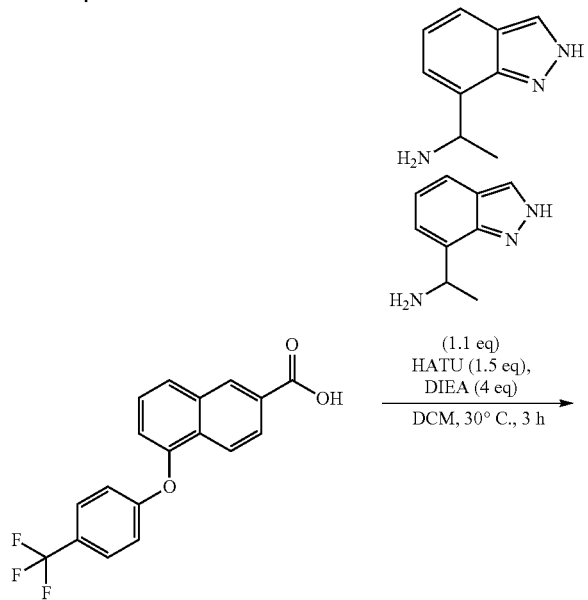

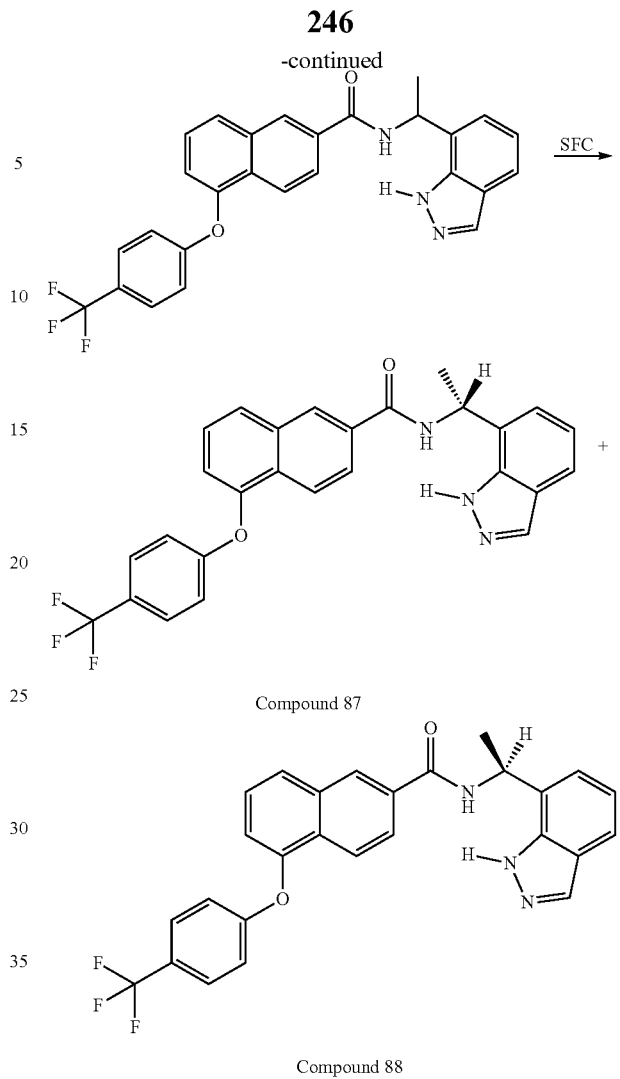

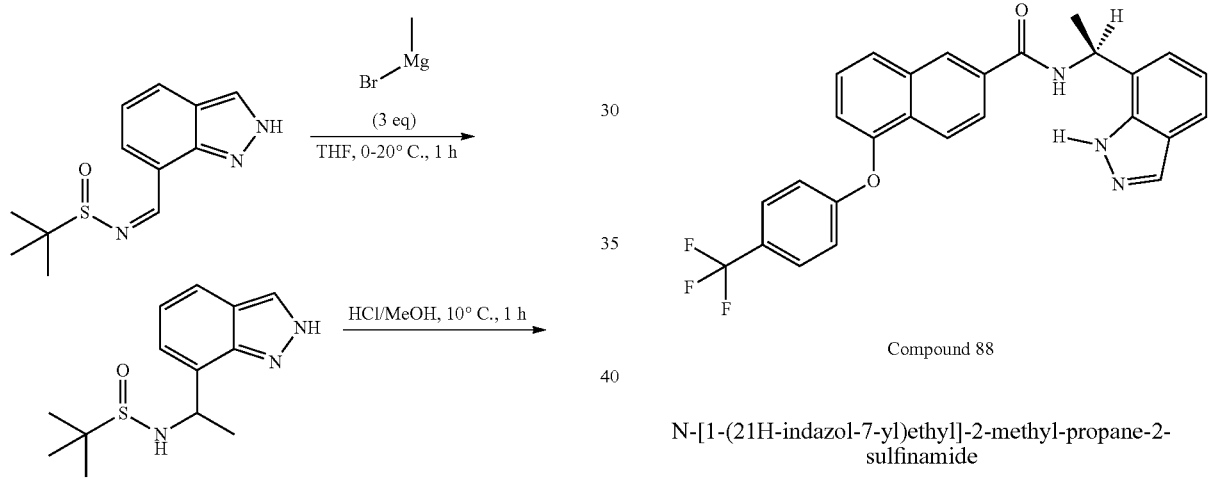

Compound 87

Compound 88

N-[1-(21H-indazol-7-yl)ethyl]-2-methyl-propane-2-sulfinamide

To a solution of (Z)-N-((2H-indazol-7-yl)methylene)-2-methylpropane-2-sulfinamide (110 mg, 0.44 mmol, 1 eq) in THF (1 mL) was added methyl magnesium bromide (3 M in THF, 0.44 mL, 3 eq) at 0° C. The mixture was stirred at 20° C. for 1 h. The mixture was diluted with H$_2$O (5 mL), extracted with EA (10 mL*3). The combined organic layer was washed with brine (10 mL), dried over Na$_2$SO$_4$, filtered and concentrated. The residue was purified by flash silica gel chromatography to give N-[1-(2H-indazol-7-yl)ethyl]-2-methyl-propane-2-sulfinamide (90 mg, 0.30 mmol, 66.9% yield).

1-(2H-indazol-7-yl)ethanamine

A mixture of N-[1-(2H-indazol-7-yl)ethyl]-2-methyl-propane-2-sulfinamide (90 mg, 0.34 mmol, 1 eq) in HCl/MeOH (2 mL) was stirred at 10° C. for 1 h. The mixture was concentrated to give 1-(2H-indazol-7-yl)ethanamine (80 mg, crude, HCl).

N-[1-(2H-indazol-7-yl)ethyl]-5-[4-(trifluoromethyl)phenoxy]naphthalene-2-carboxamide To a solution of 5-(4-(trifluoromethyl)phenoxy)-2-naphthoic acid (70 mg, 0.21 mmol, 1 eq) in DCM (2 mL) were added HATU (120.2 mg, 0.32 mmol, 1.5 eq) and DIEA (108.9 mg, 0.84 mmol, 0.15 mL, 4 eq). The mixture was stirred at 30° C. for 0.5 h. 1-(2H-indazol-7-yl)ethanamine (45.8 mg, 0.23 mmol, 1.1 eq, HCl) was added into the mixture. The mixture was stirred at 30° C. for 2 h. The mixture was diluted with H₂O (10 mL), extracted with EA (20 mL*3). The combined organic layer was washed with brine (20 mL), dried over Na₂SO₄, filtered and concentrated under reduced pressure to give a residue. The residue was purified by prep-HPLC to give N-[1-(2H-indazol-7-yl)ethyl]-5-[4-(trifluoromethyl)phenoxy]naphthalene-2-carboxamide (40 mg, 80.8 umol, 38.3% yield).

N-[(1R)-1-(1H-indazol-7-yl)ethyl]-5-[4-(trifluoromethyl)phenoxy]naphthalene-2-carboxamide (Compound 87) and N-[(1S)-1-(1H-indazol-7-yl)ethyl]-5-[4-(trifluoromethyl)phenoxy]naphthalene-2-carboxamide (Compound 88)

N-[1-(2H-indazol-7-yl)ethyl]-5-[4-(trifluoromethyl)phenoxy]naphthalene-2-carboxamide (40 mg, 84.1 umol, 1 eq) was purified by SFC to give Compound 87 (13.6 mg, 28.5 umol, 33.9% yield). LCMS (ESI): RT=1.037 min, mass calc. for $C_{27}H_{20}F_3N_3O_2$ 475.46, m/z found 476.0 [M+H]⁺; ¹H NMR (400 MHz, CDCl₃) δ 11.99-11.46 (m, 1H), 8.36 (d, J=1.0 Hz, 1H), 8.13-8.03 (m, 2H), 7.83-7.67 (m, 3H), 7.57 (d, J=8.5 Hz, 2H), 7.52-7.45 (m, 1H), 7.40 (d, J=7.0 Hz, 1H), 7.20-7.08 (m, 2H), 7.04 (d, J=8.5 Hz, 2H), 6.57 (br d, J=9.8 Hz, 1H), 6.08-5.93 (m, 1H), 1.91 (d, J=7.0 Hz, 3H); and Compound 88 (13.0 mg, 27.1 umol, 32.2% yield). LCMS (ESI): RT=1.039 min, mass calc. for $C_{27}H_{20}F_3N_3O_2$ 475.46, m/z found 476.0 [M+H]⁺; ¹H NMR (400 MHz, CDCl₃) δ 12.05-11.50 (m, 1H), 8.36 (s, 1H), 8.13-8.03 (m, 2H), 7.82-7.69 (m, 3H), 7.57 (d, J=8.8 Hz, 2H), 7.52-7.45 (m, 1H), 7.40 (d, J=7.0 Hz, 1H), 7.20-7.10 (m, 2H), 7.04 (d, J=8.5 Hz, 2H), 6.55 (br d, J=9.3 Hz, 1H), 6.08-5.90 (m, 1H), 1.91 (d, J=7.0 Hz, 3H).

Example 71: N-[(1S)-1-methylbut-2-ynyl]-5-[4-(trifluoromethyl)phenoxy]naphthalene-2-carboxamide (Compound 89) and N-[(1R)-1-methylbut-2-ynyl]-5-[4-(trifluoromethyl)phenoxy]naphthalene-2-carboxamide (Compound 90)

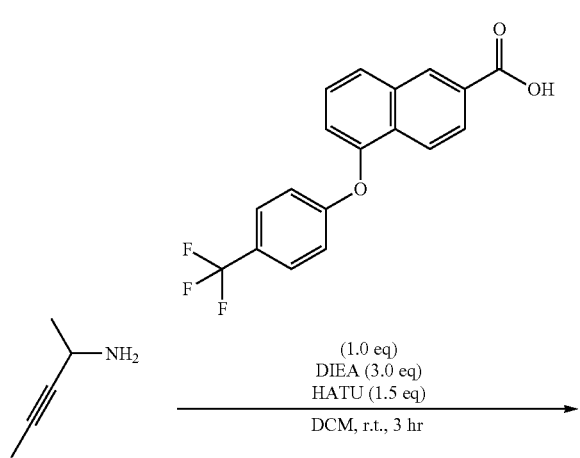

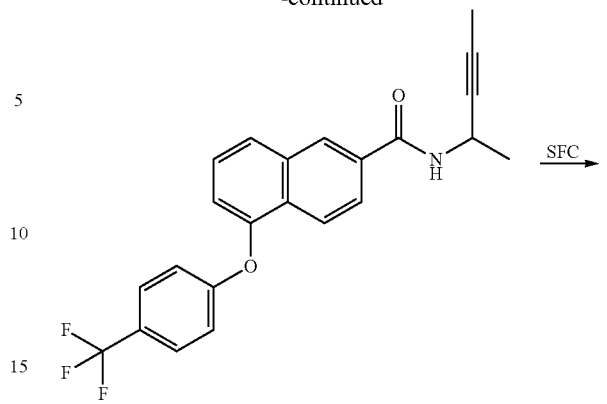

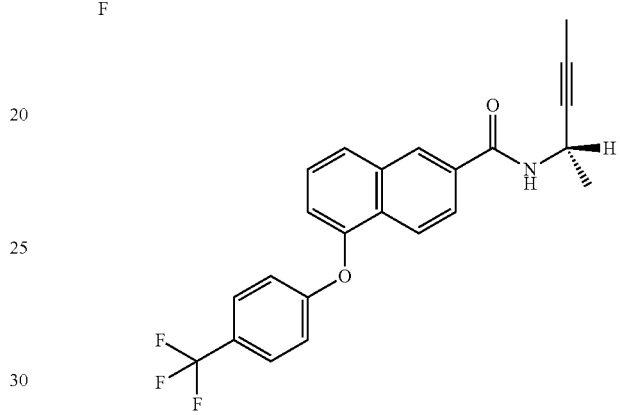

Compound 89

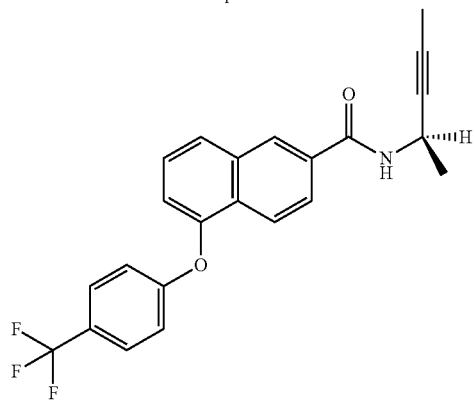

Compound 90

N-(1-methylbut-2-ynyl)-5-[4-(trifluoromethyl)phenoxy]naphthalene-2-carboxamide

A mixture of compound 5-(4-(trifluoromethyl)phenoxy)-2-naphthoic acid (160 mg, 0.48 mmol, 1 eq), HATU (274.6 mg, 0.72 mmol, 1.5 eq) in DCM (5 mL) was added DIPEA (186.7 mg, 1.4 mmol, 0.25 mL, 3 eq) at 25° C. After addition, the mixture was stirred at 25° C. for 1 hr, and then compound pent-3-yn-2-amine (80.1 mg, 0.96 mmd, 2 eq) was added. The resulting mixture was stirred at 25° C. for 2 hr. The mixture was poured into H₂O (30 mL) and stirred for 5 min. The aqueous phase was extracted with EA (20 mL*3). The combined organic phase was washed with brine (30 mL), dried with anhydrous Na₂SO₄, filtered and concentrated in vacuum. The residue was purified by flash silica gel chromatography. Compound N-(1-methylbut-2-ynyl)-5-[4-(trifluoromethyl) phenoxy] naphthalene-2-carboxamide (98 mg, 0.24 mmol, 51.21% yield) was obtained.

N-[(1S)-1-methylbut-2-ynyl]-5-[4-(trifluoromethyl) phenoxy]naphthalene-2-carboxamide (Compound 89) and N-[(1R)-1-methylbut-2-ynyl]-5-[4-(trifluoromethyl)phenoxy]naphthalene-2-carboxamide (Compound 90)

The racemic compound N-(1-methylbut-2-ynyl)-5-[4-(trifluoromethyl) phenoxy]naphthalene-2-carboxamide (98 mg, 0.25 mmd, 1 eq) was purified by SFC to give Compound 89 (36.4 mg, 90.7 umol, 36.7% yield) LCMS (ESI): RT=1.052 min, mass calcd for $C_{23}H_{18}F_3NO_2$ 397.13 m/z found 398.0 [M+H]$^+$; $^1$H NMR (400 MHz, DMSO-$d_6$) δ 9.01 (d, J=8.0 Hz, 1H), 8.58 (s, 1H), 8.04-7.94 (m, 3H), 7.75 (d, J=8.8 Hz, 2H), 7.64 (t, J=7.9 Hz, 1H), 7.33 (d, J=7.5 Hz, 1H), 7.17 (d, J=8.5 Hz, 2H), 4.97-4.83 (m, 1H), 1.81 (d, J=2.3 Hz, 3H), 1.41 (d, J=7.0 Hz, 3H); and Compound 90 (38.3 mg, 95.4 umol, 38.7% yield) LCMS (ESI): RT=1.047 min, mass calcd for $C_{23}H_{18}F_3NO_2$ 397.13 m/z found 398.0 [M+H]$^+$; $^1$H NMR (400 MHz, DMSO-$d_6$) δ 9.01 (d, J=8.0 Hz, 1H), 8.58 (s, 1H), 8.05-7.92 (m, 3H), 7.75 (d, J=8.8 Hz, 2H), 7.64 (t, J=7.9 Hz, 1H), 7.33 (d, J=7.5 Hz, 1H), 7.17 (d, J=8.8 Hz, 2H), 4.89 (m, 1H), 1.81 (d, J=2.3 Hz, 3H), 1.41 (d, J=7.0 Hz, 3H).

Example 72: N-[(1R)-1-(1-methylimidazol-4-yl) ethyl]-5-[4-(trifluoromethyl)phenoxy]naphthalene-2-carboxamide (Compound 91) and N-[(1S)-1-(1-methylimidazol-4-yl)ethyl]-5-[4-(trifluoromethyl) phenoxy]naphthalene-2-carboxamide (Compound 92)

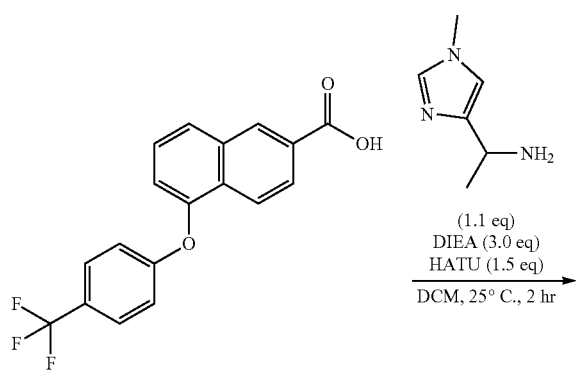

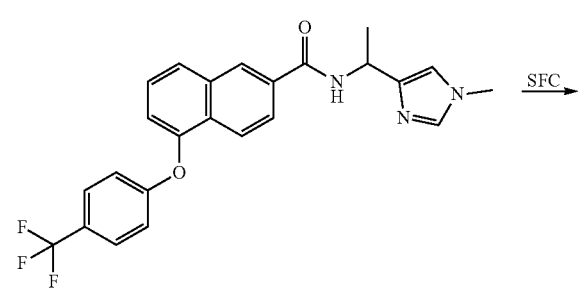

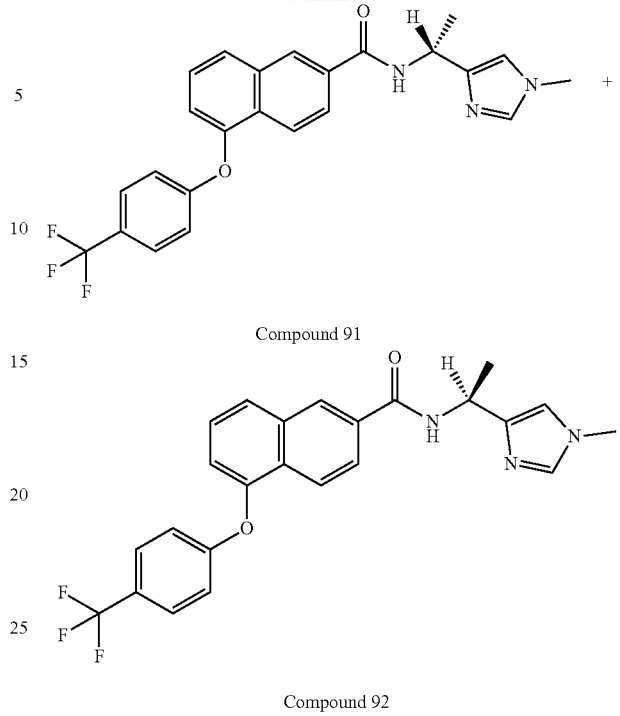

Compound 91

Compound 92

N-[1-(1-methylimidazol-4-yl)ethyl]-5-[4-(trifluoromethyl)phenoxy]naphthalene-2-carboxamide The mixture of 5-[4-(trifluoromethyl)phenoxy]naphthalene-2-carboxylic acid (100 mg, 0.30 mmol, 1 eq), 1-(1-methylimidazol-4-yl)ethanamine (41.4 mg, 0.33 mmol, 1.1 eq), DIPEA (116.6 mg, 0.90 mmol, 0.15 mL, 3 eq) and HATU (171.6 mg, 0.45 mmol, 1.5 eq) in DCM (1 mL) was stirred at 25° C. for 2 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by prep-HPLC. Compound N-[1-(1-methylimidazol-4-yl)ethyl]-5-[4-(trifluoromethyl)phenoxy]naphthalene-2-carboxamide (40 mg, 90.1 umol, 29.9% yield) was obtained.

N-[(1R)-1-(1-methylimidazol-4-yl)ethyl]-5-[4-(trifluoromethyl)phenoxy]naphthalene-2-carboxamide (Compound 91) and N-[(1S)-1-(1-methylimidazol-4-yl)ethyl]-5-[4-(trifluoromethyl)phenoxy]naphthalene-2-carboxamide (Compound 92)

The racemic compound N-[1-(1-methylimidazol-4-yl) ethyl]-5-[4-(trifluoromethyl)phenoxy]naphthalene-2-carboxamide was separated by SFC (column: YMC CHIRAL Amylose-C (250 mm*30 mm, 10 um; mobile phase: [0.1% NH$_3$H$_2$O ETOH]; B %: 45%-45%, min) to give Compound 91 (13.7 mg, 31.3 umol, 34.4% yield) LCMS (ESI): RT=0.867 min, mass calcd for $C_{24}H_{20}F_3N_3O_2$ 439.43 m/z found 440.1[M+H]$^+$; $^1$H NMR (400 MHz, CD$_3$OD) δ ppm 1.65 (d, J=6.75 Hz, 4H) 3.69 (s, 3H) 5.36 (br t, J=7.13 Hz, 1H) 6.88 (s, 1H) 7.06 (d, J=8.50 Hz, 2H) 7.11-7.23 (m, 2H) 7.47-7.53 (m, 1H) 7.59 (d, J=8.76 Hz, 2H) 7.79 (d, J=8.13 Hz, 1H) 7.89 (d, J=8.76 Hz, 1H) 8.09 (d, J=8.88 Hz, 1H) 8.41 (s, 1H); and Compound 92 (6.32 mg, 14.2 umol, 15.6% yield) LCMS (ESI): RT=0.865 min, mass calcd for $C_{24}H_{20}F_3N_3O_2$ 439.43 m/z found 440.1[M+H]+; 1H NMR (400 MHz, CD3OD) δ ppm 1.16-1.38 (m, 2H) 1.63 (br d, J=6.63 Hz, 3H) 3.66 (s, 3H) 5.31-5.39 (m, 1H) 6.85 (br s, 1H) 7.06 (d, J=8.63 Hz, 2H) 7.10-7.19 (m, 1H) 7.13 (d, J=7.63 Hz, 1H) 7.41-7.52 (m, 2H) 7.59 (d, J=8.63 Hz, 2H) 7.78 (d, J=8.25 Hz, 1H) 7.87 (br d, J=8.76 Hz, 1H) 8.09 (d, J=8.75 Hz, 1H) 8.39 (s, 1H).

Example 73: N-isopropyl-4-(4-(trifluoromethyl)phenoxy)isoquinoline-7-carboxamide (Compound 93)

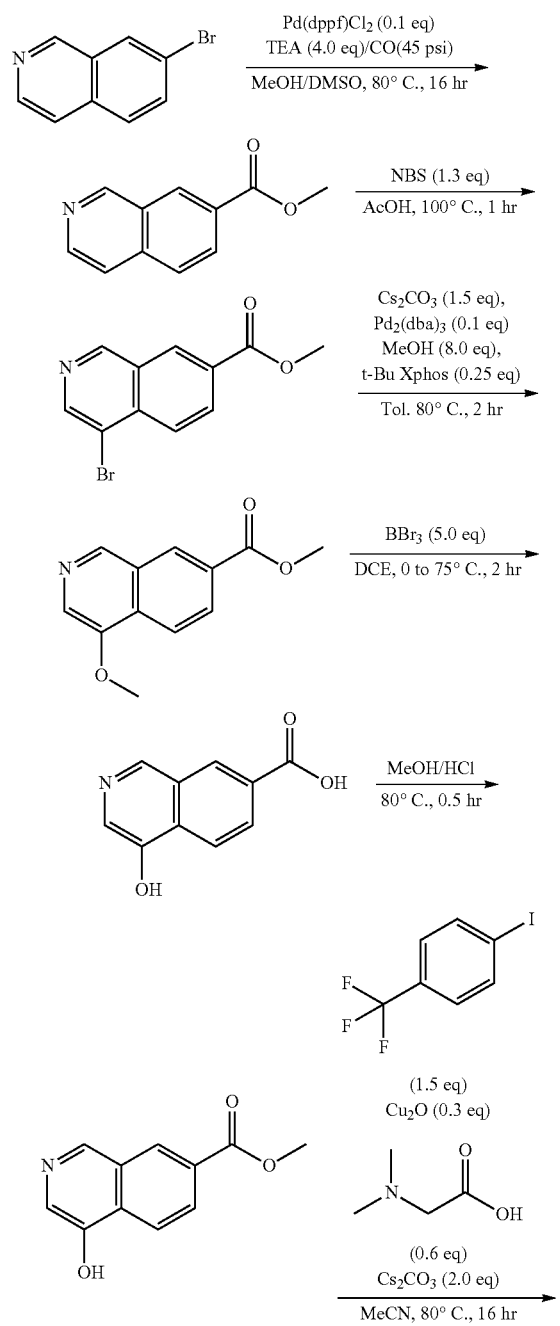

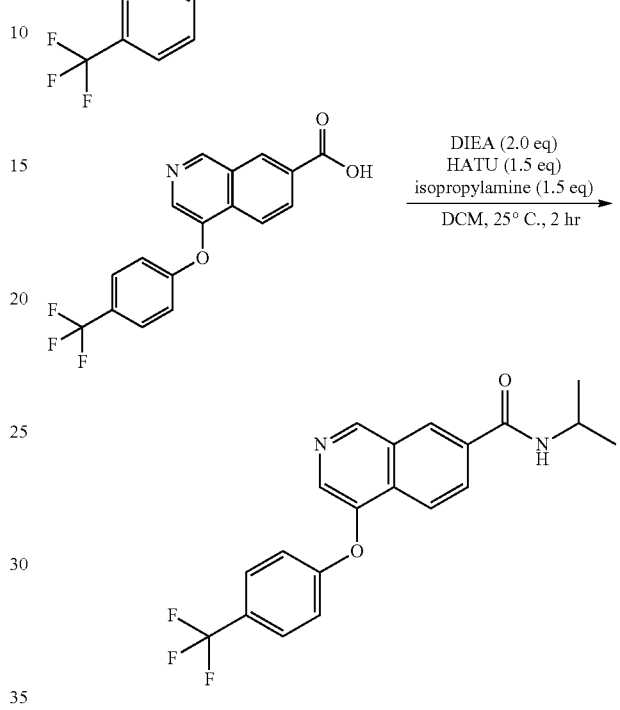

Compound 93

Methyl isoquinoline-7-carboxylate

To a solution of 7-bromoisoquinoline (1 g, 4.42 mmol, 1 eq) in MeOH (6 mL) and DMSO (8 mL) were added TEA (1.79 g, 17.69 mmol, 2.46 mL, 4.0 eq) and Pd(dppf)Cl2 (323.5 mg, 0.44 mmol, 0.1 eq) under N2. The suspension was degassed under vacuum and purged with CO several times. The mixture was stirred under CO (45 psi) at 80° C. for 16 hrs. The reaction mixture was diluted with H2O (10 mL) and extracted with EtOAc (10 mL*3). The combined organic layers were washed with brine (20 mL*3), dried over Na2SO4, filtered and concentrated under reduced pressure to give a residue. The residue was purified by silica gel column chromatography to give methyl isoquinoline-7-carboxylate (800 mg, 4.27 mmol, 96.6% yield).

Methyl 4-bromoisoquinoline-7-carboxylate

To a solution of methyl isoquinoline-7-carboxylate (400 mg, 2.14 mmol, 1 eq) in AcOH (7 mL) was added NBS (494.4 mg, 2.78 mmol, 1.3 eq). The mixture was stirred at 100° C. for 1 hr. The reaction mixture was diluted with sat. Na2CO3 (10 mL) and extracted with EtOAc (15 mL*3). The combined organic layers were washed with brine (20 mL*2), dried over Na2SO4, filtered and concentrated under reduced pressure to give a residue. The residue was purified by silica gel column chromatography to give methyl 4-bromoisoquinoline-7-carboxylate (420 mg, 1.56 mmol, 73.1% yield).

Methyl 4-methoxyisoquinoline-7-carboxylate

To a solution of methyl 4-bromoisoquinoline-7-carboxylate (420 mg, 1.56 mmol, 1 eq) and MeOH (400.5 mg, 12.50 mmol, 0.50 mL, 8.0 eq) in Tol. (8 mL) were added $Cs_2CO_3$ (763.7 mg, 2.34 mmol, 1.5 eq), t-Bu Xphos (165.8 mg, 0.39 mmol, 0.25 eq) and $Pd_2(dba)_3$ (143.0 mg, 0.15 mmol, 0.1 eq). The mixture was stirred at 80° C. for 2 hr. The reaction mixture was filtered and concentrated under reduced pressure to give a residue. The residue was purified by silica gel column chromatography to give methyl 4-methoxyisoquinoline-7-carboxylate (270 mg, 0.85 mmol, 54.8% yield).

4-hydroxyisoquinoline-7-carboxylic Acid

To a solution of methyl 4-methoxyisoquinoline-7-carboxylate (270 mg, 0.85 mmol, 1 eq) in DCE (4 mL) was added a solution of $BBr_3$ (1.07 g, 4.29 mmol, 0.41 mL, 5.0 eq) in DCE (2 mL) at 0° C. The mixture was stirred at 75° C. for 2 hr. The reaction mixture was quenched by addition sat. $NaHCO_3$ (15 mg) at 0° C., and then extracted with EtOAc (15 mL*2). The aqueous phase was concentrated under pressure to give 4-hydroxyisoquinoline-7-carboxylic acid (300 mg, crude). The crude product was used into the next step without further purification. Compound 4-hydroxyisoquinoline-7-carboxylic acid (300 mg, crude) was obtained.

Methyl 4-hydroxyisoquinoline-7-carboxylate

A solution of 4-hydroxyisoquinoline-7-carboxylic acid (300 mg, 1.59 mmol, 1 eq) in HCl/MeOH (4 M, 35.71 mL, 90.06 eq) was stirred at 80° C. for 0.5 hr. The reaction mixture was concentrated under reduced pressure to give methyl 4-hydroxyisoquinoline-7-carboxylate (250 mg, crude). The crude product was used into the next step without further purification. Compound methyl 4-hydroxyisoquinoline-7-carboxylate (250 mg, crude) was obtained.

Methyl 4-(4-(trifluoromethyl)phenoxy)isoquinoline-7-carboxylate

To a solution of methyl 4-hydroxyisoquinoline-7-carboxylate (150 mg, 0.73 mmol, 1 eq) in MeCN (4 mL) were added 1-iodo-4-(trifluoromethyl)benzene (301.2 mg, 1.11 mmol, 0.16 mL, 1.5 eq), 1H-imidazole-5-carboxylic acid (49.6 mg, 0.44 mmol, 0.6 eq), $Cs_2CO_3$ (481.0 mg, 1.48 mmol, 2.0 eq) and $Cu_2O$ (31.6 mg, 0.22 mmol, 22.6 uL, 0.3 eq). The mixture was stirred at 80° C. for 16 hr. The reaction mixture was filtered and concentrated under reduced pressure to give a residue. The residue was purified by silica gel column chromatography to give methyl 4-[4-(trifluoromethyl)phenoxy]isoquinoline-7-carboxylate (30 mg, 82.0 umol, 11.1% yield).

4-(4-(trifluoromethyl)phenoxy)isoquinoline-7-carboxylic Acid

To a solution of methyl 4-[4-(trifluoromethyl)phenoxy] isoquinoline-7-carboxylate (30 mg, 86.3 umol, 1 eq) in MeOH (1 mL) was added a solution of NaOH (13.8 mg, 0.34 mmol, 4.0 eq) in $H_2O$ (0.5 mL). The mixture was stirred at 25° C. for 1 hr. The pH of the reaction mixture was adjusted to 4-5 with HCl (2 M), then the mixture was extracted with EtOAc (15 mL*2). The combined organic was concentrated under reduced pressure to give 4-[4-(trifluoromethyl)phenoxy]isoquinoline-7-carboxylic acid (30 mg, crude). The crude product was used into the next step without further purification.

N-isopropyl-4-(4-(trifluoromethyl)phenoxy)isoquinoline-7-carboxamide

To a solution of 4-[4-(trifluoromethyl)phenoxy]isoquinoline-7-carboxylic acid (30 mg, 90.0 umol, 1 eq) in DCM (1.5 mL) was added HATU (51.3 mg, 0.13 mmol, 1.5 eq), DIPEA (23.2 mg, 0.18 mmol, 31.3 uL, 2.0 eq) and iso-propylamine (7.9 mg, 0.13 mmol, 11.6 uL, 1.5 eq). The mixture was stirred at 25° C. for 2 hr. The reaction mixture was concentrated under reduced pressure to give a residue. The residue was purified by prep-HPLC to give the title compound (3.97 mg, 10.6 umol, 11.7% yield). LCMS (ESI): RT=0.876 min, mass calcd for $C_{20}H_{17}F_3N_2O_2$ 374.36 m/z found 375.0 $[M+H]^+$; $^1H$ NMR (400 MHz, DMSO-$d_6$) δ 9.42 (s, 1H), 8.78 (s, 1H), 8.61 (br d, J=7.8 Hz, 1H), 8.44 (s, 1H), 8.24 (d, J=8.8 Hz, 1H), 8.02 (d, J=8.8 Hz, 1H), 7.76 (d, J=8.6 Hz, 2H), 7.24 (d, J=8.5 Hz, 2H), 4.16 (qd, J=6.8, 13.6 Hz, 1H), 1.21 (d, J=6.5 Hz, 6H).

Example 74: N-(3-hydroxy-1-(pyridin-2-yl)propyl)-5-(4-(trifluoromethyl)phenoxy)-2-naphthamide (Compound 94)

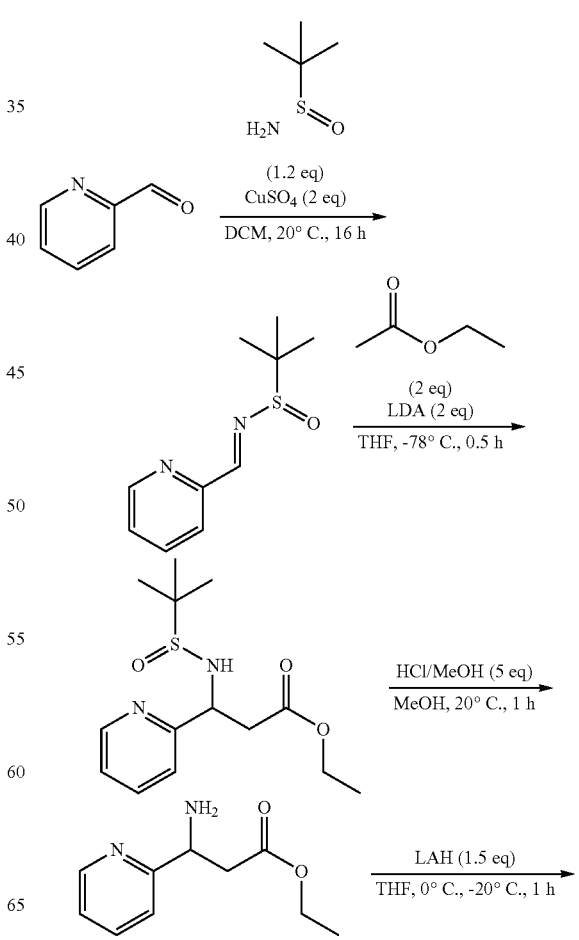

-continued

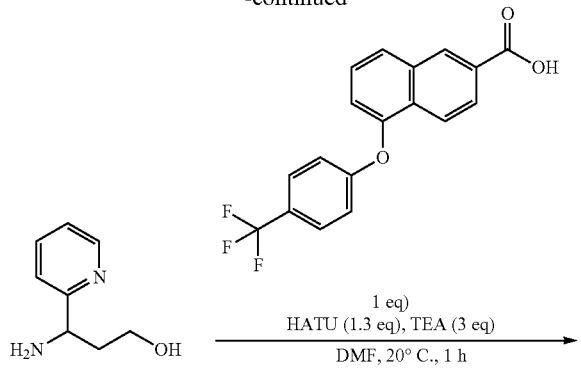

Compound 94

(E)-2-methyl-N-(pyridin-2-ylmethylene)propane-2-sulfinamide

To a solution of picolinaldehyde (3 g, 28.01 mmol, 1 eq) and 2-methylpropane-2-sulfinamide (4.07 g, 33.61 mmol, 1.2 eq) in DCM (56 mL) at 20° C. was added CuSO$_4$ (8.94 g, 56.02 mmol, 8.60 mL, 2 eq). The reaction was stirred at 20° C. for 16 h. The reaction mixture was filtered to remove the solid and the filtrate was concentrated under reduced pressure to give the residue. The residue was diluted with water (100 mL), and then extracted with EA (100 mL*3). The combined organic layers were washed with water (50 mL) and brine (50 mL), dried over anhydrous Na$_2$SO$_4$, filtered and concentrated under reduced pressure to give (E)-2-methyl-N-(pyridin-2-ylmethylene)propane-2-sulfinamide (4.32 g, 20.54 mmol, 73.3% yield), which was used for next step directly. LCMS (ESI): RT=0.640 min, mass calc. for C$_{10}$H$_{14}$N$_2$OS 210.08, m/z found 210.9 [M+H]$^+$.

Ethyl 3-(1,1-dimethylethylsulfinamido)-3-(pyridin-2-yl)propanoate

To a solution of ethyl acetate (837.9 mg, 9.51 mmol, 0.93 mL, 2 eq) in THF (5 mL) was added LDA (2 M, 4.76 mL, 2 eq) and the mixture was stirred at −78° C. for 10 min, and then a solution of (E)-2-methyl-N-(pyridin-2-ylmethylene) propane-2-sulfinamide (1.0 g, 4.76 mmol, 1 eq) in THF (5 mL) was added slowly at −78° C. into the above mixture. The reaction mixture was stirred at −78° C. for 20 min. The reaction mixture was diluted with NH$_4$Cl (3 mL) and water (40 mL) and extracted with EA (40 mL*3). The combined organic layers were washed with water (20 mL*2) and brine (20 mL*2), dried over Na$_2$SO$_4$, filtered and concentrated under reduced pressure to give ethyl 3-(1,1-dimethylethyl-sulfinamido)-3-(pyridin-2-yl)propanoate (1.1 g, 3.32 mmol, 69.8% yield), which was used directly for next step. LCMS (ESI): RT=0.803 min, mass calc. for C$_{14}$H$_{22}$N$_2$O$_3$S 298.14, m/z found 298.9 [M+H]$^+$; $^1$H NMR (400 MHz, CDCl$_3$) δ 8.55 (br d, J=4.5 Hz, 1H), 7.67 (dt, J=1.5, 7.8 Hz, 1H), 7.42 (dd, J=5.3, 7.8 Hz, 1H), 7.21-7.17 (m, 1H), 4.85 (s, 1H), 4.16-4.07 (m, 2H), 3.28-3.06 (m, 1H), 2.95-2.81 (m, 1H), 1.24 (d, J=4.8 Hz, 9H), 1.23-1.17 (m, 3H).

Ethyl 3-amino-3-(pyridin-2-yl)propanoate

To a solution of ethyl 3-(1,1-dimethylethylsulfinamido)-3-(pyridin-2-yl)propanoate (100 mg, 0.34 mmol, 1 eq) in MeOH (3 mL) at 20° C. was added HCl/MeOH (4 M, 0.42 mL, 5 eq) drop-wise, and the mixture was stirred at 20° C. for 1 h. The reaction mixture was concentrated to give ethyl 3-amino-3-(pyridin-2-yl)propanoate (65 mg, 0.33 mmd, 99.9% yield), which was used directly for next step.

3-amino-3-(pyridin-2-yl)propan-1-ol

To a solution of ethyl 3-amino-3-(pyridin-2-yl)propanoate (65 mg, 0.33 mmol, 1 eq) in THF (2 mL) at 0° C. was added LAH (19.1 mg, 0.50 mmd, 1.5 eq), and the mixture was stirred at 20° C. for 1 h. The reaction mixture was quenched at 0° C. with water (two drops) and then 2 N NaOH (two drops), diluted with EA (20 mL), dried over Na$_2$SO$_4$ and then filtered to remove the solid. The filtrate was concentrated to give 3-amino-3-(pyridin-2-yl)propan-1-ol (45 mg, 0.30 mmol, 88.4% yield), which was used directly for next step.

N-(3-hydroxy-1-(pyridin-2-yl)propyl)-5-(4-(trifluoromethyl)phenoxy)-2-naphthamide To a solution of 5-(4-(trifluoromethyl)phenoxy)-2-naphthoic acid (40 mg, 0.12 mmol, 1 eq), 3-amino-3-(pyridin-2-yl)propan-1-ol (36.6 mg, 0.24 mmol, 2 eq) and HATU (59.5 mg, 0.16 mmol, 1.3 eq) in DMF (1 mL) at 20° C. was added TEA (36.5 mg, 0.36 mmol, 50 uL, 3 eq), and the mixture was stirred at 20° C. for 1 h. The mixture was concentrated to give a residue. The residue was purified by prep-HPLC to give the title compound (15.0 mg, 29.8 umol, 24.8% yield, HCl). LCMS (ESI): RT=0.843 min, mass calc. for C$_{26}$H$_{21}$F$_3$N$_2$O$_3$ 466.15, m/z found 467.1 [M+H]$^+$; $^1$H NMR (400 MHz, CD$_3$OD) δ 8.79 (d, J=5.3 Hz, 1H), 8.63 (t, J=7.3 Hz, 1H), 8.58 (d, J=1.3 Hz, 1H), 8.19 (d, J=8.3 Hz, 1H), 8.13 (d, J=8.8 Hz, 1H), 8.01 (t, J=6.8 Hz, 1H), 7.98-7.87 (m, 2H), 7.66 (d, J=8.8 Hz, 2H), 7.61 (t, J=8.0 Hz, 1H), 7.25 (d, J=7.0 Hz, 1H), 7.14 (d, J=8.5 Hz, 2H), 5.52 (dd, J=6.3, 8.3 Hz, 1H), 3.83 (ddd, J=4.0, 7.7, 11.4 Hz, 1H), 3.72 (td, J=5.4, 11.1 Hz, 1H), 2.46-2.36 (m, 1H), 2.34-2.24 (m, 1H).

Example 75: N-[(1S)-1-(azetidin-3-yl)ethyl]-5-[4-(trifluoromethyl)phenoxy]naphthalene-2-carboxamide (Compound 95) and N-[(1R)-1-(azetidin-3-yl)ethyl]-5-[4-(trifluoromethyl)phenoxy]naphthalene-2-carboxamide (Compound 96)

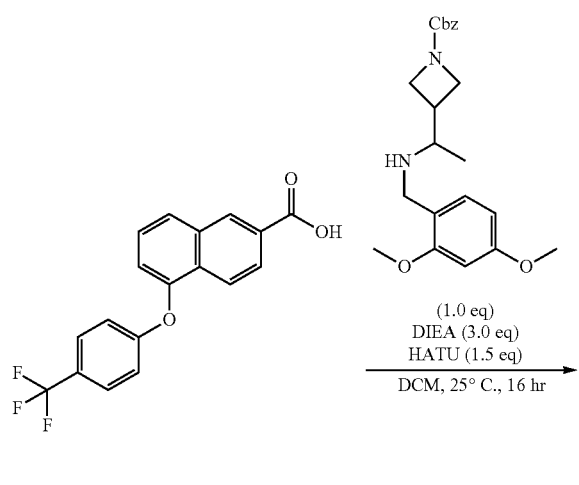

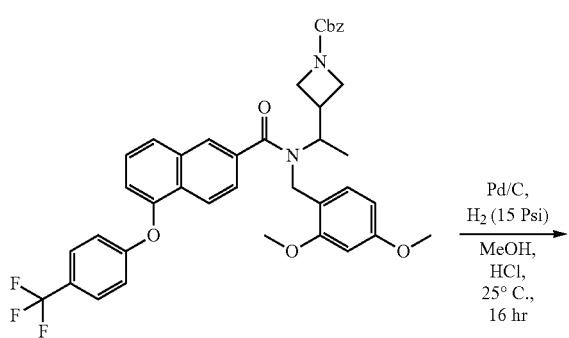

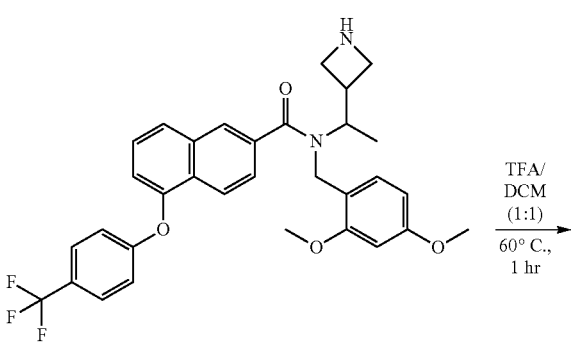

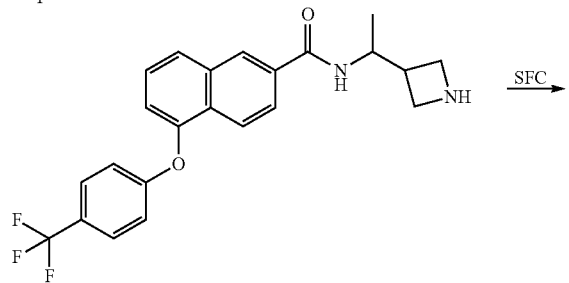

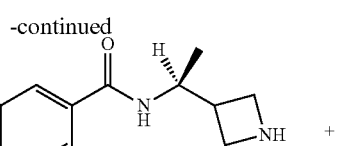

Compound 95

Compound 96

Benzyl 3-[1-[(2,4-dimethoxyphenyl)methyl-[5-[4-(trifluoromethyl)phenoxy]naphthalene-2-carbonyl]amino]ethyl]azetidine-1-carboxylate A mixture of 5-[4-(trifluoromethyl)phenoxy]naphthalene-2-carboxylic acid (1.38 g, 4.16 mmol, 1 eq), HATU (2.37 g, 6.24 mmol, 1.5 eq) in DCM (20 mL) was added DIPEA (1.61 g, 12.48 mmol, 2.17 mL, 3 eq) at 25° C. After addition, the mixture was stirred at 25° C. for 1 hr, and then benzyl 3-[1-[(2,4-dimethoxyphenyl)methylamino]ethyl]azetidine-1-carboxylate (1.6 g, 4.16 mmol, 1 eq) was added. The resulting mixture was stirred at 25° C. for 15 hr. The residue was poured into H$_2$O (50 mL) and stirred for 5 min. The aqueous phase was extracted with EA (30 mL*3). The combined organic phase was washed with brine (40 mL), dried with anhydrous Na$_2$SO$_4$, filtered and concentrated in vacuum. The residue was purified by flash silica gel chromatography. Compound benzyl 3-[1-[(2,4-dimethoxyphenyl) methyl-[5-[4-(trifluoromethyl) phenoxy] naphthalene-2-carbonyl] amino] ethyl] azetidine-1-carboxylate (2.21 g, 3.07 mmol, 73.7% yield) was obtained.

N-[1-(azetidin-3-yl)ethyl]-N-[(2,4-dimethoxyphenyl)methyl]-5-[4-(trifluoromethyl)phenoxy]naphthalene-2-carboxamide To a solution of benzyl 3-[1-[(2,4-dimethoxyphenyl)methyl-[5-[4-(trifluoromethyl)phenoxy]naphthalene-2-carbonyl]amino]ethyl]azetidine-1-carboxylate (250 mg, 0.35 mmol, 1 eq) in MeOH (5 mL) was added Pd/C (50 mg, 0.36 mmol, 10%, 1.00 eq) and HCl (12 M, 0.31 mL, 10.5 eq) under N$_2$. The suspension was degassed under vacuum and purged with H$_2$ several times. The mixture was stirred under H$_2$ (15 psi) at 25° C. for 16 hrs. The reaction mixture was filtered and the cake was washed with MeOH (10 mL*2). The filter was concentrated in vacuo to give crude product.

The crude product was used for next step without further purification. Compound N-[1-(azetidin-3-yl)ethyl]-N-[(2,4-dimethoxyphenyl)methyl]-5-[4-(trifluoromethyl)phenoxy] naphthalene-2-carboxamide (195 mg, crude) was obtained.

N-[1-(azetidin-3-yl)ethyl]-5-[4-(trifluoromethyl) phenoxy]naphthalene-2-carboxamide To a solution of N-[1-(azetidin-3-yl)ethyl]-N-[(2,4-dimethoxyphenyl)methyl]-5-[4-(trifluoromethyl)phenoxy]naphthalene-2-carboxamide (190 mg, 0.34 mmol, 1 eq) in DCM (1 mL) was added TFA (2.31 g, 20.26 mmol, 1.5 mL, 60.2 eq). The mixture was stirred at 60° C. for 1 hr. The reaction mixture was concentrated under reduced pressure to remove DCM and TFA to give crude product. The crude product was purified by prep-HPLC. Compound N-[1-(azetidin-3-yl) ethyl]-5-[4-(trifluoromethyl) phenoxy]naphthalene-2-carboxamide (91.4 mg, 0.22 mmol, 64.9% yield) was obtained.

N-[(1S)-1-(azetidin-3-yl)ethyl]-5-[4-(trifluoromethyl)phenoxy]naphthalene-2-carboxamide (Compound 95) and N-[(1R)-1-(azetidin-3-yl)ethyl]-5-[4-(trifluoromethyl)phenoxy]naphthalene-2-carboxamide (Compound 96)

The racemic compound N-[1-(azetidin-3-yl) ethyl]-5-[4-(trifluoromethyl) phenoxy]naphthalene-2-carboxamide (90 mg, 0.22 mmol, 1 eq) was purified by SFC to give Compound 95 (23.4 mg, 54.7 umol, 25.2% yield) LCMS (ESI): RT=0.822 min, mass calcd for $C_{23}H_{21}F_3N_2O_2$ 414.16 m/z found 415.1 [M+H]$^+$; $^1$H NMR (400 MHz, CD$_3$OD) δ 8.45 (s, 1H), 8.09 (d, J=8.8 Hz, 1H), 7.89 (d, J=8.8 Hz, 2H), 7.68-7.54 (m, 3H), 7.23 (d, J=7.8 Hz, 1H), 7.13 (d, J=8.8 Hz, 2H), 4.49-4.30 (m, 1H), 3.81-3.58 (m, 3H), 3.52-3.36 (m, 1H), 2.99 (m, 1H), 1.23-1.15 (m, 3H); and Compound 96 (18.3 mg, 42.8 umol, 19.7% yield) LCMS (ESI): RT=0.830 min, mass calcd for $C_{23}H_{21}F_3N_2O_2$ 414.16 m/z found 415.1 [M+H]$^+$; $^1$H NMR (400 MHz, CD$_3$OD) δ 8.47-8.40 (m, 1H), 8.11-8.03 (m, 1H), 7.89 (d, J=8.5 Hz, 2H), 7.68-7.53 (m, 3H), 7.25-7.06 (m, 3H. 4.50-4.26 (m, 1H), 3.81-3.55 (m, 2H), 3.51-3.35 (m, 1H), 3.07-2.61 (m, 1H), 1.25-1.14 (m, 3H).

Example 76: (S)-N-(1-(pyridin-2-yl)ethyl)-7-(4-(trifluoromethyl)phenoxy)benzothiophene-2-carboxamide (Compound 97)

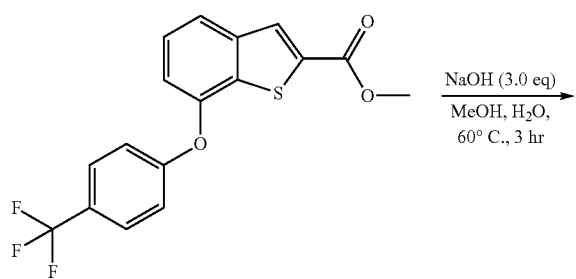

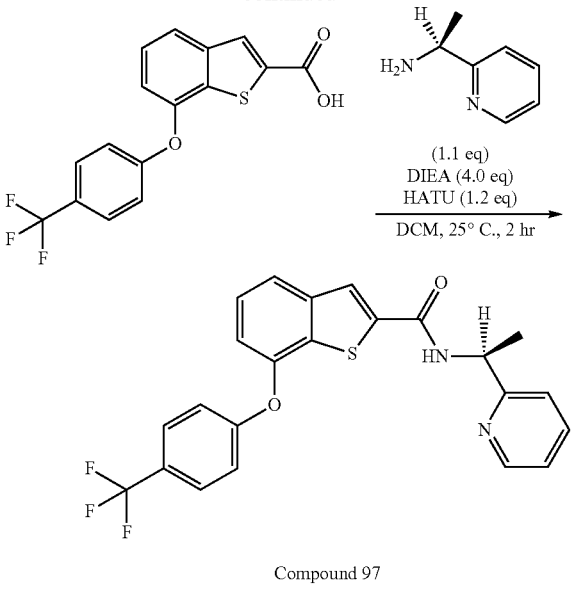

Compound 97

7-(4-(trifluoromethyl)phenoxy)benzothiophene-2-carboxylic Acid

To a solution of methyl 7-[4-(trifluoromethyl)phenoxy] benzothiophene-2-carboxylate (50 mg, 0.14 mmol, 1 eq) in MeOH (1 mL) was added NaOH (17.0 mg, 0.42 mmol, 3 eq) and H$_2$O (2.00 g, 111.02 mmol, 2 mL, 782 eq). The mixture was stirred at 60° C. for 3 hr. Iced water (5 mL) was added and the mixture was neutralized to pH=6-7 with aq. HCl (4 M). The aqueous phase was extracted with EA (15 mL*3). The combined organic phase was washed with brine (20 mL), dried with anhydrous Na$_2$SO$_4$, filtered and concentrated under reduced pressure to give a residue. Compound 7-[4-(trifluoromethyl)phenoxy]benzothiophene-2-carboxylic acid (41.3 mg, crude) was obtained.

(S)-N-(1-(pyridin-2-yl)ethyl)-7-(4-(trifluoromethyl) phenoxy)benzothiophene-2-carboxamide To a solution of 7-[4-(trifluoromethyl)phenoxy]benzothiophene-2-carboxylic acid (40 mg 0.11 mmol, 1 eq) and HATU (53.9 mg, 0.14 mmol, 1.2 eq) in DCM (2 mL) was added DIEA (61.1 mg, 0.47 mmol, 82.3 uL, 4 eq). After addition, the mixture was stirred at 25° C. for 0.5 hr, and then (1S)-1-(2-pyridyl)ethanamine (15.8 mg, 0.13 mmol, 1.1 eq) was added. The resulting mixture was stirred at 25° C. for 2 hr. The mixture was added H$_2$O (10 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC to give the title compound (9.5 mg, 21.3 umol, 18.0% yield). LCMS (ESI): RT=0.801 min, mass calcd for $C_{23}H_{17}F_3N_2O_2S$ 442.45 m/z found 443.3 [M+H]$^+$; $^1$H NMR (400 MHz, DMSO-d$_6$) δ 9.22 (br d, J=7.8 Hz, 1H), 8.53 (br d, J=4.8 Hz, 1H), 8.37 (s, 1H), 7.88 (d, J=8.0 Hz, 1H), 7.80-7.73 (m, 3H), 7.52 (t, J=7.8 Hz, 1H), 7.41 (d, J=7.9 Hz, 1H), 7.29-7.18 (m, 4H), 5.16 (quin, J=7.1 Hz, 1H), 1.52 (d, J=7.0 Hz, 3H).

Example 77: N-[(1R)-1-(2-oxo-1H-quinolin-8-yl)ethyl]-5-[4-(trifluoromethyl)phenoxy]naphthalene-2-carboxamide (Compound 98) and N-[(1S)-1-(2-oxo-1H-quinolin-8-yl)ethyl]-5-[4-(trifluoromethyl)phenoxy]naphthalene-2-carboxamide (Compound 99)
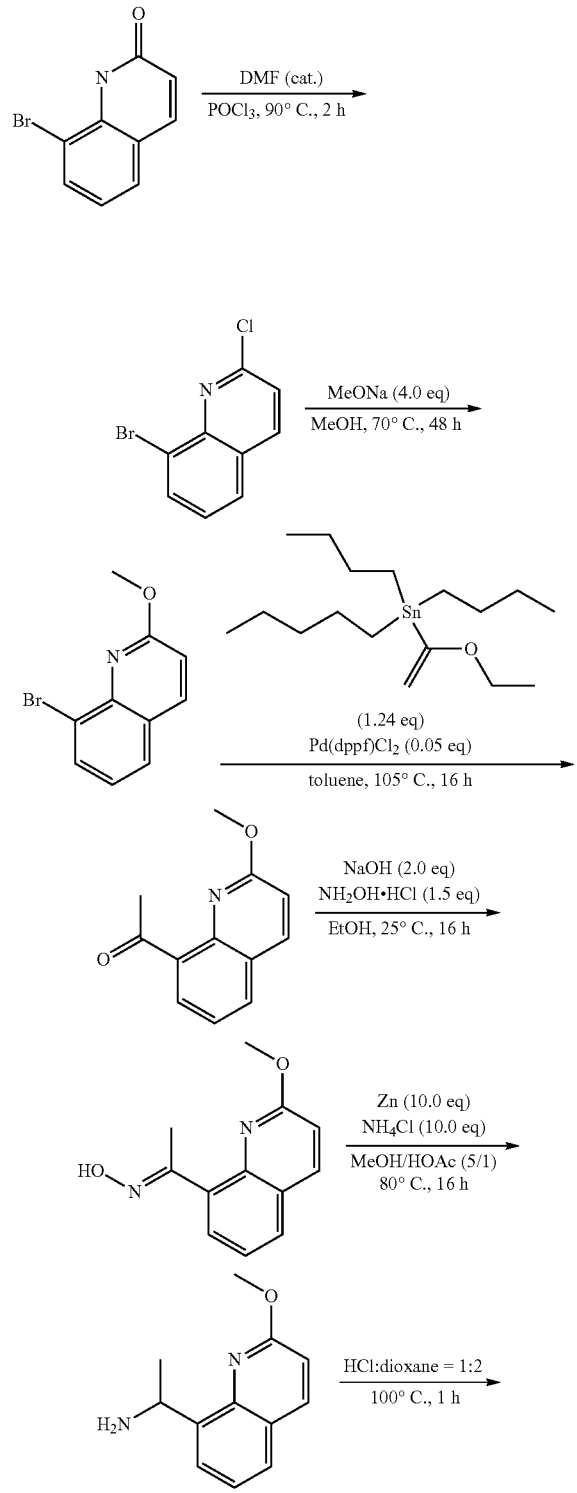
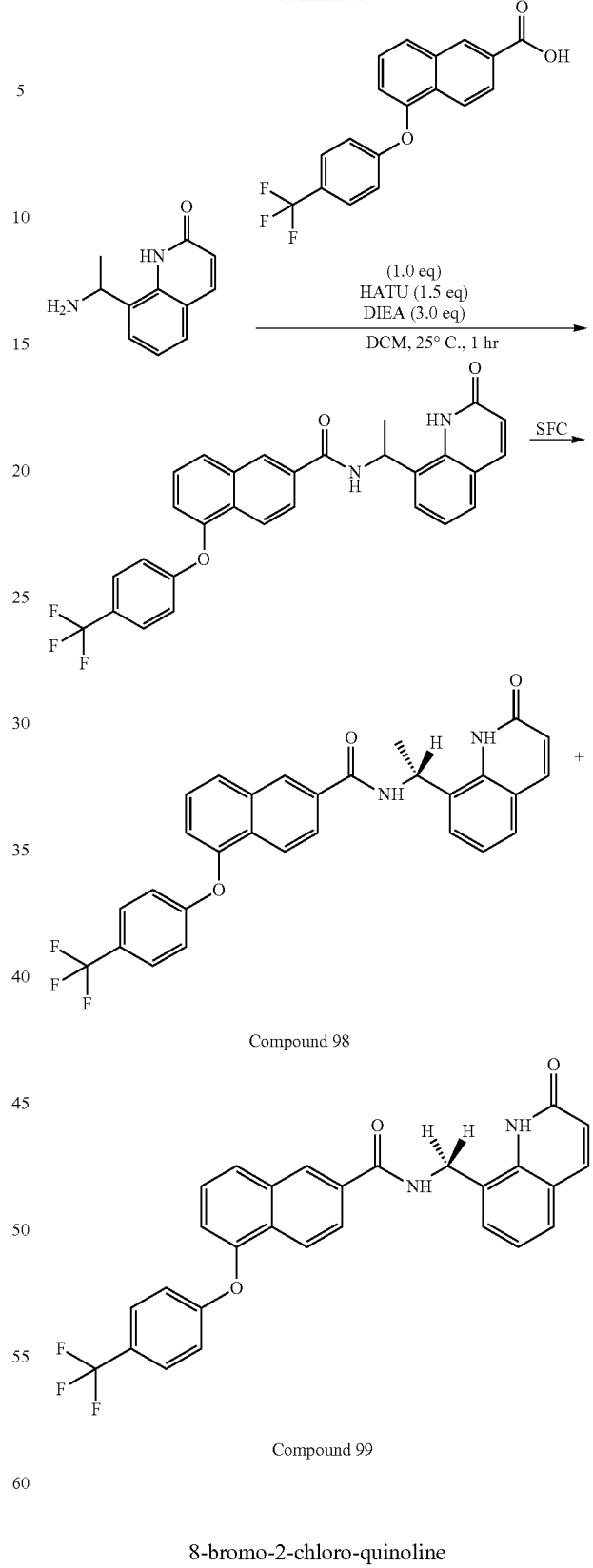
Compound 98
Compound 99
8-bromo-2-chloro-quinoline
A solution of 8-bromoquinolin-2(1H)-one (1.1 g, 4.91 mmol, 1 eq) in POCl₃ (4 mL) and DMF (0.1 mL) was heated at 90° C. for 2 hr. The reaction was cooled to 20° C., poured

8-bromo-2-methoxy-quinoline

To a solution of 8-bromo-2-chloro-quinoline (0.95 g, 3.92 mmol, 1 eq) in MeOH (15 mL) was added CH₃ONa (846.6 mg, 15.67 mmol, 4 eq). The reaction was heated at 70° C. for 48 hr. The reaction mixture was concentrated. The residue was diluted with EA (30 mL) and washed with H₂O (2*10 mL). The organic layer was dried over Na₂SO₄ and concentrated to give 8-bromo-2-methoxy-quinoline (1 g, 3.44 mmol, 87.9% yield), which was used for next step directly.

1-(2-methoxy-8-quinolyl)ethanone

To a mixture of 8-bromo-2-methoxy-quinoline (0.8 g, 3.36 mmol, 1 eq) and tributyl(1-ethoxyvinyl)stannane (1.51 g, 4.18 mmol, 1.4 mL, 1.24 eq) in toluene (10 mL) was added Pd(dppf)Cl₂ (122.9 mg, 0.16 mmol, 0.05 eq) and degassed. The reaction was heated at 105° C. for 16 hr under N₂. The reaction mixture was concentrated. 2N aq. HCl (10 mL) was added to the residue and the solution was stirred at 25° C. for 1 hr. The reaction was extracted with EA (2*50 mL). The organic layer was dried over Na₂SO₄ and concentrated. The residue was purified by silica gel column chromatography to give 1-(2-methoxy-8-quinolyl)ethanone (0.6 g, 2.83 mmol, 84.3% yield).

1-(2-methoxy-8-quinolyl)ethanone Oxime

To a mixture of NH₂OH.HCl (62.1 mg, 0.89 mmol, 1.5 eq) in EtOH (1 mL) was added NaOH (47.7 mg, 1.19 mmol, 2 eq). The mixture was filtered and the filtrate was added to a solution of 1-(2-methoxy-8-quinolyl)ethanone (120 mg, 0.59 mmol, 1 eq) in EtOH (2 mL). The reaction was stirred at 25° C. for 16 hr. The reaction was filtered to give 1-(2-methoxy-8-quinolyl)ethanone oxime (50 mg, 0.22 mmol, 38.00% yield). The filtrate was concentrated to give 1-(2-methoxy-8-quinolyl)ethanone oxime (60 mg, 0.19 mmol, 32.1% yield), which was used for next step directly.

1-(2-methoxy-8-quinolyl)ethanamine

A mixture of 1-(2-methoxy-8-quinolyl)ethanone oxime (60 mg, 0.19 mmol, 1 eq), Zn (125.1 mg, 1.91 mmol, 10 eq) and NH₄Cl (102.4 mg, 1.91 mmol, 10 eq) in MeOH (5 mL) and HOAc (1 mL) was heated at 80° C. for 16 hr. The reaction mixture was concentrated. The residue was diluted with EA (10 mL) and washed with water (5 mL). The aqueous layer was adjusted pH to 10-11 with Sat. Na₂CO₃, filtered and extracted with EA (2*10 mL). The organic layer was dried over Na₂SO₄ and concentrated to give 1-(2-methoxy-8-quinolyl)ethanamine (60 mg, 0.28 mmol, 74.3% yield), which was used for next step directly.

8-(1-aminoethyl)-1H-quinolin-2-one

A solution of 1-(2-methoxy-8-quinolyl)ethanamine (55 mg, 0.27 mmol, 1 eq) in dioxane (1 mL) and HCl (0.5 mL) was heated at 100° C. for 1 hr. The reaction mixture was concentrated to give 8-(1-aminoethyl)-1H-quinolin-2-one (60 mg, 0.24 mmol, 81.2% yield, HCl), which was used for next step directly.

N-[1-(2-oxo-1H-quinolin-8-yl)ethyl]-5-[4-(trifluoromethyl)phenoxy]naphthalene-2-carboxamide To a solution of 5-(4-(trifluoromethyl)phenoxy)-2-naphthoic acid (53.8 mg, 0.16 mmol, 1 eq), HATU (92.4 mg, 0.24 mmol, 1.5 eq) and 8-(1-aminoethyl)-1H-quinolin-2-one (40 mg, 0.16 mmol, 1 eq, HCl) in DCM (2 mL) was added DIEA (62.8 mg, 0.48 mmol, 84 uL, 3 eq). The reaction was stirred at 25° C. for 1 hr. The reaction was diluted with DCM (30 mL) and washed with H₂O (2*5 mL). The organic layer was dried over Na₂SO₄ and concentrated. The crude product was purified by prep-HPLC to give N-[1-(2-oxo-1H-quinolin-8-yl)ethyl]-5-[4-(trifluoromethyl)phenoxy]naphthalene-2-carboxamide (30 mg, 59.7 umol, 36.8% yield).

N-[(1R)-1-(2-oxo-1H-quinolin-8-yl)ethyl]-5-[4-(trifluoromethyl)phenoxy]naphthalene-2-carboxamide (Compound 98) and N-[(1S)-1-(2-oxo-1H-quinolin-8-yl)ethyl]-5-[4-(trifluoromethyl)phenoxy]naphthalene-2-carboxamide (Compound 99)

The racemic compound N-[1-(2-oxo-1H-quinolin-8-yl)ethyl]-5-[4-(trifluoromethyl)phenoxy]naphthalene-2-carboxamide (30 mg, 59.7 umol, 1 eq) was separated by chiral SFC to give Compound 98 (14.3 mg, 28.0 umol, 46.9% yield). LCMS(ESI): RT=0.970 min, mass calcd. For C₂₉H₂₁F₃N₂O₃, 502.15 m/z found 503.1 [M+H]⁺. ¹H NMR (400 MHz, CDCl₃) δ 11.33 (br s, 1H), 8.48 (d, J=1.1 Hz, 1H), 8.04 (d, J=8.8 Hz, 1H), 7.86 (dd, J=1.6, 8.8 Hz, 1H), 7.75 (d, J=9.5 Hz, 1H), 7.68 (dd, J=7.9, 11.6 Hz, 2H), 7.56 (d, J=8.6 Hz, 2H), 7.52 (d, J=7.1 Hz, 1H), 7.41 (t, J=7.9 Hz, 2H), 7.26-7.20 (m, 1H), 7.09 (d, J=7.4 Hz, 1H), 7.02 (d, J=8.5 Hz, 2H), 6.70 (d, J=9.4 Hz, 1H), 5.83-5.70 (m, 1H), 1.88 (d, J=7.0 Hz, 3H); and Compound 99 LCMS (ESI): RT=0.971 min, mass calcd. For C₂₉H₂₁F₃N₂O₃, 502.15 m/z found 503.1 [M+H]⁺. ¹H NMR (400 MHz, CDCl₃) δ 11.33 (br s, 1H), 8.48 (d, J=1.1 Hz, 1H), 8.04 (d, J=8.8 Hz, 1H), 7.86 (dd, J=1.6, 8.8 Hz, 1H), 7.75 (d, J=9.5 Hz, 1H), 7.68 (dd, J=7.9, 11.6 Hz, 2H), 7.56 (d, J=8.6 Hz, 2H), 7.52 (d, J=7.1 Hz, 1H), 7.41 (t, J=7.9 Hz, 2H), 7.26-7.20 (m, 1H), 7.09 (d, J=7.4 Hz, 1H), 7.02 (d, J=8.5 Hz, 2H), 6.70 (d, J=9.4 Hz, 1H), 5.83-5.70 (m, 1H), 1.88 (d, J=7.0 Hz, 3H).

Example 78: (S)-N-(1-(1-acetylazetidin-3-yl)ethyl)-5-(4-(trifluoromethyl)phenoxy)-2-naphthamide (Compound 100) and (R)-N-(1-(1-acetylazetidin-3-yl)ethyl)-5-(4-(trifluoromethyl)phenoxy)-2-naphthamide (Compound 101)

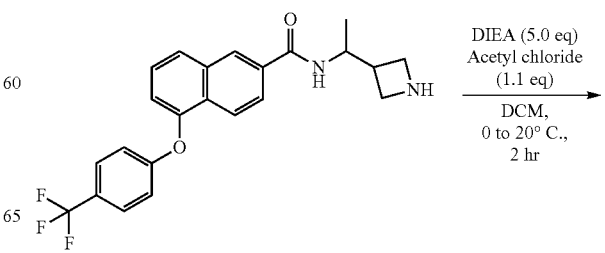

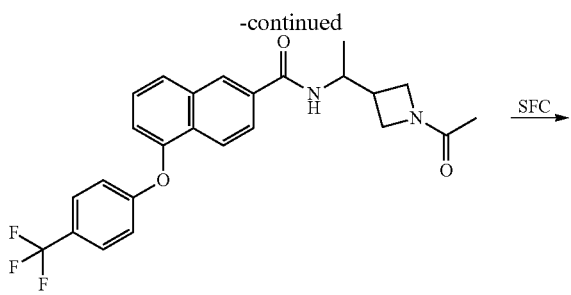

Compound 100

Compound 101

N-(1-(1-acetylazetidin-3-yl)ethyl)-5-(4-(trifluoromethyl)phenoxy)-2-naphthamide

To a solution of N-[1-(azetidin-3-yl)ethyl]-5-[4-(trifluoromethyl)phenoxy]naphthalene-2-carboxamide (150 mg, 0.36 mmol, 1 eq) and DIPEA (233.8 mg, 1.81 mmol, 0.31 mL, 5 eq) in DCM (5 mL) was added dropwise acetyl chloride (31.2 mg, 0.39 mmol, 28.4 uL, 1.1 eq)(in DCM (1 mL)) at 0° C. under $N_2$. After addition, the mixture was stirred at 20° C. for 2 hr. The residue was mixture into $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by flash silica gel chromatography. Compound N-[1-(1-acetylazetidin-3-yl)ethyl]-5-[4-(trifluoromethyl)phenoxy]naphthalene-2-carboxamide (96 mg, 0.20 mmol, 55.7% yield) was obtained.

(S)-N-(1-(1-acetylazetidin-3-yl)ethyl)-5-(4-(trifluoromethyl)phenoxy)-2-naphthamide (Compound 100) and (R)-N-(1-(1-acetylazetidin-3-yl)ethyl)-5-(4-(trifluoromethyl)phenoxy)-2-naphthamide (Compound 101)

The racemic compound N-[1-(1-acetylazetidin-3-yl)ethyl]-5-[4-(trifluoromethyl)phenoxy]naphthalene-2-carboxamide (95 mg, 0.20 mmol, 1 eq) which was further separated by SFC to give Compound 100 (32.4 mg, 68.1 umol, 32.7% yield) LCMS (ESI): RT=0.927 min, mass calcd for $C_{25}H_{23}F_3N_2O_3$ 456.46 m/z found 479.1[M+Na]$^+$; $^1$H NMR (400 MHz, CD$_3$OD) δ 8.44 (s, 1H), 8.10 (d, J=8.9 Hz, 1H), 7.89 (d, J=8.6 Hz, 2H), 7.66 (d, J=8.8 Hz, 2H), 7.59 (t, J=7.9 Hz, 1H), 7.23 (d, J=7.5 Hz, 1H), 7.13 (d, J=8.6 Hz, 2H), 4.51-4.40 (m, 1H), 4.35-4.22 (m, 1H), 4.12-3.98 (m, 2H), 3.92-3.74 (m, 1H), 2.90-2.78 (m, 1H), 1.85 (s, 3H), 1.26 (d, J=6.6 Hz, 3H); and Compound 101 (31.8 mg, 69.6 umol, 33.4% yield) LCMS (ESI): RT=0.927 min, mass calcd for $C_2H_{23}F_3N_2O_3$ 456.46 m/z found 479.1[M+Na]; $^1$H NMR (400 MHz, CD$_3$OD) δ 8.44 (s, 1H), 8.10 (d, J=8.8 Hz, 1H), 7.89 (d, J=8.5 Hz, 2H), 7.66 (d, J=8.6 Hz, 2H), 7.59 (t, J=7.9 Hz, 1H), 7.23 (d, J=7.6 Hz, 1H), 7.13 (d, J=8.6 Hz, 2H), 4.51-4.41 (m, 1H), 4.35-4.23 (m, 1H), 4.13-3.98 (m, 2H), 3.92-3.74 (m, 1H), 2.90-2.78 (m, 1H), 1.85 (d, J=1.6 Hz, 3H), 1.26 (d, J=6.6 Hz, 3H).

Example 79: (R)-5,6-difluoro-N-(1-hydroxypropan-2-yl)-8-(4-(trifluoromethyl)phenoxy)quinoline-3-carboxamide (Compound 102)

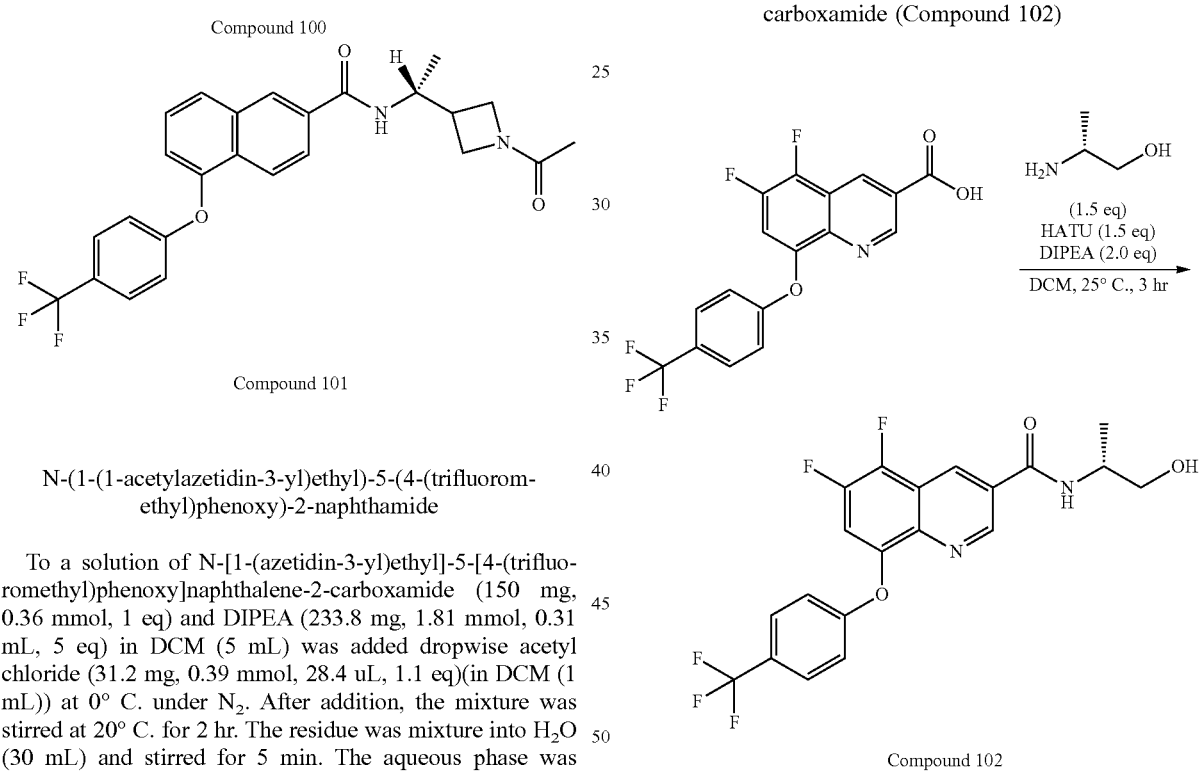

Compound 102

To a solution of 5,6-difluoro-8-(4-(trifluoromethyl)phenoxy)quinoline-3-carboxylic acid (25 mg, 67.7 umol, 1 eq) in DCM (1 mL) was added HATU (38.6 mg, 0.1 mmol, 1.5 eq), (R)-2-aminopropan-1-ol (7.6 mg, 0.1 mmol, 8.0 uL, 1.5 eq) and DIPEA (17.5 mg, 0.13 mmol, 23.5 uL, 2.0 eq). The mixture was stirred at 25° C. for 3 hr. The reaction mixture was concentrated under reduced pressure to give a residue. The residue was purified by prep-HPLC to give the title compound (3.8 mg, 8.9 umol, 13.2% yield) LCMS (ESI): RT=0.881 min, mass calcd for $C_{20}H_{15}F_5N_2O_3$ 426.10 m/z found 427.0 [M+H]$^+$; $^1$H NMR (400 MHz, MeOD) δ 9.21 (s, 1H), 9.06 (d, J=2.0 Hz, 1H), 7.67 (d, J=8.8 Hz, 2H), 7.58 (dd, J=7.3, 11.3 Hz, 1H), 7.16 (d, J=8.8 Hz, 2H), 4.33-4.17 (m, 1H), 3.65 (d, J=5.8 Hz, 2H), 1.30-1.28 (m, 3H).

Example 80: (R)-N-(1-(1H-benzo[d]imidazol-7-yl)ethyl)-8-(4-(trifluoromethyl)phenoxy)quinoline-3-carboxamide (Compound 103) and (S)-N-(1-(1H-benzo[d]imidazol-7-yl)ethyl)-8-(4-(trifluoromethyl)phenoxy)quinoline-3-carboxamide (Compound 104)

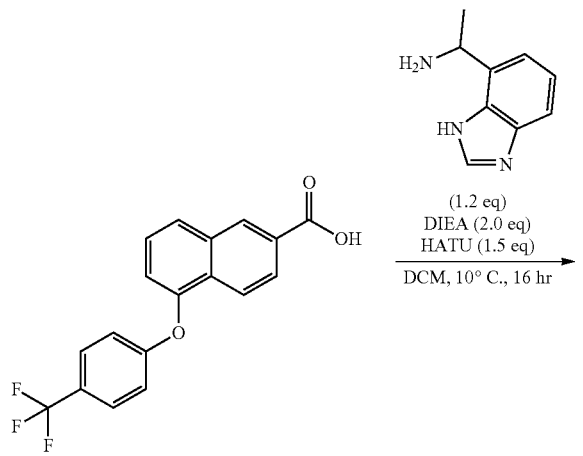

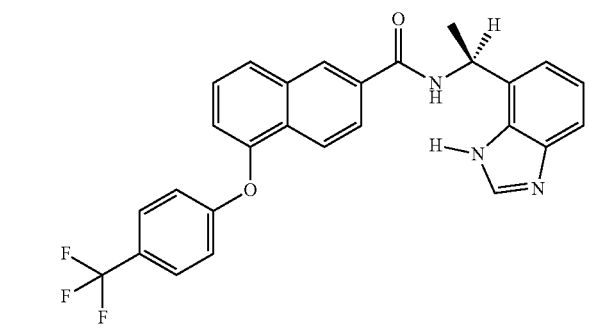

Compound 103

Compound 104

N-(1-(1H-benzo[d]imidazol-7-yl)ethyl)-5-(4-(trifluoromethyl)phenoxy)-2-naphthamide To a solution of compound 5-(4-(trifluoromethyl)phenoxy)-2-naphthoic acid (100.0 mg, 0.30 mmol, 1 eq), 1-(1H-benzo[d]imidazol-7-yl)ethan-1-amine (58.2 mg, 0.36 mmol, 1.2 eq) and HATU (171.7 mg, 0.45 mmol, 1.5 eq) in DCM (2 mL) was added DIEA (77.8 mg, 0.60 mmol, 0.10 mL, 2 eq). The mixture was stirred at 10° C. for 16 hr. The mixture was diluted with $H_2O$ (10 mL). The mixture was extracted with EA (15 mL*3). The organic layer was dried over $Na_2SO_4$, filtered and concentrated to give a residue. The residue was purified by prep-HPLC to give N-(1-(1H-benzo[d]imidazol-7-yl)ethyl)-5-(4-(trifluoromethyl)phenoxy)-2-naphthamide (30.0 mg, 63.1 umol, 20.9% yield).

(R)-N-(1-(1H-benzo[d]imidazol-7-yl)ethyl)-8-(4-(trifluoromethyl)phenoxy)quinoline-3-carboxamide (Compound 103) and (S)-N-(1-(1H-benzo[d]imidazol-7-yl)ethyl)-8-(4-(trifluoromethyl)phenoxy)quinoline-3-carboxamide (Compound 104)

N-(1-(1H-benzo[d]imidazol-7-yl)ethyl)-5-(4-(trifluoromethyl)phenoxy)-2-naphthamide (30.0 mg, 63.1 umol, 1 eq) was purified by chiral SFC to give Compound 103 (8.9 mg, 18.6 umol, 29.5% yield) LCMS (ESI): mass calc. for $C_{27}H_{20}F_3N_3O_2$ 475.15, m/z found 476.1 [M+H]$^+$; $^1$H NMR (400 MHz, CDCl$_3$) δ 8.42 (br s, 1H), 8.14-8.08 (m, 2H), 7.87 (br d, J=7.5 Hz, 1H), 7.77 (br d, J=8.3 Hz, 1H), 7.69-7.56 (m, 3H), 7.50 (t, J=7.9 Hz, 1H), 7.30-7.24 (m, 3H), 7.14 (d, J=7.3 Hz, 1H), 7.06 (br d, J=8.5 Hz, 2H), 5.87 (br s, 1H), 1.85 (br d, J=6.3 Hz, 3H); and Compound 104 (4.9 mg, 10.4 umol, 16.5% yield) LCMS(ESI): mass calc. for $C_{27}H_{20}F_3N_3O_2$ 475.15, m/z found 476.1 [M+H]$^+$; $^1$H NMR (400 MHz, DMSO-d$_6$) δ 9.32 (br d, J=7.5 Hz, 1H), 8.70-8.55 (m, 2H), 8.05-7.97 (m, 3H), 7.74 (d, J=8.8 Hz, 2H), 7.67-7.60 (m, 2H), 7.53 (br d, J=8.5 Hz, 1H), 7.34 (d, J=7.5 Hz, 2H), 7.29-7.24 (m, 1H), 7.16 (d, J=8.5 Hz, 2H), 5.74 (br t, J=7.1 Hz, 1H), 1.62 (br d, J=6.9 Hz, 3H).

Example 81: (R)-N-(1-(benzo[b]thiophen-7-yl)ethyl)-8-(4-(trifluoromethyl)phenoxy)quinoline-3-carboxamide (Compound 105) and (S)-N-(1-(benzo[b]thiophen-7-yl)ethyl)-8-(4-(trifluoromethyl)phenoxy)quinoline-3-carboxamide (Compound 106)

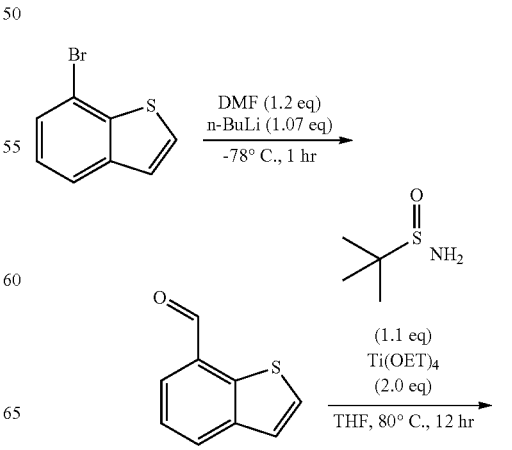

269
-continued

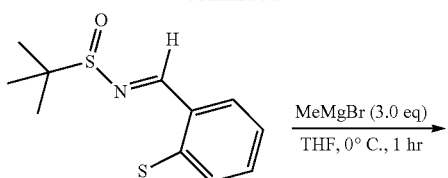

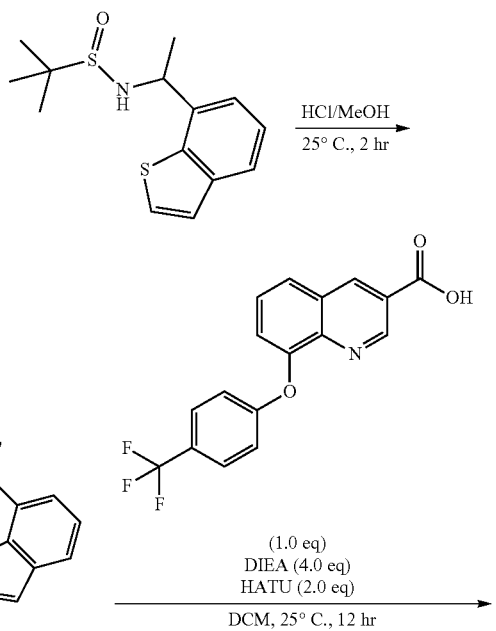

Compound 105

270
-continued

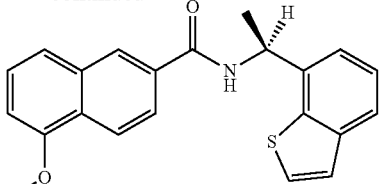

Compound 106 benzothiophene-7-carbaldehyde

To a solution of 7-bromobenzo[b]thiophene (500 mg, 2.35 mmol, 1 eq) in THF (5 mL) was added n-BuLi (2.5 M, 1 mL, 1.07 eq) at −78° C. The mixture was stirred at −78° C. for 20 min. DMF (205.8 mg, 2.82 mmol, 0.22 mL, 1.2 eq) was added into the mixture. The mixture was stirred at −78° C. for 40 min. The reaction was quenched with saturated NH$_4$Cl (10 mL). The mixture was diluted with water (10 mL) and extracted with EtOAc (30 mL*3). The combined organic layer was washed with brine (30 mL), dried over Na$_2$SO$_4$, filtered, and concentrated to give a residue. The residue was purified by column chromatography to give benzothiophene-7-carbaldehyde (120 mg, 0.74 mmol, 31.5% yield).

(E)-N-(benzo[b]thiophen-7-ylmethylene)-2-methyl-propane-2-sulfinamide

To a solution of benzothiophene-7-carbaldehyde (50 mg, 0.31 mmol, 1 eq) and 2-methylpropane-2-sulfinamide (41.1 mg, 0.34 mmol, 1.1 eq) in THF (2 mL) was added Ti(OEt)$_4$ (140.6 mg, 0.62 mmol, 0.13 mL, 2 eq). The mixture was stirred at 20° C. for 12 h. For further completion of the reaction, the mixture was stirred at 80° C. for 12 h. The mixture was cooled to room temperature, diluted with water (15 mL), and extracted with EtOAc (30 mL*3). The combined organic layer was washed with brine (30 mL), dried over Na$_2$SO$_4$, filtered, and concentrated to give a residue. The residue was purified by column chromatography to give (E)-N-(benzo[b]thiophen-7-ylmethylene)-2-methylpropane-2-sulfinamide (50 mg, 0.19 mmd, 61.1% yield). $^1$H NMR (400 MHz, CD$_3$Cl) δ 8.88 (s, 1H), 8.03 (d, J=7.2 Hz, 1H), 7.74 (d, J=7.2 Hz, 1H), 7.62 (d, J=5.2 Hz, 1H), 7.54 (t, J=7.7 Hz, 1H), 7.47 (d, J=5.5 Hz, 1H), 1.35 (s, 9H).

N-[1-(benzothiophen-7-yl)ethyl]-2-methyl-propane-2-sulfinamide

To a solution of (E)-N-(benzo[b]thiophen-7-ylmethylene)-2-methylpropane-2-sulfinamide (50 mg, 0.19 mmol, 1 eq) in THF (1 mL) was added MeMgBr (3 M, 0.19 mL, 3 eq) at 0° C. The mixture was stirred at 0° C. for 1 h. The reaction was quenched with saturated NH$_4$Cl (5 mL) and diluted with water (10 mL). The mixture was extracted with EA (30 mL*3). The combined organic layer was washed with brine (30 mL), dried over Na$_2$SO$_4$, filtered, and concentrated to give a residue. The residue was purified by column chromatography to give N-[1-(benzothiophen-7-yl)ethyl]-2-methyl-propane-2-sulfinamide (30 mg, 0.11 mmol, 56.6% yield).

1-(benzothiophen-7-yl)ethanamine

To a solution of N-[1-(benzothiophen-7-yl)ethyl]-2-methyl-propane-2-sulfinamide (30 mg, 0.11 mmol, 1 eq) in MeOH (2 mL) was added HCl/MeOH (4 M, 1 mL). The mixture was stirred at 20° C. for 0.5 h. The mixture was concentrated to give 1-(benzothiophen-7-yl)ethanamine (30 mg, crude, HCl salt). The crude compound was used directly in the next step.

N-[1-(benzothiophen-7-yl)ethyl]-5-[4-(trifluoromethyl)phenoxy]naphthalene-2-carboxamide To a solution of 5-(4-(trifluoromethyl)phenoxy)-2-naphthoic acid (45 mg, 0.14 mmol, 1 eq) and DIEA (70.0 mg, 0.54 mmol, 94.4 uL, 4 eq) in DCM (2 mL) was added HATU (103.0 mg, 0.27 mmol, 2 eq). The mixture was stirred at 20° C. for 0.5 h and 1-(benzothiophen-7-yl)ethanamine (29.0 mg, 0.14 mmol, 1 eq, HCl) was added into the mixture. The resulting mixture was stirred at 20° C. for 12 h. The mixture was diluted with water (10 mL) and extracted with EtOAc (20 mL*3). The combined organic layer was washed with brine (20 mL), dried over Na₂SO₄, filtered, and concentrated to give a residue. The residue was purified by column chromatography to give N-[1-(benzothiophen-7-yl)ethyl]-5-[4-(trifluoromethyl)phenoxy]naphthalene-2-carboxamide (40 mg, 78.9 umol, 58.3% yield).

(R)-N-(1-(benzo[b]thiophen-7-yl)ethyl)-8-(4-(trifluoromethyl)phenoxy)quinoline-3-carboxamide (Compound 105) and (S)-N-(1-(benzo[b]thiophen-7-yl)ethyl)-8-(4-(trifluoromethyl)phenoxy)quinoline-3-carboxamide (Compound 106)

N-[1-(benzothiophen-7-yl)ethyl]-5-[4-(trifluoromethyl)phenoxy]naphthalene-2-carboxamide (40 mg, 81.4 umol, 1 eq) was separated by SFC to give Compound 105 (17.6 mg, 35.5 umol, 43.7% yield) LCMS (ESI): mass calcd. for $C_{28}H_{20}F_3NO_2S$ 491.12, m/z found 492.0 [M+H]$^+$; $^1$H NMR (400 MHz, CD₃Cl) δ 8.31 (d, J=1.1 Hz, 1H), 8.03 (d, J=8.8 Hz, 1H), 7.78 (dd, J=1.6, 8.8 Hz, 1H), 7.75-7.68 (m, 2H), 7.51 (d, J=8.6 Hz, 2H), 7.46-7.31 (m, 5H), 7.06 (d, J=7.6 Hz, 1H), 6.98 (d, J=8.5 Hz, 2H), 6.55 (br d, J=7.1 Hz, 1H), 5.61 (t, J=7.1 Hz, 1H), 1.75 (d, J=6.9 Hz, 3H); and Compound 106 (16.2 mg, 32.9 umol, 40.5% yield) LCMS (ESI): mass calcd. for $C_{28}H_{20}F_3NO_2S$ 491.12, m/z found 492.0 [M+H]$^+$; $^1$H NMR (400 MHz, CD₃Cl) δ 8.38 (s, 1H), 8.10 (d, J=8.8 Hz, 1H), 7.87-7.82 (m, 1H), 7.82-7.75 (m, 2H), 7.58 (d, J=8.6 Hz, 2H), 7.53-7.34 (m, 5H), 7.13 (d, J=7.5 Hz, 1H), 7.05 (d, J=8.5 Hz, 2H), 6.62 (br d, J=7.0 Hz, 1H), 5.68 (t, J=7.0 Hz, 1H), 2.07-2.02 (m, 1H), 1.82 (d, J=6.9 Hz, 3H).

Example 82: (R)-N-(1-aminopropan-2-yl)-5-(4-(trifluoromethyl)phenoxy)-2-naphthamide (Compound 107) and (S)-N-(1-aminopropan-2-yl)-5-(4-(trifluoromethyl)phenoxy)-2-naphthamide (Compound 108)

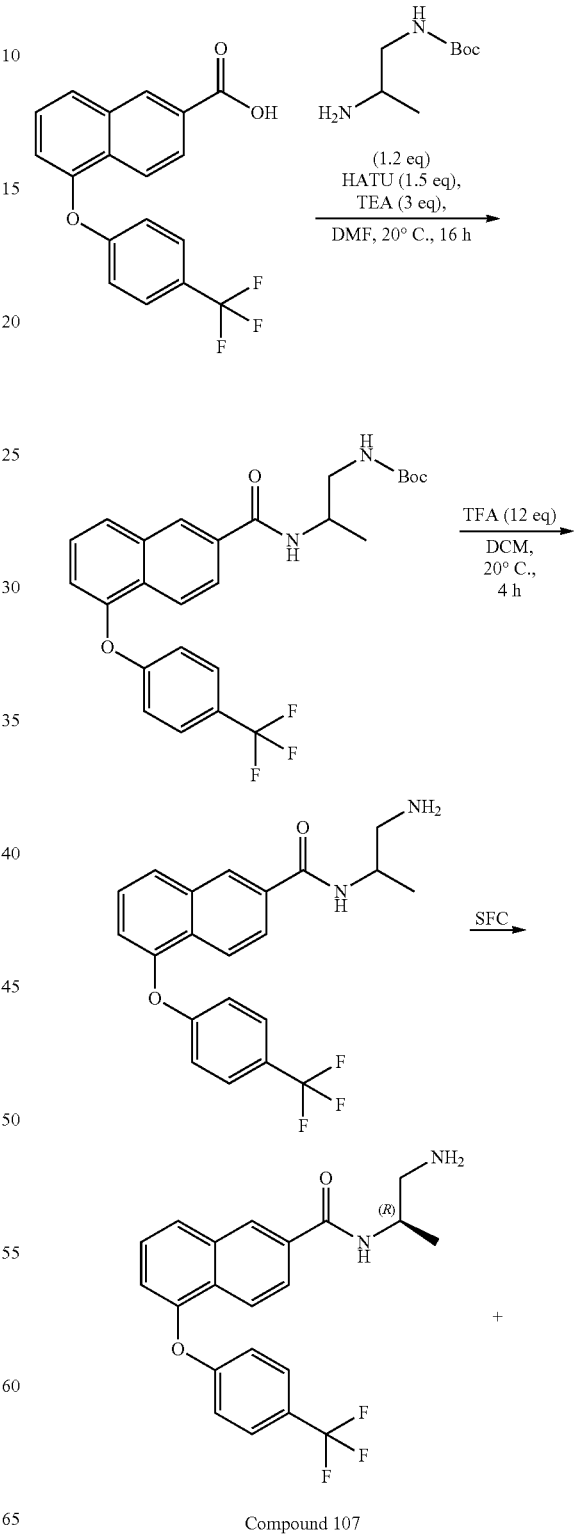

Compound 107

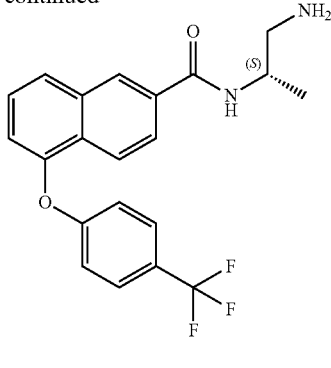

Compound 108 tert-butyl(2-(5-(4-(trifluoromethyl)phenoxy)-2-naphthamido)propyl)carbamate

To a solution of 5-(4-(trifluoromethyl)phenoxy)-2-naphthoic acid (100 mg, 0.3 mmol, 1 eq) and HATU (171.7 mg, 0.45 mmol, 1.5 eq) in DMF (1 mL) at 20° C. was added tert-butyl (2-aminopropyl)carbamate (62.9 mg, 0.36 mmol, 1.2 eq) and TEA (91.4 mg, 0.9 mmol, 0.13 mL, 3 eq). The mixture was stirred at 20° C. for 16 h. The residue was diluted with water (20 mL), and then extracted with EA (20 mL*3). The combined organic layers were washed with water (10 mL) and brine (10 mL), dried over anhydrous $Na_2SO_4$, filtered and concentrated under reduced pressure to give tert-butyl(2-(5-(4-(trifluoromethyl)phenoxy)-2-naphthamido)propyl)carbamate (130 mg, 0.27 mmol, 88.4% yield) as a yellow solid. $^1$H NMR (400 MHz, CDCl$_3$) δ 8.43 (s, 1H), 8.10 (d, J=8.9 Hz, 1H), 7.91 (br d, J=8.6 Hz, 1H), 7.79 (d, J=8.4 Hz, 1H), 7.59 (d, J=8.6 Hz, 2H), 7.50 (t, J=7.9 Hz, 1H), 7.41 (br d, J=7.0 Hz, 1H), 7.14 (d, J=7.5 Hz, 1H), 7.07 (d, J=8.6 Hz, 2H), 5.00 (brs, 1H), 4.26 (br d, J=5.9 Hz, 1H), 3.45-3.37 (m, 1H), 3.31-3.24 (m, 1H), 1.41 (s, 9H), 1.31 (d, J=6.6 Hz, 3H).

N-(1-aminopropan-2-yl)-5-(4-(trifluoromethyl)phenoxy)-2-naphthamide

To a solution of tert-butyl(2-(5-(4-(trifluoromethyl)phenoxy)-2-naphthamido)propyl)carbamate (130 mg, 0.27 mmol, 1 eq) in DCM (2 mL) at 20° C. was added TFA (364.1 mg, 3.2 mmol, 0.24 mL, 12 eq). The mixture was stirred at 20° C. for 4 h. The reaction mixture was concentrated under reduced pressure to give a residue. The residue was diluted with water (20 mL), $Na_2CO_3$ (20 mL) and extracted with EA (20 mL*3). The combined organic layers were washed with brine (20 mL), dried over $Na_2SO_4$, filtered and concentrated under reduced pressure to give a residue to give compound N-(1-aminopropan-2-yl)-5-(4-(trifluoromethyl)phenoxy)-2-naphthamide (100 mg, 0.24 umol, 91.9% yield). LCMS (ESI): RT=0.825 min, mass calc. for $C_{21}H_{19}F_3N_2O_2$ 388.14, m/z found 389.0 [M+H]$^+$.

(R)-N-(1-aminopropan-2-yl)-5-(4-(trifluoromethyl)phenoxy)-2-naphthamide (Compound 107) and (S)-N-(1-aminopropan-2-yl)-5-(4-(trifluoromethyl)phenoxy)-2-naphthamide (Compound 108)

N-(1-aminopropan-2-yl)-5-(4-(trifluoromethyl)phenoxy)-2-naphthamide (100 mg, 0.26 mmol, 1 eq) was purified by SFC. No monitoring and used for next step directly. The racemic compound was separated by SFC (column: Phenomenex-Cellulose-2 (250 mm*30 mm, 5um); mobile phase: [0.1% NH$_3$H$_2$O ETOH]; B %: 35%-35%, min) to give Compound 107 (10 mg, 25 umol, 9.90% yield) and Compound 108 (13.5 mg, 35 umol, 13.5% yield) as a white solid. Compound 107 LCMS (ESI): RT=0.827 min, mass calc. for $C_{21}H_{19}F_3N_2O_2$ 388.14, m/z found 389.0 [M+H]$^+$; $^1$H NMR (400 MHz, CDCl$_3$) δ 8.38 (s, 1H), 8.05 (d, J=8.9 Hz, 1H), 7.83 (br d, J=8.8 Hz, 1H), 7.73 (br d, J=8.4 Hz, 1H), 7.57 (br d, J=8.6 Hz, 2H), 7.45 (t, J=7.9 Hz, 1H), 7.10 (d, J=7.5 Hz, 1H), 7.07-7.02 (m, 3H), 4.33 (brs, 1H), 3.02-2.91 (m, 2H), 1.27-1.24 (m, 1H), 1.25 (br d, J=6.5 Hz, 2H). Compound 108 LCMS (ESI): RT=0.833 min, mass calc. for $C_{21}H_{19}F_3N_2O_2$ 388.14, m/z found 389.0 [M+H]$^+$; $^1$H NMR (400 MHz, CDCl$_3$) δ 8.40 (s, 1H), 8.08 (d, J=8.8 Hz, 1H), 7.85 (br d, J=8.8 Hz, 1H), 7.77 (br d, J=8.3 Hz, 1H), 7.58 (br d, J=8.5 Hz, 2H), 7.47 (t, J=7.9 Hz, 1H), 7.12 (d, J=7.5 Hz, 1H), 7.05 (br d, J=8.5 Hz, 2H), 6.92 (br d, J=7.0 Hz, 1H), 4.31 (brs, 1H), 2.94 (brs, 2H), 1.28 (br d, J=6.6 Hz, 3H).

Example 83: (R)-N-(3-hydroxy-1-(pyridin-2-yl)propyl)-5-(4-(trifluoromethyl)phenoxy)-2-naphthamide (Compound 109) and (S)-N-(3-hydroxy-1-(pyridin-2-yl)propyl)-5-(4-(trifluoromethyl)phenoxy)-2-naphthamide (Compound 110)

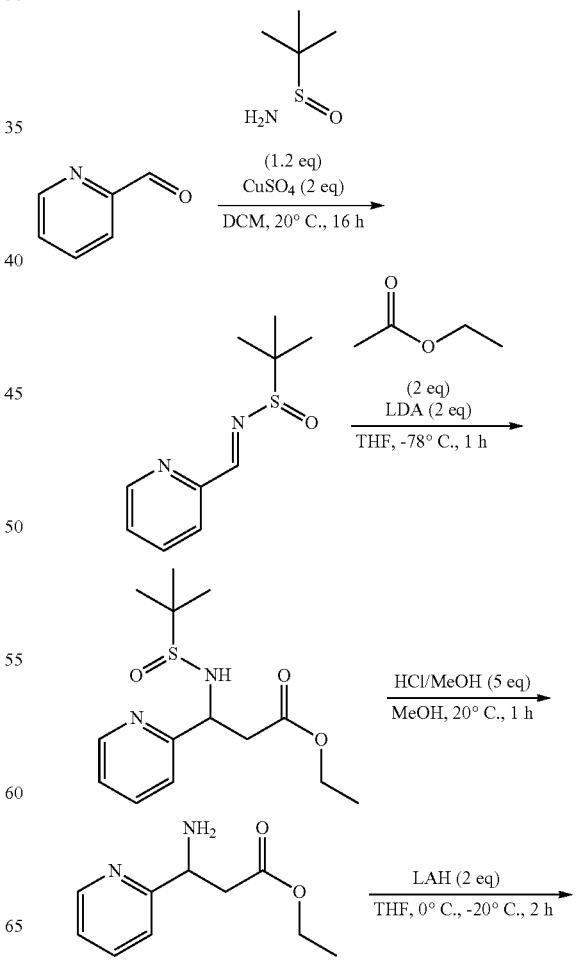

-continued

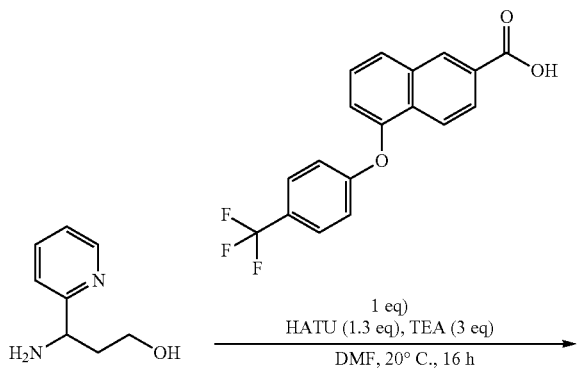

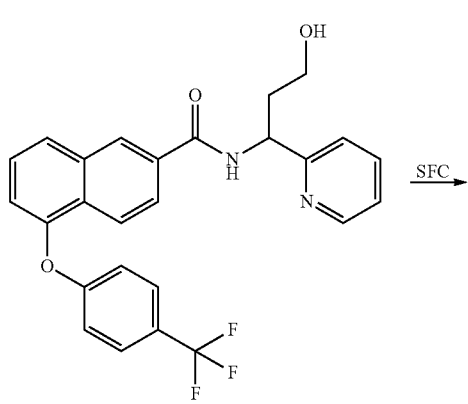

Compound 109

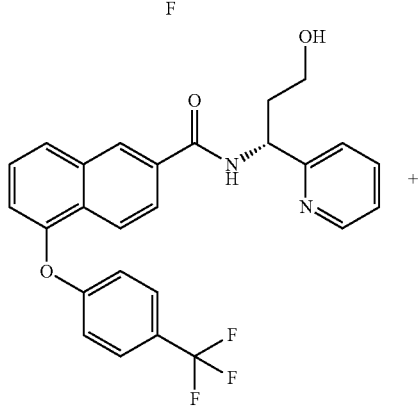

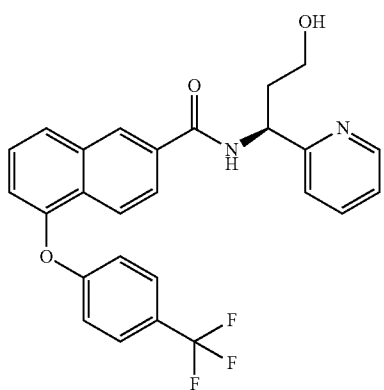

Compound 110

(E)-2-methyl-N-(pyridin-2-ylmethylene)propane-2-sulfinamide

To a solution of picolinaldehyde (3 g, 28.01 mmol, 1 eq) and 2-methylpropane-2-sulfinamide (4.07 g, 33.61 mmol, 1.2 eq) in DCM (56 mL) at 20° C. was added CuSO$_4$ (8.94 g, 56.02 mmol, 8.60 mL, 2 eq). The reaction was stirred at 20° C. for 16 h. The reaction mixture was filtered to remove the solid and the filtrate was concentrated under reduced pressure to give the residue. The residue was diluted with water (100 mL), and then extracted with EA (100 mL*3). The combined organic layers were washed with water (50 mL) and brine (50 mL), dried over anhydrous Na$_2$SO$_4$, filtered and concentrated under reduced pressure to give (E)-2-methyl-N-(pyridin-2-ylmethylene)propane-2-sulfinamide (4.32 g, 20.54 mmol, 73.3% yield) as yellow oil, which was used for next step directly. LCMS (ESI): RT=0.640 min, mass calc. for C$_{10}$H$_{14}$N$_2$OS 210.08, m/z found 210.9[M+H]$^+$.

Ethyl 3-(1,1-dimethylethylsulfinamido)-3-(pyridin-2-yl)propanoate

To a solution of ethyl acetate (838.8 mg, 9.52 mmol, 0.93 mL, 2 eq) in THF (5 mL) at −78° C. was added LDA (2 M, 4.76 mL, 2 eq) drop-wise, and the resulting mixture was stirred at −78° C. for 0.5 h. And then the solution of (E)-2-methyl-N-(pyridin-2-ylmethylene)propane-2-sulfinamide (1 g, 4.76 mmol, 1 eq) in THF (5 mL) was added into the above mixture at −78° C. The reaction mixture was stirred at −78° C. for another 0.5 h. The reaction mixture was quenched with saturated NH$_4$Cl solution (20 mL) and then extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~20% Ethyl acetate/Petroleum ether gradient @ 30 mL/min) to give ethyl 3-(1,1-dimethylethylsulfinamido)-3-(pyridin-2-yl)propanoate (1.2 g, 3.98 mmol, 83.6% yield) as a yellow solid. LCMS (ESI): RT=0.708 min, mass calc. for C$_{14}$H$_{22}$N$_2$O$_3$S 298.14, m/z found 298.9[M+H]$^+$.

Ethyl 3-amino-3-(pyridin-2-yl)propanoate

To a solution of ethyl 3-(1,1-dimethylethylsulfinamido)-3-(pyridin-2-yl)propanoate (250 mg, 0.84 mmol, 1 eq) in MeOH (2 mL) at 20° C. was added HCl/MeOH (4 M, 1.05 mL, 5 eq). The reaction mixture was stirred at 20° C. for 1 h. The reaction mixture was concentrated under reduced pressure to give ethyl 3-amino-3-(pyridin-2-yl)propanoate (162 mg, 0.83 mmol, 99.6% yield) as a yellow solid, which was used directly for next step.

3-amino-3-(pyridin-2-yl)propan-1-ol

To a solution of ethyl 3-amino-3-(pyridin-2-yl)propanoate (162 mg, 0.83 mmol, 1 eq) in THF (3 mL) at 0° C. was added LAH (63.3 mg, 1.67 mmol, 2 eq). The reaction mixture was stirred at 20° C. for 2 h. The reaction mixture was quenched with water (0.06 mL) at 0° C., then 4N NaOH (0.06 mL) and then water (0.18 mL), and then stirred at 20° C. for 0.5 h. The mixture was dried over anhydrous Na₂SO₄, and then filtered to remove the precipitate. The filtrate was concentrated under reduced pressure to give 3-amino-3-(pyridin-2-yl)propan-1-ol (110 mg, 0.72 mmol, 86.7% yield) as yellow oil, which was used directly for next step. ¹H NMR (400 MHz, CDCl₃) δ 8.57 (brs, 1H), 7.71-7.61 (m, 1H), 7.24 (s, 1H), 7.21-7.14 (m, 1H), 4.47-4.19 (m, 1H), 3.96-3.81 (m, 1H), 2.91-2.68 (m, 1H), 2.15-1.83 (m, 2H).

N-(3-hydroxy-1-(pyridin-2-yl)propyl)-5-(4-(trifluoromethyl)phenoxy)-2-naphthamide To a solution of 5-(4-(trifluoromethyl)phenoxy)-2-naphthoic acid (120 mg, 0.36 mmol, 1 eq), 3-amino-3-(pyridin-2-yl)propan-1-ol (109.9 mg, 0.72 mmol, 2 eq) in DMF (2 mL) at 20° C. was added HATU (178.5 mg, 0.47 mmol, 1.3 eq) and TEA (109.6 mg, 1.08 mmol, 0.15 mL, 3 eq). The reaction mixture was stirred at 20° C. for 16 h. The reaction mixture was concentrated under reduced pressure to give a residue. The residue was purified by prep-HPLC (column: Welch Xtimate C18 150*25 mm*5 um; mobile phase: [water (0.05% HCl)–ACN]; B %: 30%-60%, 8.5 min) to give N-(3-hydroxy-1-(pyridin-2-yl)propyl)-5-(4-(trifluoromethyl)phenoxy)-2-naphthamide (60 mg, 0.13 mmol, 35.3% yield) as yellow oil. LCMS(ESI): RT=0.843 min, mass calc. for C₂₆H₂₁F₃N₂O₃ 466.15, m/z found 467.0 [M+H]⁺.

(R)-N-(3-hydroxy-1-(pyridin-2-yl)propyl)-5-(4-(trifluoromethyl)phenoxy)-2-naphthamide (Compound 109) and (S)-N-(3-hydroxy-1-(pyridin-2-yl)propyl)-5-(4-(trifluoromethyl)phenoxy)-2-naphthamide (Compound 110)

The sample N-(3-hydroxy-1-(pyridin-2-yl)propyl)-5-(4-(trifluoromethyl)phenoxy)-2-naphthamide (60 mg, 0.13 mmol, 1 eq) was purified by SFC (column: DAICEL CHIRALPAK AD (250 mm*30 mm, 10 um); mobile phase: [0.1% NH₃H2O ETOH]; B %: 45%-45%, min) to give Compound 109 (13.1 mg, 27.6 umol, 21.5% yield) as a white solid. LCMS(ESI): RT=0.848 min, mass calc. for C₂₆H₂₁F₃N₂O₃ 466.15, m/z found 467.0 [M+H]⁺; ¹H NMR (400 MHz, CD₃OD) δ 8.55 (d, J=4.5 Hz, 1H), 8.52 (s, 1H), 8.11 (d, J=8.8 Hz, 1H), 7.96-7.89 (m, 2H), 7.83 (dt, J=1.6, 7.8 Hz, 1H), 7.66 (d, J=8.8 Hz, 2H), 7.59 (t, J=7.9 Hz, 1H), 7.53 (d, J=7.9 Hz, 1H), 7.32 (dd, J=5.4, 7.1 Hz, 1H), 7.24 (d, J=7.6 Hz, 1H), 7.14 (d, J=8.6 Hz, 2H), 5.42 (dd, J=5.9, 8.3 Hz, 1H), 3.76-3.62 (m, 2H), 2.27-2.12 (m, 2H) and Compound 110 (14.0 mg, 30.2 umol, 23.5% yield) as a white solid. LCMS (ESI): RT=0.857 min, mass calc. for C₂₆H₂₁F₃N₂O₃ 466.15, m/z found 467 [M+H]⁺; ¹H NMR (400 MHz, CD3OD) δ 8.56 (d, J=4.3 Hz, 1H), 8.52 (d, J=1.5 Hz, 1H), 8.11 (d, J=8.9 Hz, 1H), 7.96-7.89 (m, 2H), 7.87 (dt, J=1.7, 7.7 Hz, 1H), 7.66 (d, J=8.6 Hz, 2H), 7.62-7.54 (m, 2H), 7.38-7.33 (m, 1H), 7.24 (d, J=7.5 Hz, 1H), 7.14 (d, J=8.6 Hz, 2H), 5.42 (dd, J=6.1, 8.3 Hz, 1H), 3.77-3.64 (m, 2H), 2.29-2.15 (m, 2H).

Example 84: (S)-N-(4-aminobutan-2-yl)-5-(4-(trifluoromethyl)phenoxy)-2-naphthamide (Compound 111) and (R)-N-(4-aminobutan-2-yl)-5-(4-(trifluoromethyl)phenoxy)-2-naphthamide (Compound 112)

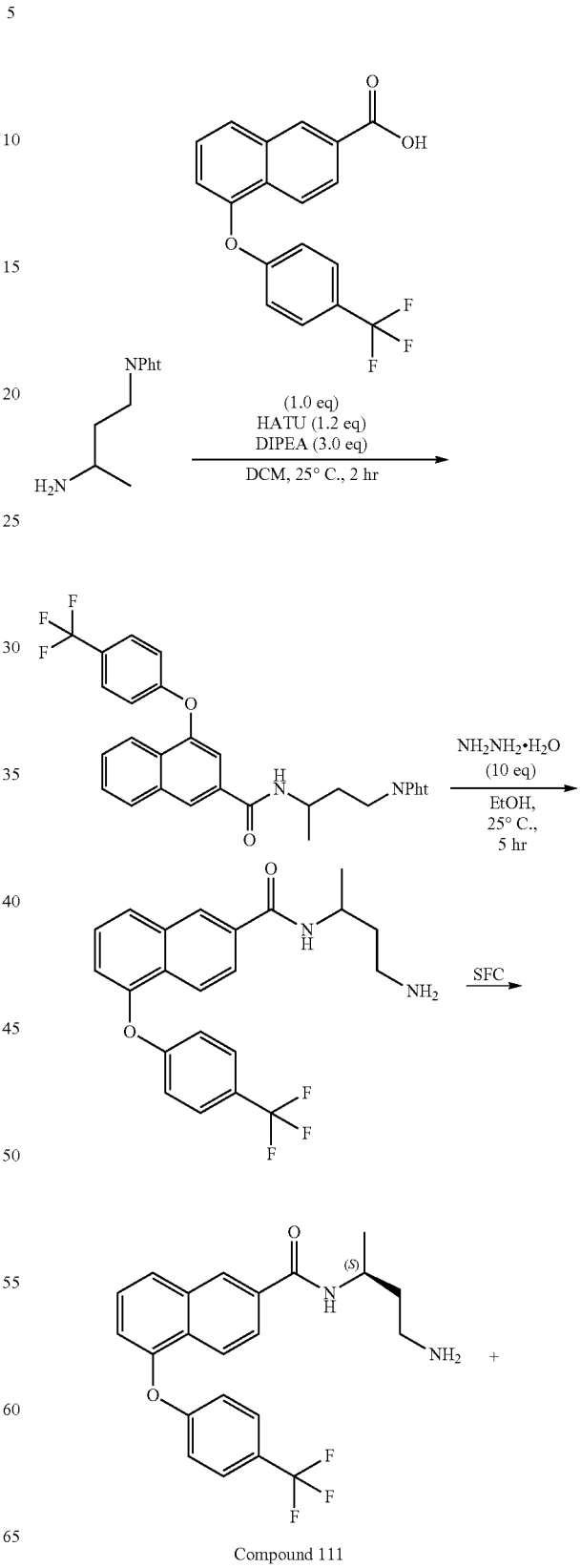

Compound 111

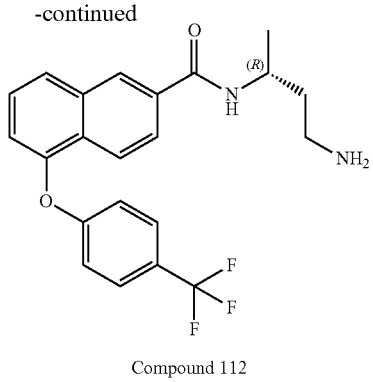

Compound 112

N-(4-(1,3-Dioxoisoindolin-2-yl)butan-2-yl)-5-(4-(trifluoromethyl)phenoxy)-2-naphthamide To a solution of 5-[4-(trifluoromethyl)phenoxy]naphthalene-2-carboxylic acid (100 mg, 0.30 mmol, 1 eq), 2-(3-aminobutyl)isoindoline-1,3-dione (76.6 mg, 0.30 mmol, 1 eq, HCl) and DIPEA (116 mg, 0.90 mmol, 3 eq) in DCM (3 mL) was added HATU (137 mg, 0.36 mmol, 1.2 eq). The reaction mixture was stirred at 25° C. for 2 hrs. LC-MS showed starting material was consumed completely and one main peak with desired MS was detected. The reaction mixture was concentrated under reduced pressure. The mixture was diluted with water (30 mL) and the resultant mixture was extracted with EA (50 mL*3). The combined organic layers were dried over $Na_2SO_4$, filtered and concentrated to dryness under reduced pressure. The residue was purified by column chromatography over silica gel (petroleum ether: ethyl acetate=1:0 to 2:1) to afford N-(4-(1,3-Dioxoisoindolin-2-yl)butan-2-yl)-5-(4-(trifluoromethyl)phenoxy)-2-naphthamide (150 mg, 92% yield) as a white solid. LCMS (ESI): RT=1.025 min, mass calcd for $C_{30}H_{23}F_3N_2O_4$ 532.16 m/z, found 533.1 [M+H]$^+$.

N-(4-Aminobutan-2-yl)-5-(4-(trifluoromethyl)phenoxy)-2-naphthamide $NH_2NH_2 \cdot H_2O$ (143 mg, 2.44 mmol, 0.14 mL, 85%, 10 eq) was added to a solution of N-[3-(1,3-dioxoisoindolin-2-yl)-1-methyl-propyl]-5-[4-(trifluoromethyl)phenoxy]naphthalene-2-carboxamide (130 mg, 0.24 mmol, 1 eq) in EtOH (8 mL). The reaction mixture was stirred at 25° C. for 5 hrs. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC (column: Welch Xtimate C18 150*25 mm*5 um; mobile phase: [water (0.05% HCl)–ACN]; B %: 20%-50%, 8.5 min) to give N-(4-Aminobutan-2-yl)-5-(4-(trifluoromethyl)phenoxy)-2-naphthamide (85 mg, 78% yield, HCl) as a white solid. LCMS (ESI): RT=0.837 min, mass calcd for $C_{22}H_{21}F_3N_2O_2$ 402.16 m/z, found 403.1 [M+H]$^+$.

(S)-N-(4-aminobutan-2-yl)-5-(4-(trifluoromethyl)phenoxy)-2-naphthamide (Compound 111) and (R)-N-(4-aminobutan-2-yl)-5-(4-(trifluoromethyl)phenoxy)-2-naphthamide (Compound 112)

N-(3-Amino-1-methyl-propyl)-5-[4-(trifluoromethyl)phenoxy]naphthalene-2-carboxamide (85 mg, 0.19 Mmol, 1 eq, HCl) was separate by SFC (column: DAICEL CHIRALCEL OD-H (250 mm*30 mm, 5 um); mobile phase: [0.1% $NH_3H_2O$ MEOH]; B %: 25%-25%, min). The pure fractions were collected and the volatiles were removed under vacuum. The residue was re-suspended in water (10 mL) and ACN (1 mL), and then the resulting mixture was lyophilized to dryness to remove the solvent residue completely. Compound 112 (32.08 mg, 79 umol, 41.1% yield) was obtain as a white solid and Compound 111 (35 mg) was obtain as a white solid. The crude product was purified by SFC (column: DAICEL CHIRALCEL OD-H (250 mm*30 mm, 5um); mobile phase: [0.1% $NH_3H_2O$ MEOH]; B %: 25%-25%, min), and then the pure fractions were collected and the volatiles were removed under vacuum. The residue was re-suspended in water (10 mL) and ACN (1 mL), and then the resulting mixture was lyophilized to dryness to remove the solvent residue completely to give Compound 111 (29.44 mg, 72 umol, 37.40% yield) as a white solid. Compound 112 LCMS (ESI): RT=0.847 min, mass calcd for $C_{22}H_{21}F_3N_2O_2$ 402.16 m/z, found 403.0 [M+H]$^+$; $^1$H NMR (400 MHz, DMSO-d$_6$) δ 8.63-8.51 (m, 2H), 8.03-7.91 (m, 3H), 7.75 (d, J=8.6 Hz, 2H), 7.64 (t, J=7.9 Hz, 1H), 7.33 (d, J=7.0 Hz, 1H), 7.16 (d, J=8.5 Hz, 2H), 4.25-4.09 (m, 1H), 2.70 (t, J=7.2 Hz, 2H), 1.81-1.61 (m, 2H), 1.22 (d, J=6.6 Hz, 3H). Compound 111 LCMS (ESI): RT=0.847 min, mass calcd for $C_{22}H_{21}F_3N_2O_2$ 402.16 m/z, found 403.1 [M+H]$^+$. $^1$H NMR (400 MHz, DMSO-d$_6$) δ 8.59-8.48 (m, 2H), 8.03-7.90 (m, 3H), 7.75 (d, J=8.6 Hz, 2H), 7.63 (t, J=7.9 Hz, 1H), 7.32 (d, J=7.3 Hz, 1H), 7.16 (d, J=8.5 Hz, 2H), 4.25-4.13 (m, 1H), 2.61 (t, J=6.8 Hz, 2H), 1.70-1.52 (m, 2H), 1.20 (d, J=6.6 Hz, 3H).

Example 85: N-Isopropyl-6-methoxy-8-(4-(trifluoromethyl)phenoxy)quinoline-3-carboxamide (Compound 113)

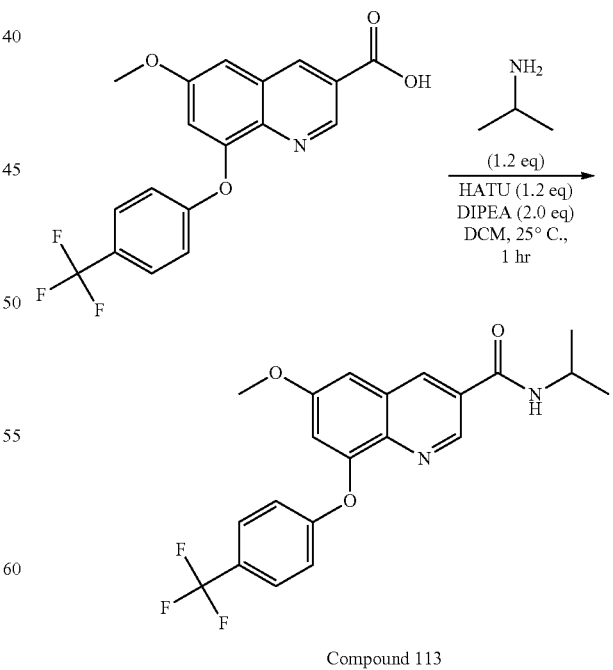

Compound 113

To a solution of 6-methoxy-8-[4-(trifluoromethyl)phenoxy]quinoline-3-carboxylic acid (20 mg, 55 umol, 1 eq), propan-2-amine (3.9 mg, 66 umol, 5.68 uL, 1.2 eq) and DIPEA (7.1 mg, 55 umol, 1 eq) in DCM (1 mL) was added HATU (25.1 mg, 66 umol, 1.2 eq). The reaction mixture was stirred at 25° C. for 1 hr. LC-MS showed starting material was consumed completely and one main peak with desired MS was detected. The reaction mixture was concentrated under reduced pressure. The mixture was diluted with water (5 mL) and the resultant mixture was extracted with EA (20 mL*3). The combined organic layers were dried over $Na_2SO_4$, filtered and concentrated to dryness under reduced pressure. The residue was purified by prep-HPLC (column: Waters Xbridge BEH C18 100*25 mm*5 um; mobile phase: [water (0.04% $NH_3H_2O$ 10 mM $NH_4HCO_3$)–ACN]; B %: 50%-80%, 7.8 min) to give the title compound as a white solid. LCMS (ESI): RT=0.911 min, mass calcd for $C_{21}H_{19}F_3N_2O_3$ 404.13 m/z, found 405.2 $[M+H]^+$. $^1H$ NMR (400 MHz, $CDCl_3$) δ 9.03 (d, J=2.3 Hz, 1H), 8.54 (d, J=2.0 Hz, 1H), 7.62 (d, J=8.5 Hz, 2H), 7.16 (d, J=8.5 Hz, 2H), 6.98 (d, J=2.5 Hz, 1H), 6.93 (d, J=2.5 Hz, 1H), 6.08 (br d, J=6.8 Hz, 1H), 4.37 (qd, J=6.7, 13.8 Hz, 1H), 3.93 (s, 3H), 1.33 (d, J=6.5 Hz, 6H).

Example 86: (R)-N-(4-hydroxybutan-2-yl)-5-(4-(trifluoromethyl)phenoxy)-2-naphthamide (Compound 114) and (S)-N-(4-hydroxybutan-2-yl)-5-(4-(trifluoromethyl)phenoxy)-2-naphthamide (Compound 115)

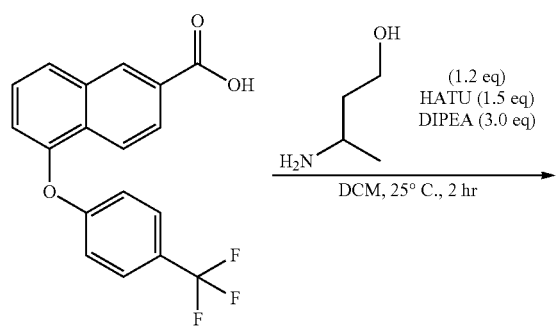

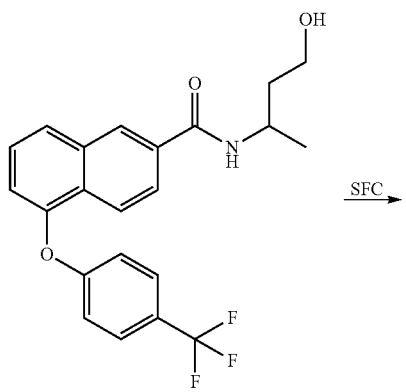

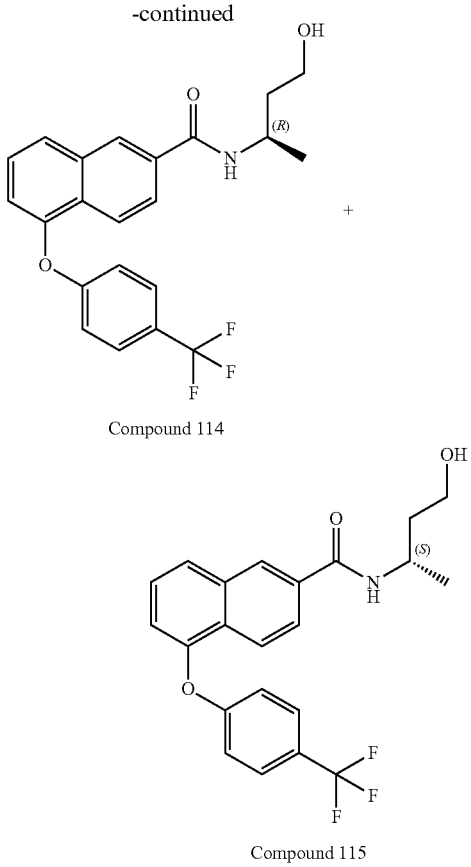

Compound 114

Compound 115

N-(3-hydroxy-1-methyl-propyl)-5-[4-(trifluoromethyl)phenoxy]naphthalene-2-carboxamide The mixture of 5-[4-(trifluoromethyl)phenoxy]naphthalene-2-carboxylic acid (90 mg, 0.27 mmol, 1 eq), 3-aminobutan-1-ol (28.9 mg, 0.32 mmol, 1.2 eq), DIPEA (105 mg, 0.81 mmol, 0.14 mL, 3 eq) and HATU (154.4 mg, 0.40 mmol, 1.5 eq) in DCM (10 mL) was stirred at 25° C. for 2 hr. The reaction mixture was diluted with $H_2O$ (10 mL) and the mixture was extracted with EA (20 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1/0 to 0/1). Compound N-(3-hydroxy-1-methyl-propyl)-5-[4-(trifluoromethyl)phenoxy]naphthalene-2-carboxamide (100 mg, 0.24 mmol, 91.5% yield) was obtained as white solid.

(R)-N-(4-hydroxybutan-2-yl)-5-(4-(trifluoromethyl)phenoxy)-2-naphthamide (Compound 114) and (S)-N-(4-hydroxybutan-2-yl)-5-(4-(trifluoromethyl)phenoxy)-2-naphthamide (Compound 115)

The racemic compound N-(3-hydroxy-1-methyl-propyl)-5-[4-(trifluoromethyl)phenoxy]naphthalene-2-carboxamide (90 mg, 0.22 mmol, 1 eq) was separated by SFC (column: Phenomenex-Cellulose-2 (250 mm*30 mm, 5 um); mobile phase: [0.1% $NH_3H_2O$ MEOH]; B %: 30%-30%, min). Compound 114 (14.6 mg, 35.5 umol, 15.9% yield) was obtained as white solid. LCMS (ESI): RT=0.927 min, mass calcd for $C_{22}H2F_3NO_3$ 403.39 m/z found 404.1$[M+H]^+$. $^1H$ NMR (400 MHz, DMSO-d$_6$) δ ppm 1.19 (d, J=6.63 Hz, 3H) 1.61-1.80 (m, 2H) 3.48 (q, J=5.75 Hz, 2H) 4.14-4.21 (m, 1H) 4.47 (t, J=5.07 Hz, 1H) 7.15 (d, J=8.63 Hz, 2H) 7.31 (d, J=7.38 Hz, 1H) 7.62 (t, J=7.88 Hz, 1H) 7.73 (d, J=8.75 Hz, 2H) 7.91-8.01 (m, 3H) 8.42 (d, J=8.13 Hz, 1H) 8.52 (s, 1H). Compound 115 (19.23 mg, 47.19 umol, 21.15% yield) was obtained as white solid. LCMS (ESI): RT=0.926 min, mass calcd for C$_{22}$H2F$_3$NO$_3$ 403.39 m/z found 404.1[M+H]$^+$. $^1$H NMR (400 MHz, DMSO-d$_6$) δ ppm 1.19 (d, J=6.63 Hz, 3H) 1.61-1.80 (m, 2H) 3.41-3.52 (m, 2H) 4.12-4.23 (m, 1H) 4.47 (t, J=5.13 Hz, 1H) 7.15 (d, J=8.63 Hz, 2H) 7.31 (d, J=7.50 Hz, 1H) 7.62 (t, J=7.94 Hz, 1H) 7.73 (d, J=8.63 Hz, 2H) 7.91-8.01 (m, 3H) 8.42 (br d, J=8.13 Hz, 1H) 8.52 (s, 1H).

Example 87: (R)-N-(1-hydroxypropan-2-yl)-6-methoxy-8-(4-(trifluoromethyl)phenoxy)quinoline-3-carboxamide (Compound 116)

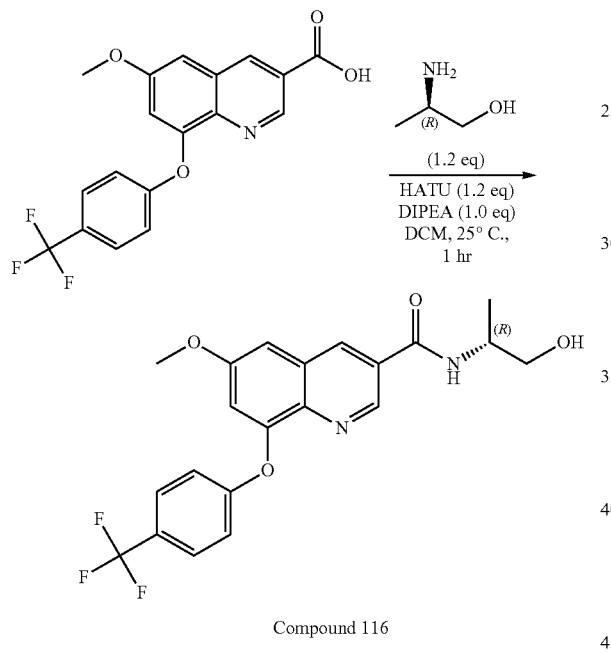

Compound 116

Example 88: 5-(4-(trifluoromethyl)phenoxy)naphthalene-2-sulfonamide (Compound 117)

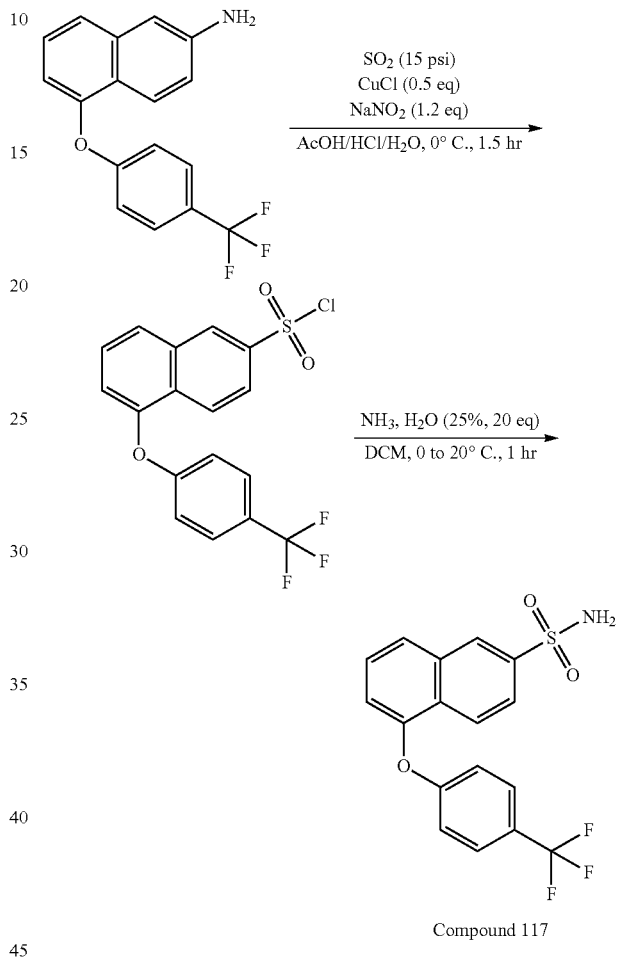

Compound 117

To a solution of 6-methoxy-8-[4-(trifluoromethyl)phenoxy]quinoline-3-carboxylic acid (20 mg, 55 umol, 1 eq), (2R)-2-aminopropan-1-ol (4.9 mg, 66 umol, 1.2 eq) and DIPEA (7.1 mg, 55 umol, 1 eq) in DCM (1 mL) was added HATU (25.1 mg, 66 umol, 1.2 eq). The reaction mixture was stirred at 25° C. for 1 hr. LC-MS showed starting material was consumed completely and one main peak with desired MS was detected. The reaction mixture was concentrated under reduced pressure. The mixture was diluted with water (5 mL) and the resultant mixture was extracted with EA (20 mL*3). The combined organic layers were dried over Na$_2$SO$_4$, filtered and concentrated to dryness under reduced pressure. The residue was purified by prep-HPLC (column: Waters Xbridge BEH C18 100*25 mm*5 um; mobile phase: [water (0.05% ammonia hydroxide v/v)–ACN]; B %: 40%-70%, 9 min) to give the title compound (9.27 mg, 39% yield) as a white solid. LCMS (ESI): RT=0.840 min, mass calcd for C$_{21}$H$_{19}$F$_3$N$_2$O$_4$ 420.13 m/z, found 421.0 [M+H]$^+$. $^1$H NMR (400 MHz, CDCl$_3$) δ 9.07 (d, J=2.0 Hz, 1H), 8.55 (d, J=2.0 Hz, 1H), 7.62 (d, J=8.5 Hz, 2H), 7.16 (d, J=8.5 Hz, 2H), 6.97 (d, J=2.5 Hz, 1H), 6.93 (d, J=2.5 Hz, 1H), 6.60 (br d, J=7.5 Hz, 1H), 4.44-4.32 (m, 1H), 3.93 (s, 3H), 3.86 (dd, J=3.5, 11.0 Hz, 1H), 3.71 (dd, J=5.5, 11.0 Hz, 1H), 1.35 (d, J=6.8 Hz, 3H).

5-[4-(trifluoromethyl)phenoxy]naphthalene-2-sulfonyl chloride

To a solution of compound 5-(4-(trifluoromethyl)phenoxy)naphthalen-2-amine (100.0 mg 0.33 mmol, 1 eq) in HCl (0.5 mL) and AcOH (1 mL) was added NaNO$_2$ (27.3 mg, 0.40 mmol, 1.2 eq) in H$_2$O (0.5 mL) at 0° C. Then the mixture was stirred at 0° C. for 30 min. Then SO$_2$ (1.00 eq) was bubbled into a solution at 0° C. for 30 min. Then CuCl (16.3 mg, 0.16 mmol, 3.9 uL, 0.5 eq) was added to the mixture and stirred for 30 min. The reaction mixture was poured into ice water (20 mL), extracted with EA (20 mL*3). The combined organic phase was washed with H$_2$O (10 mL), brine (10 mL) and dried over Na$_2$SO$_4$, filtered and concentrated in vacuum. The residue was purified by flash silica gel chromatography (ISCO®; 12 g SepaFlash® Silica Flash Column, Eluent of 0-10% Ethyl acetate/Petroleum ether gradient @ 30 mL/min). The title compound (60.0 mg, 0.16 mmol, 47.1% yield) was obtained as a brown solid. $^1$H NMR (400 MHz, CDCl$_3$) δ 8.66 (d, J=1.8 Hz, 1H), 8.40 (d, J=9.0 Hz, 1H), 8.03 (dd, J=1.9, 9.0 Hz, 1H), 7.89 (d, J=8.3 Hz, 1H), 7.71-7.62 (m, 3H), 7.27-7.24 (m, 1H), 7.13 (d, J=8.6 Hz, 2H).

5-[4-(trifluoromethyl)phenoxy]naphthalene-2-sulfonamide

To a solution of compound 5-[4-(trifluoromethyl)phenoxy]naphthalene-2-sulfonyl chloride (50.0 mg, 0.13 mmol, 1 eq) in DCM (1 mL) was added NH$_3$.H$_2$O (362.4 mg, 2.59 mmol, 0.4 mL, 20 eq) at 0° C. Then the mixture was stirred at 20° C. for 1 hr. The reaction mixture was concentrated in vacuum. The residue was purified by prep-HPLC (column: Waters Xbridge C18 150*50 mm*10 um; mobile phase: [water (0.04% NH$_3$H$_2$O+10 mM NH$_4$HCO$_3$)–ACN]; B %: 54%-84%, 9.3 min). The title compound (8.1 mg, 22 umol, 17.1% yield) was obtained as a white solid. LCMS (ESI): RT=0.878 min, mass calc. for C$_{17}$H$_{12}$F$_3$NO$_3$S 367.05, m/z found 366.0 [M–H]$^-$; 1H NMR (400 MHz, CDCl$_3$) δ 8.55 (d, J=1.8 Hz, 1H), 8.26 (d, J=8.8 Hz, 1H), 7.92 (dd, J=1.8, 8.8 Hz, 1H), 7.82 (d, J=8.5 Hz, 1H), 7.65-7.54 (m, 3H), 7.24-7.17 (m, 1H), 7.09 (d, J=8.3 Hz, 2H), 4.91 (br s, 2H).

Example 89: N-(2-Hydroxy-1-(pyridin-2-yl)ethyl)-6-methoxy-8-(4-(trifluoromethyl)phenoxy)quinoline-3-carboxamide (Compound 118)

and DIPEA (21.3 mg, 0.16 mmol, 2 eq) in DCM (1 mL) was added HATU (37.6 mg, 99.1 umol, 1.2 eq). The reaction mixture was stirred at 25° C. for 1 hr. LC-MS showed starting material was consumed completely and one peak with desired MS was detected. The reaction mixture was concentrated under reduced pressure. The mixture was diluted with water (5 mL) and the resultant mixture was extracted with EA (20 mL*3). The combined organic layers were dried over Na$_2$SO$_4$, filtered and concentrated to dryness under reduced pressure. The residue was purified by prep-HPLC (column: Waters Xbridge C18 150*50 mm*10 um; mobile phase: [water (0.04% NH$_3$H$_2$O+10 mM NH$_4$HCO$_3$)–ACN]; B %: 36%-66%, 11 min) to give the title compound (11.9 mg, 29% yield) as a white solid. LCMS (ESI): RT=0.826 min, mass calcd for C$_{25}$H$_{20}$F$_3$N$_3$O$_4$ 483.14 m/z, found 484.0 [M+H]$^+$. $^1$H NMR (400 MHz, CDCl$_3$) δ 9.19 (d, J=2.0 Hz, 1H), 8.61 (d, J=2.0 Hz, 1H), 8.57 (d, J=4.3 Hz, 1H), 8.14 (br d, J=6.8 Hz, 1H), 7.77 (dt, J=1.8, 7.7 Hz, 1H), 7.62 (d, J=8.5 Hz, 2H), 7.52 (d, J=7.8 Hz, 1H), 7.34-7.28 (m, 1H), 7.16 (d, J=8.5 Hz, 2H), 7.01 (d, J=2.5 Hz, 1H), 6.95 (d, J=2.5 Hz, 1H), 5.47-5.37 (m, 1H), 4.21-4.15 (m, 1H), 4.07 (dd, J=3.9, 11.4 Hz, 1H), 3.94 (s, 3H).

Example 90: (S)-N-(2-hydroxy-1-(pyridin-2-yl)ethyl)-5-(4-(trifluoromethyl)phenoxy)-2-naphthamide (Compound 119) and (R)-N-(2-hydroxy-1-(pyridin-2-yl)ethyl)-5-(4-(trifluoromethyl)phenoxy)-2-naphthamide (Compound 120)

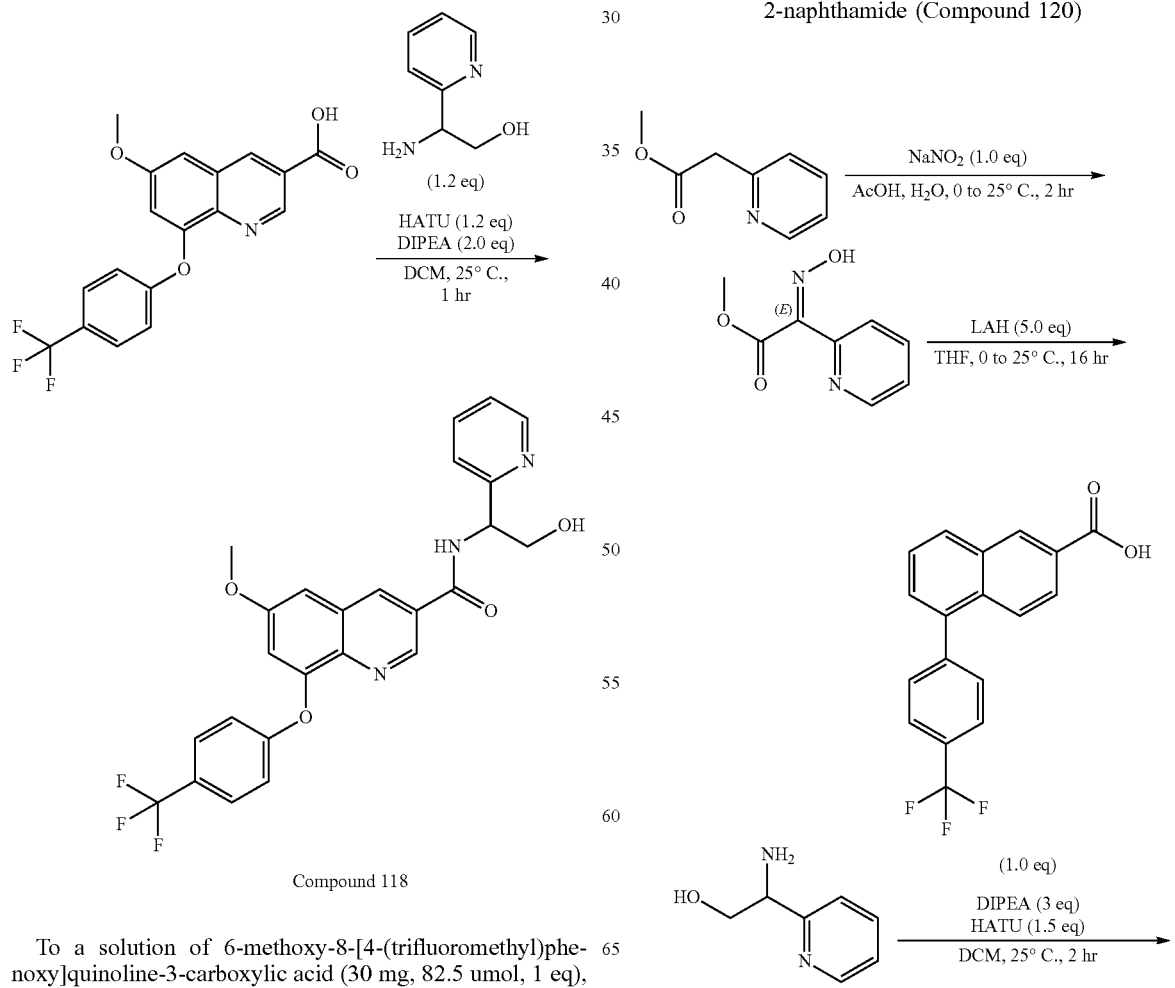

Compound 118

To a solution of 6-methoxy-8-[4-(trifluoromethyl)phenoxy]quinoline-3-carboxylic acid (30 mg, 82.5 umol, 1 eq), 2-amino-2-(2-pyridyl)ethanol (13.6 mg, 99.1 umol, 1.2 eq)

-continued

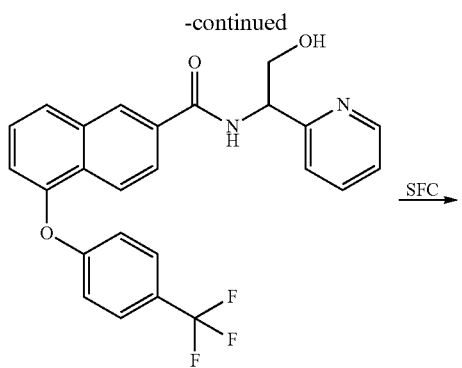

Compound 119

Compound 120

Methyl (2E)-2-hydroxyimino-2-(2-pyridyl)acetate

To a solution of methyl 2-(2-pyridyl)acetate (1 g, 6.62 mmol, 0.89 mL, 1 eq) in AcOH (1.6 mL) at 0° C. with stirring, an aqueous solution of NaNO₂ (456.4 mg, 6.62 mmol, 1 eq) in H₂O (1.40 g, 77.71 mmol, 1.4 mL, 11.75 eq) was added portion wise. After addition was completed stirring was continued for 1 hr at 25° C. H₂O (3.00 g, 166.53 mmol, 3 mL, 25.17 eq) was added and the mixture was stirred for another 1 hr. The reaction mixture was diluted with H₂O (5 mL) and the mixture was extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 1/1). Compound methyl (2E)-2-hydroxyimino-2-(2-pyridyl)acetate (670 mg, 3.61 mmol, 54.5% yield) was obtained as white solid.

2-amino-2-(2-pyridyl)ethanol

To a solution of methyl (2E)-2-hydroxyimino-2-(2-pyridyl)acetate (200 mg, 1.11 mmd, 1 eq) in THF (6 mL) was added LAH (210.6 mg, 5.55 mmd, 5 eq) at 0° C. Then the mixture was stirred at 25° C. for 16 hr. LC-MS showed the desired compound was detected. The reaction mixture was diluted with H₂O (2 mL), NaOH (2M, 2.5 ml). Then the mixture was concentrated in vacuo. No purification. Compound 2-amino-2-(2-pyridyl)ethanol (180 mg, crude) was obtained as yellow solid, which was used into the next step without further purification.

N-[2-hydroxy-1-(2-pyridyl)ethyl]-5-[4-(trifluoromethyl)phenoxy]naphthalene-2-carboxamide The mixture of 5-[4-(trifluoromethyl)phenoxy]naphthalene-2-carboxylic acid (150 mg, 0.45 mmol, 1 eq), 2-amino-2-(2-pyridyl)ethanol (68.6 mg, 0.49 mmol, 1.1 eq), DIPEA (175.0 mg, 1.35 mmol, 0.23 mL, 3 eq) and HATU (257.4 mg, 0.67 mmol, 1.5 eq) in DCM (1 mL) was stirred at 25° C. for 2 hr. The reaction mixture was diluted with H₂O (10 mL) and the mixture was extracted with EA (20 mL*3). The combined organic phase was washed with brine (10 mL*2), dried with anhydrous Na₂SO₄, filtered and concentrated in vacuum. The residue was purified by prep-HPLC (column: Xtimate C18 100*30 mm*3 um; mobile phase: [water (0.05% HCl)–ACN]; B %: 28%-58%, 8.5 min). Compound N-[2-hydroxy-1-(2-pyridyl)ethyl]-5-[4-(trifluoromethyl)phenoxy]naphthalene-2-carboxamide (15 mg, 30.5 umol, 6.7% yield) was obtained as yellow solid.

(S)-N-(2-hydroxy-1-(pyridin-2-yl)ethyl)-5-(4-(trifluoromethyl)phenoxy)-2-naphthamide (Compound 119) and (R)-N-(2-hydroxy-1-(pyridin-2-yl)ethyl)-5(4-(trifluoromethyl)phenoxy)-2-naphthamide (Compound 120)

The racemic compound N-[2-hydroxy-1-(2-pyridyl)ethyl]-5-[4-(trifluoromethyl)phenoxy]naphth alene-2-carboxamide (20 mg, 44.2 umol, 1 eq) was purified by prep-SFC (column: DAICEL CHIRALPAK AD (250 mm*30 mm, 10 um); mobile phase: [0.1% NH₃H₂O ETOH]; B %: 40%-40%, min). Compound 119 (2.4 mg, 5.4 umol, 12.3% yield) was obtained as white solid. LCMS (ESI): RT=0.801 min, mass calcd for C₂₅H₁₉F₃N₂O₃ 452.43 m/z found 453.0 [M+H]⁺. ¹H NMR (400 MHz, CDCl₃) δ 4.07 (br dd, J=11.07, 3.56 Hz, 1H) 4.20 (dd, J=11.26, 4.13 Hz, 1H) 4.36 (br s, 1H) 5.39-5.45 (m, 1H) 7.08 (d, J=8.63 Hz, 2H) 7.16 (d, J=7.50 Hz, 1H) 7.30 (dd, J=6.94, 5.44 Hz, 1H) 7.48-7.56 (m, 2H) 7.60 (d, J=8.75 Hz, 2H) 7.76 (td, J=7.66, 1.69 Hz, 1H) 7.82 (d, J=8.25 Hz, 1H) 7.92 (dd, J=8.76, 1.50 Hz, 1H) 8.04 (br d, J=7.13 Hz, 1H) 8.14 (d, J=8.75 Hz, 1H) 8.46 (s, 1H) 8.58 (br d, J=4.63 Hz, 1H). Compound 120 (2.5 mg, 5.6 umol, 12.7% yield) was obtained as white solid. LCMS (ESI): RT=0.794 min, mass calcd for C₂₅H₁₉F₃N₂O₃ 452.43 m/z found 453.0 [M+H]⁺. ¹H NMR (400 MHz, CDCl₃) δ 4.07 (dd, J=11.32, 3.69 Hz, 1H) 4.20 (dd, J=11.26, 4.25 Hz, 1H) 4.36 (br s, 1H) 5.39-5.43 (m, 1H) 7.08 (d, J=8.50 Hz, 2H) 7.16 (d, J=6.88 Hz, 1H) 7.28-7.33 (m, 1H) 7.49-7.56 (m, 2H) 7.60 (d, J=8.50 Hz, 2H) 7.76 (td, J=7.69, 1.75 Hz, 1H) 7.82 (d, =8.25 Hz, 1H) 7.92 (dd, J=8.82, 1.69 Hz, 1H) 8.04 (br d, J=6.75 Hz, 1H) 8.14 (d, J=8.75 Hz, 1H) 8.45 (d, J=1.38 Hz, 1H) 8.58 (d, J=4.25 Hz, 1H).

Example 91: N-(1,5-dihydroxypentan-3-yl)-5-(4-(trifluoromethyl)phenoxy)-2-naphthamide (Compound 121)

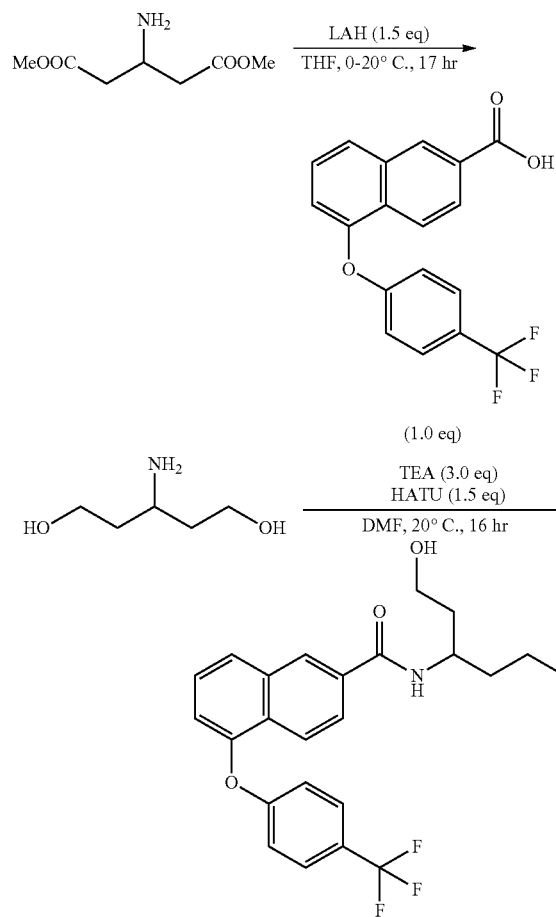

Compound 121

3-aminopentane-1,5-diol

To a solution of dimethyl 3-aminopentanedioate (120.0 mg, 0.57 mmol, 1 eq, HCl) in THF (1.5 mL) at 0° C. was added LiAlH$_4$ (32.3 mg, 0.85 mmol, 1.5 eq) portion-wise. The resulting mixture was stirred at 0° C. for 1 h and stirred at 20° C. for 16 h. The reaction mixture was quenched with water (50 μL) at 0° C. and then 2 M NaOH solution (50 μL), then diluted with water (150 μL). Then Na$_2$SO$_4$ was added into the reaction and stirred at 20° C. for 0.5 h, and the reaction was filtered and concentrated under reduced pressure to give compound 3-aminopentane-1,5-diol (20.0 mg, 0.17 mmol, 29.6% yield) as colorless oil. $^1$H NMR (400 MHz, CDCl$_3$) δ 3.87-3.76 (m, 4H), 3.23-3.11 (m, 1H), 1.76-1.68 (m, 2H), 1.62-1.56 (m, 2H).

N-(1,5-dihydroxypentan-3-yl)-5-(4-(trifluoromethyl)phenoxy)-2-naphthamide

To a solution of 5-(4-(trifluoromethyl)phenoxy)-2-naphthoic acid (38.6 mg, 0.12 mmol, 1.0 eq) and HATU (66.3 mg, 0.17 mmol, 1.5 eq) in DMF (1 mL) at 20° C. was added 3-aminopentane-1,5-diol (18.0 mg, 0.15 mmol, 1.3 eq) and TEA (35.3 mg, 0.35 mmol, 49 uL, 3 eq). The mixture was stirred at 20° C. for 16 h. The reaction mixture was concentrated to give a residue, which was purified by prep-HPLC (column: Xtimate C18 100*30 mm*3 um; mobile phase: [water (0.05% HCl)–ACN]; B %: 35%-65%, 8.5 min) to give the title compound (3.2 mg, 7 umol, 6.2% yield) as colorless oil. LCMS (ESI): RT=0.891 min, mass calc. for C$_{23}$H$_{22}$F$_3$NO$_4$ 433.15, m/z found 434.0 [M+H]$^+$; $^1$H NMR (400 MHz, CD$_3$OD) δ 8.45 (s, 1H), 8.10 (d, J=8.8 Hz, 1H), 7.90 (br d, J=8.5 Hz, 2H), 7.66 (br d, J=8.6 Hz, 2H), 7.59 (t, J=7.9 Hz, 1H), 7.23 (d, J=7.5 Hz, 1H), 7.13 (br d, J=8.5 Hz, 2H), 4.44-4.35 (m, 1H), 3.69 (br t, J=6.4 Hz, 4H), 1.97-1.77 (m, 4H).

Example 92: (R)-N-(1-(azetidin-3-yl)ethyl)-5-(4-(trifluoromethyl)phenoxy)-2-naphthamide (Compound 122) and (R)-N-(1-(1-(4-hydroxybutyl)azetidin-3-yl)ethyl)-5-(4-(trifluoromethyl)phenoxy)-2-naphthamide (Compound 123)

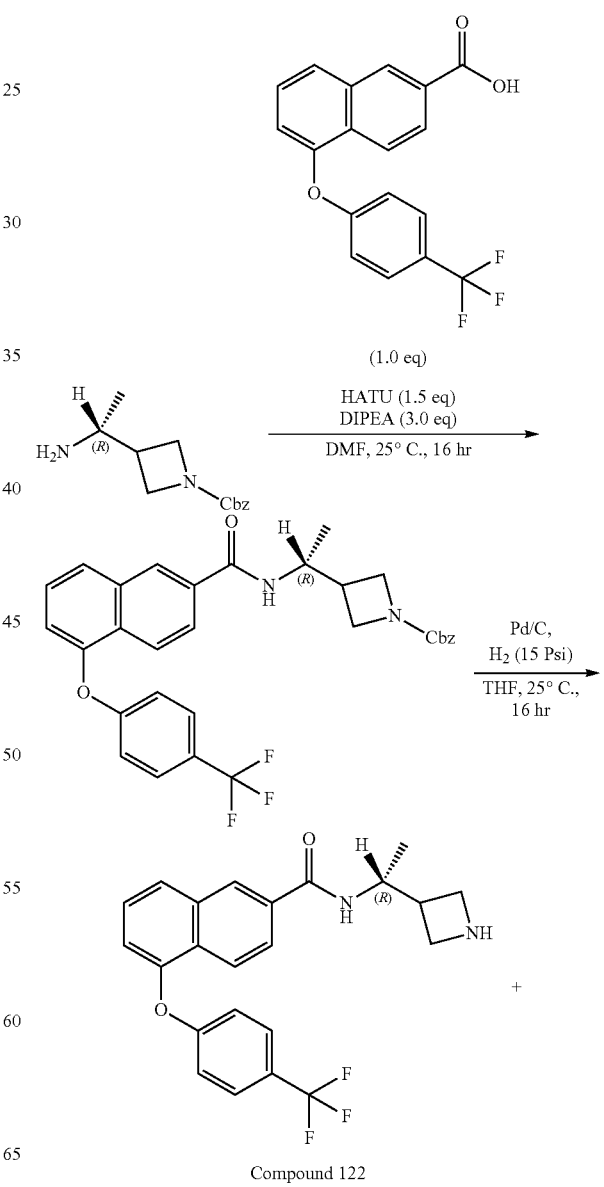

Compound 122

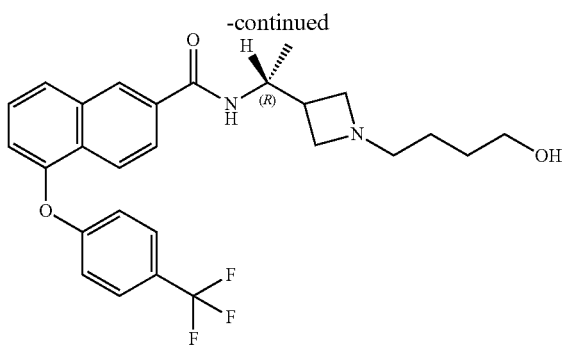

Compound 123 benzyl 3-[(1R)-1-[[5-[4-(trifluoromethyl)phenoxy]naphthalene-2-carbonyl]amino]ethyl]azetidine-1-carboxylate A mixture of 5-(4-(trifluoromethyl)phenoxy)-2-naphthoic acid (350 mg, 1.05 mmol, 1 eq), HATU (600.8 mg, 1.58 mmol, 1.5 eq) in DMF (5 mL) was added DIPEA (408.4 mg, 3.16 mmol, 0.55 mL, 3 eq) at 25° C. After addition, the mixture was stirred at 25° C. for 0.5 hr, and then benzyl (R)-3-(1-aminoethyl)azetidine-1-carboxylate (246.8 mg, 1.05 mmol, 1 eq) in DMF (3 mL) was added. The resulting mixture was stirred at 25° C. for 15.5 hr. The residue was poured into H$_2$O (30 mL) and stirred for 5 min. The aqueous phase was extracted with EA (20 mL*3). The combined organic phase was washed with brine (30 mL), dried with anhydrous Na$_2$SO$_4$, filtered and concentrated in vacuum. The residue was purified by flash silica gel chromatography (20 g SepaFlash® Silica Flash Column, EA/PE: 0-40%) to give benzyl 3-[(1R)-1-[[5-[4-(trifluoromethyl)phenoxy]naphthalene-2-carbonyl]amino]ethyl]azetidine-1-carboxylate (465 mg, 0.80 mmol, 75.6% yield) as a yellow solid.

(R)-N-(1-(azetidin-3-yl)ethyl)-5-(4-(trifluoromethyl)phenoxy)-2-naphthamide (Compound 122) and (R)-N-(1-(1-(4-hydroxy butyl)azetidin-3-yl)ethyl)-5-(4-(trifluoromethyl)phenoxy)-2-naphthamide (Compound 123)

To a solution of benzyl 3-[(1R)-1-[[5-[4-(trifluoromethyl)phenoxy]naphthalene-2-carbonyl]amino]ethyl]azetidine-1-carboxylate (350 mg, 0.64 mmol, 1 eq) in THF (2 mL) was added Pd/C (30 mg, 10%) under N$_2$. The suspension was degassed under vacuum and purged with H$_2$ several times. The mixture was stirred under H$_2$ (15 psi) at 25° C. for 16 hrs. The reaction mixture was filtered and the cake was washed with MeOH (10 mL*2). The filtrate was concentrated in vacuo to give crude product. The crude product was purified by prep-HPLC (column: Welch Xtimate C18 150*25 mm*5 um; mobile phase: [water (0.05% HCl)–ACN]; B %: 25%-55%, 8.5 min) to give 95 mg compounds, and then the compounds was purified by SFC (column: DAICEL CHIRALPAK IC (250 mm*30 mm, 5 um); mobile phase: [0.1% NH HO ETOH]; B %: 45%-45%, min) to afford Compound 122 (61.4 mg, 0.14 mmol, 22.5% yield) as a white solid. LCMS (ESI): RT=0.782 min, mass calcd for C$_{23}$H$_{21}$F$_3$N$_2$O$_2$ 414.16, m/z found 415.2 [M+H]$^+$; $^1$H NMR (400 MHz, DMSO-d$_6$) δ 8.55-8.49 (m, 1H), 8.40 (d, J=8.3 Hz, 1H), 8.01-7.91 (m, 3H), 7.77-7.70 (m, 2H), 7.68-7.58 (in, 1H), 7.35-7.27 (m, 1H), 7.19-7.08 (m, 2H), 4.34-4.12 (m, 1H), 3.51-3.43 (m, 1H), 3.30-3.26 (m, 1H), 3.26-3.10 (m, 1H), 3.01-2.81 (m, 1H), 2.81-2.69 (m, 1H), 1.12-1.03 (m, 3H). Compound 123 (7.4 mg, 13.4 umol, 2.1% yield) as a yellow solid. LCMS (ESI): RT=0.781 min, mass calcd for C$_{27}$H$_{29}$F$_3$N$_2$O$_3$ 486.21, m/z found 487.3 [M+H]$^+$; $^1$H NMR (400 MHz, CD$_3$OD) δ 8.43 (d, J=1.5 Hz, 1H), 8.09 (d, J=8.8 Hz, 1H), 7.96-7.84 (m, 2H), 7.66 (d, J=8.8 Hz, 2H), 7.58 (t, J=7.9 Hz, 1H), 7.22 (d, J=7.0 Hz, 1H), 7.13 (d, J=8.5 Hz, 2H), 4.38-4.28 (m, 1H), 3.57-3.41 (m, 4H), 3.08 (t, J=7.5 Hz, 1H), 2.96 (t, J=7.8 Hz, 11H), 2.77-2.65 (m, 1H), 2.50 (t, J=7.4 Hz, 2H), 1.57-1.49 (m, 2H), 1.48-1.39 (m, 2H), 1.35-1.23 (m, 4H), 1.20 (d, J=6.8 Hz, 3H), 0.89 (d, J=7.3 Hz, 2H).

Example 93: (R)-N-(1-(1-(2-fluoroethyl)azetidin-3-yl)ethyl)-5-(4-(trifluoromethyl)phenoxy)-2-naphthamide (Compound 124)

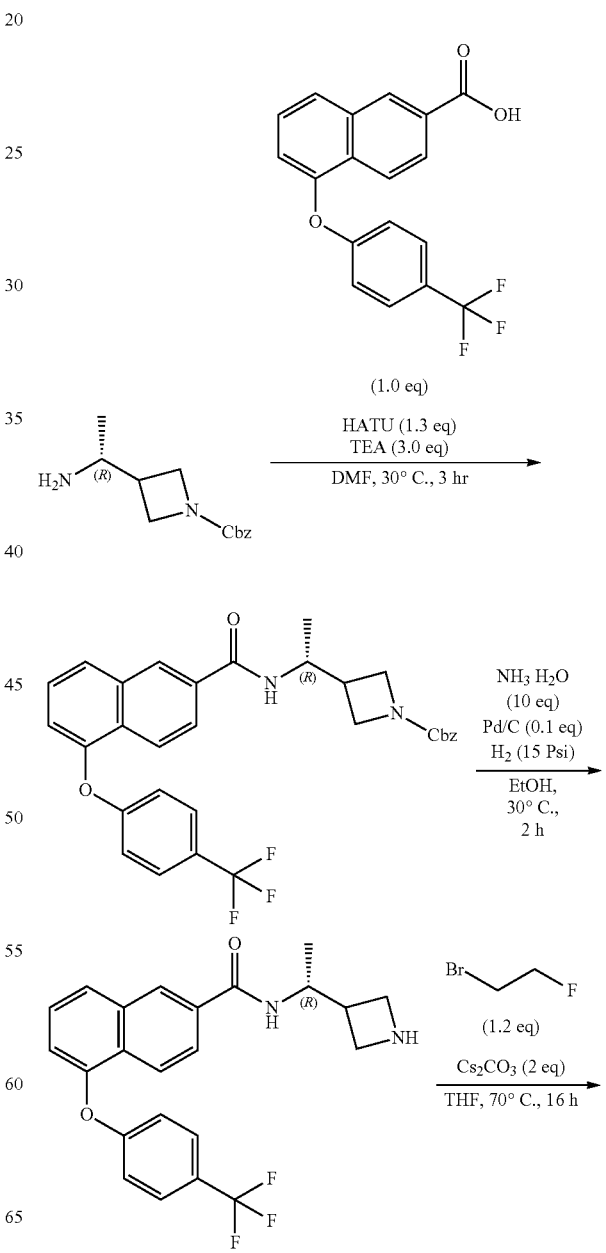

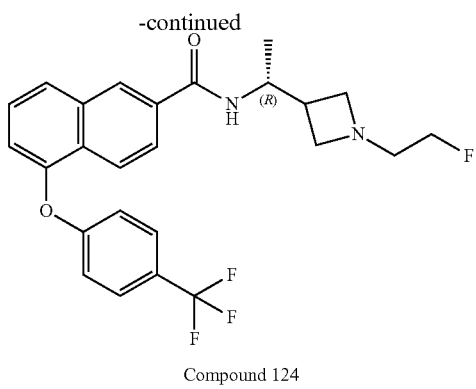

Compound 124

(R)-benzyl 3-(1-(5-(4-(trifluoromethyl)phenoxy)-2-naphthamido)ethyl)azetidine-1-carboxylate To a solution of 5-(4-(trifluoromethyl)phenoxy)-2-naphthoic acid (500 mg, 1.50 mmd, 1 eq), 1 (387.8 mg, 1.66 mmol, 1.1 eq) and HATU (743.8 mg, 1.96 mmol, 1.3 eq) in DMF (5 mL) at 30° C. was added TEA (456.8 mg, 4.51 mmd, 0.63 mL, 3 eq), and the mixture was stirred at 30° C. for 16 h. The reaction mixture was concentrated under reduced pressure to give a residue. The residue was diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @ 30 mL/min) to give (R)-benzyl 3-(1-(5-(4-(trifluoromethyl)phenoxy)-2-naphthamido)ethyl)azetidine-1-carboxylate (750 mg, 1.31 mmd, 87.2% yield) as a white solid. LCMS(ESI): RT=0.988 min, mass calc. for $C_{31}H_{27}F_3N_2O_4$ 548.19, m/z found 549.1 [M+H]$^+$.

(R)-N-(1-(azetidin-3-yl)ethyl)-5-(4-(trifluoromethyl)phenoxy)-2-naphthamide

To a solution of (R)-benzyl 3-(1-(5-(4-(trifluoromethyl)phenoxy)-2-naphthamido)ethyl)azetidine-1-carboxylate (700 mg, 1.28 mmol, 1 eq) and $NH_3.H_2O$ (1.79 g, 12.76 mmol, 1.97 mL, 25%, 10 eq) in EtOH (5 mL) at 30° C. was added Pd/C (135.8 mg, 0.13 mmol, 10%, 0.1 eq), and the mixture was purged and degassed with $H_2$ for 3 times and then stirred at 30° C. under $H_2$ (15 Psi) for 2 h. The reaction mixture was filtered to remove the solid and the filtrate was concentrated under reduced pressure to give (R)-N-(1-(azetidin-3-yl)ethyl)-5-(4-(trifluoromethyl)phenoxy)-2-naphthamide (500 mg, 1.18 mmol, 92.7% yield) as a white solid, which was used directly for next step. LCMS (ESI): RT=0.776 min, mass calc. for $C_{23}H_{21}F_3N_2O_2$ 414.16, m/z found 415.0 [M+H]$^+$; $^1$H NMR (400 MHz, CDCl$_3$) δ 8.39 (d, J=1.3 Hz, 1H), 8.10 (d, J=8.8 Hz, 1H), 7.86 (dd, J=1.7, 8.8 Hz, 1H), 7.80 (d, J=8.3 Hz, 1H), 7.59 (d, J=8.6 Hz, 2H), 7.50 (t, J=7.9 Hz, 1H), 7.14 (br dd, J=0.8, 7.6 Hz, 2H), 7.06 (d, J=8.5 Hz, 2H), 4.50-4.38 (m, 1H), 3.87-3.79 (m, 2H), 3.61 (dd, J=5.8, 7.9 Hz, 1H), 3.45 (dd, J=5.7, 7.8 Hz, 1H), 2.85-2.74 (m, 1H), 1.25 (d, J=6.6 Hz, 3H).

(R)-N-(1-(1-(2-fluoroethyl)azetidin-3-yl)ethyl)-5-(4-(trifluoromethyl)phenoxy)-2-naphthamide To a solution of (R)-N-(1-(azetidin-3-yl)ethyl)-5-(4-(trifluoromethyl)phenoxy)-2-naphthamide (50 mg, 0.12 mmol, 1 eq) and $Cs_2CO_3$ (157.2 mg, 0.48 mmd, 4 eq) in DMF (1 mL) at 30° C. was added 1-bromo-2-fluoroethane (18.4 mg, 0.14 mmol, 1.2 eq), and the mixture was stirred at 70° C. for 16 h. The reaction mixture was filtered to remove the solid and the filtrate was concentrated under reduced pressure to give a residue. The residue was purified by prep-HPLC (column: Welch Xtimate C18 150*25 mm*5 um; mobile phase: [water (0.05% HCl)–ACN]; B %: 23%-53%, 11.5 min) to give the title compound (3.1 mg, 6.2 umol, 5.2% yield, HC) as colorless oil. LCMS (ESI): RT=0.789 min, mass calc. for $C_{25}H_{24}F_4N_2O_2$ 460.18, m/z found 461.0 [M+H]$^+$; $^1$H NMR (400 MHz, DMSO-d$_6$) δ 8.58 (s, 1H), 8.45 (d, J=7.8 Hz, 1H), 8.05-7.91 (m, 3H), 7.72 (d, J=8.8 Hz, 2H), 7.65-7.58 (m, 1H), 7.29 (dd, J=0.8, 7.5 Hz, 1H), 7.18 (d, J=8.3 Hz, 2H), 4.81-4.74 (m, 1H), 4.69-4.62 (m, 1H), 4.39 (brs, 1H), 4.16 (d, J=8.5 Hz, 4H), 3.64-3.42 (m, 2H), 3.03-2.99 (m, 1H), 1.18 (d, J=6.5 Hz, 3H).

Example 94: (R)-N-(1-(1-(2,2-difluoroethyl)azetidin-3-yl)ethyl)-5-(4-(trifluoromethyl)phenoxy)-2-naphthamide (Compound 125)

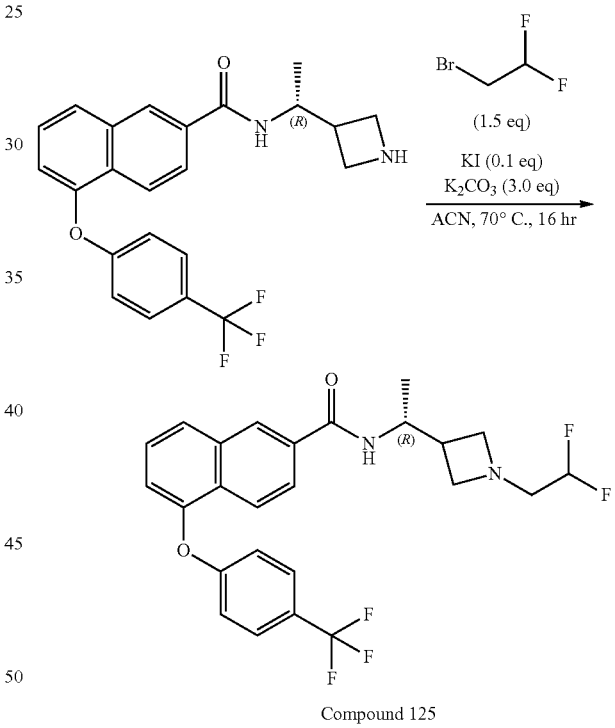

Compound 125

To a solution of (R)-N-(1-(azetidin-3-yl)ethyl)-5-(4-(trifluoromethyl)phenoxy)-2-naphthamide (50 mg, 0.12 mmol, 1 eq), KI (2.0 mg, 12.1 umol, 0.1 eq) and $K_2CO_3$ (50.0 mg, 0.36 mmol, 3 eq) in ACN (2 mL) at 30° C. was added 2-bromo-1,1-difluoroethane (26.2 mg, 0.18 mmol, 1.5 eq), and the mixture was stirred at 70° C. for 16 h. The reaction mixture was filtered to remove the solid and the filtrate was concentrated under reduced pressure to give a residue. The residue was purified by prep-HPLC (column: Waters Xbridge C18 150*50 mm*10 um; mobile phase: [water (0.04% $NH_3.H_2O$)–ACN]; B %: 52%-82%, 11 min) to give the title compound (19.9 mg, 41.2 umol, 34.1% yield) as a white solid. LCMS(ESI): RT=0.801 min, mass calc. for $C_{25}H_{23}F_5N_2O_2$ 478.17, m/z found 479.0 [M+H]$^+$; $^1$H NMR (400 MHz, DMSO-d$_6$) δ 8.51 (s, 1H), 8.44 (d, J=8.3 Hz, 1H), 8.02-7.91 (m, 3H), 7.74 (d, J=8.8 Hz, 2H), 7.63 (t, J=7.9 Hz, 1H), 7.32 (d, J=7.5 Hz, 1H), 7.15 (d, J=8.6 Hz, 2H), 6.10-5.76 (m, 1H), 4.32-4.20 (m, 1H), 3.35 (br d, J=3.6 Hz, 2H), 3.06 (t, J=6.8 Hz, 1H), 2.98 (t, J=6.8 Hz, 1H), 2.76 (dt, J=4.2, 16.2 Hz, 2H), 2.62-2.55 (m, 1H), 1.09 (d, J=6.6 Hz, 3H).

Example 95: (R)-N-(1-(1-methylazetidin-3-yl)ethyl)-5-(4-(trifluoromethyl)phenoxy)-2-naphthamide (Compound 126) and (S)-N-(1-(1-methylazetidin-3-yl)ethyl)-5-(4-(trifluoromethyl)phenoxy)-2-naphthamide (Compound 127)

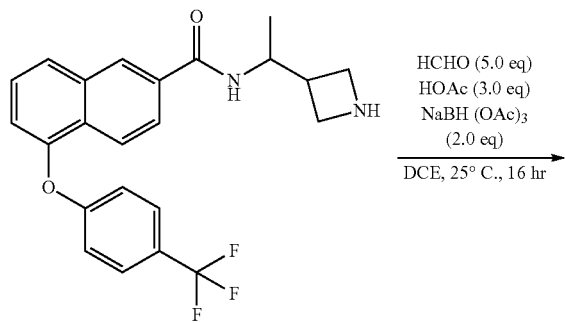

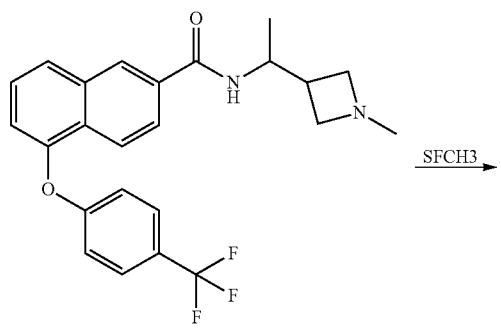

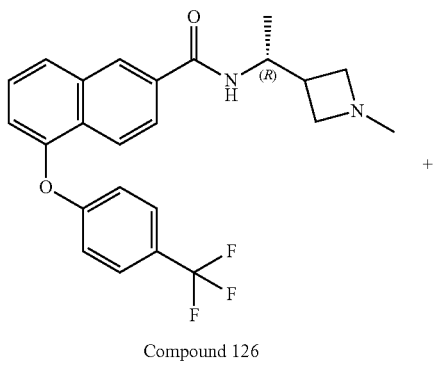

Compound 126

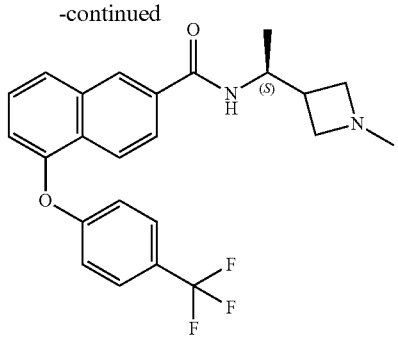

Compound 127

N-[1-(1-methylazetidin-3-yl)ethyl]-5-[4-(trifluoromethyl)phenoxy]naphthalene-2-carboxamide To a solution of N-(1-(azetidin-3-yl)ethyl)-5-(4-(trifluoromethyl)phenoxy)-2-naphthamide (150 mg, 0.36 mmol, 1 eq) and HCHO (146.9 mg, 1.81 mmol, 0.13 mL, 5 eq) in DCE (5 mL) was added HOAc (65.2 mg, 1.09 mmol, 62.1 uL, 3 eq) and stirred at 25° C. for 1 hr, and then NaBH(OAc)$_3$ (153.4 mg, 0.72 mmol, 2 eq) was added. The resulting mixture was stirred at 25° C. for 15 hr. Then iced water (30 mL) was added and the mixture was neutralized to pH=9-10 with aq. NaOH (2 M). The aqueous phase was extracted with EA (30 mL*3). The combined organic phase was washed with brine (50 mL), dried with anhydrous Na$_2$SO$_4$, filtered and concentrated in vacuo. The residue was purified by prep-HPLC (column: Welch Xtimate C18 150*25 mm*5 um; mobile phase: [water (0.05% HCl)–ACN]; B %: 21%-51%, 8.5 min) to give N-[1-(1-methylazetidin-3-yl)ethyl]-5-[4-(trifluoromethyl)phenoxy]naphthalene-2-carboxamide (54.8 mg, 0.13 mmol, 35.3% yield) as a yellow solid.

(R)-N-(1-(1-methylazetidin-3-yl)ethyl)-5-(4-(trifluoromethyl)phenoxy)-2-naphthamide (Compound 126) and (S)-N-(1-(1-methylazetidin-3-yl)ethyl)-5-(4-(trifluoromethyl)phenoxy)-2-naphthamide (Compound 127)

The N-[1-(1-methylazetidin-3-yl)ethyl]-5-[4-(trifluoromethyl)phenoxy]naphthalene-2-carboxamide (45 mg, 0.11 mmol, 1 eq) which was further separated by SFC (column: Phenomenex-Cellulose-2 (250 mm*30 mm, 5 um): mobile phase: [0.1% NH$_3$H$_2$O ETOH]; B %: 35%-35%, min) to afford Compound 126 (7.6 mg, 17.74 umol, 16.89% yield) as a yellow solid. LCMS (ESI): RT=0.795 min, mass calcd for C$_{24}$H$_{23}$F$_3$N$_2$O$_2$ 428.17, m/z found 429.1 [M+H]$^+$; $^1$H NMR (400 MHz, CD$_3$OD) δ 8.50 (d, J=1.5 Hz, 1H), 8.11 (d, J=8.8 Hz, 1H), 7.94-7.88 (m, 2H), 7.66 (d, J=8.6 Hz, 2H), 7.60 (t, J=7.9 Hz, 1H), 7.27-7.21 (m, 1H), 7.13 (d, J=8.5 Hz, 2H), 4.56-4.43 (m, 1H), 4.30-4.12 (m, 3H), 4.10-3.98 (m, 1H), 3.15-3.06 (m, 1H), 2.93 (s, 3H), 1.26 (d, J=6.8 Hz, 3H) and Compound 127 (8.8 mg, 20.3 umol, 19.4% yield) as a white solid. LCMS (ESI): RT=0.794 min, mass calcd for C$_{24}$H$_{23}$F$_3$N$_2$O 412.18, m/z found 413.1 [M+H]$^+$; $^1$H NMR (400 MHz, CD$_3$OD) δ 8.46 (s, 1H), 8.07 (d, J=7.8 Hz, 1H), 7.88-7.82 (m, 4H), 7.71-7.64 (m, 3H), 7.57 (dd, J=1.1, 7.0 Hz, 1H), 4.45-4.34 (m, 1H), 3.68 (m, 2H), 3.39-3.33 (m, 1H), 3.25 (t, J=8.1 Hz, 1H), 2.84-2.73 (m, 1H), 2.47 (s, 3H), 1.90 (s, 1H), 1.21 (d, J=6.8 Hz, 3H).

Example 96: (S)-N-(1-(1-(2-hydroxyethyl)azetidin-3-yl)ethyl)-5-(4-(trifluoromethyl)phenoxy)-2-naphthamide (Compound 128)

Example 97: (S)-N-(1-(1-(2-fluoroethyl)azetidin-3-yl)ethyl)-5-(4-(trifluoromethyl)phenoxy)-2-naphthamide (Compound 129)

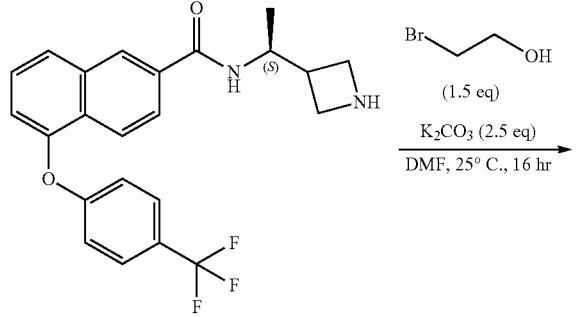
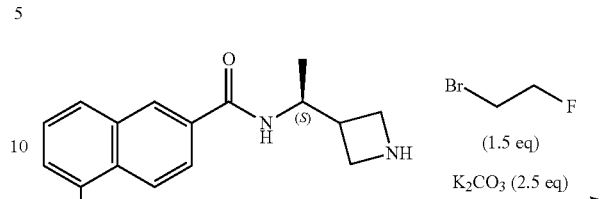

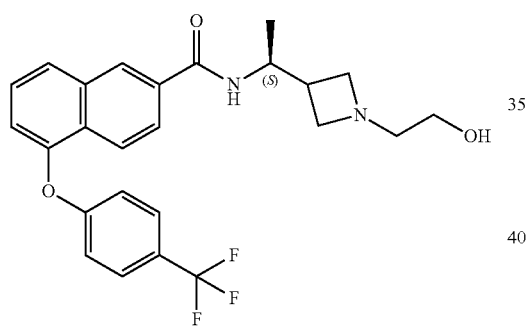

Compound 128

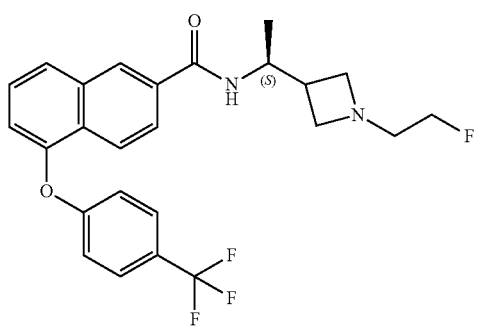

Compound 129

To a solution of (S)-N-(1-(azetidin-3-yl)ethyl)-5-(4-(trifluoromethyl)phenoxy)-2-naphthamide (50 mg, 0.12 mmol, 1 eq) in DMF (2 mL) was added $K_2CO_3$ (41.7 mg, 0.30 mmol, 2.5 eq) and 2-bromoethanol (22.6 mg, 0.18 mmol, 12.8 uL, 1.5 eq). The mixture was stirred at 25° C. for 16 hr. The reaction mixture was diluted with $H_2O$ (20 mL) and stirred for 5 min. The aqueous phase was extracted with EA (10 mL*3). The combined organic phase was washed with brine (20 mL), dried with anhydrous $Na_2SO_4$, filtered and concentrated in vacuum. The crude product was purified by prep-HPLC (column: Welch Xtimate C18 150*25 mm*5 um; mobile phase: [water (0.05% HCl)–ACN]; B %: 20%-50/o, 8.5 min) to afford the title compound (9.5 mg, 19.2 umol, 15.9% yield, HCl) as a yellow oil. LCMS (ESI): RT=0.779 min, mass calcd for $C_{23}H_{23}F_3N_2O$ 3458.18, m/z found 459.3 [M+H]$^+$; $^1$H NMR (400 MHz, DMSO-$d_6$) δ 8.58 (s, 1H), 8.49 (d, J=6.3 Hz, 1H), 8.04-7.91 (m, 3H), 7.72 (d, J=8.5 Hz, 2H), 7.62 (t, J=7.9 Hz, 1H), 7.28 (d, J=7.3 Hz, 1H), 7.17 (d, J=8.5 Hz, 2H), 4.38 (s, 1H), 4.22-3.90 (m, 4H), 3.64 (t, J=5.0 Hz, 2H), 3.11-3.03 (m, 3H), 1.17 (d, J=6.5 Hz, 3H).

To a solution of (S)-N-(1-(azetidin-3-yl)ethyl)-5-(4-(trifluoromethyl)phenoxy)-2-naphthamide (60 mg, 0.15 mmol, 1 eq) in MeCN (1 mL) was added $K_2CO_3$ (50.0 mg, 0.36 mmol, 2.5 eq) and 1-bromo-2-fluoro-ethane (27.6 mg, 0.22 mmol, 2.6 uL, 1.5 eq). The mixture was stirred at 60° C. for 16 hr. The reaction mixture was diluted with $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The crude product was purified by prep-HPLC (column: Welch Xtimate C18 150*25 mm*5 um; mobile phase: [water (0.05% HCl)–ACN]; B %: 25%-55%, 8.5 min) to afford the title compound (13.2 mg, 26.6 umol, 18.4% yield, HCl) as a white solid. LCMS (ESI): RT=0.801 min, mass calcd for $C_{25}H_{24}F_4N_2O$ 2460.18, m/z found 461.2[M+H]$^+$; $^1$H NMR (400 MHz, DMSO-$d_6$) δ 11.67-10.81 (m, 1H), 8.60 (s, 1H), 8.52 (d, J=7.0 Hz, 1H), 8.05-7.91 (m, 3H), 7.72 (d, J=8.8 Hz, 2H), 7.62 (t, J=7.9 Hz, 1H), 7.29 (d, J=7.5 Hz, 1H), 7.17 (d, J=8.8 Hz, 2H), 4.83-4.62 (m, 2H), 4.38 (m, 1H), 4.30-3.85 (m, 4H), 3.63-3.42 (m, 2H), 3.10 (m, J=7.5 Hz, 1H), 1.17 (s, 3H).

Example 98: (S)-N-(1-(1-ethylazetidin-3-yl)ethyl)-5-(4-(trifluoromethyl)phenoxy)-2-naphthamide (Compound 130) and (R)-N-(1-(1-ethylazetidin-3-yl)ethyl)-5-(4-(trifluoromethyl)phenoxy)-2-naphthamide (Compound 131)

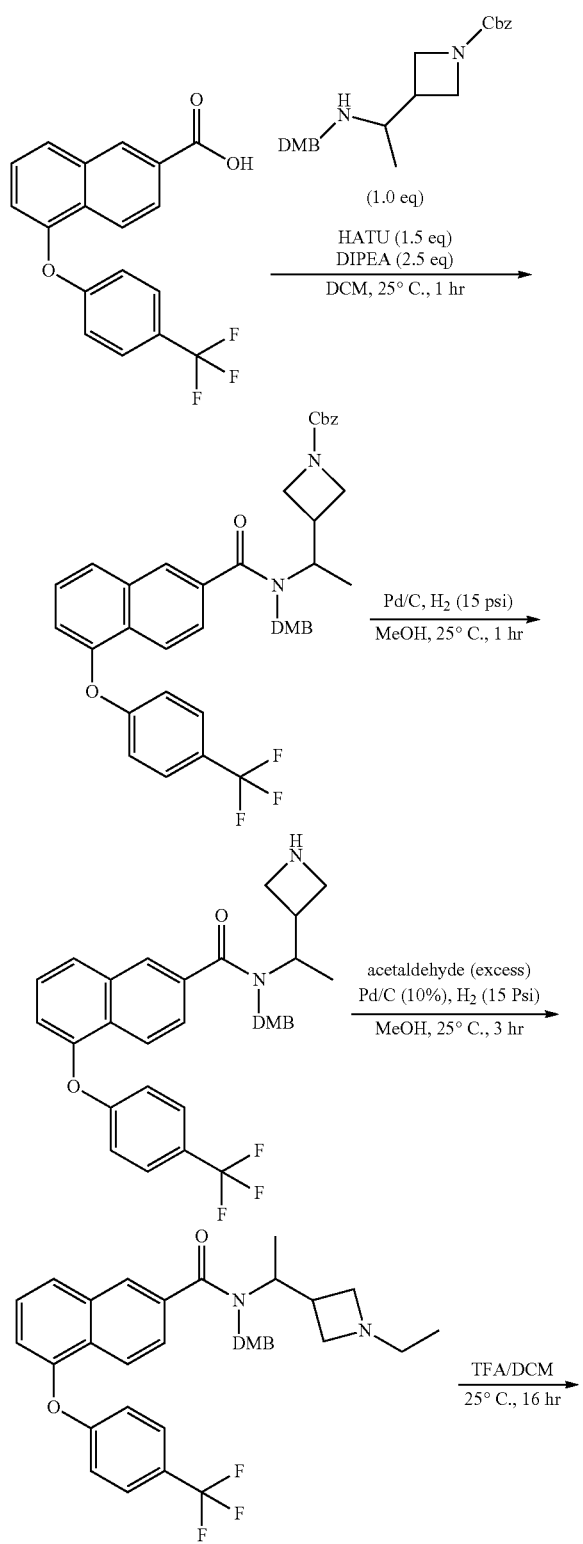

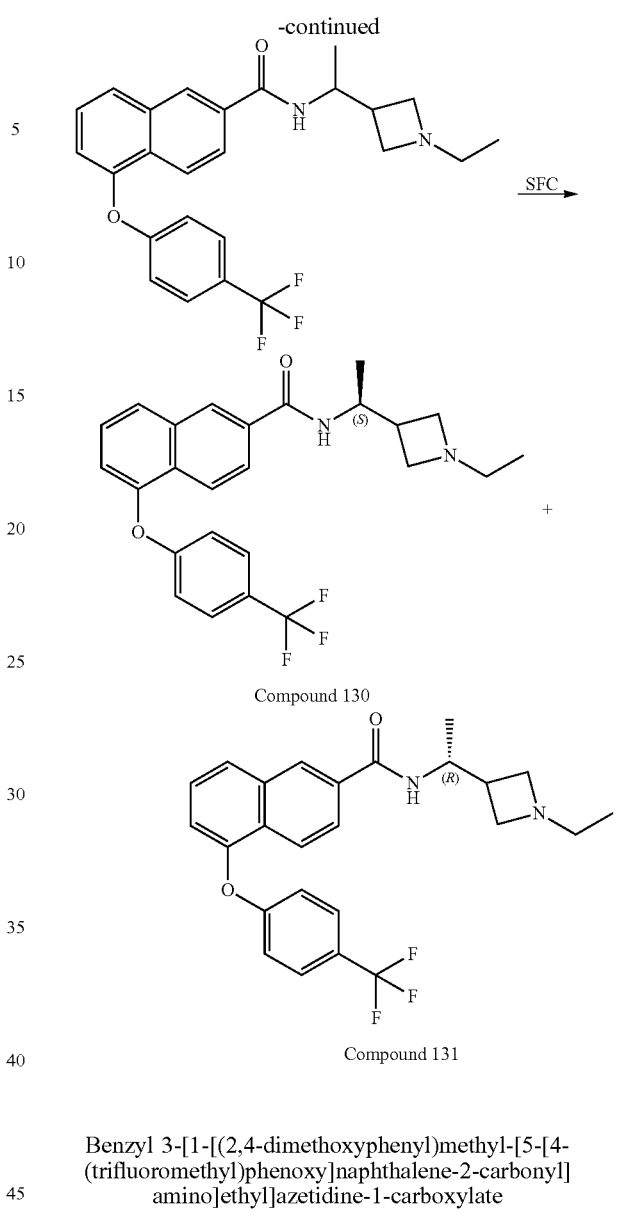

Benzyl 3-[1-[(2,4-dimethoxyphenyl)methyl-[5-[4-(trifluoromethyl)phenoxy]naphthalene-2-carbonyl]amino]ethyl]azetidine-1-carboxylate To a solution of 5-(4-(trifluoromethyl)phenoxy)-2-naphthoic acid (1 g, 3.0 mmol, 1.0 eq) in DCM (6 mL) was added HATU (1.72 g, 4.51 mmol, 1.5 eq), DIPEA (972.3 mg, 7.52 mmol, 1.31 mL, 2.5 eq) and benzyl 3-(1-((2,4-dimethoxybenzyl)amino)ethyl)azetidine-1-carboxylate (1.16 g, 3.01 mmol, 1.0 eq). The mixture was stirred at 25° C. for 1 hr. The reaction mixture was concentrated under reduced pressure to give a residue. The residue was purified by column chromatography (SiO$_2$, Petroleum ether/Ethyl acetate=100/1 to 1/1) to give benzyl 3-[1-[(2,4-dimethoxyphenyl)methyl-[5-[4-(trifluoromethyl)phenoxy]naphthalene-2-carbonyl]amino]ethyl]azetidine-1-carboxylate (1.3 g, 1.62 mmol, 53.7% yield) as a colorless oil. LCMS (ESI): RT=1.133 min, mass calcd for $C_{40}H_{37}F_3N_2O_6$ 698.26 m/z found 699.1 [M+H]$^+$.

N-[1-(Azetidin-3-yl)ethyl]-N-[(2,4-dimethoxyphenyl)methyl]-5-[4-(trifluoromethyl)phenoxy]naphthalene-2-carboxamide To a solution of benzyl 3-[1-[(2,4-dimethoxyphenyl)methyl-[5-[4-(trifluoromethyl)phenoxy]naphthalene-2-carbonyl]amino]ethyl]azetidine-1-carboxylate (0.6 g, 0.85 mmol, 1 eq) in MeOH (30 mL) was added Pd/C (0.25 g, 10%) under N₂. The suspension was degassed under vacuum and purged with H₂ several times. The mixture was stirred under H₂ (15 psi) at 25° C. for 1 hour. The reaction mixture was filtered and concentrated under reduced pressure to give a residue. The crude product was used into the next step without further purification. N-[1-(azetidin-3-yl)ethyl]-N-[(2,4-dimethoxyphenyl)methyl]-5-[4-(trifluoromethyl)phenoxy]naphthalene-2-carboxamide (400 mg, 0.70 mmol, 82.5% yield) was obtained as a white solid. LCMS (ESI): RT=0.933 min, mass calcd for $C_{32}H_{31}F_3N_2O_4$ 564.22 m/z found 565.1 [M+H]⁺.

N-[(2,4-Dimethoxy phenyl)methyl]-N-[1-(1-ethyl-azetidin-3-yl)ethyl]-5-[4-(trifluoromethyl)phenoxy]naphthalene-2-carboxamide To a solution of N-[1-(azetidin-3-yl)ethyl]-N-[(2,4-dimethoxyphenyl)methyl]-5-[4-(trifluoromethyl)phenoxy]naphthalene-2-carboxamide (200 mg, 0.35 mmol, 1 eq) in MeOH (3 mL) was added acetaldehyde (194.7 mg, 4.42 mmol, 0.24 mL, 12.48 eq) and Pd/C (50 mg, 10%). The suspension was degassed under vacuum and purged with H₂ several times. The mixture was stirred under H₂ (15 psi) at 25° C. for 1 hour. LC-MS showed 3 was consumed completely and 91% of desired compound was detected. The reaction mixture was filtered and concentrated under reduced pressure to give a residue. The crude product was used into the next step without further purification. N-[(2,4-dimethoxyphenyl)methyl]-N-[1-(1-ethylazetidin-3-yl)ethyl]-5-[4-(trifluoromethyl)phenoxy]naphthalene-2-carboxamide (150 mg, crude) was obtained as a white solid. LCMS (ESI): RT=0.958 min, mass calcd for $C_{34}H_{35}F_3N_2O_4$ 592.25 m/z found 593.1 [M+H]⁺.

N-[1-(1-Ethylazetidin-3-yl)ethyl]-5-[4-(trifluoromethyl)phenoxy]naphthalene-2-carboxamide To a solution of N-[(2,4-dimethoxyphenyl)methyl]-N-[1-(1-ethylazetidin-3-yl)ethyl]-5-[4-(trifluoromethyl)phenoxy]naphthalene-2-carboxamide (200 mg, 0.33 mmol, 1 eq) in DCM (2 mL) was added TFA (5.99 g, 52.5 mmol, 3.89 mL, 155.7 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)–ACN]; B %: 22%-52%, 9.5 min) to give N-[1-(1-ethylazetidin-3-yl)ethyl]-5-[4-(trifluoromethyl)phenoxy]naphthalene-2-carboxamide (90 mg, 0.20 mol, 60.2% yield) as a white solid. LCMS (ESI): RT=0.863 min, mass calcd for $C_{25}H_{25}F_3N_2O$ 2442.19 m/z found 433.1 [M+H]⁺.

(S)-N-(1-(1-ethylazetidin-3-yl)ethyl)-5-(4-(trifluoromethyl)phenoxy)-2-naphthamide (Compound 130) and (R)-N-(1-(1-ethylazetidin-3-yl)ethyl)-5-(4-(trifluoromethyl)phenoxy)-2-naphthamide (Compound 131)

N-[1-(1-Ethylazetidin-3-yl)ethyl]-5-[4-(trifluoromethyl)phenoxy]naphthalene-2-carboxamide (90 mg) was purified by prep-SFC (column: DAICEL CHIRALCEL OD-H (250 mm*30 mm, 5 um); mobile phase: [0.1% NH₃H₂O ETOH]; B %: 20%-20%, min) to give Compound 130 (9.6 mg, 21.5 umol, 10.5% yield) and Compound 131 (13.6 mg, 30.5 umol, 15.0% yield) as two white solids. Compound 130 LCMS (ESI): RT=0.875 min, mass calcd for $C_{23}H_{25}F_3N_2O$ 2442.19 m/z found 433.2 [M+H]⁺. ¹H NMR (400 MHz, CD₃OD) δ 8.50 (d, J=1.3 Hz, 1H), 8.10 (d, J=8.9 Hz, 1H), 7.95-7.87 (m, 2H), 7.66 (d, J=8.6 Hz, 2H), 7.59 (t, J=7.9 Hz, 1H), 7.23 (d, J=7.3 Hz, 1H), 7.12 (d, J=8.6 Hz, 2H), 4.50 (s, 1H), 4.32-3.90 (m, 4H), 3.29-3.20 (m, 1H), 3.25 (q, J=7.0 Hz, 1H), 3.11 (sxt, J=8.5 Hz, 1H), 1.27 (d, J=6.8 Hz, 3H), 1.21 (t, J=7.3 Hz, 3H). Compound 131 LCMS (ESI): RT=0.863 min, mass calcd for $C_{25}H_{25}F_3N_2O_2$ 442.19 m/z found 433.2 [M+H]⁺. ¹H NMR (400 MHz, CD₃OD) δ 8.45 (d, J=1.3 Hz, 1H), 8.09 (d, J=8.8 Hz, 1H), 7.92-7.87 (m, 2H), 7.65 (d, J=8.6 Hz, 2H), 7.58 (t, J=7.9 Hz, 1H), 7.22 (d, 0.1=7.4 Hz, 1H), 7.12 (d, J=8.6 Hz, 2H), 4.38 (dd, J=6.8, 9.3 Hz, 1H), 3.74-3.64 (m, 2H), 3.37-3.32 (m, 1H), 3.22 (t, J=8.1 Hz, 1H), 2.81 (d, J=9.0 Hz, 1H), 2.71 (q, J=7.1 Hz, 2H), 1.22 (d, J=6.6 Hz, 3H), 1.03 (t, J=7.2 Hz, 3H).

Example 99: (S)-N-(1-(1-isopropylazetidin-3-yl)ethyl)-5-(4-(trifluoromethyl)phenoxy)-2-naphthamide (Compound 132) and (R)-N-(1-(1-isopropylazetidin-3-yl)ethyl)-5-(4-(trifluoromethyl)phenoxy)-2-naphthamide (Compound 133)

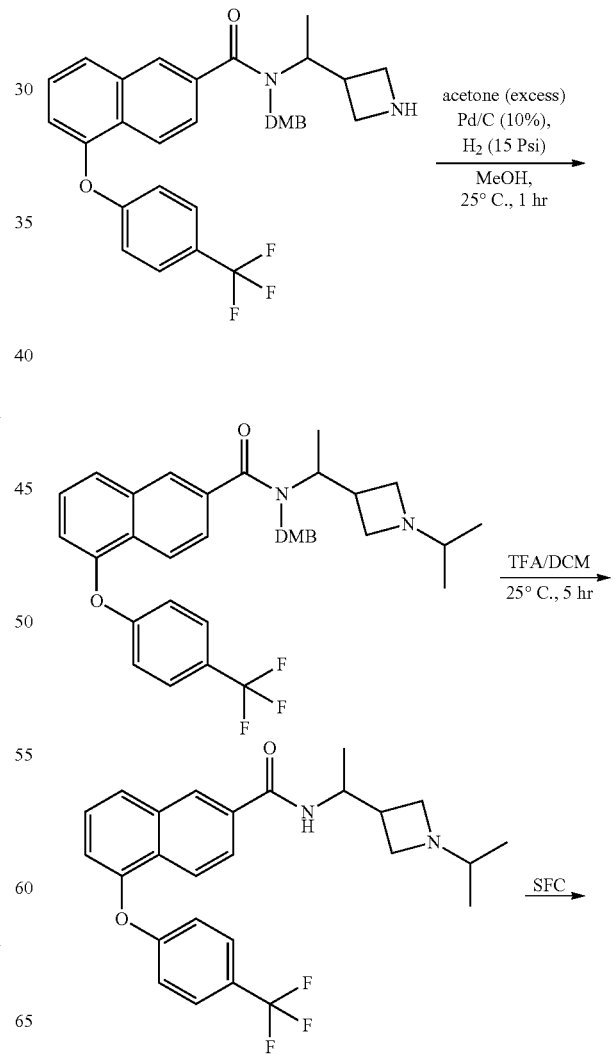

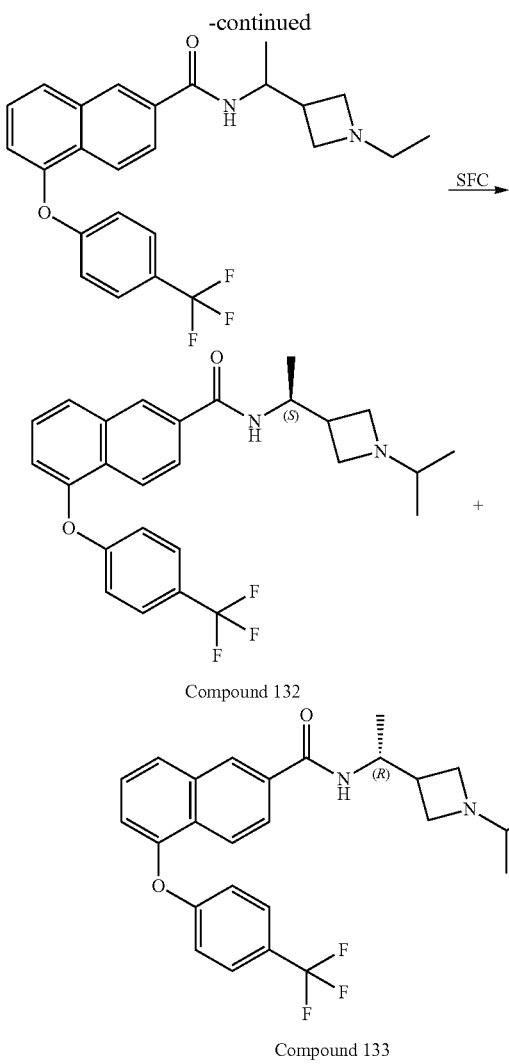

Compound 132

Compound 133

N-[(2,4-Dimethoxyphenyl)methyl]-N-[1-(1-isopropylazetidin-3-yl)ethyl]-5-[4-(trifluoromethyl)phenoxy]naphthalene-2-carboxamide To a solution of N-(1-(azetidin-3-yl)ethyl)-N-(2,4-dimethoxybenzyl)-5-(4-(trifluoromethyl)phenoxy)-2-naphthamide (200 mg, 0.35 mmol, 1 eq) in MeOH (3 mL) was added acetone (256.7 mg, 4.42 mmol, 0.32 mL, 12.48 eq) and Pd/C (100 mg, 10%). The suspension was degassed under vacuum and purged with $H_2$ several times. The mixture was stirred under $H_2$ (15 psi) at 25° C. for 1 hr. The reaction mixture was filtered and concentrated under reduced pressure to give a residue. The residue was purified by column chromatography ($SiO_2$, Ethyl acetate:Methanol=100/1 to 10/1) to give N-[(2,4-Dimethoxyphenyl)methyl]-N-[1-(1-isopropylazetidin-3-yl)ethyl]-5-[4-(trifluoromethyl)phenoxy]naphthalene-2-carboxamide (150 mg, 0.24 mmol, 69.80% yield) as a white solid. LCMS (ESI): RT=0.965 min, mass calcd for $C_{35}H_{37}F_3N_2O4$ 606.27 m/z found 607.1 [M+H]⁺.

N-[1-(1-isopropylazetidin-3-yl)ethyl]-5-[4-(trifluoromethyl)phenoxy]naphthalene-2-carboxamide To a solution of N-[(2,4-Dimethoxyphenyl)methyl]-N-[1-(1-isopropylazetidin-3-yl)ethyl]-5-[4-(trifluoromethyl)phenoxy]naphthalene-2-carboxamide (100 mg, 0.16 mmol, 1 eq) in DCM (2 mL) was added TFA (2.93 g, 25.6 mmol, 1.90 mL, 155.7 eq). The mixture was stirred at 25° C. for 5 hr. The reaction mixture was concentrated under reduced pressure to give a residue. The residue was purified by prep-HPLC (column: Welch Xtimate C18 150*25 mm*5 um; mobile phase: [water (0.05% HCl)–ACN]; B %: 25%-55%, 8.5 min) to give N-[1-(1-isopropylazetidin-3-yl)ethyl]-5-[4-(trifluoromethyl)phenoxy]naphthalene-2-carboxamide (50 mg, 0.10 mmol, 66.45% yield) as a white solid. LCMS (ESI): RT=0.885 min, mass calcd for $C_{26}H_{27}F_3N_2O_2$ 456.20 m/z found 457.0 [M+H]⁺.

(S)-N-(1-(1-isopropylazetidin-3-yl)ethyl)-5-(4-(trifluoromethyl)phenoxy)-2-naphthamide (Compound 132) and (R)-N-(1-(1-isopropylazetidin-3-yl)ethyl)-5-(4-(trifluoromethyl)phenoxy)-2-naphthamide (Compound 133)

N-[1-(1-isopropylazetidin-3-yl)ethyl]-5-[4-(trifluoromethyl)phenoxy]naphthalene-2-carboxamide (60 mg) was purified by prep-SFC (column. DAICEL CHIRALCEL OD-H (250 mm*30 mm, 5um); mobile phase: [0.1% $NH_3H_2O$ ETOH]; B %: 35%-35%, min) to give Compound 132 (5.4 mg, 11.8 umol, 9.0% yield) and Compound 133 (4.4 mg, 9.6 umol, 7.3% yield) as two white solids. Compound 132 LCMS (ESI): RT=0.907 min, mass calcd for $C_{26}H_{27}F_3N_2O_2$ 456.20 m/z found 457.0 [M+H]⁺. ¹H NMR (400 MHz, $CD_3OD$) δ 8.43 (d, J=1.3 Hz, 1H), 8.09 (d, J=8.8 Hz, 1H), 7.88 (d, J=8.5 Hz, 2H), 7.65 (d, J=8.8 Hz, 2H), 7.58 (t, J=8.0 Hz, 1H), 7.22 (d, J=7.3 Hz, 1H), 7.12 (d, J=8.5 Hz, 2H), 4.34-4.20 (m, 1H), 3.54-3.42 (m, 2H), 3.03 (t, J=7.7 Hz, 1H), 2.90 (t, J=7.8 Hz, 1H), 2.69-2.57 (m, 1H), 2.39 (spt, J=6.2 Hz, 1H), 1.19 (d, J=6.5 Hz, 3H), 0.94 (dd, J=4.1, 6.1 Hz, 6H). Compound 133 LCMS (ESI): RT=0.903 min, mass calcd for $C_{26}H_{27}F_3N_2O_2$ 456.20 m/z found 457.0 [M+H]⁺. ¹H NMR (400 MHz, $CD_3OD$) δ 8.43 (d, J=1.3 Hz, 1H), 8.09 (d, J=9.0 Hz, 1H), 7.88 (d, J=8.5 Hz, 2H), 7.65 (d, J=8.5 Hz, 2H), 7.58 (t, J=7.9 Hz, 1H), 7.22 (d, J=7.5 Hz, 1H), 7.12 (d, J=0.8 Hz, 2H), 4.42-4.20 (m, 1H), 3.55-3.41 (m, 2H), 3.03 (t, J=7.7 Hz, 1H), 2.91 (t, J=7.8 Hz, 1H), 2.69-2.57 (m, 1H), 2.44-2.35 (m, 1H), 1.19 (d, J=6.8 Hz, 3H), 0.94 (dd, J=4.1, 6.1 Hz, 6H).

Example 100: (S)-N-(1-(1-(2,2-difluoroethyl)azetidin-3-yl)ethyl)-5-(4-(trifluoromethyl)phenoxy)-2-naphthamide (Compound 134)

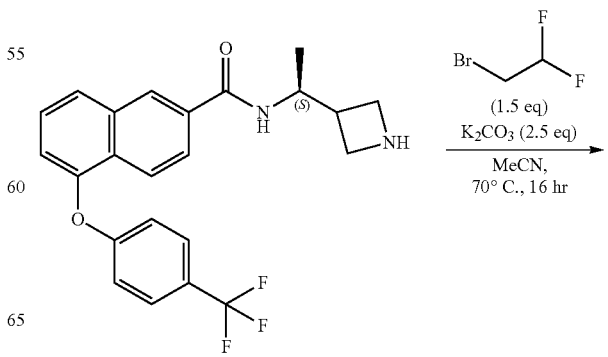

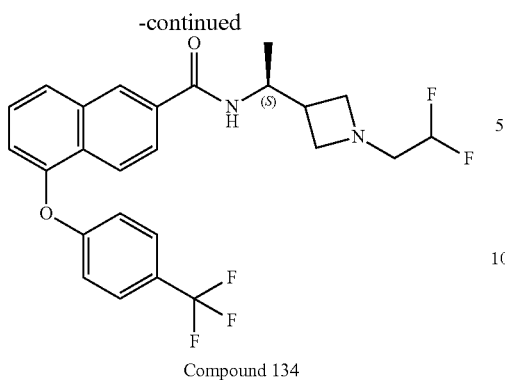

Compound 134

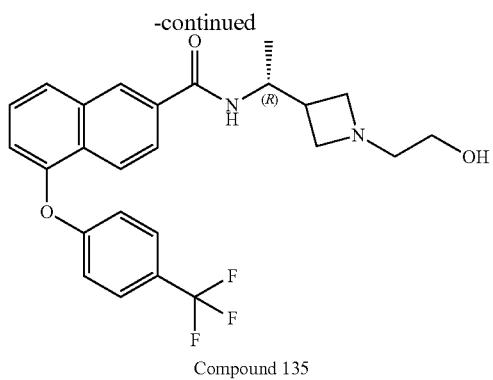

Compound 135

To a solution of (S)-N-(1-(azetidin-3-yl)ethyl)-5-(4-(trifluoromethyl)phenoxy)-2-naphthamide (75 mg, 0.18 mmol, 1 eq) in MeCN (3 mL) was added K$_2$CO$_3$ (62.5 mg, 0.45 mmol, 2.5 eq) and 2-bromo-1,1-difluoroethane (39.4 mg, 0.27 mmol, 2.6 uL, 1.5 eq). The mixture was stirred at 70° C. for 16 hr. The reaction mixture was diluted with H$_2$O (30 mL) and stirred for 5 min. The aqueous phase was extracted with EA (15 mL*3). The combined organic phase was washed with brine (20 mL), dried with anhydrous Na$_2$SO$_4$, filtered and concentrated in vacuum. The residue was purified by prep-HPLC (column: Waters Xbridge C18 150*50 mm*10 um; mobile phase: [water (0.04% NH$_3$H2O)–ACN]; B %: 51%-81%, 11 min) to afford the title compound (26.8 mg, 54.9 umol, 30.33% yield) as a white solid. LCMS (ESI): RT=0.796 min, mass calcd for C$_{25}$H$_{23}$F$_5$N$_2$O 2478.17, m/z found 479.3 [M+H]$^+$; $^1$H NMR (400 MHz, DMSO-d$_6$) δ 8.51 (s, 1H), 8.44 (d, J=8.3 Hz, 1H), 8.02-7.90 (m, 3H), 7.74 (d, J=8.8 Hz, 2H), 7.63 (t, J=7.9 Hz, 1H), 7.32 (d, J=7.0 Hz, 1H), 7.15 (d, J=8.5 Hz, 2H), 6.09-5.75 (m, 1H), 4.32-4.19 (m, 1H), 3.34 (t, J=6.8 Hz, 2H), 3.11-2.95 (m, 2H), 2.76 ((m, 2H), 2.63-2.52 (m, 2H), 1.09 (d, J=6.5 Hz, 3H).

Example 101: (R)-N-(1-(1-(2-hydroxyethyl)azetidin-3-yl)ethyl)-5-(4-(trifluoromethyl)phenoxy)-2-naphthamide (Compound 135)

To a solution of (R)-N-(1-(azetidin-3-yl)ethyl)-5-(4-(trifluoromethyl)phenoxy)-2-naphthamide (20.0 mg, 48 umol, 1 eq) in ACN (0.5 mL) were added KI (0.8 mg, 4.8 umol, 0.1 eq), K$_2$CO$_3$ (20.0 mg, 0.14 mmol, 3 eq) and 2-bromoethan-1-ol (9.1 mg, 72 umol, 5 uL, 1.5 eq) at 30° C. The reaction was stirred at 60° C. for 16 hr. The reaction was concentrated under reduced pressure to give a residue, which was purified by prep-HPLC: (column: Welch Xtimate C18 150*25 mm*5 um; mobile phase: [water (0.05% HCl)–ACN]; B %: 24%-54%, 8.5 min) to give the title compound (2.0 mg, 4.1 umol, 8.5% yield, HCl) as a white solid. LCMS (ESI): RT=0.861 min, mass calc. for C$_{25}$H$_{25}$F$_3$N$_2$O 3458.18, m/z found 459.3 [M+H]$^+$; $^1$H NMR (400 MHz, DMSO-d$_6$) δ 10.74 (brs, 1H), 8.61 (s, 1H), 8.53 (br d, J=8.0 Hz, 1H), 8.04-7.97 (m, 2H), 7.94 (d, J=8.3 Hz, 1H), 7.72 (d, J=8.6 Hz, 2H), 7.62 (t, J=7.9 Hz, 1H), 7.29 (d, J=7.4 Hz, 1H), 7.18 (d, J=8.6 Hz, 2H), 5.03 (brs, 1H), 4.39 (br d, J=6.5 Hz, 1H), 4.19-4.02 (m, 3H), 3.95 (brs, 1H), 3.65 (t, J=5.1 Hz, 2H), 3.22 (brs, 1H), 3.06-3.02 (m, 1H), 1.17 (d, J=6.8 Hz, 3H).

Example 102: (S)-N-(1-(1-cyclopropylazetidin-3-yl)ethyl)-5-(4-(trifluoromethyl)phenoxy)-2-naphthamide (Compound 136)

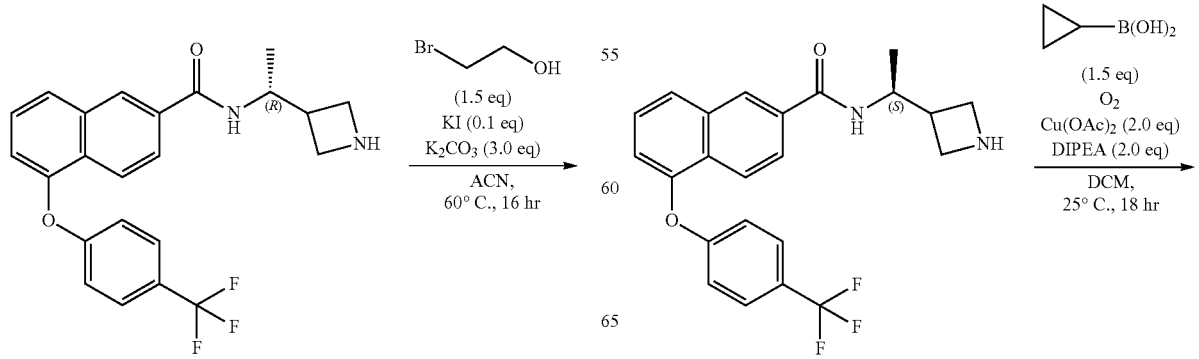

307

-continued

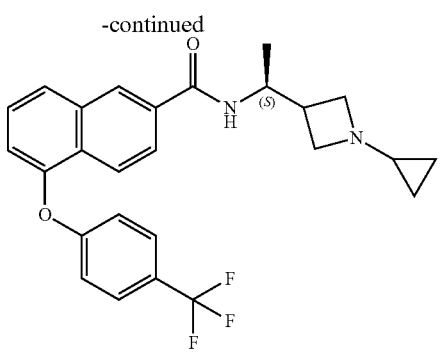

Compound 136

308

-continued

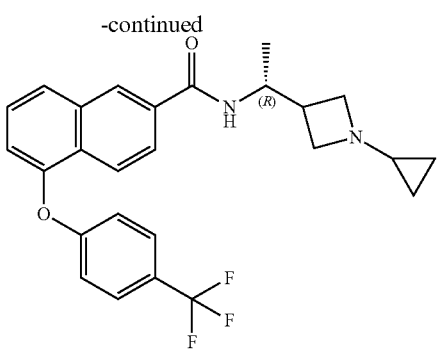

Compound 137

To a mixture of (S)-N-(1-(azetidin-3-yl)ethyl)-5-(4-(trifluoromethyl)phenoxy)-2-naphthamide (60 mg, 0.14 mmol, 1 eq) and cyclopropylboronic acid (18.7 mg, 0.22 mmol, 1.5 eq) in DCM (3 mL) was added Cu(OAc)$_2$ (52.6 mg, 0.29 mmol, 2 eq) and DIPEA (37.4 mg, 0.29 mmol, 50.4 uL, 2 eq) in one portion at 25° C. The suspension was degassed under vacuum and purged with O$_2$ several times. The mixture was stirred under O$_2$ (15 psi) at 25° C. for 18 hrs. The reaction mixture was filtered and the cake was washed with EA (10 mL*2). The filtrate was concentrated in vacuo to give crude product. The crude product was purified by prep-HPLC (column: Waters Xbridge C18 150*50 mm*10 um; mobile phase: [water (0.04% NH$_3$H$_2$O)–ACN]; B %: 55%-85%, 11 min) to afford the title compound (12.6 mg, 26.9 umol, 18.6% yield) as a white solid. LCMS (ESI): RT=0.799 min, mass calcd for C$_{26}$H$_{25}$F$_3$N$_2$O$_2$ 454.19, m/z found 455.3 [M+H]$^+$; $^1$H NMR (400 MHz, DMSO-d$_6$) δ 8.51 (s, 1H), 8.42 (d, J=8.3 Hz, 1H), 8.02-7.91 (m, 3H), 7.74 (d, J=8.8 Hz, 2H), 7.63 (t, J=7.9 Hz, 1H), 7.32 (d, J=7.3 Hz, 1H), 7.15 (d, J=8.5 Hz, 2H), 4.29-4.17 (m, 1H), 3.26 (t, J=7.2 Hz, 1H), 3.02 (t, J=6.5 Hz, 1H), 2.93 (t, J=6.7 Hz, 1H), 2.48-2.41 (m, 1H), 1.80 (m, 1H), 1.09 (d, J=6.5 Hz, 3H), 0.28 (m, 2H), 0.17 (m, 2H).

Example 103: (R)-N-(1-(1-cyclopropylazetidin-3-yl)ethyl)-5-(4-(trifluoromethyl)phenoxy)-2-naphthamide (Compound 137)

To a mixture of (R)-N-(1-(azetidin-3-yl)ethyl)-5-(4-(trifluoromethyl)phenoxy)-2-naphthamide (100.0 mg, 0.24 mmol, 1 eq) and cyclopropylboronic acid (31.1 mg, 0.36 mmol, 1.5 eq) in DCM (6 mL) was added Cu(OAc)$_2$ (87.7 mg, 0.48 mmol, 2.0 eq) and DIPEA (62.4 mg, 0.48 mmol, 84 uL, 2.0 eq) in one portion at 30° C. The suspension was degassed under vacuum and purged with O$_2$ several times. The mixture was stirred under O$_2$ (15 psi) at 30° C. for 40 hours The reaction was concentrated under reduced pressure to give a residue, which was purified by prep-HPLC: (column: Welch Xtimate C18 150*25 mm*5 um; mobile phase: [water (0.05% NH$_3$H$_2$O+10 mM NH$_4$HCO$_3$)–ACN]; B %: 65%-95%, 7.8 min) to give the title compound (9.73 mg, 21 umol, 8.7% yield) as a yellow solid. LCMS(ESI): RT=0.890 min, mass calc. for C$_{26}$H$_{25}$F$_3$N$_2$O 2454.19, m/z found 455.3 [M+H]$^+$; $^1$H NMR (400 MHz, DMSO-d$_6$) δ 8.51 (s, 1H), 8.43 (d, J=8.0 Hz, 1H), 8.01-7.90 (m, 3H), 7.74 (d, J=8.5 Hz, 2H), 7.63 (t, J=7.9 Hz, 1H), 7.33 (d, J=7.5 Hz, 1H), 7.16 (d, J=8.8 Hz, 2H), 4.29-4.14 (m, 1H), 3.28 (brs, 3H), 3.11-2.90 (m, 2H), 1.83 (brs, 1H), 1.09 (d, J=6.5 Hz, 3H), 0.35-0.24 (m, 2H), 0.19 (brs, 2H).

Example 104: (S)-N-(1-(3-hydroxyazetidin-3-yl)ethyl)-5-(4-(trifluoromethyl)phenoxy)-2-naphthamide (Compound 138)

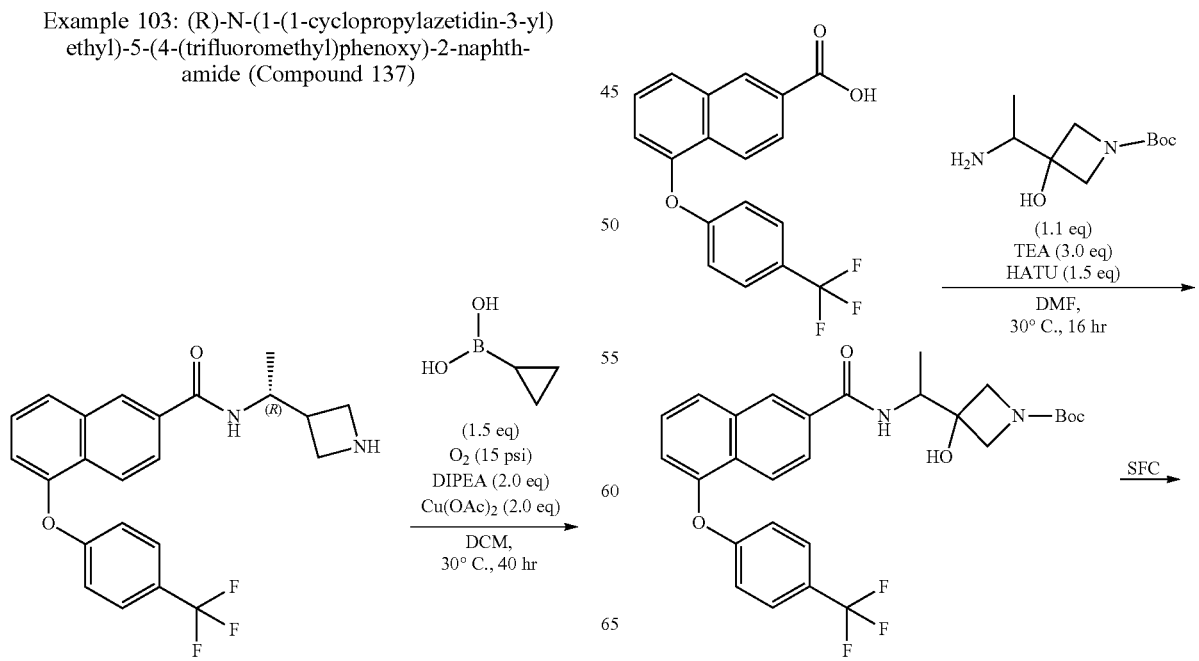

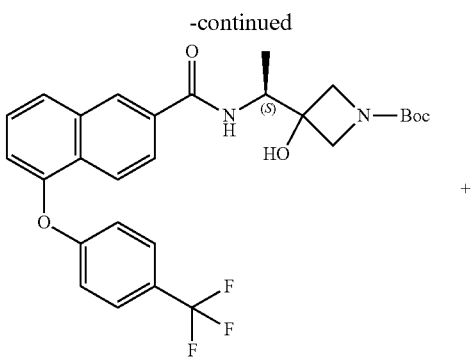

tert-butyl 3-hydroxy-3-(1-(5-(4-(trifluoromethyl) phenoxy)-2-naphthamido)ethyl)azetidine-1-carboxylate To a solution of 5-(4-(trifluoromethyl)phenoxy)-2-naphthoic acid (150.0 mg, 0.45 mmol, 1.0 eq) and HATU (257.5 mg, 0.68 mmol, 1.5 eq) in DMF (2 mL) at 30° C. were added tert-butyl 3-(1-aminoethyl)-3-hydroxyazetidine-1-carboxylate (107.4 mg, 0.50 mmol, 1.1 eq) and TEA (137.0 mg, 1.35 mmol, 0.2 mL, 3.0 eq). The mixture was stirred at 30° C. for 16 h. The reaction mixture was diluted with water (20 mL) and extracted with EA (20 mL*3). The combined organic layers were washed with water (20 mL*2) and brine (20 mL*2), dried over Na$_2$SO$_4$, filtered and concentrated under reduced pressure to give a residue. The reaction was concentrated under reduced pressure to give a residue, which was purified by flash silica gel chromatography (ISCO®; 4 g SepaFlash® Silica Flash Column, Eluent of 0-75% Ethyl acetate/Petroleum ether gradient @ 20 mL/min) to give tert-butyl 3-hydroxy-3-(1-(5-(4-(trifluoromethyl)phenoxy)-2-naphthamido)ethyl)azetidine-1-carboxylate (175.0 mg, 0.32 mmol, 70.0% yield) as a colorless oil. LCMS (ESI): RT=1.012 min, mass calc. for C$_{28}$H$_{29}$F$_3$N$_2$O$_5$ 530.20, m/z found 531.3 [M+H]$^+$.

(S)-tert-butyl 3-hydroxy-3-(1-(5-(4-(trifluoromethyl) phenoxy)-2-naphthamido)ethyl)azetidine-1-carboxylate and (R)-tert-butyl 3-hydroxy-3-(1-(5-(4-(trifluoromethyl)phenoxy)-2-naphthamido)ethyl)azetidine-1-carboxylate tert-butyl 3-hydroxy-3-(1-(5-(4-(trifluoromethyl)phenoxy)-2-naphthamido)ethyl)azetidine-1-carboxylate was purified by SFC (column: DAICEL CHIRALPAK AD-H (250 mm*30 mm, 5um); mobile phase: [0.1% NH$_3$H$_2$O IPA]; B %: 25%-25%, min) to give (S)-tert-butyl 3-hydroxy-3-(1-(5-(4-(trifluoromethyl)phenoxy)-2-naphthamido)ethyl) azetidine-1-carboxylate (50.0 mg, 90 umol, 48.0% yield) as a white solid. LCMS (ESI): RT=1.014 min, mass calc. for C$_{28}$H$_{29}$F$_3$N$_2$O$_5$ 530.20, m/z found 531.4 [M+H]$^+$ and (R)-tert-butyl 3-hydroxy-3-(1-(5-(4-(trifluoromethyl)phenoxy)-2-naphthamido)ethyl)azetidine-1-carboxylate (43 mg, 79 umol, 42.1% yield) as a white solid. LCMS (ESI): RT=1.016 min, mass calc. for C$_{28}$H$_{29}$F$_3$N$_2$O$_5$ 530.20, m/z found 531.4 [M+H]$^+$.

(S)-N-(1-(3-hydroxyazetidin-3-yl)ethyl)-5-(4-(trifluoromethyl)phenoxy)-2-naphthamide To a solution of (S)-tert-butyl 3-hydroxy-3-(1-(5-(4-(trifluoromethyl)phenoxy)-2-naphthamido)ethyl)azetidine-1-carboxylate (50.0 mg, 94.0 umol, 1.0 eq) in DCM (1 mL) at 30° C. was added TFA (154.0 mg, 1.35 mmol, 0.1 mL, 14.33 eq). The mixture was stirred at 30° C. for 2 h. The reaction was concentrated under reduced pressure to give a residue, which was purified by prep-HPLC: (column: Welch Xtimate C18 150*25 mm*5 um; mobile phase: [water (0.225% FA)-ACN]; B %: 16%-46%, 8.5 min) to give the title compound (2.06 mg, 4 umol, 4.5% yield, FA) as a white solid. LCMS (ESI): RT=0.856 min, mass calc. for C$_{23}$H$_{21}$F$_3$N$_2$O$_3$ 430.15, m/z found 431.3 [M+H]$^+$; $^1$H NMR (400 MHz, DMSO-d$_6$) δ 8.64 (s, 1H), 8.58 (br d, J=8.3 Hz, 1H), 8.37 (brs, 1H), 8.02-7.96 (m, 3H), 7.74 (br d, J=8.5 Hz, 2H), 7.64 (t, J=7.9 Hz, 1H), 7.34 (d, J=7.5 Hz, 1H), 7.15 (br d, J=8.8 Hz, 2H), 4.46-4.39 (m, 1H), 4.07 (br d, J=10.5 Hz, 1H), 3.91 (br d, J=10.0 Hz, 1H), 3.68-3.68 (m, 1H), 3.68-3.65 (m, 2H), 1.15 (br d, J=6.8 Hz, 3H).

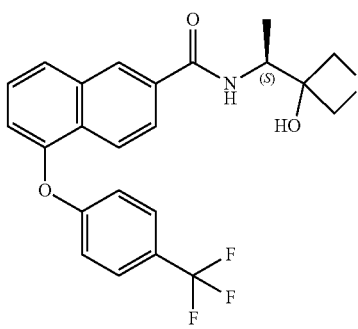

Compound 138

311

Example 105: (R)-N-(1-(3-hydroxyazetidin-3-yl)ethyl)-5-(4-(trifluoromethyl)phenoxy)-2-naphthamide (Compound 139)

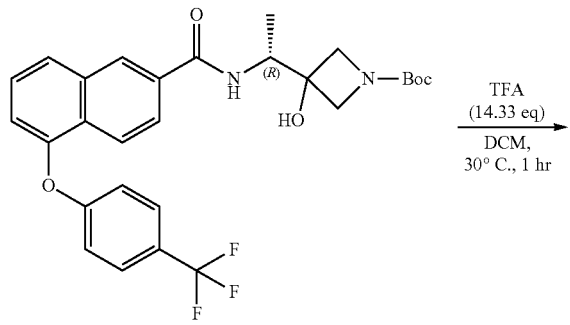

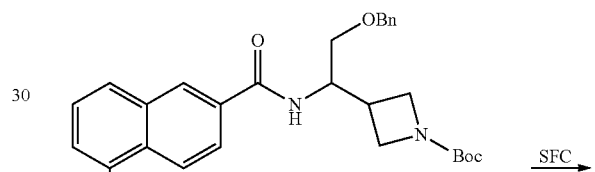

Compound 139

To a solution of tert-butyl (R)-3-hydroxy-3-(1-(5-(4-(trifluoromethyl)phenoxy)-2-naphthamido)ethyl)azetidine-1-carboxylate (43.0 mg, 81 umol, 1 eq) in DCM (1 mL) at 30° C. was added TFA (132.4 mg, 1.16 mmol, 86 uL, 14.33 eq). The mixture was stirred at 30° C. for 1 h. The reaction was concentrated under reduced pressure to give a residue, which was purified by prep-HPLC: (column: Welch Xtimate C18 150*25 mm*5 um; mobile phase: [water (0.225% FA)–ACN]; B %: 16%-46%, 8.5 min) to give the title compound (2.7 mg, 6 umol, 7.2% yield, FA) as a white solid. LCMS (ESI): RT=0.859 min, mass calc. for $C_{23}H_{21}F_3N_2O_3$ 430.15, m/z found 431.3 [M+H]$^+$; $^1$H NMR (400 MHz, DMSO-$d_6$) δ 8.66-8.57 (m, 2H), 8.39 (brs, 1H), 8.01-7.96 (m, 3H), 7.74 (br d, J=8.3 Hz, 2H), 7.64 (br t, J=7.8 Hz, 1H), 7.33 (br d, J=7.5 Hz, 1H), 7.15 (br d, J=8.5 Hz, 2H), 4.41 (brs, 1H), 4.05 (br d, J=9.8 Hz, 1H), 3.89 (br d, J=9.3 Hz, 2H), 3.64 (brs, 1H), 1.15 (br d, J=6.3 Hz, 3H).

312

Example 106: (R)-N-(1-(azetidin-3-yl)-2-hydroxyethyl)-5-(4-(trifluoromethyl)phenoxy)-2-naphthamide (Compound 140) and N-((3R)-4-(aminomethyl)tetrahydrofuran-3-yl)-5-(4-(trifluoromethyl)phenoxy)-2-naphthamide (Compound 141)

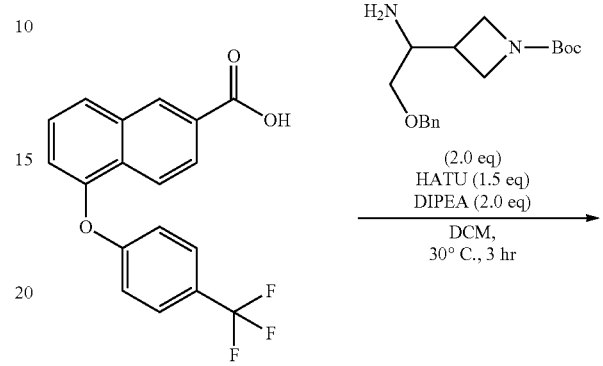

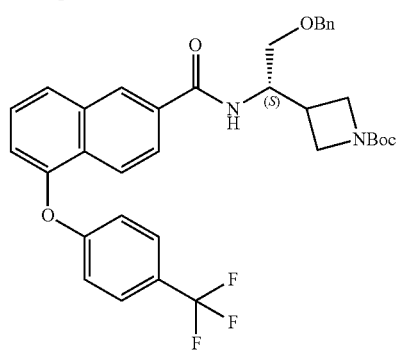

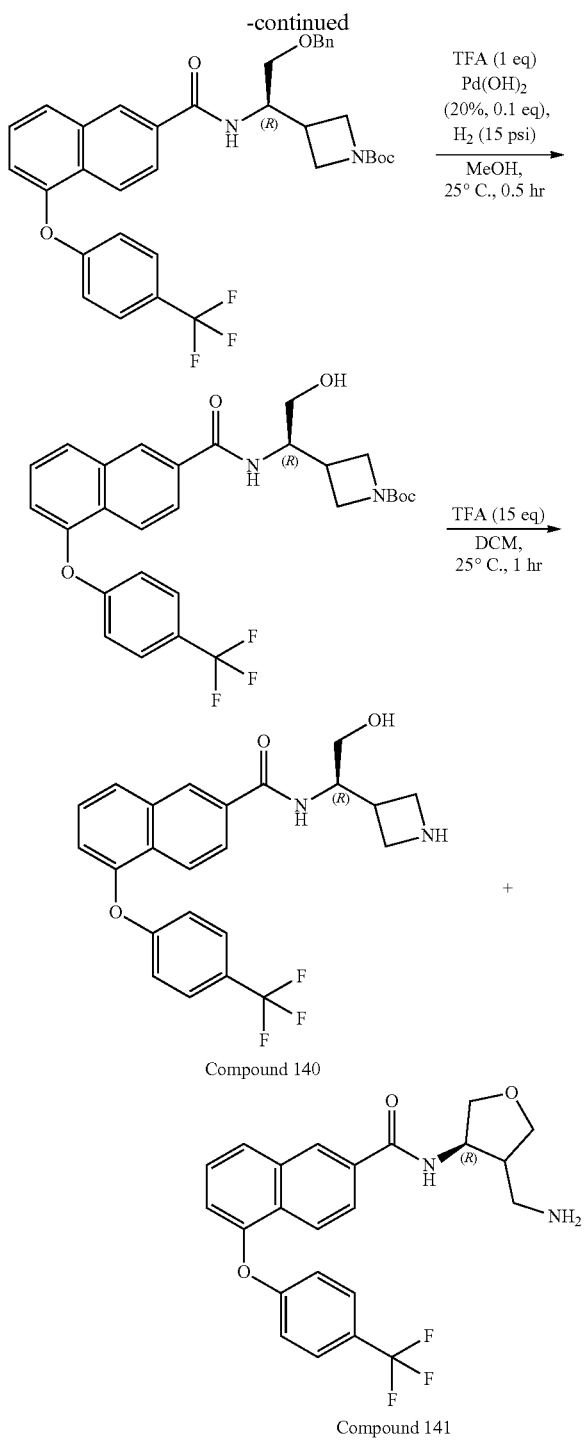

tert-butyl 3-[2-benzyloxy-1-[[5-[4-(trifluoromethyl) phenoxy]naphthalene-2-carbonyl]amino]ethyl]azetidine-1-carboxylate To a solution of compound 5-(4-(trifluoromethyl)phenoxy)-2-naphthoic acid (250 mg, 0.75 mmol, 1 eq) and HATU (429.1 mg, 1.13 mmol, 1.5 eq) in DCM (4 mL) were added compound tert-butyl 3-(1-amino-2-(benzyloxy)ethyl) azetidine-1-carboxylate (461.0 mg, 1.50 mmol, 2 eq) and DIEA (194.4 mg, 1.50 mmol, 0.26 mL, 2 eq). The mixture was stirred at 30° C. for 3 hr. The reaction mixture was concentrated in vacuum. Then the residue was diluted with EA (15 mL*3) washed with H₂O (10 ml) and brine (10 mL*2), dried over Na₂SO₄, filtered and concentrated in vacuum. The residue was purified by prep-HPLC (column: Welch Xtimate C18 150*25 mm*5 um; mobile phase: [water (0.05% HCl)–ACN]; B %: 60%-90%, 8.5 min). tert-butyl 3-[2-benzyloxy-1-[[5-[4-(trifluoromethyl)phenoxy]naphthalene-2-carbonyl] amino]ethyl]azetidine-1-carboxylate (115 mg 0.18 mml, 24.3% yield) was obtained as a yellow solid. LCMS (ESI): RT=1.055 min, mass calcd. For $C_{35}H_{35}F_3N_2O_5$, 620.25 m/z found 621.2 [M+H]⁺. ¹H NMR (400 MHz, CDCl₃) δ 8.33 (d, J=1.0 Hz, 1H), 8.13 (d, J=8.8 Hz, 1H), 7.85-7.76 (m, 2H), 7.60 (d, J=8.5 Hz, 2H), 7.53 (t, J=7.9 Hz, 1H), 7.38-7.29 (m, 5H), 7.16 (d, J=7.5 Hz, 1H), 7.08 (d, J=8.8 Hz, 2H), 6.64 (br d, J=9.0 Hz, 1H), 4.65-4.59 (m, 1H), 4.59-4.49 (m, 2H), 4.05-3.91 (m, 3H), 3.79-3.71 (m, 1H), 3.66-3.59 (m, 2H), 3.11-2.89 (m, 1H), 1.42 (s, 9H).

Tert-butyl 3-[(1R)-2-benzyloxy-1-[[5-[4-(trifluoromethyl)phenoxy]naphthalene-2-carbonyl]amino]ethyl] azetidine-1-carboxylate and tert-butyl 3-[(S)-2-benzyloxy-[[5-[4-(trifluoromethyl)phenoxy] naphthalene-2-carbonyl]amino]ethyl]azetidine-1-carboxylate The separated method of tert-butyl 3-[2-benzyloxy-1-[[5-[4-(trifluoromethyl)phenoxy]naphthalene-2-carbonyl] amino]ethyl]azetidine-1-carboxylate (115 mg, 0.18 mmol, 1 eq) was developed by SFC. The racemate was separated by chiral SFC (column: DAICEL CHIRALCEL OD-H (250 mm*30 mm, 5 um); mobile phase: [0.1% NH₃H₂O ETOH]; B %: 30%-30%, min). tert-Butyl 3-[(1R)-2-benzyloxy-1-[[5-[4-(trifluoromethyl)phenoxy]naphthalene-2-carbonyl] amino]ethyl]azetidine-1-carboxylate (52 mg, 82.9 umol, 44.7% yield) was obtained as colorless oil. LCMS (ESI): RT=1.048 min, mass calcd. For $C_{35}H_{33}F_3N_2O_5$, 620.25 m/z found 621.2 [M+H]⁺. tert-Butyl 3-[(1 S)-2-benzyloxy-1-[[5-[4-(trifluoromethyl)phenoxy]naphthalene-2-carbonyl] amino]ethyl]azetidine-1-carboxylate (50 mg, 78.9 umol, 42.6% yield) was obtained as colorless oil. LCMS (ESI): RT=1.050 min, mass calcd. For $C_{35}H_{35}F_3N_2O_5$, 620.25 m/z found 621.1 [M+H]⁺.

Tert-butyl 3-[(1R)-2-hydroxy-1-[[5-[4-(trifluoromethyl)phenoxy]naphthalene-2-carbonyl]amino]ethyl] azetidine-1-carboxylate To a solution of tert-butyl 3-[(1R)-2-benzyloxy-1-[[5-[4-(trifluoromethyl)phenoxy]naphthalene-2-carbonyl]amino] ethyl]azetidine-1-carboxylate (52 mg, 83.7 umol, 1 eq) in MeOH (2 mL) were added Pd(OH)₂ (5.8 mg, 8.3 umol, 20%, 0.1 eq) and TFA (9.5 mg, 83.7 umol, 6 uL, 1 eq). The mixture was degassed and purged with H₂ for 3 times and stirred at 25° C. for 0.5 hr under H₂ atmosphere (15 psi). The reaction mixture was filtered and the filtrate was concentrated in vacuum. The crude product was used for the next step directly. tert-Butyl 3-[(1R)-2-hydroxy-1-[[5-[4-(trifluoromethyl)phenoxy]naphthalene-2-carbonyl]amino]ethyl] azetidine-1-carboxylate (37 mg, 62.7 umol, 74.9% yield) as a white solid. LCMS (ESI): RT=0.912 min, mass calcd. For $C_{28}H_{29}F_3N_2O_5$, 530.20 m/z found 531.1 [M+H]⁺. ¹H NMR (400 MHz, CDCl₃) δ 8.37 (d, J=1.3 Hz, 1H), 8.14 (d, J=8.8 Hz, 1H), 7.85-7.77 (m, 2H), 7.62-7.58 (m, 2H), 7.55-7.50 (m, 1H), 7.16 (d, J=6.8 Hz, 1H), 7.07 (d, J=8.5 Hz, 2H), 6.73 (br d, J=8.5 Hz, 1H), 4.58-4.44 (m, 1H), 4.07 (td, J=8.7, 11.8

Hz, 2H), 3.94 (dd, J=5.8, 8.8 Hz, 1H), 3.88-3.76 (m, 3H), 3.03-2.93 (m, 1H), 1.42 (s, 9H).

(R)-N-(1-(azetidin-3-yl)-2-hydroxyethyl)-5-(4-(trifluoromethyl)phenoxy)-2-naphthamide (Compound 140) and N-((3R)-4-(aminomethyl)tetrahydrofuran-3-yl)-5-(4-(trifluoromethyl)phenoxy)-2-naphthamide (Compound 141)

To a solution of tert-butyl 3-[(1R)-2-hydroxy-1-[[5-[4-(trifluoromethyl)phenoxy]naphthalene-2-carbonyl] amino] ethyl]azetidine-1-carboxylate (35 mg, 65.9 umol, 1 eq) in DCM (2 mL) was added TFA (112.8 mg, 0.98 mmol, 73 uL, 15 eq). The mixture was stirred at 25° C. for 1 hr. The reaction mixture was concentrated in vacuum. The residue was adjusted pH=8 with saturated aq. NaHCO$_3$, extracted with EA (15 mL*3). The combined organic phase was washed with H$_2$O (10 mL), brine (10 mL) and dried over Na$_2$SO$_4$, filtered and concentrated in vacuum. The crude product was purified by prep-HPLC (column: Welch Xtimate C18 150*25 mm*5 um; mobile phase: [water (0.05% HCl)–ACN]; B %: 15%-45%, 8.5 min). Compound 141 (7.5 mg, 16.0 umol, 24.3% yield, HCl) was obtained as yellow oil. LCMS (ESI): RT=0.733 min, mass calcd. For C$_{23}$H$_{21}$F$_3$N$_2$O$_3$, 430.15 m/z found 431.1 [M+H]$^+$. $^1$H NMR (400 MHz, CD$_3$OD) δ 8.46 (s, 1H), 8.27 (d, J=8.8 Hz, 1H), 7.96 (d, J=8.3 Hz, 1H), 7.78 (dd, J=1.8, 8.8 Hz, 1H), 7.72-7.65 (m, 3H), 7.31 (d, J=7.5 Hz, 1H), 7.17 (d, J=8.8 Hz, 2H), 3.98-3.92 (m, 1H), 3.91-3.86 (m, 2H), 3.85-3.74 (m, 2H), 3.73-3.61 (m, 2H), 2.57-2.43 (m, 1H). Compound 140 (3.8 mg, 8.1 umol, 12.3% yield, HCl) was obtained as yellow oil. LCMS (ESI): RT=0.751 min, mass calcd. For C$_{23}$H$_{21}$F$_3$N$_2$O$_3$, 430.15 m/z found 431.1 [M+H]$^+$. $^1$H NMR (400 MHz, CD$_3$OD) δ 8.53 (s, 1H), 8.12 (d, J=8.8 Hz, 1H), 7.97-7.88 (m, 2H), 7.66 (d, J=8.8 Hz, 2H), 7.63-7.58 (m, 1H), 7.24 (d, J=7.5 Hz, 1H), 7.13 (d, J=8.5 Hz, 2H), 4.50 (td, J=5.5, 8.9 Hz, 1H), 4.21-4.08 (m, 4H), 3.75-3.70 (m, 1H), 3.70-3.64 (m, 1H), 3.41-3.33 (m, 1H).

Example 107: (S)-N-(1-(azetidin-3-yl)-2-hydroxyethyl)-5-(4-(trifluoromethyl)phenoxy)-2-naphthamide (Compound 142) and N-((3S)-4-(aminomethyl)tetrahydrofuran-3-yl)-5-(4-(trifluoromethyl)phenoxy)-2-naphthamide (Compound 143)

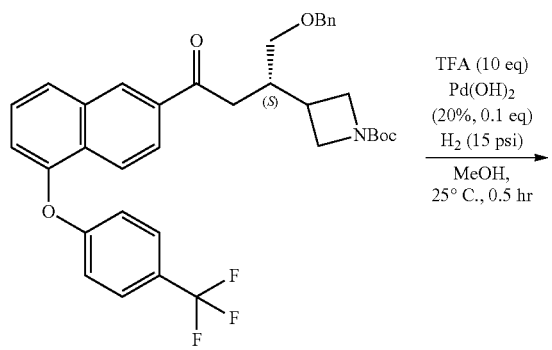

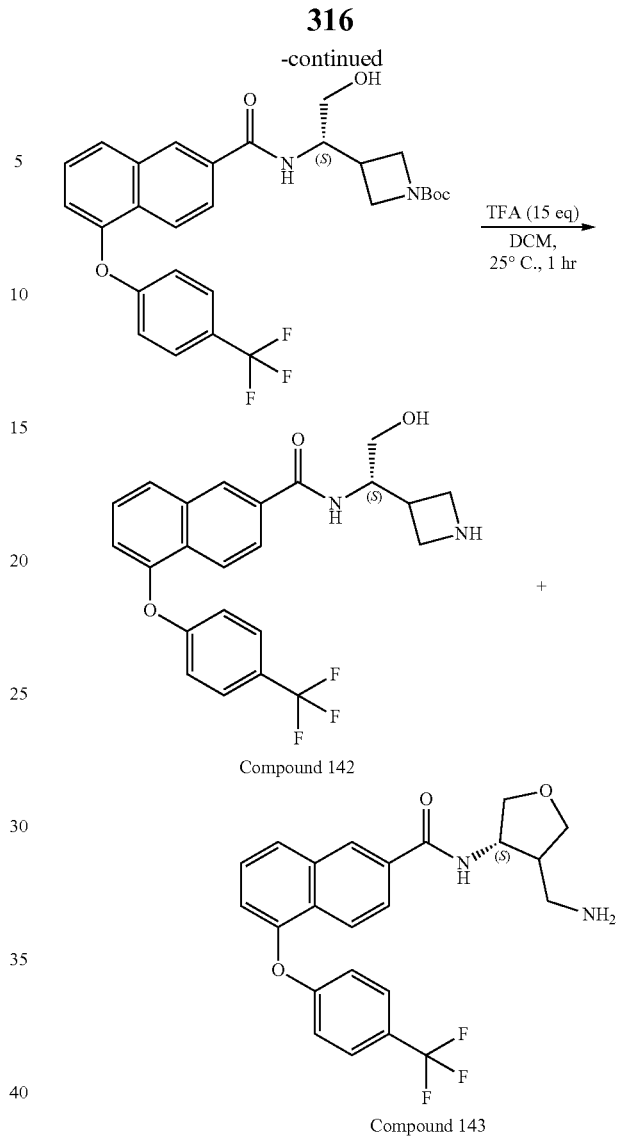

Compound 142

Compound 143

Tert-butyl 3-[(1S)-2-hydroxy-1-[[5-[4-(trifluoromethyl)phenoxy]naphthalene-2-carbonyl]amino]ethyl]azetidine-1-carboxylate To a solution of compound tert-butyl 3-[(1S)-2-benzyloxy-1-[[5-[4-(trifluoromethyl)phenoxy]naphthalene-2-carbonyl]amino]ethyl]azetidine-1-carboxylate (50 mg, 80.5 umol, 1 eq) in MeOH (2 mL) were added Pd(OH)$_2$ (5.6 mg, 8.0 umol, 20%, 0.1 eq) and TFA (91.8 mg, 0.80 mmol, 59 uL, 10 eq). The mixture was degassed and purged with H$_2$ for 3 times and stirred at 25° C. for 0.5 hr under H$_2$ atmosphere (15 psi). The reaction mixture was filtered and the filtrate was concentrated in vacuum. The crude product was used for the next step directly. tert-Butyl 3-[(1 S)-2-hydroxy-1-[[5-[4-(trifluoromethyl)phenoxy]naphthalene-2-carbonyl]amino]ethyl]azetidine-1-carboxylate (38 mg, 65.9 umol, 81.8% yield) was obtained as a white solid. LCMS (ESI): RT=0.915 min, mass calcd. For C$_{28}$H$_{29}$F$_3$N$_2$O$_5$, 530.20 m/z found 531.1 [M+H]$^+$. $^1$H NMR (400 MHz, CDCl$_3$) δ 8.37 (d, J=1.3 Hz, 1H), 8.14 (d, J=8.8 Hz, 1H), 7.85-7.77 (m, 2H), 7.60 (d, J=8.8 Hz, 2H), 7.53 (t, J=7.9 Hz, 1H), 7.16 (d, J=7.0 Hz, 1H), 7.07 (d, J=8.5 Hz, 2H), 6.73 (br d, J=8.5 Hz, 1H), 4.57-4.44 (m, 1H), 4.07 (td, J=8.6, 11.9

Hz, 2H), 3.94 (dd, J=5.6, 8.9 Hz, 1H), 3.88-3.76 (m, 3H), 3.05-2.92 (m, 1H), 1.42 (s, 9H).

(S)-N-(1-(azetidin-3-yl)-2-hydroxyethyl)-5-(4-(trifluoromethyl)phenoxy)-2-naphthamide (Compound 142) and N-((3S)-4-(aminomethyl)tetrahydrofuran-3-yl)-5-(4-(trifluoromethyl)phenoxy)-2-naphthamide (Compound 143)

To a solution of tert-butyl 3-[(1S)-2-hydroxy-1-[[5-[4-(trifluoromethyl)phenoxy]naphthalene-2-carbonyl] amino] ethyl]azetidine-1-carboxylate (35 mg, 65.9 umol, 1 eq) in DCM (2 mL) was added TFA (112.8 mg, 0.98 mmol, 73 uL, 15 eq). The mixture was stirred at 25° C. for 1 hr. The reaction mixture was concentrated in vacuum. The residue was adjusted pH=9 with saturated aq. NaHCO$_3$, extracted with EA (15 mL*3). The combined organic phase was washed with H$_2$O (10 mL), brine (10 mL) and dried over Na$_2$SO$_4$, filtered and concentrated in vacuum. The crude product was purified by prep-HPLC (column: Welch Xtimate C18 150*25 mm*5 um; mobile phase: [water (0.05% HCl)–ACN]; B %; 15%-45%, 8.5 min). Compound 143 (9.1 mg, 19.5 umol, 29.6% yield, HCl) was obtained as yellow oil. LCMS (ESI): RT=0.735 min, mass calcd. For C$_{23}$H$_{21}$F$_3$N$_2$O$_3$, 430.15 m/z found 431.1 [M+H]$^+$. $^1$H NMR (400 MHz, CD$_3$OD) δ 8.46 (s, 1H), 8.28 (d, J=8.8 Hz, 1H), 7.96 (d, J=8.3 Hz, 1H), 7.83-7.75 (m, 1H), 7.72-7.65 (m, 3H), 7.31 (dd, J=0.8, 7.5 Hz, 1H), 7.17 (d, J=8.5 Hz, 2H), 3.98-3.92 (m, 1H), 3.91-3.86 (m, 2H), 3.85-3.74 (m, 2H), 3.73-3.60 (m, 2H), 2.58-2.44 (m, 1H). Compound 142 (2.4 mg, 5.1 umol, 7.7% yield, HCl) was obtained as yellow oil. LCMS (ESI): RT=0.753 min, mass calcd. For C$_{23}$H$_{21}$F$_3$N$_2$O$_3$, 430.15 m/z found 431.1 [M+H]$^+$. $^1$H NMR (400 MHz, CD$_3$OD) δ 8.52 (d, J=1.3 Hz, 1H), 8.12 (d, J=8.8 Hz, 1H), 7.97-7.88 (m, 2H), 7.66 (d, J=8.5 Hz, 2H), 7.60 (t, J=7.9 Hz, 1H), 7.26-7.23 (m, 1H), 7.14 (d, J=8.5 Hz, 2H), 4.50 (td, J=5.5, 8.8 Hz, 1H), 4.20-4.07 (m, 4H), 3.78-3.62 (m, 2H), 3.40-3.33 (m, 1H).

Example 108: (R)-N-(4-(dimethylamino)butan-2-yl)-5-(4-(trifluoromethyl)phenoxy)-2-naphthamide (Compound 144)

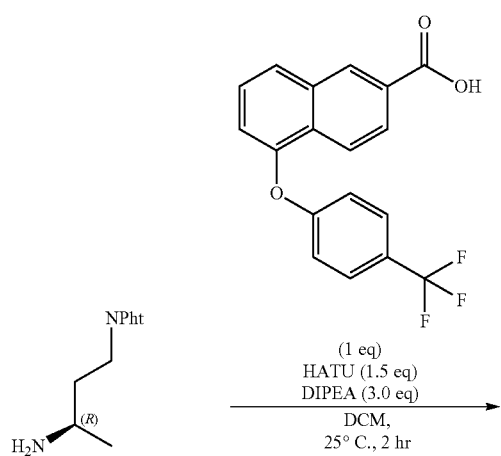

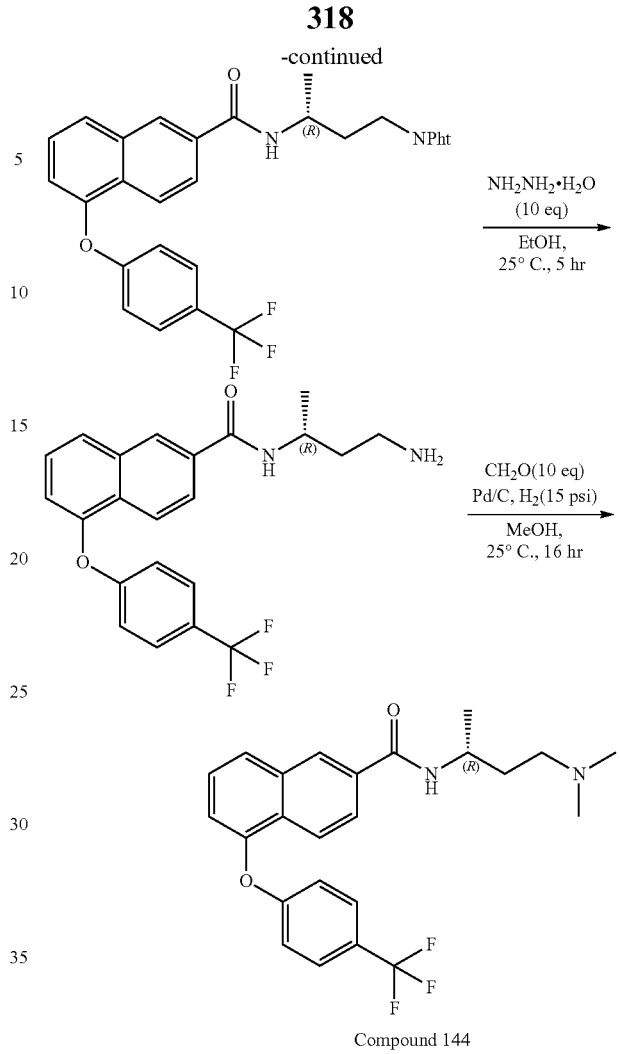

Compound 144

(R)-N-(4-(1,3-dioxoisoindolin-2-yl)butan-2-yl)-5-(4-(trifluoromethyl)phenoxy)-2-naphthamide To a solution of 5-[4-(trifluoromethyl)phenoxy]naphthalene-2-carboxylic acid (500 mg, 1.50 mmol, 1 eq) and HATU (855.5 mg, 2.25 mmol, 1.5 eq) in DCM (10 mL) was added DIPEA (581.5 mg, 4.50 mmol, 0.78 mL, 3 eq). After addition, the mixture was stirred at the same temperature (25° C.) for 0.5 hr, and then 2-[(3R)-3-aminobutyl]isoindoline-1,3-dione (327.3 mg, 1.50 mmol, 1 eq, HCl) was added. The mixture was stirred at 25° C. for 1.5 hr. The reaction mixture was added H$_2$O (20 mL) and extracted with EA (20 mL*3). The combined organic layers were washed with brine (30 mL), dried with anhydrous Na$_2$SO$_4$, filtered and concentrated under reduced pressure to give a residue. The residue was purified by flash silica gel chromatography (ISCO® 12 g SepaFlash® Silica Flash Column, Eluent of 0-30% Ethyl acetate/Petroleum ether gradient @ 30 mL/min). Compound N-[(1R)-3-(1,3-dioxoisoindolin-2-yl)-1-methyl-propyl]-5-[4-(trifluoromethyl)phenoxy]naphthalene-2-carboxamide (620 mg, 1.09 mmol, 72.9% yield) was obtained as a white solid.

(R)-N-(4-aminobutan-2-yl)-5-(4-(trifluoromethyl)phenoxy)-2-naphthamide

To a solution of N-[(1R)-3-(1,3-dioxoisoindolin-2-yl)-1-methyl-propyl]-5-[4-(trifluoromethyl)phenoxy]naphthalene-2-carboxamide (620 mg, 1.16 mmol, 1 eq) in EtOH (8 mL) was added NH$_2$NH$_2$.H$_2$O (685.7 mg, 11.64 mmol, 0.66 mL, 85%, 10 eq). The mixture was stirred at 25° C. for 6 hr. The reaction mixture was filtered. The cake was washed with EtOH (10 mL), the organic layers concentrated under reduced pressure to give a residue. The residue was added H$_2$O (10 mL) and extracted with DCM (10 mL*3). The combined organic layers were washed with brine (20 mL), dried with anhydrous Na$_2$SO$_4$, filtered and concentrated under reduced pressure to give a residue. It was used into next step without further purification. Compound N-[(1R)-3-amino-1-methyl-propyl]-5-[4-(trifluoromethyl)phenoxy] naphthalene-2-carboxamide (489 mg, 1.08 mmol, 92.8% yield) was obtained as yellow oil.

(R)-N-(4-(dimethylamino)butan-2-yl)-5-(4-(trifluoromethyl)phenoxy)-2-naphthamide To a solution of N-[(1R)-3-amino-1-methyl-propyl]-5-[4-(trifluoromethyl)phenoxy]naphthalene-2-carboxamide (50 mg, 0.12 mmol, 1 eq) and formaldehyde (100.8 mg, 1.24 mmol, 92.5 uL, 10 eq) in MeOH (1 mL) was added Pd/C (30 mg, 0.12 mmol, 10%, 1.00 eq) under H$_2$. The suspension was degassed under vacuum and purged with H$_2$ several times. The mixture was stirred under H$_2$ (15 psi) at 25° C. for 16 hours. The reaction mixture was filtered and the organic layers were concentrated under reduced pressure to give a residue. The residue was purified by prep-HPLC (column: 3_Phenomenex Luna C18 75*30 mm*3 um; mobile phase: [water (0.05% HCl)–ACN]; B %: 20%-50%, 6.5 min). The title compound (22.9 mg, 49.0 umol, 39.4% yield, HCl) was obtained as a white solid. LCMS (ESI): RT=0.867 min, mass calcd for C$_{24}$H$_{25}$F$_3$N$_2$O 2430.46 m/z found 431.3[M+H]$^+$, $^1$H NMR (400 MHz, CDCl$_3$) δ 12.08 (br s, 1H), 8.70 (br s, 1H), 8.17-8.03 (m, 2H), 7.88 (br d, J=8.3 Hz, 1H), 7.70 (br s, 1H), 7.58 (d, J=8.5 Hz, 2H), 7.49 (t, J=7.8 Hz, 1H), 7.15 (d, J=7.5 Hz, 1H), 7.05 (d, J=8.5 Hz, 2H), 4.32 (br s, 1H), 3.29-3.05 (m, 2H), 2.81 (br d, J=18.1 Hz, 6H), 2.53-2.08 (m, 2H), 1.44 (br d, J=5.3 Hz, 3H).

Example 109: (R)-N-(4-(methylamino)butan-2-yl)-5-(4-(trifluoromethyl)phenoxy)-2-naphthamide (Compound 145)

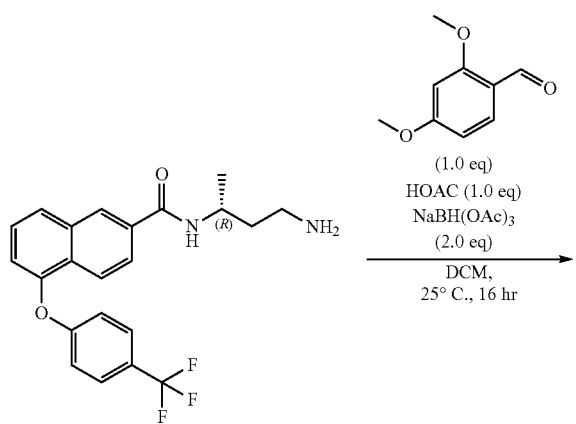

(1.0 eq)
HOAC (1.0 eq)
NaBH(OAc)$_3$ (2.0 eq)
DCM, 25° C., 16 hr

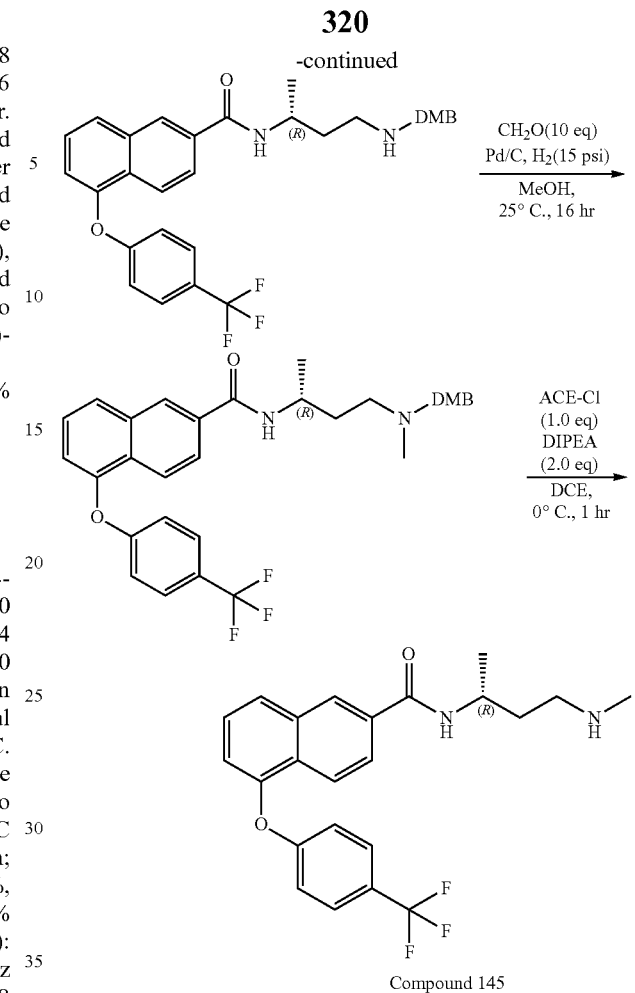

Compound 145

(R)-N-(4-((2,4-dimethoxybenzyl)amino)butan-2-yl)-5-(4-(trifluoromethyl)phenoxy)-2-naphthamide To a solution of N-[(1R)-3-amino-1-methyl-propyl]-5-[4-(trifluoromethyl)phenoxy]naphthalene-2-carboxamide (100 mg, 0.24 mmol, 1 eq) and 2,4-dimethoxybenzaldehyde (41.2 mg, 0.24 mmol, 1 eq) in DCM (5 mL) was added AcOH (14.9 mg, 0.24 mmol, 14 uL, 1 eq) and NaBH(OAc)$_3$ (105.3 mg, 0.49 mmol, 2 eq) The mixture was stirred at 25° C. for 16 hr. The reaction mixture was diluted with H$_2$O (5 mL) and neutralized to pH=7-8 with 2M NaOH, Then extracted with DCM (15 mL*3). The combined organic layers were washed with brine (10 mL), dried with anhydrous Na$_2$SO$_4$, filtered and concentrated under reduced pressure to give a residue. It was used into next step without further purification. Compound N-[(1R)-3-[(2,4-dimethoxyphenyl)methylamino]-1-methyl-propyl]-5-[4-(trifluoromethyl)phenoxy] naphthalene-2-carboxamide (122 mg, 0.16 mmd, 67.5% yield) was obtained as yellow oil.

(R)-N-(4-((2,4-dimethoxy benzyl)(methyl)amino)butan-2-yl)-5-(4-(trifluoromethyl)phenoxy)-2-naphthamide To a solution of N-[(1R)-3-[(2,4-dimethoxyphenyl)methylamino]-1-methyl-propyl]-5-[4-(trifluoromethyl)phenoxy] naphthalene-2-carboxamide (122 mg, 0.16 mmol, 1 eq) and formaldehyde (136.1 mg, 1.68 mmol, 0.12 mL, 10 eq) in MeOH (3 mL) was added Pd/C (100 mg, 0.16 mmol, 16 uL, 10%, 1 eq) under H₂. The suspension was degassed under vacuum and purged with H₂ several times. The mixture was stirred under H₂ (15 psi) at 25° C. for 3 hours. The reaction mixture was filtered and concentrated under reduced pressure to give a residue. The residue was purified by flash silica gel chromatography (ISCO®; 4 g SepaFlash® Silica Flash Column, Eluent of 0~10% DCM/MeOH @ 20 m/min). Compound N-[(1R)-3-[(2,4-dimethoxyphenyl)methyl-methyl-amino]-1-methyl-propyl]-5-[4-(trifluoromethyl)phenoxy]naphthalene-2-carboxamide (41 mg, 58.6 umol, 34.9% yield) was obtained as a colorless oil.

(R)-N-(4-(methylamino)butan-2-yl)-5-(4-(trifluoromethyl)phenoxy)-2-naphthamide

To a solution of N-[(1R)-3-[(2,4-dimethoxyphenyl)methyl-methyl-amino]-1-methyl-propyl]-5-[4-(trifluoromethyl)phenoxy]naphthalene-2-carboxamide (41 mg, 72.3 umol, 1 eq) in DCE (1 mL) were added DIPEA (18.7 mg, 0.14 mmol, 25 uL, 2 eq) and 1-chloroethyl chloroformate (ACE-Cl) (10.3 mg, 72.3 umol, 1 eq) at 0° C. Then the mixture was stirred at 0° C. for 1 hr. The reaction mixture was concentrated under reduced pressure to remove DCE to give a residue. The residue was quenched with MeOH (5 mL) and the mixture was concentrated in vacuum. The residue was purified by prep-HPLC (column: 3_Phenomenex Luna C18 75*30 mm*3 um; mobile phase: [water (0.05% HCl)–ACN]; B %: 25%-55%, 6.5 min). The title compound (6.9 mg, 14.9 umol, 20.6% yield, HCl) was obtained as a white solid. LCMS (ESI): RT=0.873 min, mass calcd for $C_{23}H_{23}F_3N_2O_2$ 416.44 m/z found 417.3[M+H]⁺. ¹H NMR (400 MHz, CDCl₃) δ 9.84 (brs, 1H), 9.14 (brs, 1H), 8.47 (brs, 1H), 8.03 (brs, 1H), 7.95-7.64 (m, 2H), 7.50 (br d, J=8.3 Hz, 2H), 7.40 (br s, 1H), 7.05 (br d, J=7.3 Hz, 1H), 6.97 (br d, J=8.3 Hz, 2H), 4.25 (br s, 1H), 3.28-2.78 (m, 2H), 2.61 (br s, 3H), 2.44-1.83 (m, 2H), 1.33 (br s, 3H).

Example 110: (R)-N-(4-(ethylamino)butan-2-yl)-5-(4-(trifluoromethyl)phenoxy)-2-naphthamide (Compound 146)

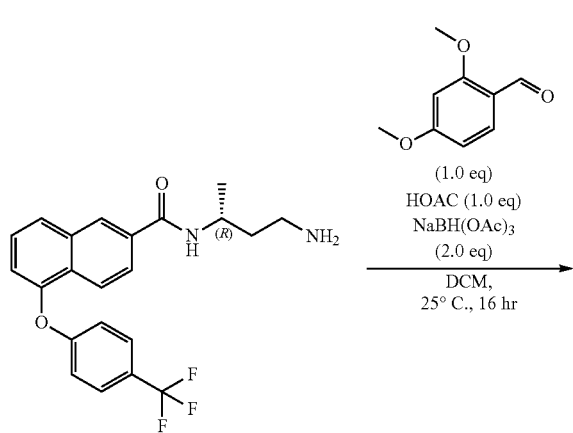

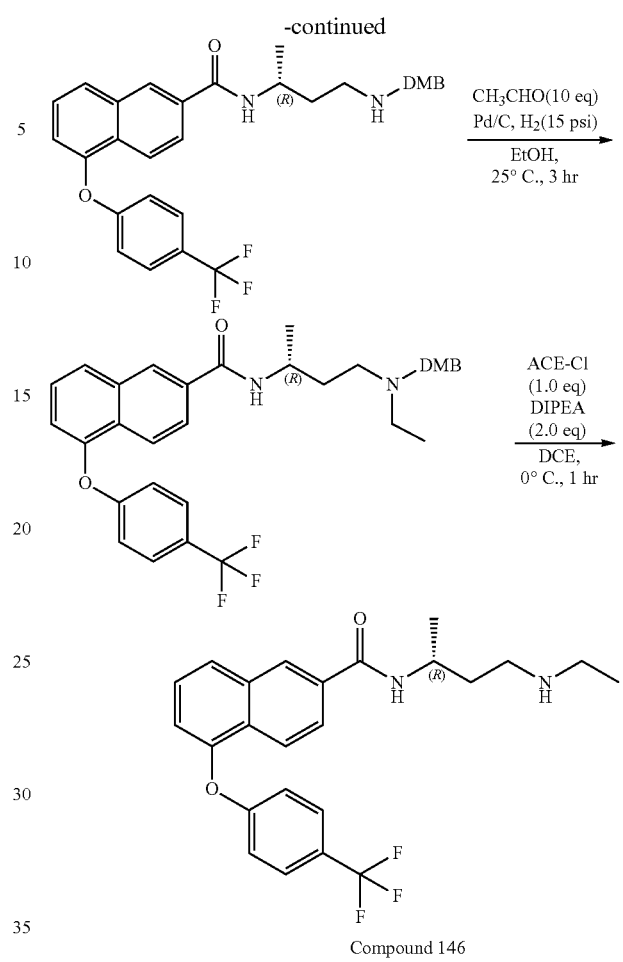

Compound 146

(R)-N-(4-((2,4-dimethoxybenzyl)amino)butan-2-yl)-5-(4-(trifluoromethyl)phenoxy)-2-naphthamide To a solution of N-[(1R)-3-amino-1-methyl-propyl]-5-[4-(trifluoromethyl)phenoxy]naphthalene-2-carboxamide (100 mg, 0.24 mmol, 1 eq) and 2,4-dimethoxybenzaldehyde (41.2 mg, 0.24 mmol, 1 eq) in DCM (5 mL) was added AcOH (14.9 mg, 0.24 mmol, 14 uL, 1 eq) and NaBH(OAc)₃ (105.3 mg, 0.49 mmol, 2 eq). The mixture was stirred at 25° C. for 16 hr. The reaction mixture was diluted with H₂O (5 mL) and neutralized to pH=7-8 with 2M NaOH, Then extracted with DCM (15 mL*3). The combined organic layers were washed with brine (10 mL), dried with anhydrous Na₂SO₄, filtered and concentrated under reduced pressure to give a residue. The residue was purified by flash silica gel chromatography (ISCO®; 4 g SepaFlash® Silica Flash Column, Eluent of 0~20% Ethyl acetate/Petroleum ether gradient @ 25 mL/min). Compound (R)-N-(4-((2,4-dimethoxybenzyl)amino)butan-2-yl)-5-(4-(trifluoromethyl)phenoxy)-2-naphthamide (112 mg, 0.16 mmol, 66.8% yield) was obtained as a colorless oil.

(R)-N-(4-((2,4-dimethoxybenzyl)(ethyl)amino)butan-2-yl)-5-(4-(trifluoromethyl)phenoxy)-2-naphthamide To a solution of N-[(1R)-3-[(2,4-dimethoxyphenyl)methylamino]-1-methyl-propyl]-5-[4-(trifluoromethyl)phenoxy]

naphthalene-2-carboxamide (112 mg, 0.16 mmol, 1 eq) and acetaldehyde (73.2 mg, 1.66 mmol, 93 uL, 10 eq) in EtOH (3 mL) was added Pd/C (100 mg, 0.16 mmol, 10%, 1.0 eq) under H$_2$. The suspension was degassed under vacuum and purged with H$_2$ several times. The mixture was stirred under H$_2$ (15 psi) at 25° C. for 3 hours. The reaction mixture was filtered and concentrated under reduced pressure to give a residue. It was used into next step without further purification. Compound (R)-N-(4-((2,4-dimethoxybenzyl)(ethyl) amino)butan-2-yl)-5-(4-(trifluoromethyl)phenoxy)-2-naphthamide (102 mg, 0.14 mmol, 84.5% yield) was obtained as yellow oil.

(R)-N-(4-(ethylamino)butan-2-yl)-5-(4-(trifluoromethyl)phenoxy)-2-naphthamide

To a solution of N-[(1R)-3-[(2,4-dimethoxyphenyl) methyl-ethyl-amino]-1-methyl-propyl]-5-[4-(trifluoromethyl)phenoxy]naphthalene-2-carboxamide (102 mg, 0.17 mmol, 1 eq) in DCE (2 mL) were added DIPEA (45.4 mg, 0.35 mmol, 61 uL, 2 eq) and 1-chloroethyl chloroformate (ACE-Cl) (25.1 mg, 0.17 mmd, 1 eq) at 0° C. Then the mixture was stirred at 0° C. for 1 hr. The reaction mixture was concentrated under reduced pressure to remove DCE to give a residue. The residue was quenched with MeOH (10 mL) and the mixture was concentrated in vacuum. The residue was purified by prep-HPLC (column: 3_Phenomenex Luna C18 75*30 mm*3 um; mobile phase: [water (0.05% HCl)-ACN]; B %: 25%-55%, 6.5 min). Then the residue was purified by prep-HPLC (column: Waters Xbridge 150*25 mm*5 um; mobile phase: [water (0.05% NH$_3$H$_2$O+10 mM NH$_4$HCO$_3$)-ACN]; B %: 53%-83%, 7.8 min). The title compound (11.9 mg, 27.7 umol, 15.7% yield) was obtained as a yellow solid. LCMS (ESI): RT=0.896 min, mass calcd for C$_{24}$H$_{25}$F$_3$N$_2$O 2430.46 m/z found 431.4[M+H]$^+$; $^1$H NMR (400 MHz, CD$_3$OD) δ 8.45 (d, J=1.0 Hz, 1H), 8.09 (d, J=8.8 Hz, 1H), 7.89 (td, J=2.3, 8.7 Hz, 2H), 7.66 (d, J=8.8 Hz, 2H), 7.58 (t, J=7.9 Hz, 1H), 7.22 (d, J=7.5 Hz, 1H), 7.13 (d, J=8.5 Hz, 2H), 4.40-4.13 (m, 1H), 2.79-2.61 (m, 4H), 1.92-1.73 (m, 2H), 1.32 (d, J=6.8 Hz, 3H), 1.15 (t, J=7.2 Hz, 3H).

Example 111: (R)-N-(4-((2-hydroxyethyl)amino)butan-2-yl)-5-(4-(trifluoromethyl)phenoxy)-2-naphthamide (Compound 147)

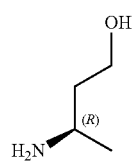

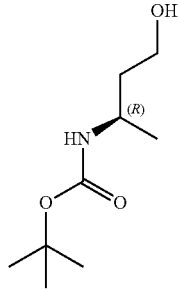

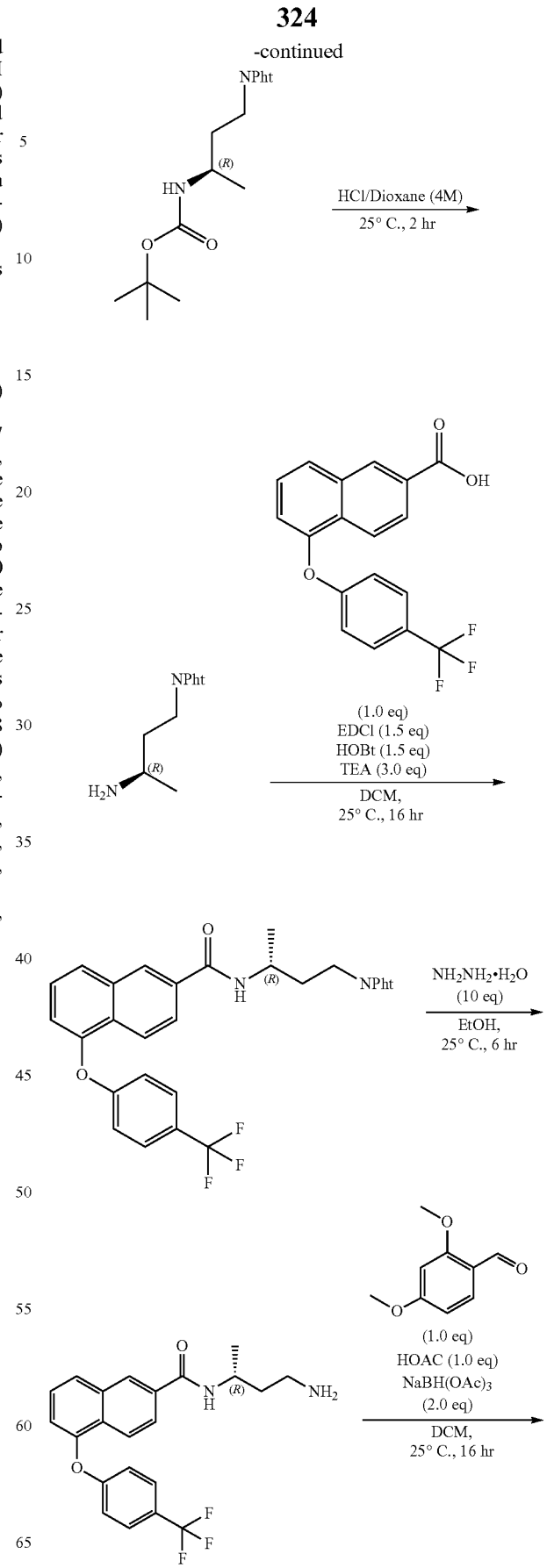

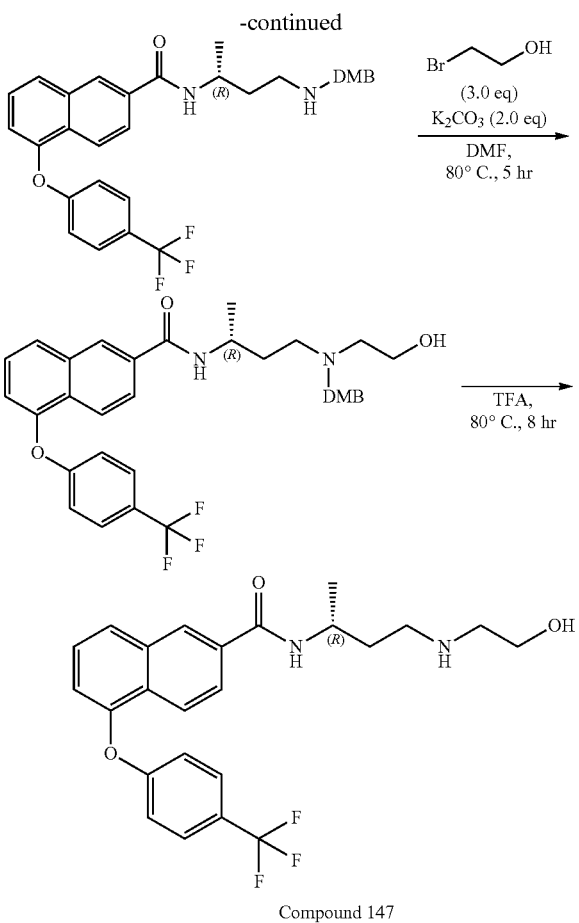

Compound 147

(R)-tert-butyl (4-hydroxybutan-2-yl)carbamate

To a solution of (3R)-3-aminobutan-1-ol (5 g, 56.09 mmol, 1 eq) in DCM (50 mL) was added TEA (6.81 g, 67.31 mmol, 9.37 mL, 1.2 eq) and tert-butoxycarbonyl tert-butyl carbonate (14.69 g, 67.31 mmol, 15.46 mL, 1.2 eq). The mixture was stirred at 25° C. for 16 hr. The reaction mixture was added H₂O (50 mL) and extracted with EA (50 mL*3). The combined organic layers were washed with brine (80 mL), dried with anhydrous Na₂SO₄, filtered and concentrated under reduced pressure to give a residue. The residue was purified by flash silica gel chromatography (ISCO®; 80 g SepaFlash® Silica Flash Column, Eluent of 0~30% Ethyl acetate/Petroleum ether gradient @ 60 mL/min). Compound tert-butyl N-[(1R)-3-hydroxy-1-methyl-propyl]carbamate (19.4 g, 102.51 mmol, 91.3% yield) was obtained as colorless oil.

(R)-tert-butyl (4-(1,3-dioxoisoindolin-2-yl)butan-2-yl)carbamate

To a solution of tert-butyl N-[(1R)-3-hydroxy-1-methyl-propyl]carbamate (5 g, 26.42 mmol, 1 eq) in THF (15 mL) was added PPh₃ (8.32 g, 31.70 mmol, 1.2 eq) and isoindoline-1,3-dione (4.28 g, 29.06 mmol, 1.1 eq). Then DEAD (5.52 g, 31.70 mmol, 5.76 mL, 1.2 eq) was added into the mixture at 0° C. in an inert atmosphere of N₂. The resulting mixture was stirred at 25° C. for 16 hr. The reaction mixture was added H₂O (20 mL) and extracted with EA (30 mL*3). The combined organic layers were washed with brine (80 mL), dried with anhydrous Na₂SO₄, filtered and concentrated under reduced pressure to give a residue. The residue was purified by flash silica gel chromatography (ISCO®; 40 g SepaFlash® Silica Flash Column, Eluent of 0~30% Ethyl acetate/Petroleum ether gradient @ 40 mL/min). Compound (R)-tert-butyl (4-(1,3-dioxoisoindolin-2-yl)butan-2-yl)carbamate (11.7 g, 27.56 mmol, 86.9% yield) was obtained as a yellow solid.

(R)-2-(3-aminobutyl)isoindoline-1,3-dione

To a solution of tert-butyl N-[(1R)-3-(1,3-dioxoisoindolin-2-yl)-1-methyl-propyl]carbamate (8.3 g, 26.07 mmol, 1 eq) in HCl/dioxane (4 M, 95.59 mL, 14.67 eq). The mixture was stirred at 25° C. for 2 hr. The reaction mixture was concentrated under reduced pressure to give a residue. It was used into next step without further purification. Compound 2-[(3R)-3-aminobutyl]isoindoline-1,3-dione (6.6 g, 25.91 mmol, 99.3% yield, HCl) was obtained as a white solid.

(R)-N-(4-(1,3-dioxoisoindolin-2-yl)butan-2-yl)-5-(4-(trifluoromethyl)phenoxy)-2-naphthamide To a solution of 5-[4-(trifluoromethyl)phenoxy]naphthalene-2-carboxylic acid (900 mg, 2.71 mmol, 1 eq), EDCI (778.8 mg, 4.06 mmol, 1.5 eq), HOBt (548.9 mg, 4.06 mmol, 1.5 eq) and TEA (822.2 mg, 8.13 mmol, 1.13 mL, 3 eq) in DCM (3 mL) at 25° C. was added. The mixture was stirred at 25° C. for 0.5 hr. Then 2-[(3R)-3-aminobutyl]isoindoline-1,3-dione (827.9 mg, 3.25 mmol, 1.2 eq, HCl) was added. The resulting mixture was stirred at 25° C. for 15.5 hr. The reaction mixture was added H₂O (10 mL) and extracted with EA (30 mL*3). The combined organic layers were washed with brine (50 mL), dried with anhydrous Na₂SO₄, filtered and concentrated under reduced pressure to give a residue. The residue was purified by flash silica gel chromatography (ISCO®; 12 g SepaFlash® Silica Flash Column, Eluent of 0~30% Ethyl acetate/Petroleum ether gradient @ 30 mL/min). Compound (R)-N-(4-(1,3-dioxoisoindolin-2-yl)butan-2-yl)-5-(4-(trifluoromethyl)phenoxy)-2-naphthamide (1.3 g, 2.37 mmol, 87.4% yield) was obtained as a white solid.

(R)-N-(4-aminobutan-2-yl)-5-(4-(trifluoromethyl)phenoxy)-2-naphthamide

To a solution of N-[(1R)-3-(1,3-dioxoisoindolin-2-yl)-1-methyl-propyl]-5-[4-(trifluoromethyl)phenoxy]naphthalene-2-carboxamide (1.3 g, 2.44 mmol, 1 eq) in EtOH (15 mL) was added NH₂NH₂.H₂O (1.44 g, 24.41 mmol, 1.40 mL, 85%, 10 eq). The mixture was stirred at 25° C. for 6 hr. The reaction mixture was filtered. The cake was washed with EtOH (10 mL), the organic layers concentrated under reduced pressure to give a residue. The residue was added H₂O (10 mL) and extracted with DCM (20 mL*3). The combined organic layers were washed with brine (30 mL), dried with anhydrous Na₂SO₄, filtered and concentrated under reduced pressure to give a residue. It was used into next step without further purification. Compound (R)-N-(4-aminobutan-2-yl)-5-(4-(trifluoromethyl)phenoxy)-2-naphthamide (905 mg, 2.19 mmol, 89.5% yield) was obtained as yellow oil.

(R)-N-(4-((2,4-dimethoxybenzyl)amino)butan-2-yl)-5-(4-(trifluoromethyl)phenoxy)-2-naphthamide To a solution of N-[(1R)-3-amino-1-methyl-propyl]-5-[4-(trifluoromethyl)phenoxy]naphthalene-2-carboxamide (855 mg, 2.12 mmol, 1 eq) and 2,4-dimethoxybenzaldehyde (353.0 mg, 2.12 mmol, 1 eq) in DCM (15 mL) was added AcOH (127.5 mg, 2.12 mmol, 0.12 mL, 1 eq) and NaBH(OAc)$_3$ (900.6 mg, 4.25 mmd, 2 eq). The mixture was stirred at 25° C. for 16 hr. The reaction mixture was added H$_2$O (10 mL) and extracted with DCM (20 mL*3). The combined organic layers were washed with brine (30 mL), dried with anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~15% DCM/MeOH @ 35 mL/min). Compound (R)-N-(4-((2,4-dimethoxybenzyl)amino)butan-2-yl)-5-(4-(trifluoromethyl)phenoxy)-2-naphthamide (1.16 g 1.91 mmol, 89.8% yield) was obtained as yellow oil.

(R)-N-(4-((2,4-dimethoxybenzyl)(2-hydroxyethyl)amino)butan-2-yl)-5-(4-(trifluoromethyl)phenoxy)-2-naphthamide To a solution of N-[(1R)-3-[(2,4-dimethoxyphenyl)methylamino]-1-methyl-propyl]-5-[4-(trifluoromethyl)phenoxy]naphthalene-2-carboxamide (100 mg, 0.18 mmd, 1 eq) in DMF (2 mL) was added K$_2$CO$_3$ (50.0 mg, 0.36 mmol, 2 eq) and 2-bromoethanol (67.8 mg, 0.54 mmol, 38.5 uL, 3 eq). The mixture was stirred at 80° C. for 5 hr. The reaction mixture was added H$_2$O (10 mL) and extracted with DCM (15 mL*3). The combined organic layers were washed with brine (20 mL), dried with anhydrous Na$_2$SO$_4$, filtered and concentrated under reduced pressure to give a residue. It was used into next step without further purification. Compound (R)-N-(4-((2,4-dimethoxybenzyl)(2-hydroxyethyl)amino)butan-2-yl)-5-(4-(trifluoromethyl)phenoxy)-2-naphthamide (142 mg, 0.20 mmol, 76.8% yield) was obtained as a yellow oil.

(R)-N-(4-((2-hydroxyethyl)amino)butan-2-yl)-5-(4-(trifluoromethyl)phenoxy)-2-naphthamide To a solution of (R)-N-(4-((2,4-dimethoxybenzyl)(2-hydroxyethyl)amino)butan-2-yl)-5-(4-(trifluoromethyl)phenoxy)-2-naphthamide (70 mg, 0.11 mmol, 1 eq) in TFA (1.08 g, 9.45 mmol, 0.70 mL, 80.5 eq). The mixture was stirred at 80° C. for 8 hr. The reaction mixture concentrated under reduced pressure to give a residue. The residue was purified by prep-HPLC (column: 3_Phenomenex Luna C18 75*30 mm*3 um; mobile phase: [water (0.05% HCl)–ACN]; B %: 20%-50%, 6.5 min). The title compound (4.2 mg, 8.4 umol, 7.2% yield, HCl) was obtained as a white solid. LCMS (ESI): RT=0.861 min, mass calcd for C$_{24}$H$_{25}$F$_3$N$_2$O 3446.46 m/z found 447.3[M+H]$^+$, $^1$H NMR (400 MHz, CD$_3$OD) δ 1.40 (d, J=6.78 Hz, 3H) 1.87-2.17 (m, 2H) 3.04-3.25 (m, 4H) 3.83 (t, J=5.14 Hz, 2H) 4.23-4.36 (m, 1H) 7.13 (d, J=8.53 Hz, 2H) 7.24 (d, J=7.53 Hz, 1H) 7.60 (t, J=8.03 Hz, 1H) 7.66 (d, J=8.78 Hz, 2H) 7.88-7.96 (m, 2H) 8.11 (d, J=8.78 Hz, 1H) 8.52 (s, 1H).

Example 112: (R)-N-(4-((2-fluoroethyl)amino)butan-2-yl)-5-(4-(trifluoromethyl)phenoxy)-2-naphthamide (Compound 148)

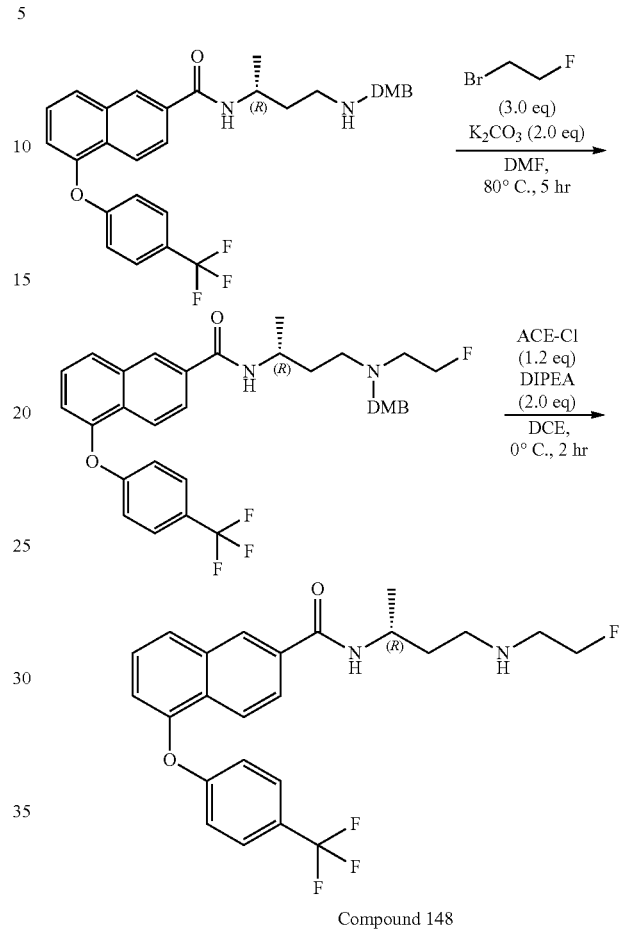

Compound 148

(R)-N-(4-((2,4-dimethoxybenzyl)(2-fluoroethyl)amino)butan-2-yl)-5-(4-(trifluoromethyl)phenoxy)-2-naphthamide To a solution of (R)-N-(4-((2,4-dimethoxybenzyl)amino)butan-2-yl)-5-(4-(trifluoromethyl)phenoxy)-2-naphthamide (150 mg, 0.27 mmol, 1 eq) in DMF (1 mL) was added K$_2$CO$_3$ (75.0 mg, 0.54 mmol, 2 eq) and 1-bromo-2-fluoroethane (103.3 mg, 0.81 mmol, 3 eq). The mixture was stirred at 80° C. for 5 hr. The reaction mixture was added H$_2$O (10 mL) and extracted with DCM (10 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~60% Ethyl acetate/Petroleum ether gradient @ 20 mL/min). Compound (R)-N-(4-((2,4-dimethoxybenzyl)(2-fluoroethyl)amino)butan-2-yl)-5-(4-(trifluoromethyl)phenoxy)-2-naphthamide (71 mg, 0.11 mmol, 41.7% yield) was obtained as a colorless oil.

(R)-N-(4-((2-fluoroethyl)amino)butan-2-yl)-5-(4-(trifluoromethyl)phenoxy)-2-naphthamide To a solution of N-[(1R)-3-[(2,4-dimethoxyphenyl)methyl-(2-fluoroethyl)amino]-1-methyl-propyl]-5-[4-(trifluoromethyl)phenoxy]naphthalene-2-carboxamide (60 mg, 0.10 mmol, 1 eq) in DCE (1 mL) were added DIPEA (25.9 mg, 0.20 mmol, 34.9 uL, 2 eq) and 1-chloroethyl chloroformate (ACE-Cl) (17.2 mg, 0.12 mmol, 1.2 eq) at 0° C. Then the mixture was stirred at 0° C. to 25° C. for 2 hr. The reaction mixture was concentrated under reduced pressure to remove DCE to give a residue. The residue was added MeOH (5 mL) and the mixture was stirred at 60° C. for 0.5 hr. The residue was purified by prep-HPLC (column: 3_Phenomenex Luna C18 75*30 mm*3 um; mobile phase: [water (0.05% HCl)–ACN]; B %: 30%-60%, 6.5 min). The title compound (23.6 mg, 48.8 umol, 48.7% yield, HCl) was obtained as a white solid. LCMS (ESI): RT=0.869 min, mass calcd for $C_{24}H_{23}F_5N_2O$ 2448.45 m/z found 449.3[M+H]$^+$; $^1$H NMR (400 MHz, CD$_3$OD) δ 1.41 (d, J=6.78 Hz, 3H) 1.86-2.17 (m, 2H) 3.09-3.26 (m, 2H) 3.36-3.50 (m, 2H) 4.23-4.41 (m, 1H) 4.70-4.85 (m, 2H) 7.14 (d, J=8.53 Hz, 2H) 7.25 (d, J=7.53 Hz, 1H) 7.60 (t, J=8.03 Hz, 1H) 7.67 (d, J=8.78 Hz, 2H) 7.88-7.99 (m, 2H) 8.11 (d, J=8.78 Hz, 1H) 8.51 (d, J=1.26 Hz, 1H).

Example 113: (R)-N-(4-((2,2-difluoroethyl)amino)butan-2-yl)-5-(4-(trifluoromethyl)phenoxy)-2-naphthamide (Compound 149)

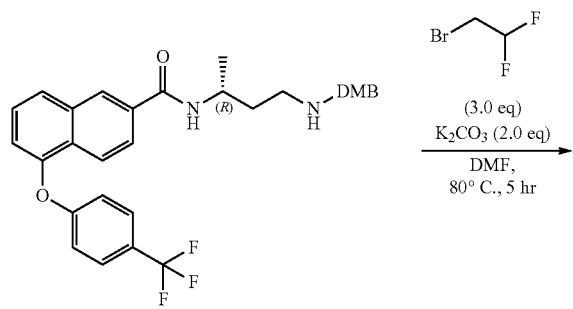

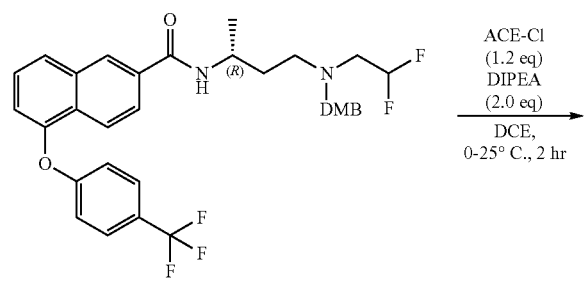

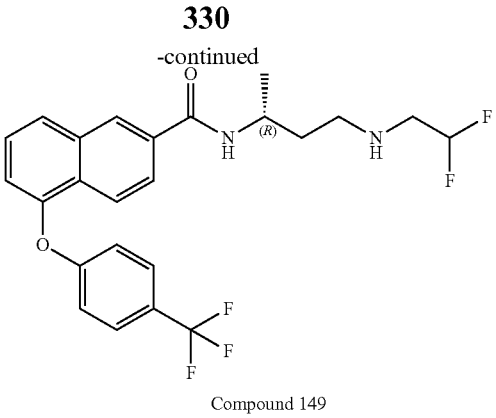

Compound 149

(R)-N-(4-((2,2-difluoroethyl)(2,4-dimethoxybenzyl)amino)butan-2-yl)-5-(4-(trifluoromethyl)phenoxy)-2-naphthamide To a solution of N-[(1R)-3-[(2,4-dimethoxyphenyl)methylamino]-1-methyl-propyl]-5-[4-(trifluoromethyl)phenoxy]naphthalene-2-carboxamide (150 mg, 0.2 mmol, 1 eq) in DMF (1 mL) was added K$_2$CO$_3$ (75.0 mg, 0.54 mmol, 2 eq) and 2-bromo-1,1-difluoro-ethane (118.0 mg, 0.81 mmol, 3 eq). The mixture was stirred at 80° C. for 5 hr. The reaction mixture was added H$_2$O (10 mL) and extracted with EA (10 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~40% Ethyl acetate/Petroleum ether gradient @ 20 mL/min). Compound N-[(1R)-3-[2,2-difluoroethyl-[(2,4-dimethoxyphenyl)methyl]amino]-1-methyl-propyl]-5-[4-(trifluoromethyl)phenoxy]naphthalene-2-carboxamide (92 mg, 96.9 umol, 35.7% yield) was obtained as a colorless oil.

(R)-N-(4-((2,2-difluoroethyl)amino)butan-2-yl)-5-(4-(trifluoromethyl)phenoxy)-2-naphthamide To a solution of N-[(1R)-3-[2,2-difluoroethyl-[(2,4-dimethoxyphenyl)methyl]amino]-1-methyl-propyl]-5-[4-(trifluoromethyl)phenoxy]naphthalene-2-carboxamide (80 mg, 0.12 mmol, 1 eq) in DCE (0.5 mL) were added DIEA (33.5 mg, 0.25 mmol, 45.2 uL, 2 eq) and 1-chloroethyl chloroformate (ACE-Cl) (22.2 mg, 0.15 mmol, 1.2 eq) at 0° C. Then the mixture was stirred at 0° C. to 25° C. for 2 hr. The reaction mixture was concentrated under reduced pressure to remove DCE to give a residue. The residue was added MeOH (5 mL) and the mixture was stirred at 60° C. for 0.5 hr. The residue was purified by prep-HPLC (column: 3_Phenomenex Luna C$_{18\ 75*30}$ mm*3 um; mobile phase: [water (0.05% HCl)–ACN]; B %: 30%-60%, 6.5 min). The title compound (15.4 mg, 30.7 umol, 23.6% yield, HCl) was obtained as a white solid. LCMS (ESI): RT=0.888 min, mass calcd for $C_{24}H_{23}F_5N_2O_2$466.44 m/z found 467.3[M+H]$^+$. $^1$H NMR (400 MHz, CD$_3$OD) δ 1.42 (d, J=6.63 Hz, 3H) 1.92-2.18 (m, 2H) 3.15-3.29 (m, 2H) 3.61 (tt, J=15.43, 3.77 Hz, 2H) 4.23-4.40 (m, 1H) 6.20-6.51 (m, 1H) 7.14 (d, J=8.63 Hz, 2H) 7.25 (d, J=7.25 Hz, 1H) 7.61 (t, J=7.94 Hz, 1H) 7.67 (d, J=8.63 Hz, 2H) 7.87-7.99 (m, 2H) 8.12 (d, J=8.75 Hz, 1H) 8.53 (d, J=1.50 Hz, 1H).

Example 114: (R)-N-(1-(piperidin-4-yl)ethyl)-5-(4-(trifluoromethyl)phenoxy)-2-naphthamide (Compound 150)

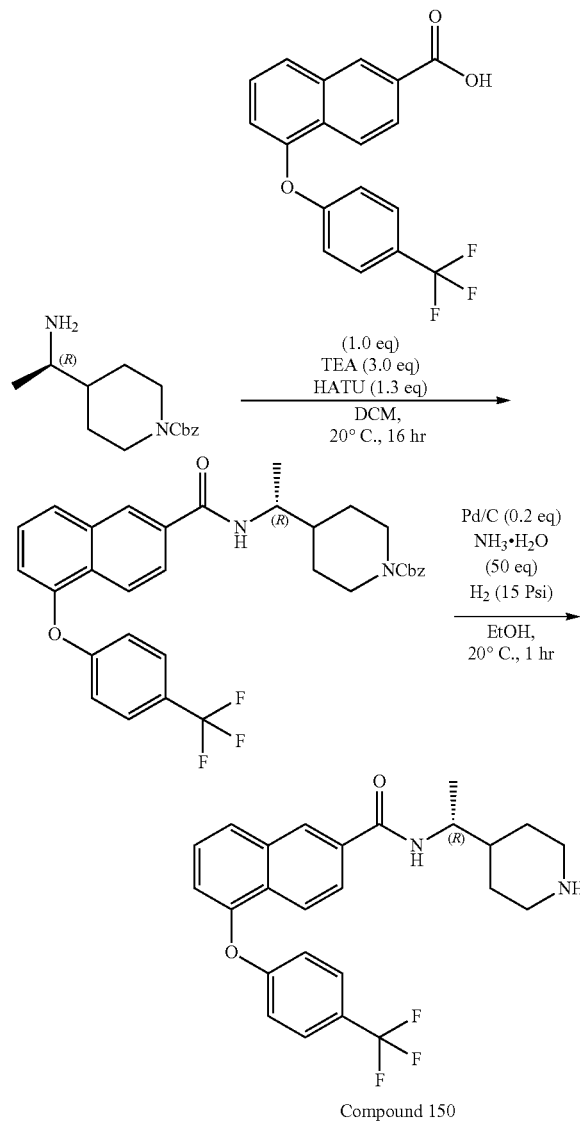

Compound 150

(R)-benzyl 4-(1-(5-(4-(trifluoromethyl)phenoxy)-2-naphthamido)ethyl)piperidine-1-carboxylate To a solution of 5-(4-(trifluoromethyl)phenoxy)-2-naphthoic acid (100 mg, 0.30 mmol, 1 eq), benzyl (R)-4-(1-aminoethyl)piperidine-1-carboxylate (86.9 mg, 0.33 mmol, 1.1 eq) and HATU (148.8 mg, 0.39 mmol, 1.3 eq) in DMF (2 mL) at 20° C. was added TEA (91.4 mg, 0.90 mmol, 0.13 mL, 3 eq) drop-wise, and the mixture was stirred at 20° C. for 16 h. The reaction mixture was diluted with water (20 mL) and extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~60% Ethyl acetate/Petroleum ether gradient @ 20 mL/min) to give (R)-benzyl 4-(1-(5-(4-(trifluoromethyl)phenoxy)-2-naphthamido)ethyl)piperidine-1-carboxylate (160 mg, 0.27 mmol, 89.4% yield) as colorless oil. LCMS (ESI): RT=1.005 min, mass calc. for C$_{33}$H$_{31}$F$_3$N$_2$O$_4$ 576.22, m/z found 577.1 [M+1]$^+$.

(R)-N-(1-(piperidin-4-yl)ethyl)-5-(4-(trifluoromethyl)phenoxy)-2-naphthamide To a solution of (R)-benzyl 4-(1-(5-(4-(trifluoromethyl)phenoxy)-2-naphthamido)ethyl)piperidine-1-carboxylate (140 mg, 0.24 mmol, 1 eq) and NH$_3$·H$_2$O (1.70 g, 12.14 mmol, 1.87 mL, 25%, 50 eq) in EtOH (2 mL) at 20° C. was added Pd/C (25.8 mg, 24.3 umol, 10%, 0.1 eq), and the mixture was purged and degassed with H$_2$ for 3 times and then stirred at 20° C. under H$_2$ (15 Psi) for 1 h. The reaction mixture was filtered to remove Pd/C and the filtrate was concentrated under reduced pressure to give the title compound (101.4 mg, 0.23 mmol, 94.4% yield) as a white solid. LCMS (ESI): RT=0.779 min, mass calc. for C$_{25}$H$_{25}$F$_3$N$_2$O$_2$ 442.19, m/z found 443.1[M+1]$^+$; $^1$H NMR (400 MHz, CDCl$_3$) δ 8.34 (s, 1H), 8.12 (d, J=8.5 Hz, 1H), 7.85-7.77 (m, 2H), 7.60 (d, J=8.3 Hz, 2H), 7.52 (t, J=7.9 Hz, 1H), 7.15 (d, J=7.0 Hz, 1H), 7.07 (d, J=8.3 Hz, 2H), 6.06 (d, J=8.8 Hz, 1H), 4.21 (dd, J=6.4, 15.4 Hz, 1H), 3.15 (d, J=9.3 Hz, 2H), 2.67-2.58 (m, 2H), 1.83-1.70 (m, 2H), 1.68-1.63 (m, 1H), 1.40-1.30 (m, 2H), 1.27 (d, J=6.8 Hz, 3H).

Example 115: (S)-N-(1-(3-fluoroazetidin-3-yl)ethyl)-5-(4-(trifluoromethyl)phenoxy)-2-naphthamide (Compound 151)

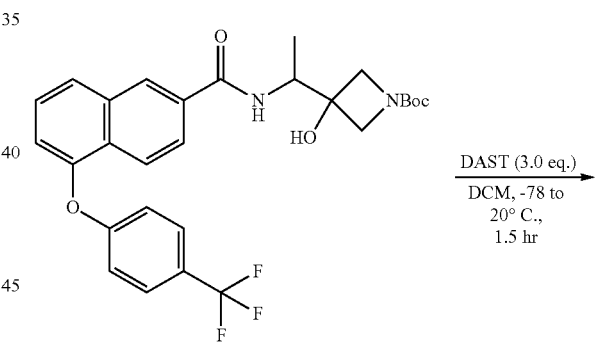

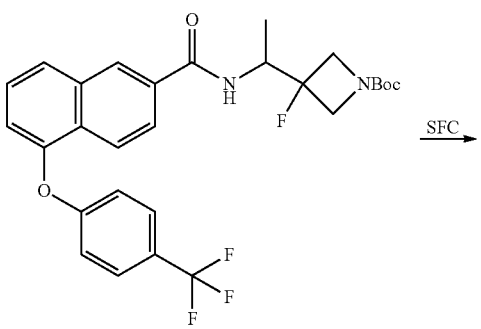

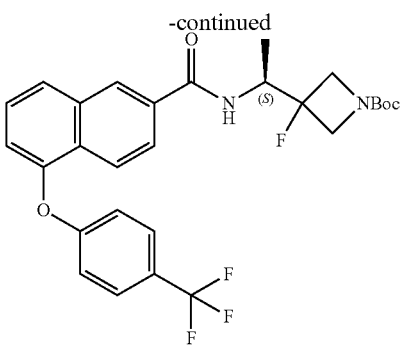

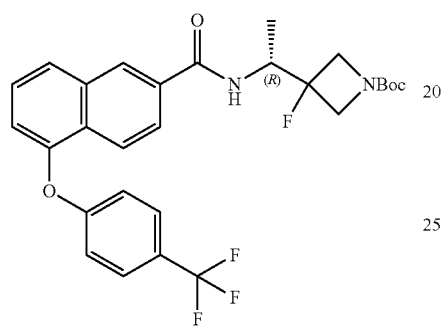

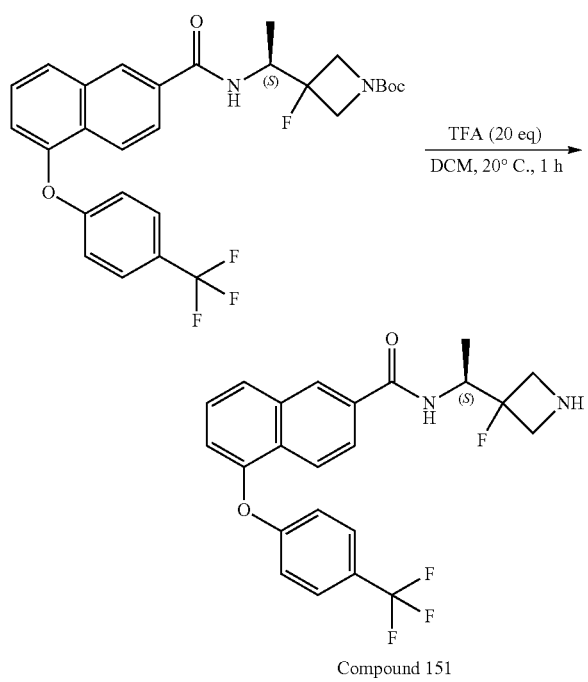

Compound 151 tert-butyl 3-fluoro-3-(1-(5-(4-(trifluoromethyl)phenoxy)-2-naphthamido)ethyl)azetidine-1-carboxylate To a solution of tert-butyl 3-hydroxy-3-(1-(5-(4-(trifluoromethyl)phenoxy)-2-naphthamido)ethyl)azetidine-1-carboxylate (450 mg, 0.85 mmol, 1 eq) in DCM (4 mL) at −78° C. was added DAST (410.2 mg, 2.54 mmol, 0.34 mL, 3 eq), and the mixture was stirred at −78° C. for 1 h and then at 20° C. for another 0.5 h. The reaction mixture was quenched with water (5 mL), then diluted with saturated NaHCO$_3$ (30 mL) and extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @ 30 mL/min) to give 400 mg sample as a yellow solid. The 400 mg sample was purified by prep-HPLC (column: Welch Xtimate C18 150*25 mm*5 um; mobile phase: [water (0.04% NH$_3$H$_2$O+10 mM NH$_4$HCO$_3$)–ACN]; B %: 60%-90%, 9.5 min) to give tert-butyl 3-fluoro-3-(1-(5-(4-(trifluoromethyl)phenoxy)-2-naphthamido)ethyl)azetidine-1-carboxylate (190 mg, 0.36 mmol, 42.1% yield) as a yellow solid. LCMS (ESI): RT=0.999 min, mass calc. for C$_{28}$H$_{28}$F$_4$N$_2$O$_4$ 532.20, m/z found 533.1 [M+1]$^+$.

(S)-tert-butyl 3-fluoro-3-(1-(5-(4-(trifluoromethyl)phenoxy)-2-naphthamido)ethyl)azetidine-1-carboxylate The sample of tert-butyl 3-fluoro-3-(1-(5-(4-(trifluoromethyl)phenoxy)-2-naphthamido)ethyl)azetidine-1-carboxylate (90 mg, 0.17 mmol, 1 eq) was purified by SFC (column: DAICEL CHIRALPAK AD (250 mm*30 mm, 10 um); mobile phase: [0.1% NH$_3$H$_2$O ETOH]; B %: 25%-25%, min) to give (S)-tert-butyl 3-fluoro-3-(1-(5-(4-(trifluoromethyl)phenoxy)-2-naphthamido)ethyl)azetidine-1-carboxylate (30 mg, 56.3 umol, 33.3% yield) and (R)-tert-butyl 3-fluoro-3-(1-(5-(4-(trifluoromethyl)phenoxy)-2-naphthamido)ethyl)azetidine-1-carboxylate (40 mg, 74.4 umol, 44.0% yield) both as a white solid. (S)-tert-butyl 3-fluoro-3-(1-(5-(4-(trifluoromethyl)phenoxy)-2-naphthamido)ethyl)azetidine-1-carboxylate: LCMS (ESI): RT=1.002 min, mass calc. for C$_{28}$H$_{28}$F$_4$N$_2$O$_4$ 532.20, m/z found 533.1 [M+1]$^+$. (R)-tert-butyl 3-fluoro-3-(1-(5-(4-(trifluoromethyl)phenoxy)-2-naphthamido)ethyl)azetidine-1-carboxylate: LCMS (ESI): RT=1.004 min, mass calc. for C$_{28}$H$_{28}$F$_4$N$_2$O$_4$ 532.20, m/z found 533.1 [M+1]$^+$.

(S)-N-(1-(3-fluoroazetidin-3-yl)ethyl)-5-(4-(trifluoromethyl)phenoxy)-2-naphthamide To a solution of (S)-tert-butyl 3-fluoro-3-(1-(5-(4-(trifluoromethyl)phenoxy)-2-naphthamido)ethyl)azetidine-1-carboxylate (25 mg, 47.0 umol, 1 eq) in DCM (0.5 mL) at 20° C. was added TFA (107.1 mg, 0.94 mmol, 70 uL, 20 eq), and the mixture was stirred at 20° C. for 1 h. The reaction mixture was concentrated under reduced pressure to give a residue. The sample was purified by prep-HPLC (column: Welch Xtimate C18 150*25 mm*5 um; mobile phase: [water (0.05% NH$_3$H$_2$O)–ACN]; B %: 59%-89%, 9.5 min) to give the title compound (5.0 mg, 11.5 umol, 24.6% yield) as a gray solid. LCMS (ESI): RT=0.784 min, mass calc. for C$_{23}$H$_{20}$F$_4$N$_2$O$_2$ 432.15, m/z found 433.0 [M+1]$^+$; $^1$H NMR (400 MHz, CDCl$_3$) δ 8.38 (s, 1H), 8.14 (d, J=8.8 Hz, 1H), 7.86-7.78 (m, 2H), 7.60 (d, J=8.5 Hz, 2H), 7.52 (t, J=7.9 Hz, 1H), 7.16 (d, J=7.5 Hz, 1H), 7.08 (br d, J=8.5 Hz, 2H), 6.77 (br s, 1H), 5.40-5.25 (m, 1H), 4.16 (br d, J=7.5 Hz, 1H), 4.00 (br d, J=9.0 Hz, 1H), 3.89 (br d, J=9.5 Hz, 2H), 1.54-1.44 (m, 3H).

Example 116: (R)-N-(1-(3-fluoroazetidin-3-yl)ethyl)-5-(4-(trifluoromethyl)phenoxy)-2-naphthamide (Compound 152)

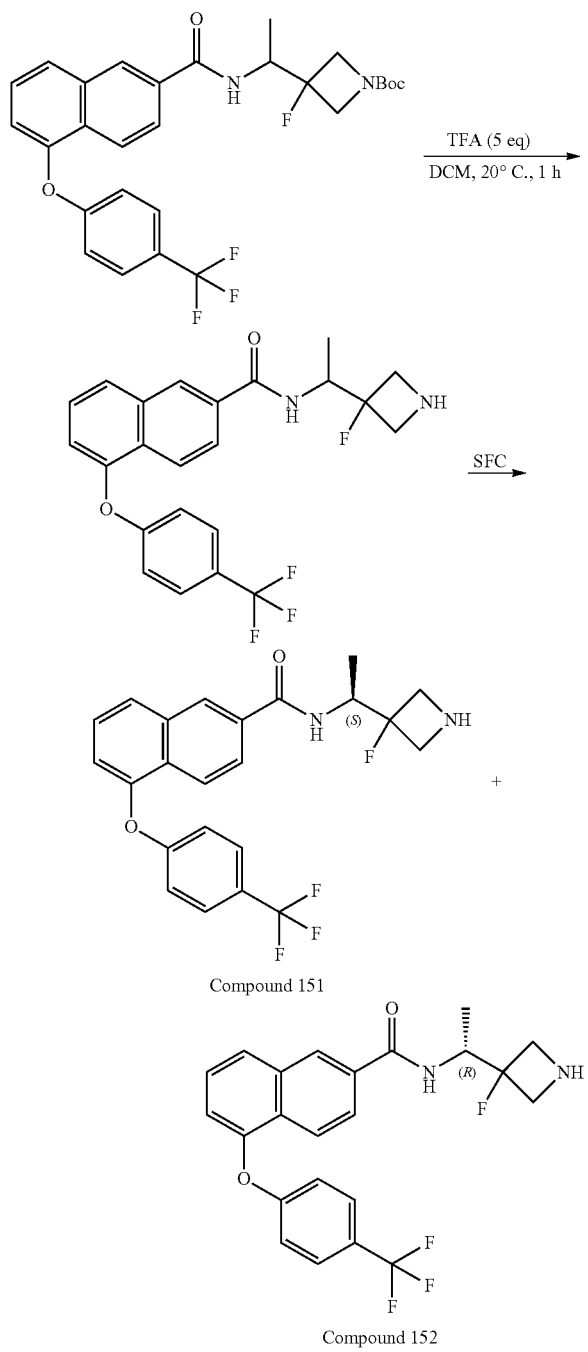

Compound 151

Compound 152

N-(1-(3-fluoroazetidin-3-yl)ethyl)-5-(4-(trifluoromethyl)phenoxy)-2-naphthamide To a solution of tert-butyl 3-fluoro-3-(1-(5-(4-(trifluoromethyl)phenoxy)-2-naphthamido)ethyl)azetidine-1-carboxylate (80 mg, 0.15 mmol, 1 eq) in DCM (0.5 mL) at 20° C. was added TFA (85.7 mg, 0.75 mmol, 56 uL, 5 eq), and the mixture was stirred at 20° C. for 1 h. The reaction mixture was concentrated under reduced pressure to give a residue. The residue was purified by prep-HPLC (column: Welch Ultimate C18 150*25 mm*5 um; mobile phase: [water (0.225% FA)–ACN]; B %: 20%-50%, 9.5 min) to give N-(1-(3-fluoroazetidin-3-yl)ethyl)-5-(4-(trifluoromethyl)phenoxy)-2-naphthamide (40 mg, 83.6 umol, 55.7% yield, FA) as colorless oil. LCMS (ESI): RT=0.785 min, mass calc. for $C_{23}H_{20}F_4N_2O_2$ 432.15, m/z found 433.0 [M+H]$^+$.

(R)-N-(1-(3-fluoroazetidin-3-yl)ethyl)-5-(4-(trifluoromethyl)phenoxy)-2-naphthamide The sample of N-(1-(3-fluoroazetidin-3-yl)ethyl)-5-(4-(trifluoromethyl)phenoxy)-2-naphthamide (40 mg, 92.5 umol, 1 eq) was purified by SFC (column: DAICEL CHIRALPAK IC (250 mm*30 mm, 5 um); mobile phase: [0.1% NH$_3$H$_2$O MEOH]; B %: 25%-25%, min) to give 15 mg P1 and 13 mg P2, both as a yellow solid. The 15 mg of P1 was further purified by prep-HPLC (column: Welch Xtimate C18 150*25 mm*5 um; mobile phase: [water (0.05% NH$_3$H$_2$O)–ACN]; B %: 59%-89%, 9.5 min) to give the title compound (5.5 mg, 12.4 umol, 13.4% yield) as a yellow solid. LCMS (ESI): RT=0.785 min, mass calc. for $C_{23}H_{20}F_4N_2O_2$ 432.15, m/z found 433.1 [M+H]$^+$; $^1$H NMR (400 MHz, CDCl$_3$) δ 8.38 (s, 1H), 8.15 (br d, J=8.5 Hz, 1H), 7.87-7.76 (m, 2H), 7.60 (br d, J=8.8 Hz, 2H), 7.52 (t, J=8.0 Hz, 1H), 7.16 (d, J=7.5 Hz, 1H), 7.08 (br d, J=8.5 Hz, 2H), 6.75 (br s, 1H), 5.39-5.25 (m, 1H), 4.17 (br d, J=8.3 Hz, 1H), 4.01 (br d, J=8.5 Hz, 1H), 3.90 (br d, J=9.5 Hz, 2H), 1.54-1.44 (m, 3H).

Example 117: (R)-N-(1-(1-(2-hydroxyethyl)piperidin-4-yl)ethyl)-5-(4-(trifluoromethyl)phenoxy)-2-naphthamide (Compound 153)

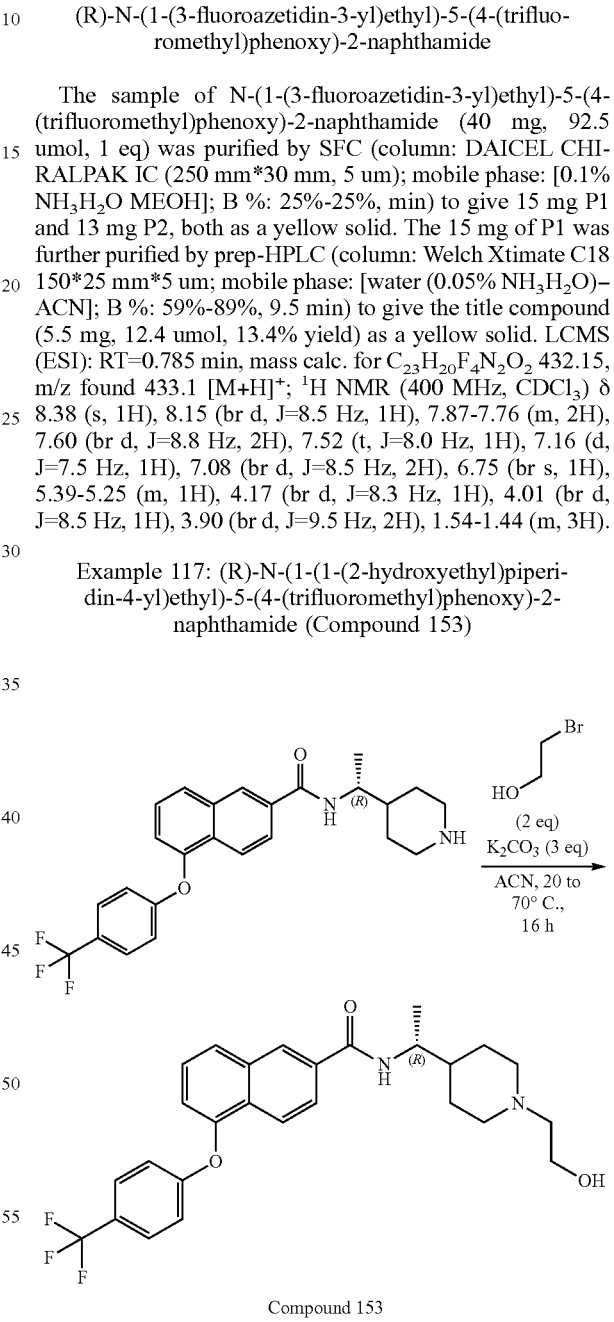

Compound 153

To a solution of (R)-N-(1-(piperidin-4-yl)ethyl)-5-(4-(trifluoromethyl)phenoxy)-2-naphthamide (40 mg, 90.4 umol, 1 eq) and 2-bromoethan-1-ol (22.6 mg, 0.18 mmol, 13 uL, 2 eq) in ACN (1 mL) was added K$_2$CO$_3$ (37.5 mg, 0.27 mmol, 3 eq) and the reaction was stirred at 70° C. for 16 h. The mixture was concentrated under reduced pressure to give a residue. The residue was purified by prep-HPLC (column: 3_Phenomenex Luna C18 75*30 mm*3 um; mobile phase: [water (0.05% HCl)–ACN]; B %: 25%-55%, 6.5 min) to give the title compound (11.7 mg, 22.5 umol, 24.9% yield, HCl) as a white solid. LCMS (ESI): RT=0.850 min, mass calc. for $C_{27}H_{29}F_3N_2O_3$ 486.21, m/z found 487.2 [M+H]$^+$; $^1$H NMR (400 MHz, DMSO-d$_6$) δ 9.52 (br s, 1H), 8.57 (s, 1H), 8.48 (br d, J=8.5 Hz, 1H), 8.00-7.94 (m, 3H), 7.75 (d, J=8.8 Hz, 2H), 7.64 (t, J=7.9 Hz, 1H), 7.34 (d, J=7.5 Hz, 1H), 7.15 (d, J=8.5 Hz, 2H), 4.02-3.94 (m, 1H), 3.74 (br t, J=5.1 Hz, 2H), 3.53 (br d, J=11.8 Hz, 2H), 3.11 (br d, J=5.0 Hz, 2H), 2.97-2.84 (m, 2H), 1.89 (br d, J=11.8 Hz, 2H), 1.63 (br s, 3H), 1.20-1.16 (m, 3H).

Example 118: (R)-N-(1-(1-(2-fluoroethyl)piperidin-4-yl)ethyl)-5-(4-(trifluoromethyl)phenoxy)-2-naphthamide (Compound 154)

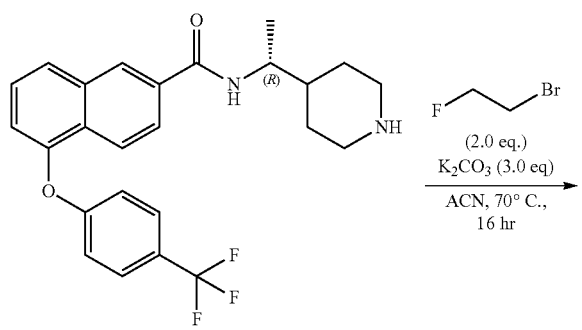

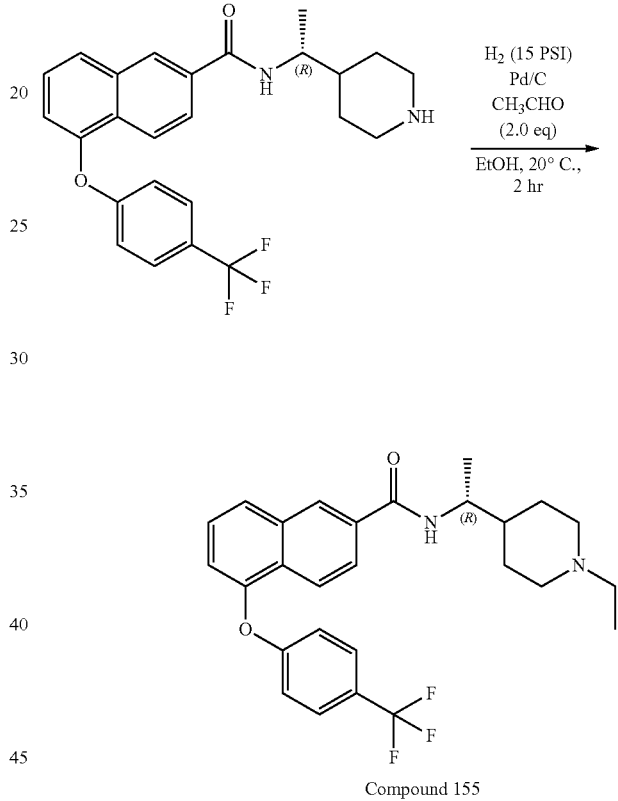

Compound 154

To a solution of (R)-N-(1-(piperidin-4-yl)ethyl)-5-(4-(trifluoromethyl)phenoxy)-2-naphthamide (50.0 mg, 0.11 mmol, 1.0 eq) and 1-bromo-2-fluoroethane (28.7 mg, 0.23 mmol, 13 uL, 2.0 eq) in ACN (1 mL) was added K$_2$CO$_3$ (46.9 mg, 0.34 mmol, 3.0 eq) and the reaction was stirred at 70° C. for 16 h. The mixture was concentrated under reduced pressure to give a residue, which was purified by prep-HPLC: (column: Welch Xtimate C18 150*25 mm*5 um; mobile phase: [water (0.05% NH$_3$H$_2$O)–ACN]; B %: 55%-85%, 7.8 min) to give the title compound (37.4 mg, 76 umol, 67.6% yield) as a white solid. LCMS (ESI): RT=0.878 min, mass calc. for $C_{27}H_{28}F_4N_2O_2$ 488.21, m/z found 489.2 [M+H]$^+$; $^1$H NMR (400 MHz, DMSO-d$_6$) δ 8.54 (s, 1H), 8.38 (br d, J=8.6 Hz, 1H), 8.00-7.93 (m, 3H), 7.74 (d, J=8.6 Hz, 2H), 7.63 (t, J=7.9 Hz, 1H), 7.32 (d, J=7.5 Hz, 1H), 7.15 (d, J=8.5 Hz, 2H), 4.62-4.43 (m, 2H), 3.97-3.86 (m, 1H), 3.47-3.35 (m, 2H), 2.96 (brs, 2H), 2.70-2.53 (m, 2H), 2.26-1.88 (m, 2H), 1.72 (br d, J=10.8 Hz, 2H), 1.45 (brs, 1H), 1.34-1.22 (m, 2H), 1.16 (d, J=6.8 Hz, 3H).

Example 119: (R)-N-(1-(1-ethylpiperidin-4-yl)ethyl)-5-(4-(trifluoromethyl)phenoxy)-2-naphthamide (Compound 155)

Compound 155

To a solution of (R)-N-(1-(piperidin-4-yl)ethyl)-5-(4-(trifluoromethyl)phenoxy)-2-naphthamide (40.0 mg, 90 umol, 1.0 eq) and acetaldehyde (19.9 mg, 0.18 mmol, 25 uL, 40%, 2.0 eq) in EtOH (1 mL) was added Pd/C (25.0 mg, 23 umol, 10%, 0.26 eq) and the reaction was purged and degassed with H$_2$ and then stirred at 20° C. for 2 h under H$_2$ (15 PSI). The mixture was concentrated under reduced pressure to give a residue, which was purified by prep-HPLC: (column: 3_Phenomenex Luna C18 75*30 mm*3 um; mobile phase: [water (0.05% HCl)–ACN]; B %: 20%-50%, 6.5 min) to give the title compound (6.19 mg, 12 umol, 13.5% yield, HCl) as a white solid. LCMS (ESI): RT=0.876 min, mass calc. for $C_{27}H_{29}F_3N_2O_2$ 470.22, m/z found 471.2 [M+H]$^+$; $^1$H NMR (400 MHz, DMSO-d$_6$) δ 10.46 (brs, 1H), 8.60 (brs, 1H), 8.56 (brs, 1H), 7.96 (brs, 3H), 7.74 (brs, 2H), 7.63 (brs, 1H), 7.33 (brs, 1H), 7.15 (brs, 2H), 3.98 (brs, 1H), 3.02 (brs, 2H), 2.80 (brs, 4H), 1.87 (brs, 2H), 1.71 (brs, 3H), 1.21 (br d, J=18.8 Hz, 8H).

Example 120: (R)-N-(1-(1-isopropylpiperidin-4-yl)ethyl)-5-(4-(trifluoromethyl)phenoxy)-2-naphthamide (Compound 156)

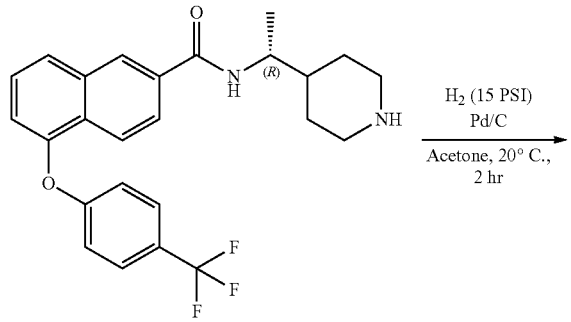

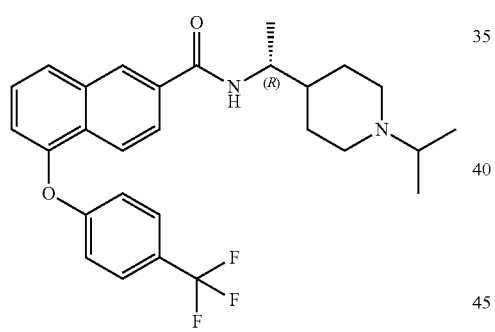

Compound 156

To a solution of (R)-N-(1-(piperidin-4-yl)ethyl)-5-(4-(trifluoromethyl)phenoxy)-2-naphthamide (40.0 mg, 90 umol, 1.0 eq) in acetone (1 mL) was added Pd/C (25.0 mg, 23 umol, 10%, 0.26 eq) and the reaction was purged and degassed with $H_2$ and then stirred at 20° C. for 2 h under $H_2$ (15 PSI). The mixture was concentrated under reduced pressure to give a residue, which was purified by prep-HPLC: (column: 3_Phenomenex Luna C18 75*30 mm*3 um; mobile phase: [water (0.05% HCl)–ACN]; B %: 20%-50%, 8.5 min) to give the title compound (2.0 mg, 4 umol, 4.25% yield, HCl) as a white solid. LCMS (ESI): RT=0.888 min, mass calc. for $C_{28}H_{31}F_3N_2O_2$ 484.23, m/z found 485.3 [M+H]$^+$; $^1$H NMR (400 MHz, DMSO-d$_6$) δ 10.33 (brs, 1H), 8.62 (brs, 1H), 8.54 (br d, J=7.8 Hz, 1H), 7.97 (brs, 3H), 7.74 (br d, J=7.8 Hz, 2H), 7.63 (brs, 1H), 7.32 (bid, J=7.0 Hz, 1H), 7.15 (br d, J=7.8 Hz, 2H), 3.99 (brs, 1H), 3.44-3.44 (m, 1H), 3.34-3.33 (m, 1H), 2.89 (brs, 3H), 1.89-1.75 (m, 5H), 1.25 (br d, J=4.8 Hz, 6H), 1.18 (br d, J=5.3 Hz, 3H).

Example 121: (R)-N-(1-(1-methylpiperidin-4-yl)ethyl)-5-(4-(trifluoromethyl)phenoxy)-2-naphthamide (Compound 157)

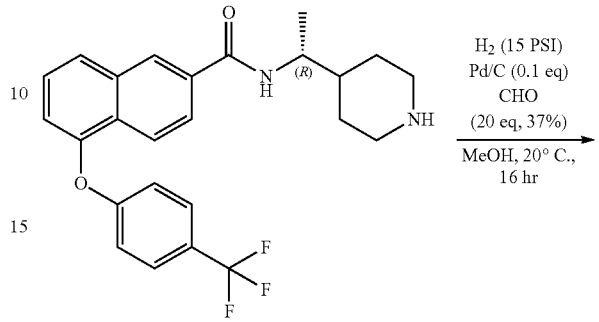

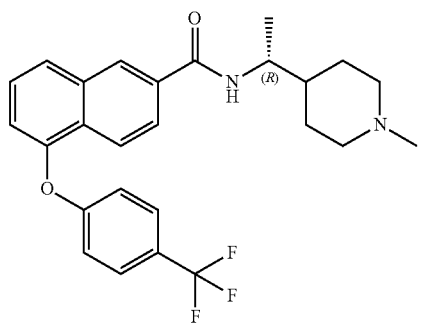

Compound 157

To a solution of (R)-N-(1-(piperidin-4-yl)ethyl)-5-(4-(trifluoromethyl)phenoxy)-2-naphthamide (40 mg, 90.4 umol, 1 eq) and formaldehyde (146.7 mg, 1.81 mmol, 0.13 mL, 37%, 20 eq) in MeOH (1 mL) at 20° C. was added Pd/C (9.6 mg, 9.0 umol, 10%, 0.1 eq), and the mixture was purged and degassed with $H_2$ for 3 times and then stirred at 20° C. under $H_2$ (15 Psi) for 16 h. The reaction mixture was filtered to remove Pd/C and the filtrate was concentrated under reduced pressure to give a residue. The residue was purified by prep-HPLC (column: 3_Phenomenex Luna C18 75*30 mm*3 um; mobile phase: [water (0.05% HCl)–ACN]; B %: 20%/6-50%, 6.5 min) to give the title compound (12.9 mg, 25.8 umol, 28.6% yield, HCl) as a yellow solid. LCMS (ESI): RT=0.786 min, mass calc. for $C_{26}H_{27}F_3N_2O_2$ 456.20, m/z found 457.1 [M+H]$^+$; $^1$H NMR (400 MHz, DMSO-d$_6$) δ 10.25 (br dd, J=2.9, 5.4 Hz, 1H), 8.58 (s, 1H), 8.51 (br d, J=8.5 Hz, 1H), 8.03-7.91 (m, 3H), 7.74 (br d, J=8.8 Hz, 2H), 7.63 (t, J=7.9 Hz, 1H), 7.33 (d, J=7.3 Hz, 1H), 7.15 (br d, J=8.5 Hz, 2H), 4.04-3.90 (m, 1H), 3.39 (br d, J=11.5 Hz, 2H), 2.97-2.78 (m, 2H), 2.69 (br d, J=4.5 Hz, 3H), 1.89 (br d, J=13.1 Hz, 2H), 1.76-1.47 (m, 3H), 1.18 (br d, J=6.8 Hz, 3H).

Example 122: (R)-N-(1-(1-(2,2-difluoroethyl)piperidin-4-yl)ethyl)-5-(4-(trifluoromethyl)phenoxy)-2-naphthamide (Compound 162)

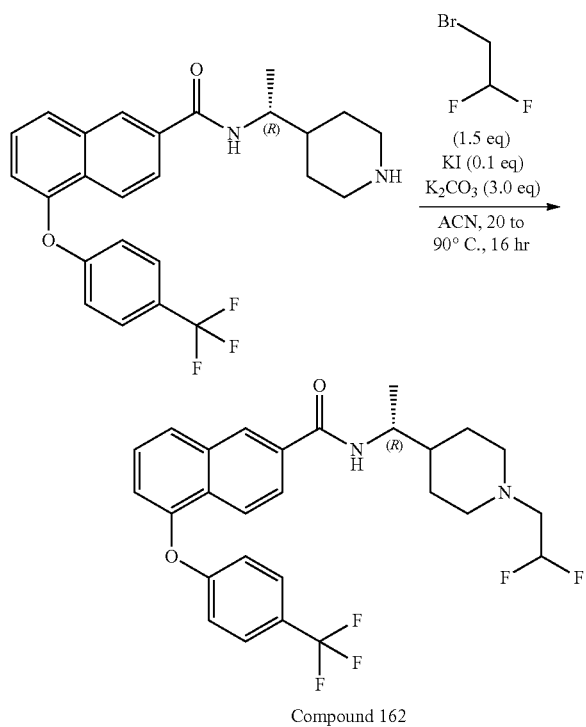

Compound 162

To a solution of (R)-N-(1-(piperidin-4-yl)ethyl)-5-(4-(trifluoromethyl)phenoxy)-2-naphthamide (50 mg, 0.11 mmol, 1 eq), 2-bromo-1,1-difluoroethane (24.6 mg, 0.17 mmol, 1.5 eq) and $K_2CO_3$ (46.9 mg, 0.34 mmol, 3 eq) in ACN (2 mL) at 20° C. was added KI (1.9 mg, 11.3 umol, 0.1 eq), and the resulting mixture was stirred at 90° C. for 16 h. The reaction mixture was concentrated under reduced pressure to give a residue. The residue was purified by prep-HPLC (column: Welch Xtimate C18 150*25 mm*5 um; mobile phase: [water (0.05% ammonia hydroxide v/v)–ACN]; B %: 55%-85%, 7.8 min) to give the title compound (17.4 mg, 33.8 umol, 29.9% yield) as a white solid. LCMS (ESI): RT=0.807 min, mass calc. for $C_{27}H_{27}F_5N_2O_2$ 506.20, m/z found 507.1 $[M+H]^+$; $^1H$ NMR (400 MHz, $CDCl_3$) δ 8.33 (d, J=1.3 Hz, 1H), 8.12 (d, J=8.8 Hz, 1H), 7.81 (d, J=8.8 Hz, 2H), 7.60 (d, J=8.8 Hz, 2H), 7.52 (t, J=8.0 Hz, 1H), 7.15 (d, J=7.5 Hz, 1H), 7.07 (d, J=8.5 Hz, 2H), 6.08-6.02 (m, 1H), 6.01-5.73 (m, 1H), 4.27-4.20 (m, 1H), 3.01 (d, J=11.0 Hz, 2H), 2.81-2.68 (m, 3H), 2.24-2.16 (m, 2H), 1.84-1.69 (m, 2H), 1.54-1.43 (m, 3H), 1.27 (d, J=6.8 Hz, 3H).

II. Biological Evaluation

Example A1: YAP Reporter Assay

HEK293T cells stably transfected with 8XTBD luciferase reporter and pRLTK in 384-well plates were treated with the test compounds, starting from 3 μM (final concentration in assay plate), 1:3 dilution, and 10 points in quadruplicates. Post 24-hr incubation with compounds at 37° C. and 5% $CO_2$, cells were lysed and 8XTBD-driven firefly luciferase and control TK-driven renilla luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLUTAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1*D-PBS, 0.05% trypsin-EDTA. The cells were trypsinized after removing all media, then washed with 1*sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/ml). The cell suspension was then diluted with Assay Medium to a concentration of 6×104 cells/ml. 50 ul cells suspension was then plated to 384-well plate (Perkin Elmer-6007480), 3×103 cells/well and the cells were incubated in an incubator at 37° C., 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C., 5% CO2 incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring renilla luciferase activity: 20 ul Stop-Glo Reagent was added to the 384-well plates. The plates were shaken for 1 min and then centrifuged at 1000 rpm for 30 seconds. After waiting at least 10 minutes, the renilla luminescence was measured by Envision.

Compound $IC_{50}$ and maximum inhibition on the firefly luciferase and renilla luciferase activities were reported separately. $IC_{50}$ for firefly luciferase activity are shown in Table 2.

TABLE 2

| Compound # | Name | Firefly Luciferase IC$_{50}$ (μM) |
|---|---|---|
| 1 | 5-(4-chlorophenoxy)-N-isopropyl-2-naphthamide | A |
| 2 | 5-(3-chlorophenoxy)-N-isopropyl-2-naphthamide | A |
| 3 | 5-(3,4-dichlorophenoxy)-N-isopropyl-naphthalene-2-carboxamide | A |
| 4 | N-isopropyl-5-(4-(trifluoromethyl)phenoxy)-2-naphthamide | A |
| 5 | N-(methylsulfonyl)-5-(4-(trifluoromethyl)phenoxy)-2-naphthamide | A |
| 6 | 5-(3,4-dichlorophenoxy)-N-(methylsulfonyl)-2-naphthamide | A |
| 7 | N-methyl-5-(4-(trifluoromethyl)phenoxy)naphthalene-2-sulfonamide | A |
| 8 | 5-(3,4-difluorophenoxy)-N-isopropyl-2-naphthamide | A |
| 9 | 5-(3,4-dichlorophenoxy)-N-methylnaphthalene-2-sulfonamide | A |
| 10 | 5-(3,4-difluorophenoxy)-N-(methylsulfonyl)-2-naphthamide | A |
| 11 | N-isopropyl-1-[4-(trifluoromethyl)phenoxy]isoquinoline-6-carboxamide | A |
| 12 | N-[(1R)-2-hydroxy-1-methyl-ethyl]-1-[4-(trifluoromethyl)phenoxy]isoquinoline-6-carboxamide | A |
| 13 | N-isopropyl-8-[4-(trifluoromethyl)phenoxy]quinoline-3-carboxamide | A |
| 14 | N-[2-hydroxy-1-(2-pyridyl)ethyl]-8-[4-(trifluoromethyl)phenoxy]quinoline-3-carboxamide | A |
| 15 | N-[(1R)-2-hydroxy-1-methyl-ethyl]-8-[4-(trifluoromethyl)phenoxy]quinoline-3-carboxamide | A |
| 16 | N-[(1R)-2-methoxy-1-methyl-ethyl]-8-[4-(trifluoromethyl)phenoxy]quinoline-3-carboxamide | B |
| 17 | N-[(1R)-1-(2-pyridyl)ethyl]-8-[4-(trifluoromethyl)phenoxy]quinoline-3-carboxamide | B |
| 18 | N-[(1S)-2-methoxy-1-methyl-ethyl]-8-[4-(trifluoromethyl)phenoxy]quinoline-3-carboxamide | A |
| 19 | N-[(1S)-1-(2-pyridyl)ethyl]-8-[4-(trifluoromethyl)phenoxy]quinoline-3-carboxamide | A |
| 20 | N-(prop-2-yn-1-yl)-5-(4-(trifluoromethyl)phenoxy)-2-naphthamide | A |
| 21 | N-(but-3-yn-1-yl)-5-(4-(trifluoromethyl)phenoxy)-2-naphthamide | A |
| 22 | N-(cyanomethyl)-5-(4-(trifluoromethyl)phenoxy)-2-naphthamide | A |
| 23 | N-(2-cyanoethyl)-5-(4-(trifluoromethyl)phenoxy)-2-naphthamide | A |
| 24 | (R)-N-(1-hydroxypropan-2-yl)-5-(4-(trifluoromethyl)phenoxy)-2-naphthamide | A |
| 25 | N-(2-hydroxy-1-pyridin-2-yl)ethyl)-5-(4-(trifluoromethyl)phenoxy)-2-naphthamide | A |
| 26 | (R)-N-(1-methoxypropan-2-yl)-5-(4-(trifluoromethyl)phenoxy)-2-naphthamide | A |
| 27 | N-[(1R)-1-(2-pyridyl)ethyl]-5-[4-(trifluoromethyl)phenoxy]naphthalene-2-carboxamide | B |
| 28 | (S)-N-(1-methoxypropan-2-yl)-5-(4-(trifluoromethyl)phenoxy)-2-naphthamide | A |
| 29 | (S)-N-(1-(pyridin-2-yl))-5-(4-(trifluoromethyl)phenoxy)-2-naphthamide | A |
| 30 | N-(2-(methylamino)ethyl)-5-(4-(trifluoromethyl)phenoxy)-2-naphthamide | B |
| 31 | N-(2-(N-methylcyanamido)ethyl)-5-(4-(trifluoromethyl)phenoxy)-2-naphthamide | A |
| 32 | N-isopropyl-7-(4-(trifluoromethyl)phenoxy)benzo[b]thiophene-2-carboxamide | A |
| 33 | (R)-N-(1-hydroxypropan-2-yl)-7-(4-(trifluoromethyl)phenoxy)benzo[b]thiophene-2-carboxamide | A |
| 34 | N-(3-(methylamino)propyl)-5-(4-(trifluoromethyl)phenoxy)-2-naphthamide | A |
| 35 | N-(3-(N-methylcyanamido)propyl)-5-(4-(trifluoromethyl)phenoxy)-2-naphthamide | A |
| 36 | N-(1-phenylcyclopropyl)-5-[4-(trifluoromethyl)phenoxy]naphthalene-2-carboxamide | A |
| 37 | N-(3-phenyloxetan-3-yl)-5-(4-(trifluoromethyl)phenoxy)-2-naphthamide | A |
| 38 | (R)-N-(1-cyclopropylethyl)-5-(4-(trifluoromethyl)phenoxy)-2-naphthamide | A |
| 39 | (S)-N-(1-cyclopropylethyl)-5-(4-(trifluoromethyl)phenoxy)-2-naphthamide | A |
| 40 | (R)-N-(1-(oxetan-3-yl)ethyl)-5-(4-(trifluoromethyl)phenoxy)-2-naphthamide | A |
| 41 | (S)-N-(1-(oxetan-3-yl)ethyl)-5-(4-(trifluoromethyl)phenoxy)-2-naphthamide | A |
| 42 | (R)-6-methoxy-N-(1-(pyridin-2-yl)ethyl)-8-(4-(trifluoromethyl)phenoxy)quinoline-3-carboxamide | B |
| 43 | (S)-6-methoxy-N-(1-(pyridin-2-yl)ethyl)-8-(4-(trifluoromethyl)phenoxy)quinoline-3-carboxamide | A |
| 44 | (R)-6-methoxy-N-(1-methoxypropan-2-yl)-8-(4-(trifluoromethyl)phenoxy)quinoline-3-carboxamide | A |
| 45 | (S)-6-methoxy-N-(1-methoxypropan-2-yl)-8-(4-(trifluoromethyl)phenoxy)quinoline-3-carboxamide | A |
| 46 | (R)-N-(1-(pyrazin-2-yl)ethyl)-5-(4-(trifluoromethyl)phenoxy)-2-naphthamide | A |
| 47 | (S)-N-(1-(pyrazin-2-yl)ethyl)-5-(4-(trifluoromethyl)phenoxy)-2-naphthamide | B |
| 48 | (R)-N-(1-(1H-imidazol-4-yl)ethyl)-5-(4-(trifluoromethyl)phenoxy)-2-naphthamide | A |
| 49 | (S)-N-(1-(1H-imidazol-4-yl)ethyl)-5-(4-(trifluoromethyl)phenoxy)-2-naphthamide | A |
| 50 | S)-N-(1-amino-1-oxopropan-2-yl)-5-(4-(trifluoromethyl)phenoxy)-2-naphthamide | A |
| 51 | (R)-N-(1-amino-1-oxopropan-2-yl)-5-(4-(trifluoromethyl)phenoxy)-2-naphthamide | A |
| 52 | (S)-N-(1-(2H-tetrazol-5-yl)ethyl)-5-(4-(trifluoromethyl)phenoxy)-2-naphthamide | C |
| 54 | N-(1-(pyridin-2-yl)cyclopropyl)-5-(4-(trifluoromethyl)phenoxy)-2-naphthamide | A |
| 55 | (S)-N-(1-(1-methyl-1H-tetrazol-5-yl)ethyl)-5-(4-(trifluoromethyl)phenoxy)-2-naphthamide | B |
| 56 | (R)-N-(1-(1-methyl-1H-tetrazol-5-yl)ethyl)-5-(4-(trifluoromethyl)phenoxy)-2-naphthamide | B |
| 57 | (R)-N-(1-(2-methyl-2H-tetrazol-5-yl)ethyl)-5-(4-(trifluoromethyl)phenoxy)-2-naphthamide | B |
| 58 | (S)-N-(1-(2-methyl-2H-tetrazol-5-yl)ethyl)-5-(4-(trifluoromethyl)phenoxy)-2-naphthamide | A |
| 59 | (R)-N-(1-cyclobutylethyl)-5-(4-(trifluoromethyl)phenoxy)-2-naphthamide | A |
| 60 | (S)-N-(1-cyclobutylethyl)-5-(4-(trifluoromethyl)phenoxy)-2-naphthamide | A |
| 61 | (R)-N-(but-3-yn-2-yl)-5-(4-(trifluoromethyl)phenoxy)-2-naphthamide | A |
| 62 | (S)-N-(but-3-yn-2-yl)-5-(4-(trifluoromethyl)phenoxy)-2-naphthamide | A |
| 63 | (S)-N-(1-(1H-imidazol-2-yl)ethyl)-5-(4-(trifluoromethyl)phenoxy)-2-naphthamide | B |
| 64 | (R)-N-(1-(1H-imidazol-2-yl)ethyl)-5-(4-(trifluoromethyl)phenoxy)-2-naphthamide | A |
| 65 | (S)-N-(1-(6-aminopyridin-2-yl)ethyl)-5-(4-(trifluoromethyl)phenoxy)-2-naphthamide | B |
| 66 | (R)-N-(1-(6-aminopyridin-2-yl)ethyl)-5-(4-(trifluoromethyl)phenoxy)-2-naphthamide | A |
| 67 | N-Isopropyl-4-(4-(trifluoromethyl)phenoxy)quinoline-7-carboxamide | B |
| 68 | (R)-N-(1-(1-methyl-1H-imidazol-2-yl)ethyl)-5-(4-(trifluoromethyl)phenoxy)-2-naphthamide | B |
| 69 | (S)-N-(1-(1-methyl-1H-imidazol-2-yl)ethyl)-5-(4-(trifluoromethyl)phenoxy)-2-naphthamide | B |
| 70 | N-Isopropyl-5-(4-(trifluoromethyl)phenoxy)quinoline-2-carboxamide | A |
| 71 | (S)-N-(1-(4-aminopyridin-2-yl)ethyl)-5-(4-(trifluoromethyl)phenoxy)-2-naphthamide | B |
| 72 | (R)-N-(1-(4-aminopyridin-2-yl)ethyl)-5-(4-(trifluoromethyl)phenoxy)-2-naphthamide | A |
| 73 | (S)-N-(1-(4-(dimethylamino)pyridin-2-yl)ethyl)-5-(4-(trifluoromethyl)phenoxy)-2-naphthamide | B |
| 74 | (R)-N-(1-(4-(dimethylamino)pyridin-2-yl)ethyl)-5-(4-(trifluoromethyl)phenoxy)-2-naphthamide | C |
| 75 | N-(1-(4-bromopyridin-2-yl)ethyl)-5-(4-(trifluoromethyl)phenoxy)-2-naphthamide | A |
| 76 | (S)-N-(1-(6-(dimethylamino)pyridin-2-yl)ethyl)-5-(4-(trifluoromethyl)phenoxy)-2-naphthamide | B |
| 77 | (R)-N-(1-(6-(dimethylamino)pyridin-2-yl)ethyl)-5-(4-(trifluoromethyl)phenoxy)-2-naphthamide | A |

TABLE 2-continued

| Compound # | Name | Firefly Luciferase IC$_{50}$ (μM) |
|---|---|---|
| 78 | (S)-N-(1-(2-aminopyridin-3-yl)ethyl)-5-(4-(trifluoromethyl)phenoxy)-2-naphthamide | A |
| 79 | (R)-N-(1-(2-aminopyridin-3-yl)ethyl)-5-(4-(trifluoromethyl)phenoxy)-2-naphthamide | C |
| 80 | N-[1-(hydroxymethyl)-2-(2-pyridyl)ethyl]-5-[4-(trifluoromethyl)phenoxy]naphthalene-2-carboxamide | A |
| 81 | 5,6-difluoro-N-isopropyl-8-(4-(trifluoromethyl)phenoxy)quinoline-3-carboxamide | A |
| 83 | (S)-N-(1-(2-chlorophenyl)ethyl)-5-(4-(trifluoromethyl)phenoxy)-2-naphthamide | A |
| 84 | 5-(2-fluoro-4-(trifluoromethyl)phenoxy)-N-isopropyl-2-naphthamide | A |
| 85 | 5-(2-chloro-4-(trifluoromethyl)phenoxy)-N-isopropyl-2-naphthamide | A |
| 86 | N-cyano-5-[4-(trifluoromethyl)phenoxy]naphthalene-2-carboxamide | B |
| 87 | N-[(1R)-1-(1H-indazol-7-yl)ethyl]-5-[4-(trifluoromethyl)phenoxy]naphthalene-2-carboxamide | A |
| 89 | N-[(1S)-1-methylbut-2-ynyl]-5-[4-(trifluoromethyl)phenoxy]naphthalene-2-carboxamide | A |
| 90 | N-[(1R)-1-methylbut-2-ynyl]-5-[4-(trifluoromethyl)phenoxy]naphthalene-2-carboxamide | A |
| 91 | N-[(1R)-1-(1-methylimidazol-4-yl)ethyl]-5-[4-(trifluoromethyl)phenoxy]naphthalene-2-carboxamide | A |
| 92 | N-[(1S)-1-(1-methylimidazol-4-yl)ethyl]-5-[4-(trifluoromethyl)phenoxy]naphthalene-2-carboxamide | B |
| 93 | N-isopropyl-4-(4-(trifluoromethyl)phenoxy)isoquinoline-7-carboxamide | A |
| 94 | N-(3-hydroxy-1-(pyridin-2-yl)propyl)-5-(4-(trifluoromethyl)phenoxy)-2-naphthamide | A |
| 95 | N-[(1R)-1-(azetidin-3-yl)ethyl]-5-[4-(trifluoromethyl)phenoxy]naphthalene-2-carboxamide | A |
| 96 | N-[(1S)-1-(azetidin-3-yl)ethyl]-5-[4-(trifluoromethyl)phenoxy]naphthalene-2-carboxamide | A |
| 97 | (S)-N-(1-(pyridin-2-yl)ethyl)-7-(4-(trifluoromethyl)phenoxy)benzothiophene-2-carboxamide | A |
| 98 | N-[(1R)-1-(2-oxo-1H-quinolin-8-yl)ethyl]-5-[4-(trifluoromethyl)phenoxy]naphthalene-2-carboxamide | A |
| 100 | (S)-N-(1-(1-acetylazetidin-3-yl)ethyl)-5-(4-(trifluoromethyl)phenoxy)-2-naphthamide | B |
| 101 | (R)-N-(1-(1-acetylazetidin-3-yl)ethyl)-5-(4-(trifluoromethyl)phenoxy)-2-naphthamide | B |
| 102 | (R)-5,6-difluoro-N-(1-hydroxypropan-2-yl)-8-(4-(trifluoromethyl)phenoxy)quinoline-3-carboxamide | A |
| 103 | (R)-N-(1-(1H-benzo[d]imidazol-7-yl)ethyl)-8-(4-(trifluoromethyl)phenoxy)quinoline-3-carboxamide | B |
| 104 | (S)-N-(1-(1H-benzo[d]imidazol-7-yl)ethyl)-8-(4-(trifluoromethyl)phenoxy)quinoline-3-carboxamide | A |
| 105 | (R)-N-(1-(benzo[b]thiophen-7-yl)ethyl)-8-(4-(trifluoromethyl)phenoxy)quinoline-3-carboxamide | B |
| 107 | (R)-N-(1-aminopropan-2-yl)-5-(4-(trifluoromethyl)phenoxy)-2-naphthamide | B |
| 108 | (S)-N-(1-aminopropan-2-yl)-5-(4-(trifluoromethyl)phenoxy)-2-naphthamide | A |
| 109 | (R)-N-(3-hydroxy-1-(pyridin-2-yl)propyl)-5-(4-(trifluoromethyl)phenoxy)-2-naphthamide | B |
| 110 | (S)-N-(3-hydroxy-1-(pyridin-2-yl)propyl)-5-(4-(trifluoromethyl)phenoxy)-2-naphthamide | A |
| 111 | (S)-N-(4-aminobutan-2-yl)-5-(4-(trifluoromethyl)phenoxy)-2-naphthamide | A |
| 112 | (R)-N-(4-aminobutan-2-yl)-5-(4-(trifluoromethyl)phenoxy)-2-naphthamide | A |
| 113 | N-Isopropyl-6-methoxy-8-(4-(trifluoromethyl)phenoxy)quinoline-3-carboxamide | A |
| 114 | (R)-N-(4-hydroxybutan-2-yl)-5-(4-(trifluoromethyl)phenoxy)-2-naphthamide | A |
| 115 | (S)-N-(4-hydroxybutan-2-yl)-5-(4-(trifluoromethyl)phenoxy)-2-naphthamide | A |
| 116 | (R)-N-(1-hydroxypropan-2-yl)-6-methoxy-8-(4-(trifluoromethyl)phenoxy)quinoline-3-carboxamide | A |
| 117 | 5-(4-(trifluoromethyl)phenoxy)naphthalene-2-sulfonamide | A |
| 118 | N-(2-Hydroxy-1-(pyridin-2-yl)ethyl)-6-methoxy-8-(4-(trifluoromethyl)phenoxy)quinoline-3-carboxamide | A |
| 119 | (S)-N-(2-hydroxy-1-(pyridin-2-yl)ethyl)-5-(4-(trifluoromethyl)phenoxy)-2-naphthamide | A |
| 120 | (R)-N-(2-hydroxy-1-(pyridin-2-yl)ethyl)-5-(4-(trifluoromethyl)phenoxy)-2-naphthamide | B |
| 121 | N-(1,5-dihydroxypentan-3-yl)-5-(4-(trifluoromethyl)phenoxy)-2-naphthamide | A |
| 123 | (R)-N-(1-(1-(4-hydroxybutyl)azetidin-3-yl)ethyl)-5-(4-(trifluoromethyl)phenoxy)-2-naphthamide | B |
| 124 | (R)-N-(1-(1-(2-fluoroethyl)azetidin-3-yl)ethyl)-5-(4-(trifluoromethyl)phenoxy)-2-naphthamide | A |
| 125 | (R)-N-(1-(1-(2,2-difluoroethyl)azetidin-3-yl)ethyl)-5-(4-(trifluoromethyl)phenoxy)-2-naphthamide | A |
| 126 | (R)-N-(1-(1-methylazetidin-3-yl)ethyl)-5-(4-(trifluoromethyl)phenoxy)-2-naphthamide | B |
| 127 | (S)-N-(1-(1-methylazetidin-3-yl)ethyl)-5-(4-(trifluoromethyl)phenoxy)-2-naphthamide | C |
| 128 | (S)-N-(1-(1-(2-hydroxyethyl)azetidin-3-yl)ethyl)-5-(4-(trifluoromethyl)phenoxy)-2-naphthamide | B |
| 129 | (S)-N-(1-(1-(2-fluoroethyl)azetidin-3-yl)ethyl)-5-(4-(trifluoromethyl)phenoxy)-2-naphthamide | C |
| 130 | (S)-N-(1-(1-ethylazetidin-3-yl)ethyl)-5-(4-(trifluoromethyl)phenoxy)-2-naphthamide | B |
| 131 | (R)-N-(1-(1-ethylazetidin-3-yl)ethyl)-5-(4-(trifluoromethyl)phenoxy)-2-naphthamide | B |
| 132 | (S)-N-(1-(1-isopropylazetidin-3-yl)ethyl)-5-(4-(trifluoromethyl)phenoxy)-2-naphthamide | B |
| 133 | (R)-N-(1-(1-isopropylazetidin-3-yl)ethyl)-5-(4-(trifluoromethyl)phenoxy)-2-naphthamide | C |
| 134 | (S)-N-(1-(1-(2,2-difluoroethyl)azetidin-3-yl)ethyl)-5-(4-(trifluoromethyl)phenoxy)-2-naphthamide | C |
| 135 | (R)-N-(1-(1-(2-hydroxyethylazetidin-3-yl)ethyl)-5-(4-(trifluoromethyl)phenoxy)-2-naphthamide | B |
| 136 | (S)-N-(1-(1-cyclopropylazetidin-3-yl)ethyl)-5-(4-(trifluoromethyl)phenoxy)-2-naphthamide | C |
| 137 | (R)-N-(1-(1-cyclopropylazetidin-3-yl)ethyl)-5-(4-(trifluoromethyl)phenoxy)-2-naphthamide | A |
| 138 | (S)-N-(1-(3-hydroxyazetidin-3-yl)ethyl)-5-(4-(trifluoromethyl)phenoxy)-2-naphthamide | B |
| 139 | (R)-N-(1-(3-hydroxyazetidin-3-yl)ethyl)-5-(4-(trifluoromethyl)phenoxy)-2-naphthamide | A |
| 140 | (R)-N-(1-(azetidin-3-yl)-2-hydroxyethyl)-5-(4-(trifluoromethyl)phenoxy)-2-naphthamide | C |
| 142 | (S)-N-(1-(azetidin-3-yl)-2-hydroxyethyl)-5-(4-(trifluoromethyl)phenoxy)-2-naphthamide | B |
| 144 | (R)-N-(4-(dimethylamino)butan-2-yl)-5-(4-(trifluoromethyl)phenoxy)-2-naphthamide | A |
| 145 | (R)-N-(4-(methylamino)butan-2-yl)-5-(4-(trifluoromethyl)phenoxy)-2-naphthamide | A |
| 146 | (R)-N-(4-(ethylamino)butan-2-yl)-5-(4-(trifluoromethyl)phenoxy)-2-naphthamide | A |
| 147 | (R)-N-(4-((2-hydroxyethyl)amino)butan-2-yl)-5-(4-(trifluoromethyl)phenoxy)-2-naphthamide | A |
| 148 | (R)-N-(4-((2-fluoroethyl)amino)butan-2-yl)-5-(4-(trifluoromethyl)phenoxy)-2-naphthamide | A |
| 149 | (R)-N-(4-((2,2-difluoroethyl)amino)butan-2-yl)-5-(4-(trifluoromethyl)phenoxy)-2-naphthamide | A |
| 150 | (R)-N-(1-(piperidin-4-yl)ethyl)-5-(4-(trifluoromethyl)phenoxy)-2-naphthamide | A |
| 151 | (S)-N-(1-(3-fluoroazetidin-3-yl)ethyl)-5-(4-(trifluoromethyl)phenoxy)-2-naphthamide | C |
| 152 | (R)-N-(1-(3-fluoroazetidin-3-yl)ethyl)-5-(4-(trifluoromethyl)phenoxy)-2-naphthamide | B |
| 153 | (R)-N-(1-(1-(2-hydroxyethyl)piperidin-4-yl)ethyl)-5-(4-(trifluoromethyl)phenoxy)-2-naphthamide | B |
| 154 | (R)-N-(1-(1-(2-fluoroethyl)piperidin-4-yl)ethyl)-5-(4-(trifluoromethyl)phenoxy)-2-naphthamide | B |
| 155 | (R)-N-(1-(1-ethylpiperidin-4-yl)ethyl)-5-(4-(trifluoromethyl)phenoxy)-2-naphthamide | B |
| 156 | (R)-N-(1-(1-isopropylpiperidin-4-yl)ethyl)-5-(4-(trifluoromethyl)phenoxy)-2-naphthamide | B |
| 157 | (R)-N-(1-(1-methylpiperidin-4-yl)ethyl)-5-(4-(trifluoromethyl)phenoxy)-2-naphthamide | A |

TABLE 2-continued

| Compound # | Name | Firefly Luciferase IC$_{50}$ (μM) |
|---|---|---|
| 162 | (R)-N-(1-(1-(2,2-difluoroethyl)piperidin-4-yl)ethyl)-5-(4-(trifluoromethyl)phenoxy)-2-naphthamide | B |

Note:
Biochemical assay IC$_{50}$ data are designated within the following ranges:
A: ≤0.1 μM
B: >0.1 μM to ≤1.0 μM
C: >1.0 μM to ≤3 μM
D: >3 μM ≤ 10 μM Example A2: Tumor Suppression Assay The procedures described herein for the tumor suppression assay is as described in PCT/US2013/043752 (WO 2013/188138). Mouse procedures are performed according to the guidelines of approved animal protocol and based on the methods. After the cells are grown to 90%>confluence, these cells are harvested by trypsinization, washed in phosphate-buffered saline (PBS), and resuspended in PBS supplemented with 50% Matrigel (BD Biosciences). An appropriate amount of cells is prepared for administration, such as 200 μL per injection site. Immuno-compromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24 h before drug treatment. Post incubation for various time periods with the test compounds, starting from 3 μM (final concentration in assay plate), 1:3 dilution, and 10 points in duplicates, the number of viable cells and proliferative cells are determined using CellTiter-Glo® Luminescent Cell Viability Assay Kit (Promega) and Click-iT EdU HCS Assay Kit (Invitrogen) according to the manufacturers' protocols. The IC$_{50}$ values and maximum % inhibition of the test compounds are calculated using the dose response curves.

The examples and embodiments described herein are for illustrative purposes only and various modifications or changes suggested to persons skilled in the art are to be included within the spirit and purview of this application and scope of the appended claims.

NUMBERED EMBODIMENTS

Embodiment 1 is a compound of Formula (I), or a pharmaceutically acceptable salt or solvate thereof:

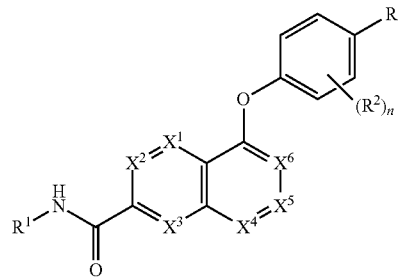

Formula (I)

wherein,
each $X^1$, $X^4$, $X^5$, and $X^6$, is independently N or $CR^X$;
each $X^2$ and $X^3$ is independently N or $CR^Y$;
each $R^X$ is independently hydrogen, halogen, nitro, —OR$^3$, —SR$^3$, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted C$_1$-C$_6$alkyl, substituted or unsubstituted C$_1$-C$_6$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
each $R^Y$ is independently hydrogen, halogen, nitro, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted C$_1$-C$_6$alkyl, substituted or unsubstituted C$_1$-C$_6$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
R is halogen, nitro, —CN, —OR$^3$, —SR$^3$, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl;
$R^1$ is substituted or unsubstituted C$_1$-C$_6$alkyl, substituted or unsubstituted C$_1$-C$_6$fluoroalkyl, substituted or unsubstituted C$_2$-C$_6$alkenyl, substituted or unsubstituted C$_2$-C$_6$alkynyl, substituted or unsubstituted C$_3$-C$_{10}$cycloalkyl, substituted or unsubstituted C$_2$-C$_{10}$heterocycloalkyl, substituted or unsubstituted C$_1$-C$_6$heteroalkyl, —CN, or —S(=O)$_2$R$^4$;
each $R^2$ is independently halogen, nitro, —N$_3$, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted C$_1$-C$_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_2$ heterocycloalkyl;

$R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —$NH_2$; and n is 0, 1, 2, 3, or 4.

Embodiment 2 is the compound or pharmaceutically acceptable salt or solvate thereof of embodiment 1, wherein: $X^1$ is $CR^X$; and each $X^2$ and $X^3$ is $CR^Y$.

Embodiment 3 is the compound or pharmaceutically acceptable salt or solvate thereof of embodiment 1, wherein: $X^1$ is N; and each $X^2$ and $X^3$ is $CR^Y$.

Embodiment 4 is the compound or pharmaceutically acceptable salt or solvate thereof of embodiment 1, wherein: $X^1$ is $CR^X$; $X^2$ is $CR^Y$; and $X^3$ is N.

Embodiment 5 is the compound or pharmaceutically acceptable salt or solvate thereof of any one of embodiments 1-4, wherein: each $X^4$, $X^5$, and $X^6$ is $CR^X$.

Embodiment 6 is the compound or pharmaceutically acceptable salt or solvate thereof of any one of embodiments 1-4, wherein: $X^4$ is N; and each $X^5$ and $X^6$ is $CR^X$.

Embodiment 7 is the compound or pharmaceutically acceptable salt or solvate thereof of any one of embodiments 1-4, wherein: each $X^4$ and $X^5$ is $CR^X$; and $X^6$ is N.

Embodiment 8 is the compound or pharmaceutically acceptable salt or solvate thereof of any one of embodiments 1-7, wherein: each $R^X$ is independently hydrogen, halogen, —$OR^3$, —$SR^3$, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 9 is the compound or pharmaceutically acceptable salt or solvate thereof of any one of embodiments 1-7, wherein: each $R^X$ is independently hydrogen, halogen, —$OR^3$, —$SR^3$, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 10 is the compound or pharmaceutically acceptable salt or solvate thereof of any one of embodiments 1-7, wherein: each $R^X$ is independently hydrogen, F, Cl, Br, I, —$CH_3$, —$CH_2CH_3$, —$CH_2OH$, —$CH_2CH_2OH$, —$CH_2CN$, —$CH_2C$(=O)OH, —$CH_2C$(=O)O$CH_3$, —$CH_2C$(=O)O$CH_2CH_3$, —$CH_2C$(=O)$NH_2$, —$CH_2C$(=O)NH$CH_3$, —$CH_2C$(=O)N($CH_3$)$_2$, —$CH_2NH_2$, —$CH_2NHCH_3$, —$CH_2N(CH_3)_2$, —$CH_2F$, —$CHF_2$, —$CF_3$, —CH=$CH_2$, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —C(=O)OH, —C(=O)$OCH_3$, —C(=O)$OCH_2CH_3$, —C(=O)$NH_2$, —C(=O)NH$CH_3$, —C(=O)N($CH_3$)$_2$, —$NH_2$, —NH$CH_3$, —N($CH_3$)$_2$, —NHC(=O)$CH_3$, —N($CH_3$)C(=O)$CH_3$, —NHC(=O)$OCH_3$, —N($CH_3$)C(=O)$OCH_3$, —S(=O)$CH_3$, —S(=O)$_2CH_3$, —NHS(=O)$_2CH_3$, or —N($CH_3$)S(=O)$_2CH_3$.

Embodiment 11 is the compound or pharmaceutically acceptable salt or solvate thereof of any one of embodiments 1-7, wherein: each $R^X$ is independently hydrogen, F, Cl, Br, I, —$CH_3$, —$CH_2CH_3$, cyclopropyl, —C≡CH, —OH, —$OCH_3$, —$OCH_2CH_3$, —$OCF_3$, —$SCH_3$, cyclopropyloxy, —$NH_2$, —NHC(=O)$CH_3$, —N($CH_3$)C(=O)$CH_3$, —NHS(=O)$_2CH_3$, —N($CH_3$)S(=O)$_2CH_3$, —S(=O)$CH_3$, or —S(=O)$_2CH_3$.

Embodiment 12 is the compound or pharmaceutically acceptable salt or solvate thereof of any one of embodiments 1-7, wherein: each $R^X$ is independently hydrogen, F, Cl, Br, I, —$CH_3$, —$CH_2CH_3$, cyclopropyl, —OH, —$OCH_3$, —$OCH_2CH_3$, —$OCF_3$, cyclopropyloxy, —$NH_2$, —NHC(=O)$CH_3$, —NHS(=O)$_2CH_3$, —S(=O)$CH_3$, or —S(=O)$_2$ $CH_3$.

Embodiment 13 is the compound or pharmaceutically acceptable salt or solvate thereof of any one of embodiments 1-7, wherein: each $R^X$ is independently hydrogen, F, Cl, Br, —$CH_3$, —OH, —$OCH_3$, or —$OCF_3$.

Embodiment 14 is the compound or pharmaceutically acceptable salt or solvate thereof of any one of embodiments 1-7, wherein: each $R^X$ is independently hydrogen, F, Cl, —$CH_3$, —$OCH_3$, or —$OCF_3$.

Embodiment 15 is the compound or pharmaceutically acceptable salt or solvate thereof of any one of embodiments 1-7, wherein: each $R^X$ is independently hydrogen, F, or —$OCH_3$.

Embodiment 16 is the compound or pharmaceutically acceptable salt or solvate thereof of any one of embodiments 1-7, wherein: each $R^X$ is hydrogen.

Embodiment 17 is the compound or pharmaceutically acceptable salt or solvate thereof of any one of embodiments 1-16, wherein: each $R^Y$ is independently hydrogen, halogen, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 18 is the compound or pharmaceutically acceptable salt or solvate thereof of any one of embodiments 1-16, wherein: each $R^Y$ is independently hydrogen, halogen, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or un substituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 19 is the compound or pharmaceutically acceptable salt or solvate thereof of any one of embodiments 1-16, wherein: each $R^Y$ is independently hydrogen, F, Cl, Br, I, —$CH_3$, —$CH_2CH_3$, —$CH_2OH$, —$CH_2CH_2OH$, —$CH_2CN$, —$CH_2C(=O)OH$, —$CH_2C(=O)OCH_3$, —$CH_2C(=O)OCH_2CH_3$, —$CH_2C(=O)NH_2$, —$CH_2C(=O)NHCH_3$, —$CH_2C(=O)N(CH_3)_2$, —$CH_2NH_2$, —$CH_2NHCH_3$, —$CH_2N(CH_3)_2$, —$CH_2F$, —$CHF_2$, —$CF_3$, —$CH=CH_2$, —$C\equiv CH$, —$C(=O)NH_2$, —$C(=O)NHCH_3$, —$C(=O)N(CH_3)_2$, —$NH_2$, —$NHCH_3$, —$N(CH_3)_2$, —$NHC(=O)CH_3$, —$N(CH_3)C(=O)CH_3$, —$NHC(=O)OCH_3$, —$N(CH_3)C(=O)OCH_3$, —$S(=O)CH_3$, —$S(=O)_2CH_3$, —$NHS(=O)_2CH_3$, or —$N(CH_3)S(=O)_2CH_3$.

Embodiment 20 is the compound or pharmaceutically acceptable salt or solvate thereof of any one of embodiments 1-16, wherein: each $R^Y$ is independently hydrogen, F, Cl, Br, I, —$CH_3$, —$CH_2CH_3$, cyclopropyl, —$C\equiv CH$, —$NH_2$, —$NHC(=O)CH_3$, —$N(CH_3)C(=O)CH_3$, —$NHS(=O)_2CH_3$, —$N(CH_3)S(=O)_2CH_3$, —$S(=O)CH_3$, or —$S(=O)_2CH_3$.

Embodiment 21 is the compound or pharmaceutically acceptable salt or solvate thereof of any one of embodiments 1-16, wherein: each $R^Y$ is independently hydrogen, F, Cl, Br, I, —$CH_3$, —$CH_2CH_3$, cyclopropyl, —$NH_2$, —$NHC(=O)CH_3$, —$NHS(=O)_2CH_3$, —$S(=O)CH_3$, or —$S(=O)_2CH_3$.

Embodiment 22 is the compound or pharmaceutically acceptable salt or solvate thereof of any one of embodiments 1-16, wherein: each $R^Y$ is independently hydrogen, F, Cl, or —$CH_3$.

Embodiment 23 is the compound or pharmaceutically acceptable salt or solvate thereof of any one of embodiments 1-16, wherein: each $R^Y$ is independently hydrogen or F.

Embodiment 24 is the compound or pharmaceutically acceptable salt or solvate thereof of any one of embodiments 1-16, wherein: each $R^Y$ is hydrogen.

Embodiment 25 is the compound or pharmaceutically acceptable salt or solvate thereof of any one of embodiments 1-24, wherein: $R^1$ is substituted or unsubstituted $C_1$-$C_6$alkyl.

Embodiment 26 is the compound or pharmaceutically acceptable salt or solvate thereof of any one of embodiments 1-24, wherein: $R^1$ is $C_1$-$C_6$alkyl substituted with substituted or unsubstituted $C_2$-$C_6$alkenyl, substituted or unsubstituted $C_2$-$C_6$alkynyl, or —CN.

Embodiment 27 is the compound or pharmaceutically acceptable salt or solvate thereof of any one of embodiments 1-24, wherein: $R^1$ is $C_1$-$C_6$alkyl substituted with —$OR^3$; and $R^3$ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl.

Embodiment 28 is the compound or pharmaceutically acceptable salt or solvate thereof of any one of embodiments 1-24, wherein: $R^1$ is $C_1$-$C_6$alkyl substituted with —$C(=O)N(R^5)_2$ or —$N(R^5)_2$; wherein each $R^5$ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —CN; or two $R^5$ are taken together with the nitrogen atom to which they are attached to form a substituted or unsubstituted $C_3$-$C_7$ heterocycloalkyl.

Embodiment 29 is the compound or pharmaceutically acceptable salt or solvate thereof of any one of embodiments 1-24, wherein: $R^1$ is $C_1$-$C_6$alkyl substituted with substituted or unsubstituted $C_3$-$C_8$cycloalkyl or substituted or unsubstituted $C_2$-$C_7$heterocycloalkyl.

Embodiment 30 is the compound or pharmaceutically acceptable salt or solvate thereof of embodiment 29, wherein: $R^1$ is $C_1$-$C_6$alkyl substituted with cyclopropyl, cyclobutyl, cyclopentyl, or cyclohexyl.

Embodiment 31 is the compound or pharmaceutically acceptable salt or solvate thereof of embodiment 29, wherein: $R^1$ is $C_1$-$C_6$alkyl substituted with oxetanyl, tetrahydrofuranyl, tetrahydropyranyl, azetidinyl, pyrrolidinyl, or piperidinyl.

Embodiment 32 is the compound or pharmaceutically acceptable salt or solvate thereof of any one of embodiments 1-24, wherein: $R^1$ is $C_1$-$C_6$alkyl substituted with substituted or unsubstituted phenyl, wherein if phenyl is substituted, then it is substituted with 1, 2, 3, or 4 substituents selected from halogen, nitro, —CN, —$OR^3$, —$N(R^3)_2$, —$C(=O)R^3$, —$C(=O)N(R^3)_2$, —$C(=O)OR^3$, substituted or unsubstituted $C_1$-$C_6$alkyl, and substituted or unsubstituted $C_1$-$C_6$fluoroalkyl; and each $R^3$ is independently hydrogen, substituted or unsubstituted $C_1$-$C_6$alkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 33 is the compound or pharmaceutically acceptable salt or solvate thereof of any one of embodiments 1-24, wherein: $R^1$ is $C_1$-$C_6$alkyl substituted with 5-membered heteroaryl ring containing at least one nitrogen atom.

Embodiment 34 is the compound or pharmaceutically acceptable salt or solvate thereof of any one of embodiments 1-24, wherein: $R^1$ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.

Embodiment 35 is the compound or pharmaceutically acceptable salt or solvate thereof of any one of embodiments 1-24, wherein: $R^1$ is $C_1$-$C_6$alkyl substituted with 5-membered heteroaryl ring selected from

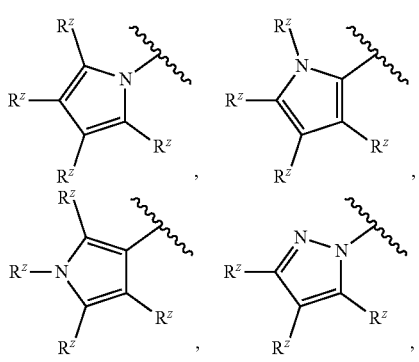

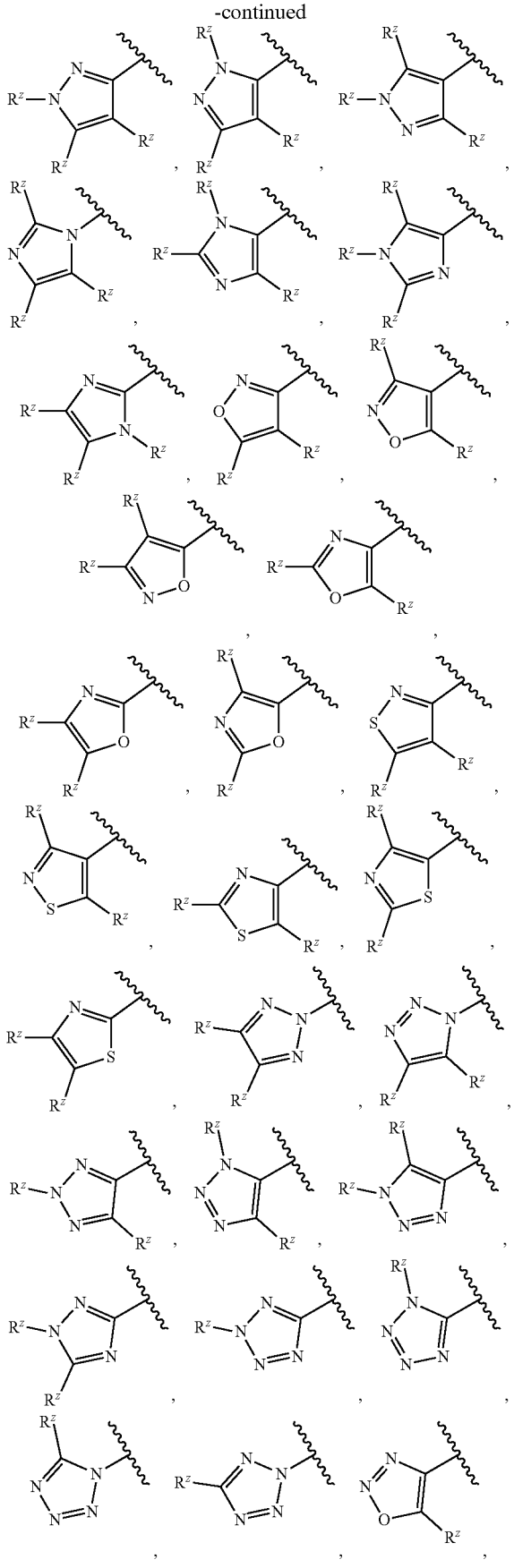
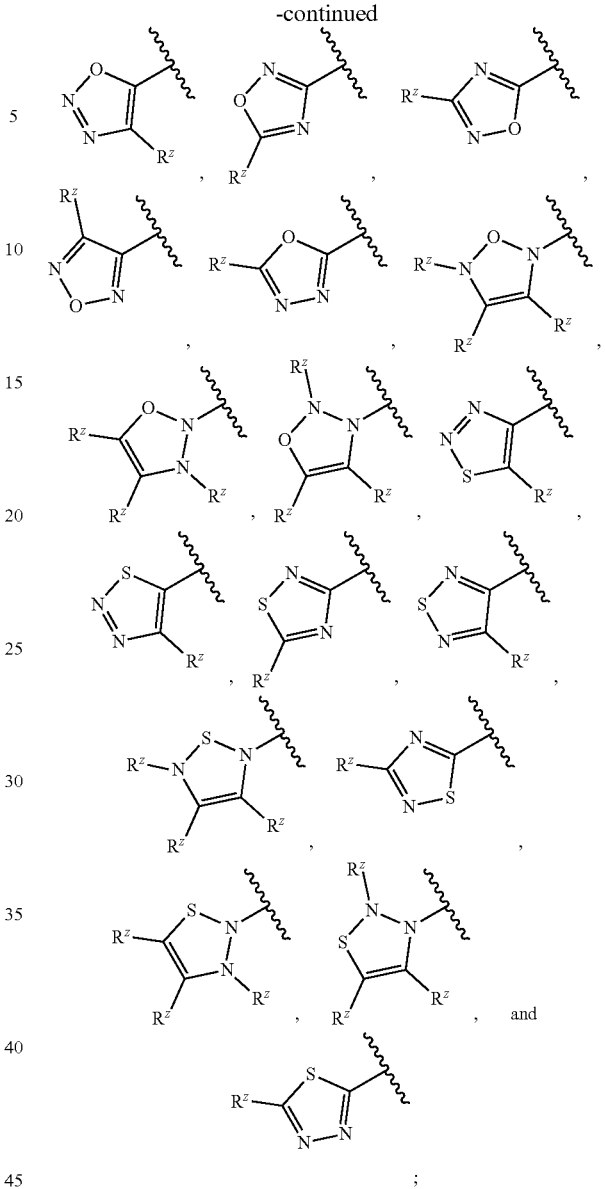

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 36 is the compound or pharmaceutically acceptable salt or solvate thereof of any one of embodiments 1-24, wherein: $R^1$ is $C_1$-$C_6$alkyl substituted with a substituted or unsubstituted monocyclic 6-membered heteroaryl ring containing at least one nitrogen atom.

Embodiment 37 is the compound or pharmaceutically acceptable salt or solvate thereof of any one of embodiments 1-24, wherein: $R^1$ is $C_1$-$C_6$alkyl substituted with a substituted or unsubstituted monocyclic 6-membered heteroaryl ring containing 1, 2, or 3 nitrogen atoms.

Embodiment 38 is the compound or pharmaceutically acceptable salt or solvate thereof of any one of embodiments 1-24, wherein: $R^1$ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl.

Embodiment 39 is the compound or pharmaceutically acceptable salt or solvate thereof of any one of embodiments 1-24, wherein: $R^1$ is $C_1$-$C_6$alkyl substituted with 6-membered heteroaryl ring selected from

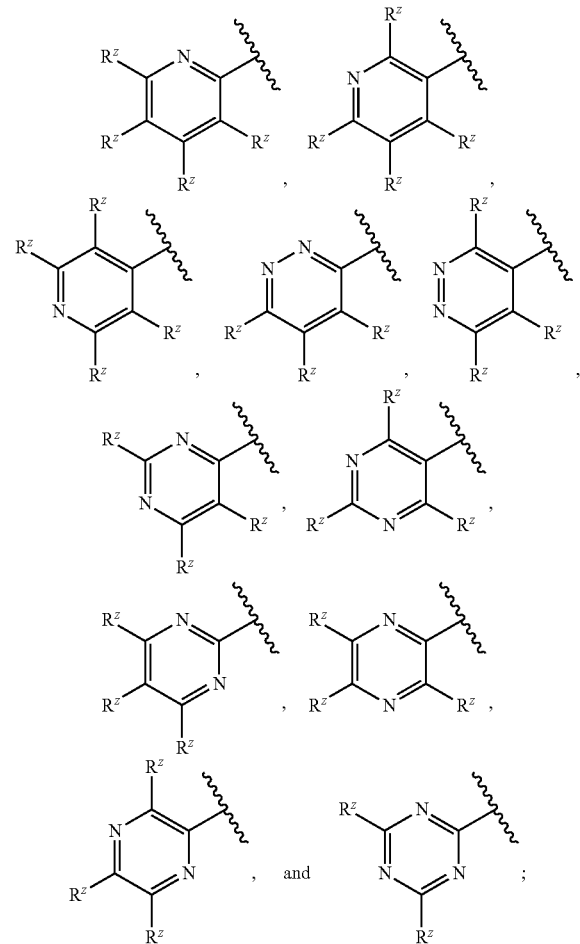

wherein
each $R^z$ is independently hydrogen, halogen, —CN, —$OR^3$, —$SR^3$, —$S(=O)_2R^3$, —$N(R^3)_2$, —$C(=O)OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 40 is the compound or pharmaceutically acceptable salt or solvate thereof of any one of embodiments 1-24, wherein: $R^1$ is $C_1$-$C_6$alkyl substituted with bicyclic 6/5 fused heteroaryl ring.

Embodiment 41 is the compound or pharmaceutically acceptable salt or solvate thereof of any one of embodiments 1-24, wherein: $R^1$ is $C_1$-$C_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzooxadiazolyl, substituted or unsubstituted benzothiadiazolyl, substituted or unsubstituted indolizinyl, and substituted or unsubstituted imidazopyridinyl.

Embodiment 42 is the compound or pharmaceutically acceptable salt or solvate thereof of any one of embodiments 1-24, wherein: $R^1$ is $C_1$-$C_6$alkyl substituted with bicyclic 6/5 fused heteroaryl ring selected from

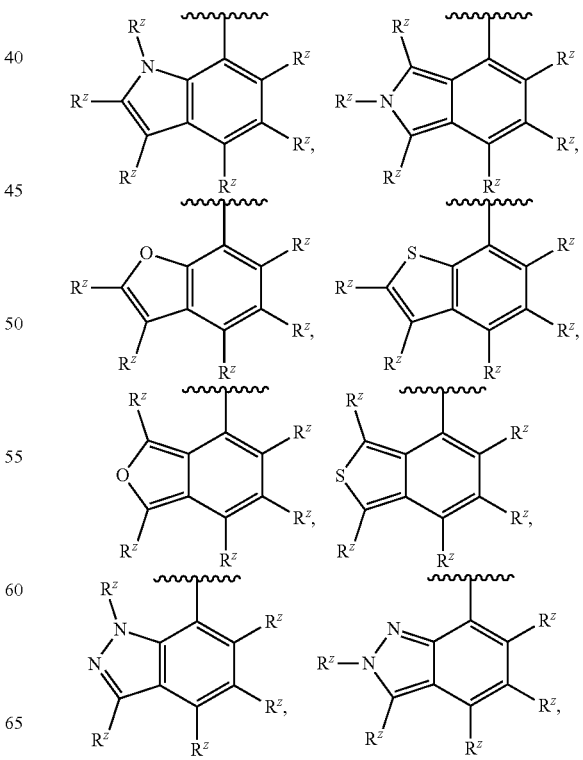

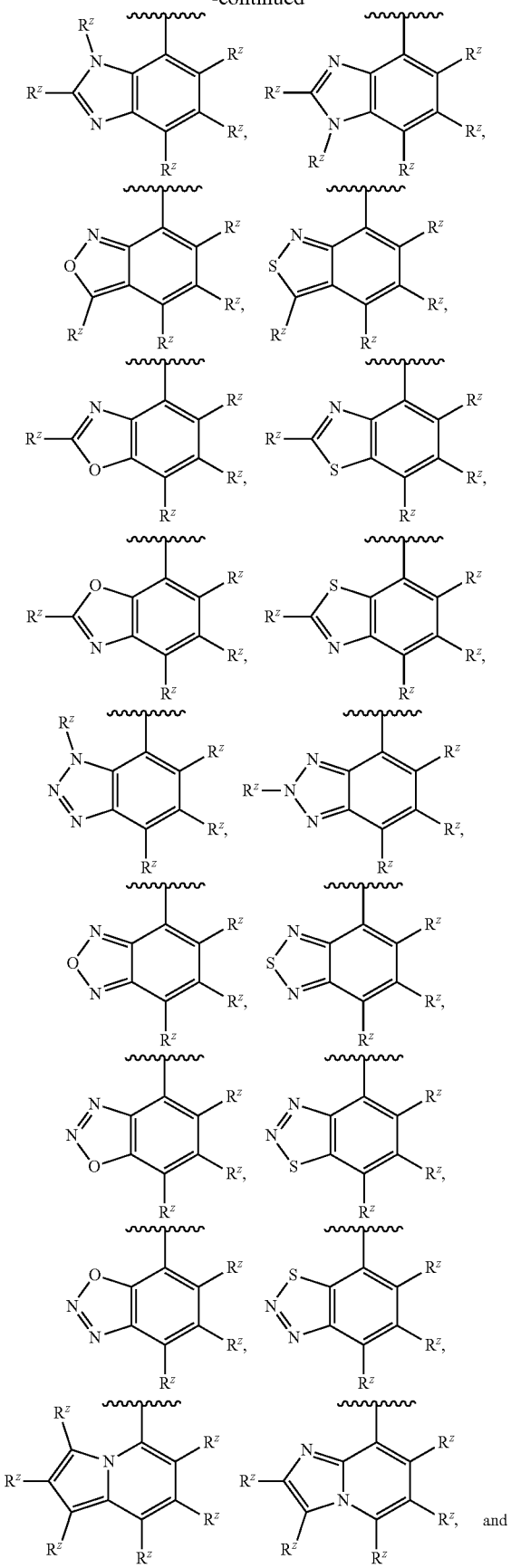

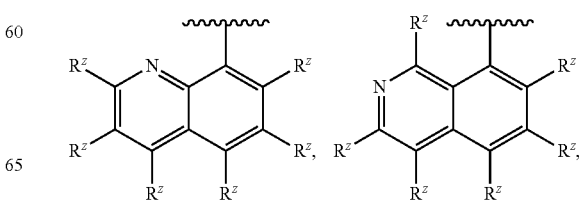

wherein each $R^z$ is independently hydrogen, halogen, —CN, —OR$^3$, —SR$^3$, —S(=O)$_2$R$^3$, —N(R$^3$), —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_1$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment 43 is the compound or pharmaceutically acceptable salt or solvate thereof of any one of embodiments 1-24, wherein: $R^1$ is C$_1$-C$_6$alkyl substituted with a substituted or unsubstituted bicyclic 6/6 fused heteroaryl ring containing at least one nitrogen atom.

Embodiment 44 is the compound or pharmaceutically acceptable salt or solvate thereof of any one of embodiments 1-24, wherein: $R^1$ is C$_1$-C$_6$alkyl substituted with a substituted or unsubstituted bicyclic 6/6 fused heteroaryl ring containing 1, 2, 3, or 4 nitrogen atoms.

Embodiment 45 is the compound or pharmaceutically acceptable salt or solvate thereof of any one of embodiments 1-24, wherein: $R^1$ is C$_1$-C$_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or unsubstituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyridazinyl, substituted or unsubstituted pyrimidopyrimidinyl, and substituted or unsubstituted pteridinyl.

Embodiment 46 is the compound or pharmaceutically acceptable salt or solvate thereof of any one of embodiments 1-24, wherein: $R^1$ is C$_1$-C$_6$alkyl substituted with 6/6 fused heteroaryl ring selected from

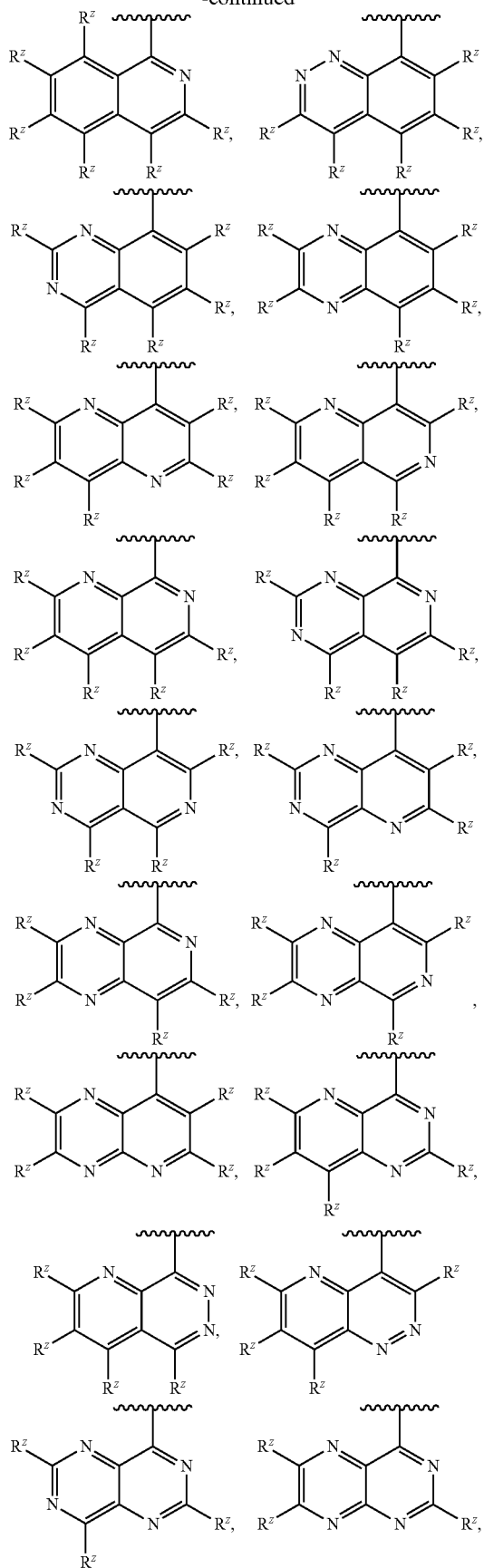

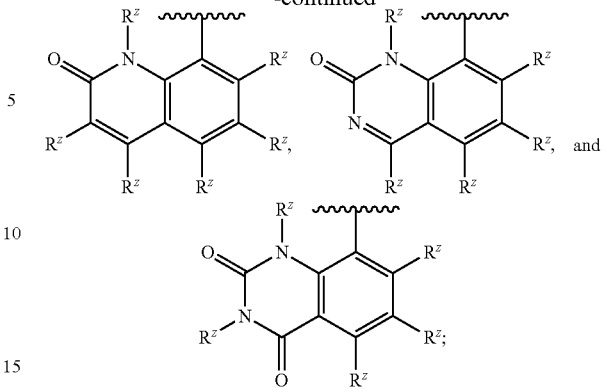

wherein
each $R^z$ is independently hydrogen, halogen, —CN, —OR³, —SR³, —S(═O)₂R³, —N(R³)₂, —C(═O)OR³, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl; and
each $R^3$ is independently hydrogen, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, or substituted or unsubstituted C₂-C₁₀heterocycloalkyl; or if two R³ are on the same nitrogen atom, then two R³ are taken together with the nitrogen atom to which they are attached to form a substituted or unsubstituted C₃-C₇ heterocycloalkyl.

Embodiment 47 is the compound or pharmaceutically acceptable salt or solvate thereof of any one of embodiments 35, 39, 42, or 46, wherein: each $R^z$ is independently hydrogen, F, Cl, Br, —CH₃, —CH₂CH₃, —CH₂F, —CHF₂, —CF₃, —CN, —OH, —OCH₃, —OCH₂CH₃, —OCF₃, —NH₂, —NHCH₃, or —N(CH₃)₂.

Embodiment 48 is the compound or pharmaceutically acceptable salt or solvate thereof of any one of embodiments 35, 39, 42, or 46, wherein: each $R^z$ is independently hydrogen, Cl, Br, —CH₃, —OCH₃, —NH₂, or —N(CH₃)₂.

Embodiment 49 is the compound or pharmaceutically acceptable salt or solvate thereof of any one of embodiments 35, 39, 42, or 46, wherein: each $R^z$ is hydrogen.

Embodiment 50 is the compound or pharmaceutically acceptable salt or solvate thereof of any one of embodiments 1-24, wherein: R¹ is C₁-C₆alkyl substituted with halogen, —CN, —OR³, —SR³, —S(═O) R³, —S(═O)₂R³, —N(R³)₂, —C(═O)OR³, —C(═O)N(R³)₂, —CR³═C (R³)₂, —C≡CR³, substituted or unsubstituted C₃-C₁₀cycloalkyl, substituted or unsubstituted C₂-C₁₀heterocycloalkyl, or substituted or unsubstituted aryl; and
each R³ is independently hydrogen, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, or substituted or unsubstituted C₂-C₁₀heterocycloalkyl; or if two R³ are on the same nitrogen atom, then two R³ are taken together with the nitrogen atom to which they are attached to form a substituted or unsubstituted C₃-C₇ heterocycloalkyl.

Embodiment 51 is the compound or pharmaceutically acceptable salt or solvate thereof of any one of embodiments 1-24, wherein: $R^1$ is substituted or unsubstituted $C_3$-$C_{10}$cycloalkyl or substituted or unsubstituted $C_2$-$C_{10}$heterocycloalkyl.

Embodiment 52 is the compound or pharmaceutically acceptable salt or solvate thereof of embodiment 51, wherein: $R^1$ is $C_3$-$C_6$cycloalkyl or $C_3$-$C_5$heterocycloalkyl substituted with $C_1$-$C_6$alkyl, phenyl, pyridinyl, pyrazinyl, pyrimidinyl, pyridazinyl, or triazinyl.

Embodiment 53 is the compound or pharmaceutically acceptable salt or solvate thereof of embodiment 51, wherein: $R^1$ is $C_3$-$C_6$cycloalkyl or $C_3$-$C_5$heterocycloalkyl substituted with $C_1$-$C_6$alkyl, phenyl, or pyridinyl.

Embodiment 54 is the compound or pharmaceutically acceptable salt or solvate thereof of any one of embodiments 1-53, wherein: R is halogen, nitro, —CN, —OR$^3$, —C(=O)R$^3$, —C(=O)N(R$^3$)$_2$, —C(=O)OR$^3$, —S(=O)R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted $C_1$-$C_6$fluoroalkyl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 55 is the compound or pharmaceutically acceptable salt or solvate thereof of any one of embodiments 1-53, wherein: R is F, Cl, Br, I, nitro, —CN, —OCH$_2$F, —OCHF$_2$, —OCF$_3$, —C(=O)CH$_3$, —C(=O)OCH$_3$—C(=O)NH$_2$, —C(=O)NHCH$_3$, —C(=O)N(CH$_3$)$_2$, —S(=O)CH$_3$, —S(=O)$_2$CH$_3$, —NHS(=O)$_2$CH$_3$, —N(CH$_3$)S(=O)$_2$CH$_3$, —NHC(=O)CH$_3$, —N(CH$_3$)C(=O)CH$_3$, —NHC(=O)OCH$_3$, —N(CH$_3$)C(=O)OCH$_3$, —CH$_2$F, —CHF$_2$, or —CF$_3$.

Embodiment 56 is the compound or pharmaceutically acceptable salt or solvate thereof of any one of embodiments 1-53, wherein: R is F, Cl, —CN, —OCF$_3$, —CHF$_2$, or —CF$_3$.

Embodiment 57 is the compound or pharmaceutically acceptable salt or solvate thereof of any one of embodiments 1-53, wherein: R is F, Cl, —OCF$_3$, —CHF$_2$, or —CF$_3$.

Embodiment 58 is the compound or pharmaceutically acceptable salt or solvate thereof of any one of embodiments 1-53, wherein: R is F, Cl, or —CF$_3$.

Embodiment 59 is the compound or pharmaceutically acceptable salt or solvate thereof of any one of embodiments 1-58, wherein: each $R^2$ is independently halogen, nitro, —CN, —OR$^3$, —SR$^3$, —S(=O)$_2$R$^3$, —N(R$^3$)$_2$, —C(=O)OR$^3$, substituted or unsubstituted $C_1$-$C_6$alkyl, or substituted or unsubstituted $C_1$-$C_6$fluoroalkyl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 60 is the compound or pharmaceutically acceptable salt or solvate thereof of any one of embodiments 1-58, wherein: each $R^2$ is independently F, Cl, Br, nitro, —CN, —OH, —OCH$_3$, —OCH$_2$CH$_3$, —OCH$_2$CH$_2$OH, —OCH$_2$CN, —OCF$_3$, —S(=O)$_2$CH$_3$, —NH$_2$, —NHCH$_3$, —N(CH$_3$)$_2$, —C(=O)OCH$_3$, —CH$_3$, —CH$_2$CH$_3$, —CH$_2$F, —CHF$_2$, or —CF$_3$.

Embodiment 61 is the compound or pharmaceutically acceptable salt or solvate thereof of any one of embodiments 1-58, wherein: each $R^2$ is independently F, Cl, —CN, —OCH$_3$, —OCF$_3$, —C(=O)OCH$_3$, —CH$_3$, or —CF$_3$.

Embodiment 62 is the compound or pharmaceutically acceptable salt or solvate thereof of any one of embodiments 1-58, wherein: each $R^2$ is independently F, Cl, —OCF$_3$, or —CF$_3$.

Embodiment 63 is the compound or pharmaceutically acceptable salt or solvate thereof of any one of embodiments 1-58, wherein: each $R^2$ is independently F or Cl.

Embodiment 64 is a compound of Formula (II), or a pharmaceutically acceptable salt or solvate thereof:

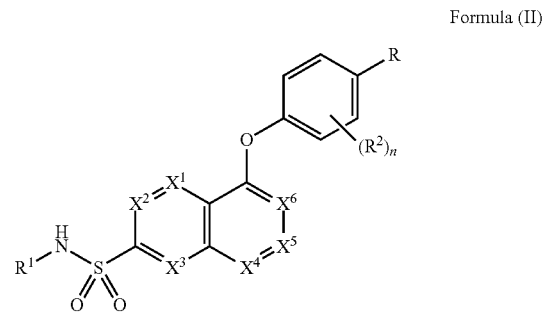

Formula (II)

wherein,
each $X^1$, $X^2$, $X^3$, $X^4$, $X^5$, and $X^6$ is independently N or CR$^X$;
each $R^X$ is independently hydrogen, halogen, nitro, —OR$^3$, —SR$^3$, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
R is halogen, nitro, —CN, —OR$^3$, —SR$^3$, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, or substituted or unsubstituted $C_1$-$C_6$fluoroalkyl;
$R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)$_2$R$^4$;
each $R^2$ is independently halogen, nitro, —N$_3$, —CN, —OR$^3$, —SR$^3$, —S(=O)$_2$R$^3$, —N(R$^3$)$_2$, —C(=O)OR$^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl;

$R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —$NH_2$; and n is 0, 1, 2, 3, or 4.

Embodiment 65 is the compound or pharmaceutically acceptable salt or solvate thereof of embodiment 64, wherein: each $X^1$, $X^2$, and $X^3$ is $CR^X$.

Embodiment 66 is the compound or pharmaceutically acceptable salt or solvate thereof of embodiment 64, wherein: $X^1$ is N; and each $X^2$ and $X^3$ is $CR^X$.

Embodiment 67 is the compound or pharmaceutically acceptable salt or solvate thereof of embodiment 64, wherein: each $X^1$ and $X^2$ is $CR^X$; and $X^3$ is N.

Embodiment 68 is the compound or pharmaceutically acceptable salt or solvate thereof of any one of embodiments 64-67, wherein: each $X^4$, $X^5$, and $X^6$ is $CR^X$.

Embodiment 69 is the compound or pharmaceutically acceptable salt or solvate thereof of any one of embodiments 64-67, wherein: $X^4$ is N; and each $X^5$ and $X^6$ is $CR^X$.

Embodiment 70 is the compound or pharmaceutically acceptable salt or solvate thereof of any one of embodiments 64-67, wherein: each $X^4$ and $X^5$ is $CR^X$; and $X^6$ is N.

Embodiment 71 is the compound or pharmaceutically acceptable salt or solvate thereof of any one of embodiments 64-70, wherein: each $R^X$ is independently hydrogen, halogen, —$OR^3$, —$SR^3$, —CN, —$S(=O)R^3$, —$S(=O)_2R^3$, —$N(R^3)_2$, —$NR^3S(=O)_2R^3$, —$NR^3C(=O)R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_2$ heterocycloalkyl.

Embodiment 72 is the compound or pharmaceutically acceptable salt or solvate thereof of any one of embodiments 64-70, wherein: each $R^X$ is independently hydrogen, halogen, —$OR^3$, —$SR^3$, —$S(=O)R^3$, —$S(=O)_2R^3$, —$N(R^3)_2$, —$NR^3S(=O)_2R^3$, —$NR^3C(=O)R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 73 is the compound or pharmaceutically acceptable salt or solvate thereof of any one of embodiments 64-70, wherein: each $R^X$ is independently hydrogen, F, Cl, Br, I, —$CH_3$, —$CH_2CH_3$, —$CH_2OH$, —$CH_2CH_2OH$, —$CH_2CN$, —$CH_2C(=O)OH$, —$CH_2C(=O)OCH_3$, —$CH_2C(=O)OCH_2CH_3$, —$CH_2C(=O)NH_2$, —$CH_2C(=O)NHCH_3$, —$CH_2C(=O)N(CH_3)_2$, —$CH_2NH_2$, —$CH_2NHCH_3$, —$CH_2N(CH_3)_2$, —$CH_2F$, —$CHF_2$, —$CF_3$, —$CH=CH_2$, —$C≡CH$, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —$C(=O)OH$, —$C(=O)OCH_3$, —$C(=O)OCH_2CH_3$, —$C(=O)NH_2$, —$C(=O)NHCH_3$, —$C(=O)N(CH_3)_2$, —$NH_2$, —$NHCH_3$, —$N(CH_3)_2$, —$NHC(=O)CH_3$, —$N(CH_3)C(=O)CH_3$, —$NHC(=O)OCH_3$, —$N(CH_3)C(=O)OCH_3$, —$S(=O)CH_3$, —$S(=O)_2CH_3$, —$NHS(=O)_2CH_3$, or —$N(CH_3)S(=O)_2CH_3$.

Embodiment 74 is the compound or pharmaceutically acceptable salt or solvate thereof of any one of embodiments 64-70, wherein: each $R^X$ is independently hydrogen, F, Cl, Br, I, —$CH_3$, —$CH_2CH_3$, cyclopropyl, —$C≡CH$, —OH, —$OCH_3$, —$OCH_2CH_3$, —$OCF_3$, —$SCH_3$, cyclopropyloxy, —$NH_2$, —$NHC(=O)CH_3$, —$N(CH_3)C(=O)CH_3$, —$NHS(=O)_2CH_3$, —$N(CH_3)S(=O)_2CH_3$, —$S(=O)CH_3$, or —$S(=O)_2CH_3$.

Embodiment 75 is the compound or pharmaceutically acceptable salt or solvate thereof of any one of embodiments 64-70, wherein: each $R^X$ is independently hydrogen, F, Cl, Br, I, —$CH_3$, —$CH_2CH_3$, cyclopropyl, —OH, —$OCH_3$, —$OCH_2CH_3$, —$OCF_3$, cyclopropyloxy, —$NH_2$, —$NHC(=O)CH_3$, —$NHS(=O)_2CH_3$, —$S(=O)CH_3$, or —$S(=O)_2CH_3$.

Embodiment 76 is the compound or pharmaceutically acceptable salt or solvate thereof of any one of embodiments 64-70, wherein: each $R^X$ is independently hydrogen, F, Cl, Br, —$CH_3$, —OH, —$OCH_3$, or —$OCF_3$.

Embodiment 77 is the compound or pharmaceutically acceptable salt or solvate thereof of any one of embodiments 64-70, wherein: each $R^X$ is independently hydrogen, F, Cl, —$CH_3$, —$OCH_3$, or —$OCF_3$.

Embodiment 78 is the compound or pharmaceutically acceptable salt or solvate thereof of any one of embodiments 64-70, wherein: each $R^X$ is independently hydrogen, F, or —$OCH_3$.

Embodiment 79 is the compound or pharmaceutically acceptable salt or solvate thereof of any one of embodiments 64-70, wherein: each $R^X$ is hydrogen.

Embodiment 80 is the compound or pharmaceutically acceptable salt or solvate thereof of any one of embodiments 64-79, wherein: $R^1$ is substituted or unsubstituted $C_1$-$C_6$alkyl.

Embodiment 81 is the compound or pharmaceutically acceptable salt or solvate thereof of any one of embodiments 64-79, wherein: $R^1$ is $C_1$-$C_6$alkyl substituted with substituted or unsubstituted $C_2$-$C_6$alkenyl, substituted or unsubstituted $C_2$-$C_6$alkynyl, or —CN.

Embodiment 82 is the compound or pharmaceutically acceptable salt or solvate thereof of any one of embodiments 64-79, wherein: $R^1$ is $C_1$-$C_6$alkyl substituted with —$OR^3$; and $R^3$ is hydrogen, substituted or unsubstituted $C_1$-$C_6$alkyl, substituted or unsubstituted $C_1$-$C_6$fluoroalkyl, or substituted or un substituted $C_3$-$C_{10}$cycloalkyl.

Embodiment 83 is the compound or pharmaceutically acceptable salt or solvate thereof of any one of embodiments 64-79, wherein: R¹ is $C_1$-$C_6$alkyl substituted with —C(=O)N($R^5$)$_2$ or —N($R^5$)$_2$; wherein each $R^5$ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —CN; or two $R^5$ are taken together with the nitrogen atom to which they are attached to form a substituted or unsubstituted $C_3$-$C_7$ heterocycloalkyl.

Embodiment 84 is the compound or pharmaceutically acceptable salt or solvate thereof of any one of embodiments 64-79, wherein: R¹ is $C_1$-$C_6$alkyl substituted with substituted or unsubstituted $C_3$-$C_8$cycloalkyl or substituted or unsubstituted $C_2$-$C_7$heterocycloalkyl.

Embodiment 85 is the compound or pharmaceutically acceptable salt or solvate thereof of embodiment 84, wherein: R¹ is $C_1$-$C_6$alkyl substituted with cyclopropyl, cyclobutyl, cyclopentyl, or cyclohexyl.

Embodiment 86 is the compound or pharmaceutically acceptable salt or solvate thereof of embodiment 84, wherein: R¹ is $C_1$-$C_6$alkyl substituted with oxetanyl, tetrahydrofuranyl, tetrahydropyranyl, azetidinyl, pyrrolidinyl, or piperidinyl.

Embodiment 87 is the compound or pharmaceutically acceptable salt or solvate thereof of any one of embodiments 64-79, wherein: R¹ is $C_1$-$C_6$alkyl substituted with substituted or unsubstituted phenyl, wherein if phenyl is substituted, then it is substituted with 1, 2, 3, or 4 substituents selected from halogen, nitro, —CN, —$OR^3$, —N($R^3$)$_2$, —C(=O)$R^3$, —C(=O)N($R^3$)$_2$, —C(=O)$OR^3$, substituted or unsubstituted $C_1$-$C_6$alkyl, and substituted or unsubstituted $C_1$-$C_6$fluoroalkyl; and each $R^3$ is independently hydrogen, substituted or unsubstituted $C_1$-$C_6$alkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 88 is the compound or pharmaceutically acceptable salt or solvate thereof of any one of embodiments 64-79, wherein: R¹ is $C_1$-$C_6$alkyl substituted with 5-membered heteroaryl ring containing at least one nitrogen atom.

Embodiment 89 is the compound or pharmaceutically acceptable salt or solvate thereof of any one of embodiments 64-79, wherein: R¹ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.

Embodiment 90 is the compound or pharmaceutically acceptable salt or solvate thereof of any one of embodiments 64-79, wherein: R¹ is $C_1$-$C_6$alkyl substituted with 5-membered heteroaryl ring selected from

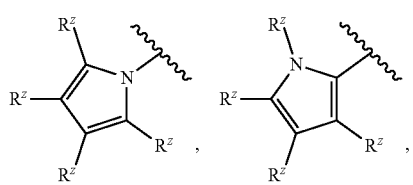

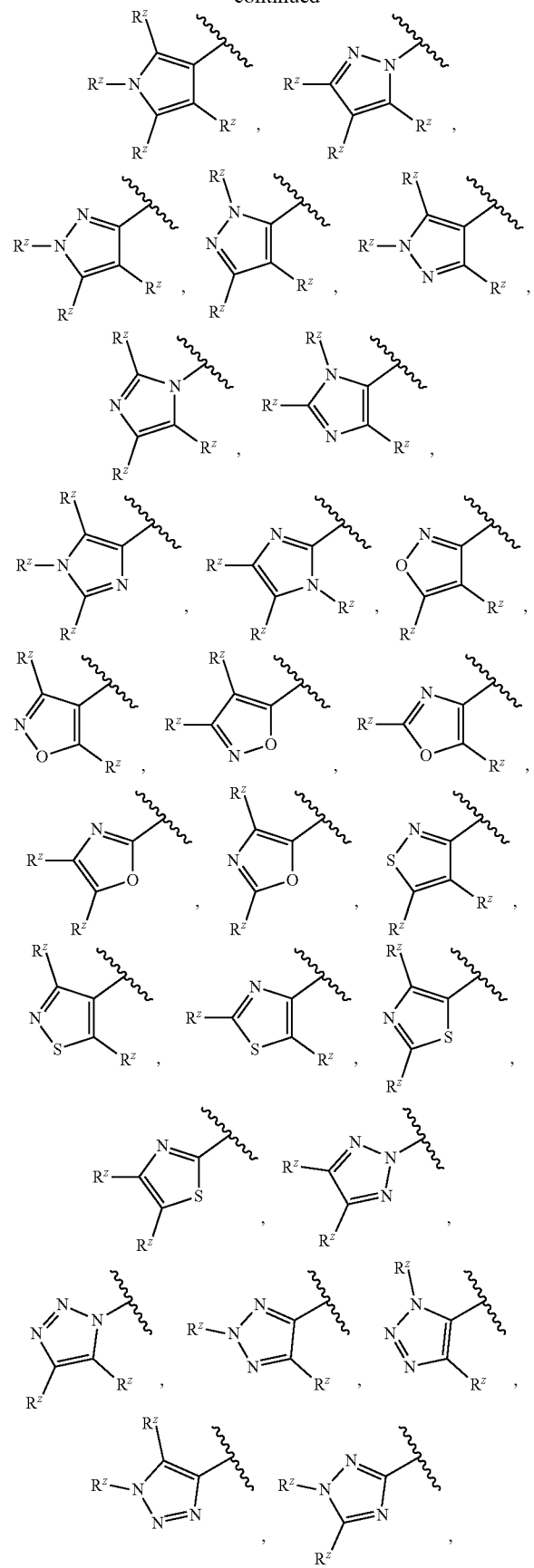

-continued

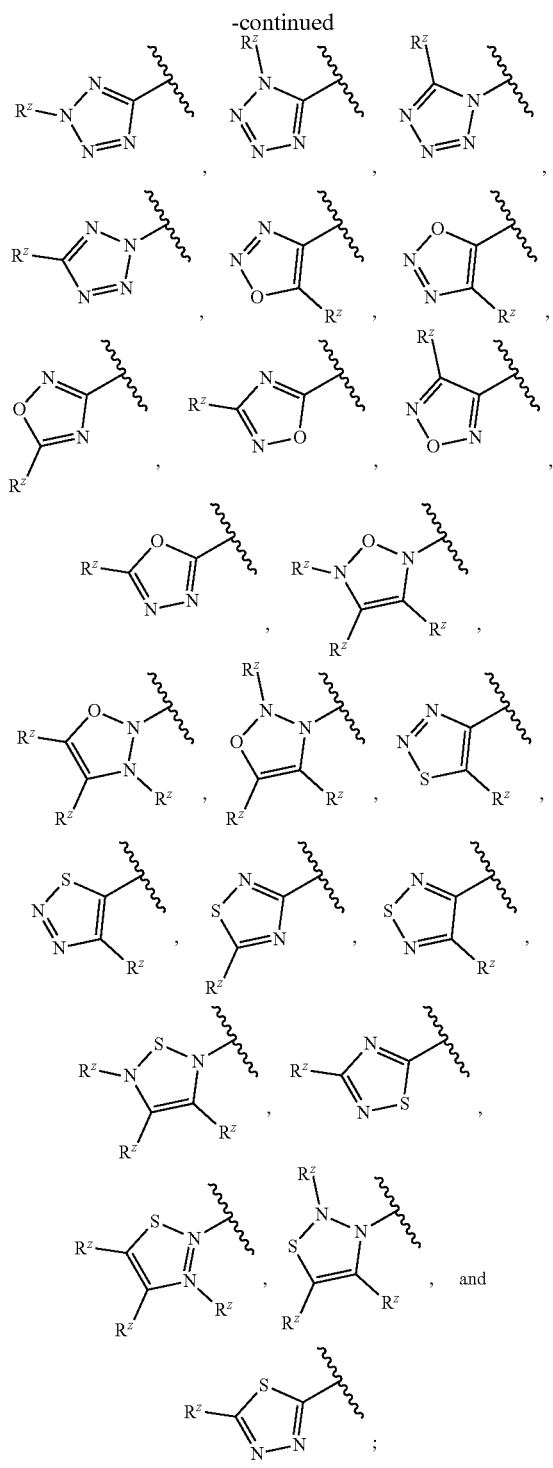

wherein each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment 91 is the compound or pharmaceutically acceptable salt or solvate thereof of any one of embodiments 64-79, wherein: $R^1$ is C$_1$-C$_6$alkyl substituted with a substituted or unsubstituted monocyclic 6-membered heteroaryl ring containing at least one nitrogen atom.

Embodiment 92 is the compound or pharmaceutically acceptable salt or solvate thereof of any one of embodiments 64-79, wherein: $R^1$ is C$_1$-C$_6$alkyl substituted with a substituted or unsubstituted monocyclic 6-membered heteroaryl ring containing 1, 2, or 3 nitrogen atoms.

Embodiment 93 is the compound or pharmaceutically acceptable salt or solvate thereof of any one of embodiments 64-79, wherein:

$R^1$ is C$_1$-C$_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl.

Embodiment 94 is the compound or pharmaceutically acceptable salt or solvate thereof of any one of embodiments 64-79, wherein: $R^1$ is C$_1$-C$_6$alkyl substituted with 6-membered heteroaryl ring selected from

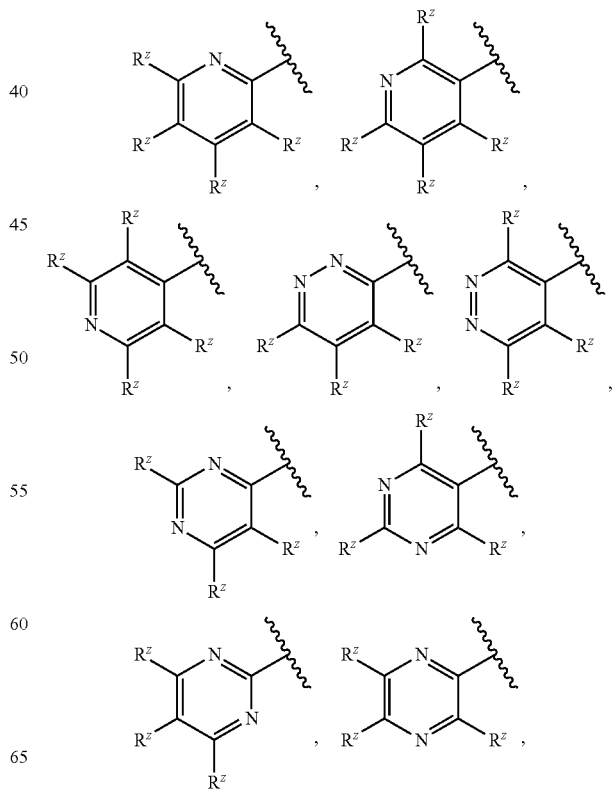

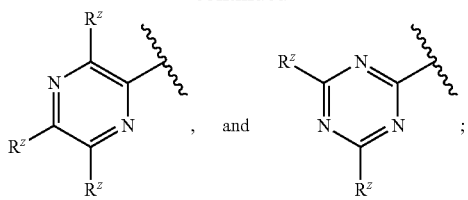
, and wherein each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 95 is the compound or pharmaceutically acceptable salt or solvate thereof of any one of embodiments 64-79, wherein: $R^1$ is $C_1$-$C_6$alkyl substituted with bicyclic 6/5 fused heteroaryl ring.

Embodiment 96 is the compound or pharmaceutically acceptable salt or solvate thereof of any one of embodiments 64-79, wherein: $R^1$ is $C_1$-$C_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzooxadiazolyl, substituted or unsubstituted benzothiadiazolyl, substituted or unsubstituted indolizinyl, and substituted or unsubstituted imidazopyridinyl.

Embodiment 97 is the compound or pharmaceutically acceptable salt or solvate thereof of any one of embodiments 64-79, wherein: $R^1$ is $C_1$-$C_6$alkyl substituted with bicyclic 6/5 fused heteroaryl ring selected from

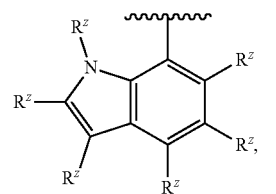

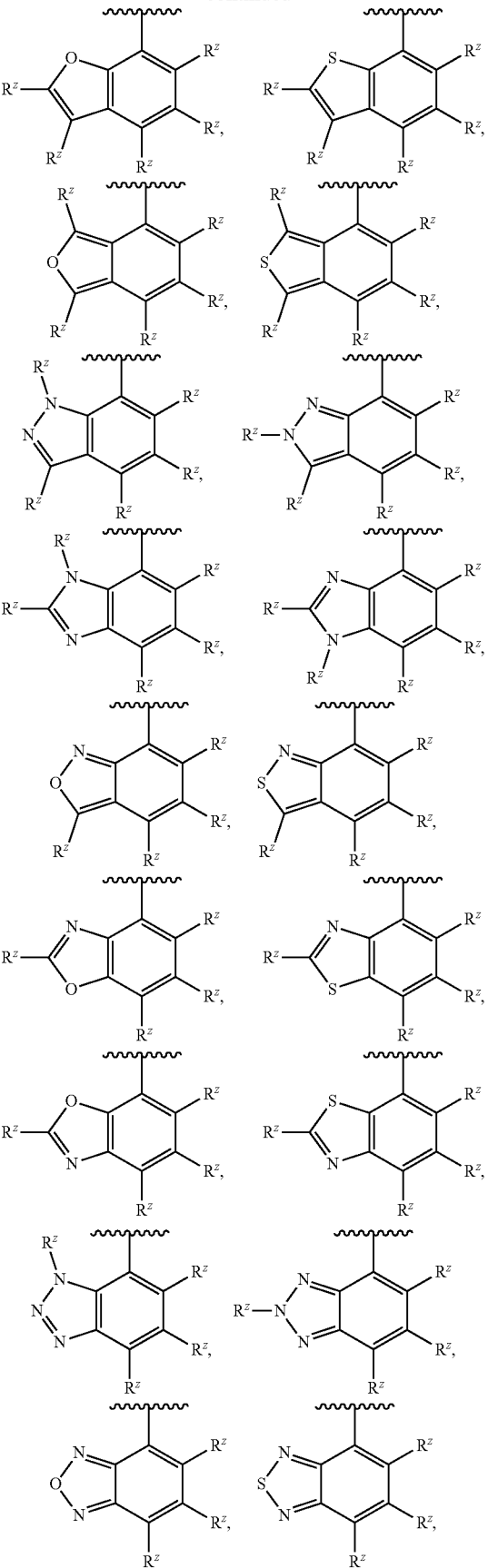

-continued

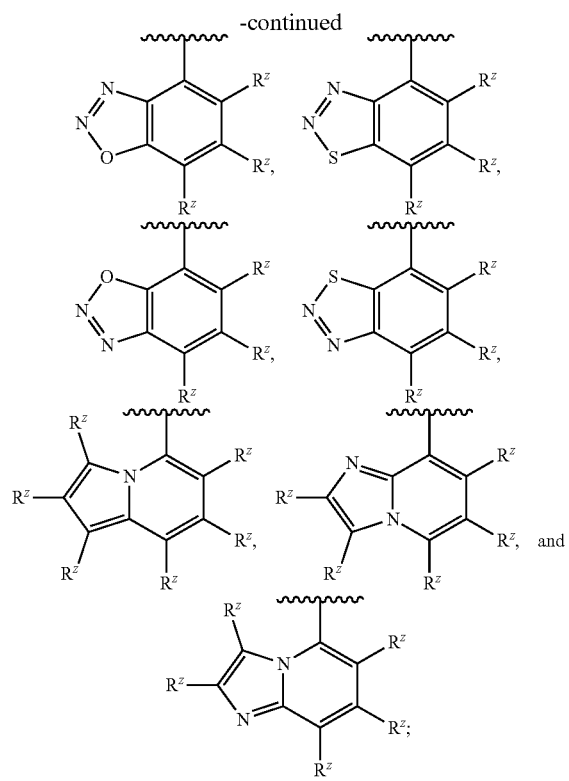

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment 98 is the compound or pharmaceutically acceptable salt or solvate thereof of any one of embodiments 64-79, wherein: $R^1$ is C$_1$-C$_6$alkyl substituted with a substituted or unsubstituted bicyclic 6/6 fused heteroaryl ring containing at least one nitrogen atom.

Embodiment 99 is the compound or pharmaceutically acceptable salt or solvate thereof of any one of embodiments 64-79, wherein: $R^1$ is C$_1$-C$_6$alkyl substituted with a substituted or unsubstituted bicyclic 6/6 fused heteroaryl ring containing 1, 2, 3, or 4 nitrogen atoms.

Embodiment 100 is the compound or pharmaceutically acceptable salt or solvate thereof of any one of embodiments 64-79, wherein: $R^1$ is C$_1$-C$_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or unsubstituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyridazinyl, substituted or unsubstituted pyrimidopyrimidinyl, and substituted or unsubstituted pteridinyl.

Embodiment 101 is the compound or pharmaceutically acceptable salt or solvate thereof of any one of embodiments 64-79, wherein: $R^1$ is C$_1$-C$_6$alkyl substituted with 6/6 fused heteroaryl ring selected from

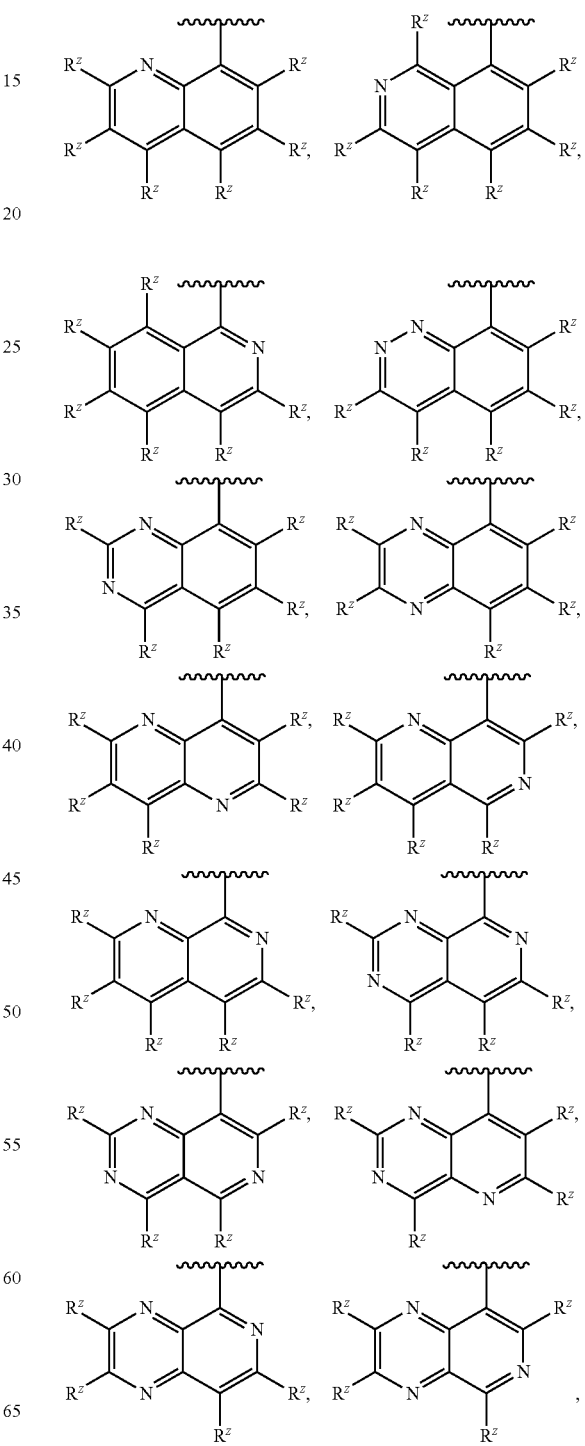

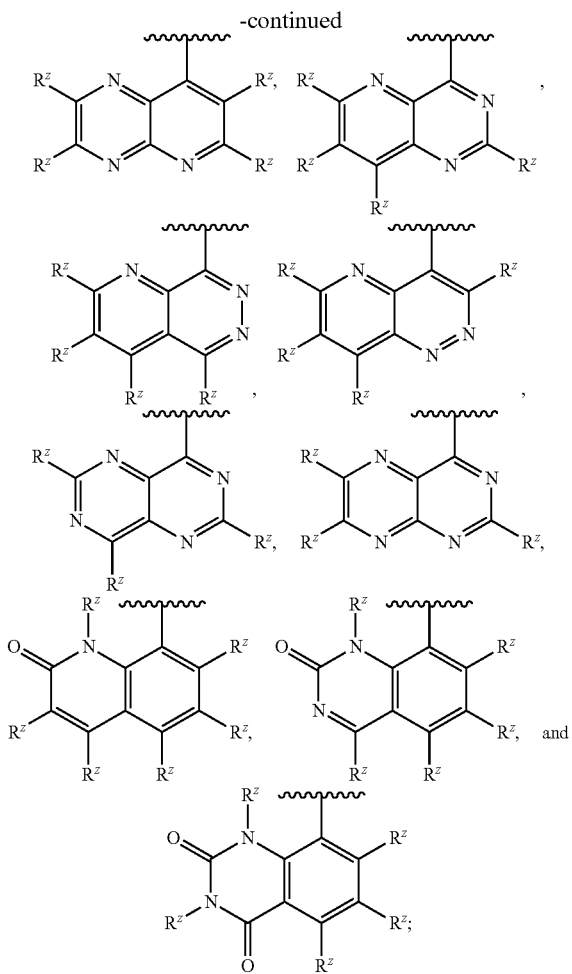

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 102 is the compound or pharmaceutically acceptable salt or solvate thereof of any one of embodiments 90, 94, 97, or 101, wherein: each R$^z$ is independently hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, —OCF$_3$, —NH$_2$, —NHCH$_3$, or —N(CH$_3$)$_2$.

Embodiment 103 is the compound or pharmaceutically acceptable salt or solvate thereof of any one of embodiments 90, 94, 97, or 101, wherein: each R$^z$ is independently hydrogen, Cl, Br, —CH$_3$, —OCH$_3$, —NH$_2$, or —N(CH$_3$)$_2$.

Embodiment 104 is the compound or pharmaceutically acceptable salt or solvate thereof of any one of embodiments 90, 94, 97, or 101, wherein: each R$^z$ is hydrogen.

Embodiment 105 is the compound or pharmaceutically acceptable salt or solvate thereof of any one of embodiments 64-79, wherein: R$^1$ is C$_1$-C$_6$alkyl substituted with halogen, —CN, —OR$^3$, —SR$^3$, —S(=O) R$^3$, —S(=O)$_2$R$^3$, —N(R$^3$)$_2$, —C(=O)OR$^3$, —C(=O)N(R$^3$)$_2$, —CR$^3$=C(R$^3$)$_2$, —C≡CR$^3$, substituted or unsubstituted C$_3$-C$_{10}$cycloalkyl, substituted or unsubstituted C$_2$-C$_{10}$heterocycloalkyl, or substituted or unsubstituted aryl; and
each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 106 is the compound or pharmaceutically acceptable salt or solvate thereof of any one of embodiments 64-79, wherein: R$^1$ is substituted or unsubstituted C$_3$-C$_{10}$cycloalkyl or substituted or unsubstituted C$_2$-C$_{10}$heterocycloalkyl.

Embodiment 107 is the compound or pharmaceutically acceptable salt or solvate thereof of embodiment 106, wherein: R$^1$ is C$_3$-C$_6$cycloalkyl or C$_3$-C$_5$heterocycloalkyl substituted with C$_1$-C$_6$alkyl, phenyl, pyridinyl, pyrazinyl, pyrimidinyl, pyridazinyl, or triazinyl.

Embodiment 108 is the compound or pharmaceutically acceptable salt or solvate thereof of embodiment 106, wherein: R$^1$ is C$_3$-C$_6$cycloalkyl or C$_3$-C$_5$heterocycloalkyl substituted with C$_1$-C$_6$alkyl, phenyl, or pyridinyl.

Embodiment 109 is the compound or pharmaceutically acceptable salt or solvate thereof of any one of embodiments 64-108, wherein: R is halogen, nitro, —CN, —OR$^3$, —C(=O)R$^3$, —C(=O)N(R$^3$)$_2$, —C(=O)OR$^3$, —S(=O) R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl; and
each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 110 is the compound or pharmaceutically acceptable salt or solvate thereof of any one of embodiments 64-108, wherein: R is F, Cl, Br, I, nitro, —CN, —OCH$_2$F, —OCHF$_2$, —OCF$_3$, —C(=O)CH$_3$, —C(=O)OCH$_3$—C(=O)NH$_2$, —C(=O)NHCH$_3$, —C(=O)N(CH$_3$)$_2$, —S(=O)CH$_3$, —S(=O)$_2$CH$_3$, —NHS(=O)$_2$CH$_3$, —N(CH$_3$)S(=O)$_2$CH$_3$, —NHC(=O)CH$_3$, —N(CH$_3$)C(=O)CH$_3$, —NHC(=O)OCH$_3$, —N(CH$_3$)C(=O)OCH$_3$, —CH$_2$F, —CHF$_2$, or —CF$_3$.

Embodiment 111 is the compound or pharmaceutically acceptable salt or solvate thereof of any one of embodiments 64-108, wherein: R is F, Cl, —CN, —OCF$_3$, —CHF$_2$, or —CF$_3$.

Embodiment 112 is the compound or pharmaceutically acceptable salt or solvate thereof of any one of embodiments 64-108, wherein: R is F, Cl, —OCF$_3$, —CHF$_2$, or —CF$_3$.

Embodiment 113 is the compound or pharmaceutically acceptable salt or solvate thereof of any one of embodiments 64-108, wherein: R is F, Cl, or —CF$_3$.

Embodiment 114 is the compound or pharmaceutically acceptable salt or solvate thereof of any one of embodiments 64-113, wherein: each R$^2$ is independently halogen, nitro, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, or substituted or unsubstituted C$_1$-C$_6$fluoroalkyl; and
each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_2$ heterocycloalkyl.

Embodiment 115 is the compound or pharmaceutically acceptable salt or solvate thereof of any one of embodiments 64-113, wherein: each R$^2$ is independently F, Cl, Br, nitro, —CN, —OH, —OCH$_3$, —OCH$_2$CH$_3$, —OCH$_2$CH$_2$OH, —OCH$_2$CN, —OCF$_3$, —S(=O)$_2$CH$_3$, —NH$_2$, —NHCH$_3$, —N(CH$_3$)$_2$, —C(=O)OCH$_3$, —CH$_3$, —CH$_2$CH$_3$, —CH$_2$F, —CHF$_2$, or —CF$_3$.

Embodiment 116 is the compound or pharmaceutically acceptable salt or solvate thereof of any one of embodiments 64-113, wherein: each R$^2$ is independently F, Cl, —CN, —OCH$_3$, —OCF$_3$, —C(=O)OCH$_3$, —CH$_3$, or —CF$_3$.

Embodiment 117 is the compound or pharmaceutically acceptable salt or solvate thereof of any one of embodiments 64-113, wherein: each R$^2$ is independently F, Cl, —OCF$_3$, or —CF$_3$.

Embodiment 118 is the compound or pharmaceutically acceptable salt or solvate thereof of any one of embodiments 64-113, wherein: each R$^2$ is independently F or Cl.

Embodiment 119 is a compound of Formula (III), or a pharmaceutically acceptable salt or solvate thereof:

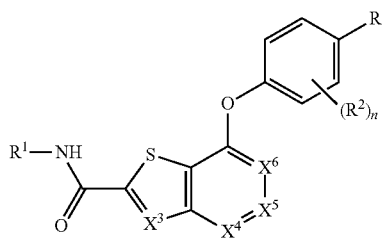

Formula (III)

wherein,
each X$^3$, X$^3$, and X$^6$ is independently N or CR$^X$;
X$^4$ is CR$^X$;
each R$^X$ is independently hydrogen, halogen, nitro, —OR$^3$, —SR$^3$, —CN, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted C$_1$-C$_6$alkyl, substituted or unsubstituted C$_1$-C$_6$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
R is halogen, nitro, —CN, —OR$^3$, —SR$^3$, —C(=O)R$^3$, —C(=O)N(R$^3$)$_2$, —C(=O)OR$^3$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl;
R$^1$ is substituted or unsubstituted C$_1$-C$_6$alkyl, substituted or unsubstituted C$_1$-C$_6$fluoroalkyl, substituted or unsubstituted C$_2$-C$_6$alkenyl, substituted or unsubstituted C$_2$-C$_6$alkynyl, substituted or unsubstituted C$_1$-C$_{10}$cycloalkyl, substituted or unsubstituted C$_2$-C$_{10}$heterocycloalkyl, substituted or unsubstituted C$_1$-C$_6$heteroalkyl, —CN, or —S(=O)$_2$R$^4$;
each R$^2$ is independently halogen, nitro, —N$_3$, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; or if two R$^3$ are on the same nitrogen atom, then two R$^3$ are taken together with the nitrogen atom to which they are attached to form a substituted or unsubstituted C$_3$-C$_7$ heterocycloalkyl;
R$^4$ is substituted or unsubstituted C$_1$-C$_6$alkyl, substituted or unsubstituted C$_1$-C$_6$fluoroalkyl, substituted or unsubstituted C$_3$-C$_{10}$cycloalkyl, or —NH$_2$; and
n is 0, 1, 2, 3, or 4.

Embodiment 120 is the compound or pharmaceutically acceptable salt or solvate thereof of embodiment 119, wherein: X$^3$ is CR$^X$.

Embodiment 121 is the compound or pharmaceutically acceptable salt or solvate thereof of embodiment 119, wherein: X$^3$ is N.

Embodiment 122 is the compound or pharmaceutically acceptable salt or solvate thereof of any one of embodiments 119-121, wherein: each X$^5$ and X$^6$ is CR$^X$.

Embodiment 123 is the compound or pharmaceutically acceptable salt or solvate thereof of any one of embodiments 119-121, wherein: X$^5$ is N; and X$^6$ is CR$^X$.

Embodiment 124 is the compound or pharmaceutically acceptable salt or solvate thereof of any one of embodiments 119-121, wherein: X$^5$ is CR$^X$; and X$^6$ is N.

Embodiment 125 is the compound or pharmaceutically acceptable salt or solvate thereof of any one of embodiments 119-124, wherein: each R$^X$ is independently hydrogen, halogen, —OR$^3$, —SR$^3$, —CN, —S(=O)R$^3$, —S(=O)$_2$R$^3$, —N(R$^3$)$_2$, —NR$^3$S(=O)$_2$R$^3$, —NR$^3$C(=O)R$^3$, substituted or unsubstituted C$_1$-C$_6$alkyl, substituted or unsubstituted C$_1$-C$_6$fluoroalkyl, substituted or unsubstituted C$_2$-C$_4$alkenyl, substituted or unsubstituted C$_2$-C$_4$alkynyl, or substituted or unsubstituted C$_1$-C$_6$heteroalkyl; and
each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 126 is the compound or pharmaceutically acceptable salt or solvate thereof of any one of embodiments 119-124, wherein: each $R^X$ is independently hydrogen, halogen, —$OR^3$, —$SR^3$, —$S(=O)R^3$, —$S(=O)_2R^3$, —$N(R^3)_2$, —$NR^3S(=O)_2R^3$, —$NR^3C(=O)R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 127 is the compound or pharmaceutically acceptable salt or solvate thereof of any one of embodiments 119-124, wherein; each $R^X$ is independently hydrogen, F, Cl, Br, I, —$CH_3$, —$CH_2CH_3$, —$CH_2OH$, —$CH_2CH_2OH$, —$CH_2CN$, —$CH_2C(=O)OH$, —$CH_2C(=O)OCH_3$, —$CH_2C(=O)OCH_2CH_3$, —$CH_2C(=O)NH_2$, —$CH_2C(=O)NHCH_3$, —$CH_2C(=O)N(CH_3)_2$, —$CH_2NH_2$, —$CH_2NHCH_3$, —$CH_2N(CH_3)_2$, —$CH_2F$, —$CHF_2$, —$CF_3$, —$CH=CH_2$, —$C\equiv CH$, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —$CN$, —$OH$, —$OCH_3$, —$OCH_2CH_3$, —$OCH_2CH_2OH$, —$OCH_2CN$, —$OCF_3$, —$C(=O)OH$, —$C(=O)OCH_3$, —$C(=O)OCH_2CH_3$, —$C(=O)NH_2$, —$C(=O)NHCH_3$, —$C(=O)N(CH_3)_2$, —$NH_2$, —$NHCH_3$, —$N(CH_3)_2$, —$NHC(=O)CH_3$, —$N(CH_3)C(=O)CH_3$, —$NHC(=O)OCH_3$, —$N(CH_3)C(=O)OCH_3$, —$S(=O)CH_3$, —$S(=O)_2CH_3$, —$NHS(=O)_2CH_3$, or —$N(CH_3)S(=O)_2CH_3$.

Embodiment 128 is the compound or pharmaceutically acceptable salt or solvate thereof of any one of embodiments 119-124, wherein: each $R^X$ is independently hydrogen, F, Cl, Br, I, —$CH_3$, —$CH_2CH_3$, cyclopropyl, —$C\equiv CH$, —$OH$, —$OCH_3$, —$OCH_2CH_3$, —$OCF_3$, —$SCH_3$, cyclopropyloxy, —$NH_2$, —$NHC(=O)CH_3$, —$N(CH_3)C(=O)CH_3$, —$NHS(=O)_2CH_3$, —$N(CH_3)S(=O)_2CH_3$, —$S(=O)CH_3$, or —$S(=O)_2CH_3$.

Embodiment 129 is the compound or pharmaceutically acceptable salt or solvate thereof of any one of embodiments 119-124, wherein: each $R^X$ is independently hydrogen, F, Cl, Br, I, —$CH_3$, —$CH_2CH_3$, cyclopropyl, —$OH$, —$OCH_3$, —$OCH_2CH_3$, —$OCF_3$, cyclopropyloxy, —$NH_2$, —$NHC(=O)CH_3$, —$NHS(=O)_2CH_3$, —$S(=O)CH_3$, or —$S(=O)_2 CH_3$.

Embodiment 130 is the compound or pharmaceutically acceptable salt or solvate thereof of any one of embodiments 119-124, wherein: each $R^X$ is independently hydrogen, F, Cl, Br, —$CH_3$, —$OH$, —$OCH_3$, or —$OCF_3$.

Embodiment 131 is the compound or pharmaceutically acceptable salt or solvate thereof of any one of embodiments 119-124, wherein: each $R^X$ is independently hydrogen, F, Cl, —$CH_3$, —$OCH_3$, or —$OCF_3$.

Embodiment 132 is the compound or pharmaceutically acceptable salt or solvate thereof of any one of embodiments 119-124, wherein: each $R^X$ is independently hydrogen, F, or —$OCH_3$.

Embodiment 133 is the compound or pharmaceutically acceptable salt or solvate thereof of any one of embodiments 119-124, wherein: each $R^X$ is hydrogen.

Embodiment 134 is the compound or pharmaceutically acceptable salt or solvate thereof of any one of embodiments 119-133, wherein $R^1$ is substituted or unsubstituted $C_1$-$C_6$alkyl.

Embodiment 135 is the compound or pharmaceutically acceptable salt or solvate thereof of any one of embodiments 119-133, wherein: $R^1$ is $C_1$-$C_6$alkyl substituted with substituted or unsubstituted $C_2$-$C_6$alkenyl, substituted or unsubstituted $C_2$-$C_6$alkynyl, or —$CN$.

Embodiment 136 is the compound or pharmaceutically acceptable salt or solvate thereof of any one of embodiments 119-133, wherein: $R^1$ is $C_1$-$C_6$alkyl substituted with —$OR^3$; and $R^3$ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl.

Embodiment 137 is the compound or pharmaceutically acceptable salt or solvate thereof of any one of embodiments 119-133, wherein: $R^1$ is $C_1$-$C_6$alkyl substituted with —$C(=O)N(R^5)_2$ or —$N(R^5)_2$; wherein each $R^5$ is independently hydrogen, substituted or unsubstituted $C_1$-$C_6$alkyl, substituted or unsubstituted $C_1$-$C_6$fluoroalkyl, substituted or unsubstituted $C_3$-$C_{10}$cycloalkyl, substituted or unsubstituted $C_2$-$C_6$alkenyl, substituted or unsubstituted $C_2$-$C_6$alkynyl, or —$CN$; or two $R^5$ are taken together with the nitrogen atom to which they are attached to form a substituted or unsubstituted $C_3$-$C_7$ heterocycloalkyl.

Embodiment 138 is the compound or pharmaceutically acceptable salt or solvate thereof of any one of embodiments 119-133, wherein: $R^1$ is $C_1$-$C_6$alkyl substituted with substituted or unsubstituted $C_3$-$C_8$cycloalkyl or substituted or unsubstituted $C_3$-$C_7$heterocycloalkyl.

Embodiment 139 is the compound or pharmaceutically acceptable salt or solvate thereof of embodiment 138, wherein: $R^1$ is $C_1$-$C_6$alkyl substituted with cyclopropyl, cyclobutyl, cyclopentyl, or cyclohexyl.

Embodiment 140 is the compound or pharmaceutically acceptable salt or solvate thereof of embodiment 138, wherein: $R^1$ is $C_1$-$C_6$alkyl substituted with oxetanyl, tetrahydrofuranyl, tetrahydropyranyl, azetidinyl, pyrrolidinyl, or piperidinyl.

Embodiment 141 is the compound or pharmaceutically acceptable salt or solvate thereof of any one of embodiments 119-133, wherein: $R^1$ is $C_1$-$C_6$alkyl substituted with substituted or unsubstituted phenyl, wherein if phenyl is substituted, then it is substituted with 1, 2, 3, or 4 substituents selected from halogen, nitro, —$CN$, —$OR^3$, —$N(R^3)_2$, —$C(=O)R^3$, —$C(=O)N(R^3)_2$, —$C(=O)OR^3$, substituted or unsubstituted $C_1$-$C_6$alkyl, and substituted or unsubstituted $C_1$-$C_6$fluoroalkyl; and each $R^3$ is independently hydrogen, substituted or unsubstituted $C_1$-$C_6$alkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 142 is the compound or pharmaceutically acceptable salt or solvate thereof of any one of embodiments 119-133, wherein: $R^1$ is $C_1$-$C_6$alkyl substituted with 5-membered heteroaryl ring containing at least one nitrogen atom.

Embodiment 143 is the compound or pharmaceutically acceptable salt or solvate thereof of any one of embodiments 119-133, wherein: $R^1$ is $C_1$-$C_6$alkyl substituted with 5-membered heteroaryl ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, and substituted or unsubstituted thiadiazolyl.
Embodiment 144 is the compound or pharmaceutically acceptable salt or solvate thereof of any one of embodiments 119-133, wherein: $R^1$ is $C_1$-$C_6$alkyl substituted with 5-membered heteroaryl ring selected from
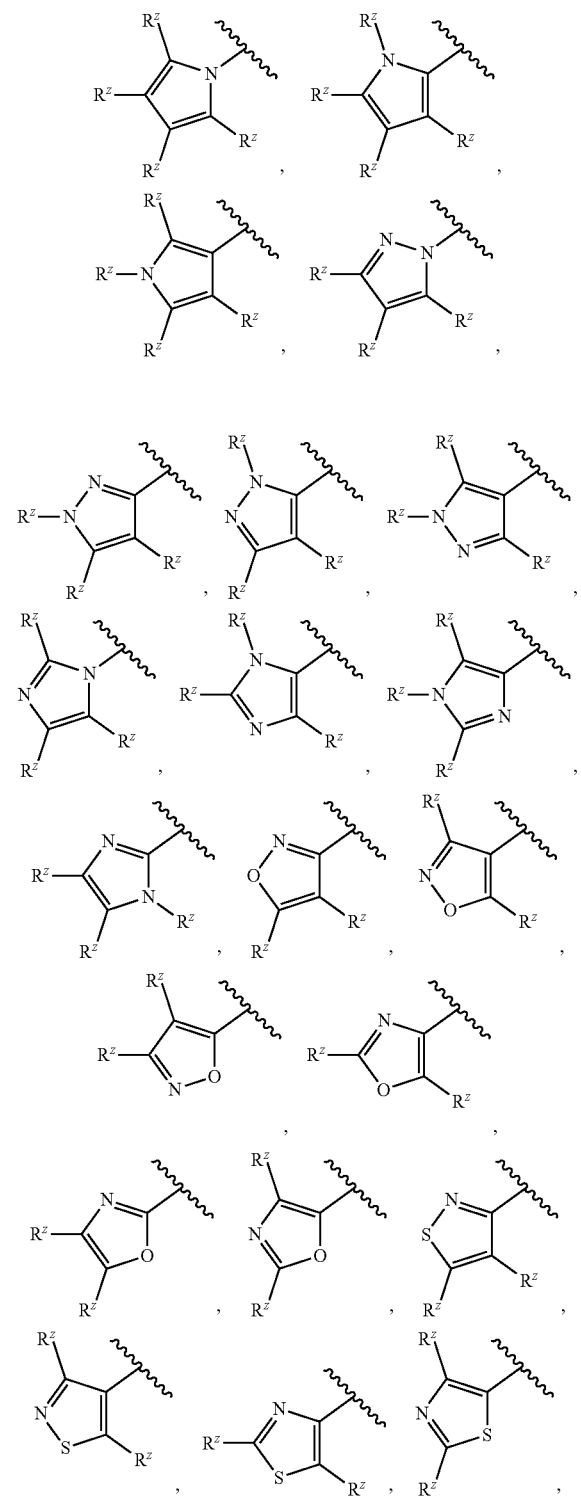
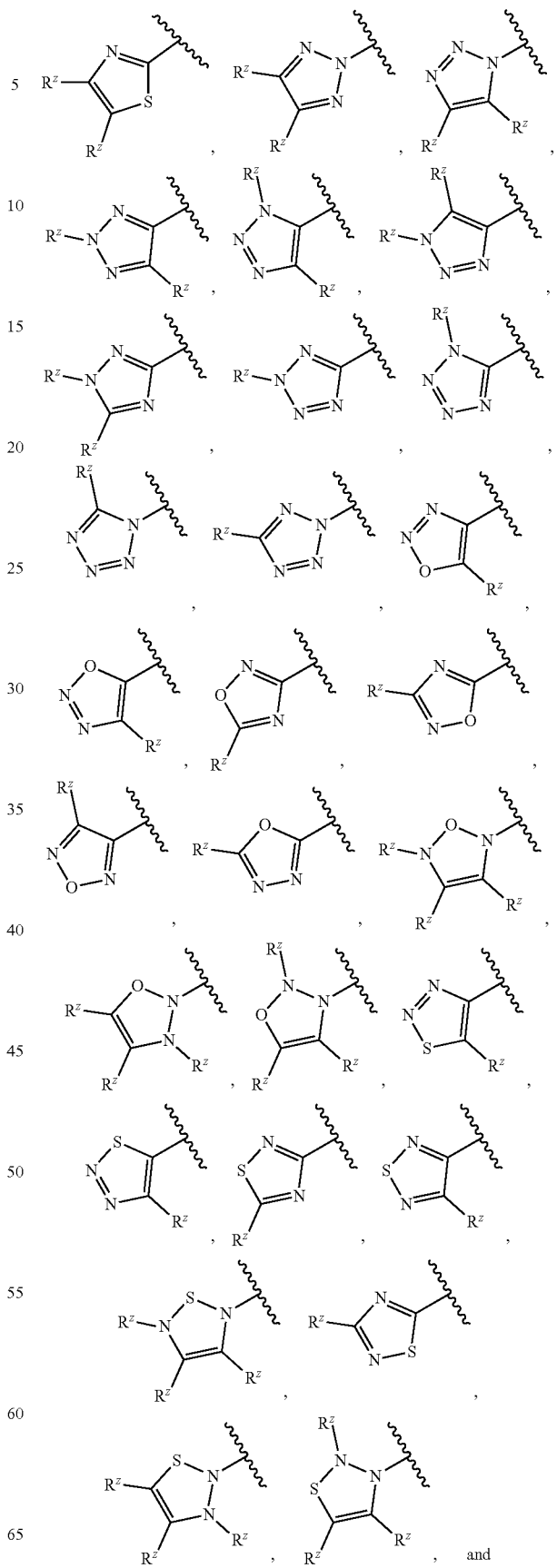
and -continued

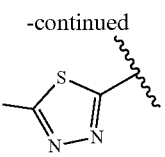

;

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment 145 is the compound or pharmaceutically acceptable salt or solvate thereof of any one of embodiments 119-133, wherein: $R^1$ is C$_1$-C$_6$alkyl substituted with a substituted or unsubstituted monocyclic 6-membered heteroaryl ring containing at least one nitrogen atom.

Embodiment 146 is the compound or pharmaceutically acceptable salt or solvate thereof of any one of embodiments 119-133, wherein: $R^1$ is C$_1$-C$_6$alkyl substituted with a substituted or unsubstituted monocyclic 6-membered heteroaryl ring containing 1, 2, or 3 nitrogen atoms.

Embodiment 147 is the compound or pharmaceutically acceptable salt or solvate thereof of any one of embodiments 119-133, wherein: $R^1$ is C$_1$-C$_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl.

Embodiment 148 is the compound or pharmaceutically acceptable salt or solvate thereof of any one of embodiments 119-133, wherein: $R^1$ is C$_1$-C$_6$alkyl substituted with 6-membered heteroaryl ring selected from

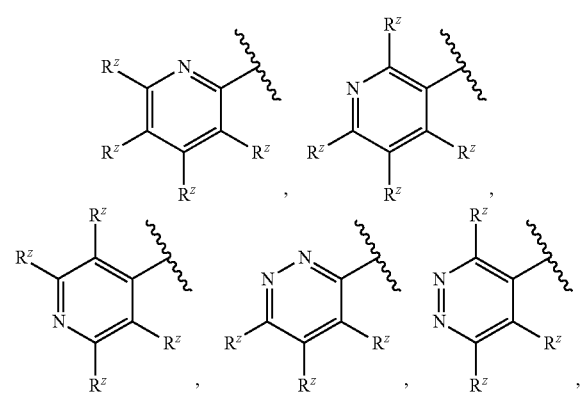

-continued

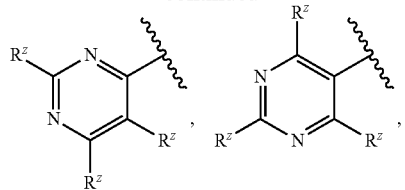

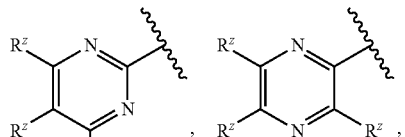

, and

;

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment 149 is the compound or pharmaceutically acceptable salt or solvate thereof of any one of embodiments 119-133, wherein: $R^1$ is C$_1$-C$_6$alkyl substituted with bicyclic 6/5 fused heteroaryl ring.

Embodiment 150 is the compound or pharmaceutically acceptable salt or solvate thereof of any one of embodiments 119-133, wherein: $R^1$ is C$_1$-C$_6$alkyl substituted with bicyclic 6/5 fused heteroaryl ring selected from substituted or unsubstituted indolyl, substituted or unsubstituted isoindolyl, substituted or unsubstituted benzofuranyl, substituted or unsubstituted isobenzofuranyl, substituted or unsubstituted benzothiophenyl, substituted or unsubstituted indazolyl, substituted or unsubstituted benzoimidazolyl, substituted or unsubstituted benzooxazolyl, substituted or unsubstituted benzoisoxazolyl, substituted or unsubstituted benzothiazolyl, substituted or unsubstituted benzoisothiazolyl, substituted or unsubstituted benzotriazolyl, substituted or unsubstituted benzooxadiazolyl, substituted or unsubstituted benzothiadiazolyl, substituted or unsubstituted indolizinyl, and substituted or unsubstituted imidazopyridinyl.

Embodiment 151 is the compound or pharmaceutically acceptable salt or solvate thereof of any one of embodiments 119-133, wherein: $R^1$ is C$_1$-C$_6$alkyl substituted with bicyclic 6/5 fused heteroaryl ring selected from

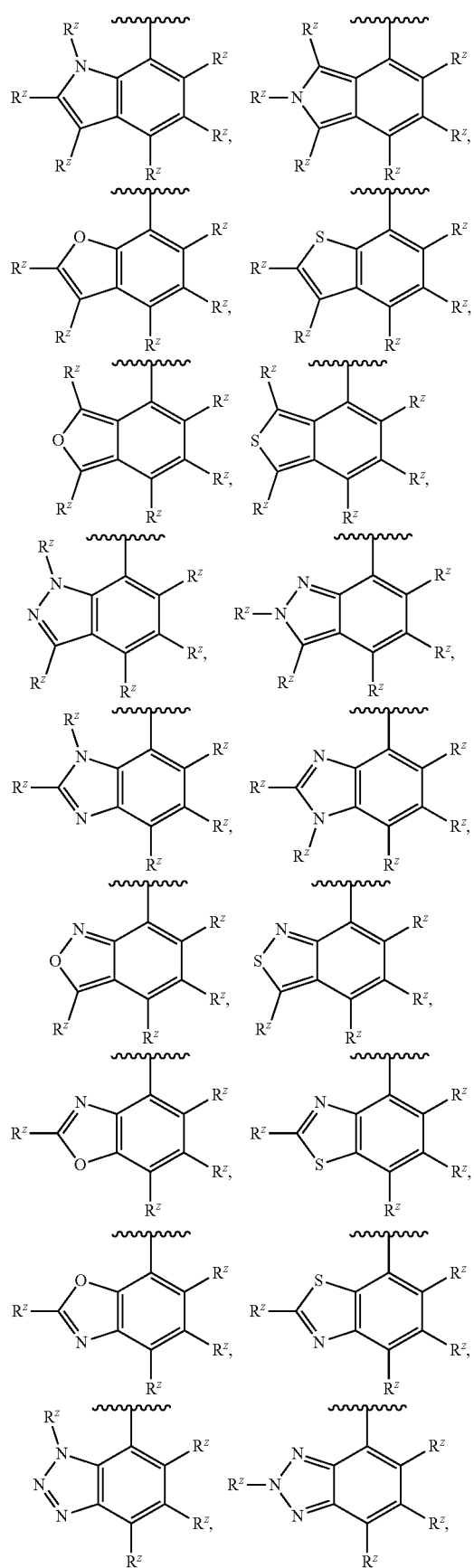
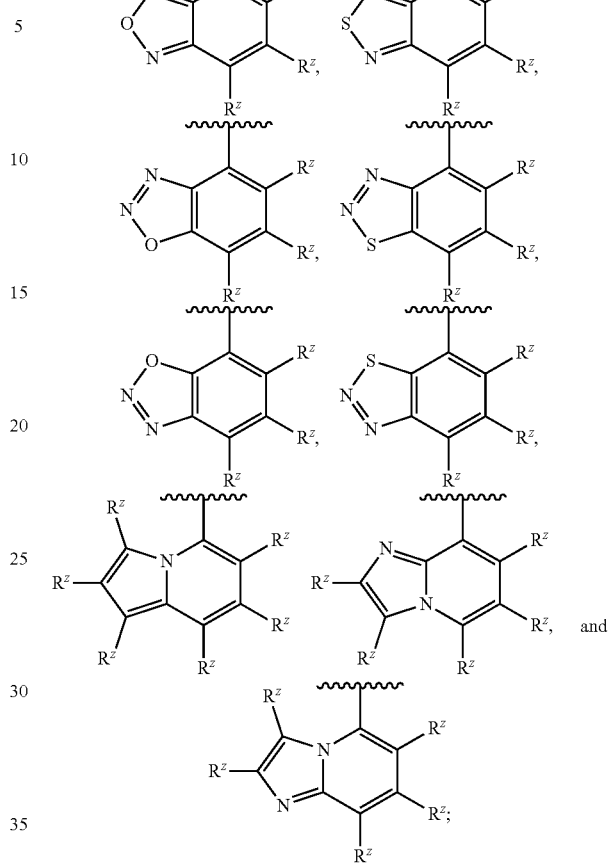

wherein
each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 152 is the compound or pharmaceutically acceptable salt or solvate thereof of any one of embodiments 119-133, wherein: $R^1$ is $C_1$-$C_6$alkyl substituted with a substituted or unsubstituted bicyclic 6/6 fused heteroaryl ring containing at least one nitrogen atom.

Embodiment 153 is the compound or pharmaceutically acceptable salt or solvate thereof of any one of embodiments 119-133, wherein: $R^1$ is $C_1$-$C_6$alkyl substituted with a substituted or unsubstituted bicyclic 6/6 fused heteroaryl ring containing 1, 2, 3, or 4 nitrogen atoms.

Embodiment 154 is the compound or pharmaceutically acceptable salt or solvate thereof of any one of embodiments 119-133, wherein: $R^1$ is $C_1$-$C_6$alkyl substituted with bicyclic 6/6 fused heteroaryl ring selected from substituted or unsubstituted quinolinyl, substituted or unsubstituted isoquinolinyl, substituted or unsubstituted cinnolinyl, substituted or unsubstituted quinazolinyl, substituted or unsubstituted quinoxalinyl, substituted or unsubstituted naphthyridinyl, substituted or unsubstituted pyridopyrimidinyl, substituted or unsubstituted pyridopyrazinyl, substituted or unsubstituted pyridopyridazinyl, substituted or unsubstituted pyrimidopyrimidinyl, and substituted or unsubstituted pteridinyl.

Embodiment 155 is the compound or pharmaceutically acceptable salt or solvate thereof of any one of embodiments 119-133, wherein: $R^1$ is $C_1$-$C_6$alkyl substituted with 6/6 fused heteroaryl ring selected from

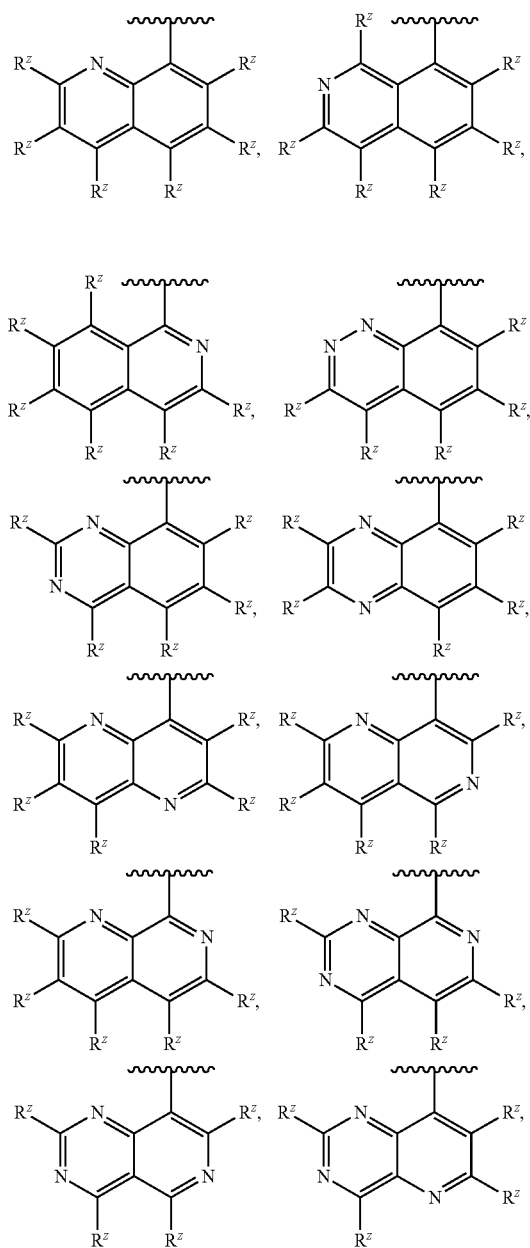

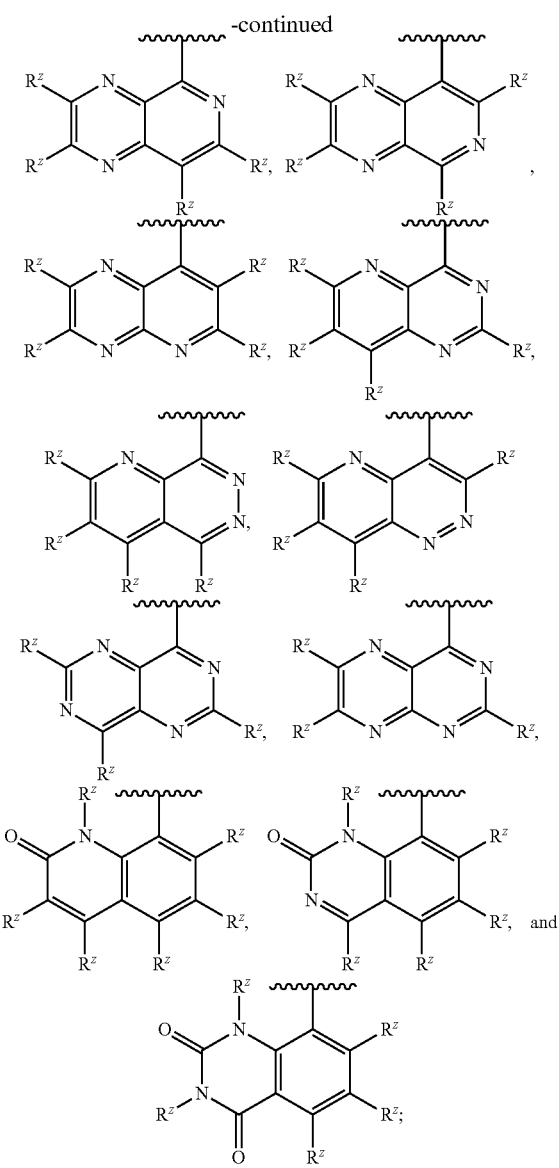

wherein
each $R^z$ is independently hydrogen, halogen, —CN, —$OR^3$, —$SR^3$, —S(=O)$_2R^3$, —N($R^3$)$_2$, —C(=O)$OR^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; or if two $R^3$ are on the same nitrogen atom, then two $R^3$ are taken together with the nitrogen atom to which they are attached to form a substituted or unsubstituted $C_3$-$C_7$ heterocycloalkyl.

Embodiment 156 is the compound or pharmaceutically acceptable salt or solvate thereof of any one of embodiments 144, 148, 151, or 155, wherein: each $R^z$ is independently hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, —OCF$_3$, —NH$_2$, —NHCH$_3$, or —N(CH$_3$)$_2$.

Embodiment 157 is the compound or pharmaceutically acceptable salt or solvate thereof of any one of embodiments 144, 148, 151, or 155, wherein: each $R^z$ is independently hydrogen, Cl, Br, —CH$_3$, —OCH$_3$, —NH$_2$, or —N(CH$_3$)$_2$.

Embodiment 158 is the compound or pharmaceutically acceptable salt or solvate thereof of any one of embodiments 144, 148, 151, or 155, wherein: each $R^z$ is hydrogen.

Embodiment 159 is the compound or pharmaceutically acceptable salt or solvate thereof of any one of embodiments 119-133, wherein: $R^1$ is C$_1$-C$_6$alkyl substituted with halogen, —CN, —OR$^3$, —SR$^3$, —S(=O) R$^3$, —S(=O)$_2$R$^3$, —N(R$^3$)$_2$, —C(=O)OR$^3$, —C(=O)N(R$^3$)$_2$, —CR$^3$=C(R$^3$)$_2$, —C≡CR$^3$, substituted or unsubstituted C$_3$-C$_{10}$cycloalkyl, substituted or unsubstituted C$_2$-C$_{10}$heterocycloalkyl, or substituted or unsubstituted aryl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 160 is the compound or pharmaceutically acceptable salt or solvate thereof of any one of embodiments 119-133, wherein: $R^1$ is substituted or unsubstituted C$_3$-C$_{10}$cycloalkyl or substituted or unsubstituted C$_2$-C$_{10}$heterocycloalkyl.

Embodiment 161 is the compound or pharmaceutically acceptable salt or solvate thereof of embodiment 160, wherein: $R^1$ is C$_3$-C$_6$cycloalkyl or C$_3$-C$_5$heterocycloalkyl substituted with C$_1$-C$_6$alkyl, phenyl, pyridinyl, pyrazinyl, pyrimidinyl, pyridazinyl, or triazinyl.

Embodiment 162 is the compound or pharmaceutically acceptable salt or solvate thereof of embodiment 160, wherein: $R^1$ is C$_3$-C$_6$cycloalkyl or C$_3$-C$_5$heterocycloalkyl substituted with C$_1$-C$_6$alkyl, phenyl, or pyridinyl.

Embodiment 163 is the compound or pharmaceutically acceptable salt or solvate thereof of any one of embodiments 119-162, wherein: R is halogen, nitro, —CN, —OR$^3$, —C(=O)R$^3$, —C(=O)N(R$^3$)$_2$, —C(=O)OR$^3$, —S(=O) R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl; and each R$^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 164 is the compound or pharmaceutically acceptable salt or solvate thereof of any one of embodiments 119-162, wherein: R is F, Cl, Br, I, nitro, —CN, —OCH$_2$F, —OCHF$_2$, —OCF$_3$, —C(=O)CH$_3$, —C(=O)OCH$_3$, —C(=O)NH$_2$, —C(=O)NHCH$_3$, —C(=O)N(CH$_3$)$_2$, —S(=O)CH$_3$, —S(=O)$_2$CH$_3$, —NHS(=O)$_2$CH$_3$, —N(CH$_3$)S(=O)$_2$CH$_3$, —NHC(=O)CH$_3$, —N(CH$_3$)C(=O)CH$_3$, —NHC(=O)OCH$_3$, —N(CH$_3$)C(=O)OCH$_3$, —CH$_2$F, —CHF$_2$, or —CF$_3$.

Embodiment 165 is the compound or pharmaceutically acceptable salt or solvate thereof of any one of embodiments 119-162, wherein: R is F, Cl, —CN, —OCF$_3$, —CHF$_2$, or —CF$_3$.

Embodiment 166 is the compound or pharmaceutically acceptable salt or solvate thereof of any one of embodiments 119-162, wherein: R is F, Cl, —OCF$_3$, —CHF$_2$, or —CF$_3$.

Embodiment 167 is the compound or pharmaceutically acceptable salt or solvate thereof of any one of embodiments 119-162, wherein: R is F, Cl, or —CF$_3$.

Embodiment 168 is the compound or pharmaceutically acceptable salt or solvate thereof of any one of embodiments 119-167, wherein:

each $R^2$ is independently halogen, nitro, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, or substituted or unsubstituted C$_1$-C$_6$fluoroalkyl; and each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two R$^3$ are on the same nitrogen atom, then two R$^3$ are taken together with the nitrogen atom to which they are attached to form a substituted or unsubstituted C$_3$-C$_7$ heterocycloalkyl.

Embodiment 169 is the compound or pharmaceutically acceptable salt or solvate thereof of any one of embodiments 119-167, wherein: each $R^2$ is independently F, Cl, Br, nitro, —CN, —OH, —OCH$_3$, —OCH$_2$CH$_3$, —OCH$_2$CH$_2$OH, —OCH$_2$CN, —OCF$_3$, —S(=O)$_2$CH$_3$, —NH$_2$, —NHCH$_3$, —N(CH$_3$)$_2$, —C(=O)OCH$_3$, —CH$_3$, —CH$_2$CH$_3$, —CH$_2$F, —CHF$_2$, or —CF$_3$.

Embodiment 170 is the compound or pharmaceutically acceptable salt or solvate thereof of any one of embodiments 119-167, wherein: each $R^2$ is independently F, Cl, —CN, —OCH$_3$, —OCF$_3$, —C(=O)OCH$_3$, —CH$_3$, or —CF$_3$.

Embodiment 171 is the compound or pharmaceutically acceptable salt or solvate thereof of any one of embodiments 119-167, wherein: each $R^2$ is independently F, Cl, —OCF$_3$, or —CF$_3$.

Embodiment 172 is the compound or pharmaceutically acceptable salt or solvate thereof of any one of embodiments 119-167, wherein: each $R^2$ is independently F or Cl.

Embodiment 173 is the compound or pharmaceutically acceptable salt or solvate thereof of any one of embodiments 1-172, wherein: n is 0.

Embodiment 174 is the compound or pharmaceutically acceptable salt or solvate thereof of any one of embodiments 1-172, wherein: n is 1 or 2.

Embodiment 175 is the compound or pharmaceutically acceptable salt or solvate thereof of any one of embodiments 1-174, wherein the compound exhibits an IC$_{50}$ of no more than 3 µM.

Embodiment 176 is a compound or pharmaceutically acceptable salt or solvate thereof, wherein the compound is a compound from Table 1, or a pharmaceutically acceptable salt or solvate thereof.

Embodiment 177 is a pharmaceutical composition comprising a pharmaceutically acceptable excipient and a compound of any one of embodiments 1-176, or a pharmaceutically acceptable salt or solvate thereof.

Embodiment 178 is a method for treating a cancer in a subject in need thereof comprising administering a therapeutically effective amount of a compound of anyone of embodiments 1-176, or a pharmaceutically acceptable salt or solvate thereof.

Embodiment I is a compound of Formula (I), or a pharmaceutically acceptable salt or solvate thereof:

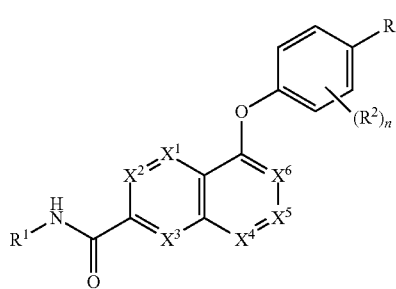

Formula (I)

wherein,
each $X^1$, $X^4$, $X^5$, and $X^6$, is independently N or $CR^X$;
each $X^2$ and $X^3$ is independently N or $CR^Y$;
each $R^X$ is independently hydrogen, halogen, nitro, —$OR^3$, —$SR^3$, —CN, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^Y$ is independently hydrogen, halogen, nitro, —CN, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
R is halogen, nitro, —CN, —$OR^3$, —$SR^3$, —C(=O)$R^3$, —C(=O)N($R^3$)$_2$, —C(=O)O$R^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)O$R^3$, or substituted or unsubstituted $C_1$-$C_6$fluoroalkyl;
$R^1$ is substituted or unsubstituted $C_1$-$C_6$alkyl, substituted or unsubstituted $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_{10}$cycloalkyl, substituted or unsubstituted $C_2$-$C_{10}$heterocycloalkyl, substituted or unsubstituted $C_1$-$C_6$heteroalkyl, —CN, or —S(=O)$_2R^4$;
each $R^2$ is independently halogen, nitro, —$N_3$, —CN, —$OR^3$, —$SR^3$, —S(=O)$_2R^3$, —N($R^3$)$_2$, —C(=O)O$R^3$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_2$ heterocycloalkyl;
$R^4$ is substituted or unsubstituted $C_1$-$C_6$alkyl, substituted or unsubstituted $C_1$-$C_6$fluoroalkyl, substituted or unsubstituted $C_3$-$C_{10}$cycloalkyl, or —$NH_2$; and
n is 0, 1, 2, 3, or 4.

Embodiment II is the compound or pharmaceutically acceptable salt or solvate thereof of embodiment I, wherein: $X^1$ is $CR^X$; and each $X^2$ and $X^3$ is $CR^Y$.

Embodiment III is the compound or pharmaceutically acceptable salt or solvate thereof of embodiment I or II, wherein:
each $X^4$, $X^5$, and $X^6$ is $CR^X$.

Embodiment IV is the compound or pharmaceutically acceptable salt or solvate thereof of any one of embodiments I-III, wherein:
each $R^X$ is independently hydrogen, halogen, —$OR^3$, —$SR^3$, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and
each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_3$—C; heterocycloalkyl.

Embodiment V is the compound or pharmaceutically acceptable salt or solvate thereof of any one of embodiments I-III, wherein:
each $R^X$ is independently hydrogen, F, Cl, Br, —$CH_3$, —OH, —$OCH_3$, or —$OCF_3$.

Embodiment VI is the compound or pharmaceutically acceptable salt or solvate thereof of any one of embodiments I-III, wherein:
each $R^X$ is hydrogen.

Embodiment VII is the compound or pharmaceutically acceptable salt or solvate thereof of any one of embodiments 1-VI, wherein:
each $R^Y$ is independently hydrogen, halogen, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$fluoroalkyl, or substituted or unsubstituted $C_2$-$C_4$alkynyl; and
each $R^3$ is independently hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl; or if two $R^3$ are on the same nitrogen atom, then two $R^3$ are taken together with the nitrogen atom to which they are attached to form a substituted or unsubstituted $C_rC$, heterocycloalkyl.

Embodiment VIII is the compound or pharmaceutically acceptable salt or solvate thereof of any one of embodiments I-VI, wherein:
each $R^Y$ is independently hydrogen, F, Cl, or —CH$_3$.

Embodiment IX is the compound or pharmaceutically acceptable salt or solvate thereof of any one of embodiments I-VI, wherein:
each $R^Y$ is hydrogen.

Embodiment X is the compound or pharmaceutically acceptable salt or solvate thereof of any one of embodiments I-IX, wherein: $R^1$ is substituted or unsubstituted C$_1$-C$_6$alkyl.

Embodiment XI is the compound or pharmaceutically acceptable salt or solvate thereof of any one of embodiments I-X, wherein:
$R^1$ is C$_1$-C$_6$alkyl substituted with —OR$^3$; and $R^3$ is hydrogen, substituted or unsubstituted C$_1$-C$_6$alkyl, substituted or unsubstituted C$_1$-C$_6$fluoroalkyl, or substituted or unsubstituted C$_3$-C$_{10}$cycloalkyl.

Embodiment XII is the compound or pharmaceutically acceptable salt or solvate thereof of embodiment XI, wherein:
$R^1$ is C$_1$-C$_6$alkyl substituted with —OH.

Embodiment XIII is the compound or pharmaceutically acceptable salt or solvate thereof of any one of embodiments I-X, wherein:
$R^1$ is C$_1$-C$_6$alkyl substituted with 6-membered heteroaryl ring selected from substituted or unsubstituted pyridinyl, substituted or unsubstituted pyrazinyl, substituted or unsubstituted pyrimidinyl, substituted or unsubstituted pyridazinyl, and substituted or unsubstituted triazinyl.

Embodiment XIV is the compound or pharmaceutically acceptable salt or solvate thereof of embodiment XIII, wherein:
$R^1$ is C$_1$-C$_6$alkyl substituted with pyridinyl.

Embodiment XV is the compound or pharmaceutically acceptable salt or solvate thereof of any one of embodiments I-X, wherein:
$R^1$ is C$_1$-C$_6$alkyl substituted with 1, 2, or 3 substituents each independently selected from —OH, —OCH$_3$, —NH$_2$, —NHCH$_3$, —N(CH$_3$)$_2$, and pyridinyl.

Embodiment XVI is the compound or pharmaceutically acceptable salt or solvate thereof of any one of embodiments I-XV, wherein:
R is halogen, nitro, —CN, —OR$^3$, —C(=O)R$^3$, —C(=O)N(R$^3$)$_2$, —C(=O)OR$^3$, —S(=O)R$^3$, —S(=O)$_2$R$^3$, —NR$^3$S(=O)$_2$R$^3$, —NR$^3$C(=O)R$^3$, —NR$^3$C(=O)OR$^3$, or substituted or unsubstituted C$_1$-C$_6$fluoroalkyl; and
each $R^3$ is independently hydrogen, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; or if two $R^3$ are on the same nitrogen atom, then two $R^3$ are taken together with the nitrogen atom to which they are attached to form a substituted or unsubstituted C$_3$-C$_7$ heterocycloalkyl.

Embodiment XVII is the compound or pharmaceutically acceptable salt or solvate thereof of any one of embodiments I-XV, wherein:
R is F, Cl, —CN, —OCF$_3$, —CHF$_2$, or —CF$_3$.

Embodiment XVIII is the compound or pharmaceutically acceptable salt or solvate thereof of any one of embodiments I-XV, wherein:
R is F, Cl, or —CF$_3$.

Embodiment XIX is the compound or pharmaceutically acceptable salt or solvate thereof of any one of embodiments I-XV, wherein:
R is —CF$_3$.

Embodiment XX is the compound or pharmaceutically acceptable salt or solvate thereof of any one of embodiments I-XIX, wherein:
each $R^2$ is independently F, Cl, —OCF$_3$, or —CF$_3$.

Embodiment XXI is the compound or pharmaceutically acceptable salt or solvate thereof of any one of embodiments I-XIX, wherein:
each $R^2$ is independently F or Cl.

Embodiment XXII is the compound or pharmaceutically acceptable salt or solvate thereof of any one of embodiments I-XXI, wherein: n is 0.

Embodiment XXIII is the compound or pharmaceutically acceptable salt or solvate thereof of any one of embodiments I-XXI, wherein: n is 1 or 2.

Embodiment XXIV is a compound or pharmaceutically acceptable salt or solvate thereof, wherein the compound is a compound from Table 1, or a pharmaceutically acceptable salt or solvate thereof.

Embodiment XXV is a pharmaceutical composition comprising a pharmaceutically acceptable excipient and a compound of any one of embodiments I-XXIV, or a pharmaceutically acceptable salt or solvate thereof.

Embodiment XXVI is a method of inhibiting one or more of proteins encompassed by, or related to, the Hippo pathway, comprising administering to a subject in need thereof a therapeutically effective amount of a compound of any one of embodiments I-XXIV, or a pharmaceutically acceptable salt thereof.

Embodiment XXVII is a method of inhibiting transcriptional coactivator with PDZ binding motif/Yes-associated protein transcriptional coactivator (TAZ/YAP) comprising administering to a subject in need thereof a therapeutically effective amount of a compound of any one of embodiments I-XXIV, or a pharmaceutically acceptable salt thereof.

Embodiment XXVIII is a method of treating cancer in a subject in need thereof comprising administering to the subject in need thereof a therapeutically effective amount of a compound of any one of embodiments I-XXIV, or a pharmaceutically acceptable salt thereof.

Embodiment XXIX is the method of embodiment XXVIII, wherein the cancer is selected from mesothelioma, hepatocellular carcinoma, meningioma, malignant peripheral nerve sheath tumor, Schwannoma, lung cancer, bladder carcinoma, cutaneous neurofibromas, prostate cancer, pancreatic cancer, glioblastoma, endometrial adenosquamous carcinoma, anaplastic thyroid carcinoma, gastric adenocarcinoma, esophageal adenocarcinoma, ovarian cancer, ovarian serous adenocarcinoma, melanoma, and breast cancer.

Embodiment XXX is a method of treating polycystic kidney disease or liver fibrosis in a subject in need thereof comprising administering to the subject in need thereof a therapeutically effective amount of a compound of any one of embodiments I-XXIV, or a pharmaceutically acceptable salt thereof.

What is claimed is:
1. A method of treating a cancer mediated by activation of transcriptional coactivator with PDZ binding motif/Yes-associated protein transcription coactivator (TAZ/YAP) in a subject in need thereof comprising administering to the subject in need thereof a therapeutically effective amount of a compound of Formula (I), or a pharmaceutically acceptable salt thereof,

Formula (I)

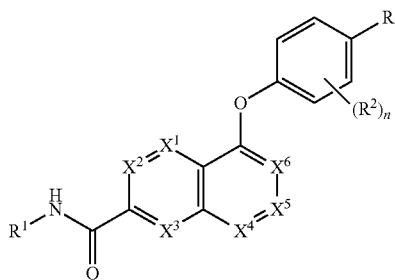

wherein, $X^1$ is $CR^X$; and each $X^2$ and $X^3$ is $CR^Y$;

each $X^4$, $X^5$, and $X^6$, is independently N or $CR^X$;

each $R^X$ is independently hydrogen, halogen, nitro, —OR³, —SR³, —CN, —C(=O)R³, —C(=O)N(R³)₂, —C(=O)OR³, —S(=O)R³, —S(=O)₂R³, —N(R³)₂, —NR³S(=O)₂R³, —NR³C(=O)R³, —NR³C(=O)OR³, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^Y$ is independently hydrogen, halogen, nitro, —CN, —C(=O)R³, —C(=O)N(R³)₂, —C(=O)OR³, —S(=O)R³, —S(=O)₂R³, —N(R³)₂, —NR³S(=O)₂R³, —NR³C(=O)R³, —NR³C(=O)OR³, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

R is halogen, nitro, —CN, —OR³, —SR³, —C(=O)R³, —C(=O)N(R³)₂, —C(=O)OR³, —S(=O)R³, —S(=O)₂R³, —N(R³)₂, —NR³S(=O)₂R³, —NR³C(=O)R³, —NR³C(=O)OR³, or substituted or unsubstituted $C_1$-$C_6$fluoroalkyl;

$R^1$ is $C_1$-$C_{10}$alkyl substituted with —OR³; and R³ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl;

each $R^2$ is independently halogen, nitro, —N₃, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two R³ are on the same nitrogen atom, then two R³ are taken together with the nitrogen atom to which they are attached to form a substituted or unsubstituted $C_3$-$C_7$ heterocycloalkyl; and n is 0, 1, 2, 3, or 4; and wherein the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma-, head and neck cancer, prostate cancer, and meningioma, and wherein the treatment is for therapeutic benefit.

2. The method of claim 1, wherein: R is —CF₃ and n is 0.

3. The method of claim 1, wherein:
each $X^4$, $X^5$, and $X^6$ is $CR^X$;
or $X^4$ is N; and each $X^5$ and $X^6$ is $CR^X$;
or $X^4$ and $X^5$ is $CR^X$; and $X^6$ is N;
each $R^X$ is independently hydrogen, F, Cl, Br, —CH₃, —OH, —OCH₃, or —OCF₃,
and each $R^Y$ is hydrogen.

4. The method of claim 1, wherein:
$R^1$ is $C_1$-$C_6$alkyl substituted with —OR³; and R³ is hydrogen or unsubstituted $C_1$-$C_6$alkyl;
R is —CF₃; and
n is 0.

5. The method of claim 1, wherein the compound of Formula (I) is selected from the group consisting of:

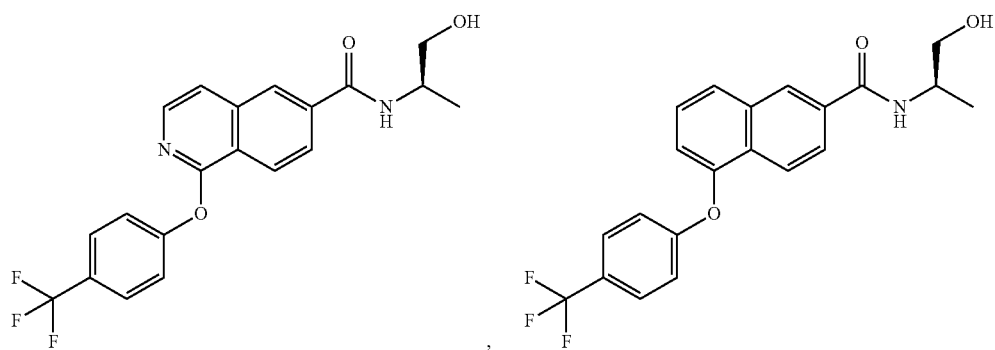

,

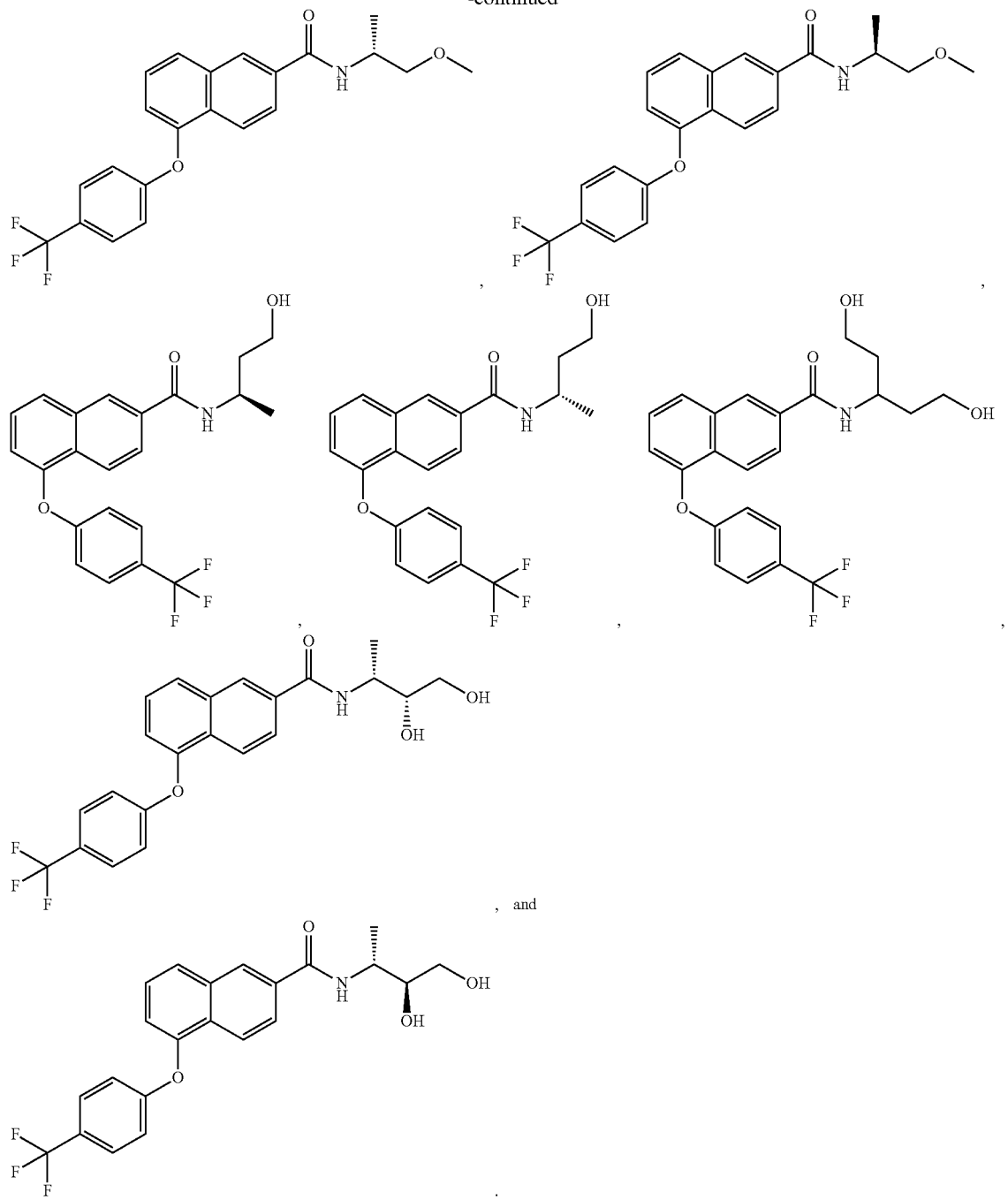

6. The method of claim 1, wherein the cancer is uveal melanoma, mesothelioma, esophageal cancer, or liver cancer.

7. The method of claim 6, wherein the cancer is uveal melanoma.

8. The method of claim 6, wherein the cancer is mesothelioma.

9. The method of claim 6, wherein the cancer is esophageal cancer.

10. The method of claim 6, wherein the cancer is liver cancer.

11. The method of claim 1, wherein the cancer is a relapsed or refractory cancer.

12. The method of claim 1, wherein the cancer is a metastasized cancer.

13. The method of claim 12, wherein the metastasized cancer is a metastatic solid tumor.

14. The method of claim 11, wherein the cancer is a refractory solid tumor.

15. A method of inhibiting an interaction of transcriptional enhancer associate domain (TEAD) transcription factors with transcriptional coactivator with PDZ binding motif/Yes-associated protein transcription coactivator (TAZ/YAP) in a mammal comprising administering to a subject in need thereof a therapeutically effective amount of a compound of Formula (I), or a pharmaceutically acceptable salt thereof, Formula (I)

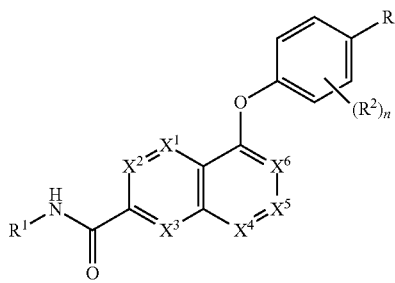

wherein, $X^1$ is $CR^X$; and each $X^2$ and $X^3$ is $CR^Y$;

each $X^4$, $X^5$, and $X^6$, is independently N or $CR^X$;

each $R^X$ is independently hydrogen, halogen, nitro, —$OR^3$, —$SR^3$, —CN, —C(=O)$R^3$, —C(=O)N($R^3$)$_2$, —C(=O)$OR^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)$OR^3$, substituted or unsubstituted $C_1$-$C_6$alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^Y$ is independently hydrogen, halogen, nitro, —CN, —C(O=O)$R^3$, —C(=O)N($R^3$)$_2$, —C(=O)$OR^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

R is halogen, nitro, —CN, —$OR^3$, —$SR^3$, —C(=O)$R^3$, -C(=O)N($R^3$)$_2$, —C(=O)$OR^3$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)$OR^3$, or substituted or unsubstituted $C_1$-$C_6$fluoroalkyl;

$R^1$ is $C_1$-$C_6$alkyl substituted with —$OR^3$; and $R^3$ is hydrogen, substituted or unsubstituted $C_1$-$C_6$alkyl, substituted or unsubstituted $C_1$-$C_6$fluoroalkyl, or substituted or unsubstituted $C_3$-$C_{10}$cycloalkyl;

each $R^2$ is independently halogen, nitro, —$N_3$, —CN, —$OR^3$, —$SR^3$, —S(=O)$_2R^3$, —N($R^3$)$_2$, —C(=O)$OR^3$, substituted or unsubstituted $C_1$-$C_6$alkyl, substituted or unsubstituted $C_1$-$C_{10}$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl, each $R^3$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; or if two $R^3$ are on the same nitrogen atom, then two $R^3$ are taken together with the nitrogen atom to which they are attached to form a substituted or unsubstituted $C_3$-$C_7$ heterocycloalkyl; and n is 0, 1, 2, 3, or 4.

16. The method of claim 15, wherein the mammal has a cancer.

17. The method of claim 16, wherein the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma.

* * * * *